US012753182B2

(12) United States Patent
Komatsu et al.

(10) Patent No.: US 12,753,182 B2
(45) Date of Patent: Oct. 6, 2026

(54) ORGANIC COMPOUND, LIGHT-EMITTING DEVICE, LIGHT-EMITTING APPARATUS, ELECTRONIC APPLIANCE, AND LIGHTING DEVICE

(71) Applicant: SEMICONDUCTOR ENERGY LABORATORY CO., LTD., Atsugi (JP)

(72) Inventors: Nozomi Komatsu, Atsugi (JP); Sachiko Kawakami, Atsugi (JP); Hiromitsu Kido, Atsugi (JP); Masatoshi Takabatake, Atsugi (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 942 days.

(21) Appl. No.: 18/047,000

(22) Filed: Oct. 17, 2022

(65) Prior Publication Data

US 2023/0147615 A1 May 11, 2023

(30) Foreign Application Priority Data

Oct. 22, 2021 (JP) ................................ 2021-172966
Jun. 27, 2022 (JP) ................................ 2022-102968

(51) Int. Cl.
*H01L 51/50* (2006.01)
*C07D 491/048* (2006.01)
(Continued)

(52) U.S. Cl.
CPC ....... *C07D 491/048* (2013.01); *C07D 495/04* (2013.01); *H10K 85/113* (2023.02); *H10K 85/657* (2023.02)

(58) Field of Classification Search
None
See application file for complete search history.

(56) References Cited

U.S. PATENT DOCUMENTS 8,431,245 B2 4/2013 Meng et al.
8,497,495 B2 7/2013 Lecloux et al.
(Continued)

FOREIGN PATENT DOCUMENTS

CN 109678868 A 4/2019
CN 112979616 A 6/2021
(Continued)

*Primary Examiner* — Gregory D Clark
(74) *Attorney, Agent, or Firm* — Fish & Richardson P.C.

(57) ABSTRACT

An organic compound that is stable in an excited state and has high emission efficiency is provided. An organic compound represented by General Formula (G1) is provided. Note that in General Formula (G1), $Q^1$ represents sulfur or oxygen. $R^1$ to $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms. In addition, $A^1$ represents an aryl group having 6 to 100 carbon atoms and including a substituted or unsubstituted substituent, or a heteroaryl group having 2 to 100 carbon atoms and including a substituted or unsubstituted substituent. Deuterium is substituted for at least one of hydrogen contained in $R^1$ to $R^5$ and $A^1$.

(Continued)

(G1)

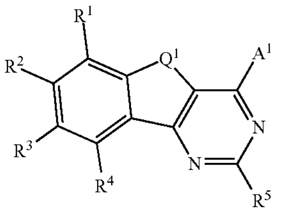

23 Claims, 73 Drawing Sheets

(51) Int. Cl.

| | |
|---|---|
| ***C07D 495/04*** | (2006.01) |
| ***H10K 85/10*** | (2023.01) |
| ***H10K 85/60*** | (2023.01) |

(56) References Cited

U.S. PATENT DOCUMENTS

| | | | | |
|---|---|---|---|---|
| 8,531,100 | B2 | 9/2013 | Herron et al. | |
| 8,592,239 | B2 | 11/2013 | Fennimore et al. | |
| 8,759,818 | B2 | 6/2014 | LeCloux et al. | |
| 8,968,883 | B2 | 3/2015 | Rostovtsev et al. | |
| 9,166,174 | B2 | 10/2015 | Herron et al. | |
| 9,306,185 | B2 | 4/2016 | Fennimore et al. | |
| 9,577,199 | B2 | 2/2017 | LeCloux et al. | |
| 9,905,782 | B2 | 2/2018 | Inoue et al. | |
| 10,586,931 | B2 | 3/2020 | Kanamoto et al. | |
| 11,189,802 | B2 | 11/2021 | Ogawa et al. | |
| 11,456,424 | B2 | 9/2022 | Hara et al. | |
| 11,530,225 | B2 | 12/2022 | Kim et al. | |
| 11,746,117 | B2 | 9/2023 | Jung et al. | |
| 12,022,730 | B2 | 6/2024 | Jung et al. | |
| 12,037,337 | B2 | 7/2024 | Jung et al. | |
| 12,098,156 | B2 | 9/2024 | Jung et al. | |
| 12,275,736 | B2 | 4/2025 | Jung et al. | |
| 2011/0057173 | A1 | 3/2011 | LeCloux et al. | |
| 2011/0121269 | A1 | 5/2011 | Lecloux et al. | |
| 2018/0282276 | A1 | 10/2018 | Mun et al. | |
| 2020/0199135 | A1 | 6/2020 | Kurihara et al. | |
| 2022/0006022 | A1 | 1/2022 | Suh et al. | |
| 2022/0181572 | A1 | 6/2022 | Ohsawa et al. | |
| 2022/0209162 | A1 | 6/2022 | Seo et al. | |
| 2022/0367831 | A1* | 11/2022 | Ohsawa | H10K 50/16 |
| 2023/0143281 | A1 | 5/2023 | Yoshiyasu et al. | |

FOREIGN PATENT DOCUMENTS

| | | | | |
|---|---|---|---|---|
| EP | 3553049 A | | 10/2019 | |
| EP | 3842428 A | | 6/2021 | |
| EP | 3854792 A | | 7/2021 | |
| JP | 2013-503860 | | 2/2013 | |
| JP | 2020-505338 | | 2/2020 | |
| KR | 2018-0022608 A | | 3/2018 | |
| KR | 10-2054806 | | 12/2019 | |
| KR | 2020-0050890 A | | 5/2020 | |
| KR | 2020-0063048 A | | 6/2020 | |
| KR | 2020-0063050 A | | 6/2020 | |
| KR | 2020-0063052 A | | 6/2020 | |
| KR | 2020-0076586 A | | 6/2020 | |
| KR | 2020-0133423 A | | 11/2020 | |
| KR | 20200136072 A | * | 12/2020 | H10K 50/11 |
| KR | 2021-0019968 A | | 2/2021 | |
| KR | 2021-0029028 A | | 3/2021 | |
| KR | 2021-0031205 A | | 3/2021 | |
| WO | WO-2018/123783 | | 7/2018 | |
| WO | WO-2018/198844 | | 11/2018 | |
| WO | WO-2021/191720 | | 9/2021 | |

* cited by examiner

ORGANIC COMPOUND, LIGHT-EMITTING DEVICE, LIGHT-EMITTING APPARATUS, ELECTRONIC APPLIANCE, AND LIGHTING DEVICE

BACKGROUND OF THE INVENTION

1. Field of the Invention

One embodiment of the present invention relates to an organic compound, a light-emitting device, a light-emitting apparatus, a light-emitting and light-receiving apparatus, a display device, an electronic appliance, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid-crystal display device, a light-emitting apparatus, a lighting device, a power storage device, a memory device, an imaging device, a driving method thereof, and a manufacturing method thereof.

2. Description of the Related Art

Light-emitting devices (organic EL elements) including organic compounds and utilizing electroluminescence (EL) have been put to more practical use. In the basic structure of such light-emitting devices, an organic compound layer containing a light-emitting material (an EL layer) is located between a pair of electrodes. Carriers are injected by application of voltage to the element, and recombination energy of the carriers is used, whereby light emission can be obtained from the light-emitting material.

Since such light-emitting devices are of self-emission type, displays including the light-emitting devices have higher visibility than liquid crystal displays; thus, the light-emitting devices are preferably used for pixels of a display. Displays including such light-emitting devices are also highly advantageous in that they can be thin and lightweight because a backlight is not needed. Moreover, such light-emitting devices also have a feature that response speed is extremely fast.

Since light-emitting layers of such light-emitting devices can be successively formed two-dimensionally, planar light emission can be achieved. This feature is difficult to realize with point light sources typified by incandescent lamps or LEDs or linear light sources typified by fluorescent lamps; thus, such light-emitting devices also have great potential as planar light sources, which can be applied to lighting devices and the like.

Displays or lighting devices including light-emitting devices can be suitably used for a variety of electronic appliances as described above, and research and development of light-emitting devices have progressed for higher efficiency or longer lifetimes.

Although the characteristics of light-emitting devices have been improved considerably, advanced requirements for various characteristics including efficiency and durability are not yet satisfied. In particular, to solve a problem such as burn-in that is an issue peculiar to EL, it is preferable to inhibit a reduction in efficiency due to deterioration as much as possible.

Deterioration largely depends on an emission center substance and its surrounding materials; therefore, host materials having good characteristics have been actively developed.

For example, an organic compound having an indolocarbazole skeleton is disclosed as a host material (Patent Document 1 and Patent Document 2). The organic compound having an indolocarbazole skeleton has a high glass transition point; thus, when the organic compound is used for a light-emitting device, favorable characteristics can be obtained. However, a material with higher heat resistance and a longer lifetime is required to inhibit deterioration of a light-emitting device.

In addition, a technique for substituting deuterium for hydrogen contained in a host material (a deuteration technique) is disclosed (Patent Document 3). Although deuteration of a host material is effective for a longer lifetime of a light-emitting device, a complicated synthesis pathway, necessity of high temperature and high pressure for synthesis, or the like is a problem.

REFERENCE

[Patent Document 1] PCT International Publication No. WO2018/198844

[Patent Document 2] PCT International Publication No. WO2018/123783

[Patent Document 3] Japanese Translation of PCT International Application No. 2013-503860

SUMMARY OF THE INVENTION

An object of one embodiment of the present invention is to provide a novel organic compound. Another object of one embodiment of the present invention is to provide an organic compound that is stable in an excited state. Another object of one embodiment of the present invention is to provide an organic compound that can be used as a host material in which a light-emitting substance is dispersed. Another object of one embodiment of the present invention is to provide an organic compound easy to synthesize. Another object of one embodiment of the present invention is to provide a light-emitting device with a long driving lifetime. Another object of one embodiment of the present invention is to provide a novel light-emitting device. Another object of one embodiment of the present invention is to reduce manufacturing costs of a light-emitting device. Another object of one embodiment of the present invention is to provide a light-emitting apparatus, an electronic appliance, or a lighting device having low power consumption.

Another object of one embodiment of the present invention is to provide an organic compound in which a partial structure is selectively deuterated. Another object of one embodiment of the present invention is to provide an organic compound in which a partial structure having an effect of a longer lifetime is selectively deuterated. Another object of one embodiment of the present invention is to perform a molecular design with which the degree of complexity of a synthesis pathway can be reduced and the temperature, pressure, and the like for synthesis can be lowered, and synthesize an organic compound with such a molecular design.

Note that the description of these objects does not preclude the existence of other objects. One embodiment of the present invention does not need to achieve all these objects. Other objects will be apparent from and can be derived from the descriptions of the specification, the drawings, the claims, and the like.

One embodiment of the present invention is an organic compound represented by General Formula (G1).

[Chemical Formula 1]

(G1)

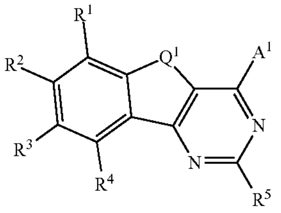

In General Formula (G1) above, $Q^1$ represents sulfur or oxygen, $R^1$ to $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, $A^1$ represents an aryl group having 6 to 100 carbon atoms and including a substituted or unsubstituted substituent, or a heteroaryl group having 2 to 100 carbon atoms and including a substituted or unsubstituted substituent, and deuterium is substituted for at least one of hydrogen contained in $R^1$ to $R^5$ and $A^1$.

One embodiment of the present invention is an organic compound represented by General Formula (G1).

[Chemical Formula 2]

(G1)

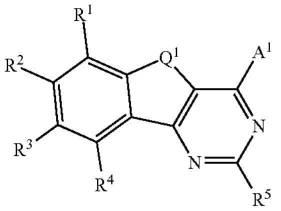

Note that in General Formula (G1) above, $Q^1$ represents sulfur or oxygen, $R^1$, $R^2$, $R^4$, and $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, $A^1$ represents an aryl group having 6 to 100 carbon atoms and including a substituted or unsubstituted substituent, or a heteroaryl group having 2 to 100 carbon atoms and including a substituted or unsubstituted substituent, $R^3$ represents an aryl group having 6 to 100 carbon atoms and including a substituted or unsubstituted substituent, or a heteroaryl group having 2 to 100 carbon atoms and including a substituted or unsubstituted substituent, and deuterium is substituted for at least one of hydrogen contained in $A^1$ or at least one of hydrogen contained in $R^1$ to $R^5$.

One embodiment of the present invention is an organic compound represented by General Formula (G2).

[Chemical Formula 3]

(G2)

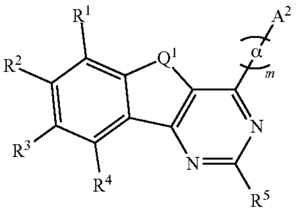

Note that in General Formula (G2) above, $Q^1$ represents sulfur or oxygen, $R^1$, $R^2$, $R^4$, and $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, a represents substituted or unsubstituted an arylene group having 6 to 25 carbon atoms, or a substituted or unsubstituted heteroarylene group having 2 to 25 carbon atoms, m represents an integer of 0 to 4, $A^2$ represents a substituted or unsubstituted aryl group having 6 to 30 carbon atoms, or a substituted or unsubstituted heteroaryl group having 2 to 30 carbon atoms, $R^3$ represents an aryl group having 6 to 100 carbon atoms and including a substituted or unsubstituted substituent, or a heteroaryl group having 2 to 100 carbon atoms and including a substituted or unsubstituted substituent, and at least one of hydrogen contained in a, $A^2$, and $R^3$ is deuterium.

One embodiment of the present invention is an organic compound with any of the above structures in which each of the arylene group having 6 to 25 carbon atoms and the heteroarylene group having 2 to 25 carbon atoms that are represented as a is independently represented by any one of Formulae (α-1) to (α-20).

[Chemical Formula 4]

(α-1)

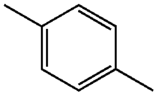

(α-2)

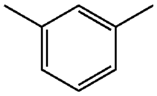

(α-3)

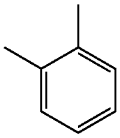

(α-4)

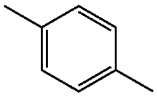

-continued
(α-5)
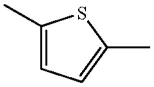
(α-6)
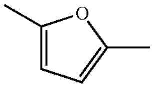
(α-7)
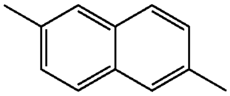
(α-8)
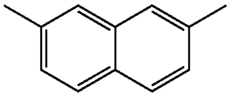
(α-9)
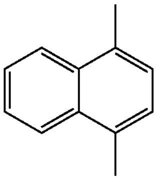
(α-10)
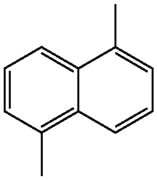
(α-11)
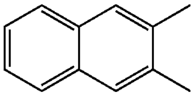
(α-12)
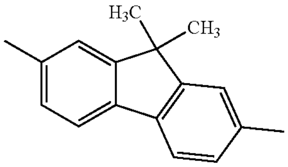
(α-13)
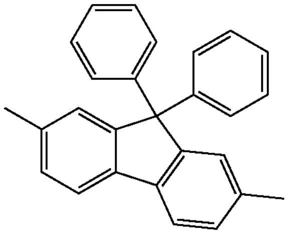
-continued
(α-14)
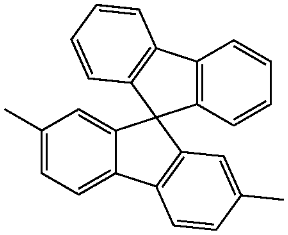
(α-15)
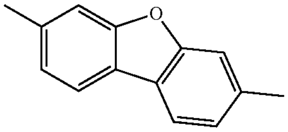
(α-16)
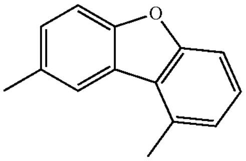
(α-17)
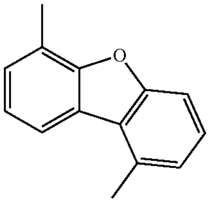
(α-18)
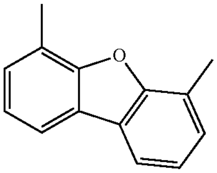
(α-19)
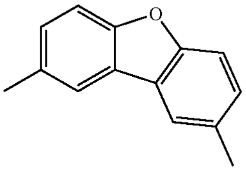
(α-20)
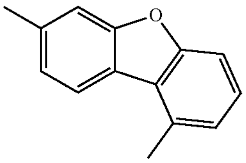

One embodiment of the present invention is an organic compound represented by General Formula (G3).

[Chemical Formula 5]

(G3)

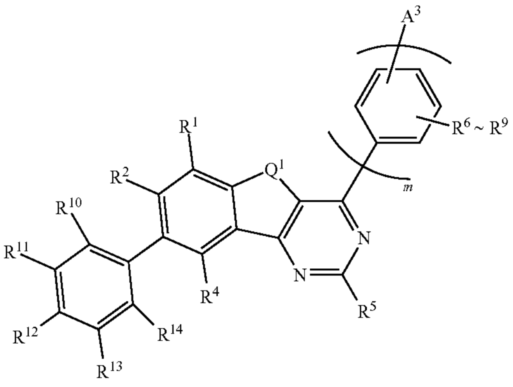

Note that in General Formula (G3) above, $Q^1$ represents sulfur or oxygen, $R^1$, $R^2$, and $R^4$ to $R^{14}$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, $A^3$ represents a substituted or unsubstituted aryl group having 6 to 30 carbon atoms, or a substituted or unsubstituted heteroaryl group having 2 to 30 carbon atoms, m represents an integer of 0 to 4, and at least one of hydrogen contained in $A^3$ and $R^1$, $R^2$, and $R^4$ to $R^{14}$ is deuterium.

One embodiment of the present invention is an organic compound represented by General Formula (G4).

[Chemical Formula 6]

(G4)

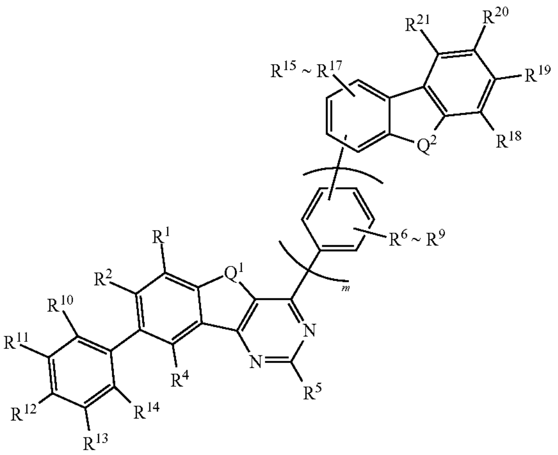

Note that in General Formula (G4) above, $Q^1$ and $Q^2$ each independently represent sulfur or oxygen, $R^1$, $R^2$, and $R^4$ to $R^{21}$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, m represents an integer of 0 to 4, and at least one of $R^1$, $R^2$, and $R^4$ to $R^{21}$ is deuterium.

One embodiment of the present invention is an organic compound in which $A^1$ and $R^3$ have the same structure.

One embodiment of the present invention is an organic compound with any of the above structures in which one or more hydrogen other than hydrogen directly bonded to a benzofuropyrimidine skeleton is deuterium.

One embodiment of the present invention is an organic compound with any of the above structures in which all hydrogen contained in a molecule structure is deuterium.

One embodiment of the present invention is an organic compound with any of the above structures in which each of the aryl group having 6 to 30 carbon atoms and the heteroaryl group having 2 to 30 carbon atoms is independently represented by any one of Formulae (Ar-1) to (Ar-80).

[Chemical Formula 7]

(Ar-1)

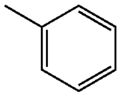

(Ar-2)

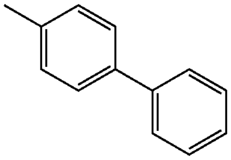

(Ar-3)

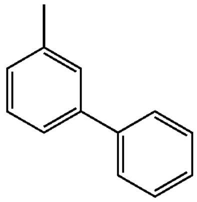

(Ar-4)

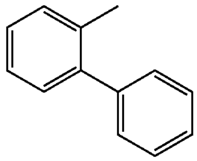

(Ar-5)

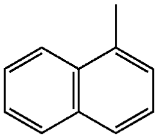

(Ar-6)

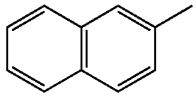

-continued
(Ar-7)
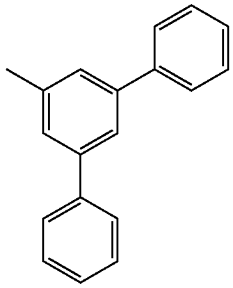
(Ar-8)
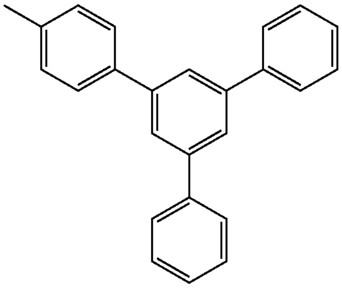
(Ar-9)
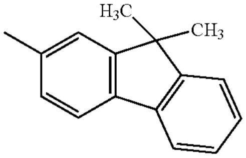
(Ar-10)
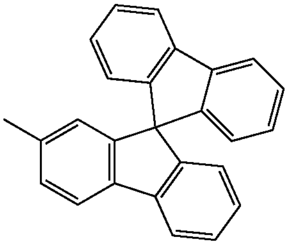
(Ar-11)
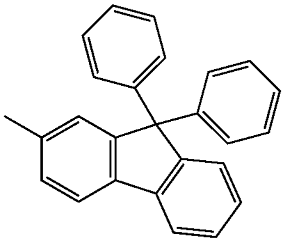
(Ar-12)
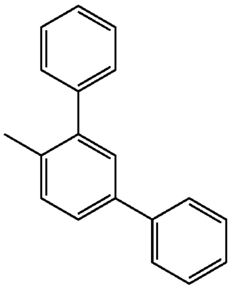
-continued
(Ar-13)
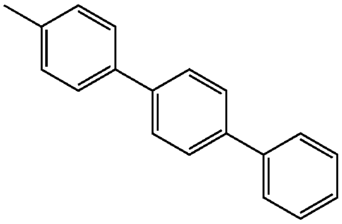
(Ar-14)
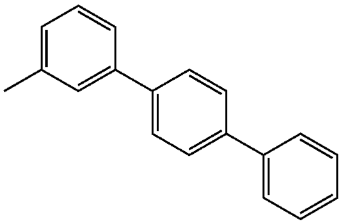
(Ar-15)
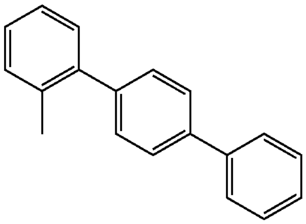
(Ar-16)
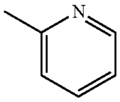
(Ar-17)
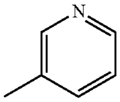
(Ar-18)
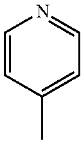
(Ar-19)
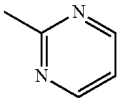
(Ar-20)
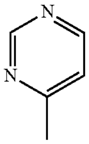
(Ar-21)
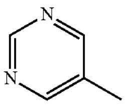
(Ar-22)
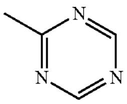

-continued
(Ar-23)
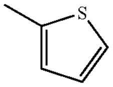
(Ar-24)
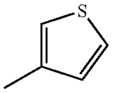
(Ar-25)
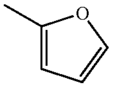
(Ar-26)
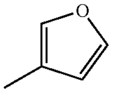
(Ar-27)
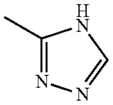
(Ar-28)
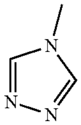
[Chemical Formula 8]
(Ar-29)
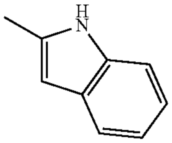
(Ar-30)
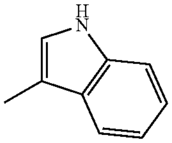
(Ar-31)
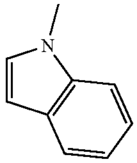
(Ar-32)
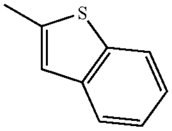
(Ar-33)
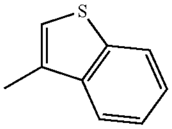
(Ar-34)
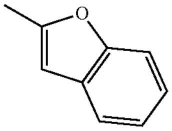
-continued
(Ar-35)
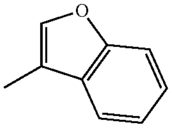
(Ar-36)
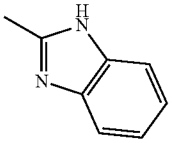
(Ar-37)
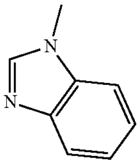
(Ar-38)
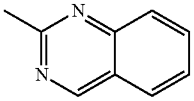
(Ar-39)
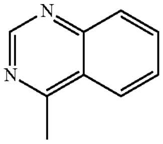
(Ar-40)
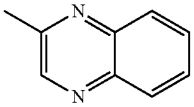
(Ar-41)
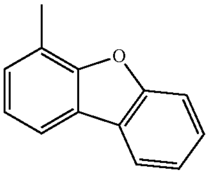
(Ar-42)
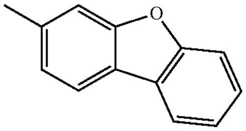
(Ar-43)
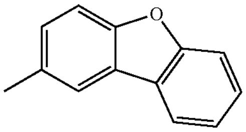
(Ar-44)
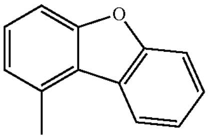

-continued
(Ar-45)
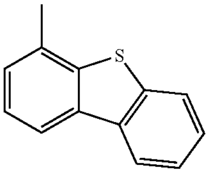
(Ar-46)
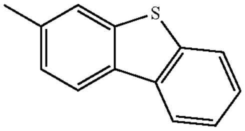
(Ar-47)
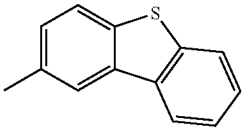
(Ar-48)
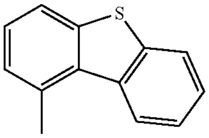
(Ar-49)
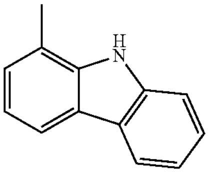
(Ar-50)
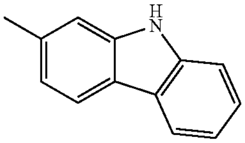
(Ar-51)
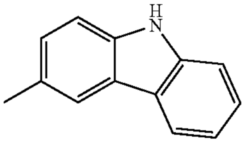
(Ar-52)
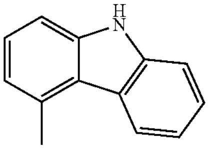
(Ar-53)
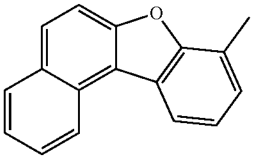
(Ar-54)
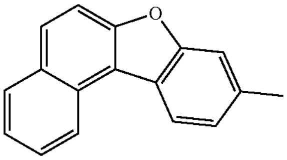
-continued
(Ar-55)
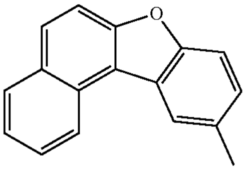
(Ar-56)
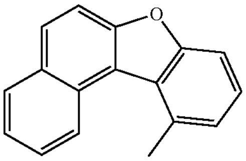
(Ar-57)
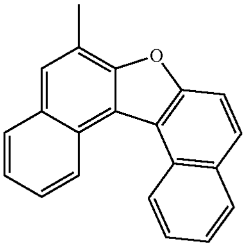
(Ar-58)
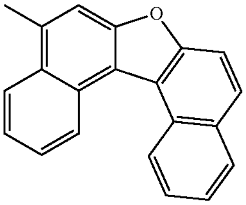
[Chemical Formula 9]
(Ar-59)
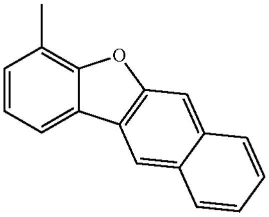
(Ar-60)
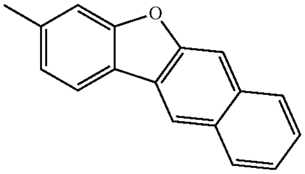
(Ar-61)
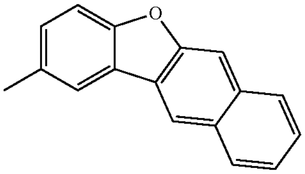
(Ar-62)
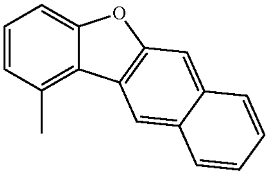

-continued
(Ar-63)
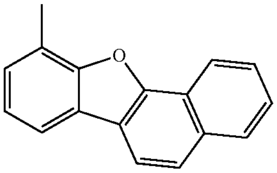
(Ar-64)
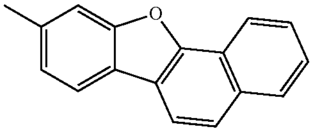
(Ar-65)
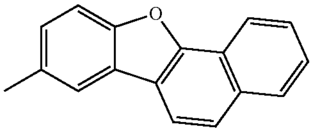
(Ar-66)
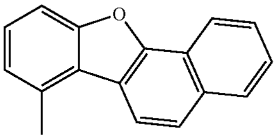
(Ar-67)
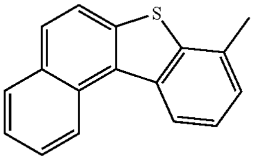
(Ar-68)
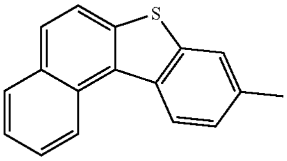
(Ar-69)
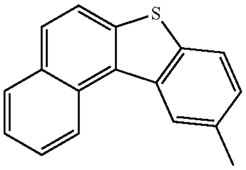
(Ar-70)
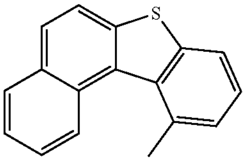
(Ar-71)
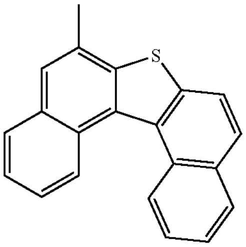
-continued
(Ar-72)
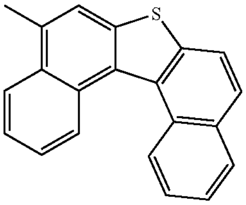
(Ar-73)
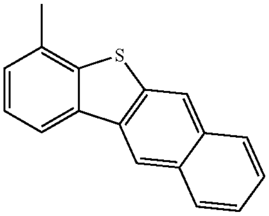
(Ar-74)
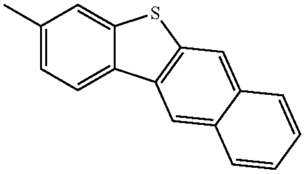
(Ar-75)
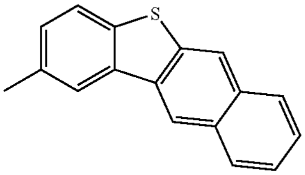
(Ar-76)
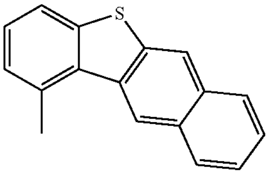
(Ar-77)
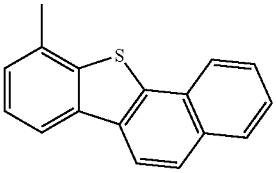
(Ar-78)
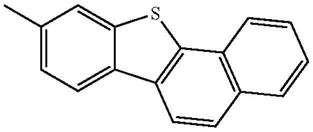
(Ar-79)
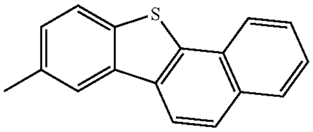
(Ar-80)
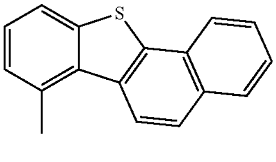

One embodiment of the present invention is an organic compound represented by Structural Formula (100), (101), or (128).

[Chemical Formula 10]

(100)

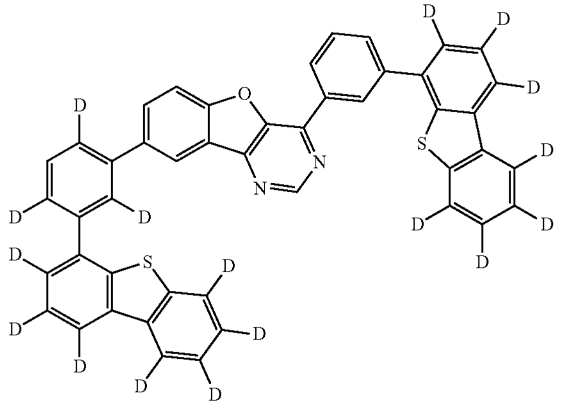

(101)

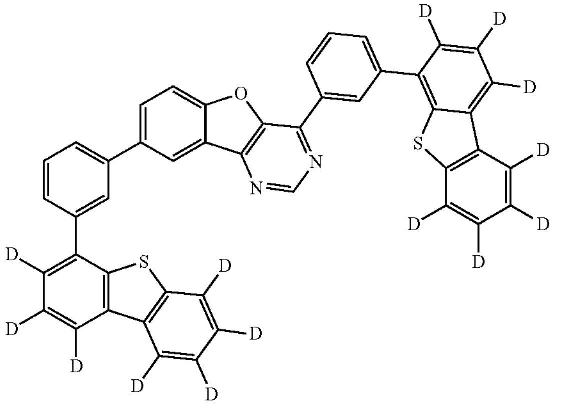

(128)

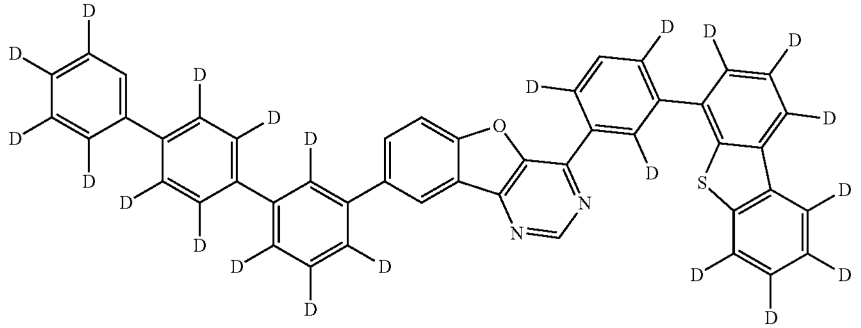

One embodiment of the present invention is a light-emitting device containing the organic compound having any of the above structures.

One embodiment of the present invention is a light-emitting apparatus including the light-emitting device having the above structure, and at least one of a transistor and a substrate.

One embodiment of the present invention is an electronic appliance including the above light-emitting apparatus, and at least one of a sensor unit, an input unit, and a communication unit.

One embodiment of the present invention is a lighting device including the above light-emitting apparatus, the above electronic appliance, and a housing.

According to one embodiment of the present invention, a novel organic compound can be provided. According to one embodiment of the present invention, an organic compound that is less likely to react in an excited state and stable can be provided. According to one embodiment of the present invention, an organic compound that can be used as a host material can be provided. According to one embodiment of the present invention, an organic compound easy to synthesize can be provided. According to one embodiment of the present invention, a novel light-emitting device can be provided. According to one embodiment of the present invention, a light-emitting device with a long driving lifetime can be provided. According to one embodiment of the present invention, manufacturing costs of a light-emitting device can be reduced. According to one embodiment of the present invention, a light-emitting apparatus, an electronic appliance, or a lighting device having low power consumption can be provided.

According to one embodiment of the present invention, an organic compound in which a partial structure is selectively deuterated can be provided. According to one embodiment of the present invention, an organic compound in which a partial structure having an effect of a longer lifetime is selectively deuterated can be provided. As a result, the degree of complexity of a synthesis pathway and the temperature, pressure, and the like in the synthesis pathway that are caused in substituting deuterium for all hydrogen of an organic compound can be reduced or lowered.

Note that the description of these effects does not preclude the existence of other effects. One embodiment of the present invention does not necessarily have all the effects. Other effects will be apparent from and can be derived from the descriptions of the specification, the drawings, the claims, and the like.

DETAILED DESCRIPTION OF THE INVENTION

Embodiment 1

Figure 1A:
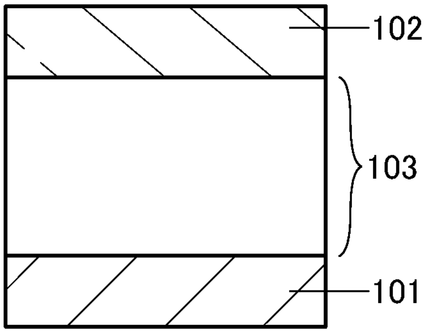
FIGS. 1A to 1E illustrate structures of light-emitting devices of an embodiment.

In this embodiment, organic compounds and thin films of embodiments of the present invention will be described.

One embodiment of the present invention is an organic compound that is a bipolar substance having both a hole-transport skeleton and an electron-transport skeleton, in which the hole-transport skeleton is deuterated. Specifically, one embodiment of the present invention is a bipolar substance that has a benzofuropyrimidine skeleton as an electron-transport skeleton, and a deuterated dibenzothiophene skeleton or a deuterated dibenzofuran skeleton as a hole-transport skeleton. One embodiment of the present invention has both a hole-transport skeleton and an electron-transport skeleton, thereby having both a hole-transport property and an electron-transport property. Accordingly, one embodiment of the present invention can be suitably used as a host material for a light-emitting layer of a light-emitting device, for example. Furthermore, one embodiment of the present invention can be suitably used for a hole-transport layer and an electron-transport layer as a transport layer in contact with a light-emitting layer.

Note that in this specification and the like, deuteration means that deuterium (D) is substituted for at least one of hydrogen (H) of an organic compound. The bond dissociation energy of a bond between carbon and deuterium (C-D bond) is higher than the bond dissociation energy of a bond between carbon and hydrogen (C—H bond), and thus the C-D bond is stable and not easily cut. Accordingly, in one embodiment of the present invention, when a hole-transport skeleton is deuterated, carbon-hydrogen bond dissociation in a hole-transport skeleton in a ground state or an excited state can be inhibited. Deterioration or a change in quality of an organic compound due to carbon-hydrogen bond dissociation in a hole-transport skeleton can be inhibited.

The organic compound of one embodiment of the present invention has a hole-transport skeleton; therefore, when the organic compound of one embodiment of the present invention is used for a light-emitting device as a host material, for example, the hole-transport skeleton receives a hole in some cases. Carbon-hydrogen bond dissociation easily occurs in hole transfer in some cases; however, a hole-transport skeleton is deuterated in the organic compound of one embodiment of the present invention, and thus carbon-hydrogen bond dissociation can be inhibited.

Note that in synthesis of an organic compound in which the whole structure of a bipolar substance having a hole-transport skeleton and an electron-transport skeleton is deuterated, a complicated synthesis pathway, necessity of high temperature and high pressure, or the like is a problem. Accordingly, one embodiment of the present invention can be easily synthesized by selectively deuterating only a hole-transport skeleton, leading to cost reduction.

In this specification and the like, the deuteration rate of a hole-transport skeleton refers to a rate of substitution of deuterium for hydrogen directly bonded to a hole-transport skeleton. For example, in the case where deuterium is substituted for 10% of hydrogen directly bonded to a hole-transport skeleton, the deuteration rate of the hole-transport skeleton is 10%. Furthermore, in the case where a hole-transport skeleton has a substituent, hydrogen or deuterium of the substituent is not used for the calculation of the deuteration rate of the hole-transport skeleton. In the case where only deuterium and a phenyl group directly bond to a hole-transport skeleton, for example, the deuteration rate of the hole-transport skeleton is 100%, regardless of the rates of hydrogen and deuterium in the phenyl group.

Note that a specific example of the benzofuropyrimidine skeleton is, but not limited to, a benzofuro[3,2-d]pyrimidine skeleton.

The organic compound of one embodiment of the present invention has an excellent carrier transport property. Thus, a light-emitting device with low driving voltage can be provided. Furthermore, an electronic device with low power consumption can be provided.

The organic compound of one embodiment of the present invention has a high triplet excitation level (T1 level) and thus can be suitably applied to a light-emitting device containing a phosphorescent substance. Specifically, the organic compound of one embodiment of the present invention is preferably used for a light-emitting device as a host material.

In the case where the organic compound of one embodiment of the present invention is used as a host material, when the organic compound has a high triplet excitation level (T1 level), excitation energy of a phosphorescent substance is inhibited from transferring to the organic compound, and thus the excitation energy can be effectively converted into light emission. Note that an iridium complex can be used as a phosphorescent substance, for example. Consequently, a light-emitting device with high efficiency can be provided.

Furthermore, the organic compound of one embodiment of the present invention can be suitably used not only as a host material in a light-emitting layer, but also for a carrier-transport layer (hole-transport layer or electron-transport layer).

The organic compound of one embodiment of the present invention has a hole-transport skeleton; therefore, when the organic compound of one embodiment of the present invention is used for a light-emitting device as a host material in which a light-emitting substance is dispersed, for example, the hole-transport skeleton receives a hole in some cases. Carbon-hydrogen bond dissociation easily occurs in hole transfer in some cases; however, a hole-transport skeleton is deuterated in the organic compound of one embodiment of the present invention, and thus carbon-hydrogen bond dissociation can be inhibited. The organic compound of one embodiment of the present invention has both a hole-transport skeleton and an electron-transport skeleton, and thus can receive both an electron and a hole. Accordingly, the organic compound of one embodiment of the present invention can be efficiently in an excited state due to carrier recombination. Therefore, the organic compound of one embodiment of the present invention is used for a light-emitting device as a host material in which a light-emitting substance is dispersed, whereby a light-emitting device with high efficiency can be provided.

Example 1 of Organic Compound

One embodiment of the present invention is an organic compound represented by General Formula (G1).

[Chemical Formula 11]

(G1)

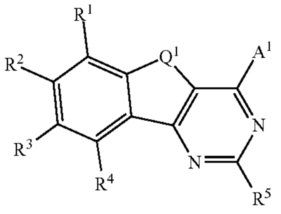

Note that $Q^1$ represents sulfur or oxygen in General Formula (G1) above. In General Formula (G1), $R^1$ to $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms. Furthermore, $A^1$ represents an aryl group having 6 to 100 carbon atoms and including a substituted or unsubstituted substituent, or a heteroaryl group having 2 to 100 carbon atoms and including a substituted or unsubstituted substituent. Deuterium is substituted for at least one of hydrogen contained in $R^1$ to $R^5$ and $A^1$.

Examples of the alkyl group substituted for $R^1$ to $R^5$ in General Formula (G1) above can include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

Examples of the cycloalkyl group or the polycyclic alkyl group substituted for $R^1$ to $R^5$ in General Formula (G1) above can include a cyclopropyl group, a cyclobutyl group, a cyclopentyl group, a cyclohexyl group, a 1-methylcyclohexyl group, a cycloheptyl group, and an adamantyl group.

Examples of the aryl group or the heteroaryl group substituted for $A^1$ or $R^1$ to $R^5$ in General Formula (G1) above can include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, an acenaphthylenyl group, an anthryl group, a phenanthryl group, a biphenyl group, a terphenyl group, a triphenylenyl group, a pyrimidinyl group, a pyrazinyl group, a pyridazinyl group, a triadinyl group, a bipyridinyl group, a phenanthrolinyl group, a quinoxalinyl group, a dibenzoquinoxalinyl group, a quinazolinyl group, a benzoquinazolinyl group, a dibenzoquinazolinyl group, an imidazolyl group, a triazolyl group, an oxadiazolyl group, a benzoimidazolyl group, a furopyrimidyl group, a furopyrazyl group, a furopyridazyl group, a benzofuropyrimidinyl group, a benzofuropyrazinyl group, a benzofuropyridazinyl group, a thienyl group, a furanyl group, a benzothiophen-yl group, a benzofuran-yl group, a dibenzothiophen-yl group, a dibenzofuran-yl group, a benzonaphthothiophen-yl group, a benzonaphthofuran-yl group, a dinaphthothiophen-yl group, and a dinaphthofuran-yl group.

In the organic compound represented by General Formula (G1) above, which is one embodiment of the present invention, deuterium is substituted for at least one of hydrogen contained in $R^1$ to $R^5$ and $A^1$, and thus deterioration or a change in quality of the organic compound can be inhibited. Furthermore, since carbon-hydrogen bond dissociation in an excited state can be inhibited, the organic compound of one embodiment of the present invention can be suitably used as a host material of a light-emitting device in which a light-emitting substance is dispersed.

When the organic compound of one embodiment of the present invention is used for a light-emitting device as a host material, for example, a hole-transport skeleton receives a hole in some cases. Carbon-hydrogen bond dissociation tends to easily occur in hole transfer; however, a hole-transport skeleton is deuterated in the organic compound of one embodiment of the present invention, and thus carbon-hydrogen bond dissociation can be inhibited, which is preferable.

Example 2 of Organic Compound

One embodiment of the present invention is an organic compound represented by General Formula (G1).

[Chemical Formula 12]

(G1)

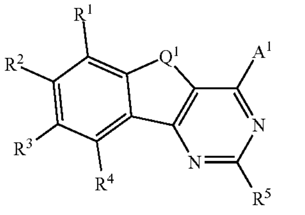

Note that $Q^1$ represents sulfur or oxygen in General Formula (G1) above. $R^1$, $R^2$, $R^4$, and $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms. Furthermore, $A^1$ represents an aryl group having 6 to 100 carbon atoms and including a substituted or unsubstituted substituent, or a heteroaryl group having 2 to 100 carbon atoms and including a substituted or unsubstituted substituent. Moreover, $R^3$ represents an aryl group having 6 to 100 carbon atoms and including a substituted or unsubstituted substituent, or a heteroaryl group having 2 to 100 carbon atoms and including a substituted or unsubstituted substituent. Deuterium is substituted for at least one of hydrogen contained in $A^1$ or at least one of hydrogen contained in $R^1$ to $R^5$.

Note that in General Formula (G1) above, as substituents substituted for $A^1$, $R^1$, $R^2$, $R^4$, and $R^5$, the same substituents as the substituents with the corresponding symbols of General Formula (G1) in <Example 1 of organic compound> described above can be given; thus, the above description can be referred to.

In General Formula (G1) above, examples of the aryl group substituted for $R^3$ can include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, an acenaphthylenyl group, an anthryl group, a phenanthryl group, a terphenyl group, and a triphenylenyl group. Examples of the heteroaryl group can include a pyrimidinyl group, a pyrazinyl group, a pyridazinyl group, a triadinyl group, a bipyridinyl group, a phenanthrolinyl group, a quinoxalinyl group, a dibenzoquinoxalinyl group, a quinazolinyl group, a benzoquinazolinyl group, a dibenzoquinazolinyl group, an imidazolyl group, a triazolyl group, an oxadiazolyl group, a benzoimidazolyl group, a furopyrimidyl group, a furopyrazyl group, a furopyridazyl group, a benzofuropyrimidinyl group, a benzofuropyrazinyl group, a benzofuropyridazinyl group, a thienyl group, a furanyl group, a benzothiophen-yl group, a benzofuran-yl group, a dibenzothiophen-yl group, a dibenzofuran-yl group, a benzonaphthothiophen-yl group, a benzonaphthofuran-yl group, a dinaphthothiophen-yl group, and a dinaphthofuran-yl group.

In the organic compound represented by General Formula (G1) above, which is one embodiment of the present invention, deuterium is substituted for at least one of hydrogen contained in $R^1$ to $R^5$ and $A^1$, and thus deterioration or a change in quality of the organic compound can be inhibited. Furthermore, since carbon-hydrogen bond dissociation in an excited state can be inhibited, the organic compound of one embodiment of the present invention can be suitably used as a host material of a light-emitting device in which a light-emitting substance is dispersed.

When the organic compound one embodiment of the present invention is used for a light-emitting device as a host material, for example, hole-transport skeleton receives a hole in some cases. Carbon-hydrogen bond dissociation tends to easily occur in hole transfer in some cases; however, a hole-transport skeleton is deuterated in the organic compound of one embodiment of the present invention, and carbon-hydrogen bond dissociation can be inhibited, which is preferable.

Example 3 of Organic Compound

One embodiment of the present invention is an organic compound represented by General Formula (G2).

[Chemical Formula 13]

(G2)

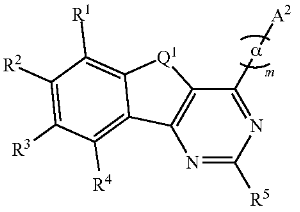

Note that $Q^1$ represents sulfur or oxygen in General Formula (G2) above. $R^1$, $R^2$, $R^4$, and $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms. In addition, a represents a substituted or unsubstituted arylene group having 6 to 25 carbon atoms or a substituted or unsubstituted heteroarylene group having 2 to 25 carbon atoms. Moreover, m represents an integer of 0 to 4. Furthermore, $A^2$ represents a substituted or unsubstituted aryl group having 6 to 30 carbon atoms, or a substituted or unsubstituted heteroaryl group having 2 to 30 carbon atoms. $R^3$ represents an aryl group having 6 to 100 carbon atoms and including a substituted or unsubstituted substituent, or a heteroaryl group having 2 to 100 carbon atoms and including a substituted or unsubstituted substituent. Furthermore, at least one of hydrogen contained in a, $A^2$, and $R^3$ is deuterium.

Note that the substituents that can be represented by the same symbols in General Formula (G1) described above in <Example 1 of organic compound> or <Example 2 of organic compound> are referred to for the substituents substituted for any of $A^1$ and $R^1$ to $R^5$ in General Formula (G2) above.

In General Formula (G2) above, examples of the aryl group substituted for $A^2$ can include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, an acenaphthylenyl group, an anthryl group, a phenanthryl group, a biphenyl group, a terphenyl group, and a triphenylenyl group. Examples of the heteroaryl group can include a pyrimidinyl group, a pyrazinyl group, a pyridazinyl group, a triadinyl group, a bipyridinyl group, a phenanthrolinyl group, a quinoxalinyl group, a dibenzoquinoxalinyl group, a quinazolinyl group, a benzoquinazolinyl group, a dibenzoquinazolinyl group, an imidazolyl group, a triazolyl group, an oxadiazolyl group, a benzoimidazolyl group, a furopyrimidyl group, a furopyrazyl group, a furopyridazyl group, a benzofuropyrimidinyl group, a benzofuropyrazinyl group, a benzofuropyridazinyl group, a thienyl group, a furanyl group, a benzothiophen-yl group, a benzofuran-yl group, a dibenzothiophen-yl group, a dibenzofuran-yl group, a benzonaphthothiophen-yl group, a benzonaphthofuran-yl group, a dinaphthothiophen-yl group, and a dinaphthofuran-yl group.

In General Formula (G2) above, examples of the arylene group substituted for a can include a phenylene group, a toluylene group, a dimethylphenylene group, a trimethylphenylene group, a tetramethylphenylene group, a biphenylene group, a terphenylene group, a quaterphenylene group, a naphthylene group, a fluorenylene group, a phenanthrenylene group, a triphenylenylene group, a benzo[a]phenanthrenylene group, and a benzo[c]phenanthrenylene group. Examples of the heteroarylene group can be include a pyrimidine-diyl group, a pyrazine-diyl group, a pyridazine-diyl group, a triazine-diyl group, a bipyridine-diyl group, a phenanthroline-diyl group, a quinoxaline-diyl group, a dibenzoquinoxaline-diyl group, a quinazoline-diyl group, a benzoquinazoline-diyl group, a dibenzoquinazoline-diyl group, an imidazole-diyl group, a triazole-diyl group, an oxadiazole-diyl group, a benzimidazole-diyl group, a furodiazine-diyl group, a benzofuropyrimidine-diyl group, a thiophene-diyl group, a furan-diyl group, a benzothiophene-diyl group, a benzofuran-diyl group, a dibenzothiophene-diyl group, a dibenzofuran-diyl group, a benzonaphthothiophene-diyl group, a benzonaphthofuran-diyl group, a dinaphthothiophene-diyl group, and a dinaphthofuran-diyl group.

Note that in General Formula (G2) above, when m is 0, the highest occupied molecular orbital (HOMO) level tends to be deep; when m is greater than or equal to 1 and less than or equal to 4, the HOMO level tends to be shallow. In such a manner, the HOMO level of the organic compound can be changed by changing m. In the case where m is greater than or equal to 2 and less than or equal to 4, the molecular weight becomes large compared with the case where m is 0 or 1 and thus heat resistance becomes high, and crystallization does not tend to occur and film quality becomes stable in the case of making a film thinner, which is preferable. As a result, a device with high reliability can be provided.

Meanwhile, when m is 0 or 1, a sublimation property can be high because the molecular weight is not too large, and decomposition in evaporation can be prevented, which is preferable because a highly-purified thin film can be provided. As a result, a device with high reliability can be provided.

In General Formula (G1) and General Formula (G2) above, it is preferable that each of an arylene group having 6 to 30 carbon atoms and a heteroarylene group having 2 to 30 carbon atoms be independently represented by any one of Structural Formulae (α-1) to (α-20).

[Chemical Formula 14]

(α-1)

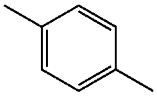

(α-2)

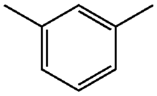

(α-3)

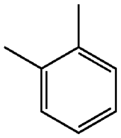

(α-4)

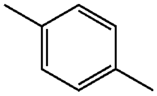

(α-5)

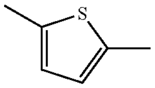

(α-6)

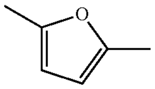

(α-7)

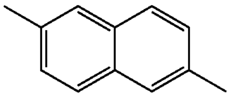

(α-8)

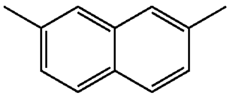

(α-9)

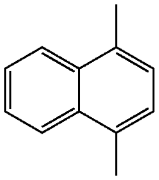

(α-10)

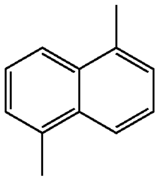

(α-11)

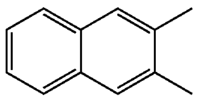

(α-12)

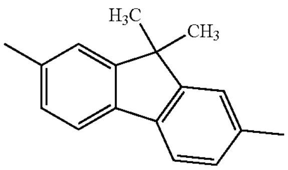

-continued (α-13)

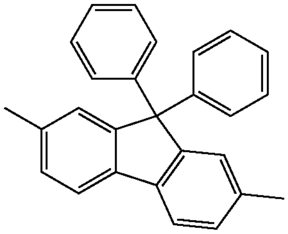

(α-14)

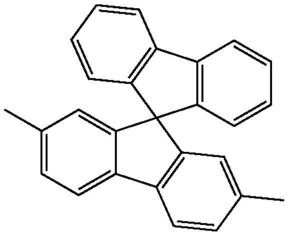

(α-15)

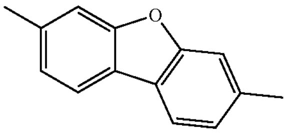

(α-16)

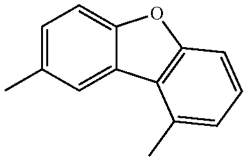

(α-17)

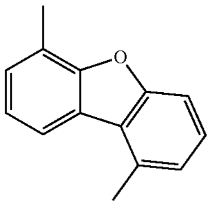

(α-18)

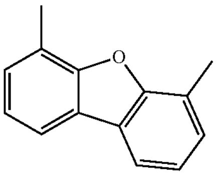

(α-19)

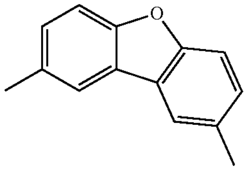

(α-20)

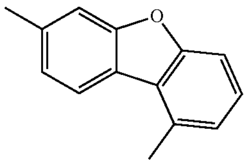

Note that substituents represented by Structural Formulae (α-1) to (α-20) above are examples of an arylene group having 6 to 25 carbon atoms or a heteroarylene group having 2 to 25 carbon atoms; however, an arylene group having 6 to 25 carbon atoms or a heteroarylene group having 2 to 25 carbon atoms that can be used for General Formula (G2) above is not limited thereto. When an arylene group or a heteroarylene group is included as a substituent, carrier balance can be adjusted by changing the HOMO level or heat resistance can be improved.

In General Formula (G2) above, when an arylene group having 6 to 25 carbon atoms or a heteroarylene group having 2 to 25 carbon atoms has a substituent, the substituent is a straight-chain alkyl group having 1 to 6 carbon atoms, a branched alkyl group having 1 to 6 carbon atoms, a cyclic or polycyclic alkyl group having 3 to 10 carbon atoms, or a substituted or unsubstituted aryl group having 6 to 13 carbon atoms. When an alkyl group is included as a substituent, the organic compound represented by General Formula (G2) can have lower refractive index. When an aryl group is included as a substituent, the organic compound represented by General Formula (G2) can have improved heat resistance.

In the organic compound represented by General Formula (G2) above, which is one embodiment of the present invention, deuterium is substituted for at least one of hydrogen contained in a, $A^2$, and $R^3$, and thus deterioration or a change in a molecular structure of the organic compound can be inhibited. Furthermore, since carbon-hydrogen bond dissociation in an excited state can be inhibited, a compound with a stable excited state can be provided. It is preferable to use such a compound as a host material of a light-emitting device in which a light-emitting substance is dispersed because a highly reliable device with a long driving lifetime can be provided.

When the organic compound of one embodiment of the present invention is used for a light-emitting device as a host material, for example, a hole-transport skeleton receives a hole in some cases. Carbon-hydrogen bond dissociation easily occurs in hole transfer in some cases; however, a hole-transport skeleton is deuterated in the organic compound of one embodiment of the present invention, and thus carbon-hydrogen bond dissociation can be inhibited in hole transfer, which is preferable.

Example 4 of Organic Compound

One embodiment of the present invention is an organic compound represented by General Formula (G3).

[Chemical Formula 15]

(G3)

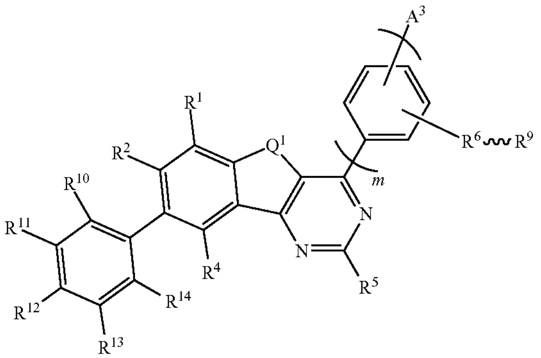

Note that $Q^1$ represents sulfur or oxygen in General Formula (G3) above. $R^1$, $R^2$, and $R^4$ to $R^{14}$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms. Furthermore, $A^3$ represents a substituted or unsubstituted aryl group having 6 to 30 carbon atoms or a substituted or unsubstituted heteroaryl group having 2 to 30 carbon atoms. Moreover, m represents an integer of 0 to 4, at least one of hydrogen contained in $A^3$ and $R^1$, $R^2$, and $R^4$ to $R^{14}$ is deuterium.

Note that in General Formula (G3) above, as substituents substituted for $A^1$, $A^2$, $R^1$, $R^2$, $R^4$, and $R^5$, the same substituents as the substituents with the corresponding symbols of General Formula (G1) in <Example 1 of organic compound> described above can be given; thus, the above description can be referred to.

In General Formula (G3) above, examples of the aryl group substituted for $A^3$ can include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, an acenaphthylenyl group, an anthryl group, a phenanthryl group, a biphenyl group, a terphenyl group, and a triphenylenyl group. Examples of the heteroaryl group can include a pyrimidinyl group, a pyrazinyl group, a pyridazinyl group, a triadinyl group, a bipyridinyl group, a phenanthrolinyl group, a quinoxalinyl group, a dibenzoquinoxalinyl group, a quinazolinyl group, a benzoquinazolinyl group, a dibenzoquinazolinyl group, an imidazolyl group, a triazolyl group, an oxadiazolyl group, a benzoimidazolyl group, a furopyrimidyl group, a furopyrazyl group, a furopyridazyl group, a benzofuropyrimidinyl group, a benzofuropyrazinyl group, a benzofuropyridazinyl group, a thienyl group, a furanyl group, a benzothiophen-yl group, a benzofuran-yl group, a dibenzothiophen-yl group, a dibenzofuran-yl group, a benzonaphthothiophen-yl group, a benzonaphthofuran-yl group, a dinaphthothiophen-yl group, and a dinaphthofuran-yl group.

Examples of the straight-chain or branched alkyl group substituted for $R^6$ to $R^{14}$ in General Formula (G3) above can include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

Examples of the cycloalkyl group or the polycyclic alkyl group substituted for $R^6$ to $R^{14}$ in General Formula (G3) above can include a cyclopropyl group, a cyclo butyl group, a cyclopentyl group, a cyclohexyl group, a 1-methylcyclohexyl group, a cycloheptyl group, and an adamantyl group.

In General Formula (G3) above, examples of the aryl group substituted for $R^6$ to $R^{14}$ can include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, an acenaphthylenyl group, an anthryl group, a phenanthryl group, a biphenyl group, a terphenyl group, and a triphenylenyl group. Examples of the heteroaryl group can include a pyrimidinyl group, a pyrazinyl group, a pyridazinyl group, a triadinyl group, a bipyridinyl group, a phenanthrolinyl group, a quinoxalinyl group, a dibenzoquinoxalinyl group, a quinazolinyl group, a benzoquinazolinyl group, a dibenzoquinazolinyl group, an imidazolyl group, a triazolyl group, an oxadiazolyl group, a benzoimidazolyl group, a furopyrimidyl group, a furopyrazyl group, a furopyridazyl group, a benzofuropyrimidinyl group, a benzofuropyrazinyl group, a benzofuropyridazinyl group, and a benzofuropyrimidinyl group.

In the organic compound represented by General Formula (G3) above, which is one embodiment of the present invention, deuterium is substituted for at least one of hydrogen contained in $A^3$ and hydrogen contained in $R^1$, $R^2$, and $R^4$ to $R^{14}$, and thus deterioration or a change in quality of the organic compound can be inhibited. Furthermore, since carbon-hydrogen bond dissociation in an excited state can be inhibited, the organic compound of one embodiment of the present invention is suitably used for a host material of a light-emitting device in which a light-emitting substance is dispersed.

When the organic compound of one embodiment of the present invention is used for a light-emitting device as a host material, for example, a hole-transport skeleton receives a hole in some cases. Carbon-hydrogen bond dissociation tends to easily occur in hole transfer; however, a hole-transport skeleton is deuterated in the organic compound of one embodiment of the present invention, and carbon-hydrogen bond dissociation can be inhibited, which is preferable.

Example 5 of Organic Compound

One embodiment of the present invention is an organic compound represented by General Formula (G4).

[Chemical Formula 16]

(G4)

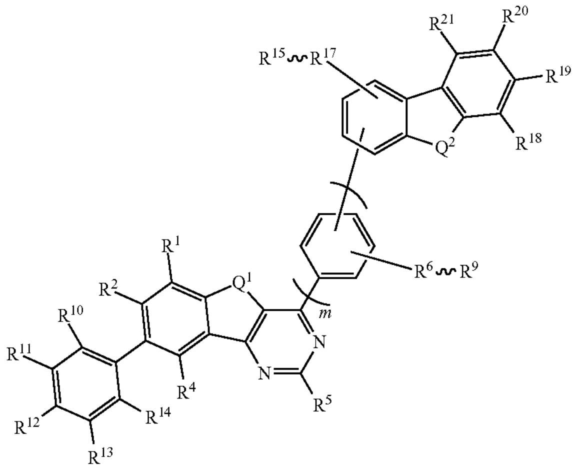

Note that $Q^1$ and $Q^2$ each independently represent sulfur or oxygen in General Formula (G4) above. $R^1$, $R^2$, and $R^4$ to $R^{21}$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms. Moreover, m represents an integer of 0 to 4. At least one of $R^1$, $R^2$, and $R^4$ to $R^{21}$ is deuterium.

Examples of the alkyl group substituted for $R^1$, $R^2$, and $R^4$ to $R^{21}$ in General Formula (G4) above can include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

Examples of the cycloalkyl group or polycyclic alkyl group substituted for $R^1$, $R^2$, and $R^4$ to $R^{21}$ in General Formula (G4) above can include a cyclopropyl group, a cyclobutyl group, a cyclopentyl group, a cyclohexyl group, a 1-methylcyclohexyl group, a cycloheptyl group, and an adamantyl group.

In General Formula (G4) above, examples of the aryl group substituted for $R^1$, $R^2$, and $R^4$ to $R^{21}$ can include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, an acenaphthylenyl group, an anthryl group, a phenanthryl group, a biphenyl group, a terphenyl group, and a triphenylenyl group. Examples of the heteroaryl group can include a pyrimidinyl group, a pyrazinyl group, a pyridazinyl group, a triadinyl group, a bipyridinyl group, a phenanthrolinyl group, a quinoxalinyl group, a dibenzoquinoxalinyl group, a quinazolinyl group, a benzoquinazolinyl group, a dibenzoquinazolinyl group, an imidazolyl group, a triazolyl group, an oxadiazolyl group, a benzoimidazolyl group, a furopyrimidyl group, a furopyrazyl group, a furopyridazyl group, a benzofuropyrimidinyl group, a benzofuropyrazinyl group, a benzofuropyridazinyl group, a thienyl group, a furanyl group, a benzothiophen-yl group, a benzofuran-yl group, a dibenzothiophen-yl group, a dibenzofuran-yl group, a benzonaphthothiophen-yl group, a benzonaphthofuran-yl group, a dinaphthothiophen-yl group, and a dinaphthofuran-yl group.

In the organic compound represented by General Formula (G4) above, which is one embodiment of the present invention, deuterium is substituted for at least one of hydrogen contained in $R^1$, $R^2$, and $R^4$ to $R^{21}$, and thus deterioration or a change in quality of the organic compound can be inhibited. Furthermore, since carbon-hydrogen bond dissociation in an excited state can be inhibited, the organic compound of one embodiment of the present invention is suitably used as a host material of a light-emitting device in which a light-emitting substance is dispersed.

When the organic compound of one embodiment of the present invention is used for a light-emitting device as a host material, for example, a hole-transport skeleton receives a hole in some cases. Carbon-hydrogen bond dissociation tends to easily occur in hole transfer; however, a hole-transport skeleton is deuterated in the organic compound of one embodiment of the present invention, and thus carbon-hydrogen bond dissociation can be inhibited, which is preferable.

In General Formula (G1) to General Formula (G4) described in <Example 1 of organic compound> to <Example 5 of organic compound> above, it is preferable that each of the aryl group having 6 to 100 carbon atoms and the heteroaryl group having 2 to 100 carbon atoms be independently represented by any one of Structural Formulae (Ar-1) to (Ar-80).

[Chemical Formula 17]

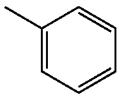
(Ar-1)

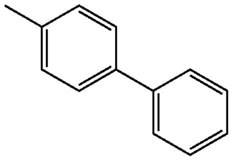
(Ar-2)

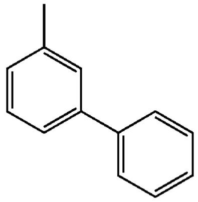
(Ar-3)

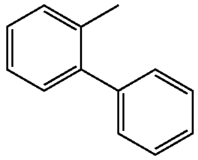
(Ar-4)

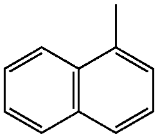
(Ar-5)

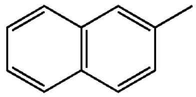
(Ar-6)

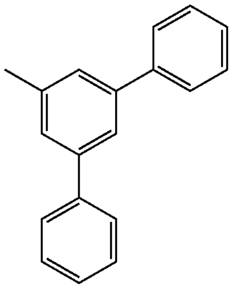
(Ar-7)

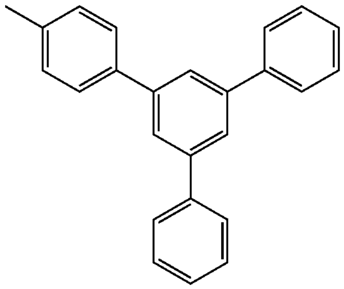
(Ar-8)

-continued
(Ar-9)
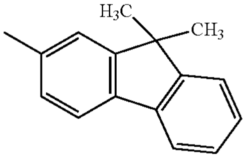
(Ar-10)
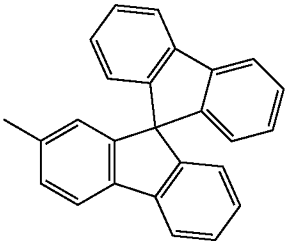
(Ar-11)
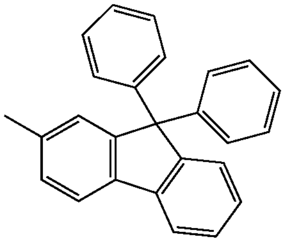
(Ar-12)
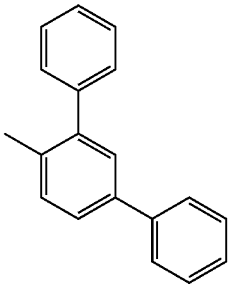
(Ar-13)
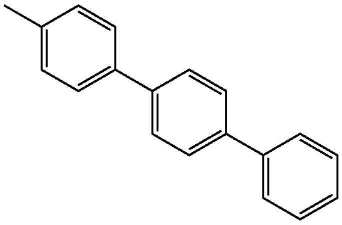
(Ar-14)
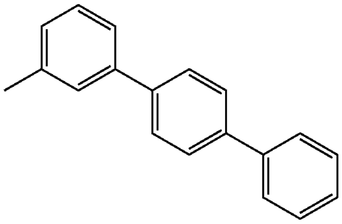
-continued
(Ar-15)
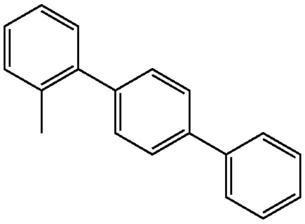
(Ar-16)
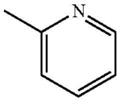
(Ar-17)
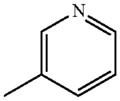
(Ar-18)
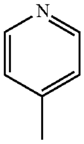
(Ar-19)
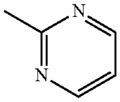
(Ar-20)
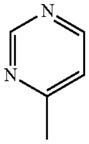
(Ar-21)
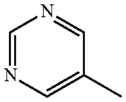
(Ar-22)
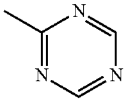
(Ar-23)
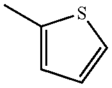
(Ar-24)
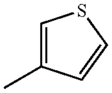
(Ar-25)
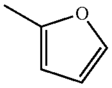
(Ar-26)
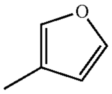

-continued
(Ar-27)
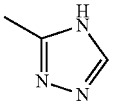
(Ar-28)
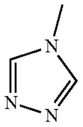
[Chemical Formula 18]
(Ar-29)
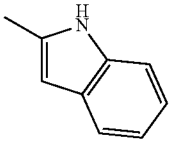
(Ar-30)
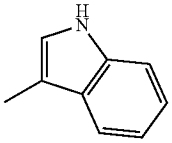
(Ar-31)
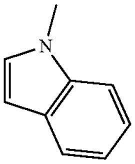
(Ar-32)
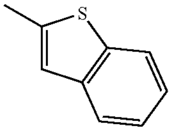
(Ar-33)
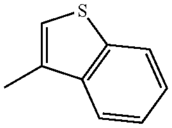
(Ar-34)
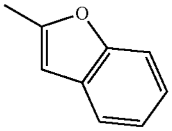
(Ar-35)
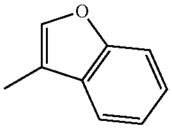
(Ar-36)
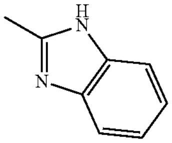
-continued
(Ar-37)
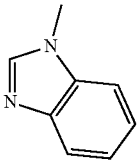
(Ar-38)
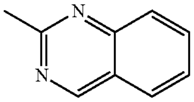
(Ar-39)
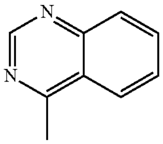
(Ar-40)
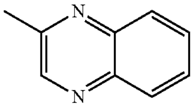
(Ar-41)
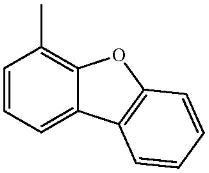
(Ar-42)
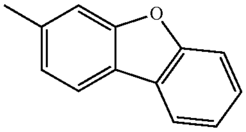
(Ar-43)
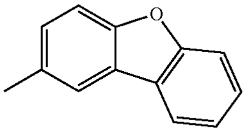
(Ar-44)
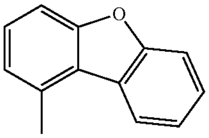
(Ar-45)
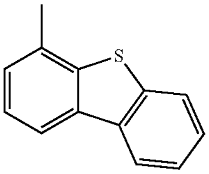
(Ar-46)
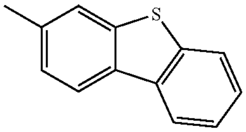

-continued
(Ar-47)
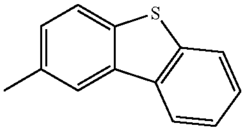
(Ar-48)
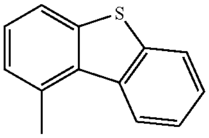
(Ar-49)
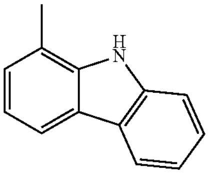
(Ar-50)
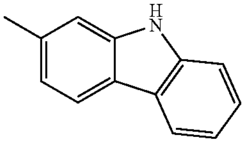
(Ar-51)
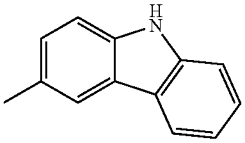
(Ar-52)
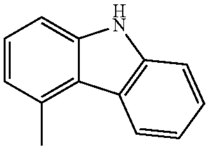
(Ar-53)
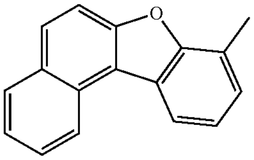
(Ar-54)
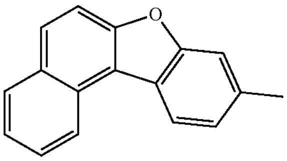
(Ar-55)
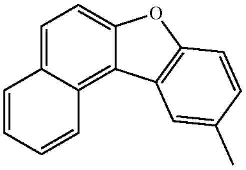
-continued
(Ar-56)
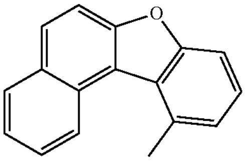
(Ar-57)
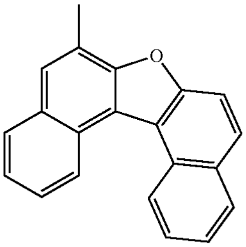
(Ar-58)
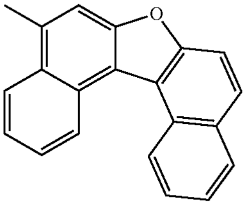
[Chemical Formula 19]
(Ar-59)
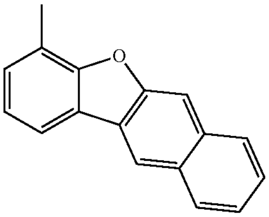
(Ar-60)
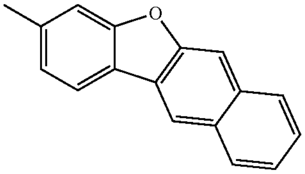
(Ar-61)
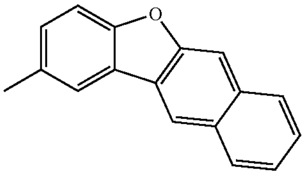
(Ar-62)
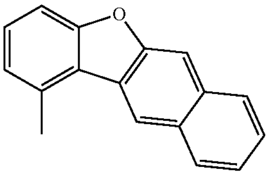
(Ar-63)
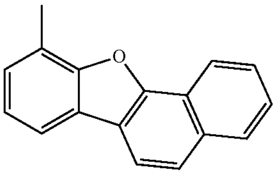

-continued (Ar-64)

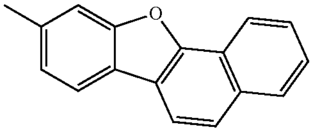

(Ar-65)

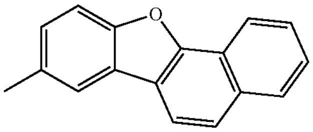

(Ar-66)

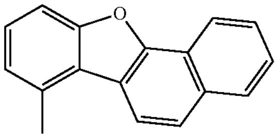

(Ar-67)

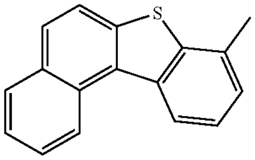

(Ar-68)

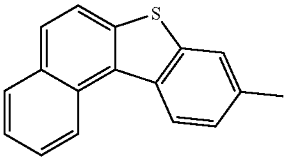

(Ar-69)

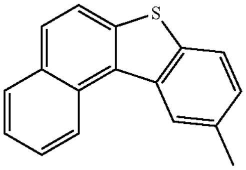

(Ar-70)

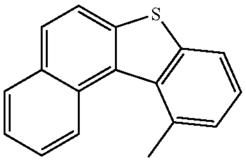

(Ar-71)

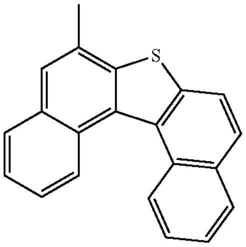

(Ar-72)

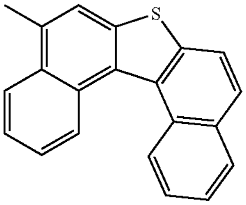

-continued (Ar-73)

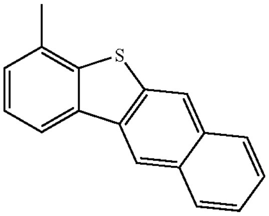

(Ar-74)

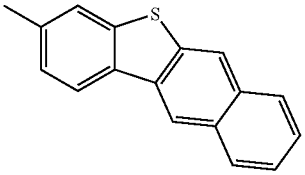

(Ar-75)

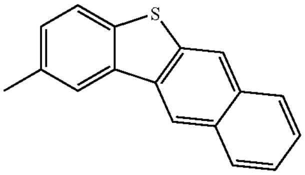

(Ar-76)

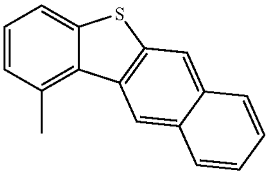

(Ar-77)

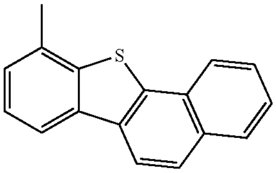

(Ar-78)

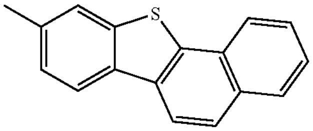

(Ar-79)

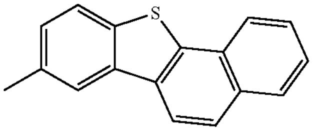

(Ar-80)

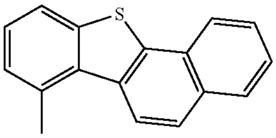

Note that the substituents represented by Structural Formulae (Ar-1) to (Ar-80) above are examples of the aryl group and the heteroaryl group; however, the aryl group and the heteroaryl group that can be used in General Formulae (G1) to (G4) above are not limited to the substituents represented by General Formulae (Ar-1) to (Ar-80) above.

In General Formula (G1) to General Formula (G4) above, when any one or more of $R^1$ to $R^{21}$ are a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, these groups may be deuterated or not.

In General Formula (G1) to General Formula (G4) above, at least one of hydrogen contained in $A^1$ to $A^3$, or at least one of $R^1$ to $R^{21}$ is deuterium, whereby carbon-hydrogen bond dissociation can be inhibited.

Furthermore, in General Formula (G4) above, it is further preferable that some or all of $R^1$ to $R^{21}$ be deuterium. Particularly, when all of $R^1$ to $R^{21}$ are deuterium, dissociation of all carbon-hydrogen bonds in a hole-transport skeleton can be prevented. Note that even when deuteration rate is less than 100%, the effect of preventing carbon-hydrogen bond dissociation can be obtained.

Note that in this specification and the like, in a hole-transport skeleton, i.e., the benzofuropyrimidine skeleton in General Formula (G1) above, the deuteration rate of a benzofuropyrimidine skeleton refers to a rate of substitution of deuterium for hydrogen directly bonded to the benzofuropyrimidine skeleton. For example, in the case where all of $R^1$ to $R^{21}$ are deuterium, the deuteration rate of the benzofuropyrimidine skeleton is 100%. Furthermore, in the case where some of $R^1$ to $R^{21}$ are not hydrogen or deuterium, that is, in the case where some of $R^1$ to $R^{21}$ are a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, hydrogen or deuterium contained in the substituents is not used to calculate the deuteration rate of the benzofuropyrimidine skeleton.

In General Formula (G1) to General Formula (G4) above, the deuteration rate of an indolocarbazole skeleton is preferably greater than or equal to 50% and less than or equal to 100%. For example, the effect of preventing carbon-hydrogen bond dissociation is obtained also when deuterium occupies 50% and hydrogen occupies 50% in $R^1$ in General Formula (G1) to General Formula (G4). The same is applied to $R^2$ to $R^{10}$. Note that the deuteration rate of the indolocarbazole skeleton is preferably greater than or equal to 60%, further preferably greater than or equal to 70%, still further preferably greater than or equal to 80%, yet still further preferably greater than or equal to 90%.

In General Formula (G1) to General Formula (G4) above, it is further preferable that at least one of hydrogen contained in $A^1$ to $A^3$ or some or all of $R^1$ to $R^{21}$ be deuterium. Particularly, when all of $R^1$ to $R^{21}$ are deuterium, dissociation of all carbon-hydrogen bonds does not easily occur, which is preferable.

When the organic compound of one embodiment of the present invention, which has any of the structures represented by General Formulae (G1) to (G4) above, is used for a light-emitting device, a thin film (also referred to as an organic compound layer) is preferably used. The thin film containing the organic compound of one embodiment of the present invention can be suitably used as a light-emitting layer, a hole-transport layer, an electron-transport layer, or a cap layer in a light-emitting device. In addition, the organic compound of one embodiment of the present invention can be used also for a non-light-emitting device. As the non-light-emitting device, a device such as a light-receiving device can be given, for example.

Note that the structure in the case of using the organic compound of one embodiment of the present invention for a light-emitting layer, a hole-transport layer, an electron-transport layer, or a cap layer in a light-emitting device, or in the case of using the organic compound of one embodiment of the present invention for a light-receiving device is described in detail in Embodiment 2.

Specific Example 1

The following are specific examples of the organic compounds of one embodiment of the present invention having the structures represented by General Formulae (G1) to (G4) above. Note that in the following examples, $Q^1$ and $Q^2$ represent oxygen.

[Chemical Formula 20]

(100)

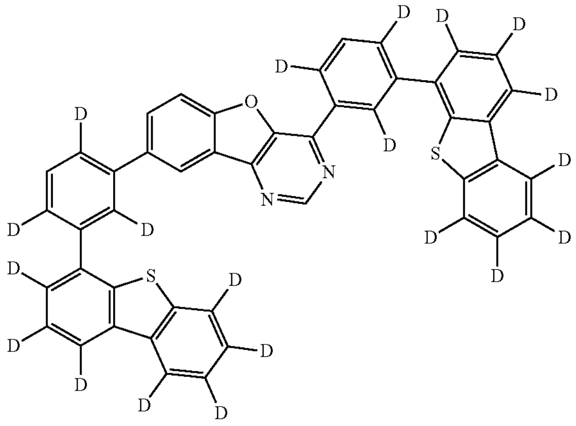

(101)

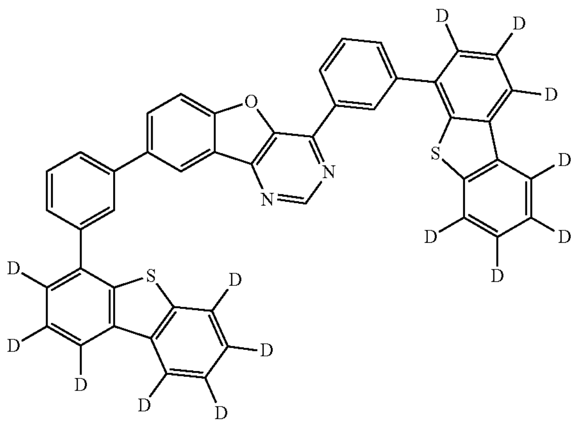

-continued
(102)
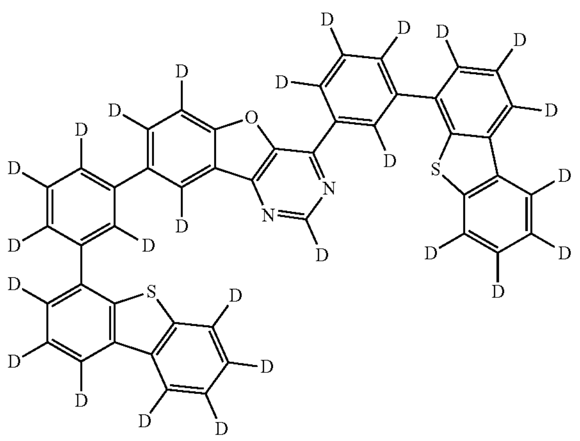
(103)
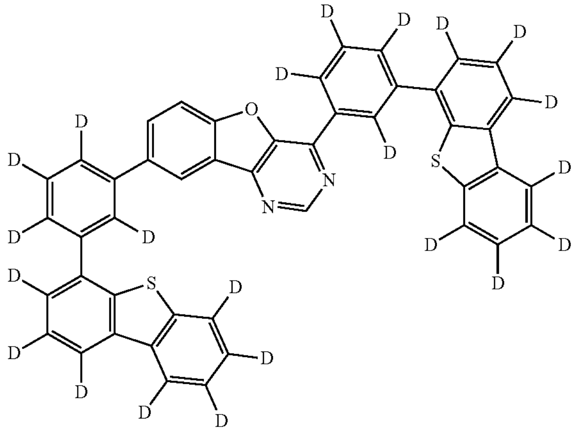
(104)
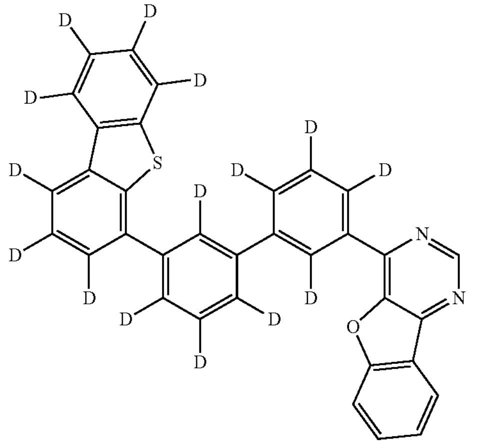
-continued
(105)
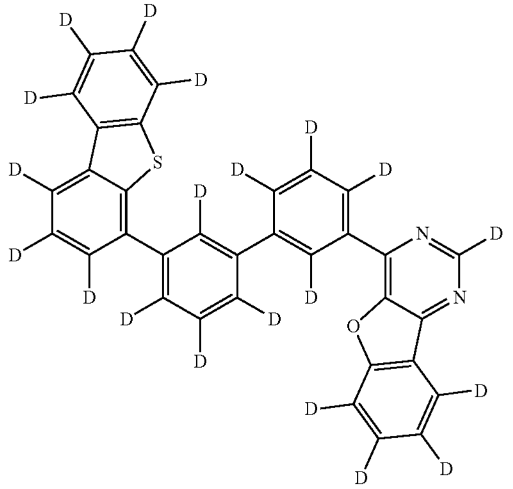
(106)
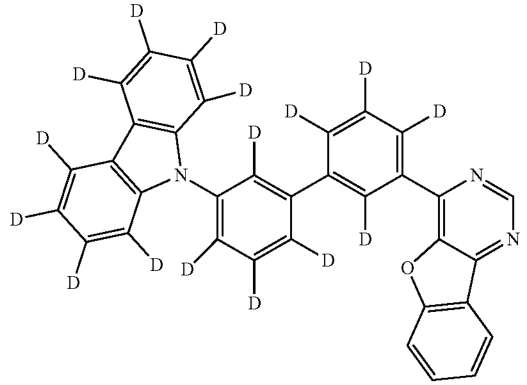
(107)
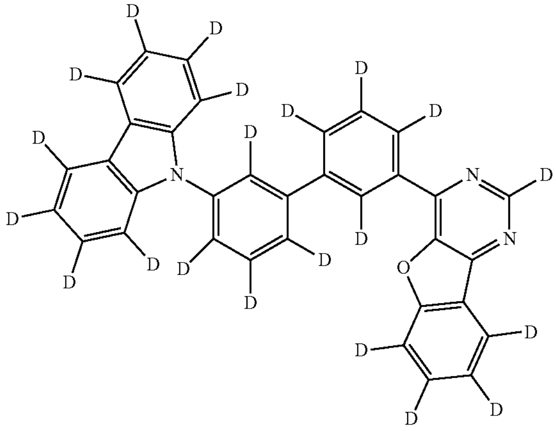

[Chemical Formula 21]
(108)
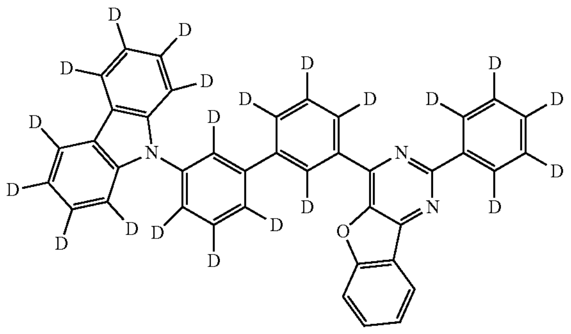
(109)
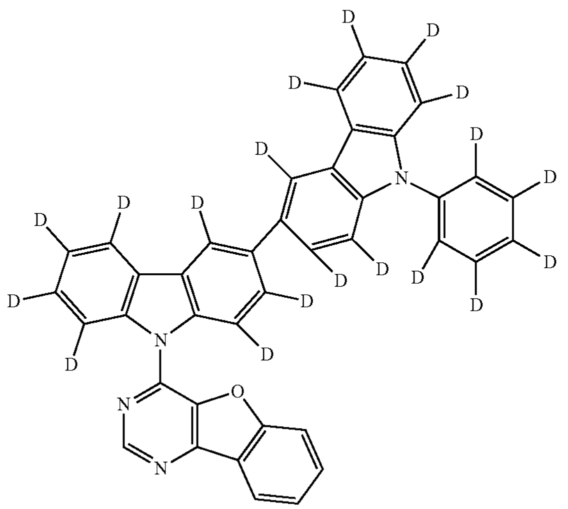
(110)
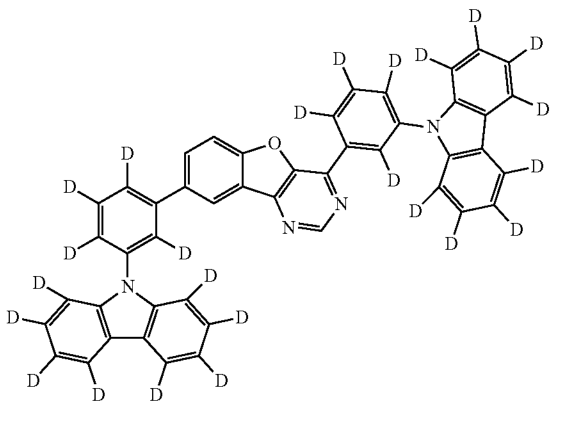
(111)
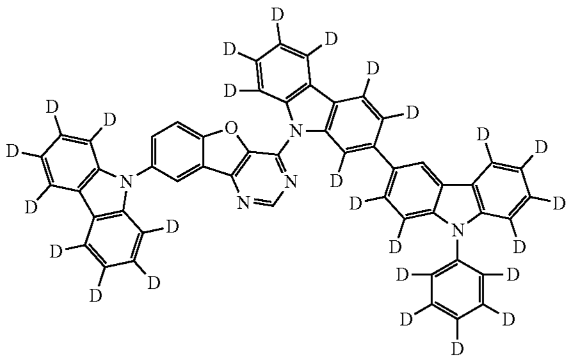
(112)
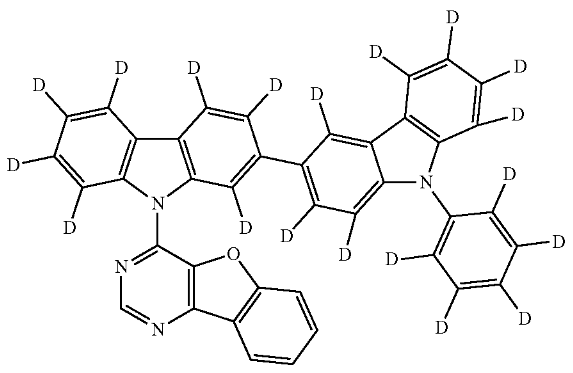
(113)
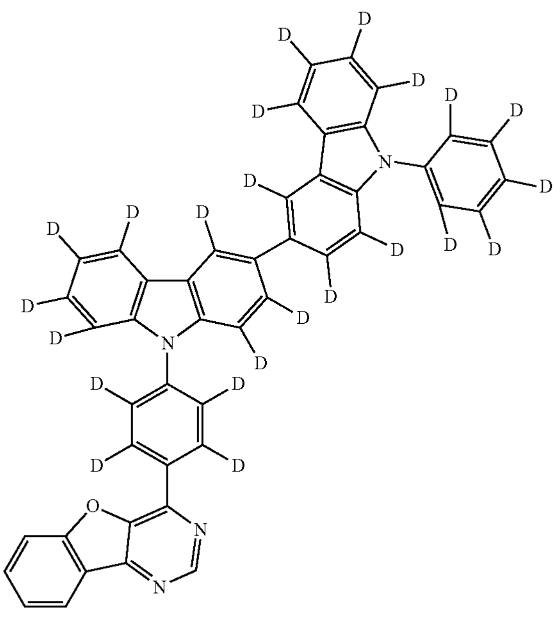

-continued
(114)
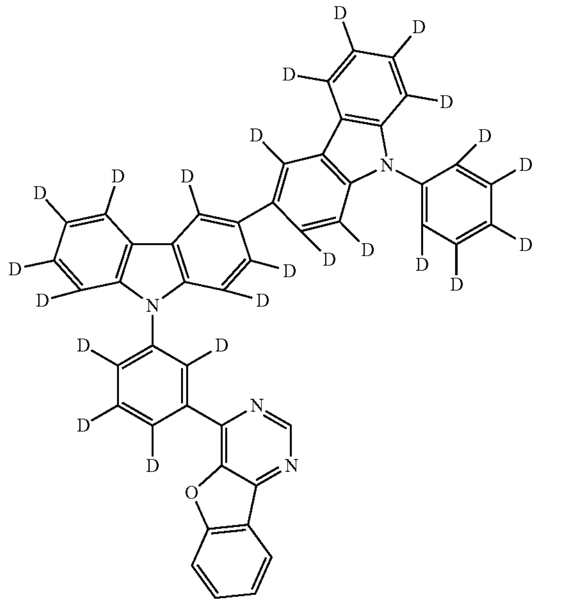
-continued
(115)
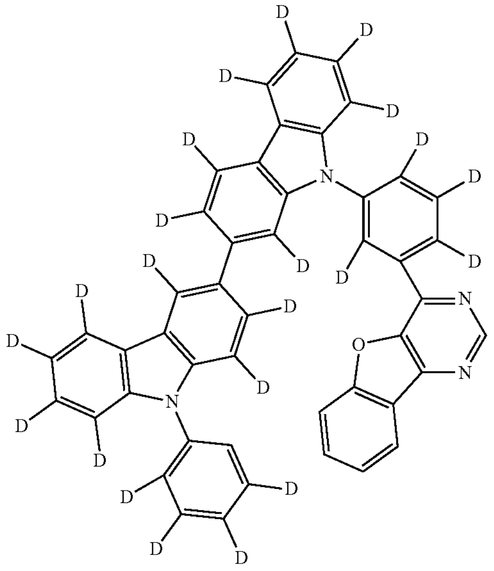
[Chemical Formula 22]
(116)
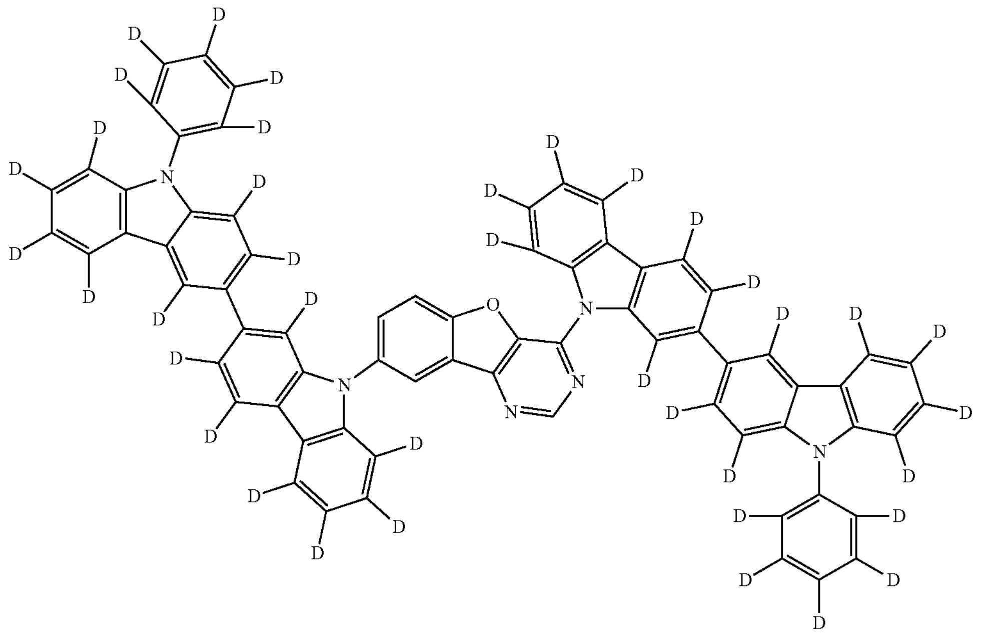

-continued
(117)
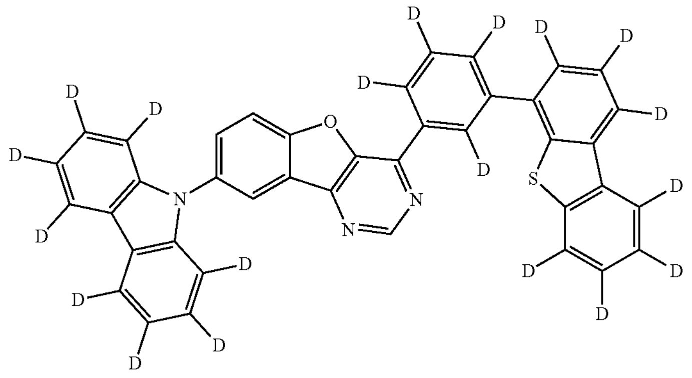
(118)
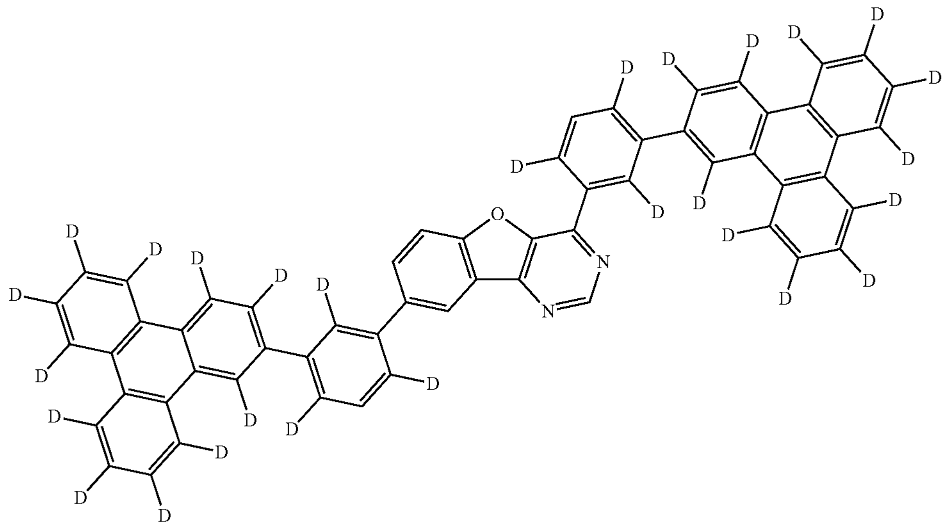
(119)
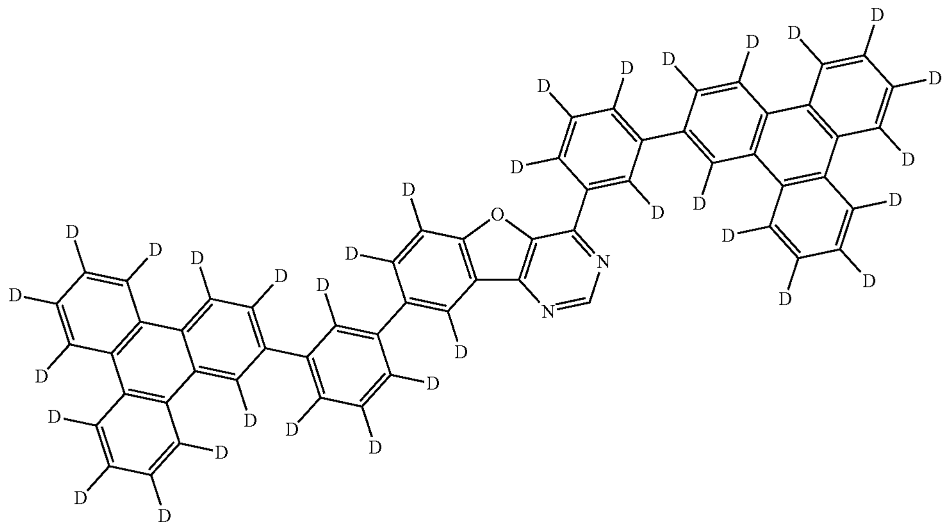

-continued
(120)
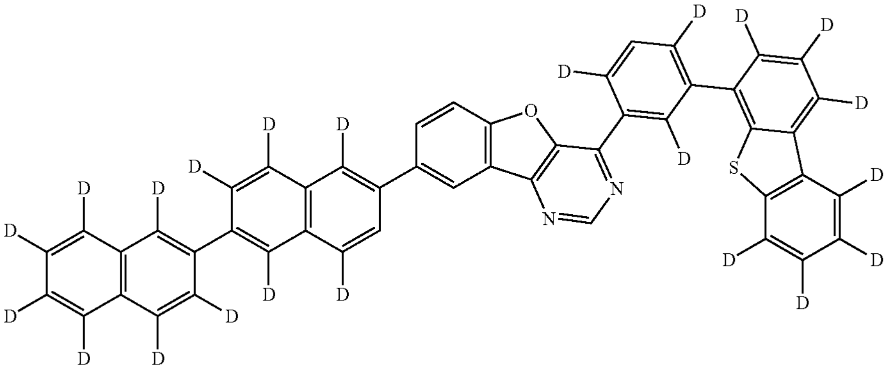
(121)
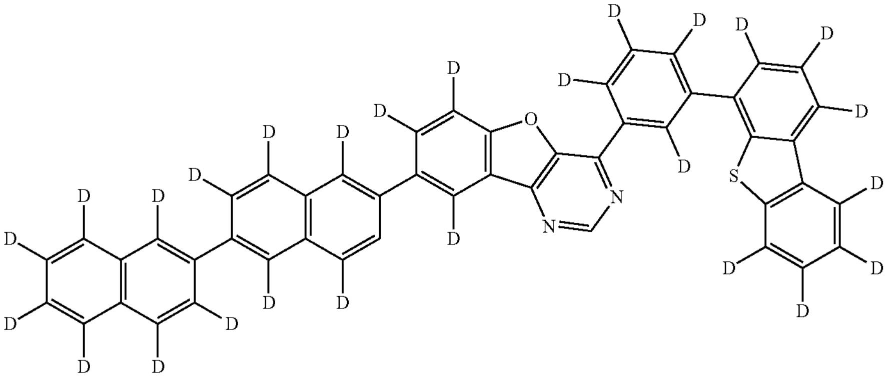
[Chemical Formula 23]
(122)
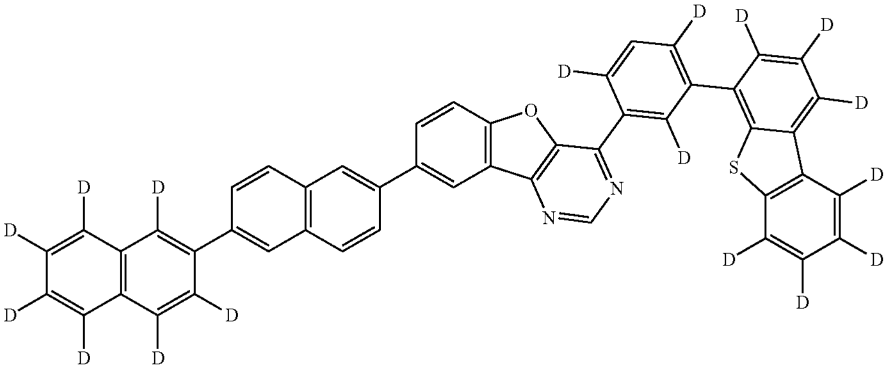
(123)
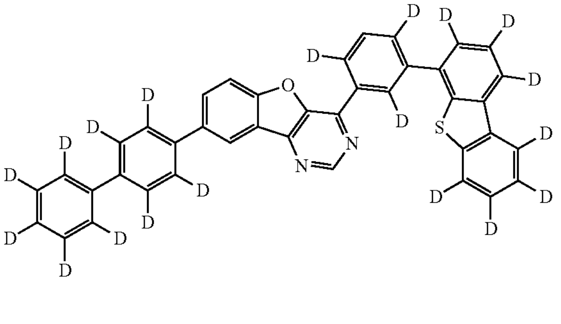
(124)
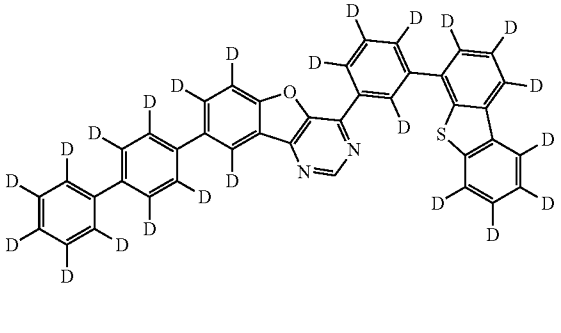

-continued
(125)
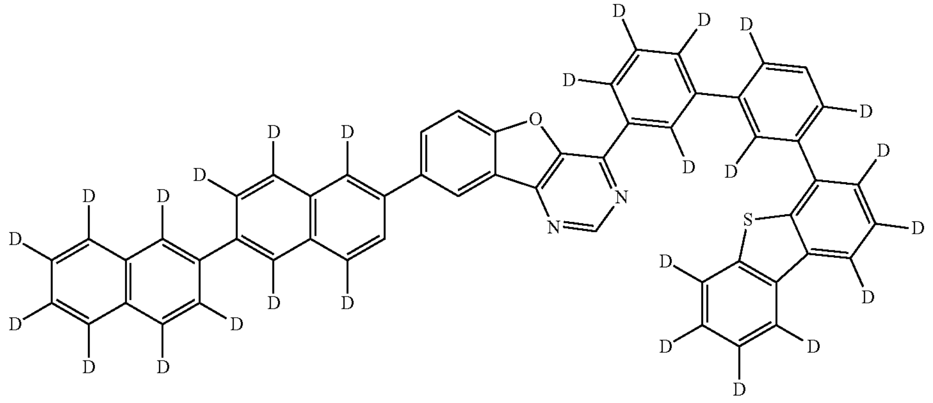
(126)
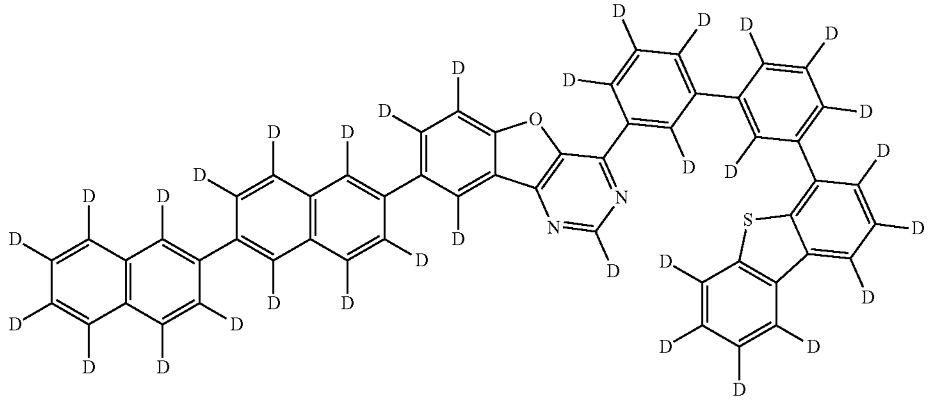
(127)
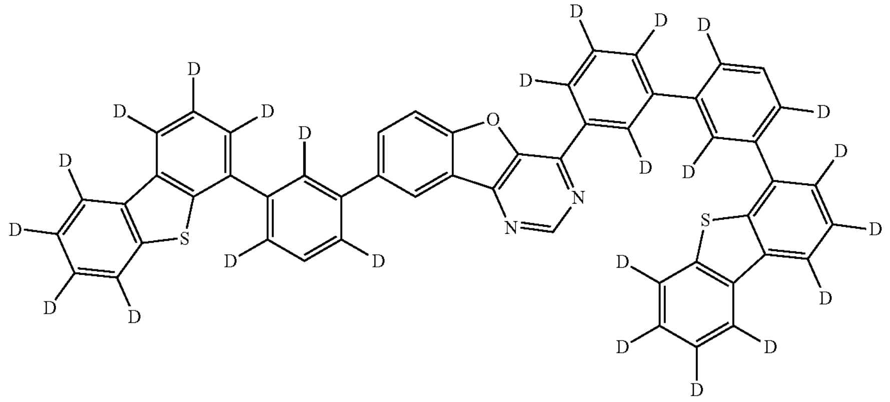
(128)
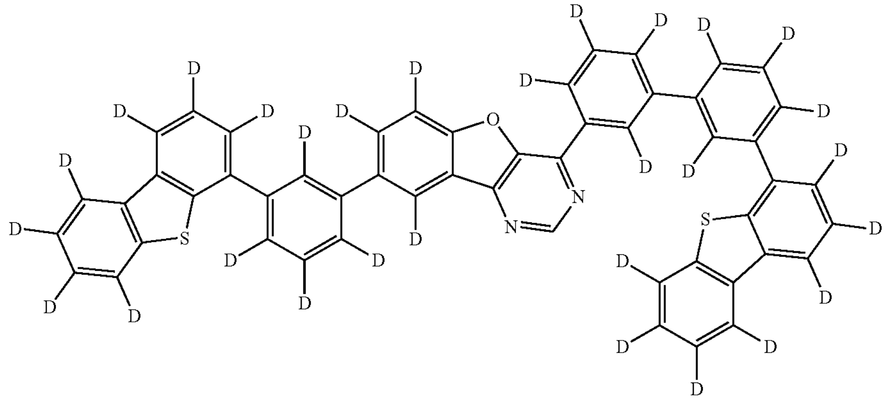

-continued
[Chemical Formula 24]
(128)
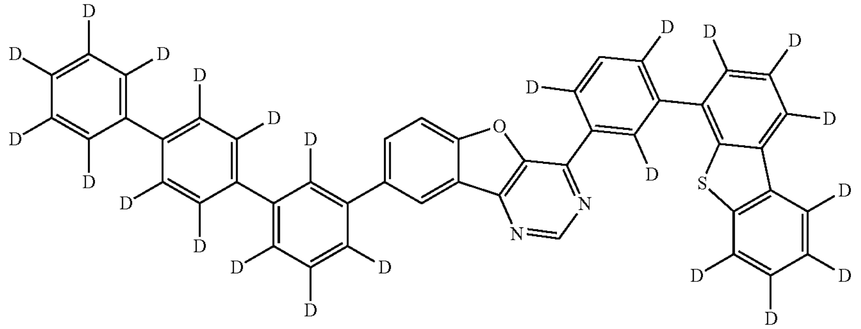
(129)
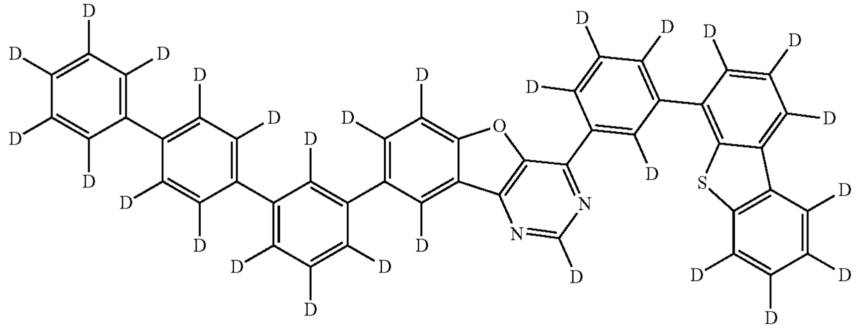
(130)
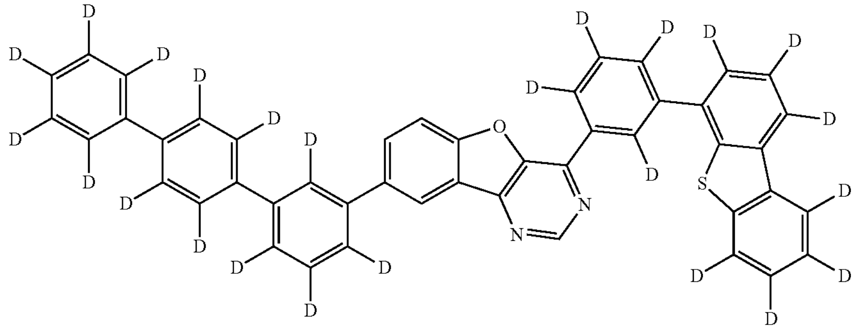
(131)
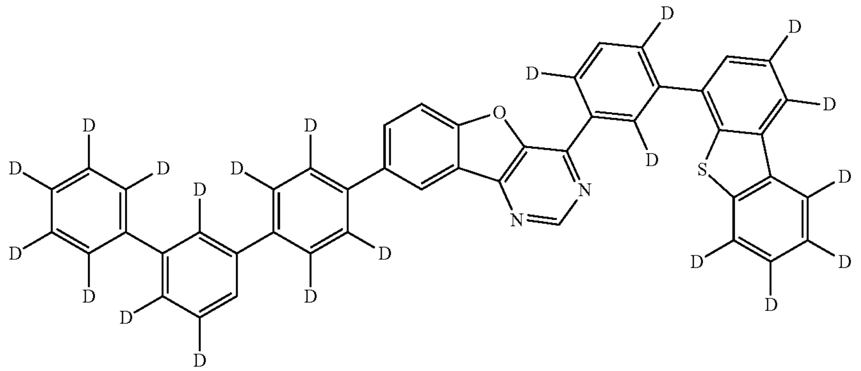

-continued
(132)
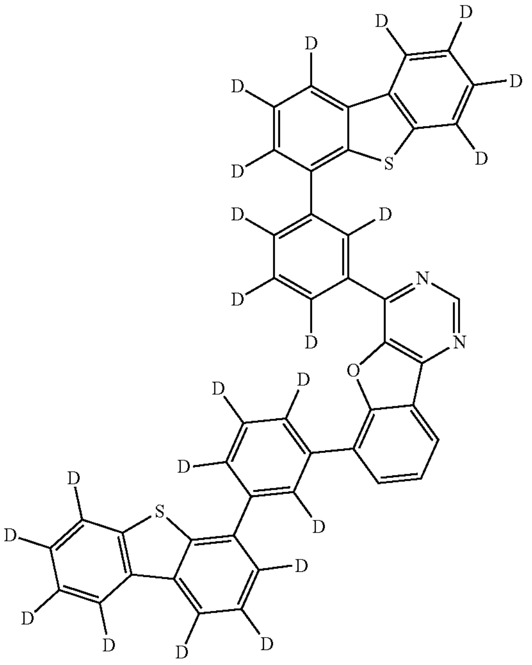
(133)
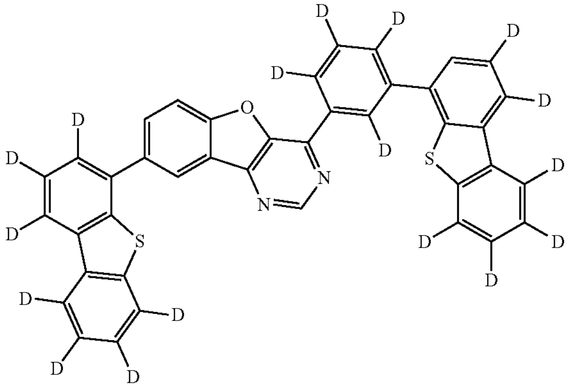
(134)
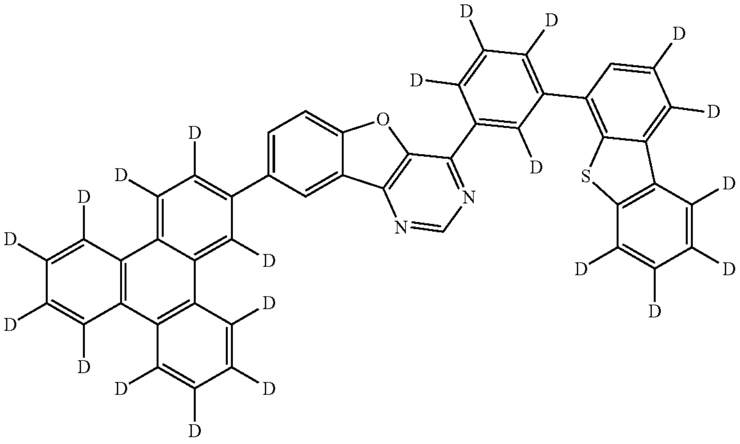

-continued
(135)
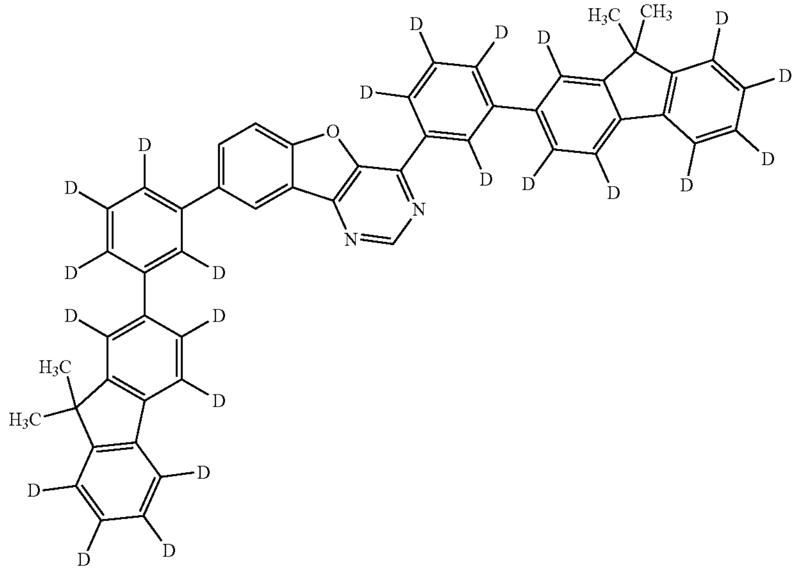
[Chemical Formula 25]
(136)
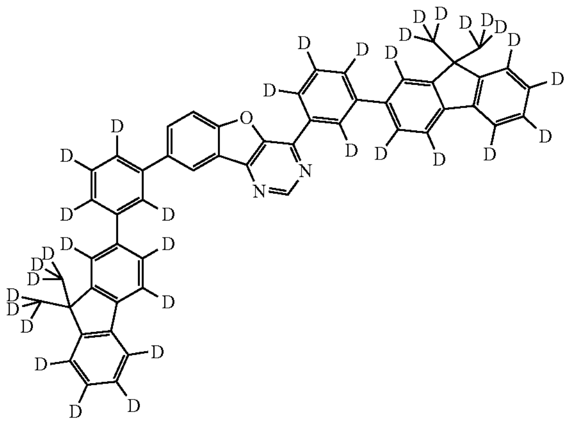
(137)
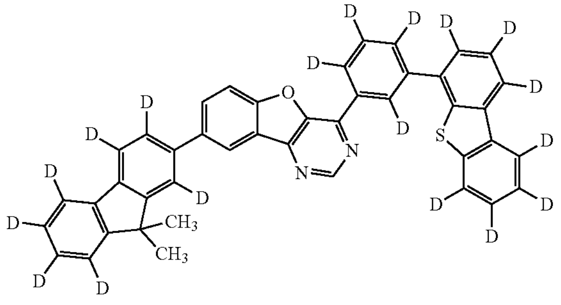
-continued
(138)
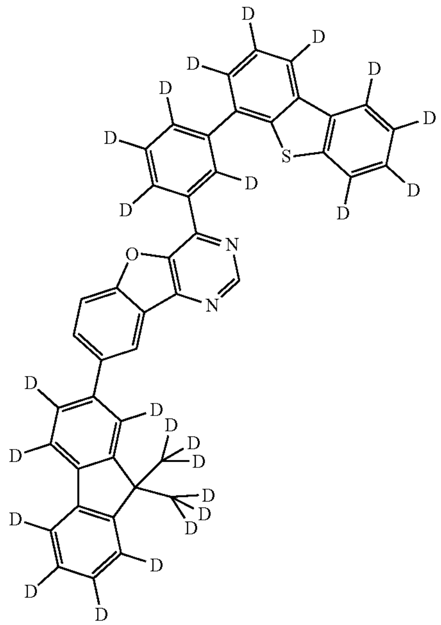

-continued
(139)
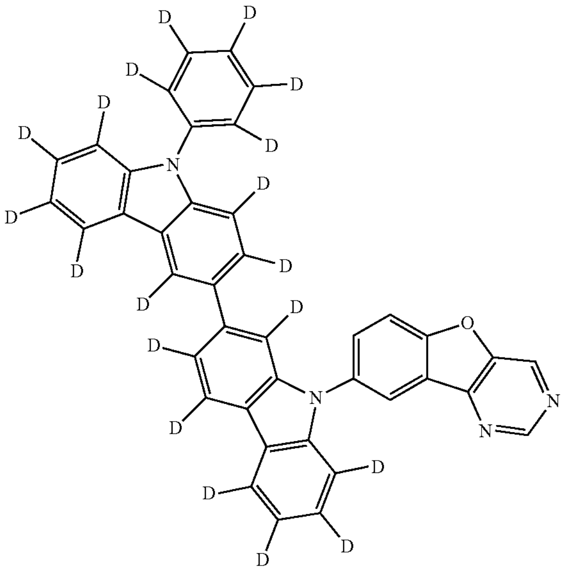
(140)
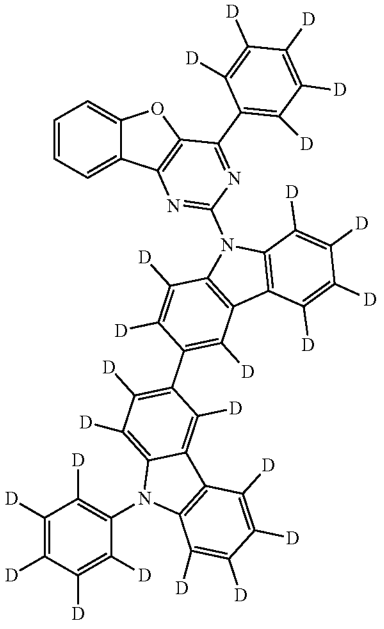
(141)
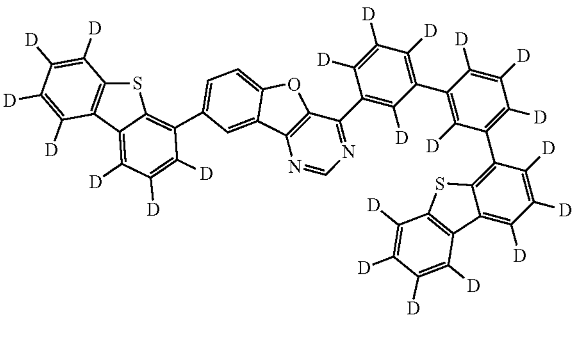
-continued
(142)
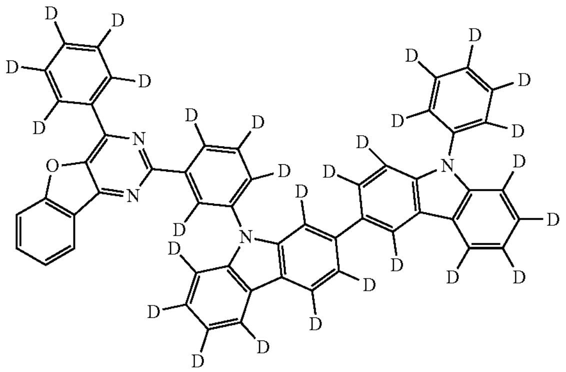
(143)
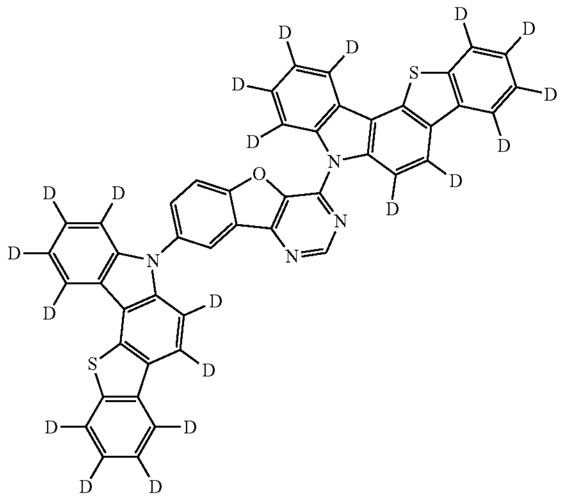
(144)
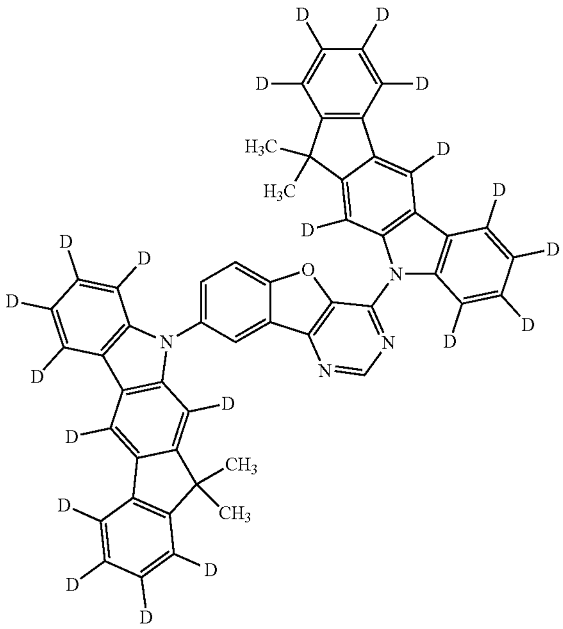

-continued
[Chemical Formula 26]
(145)
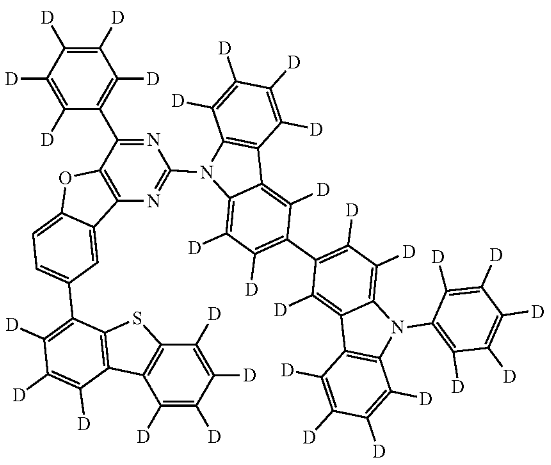
(146)
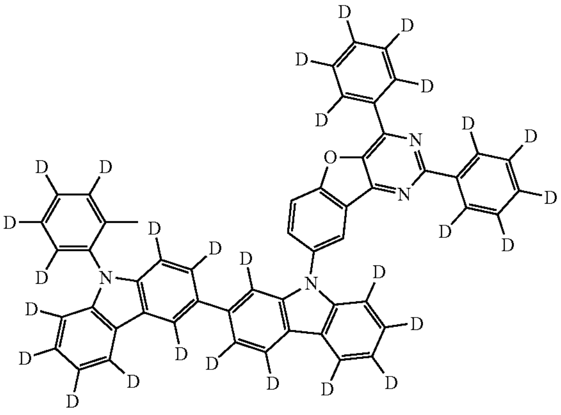
(147)
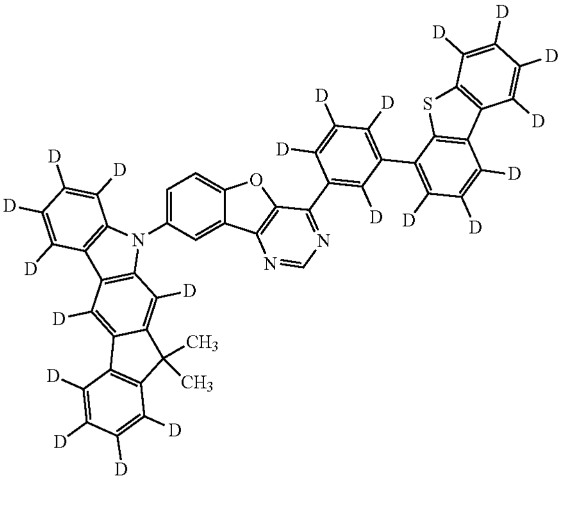
-continued
(148)
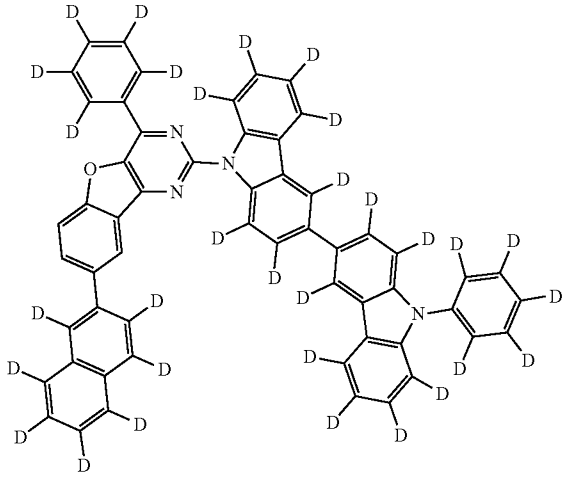
(149)
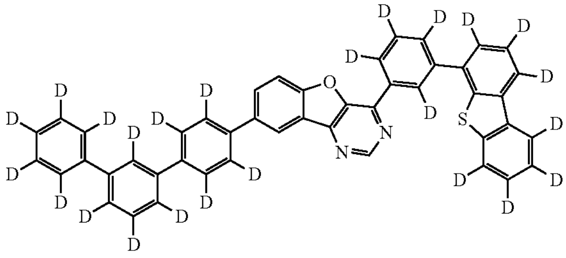
(150)
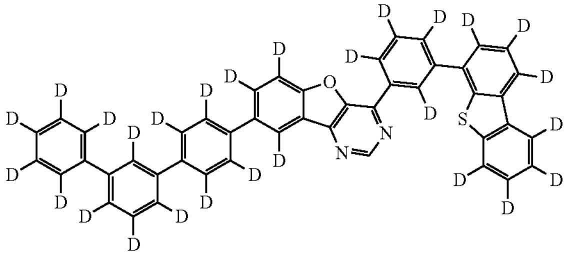
(151)
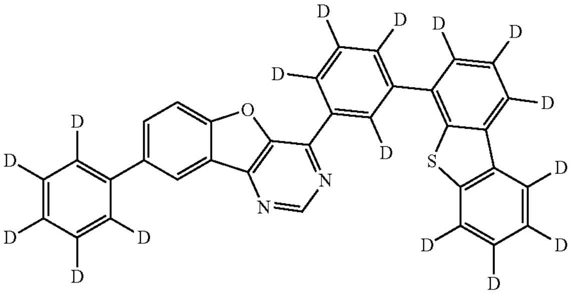
(152)
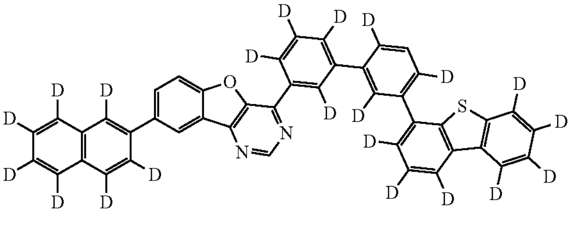

[Chemical Formula 27]
(153)
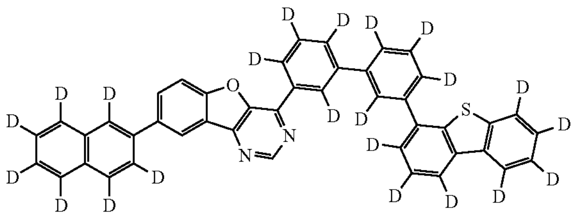
(154)
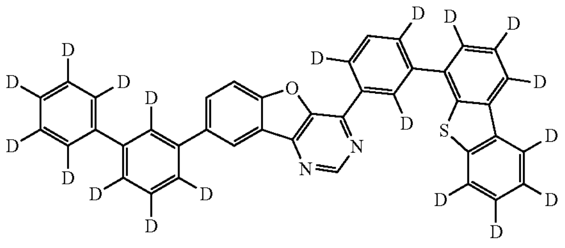
(155)
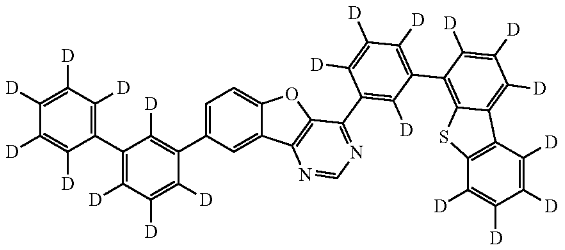
(156)
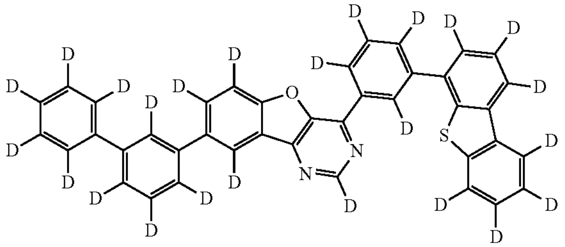
(157)
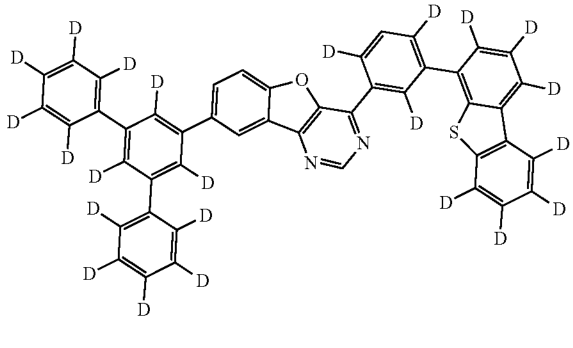
(158)
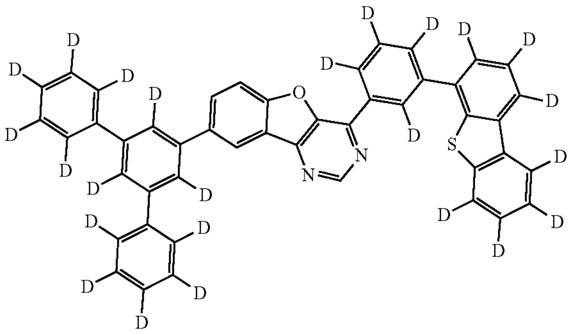
(159)
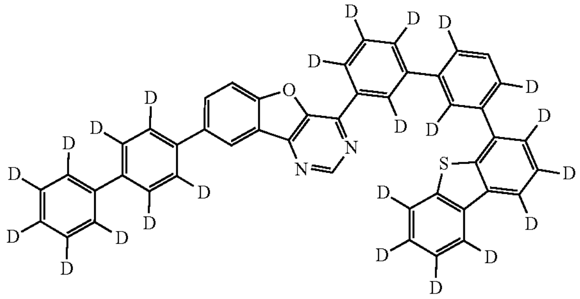
(160)
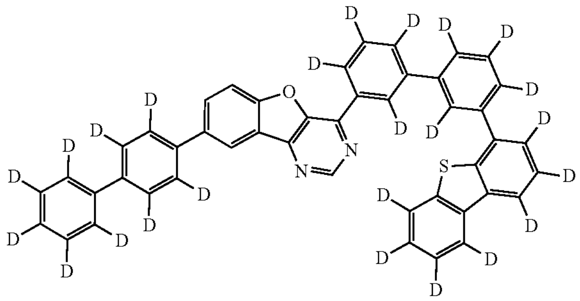
(161)
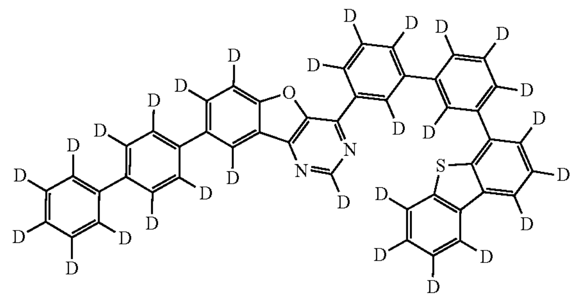
(162)
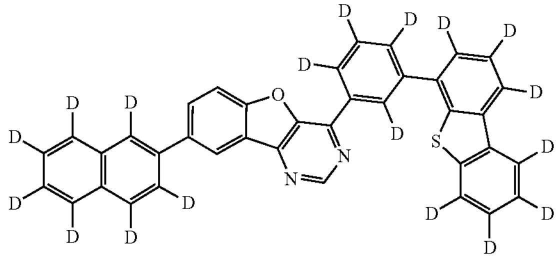

[Chemical Formula 28]
163
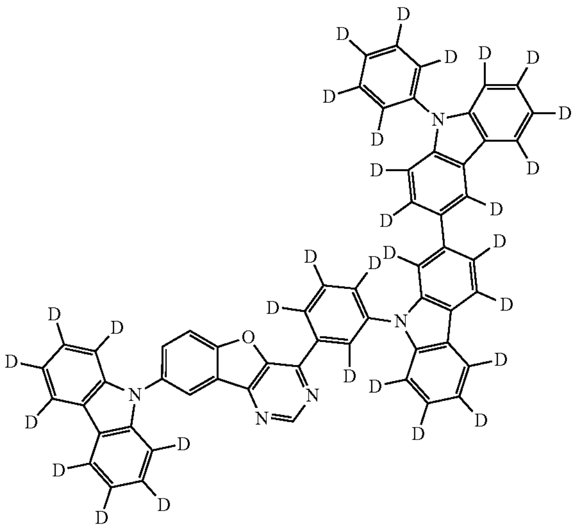
164
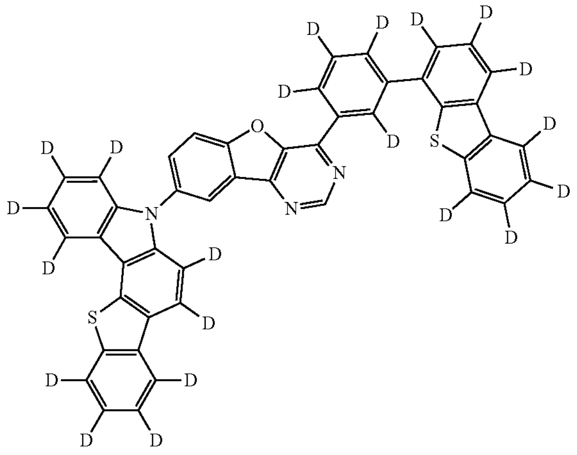
165
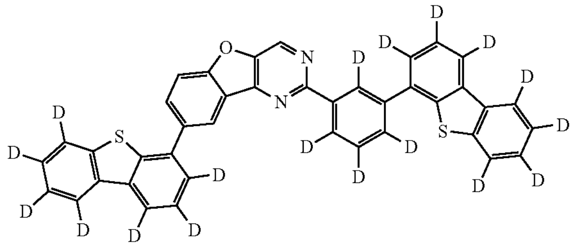
-continued
166
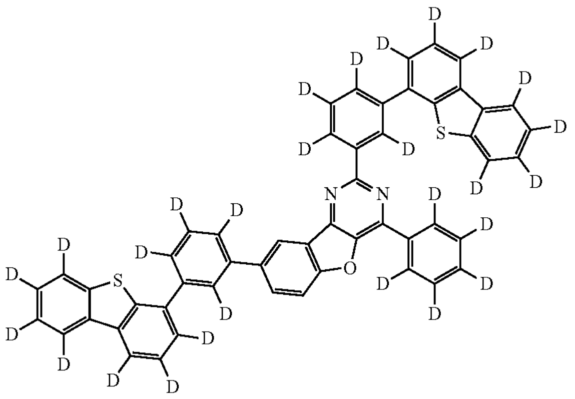
167
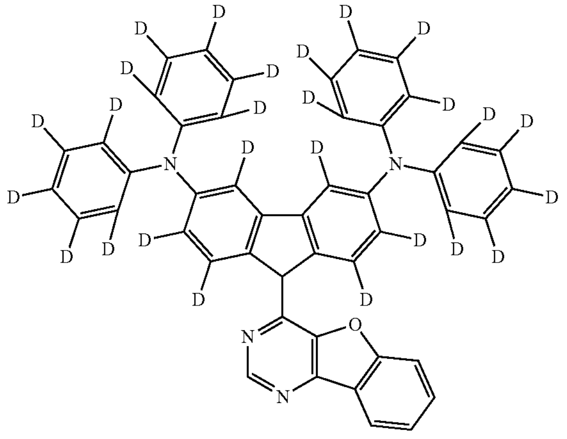
168
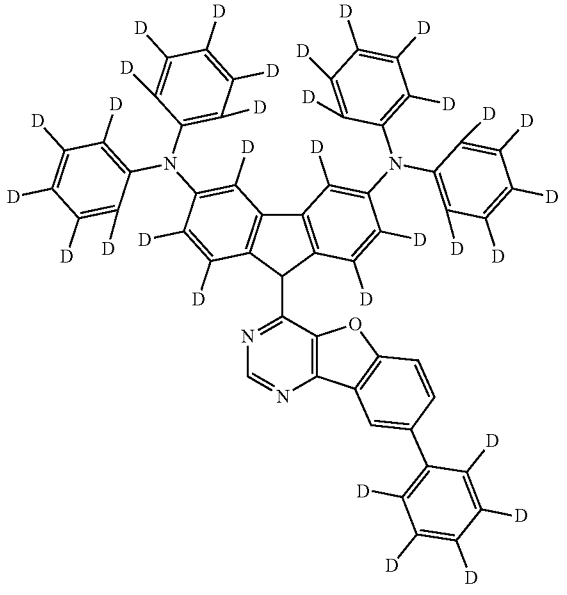

-continued
169
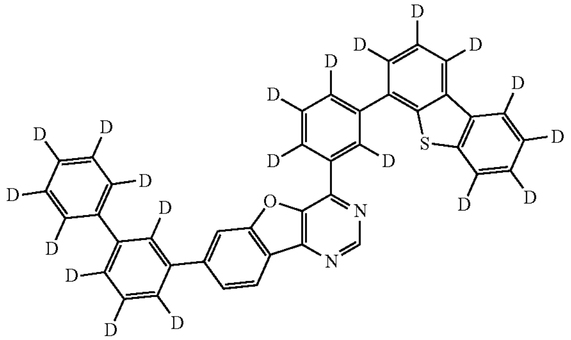
170
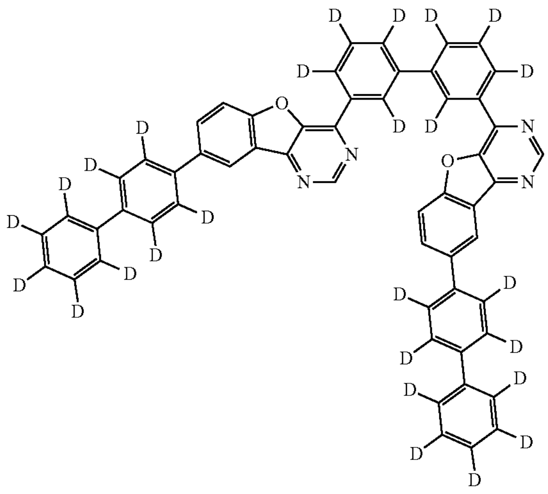
[Chemical Formula 29]
171
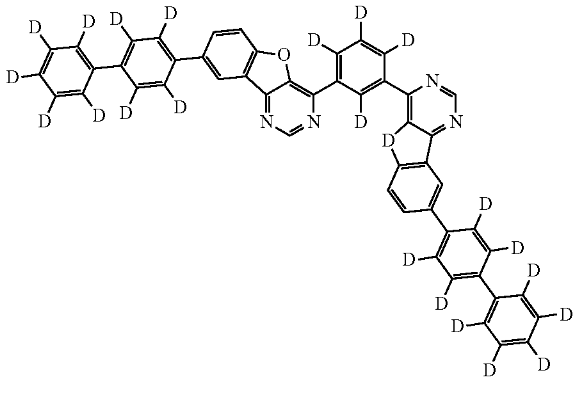
-continued
172
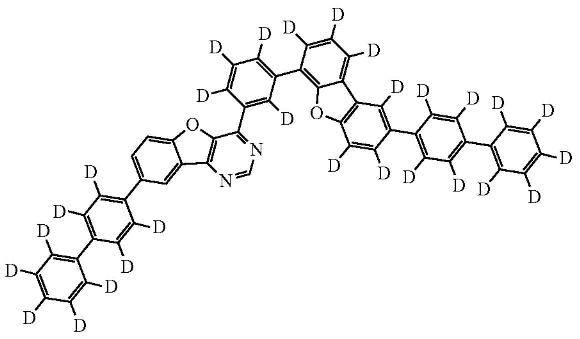
173
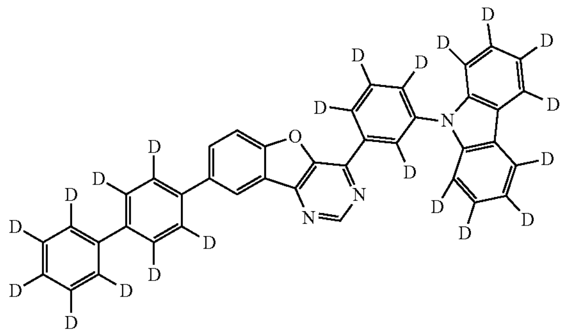
174
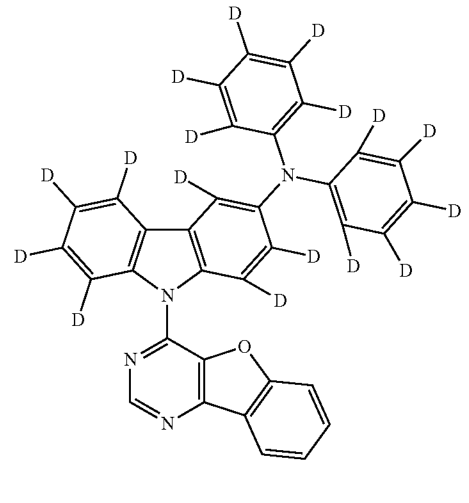
175
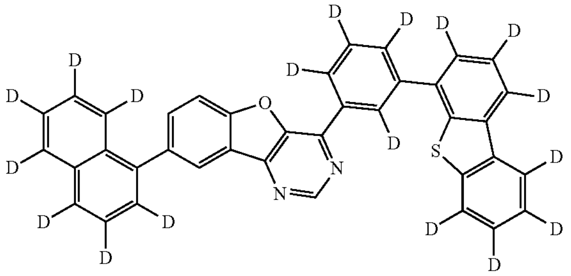

-continued
176
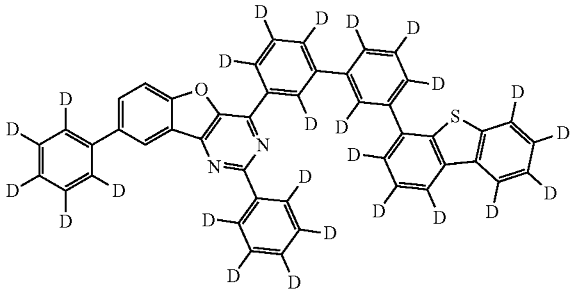
177
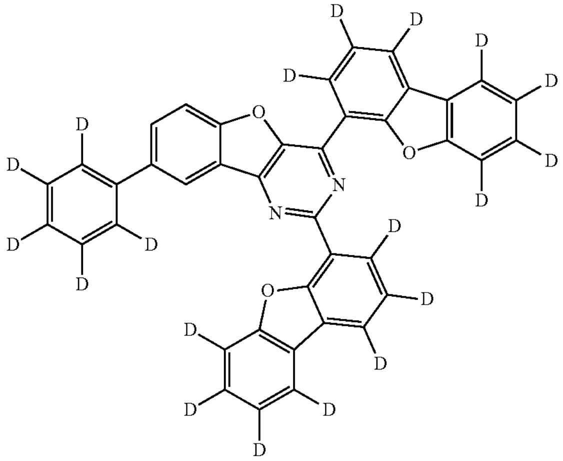
178
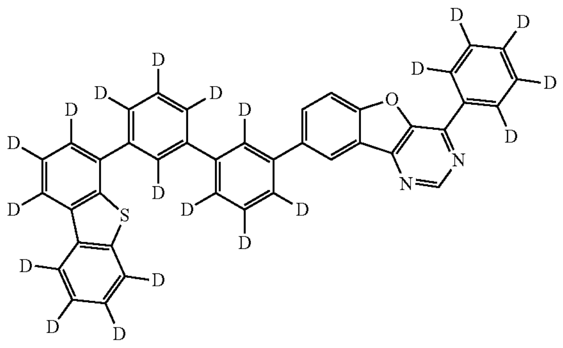
179
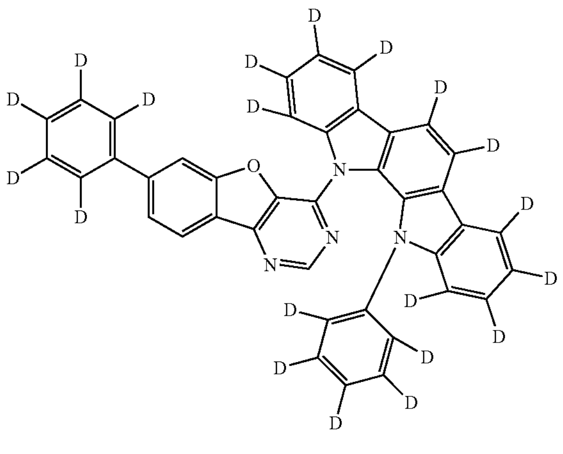
-continued
[Chemical Formula 30]
180
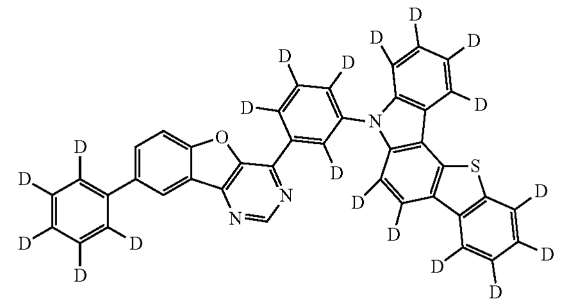
181
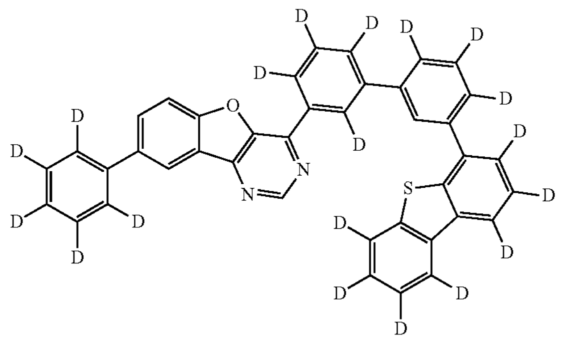
182
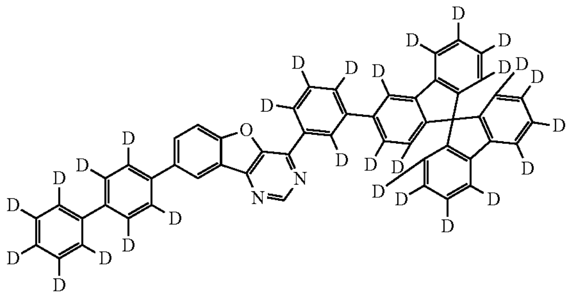
183
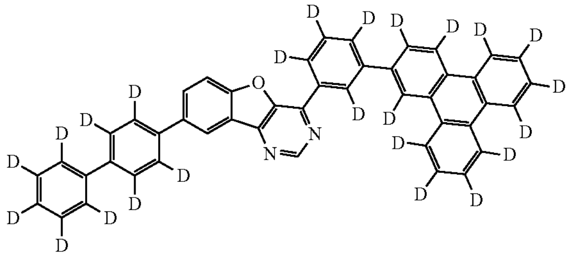
184
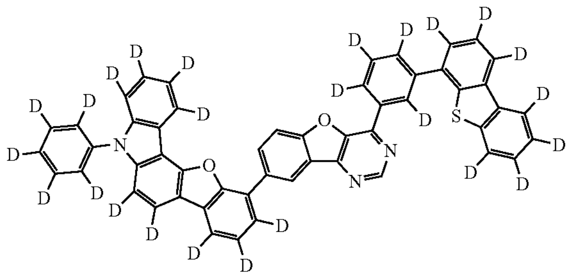

-continued
185
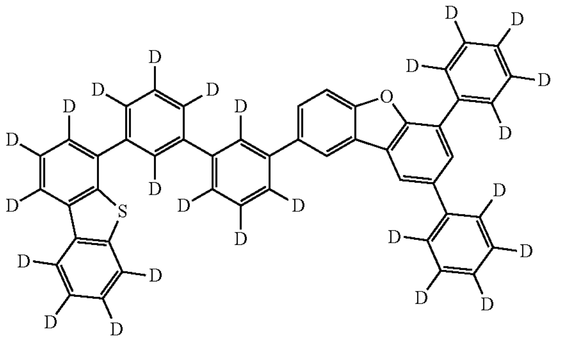
186
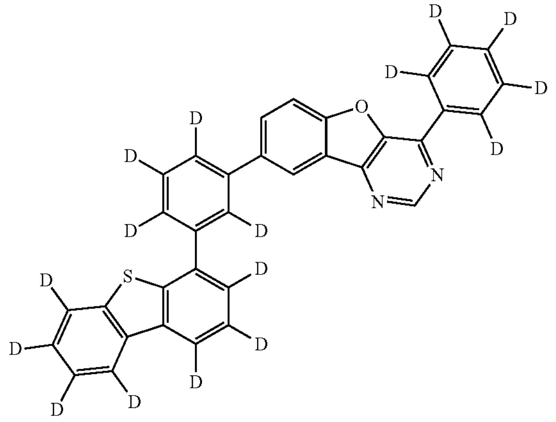
187
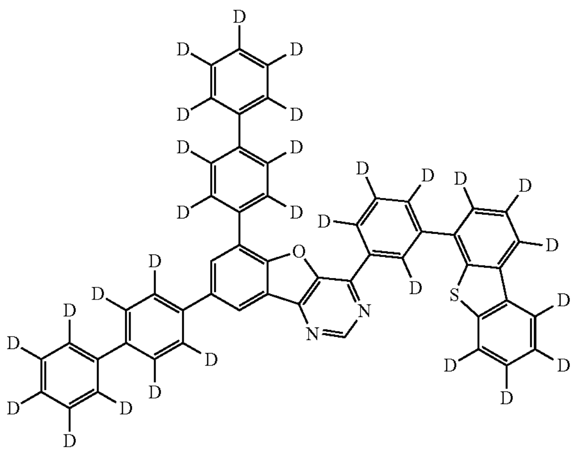
[Chemical Formula 31]
(188)
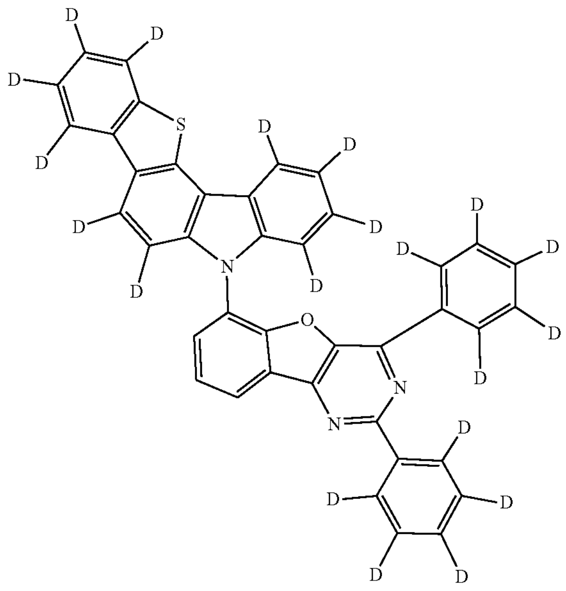
(189)
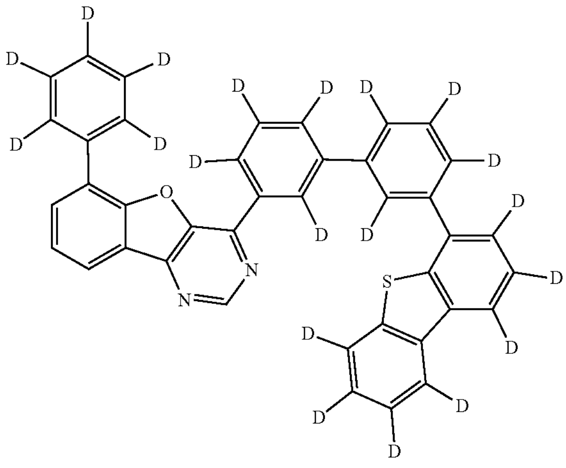
(190)
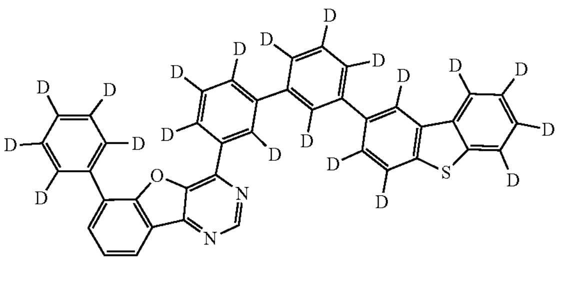

-continued
(191)
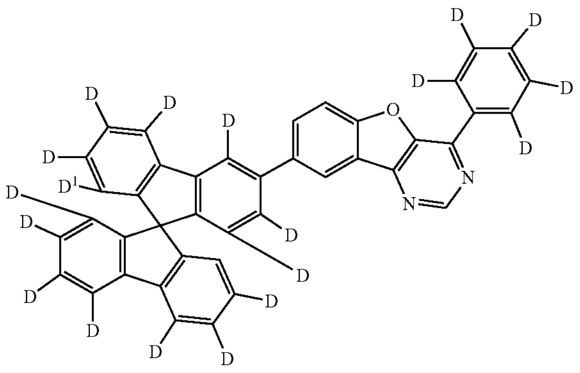
(192)
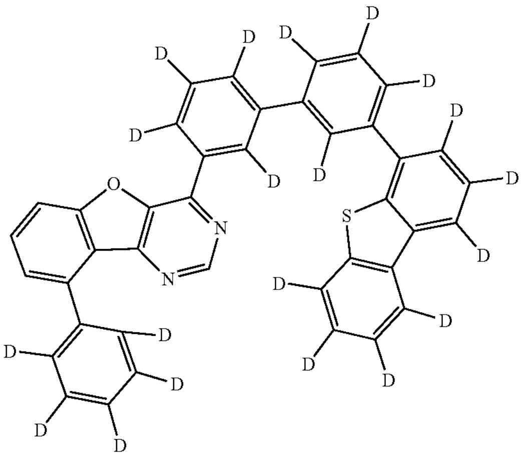
(193)
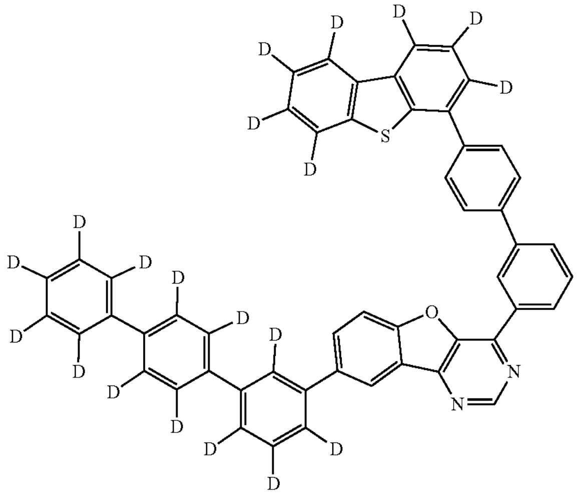
-continued
(194)
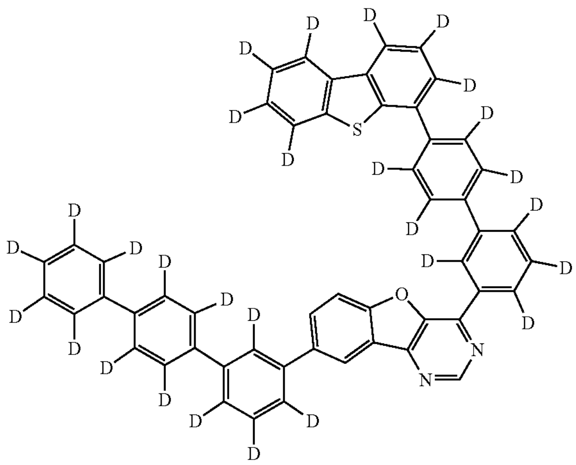
(195)
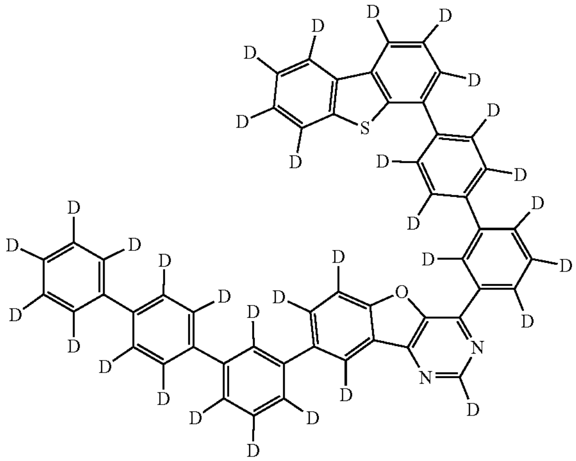
[Chemical Formula 32]
(501)
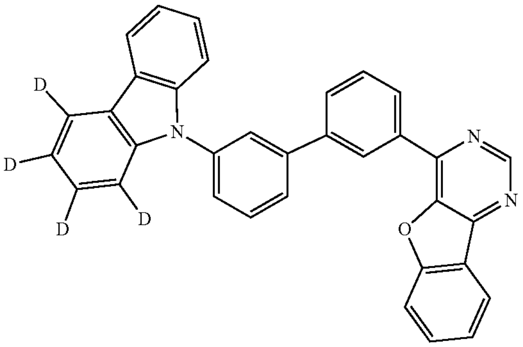

-continued
(502)
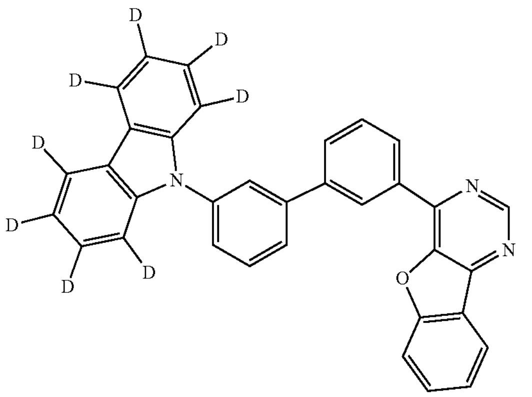
(503)
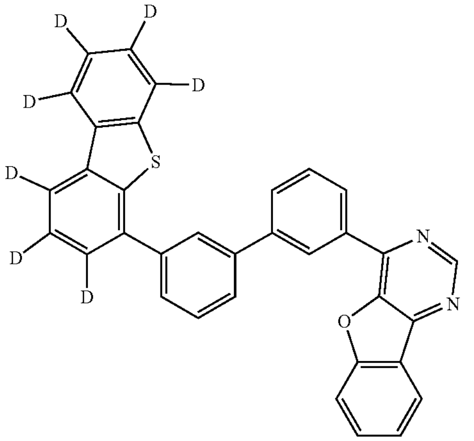
(504)
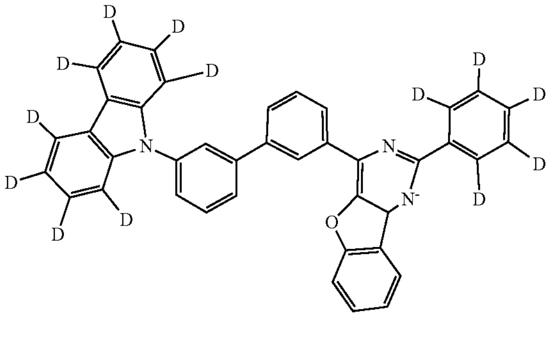
(505)
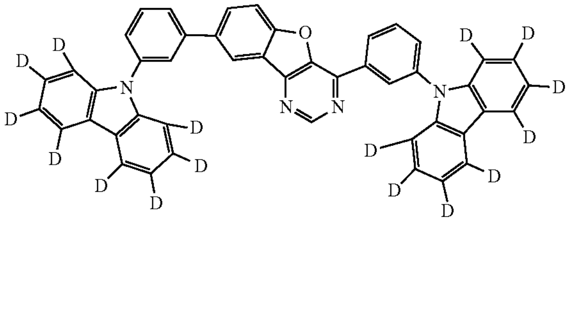
-continued
(506)
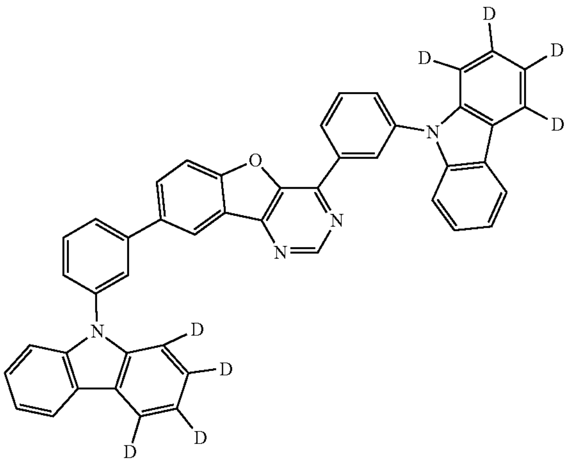
(507)
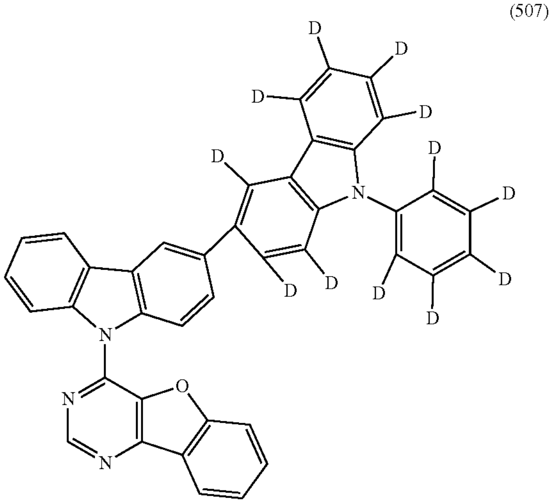
(508)
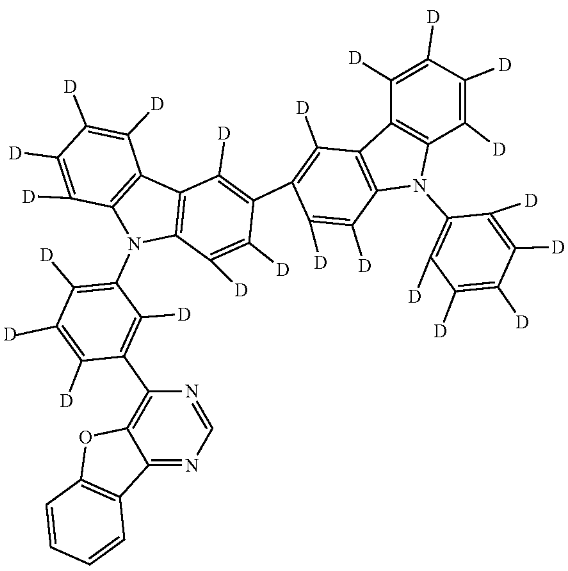

-continued
(509)
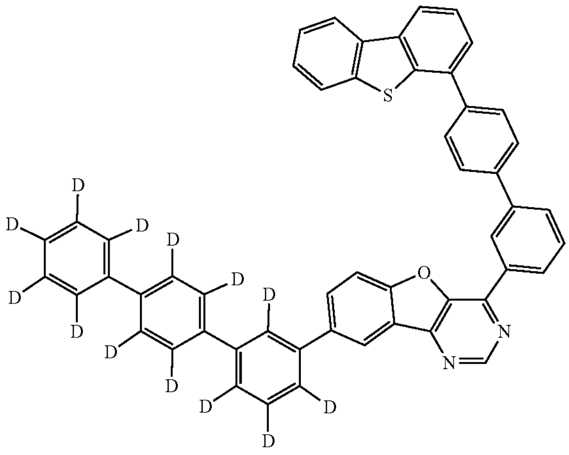
(510)
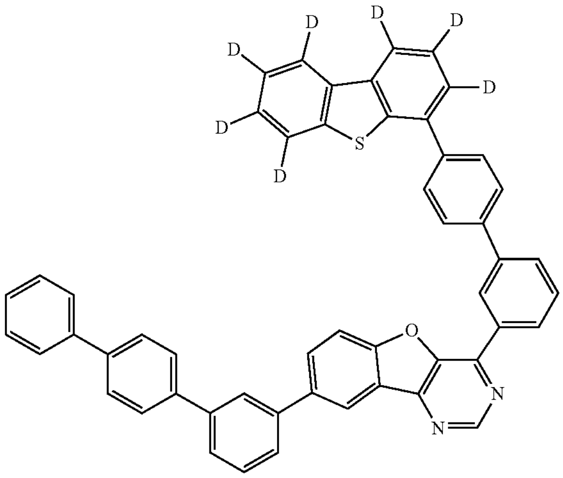
(511)
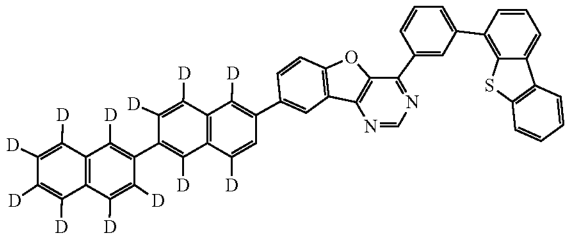
(512)
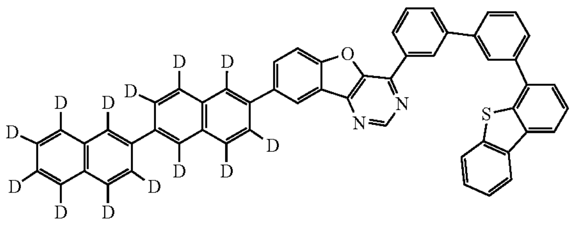
-continued
[Chemical Formula 33]
(513)
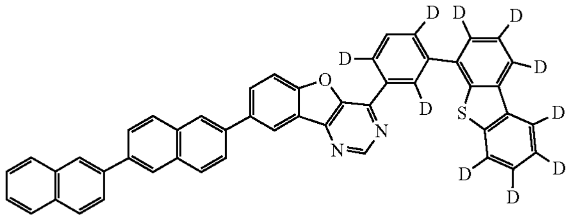
(514)
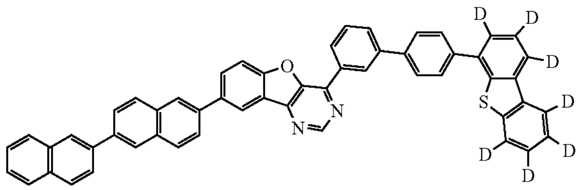
(515)
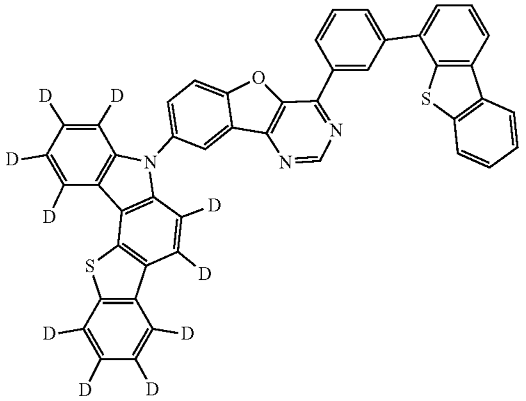
(516)
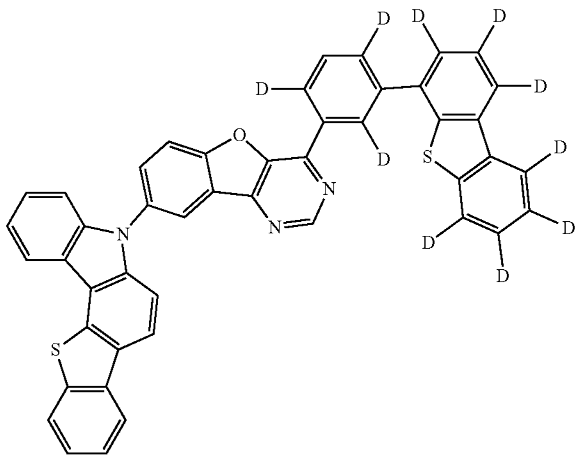

-continued
(516)
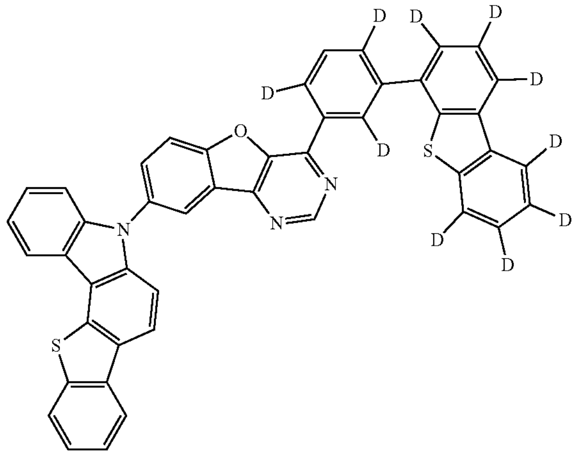
(517)
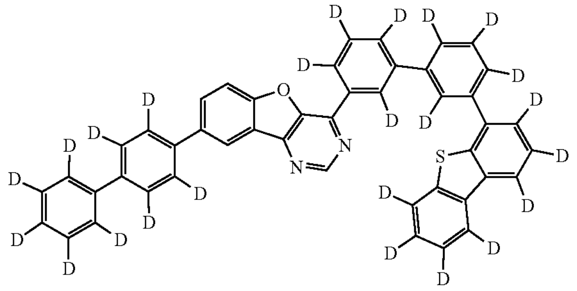
(518)
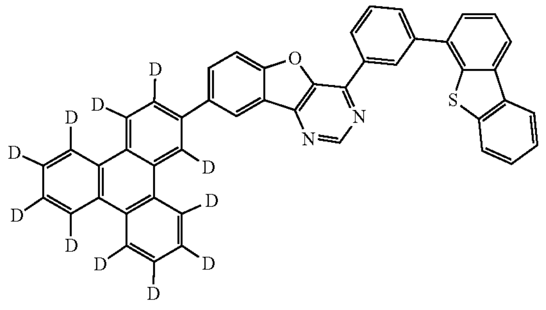
-continued
(519)
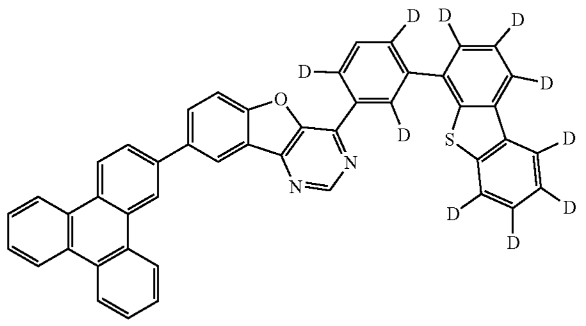
(520)
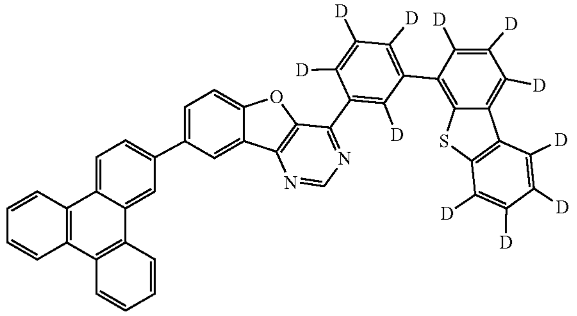
(521)
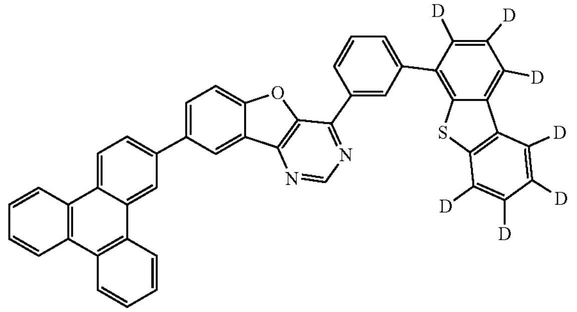
[Chemical Formula 34]
(522)
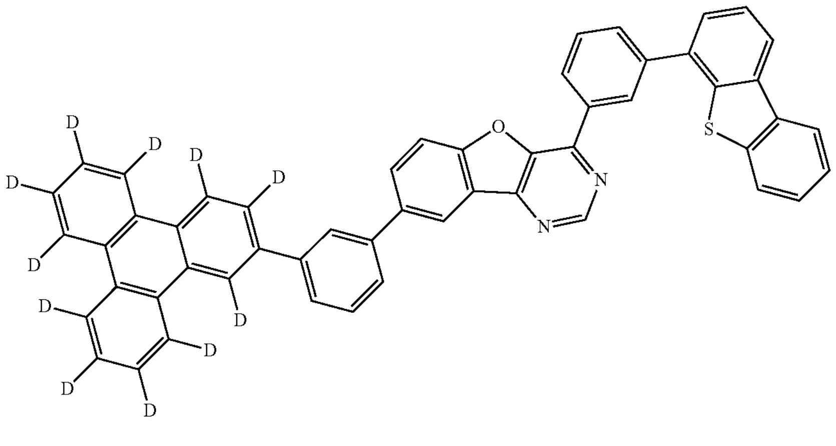

-continued
(523)
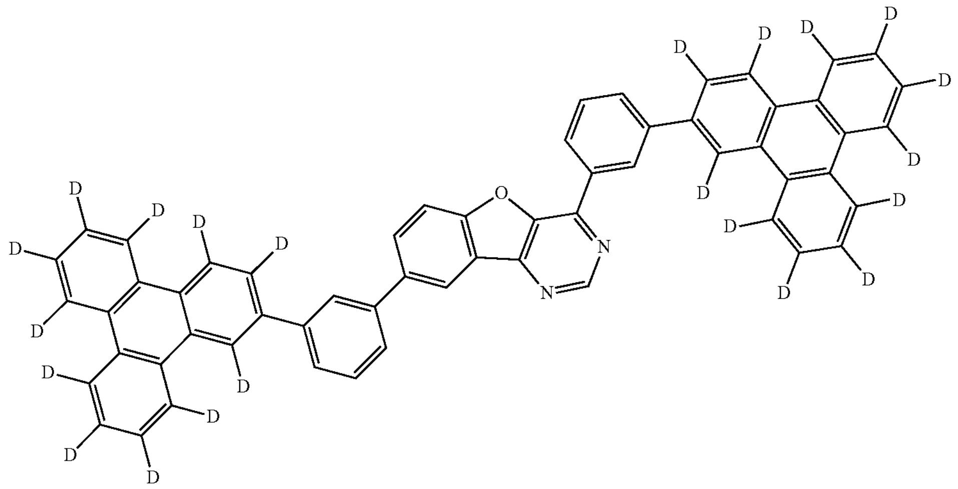
(524)
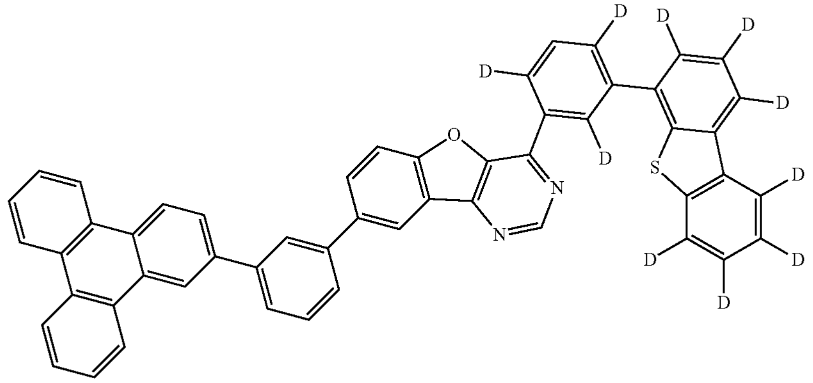
(525)
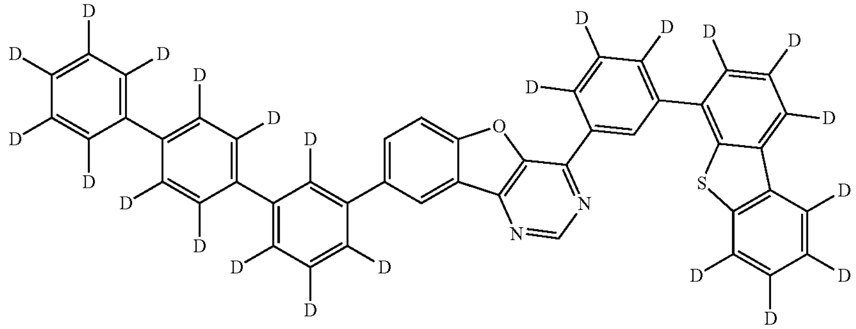
(526)
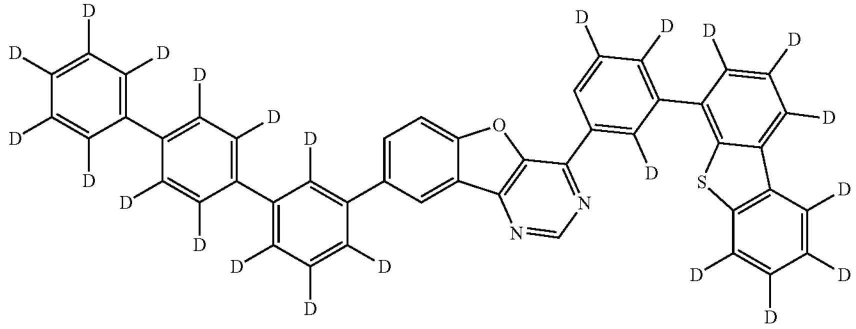

-continued
(527)
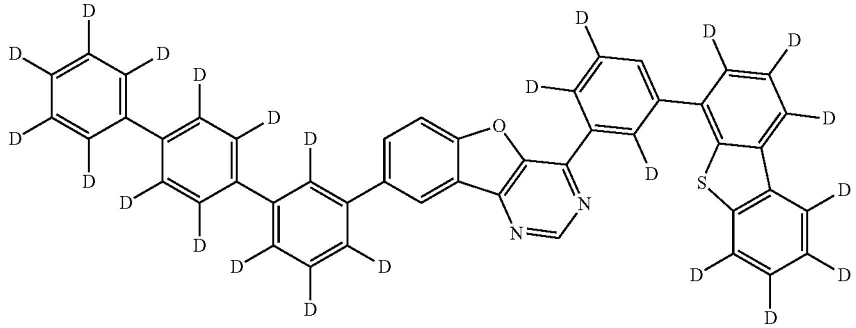
(528)
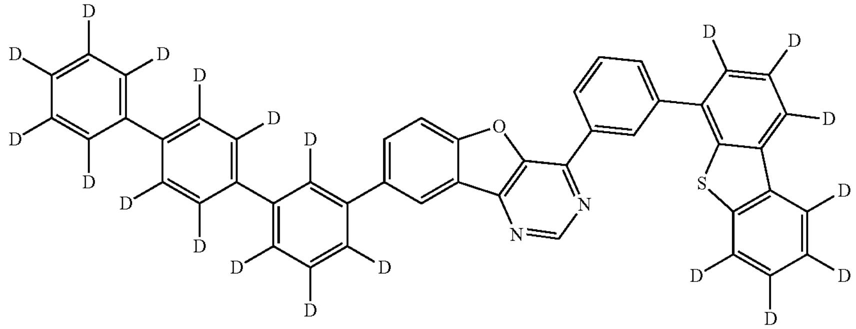
[Chemical Formula 35]
(529)
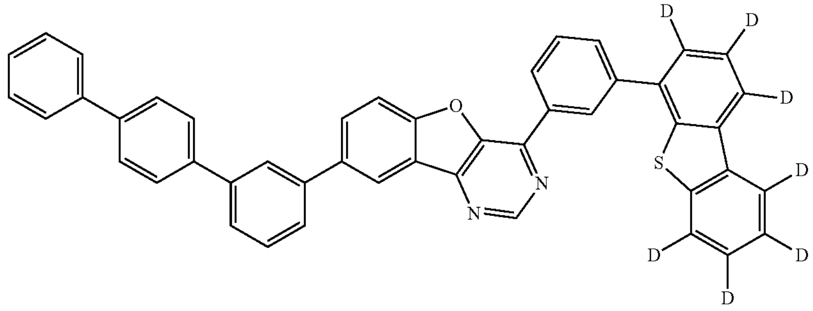
(531)
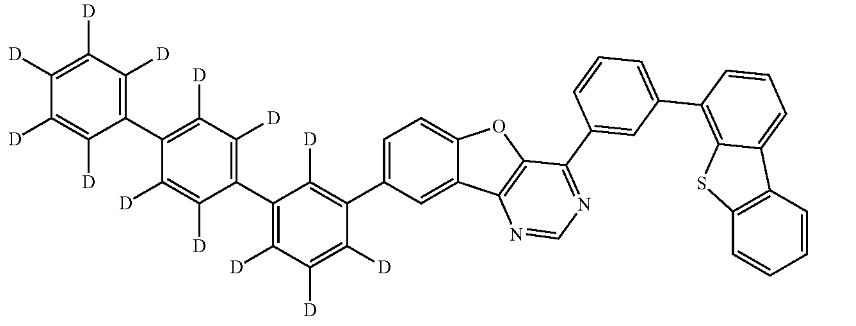

-continued
(530)
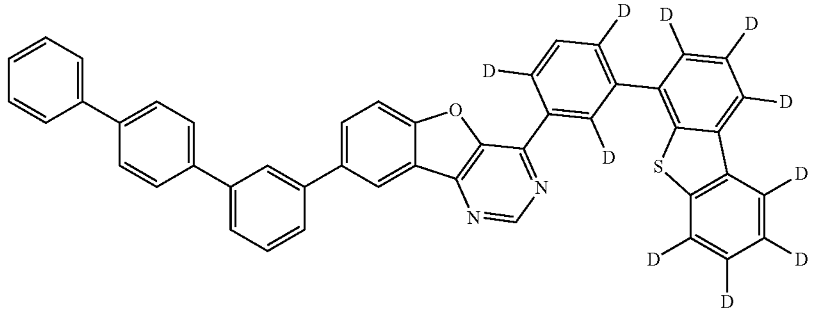
(532)
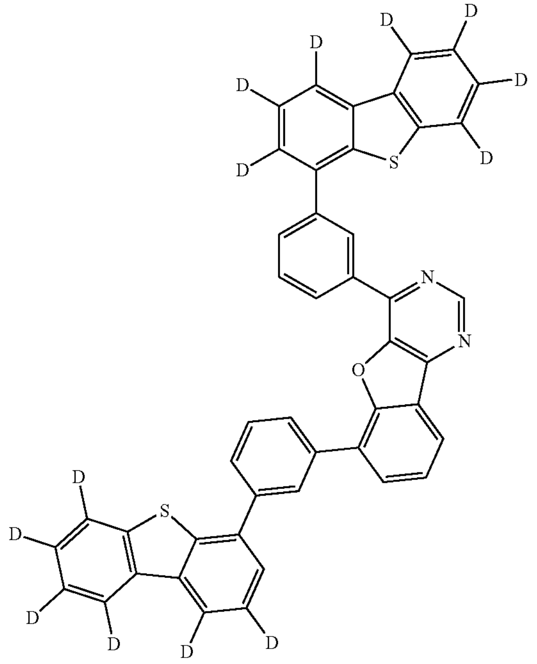
(533)
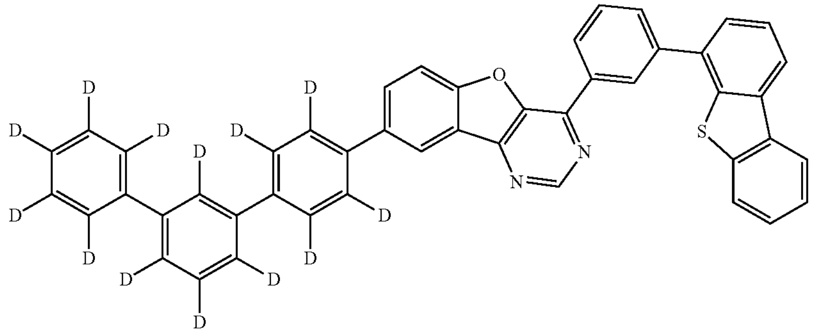
(534)
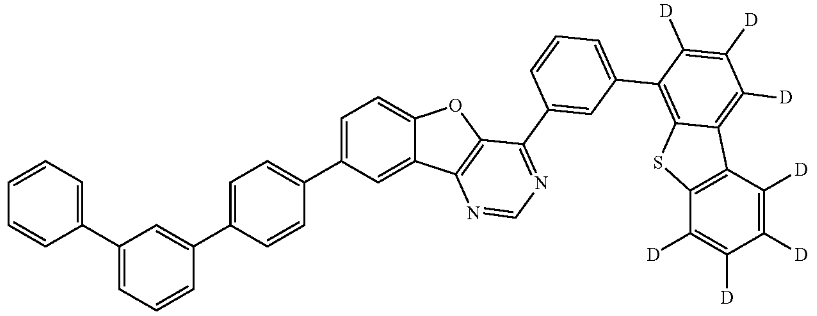

-continued
(535)
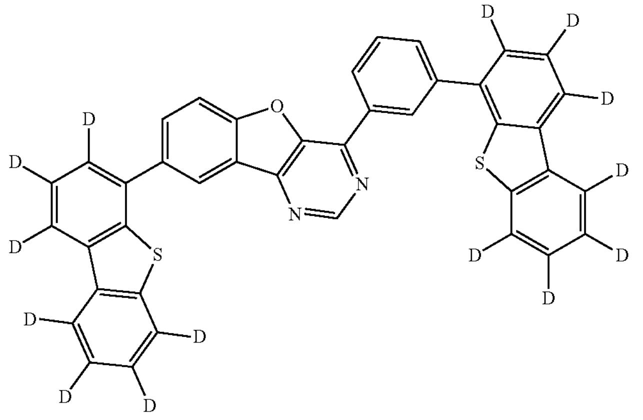
(536)
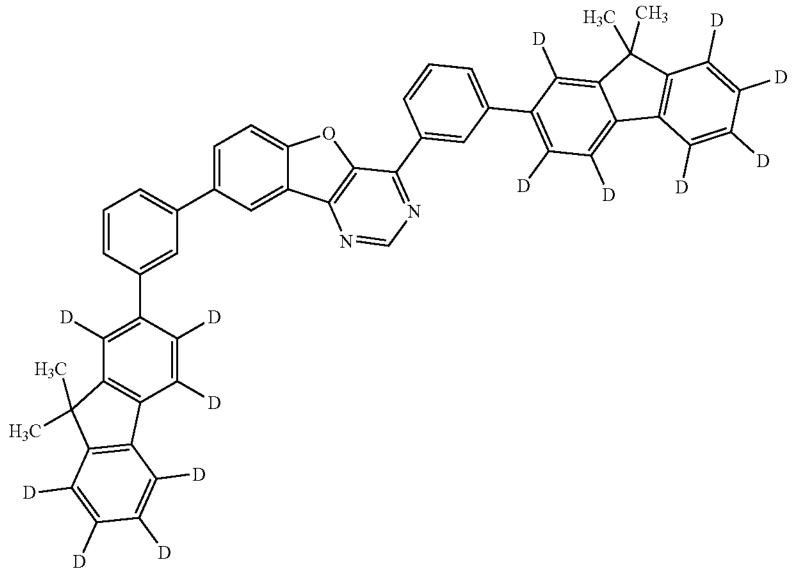
(537)
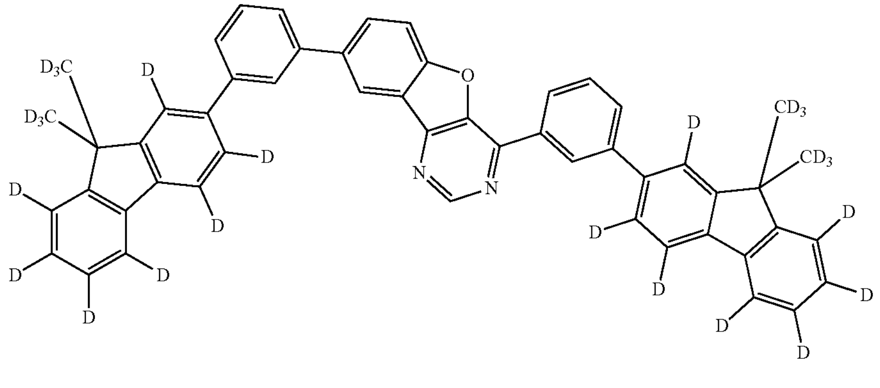

-continued
[Chemical Formula 36]
(538)
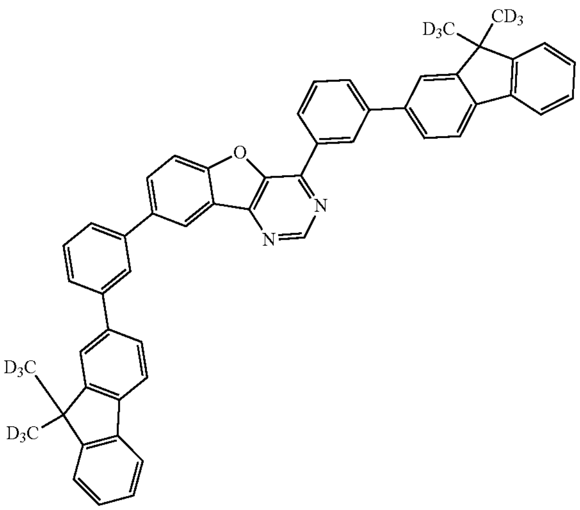
(539)
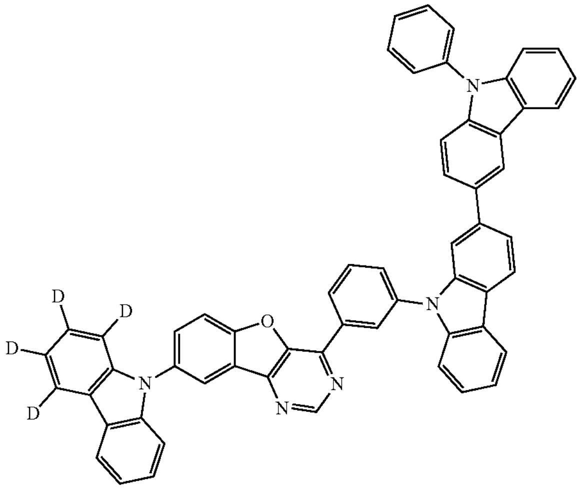
(540)
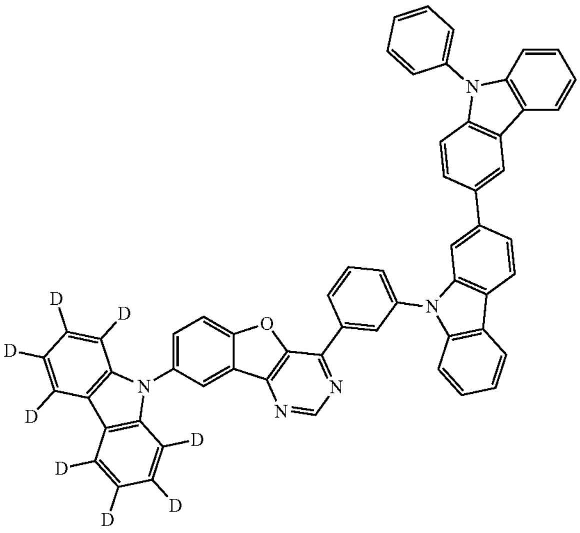
(541)
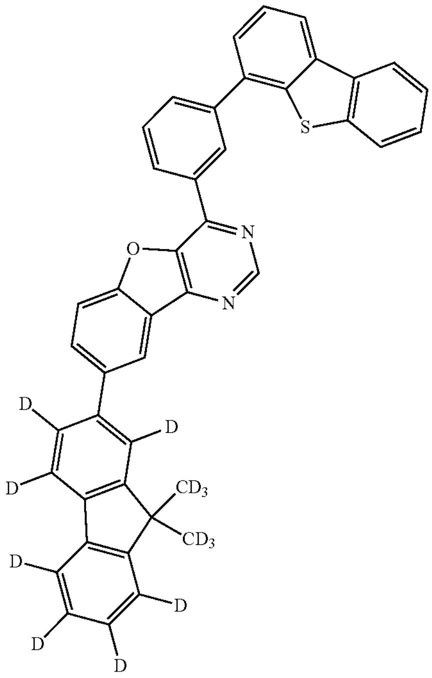

-continued
(542)
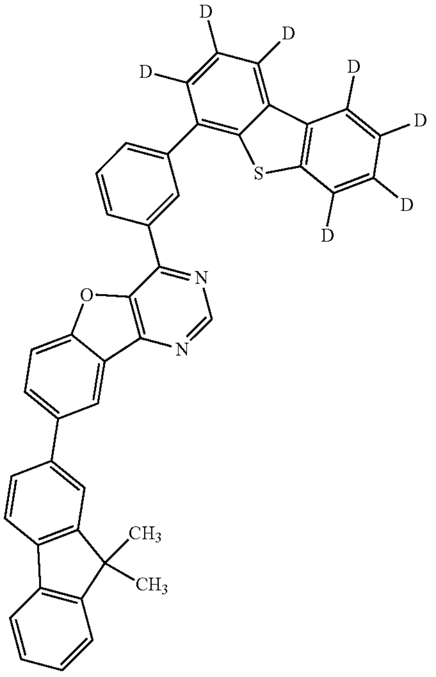
(543)
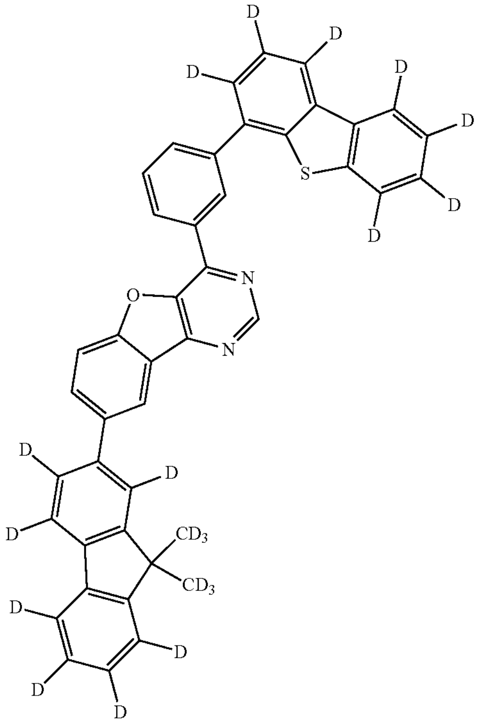
(546)
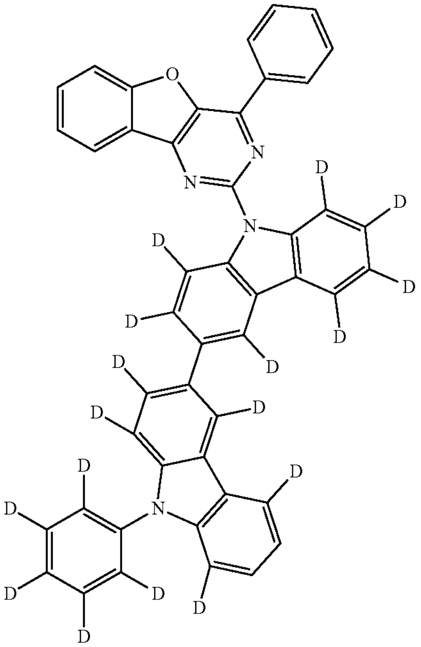
(544)
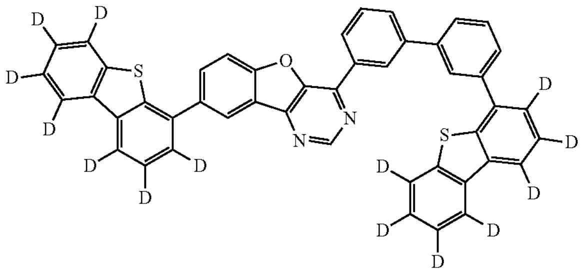

-continued
(545)
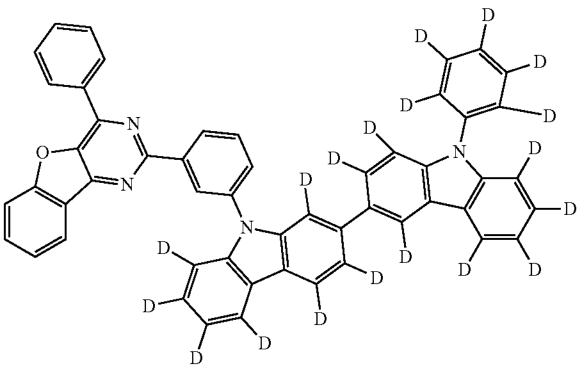
(547)
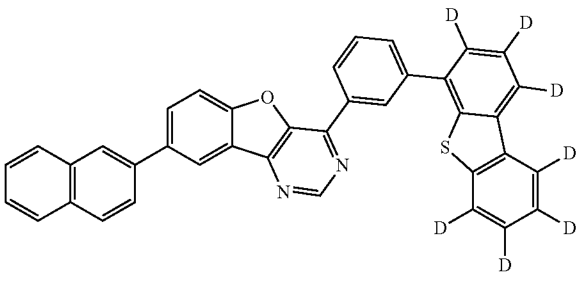
(548)
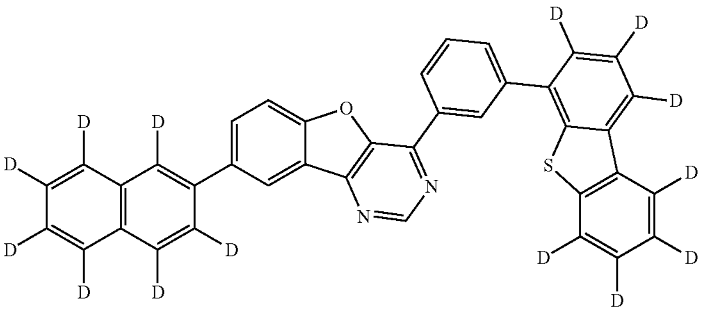
[Chemical Formula 37]
(549)
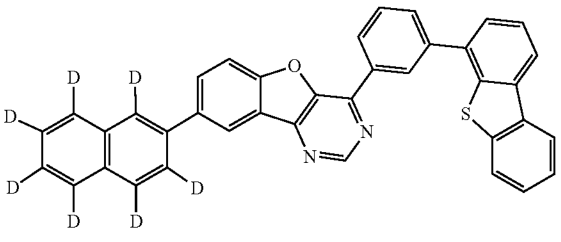
(550)
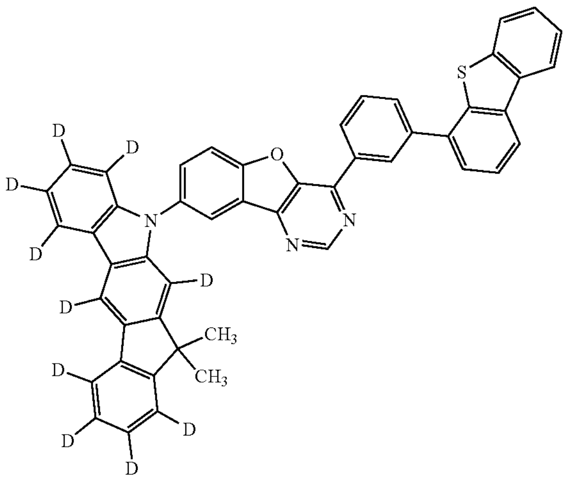

-continued
(551)
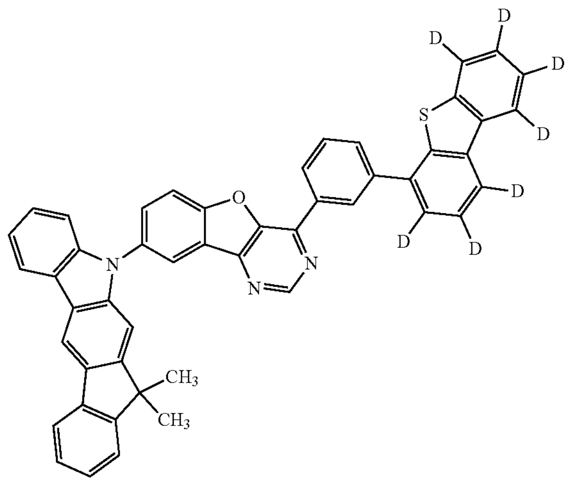
(552)
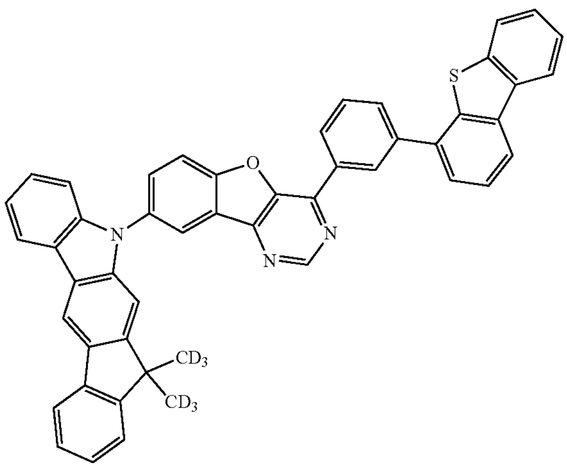
(553)
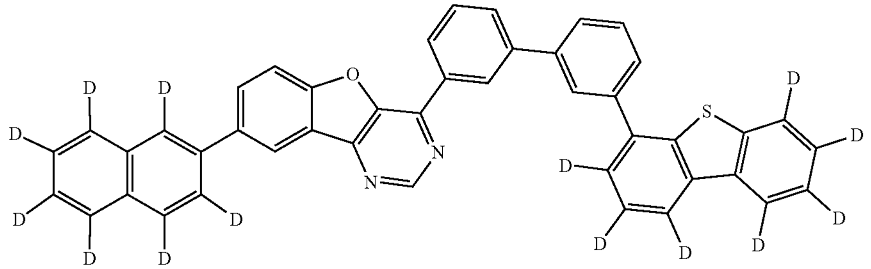
(554)
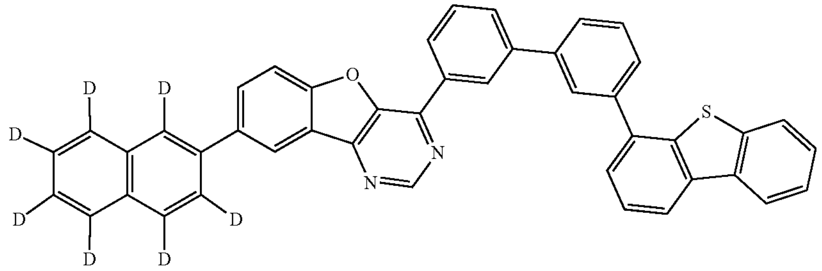
(555)
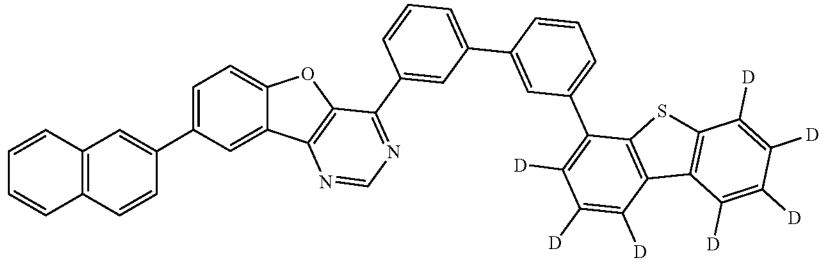
(556)
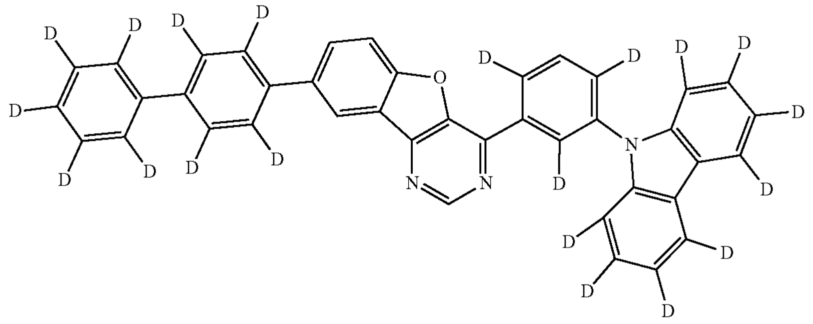

-continued
(557)
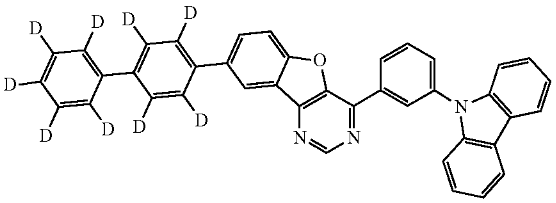
(558)
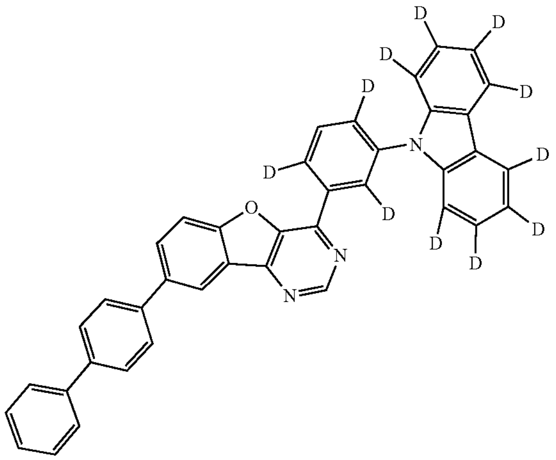
(559)
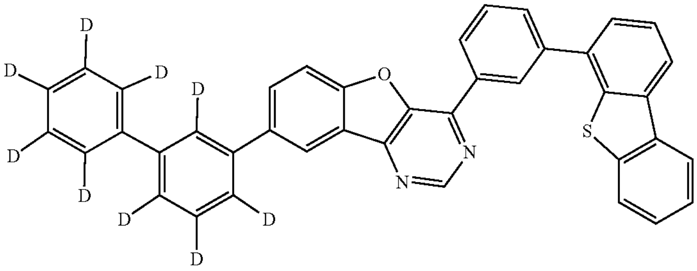
[Chemical Formula 38]
(560)
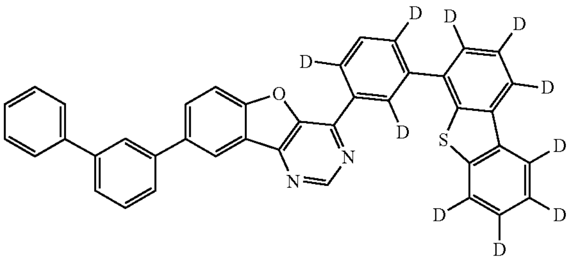
(561)
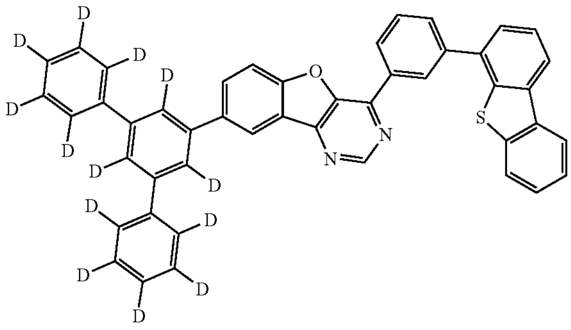
(562)
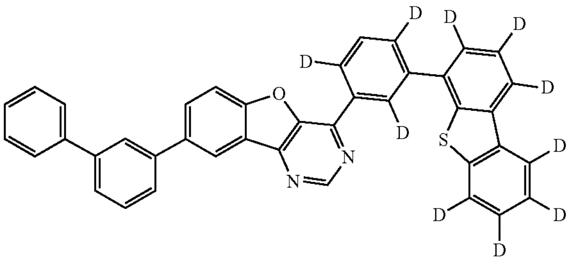
(563)
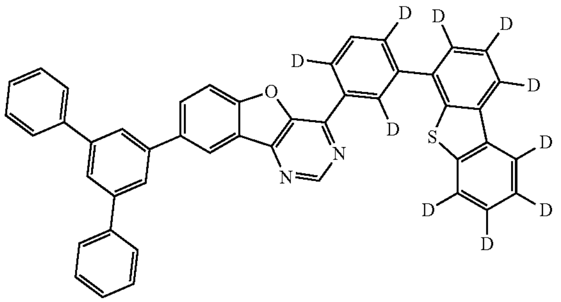

-continued
(564)
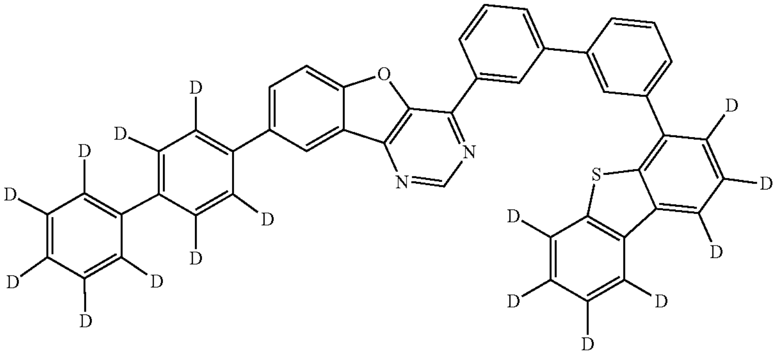
(565)
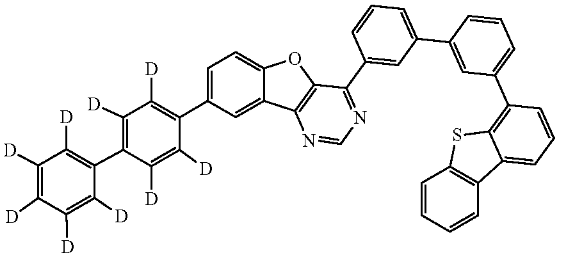
(566)
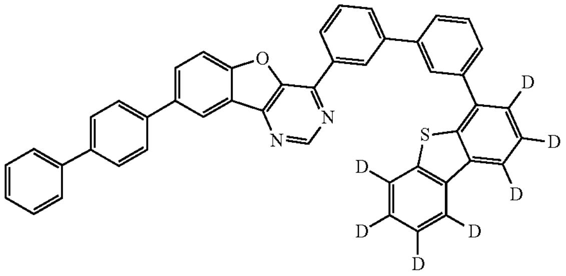
(567)
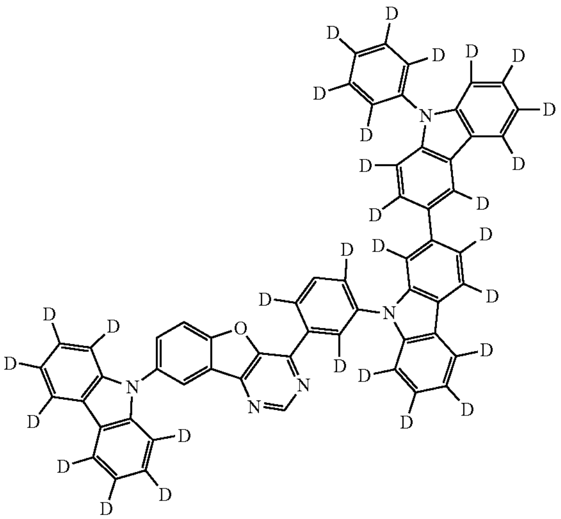
(568)
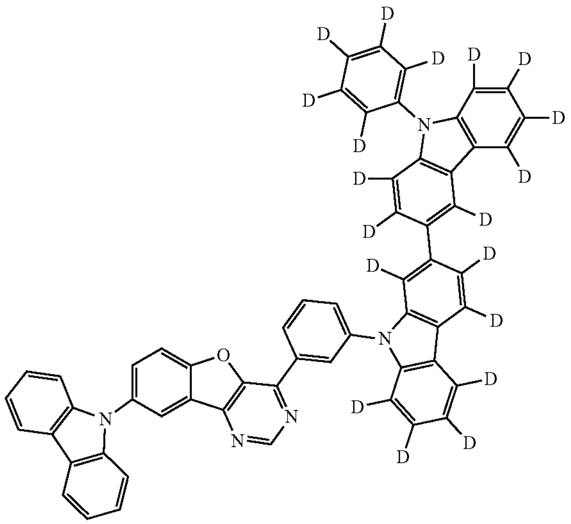
(569)
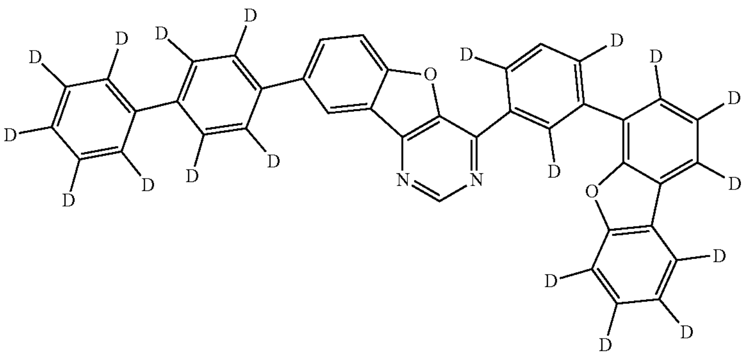

-continued
[Chemical Formula 39]
(570)
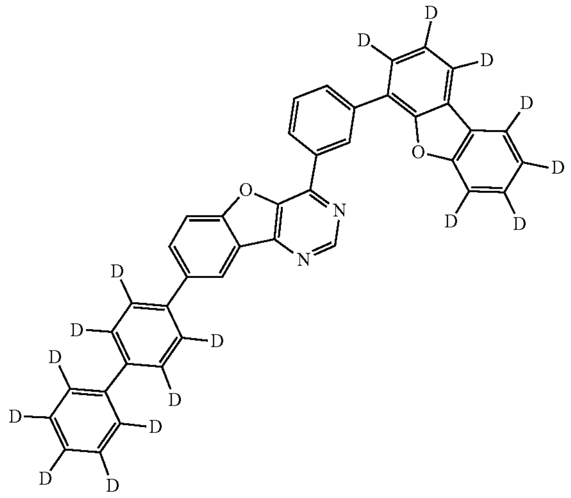
(571)
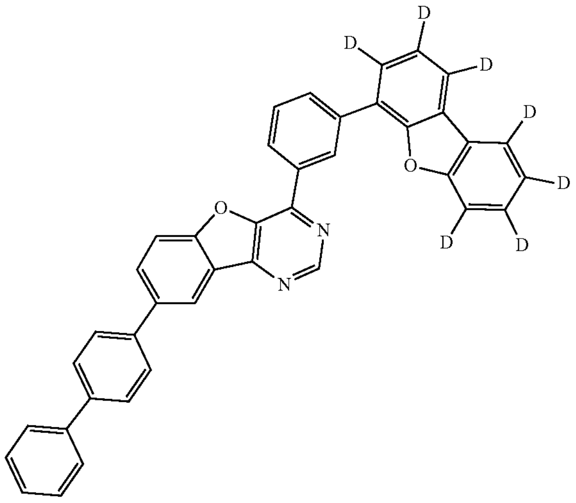
(572)
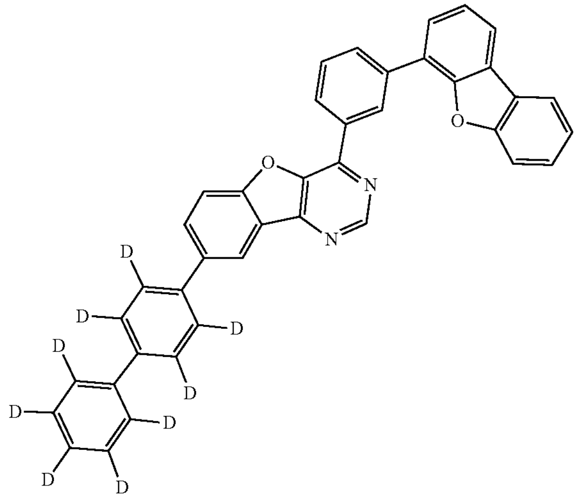
(573)
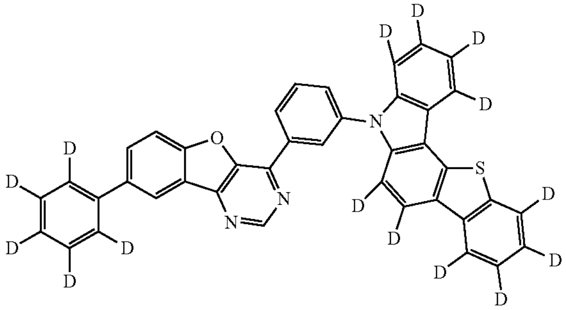
(574)
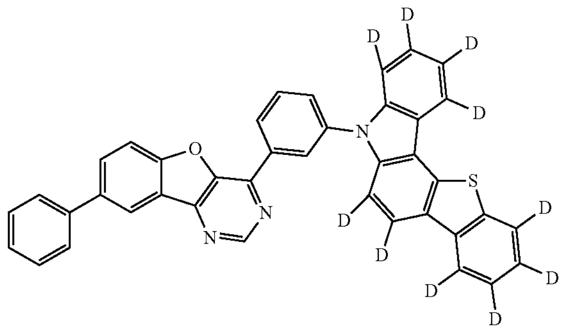
(575)
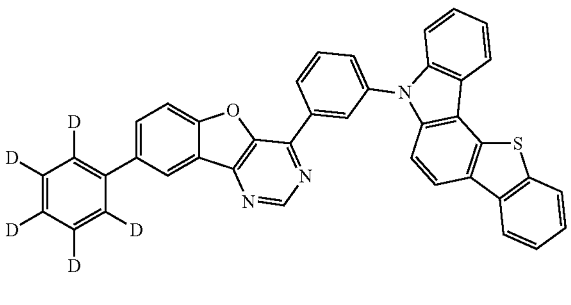

-continued
(576)
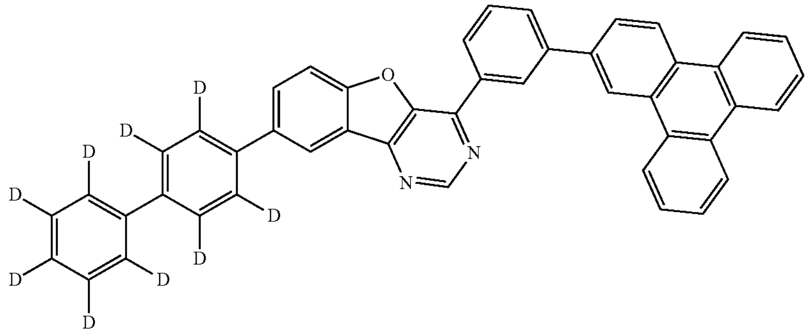
(577)
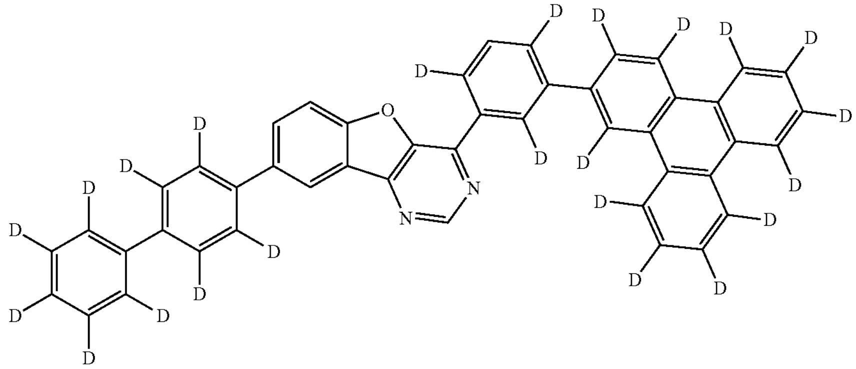
(578)
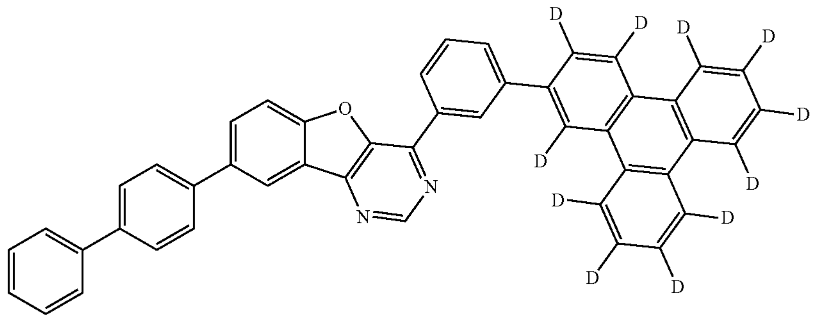
(579)
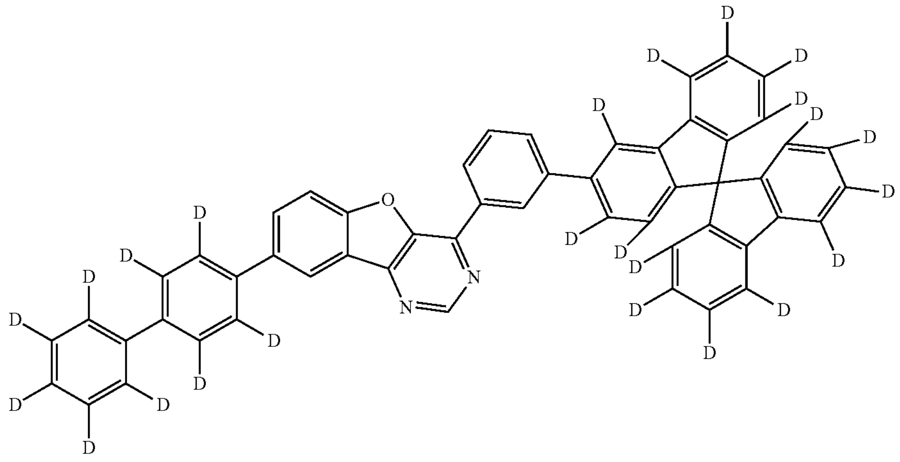

-continued
(580)
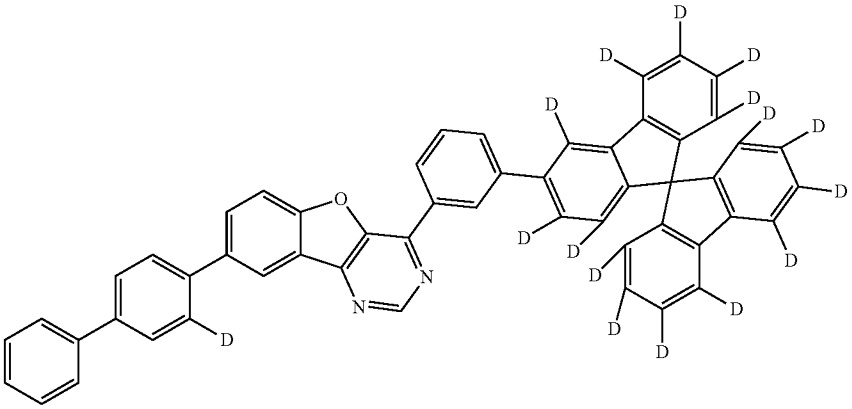
[Chemical Formula 40]
(581)
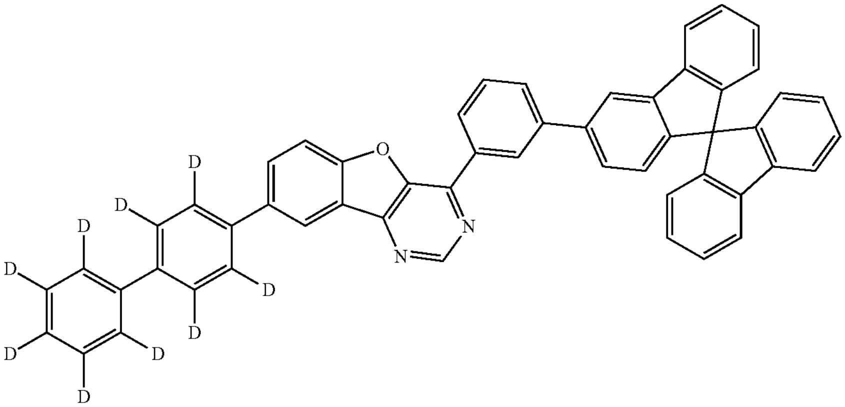
(582)
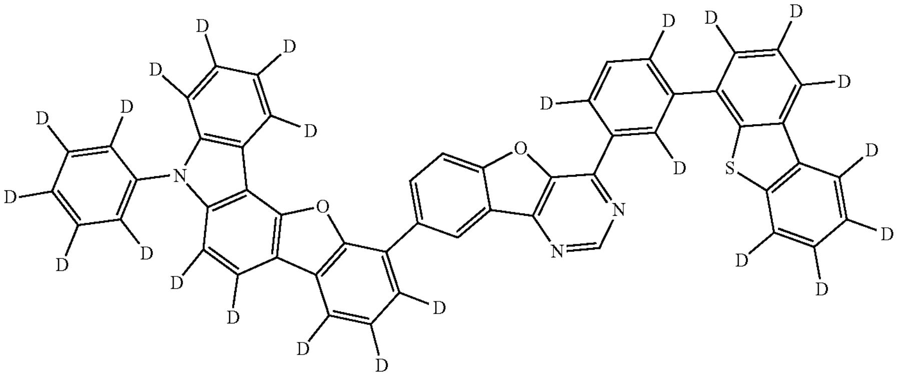
(583)
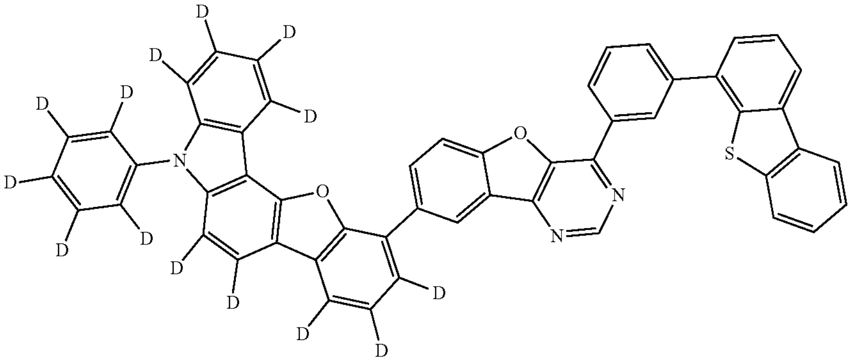

-continued
(584)
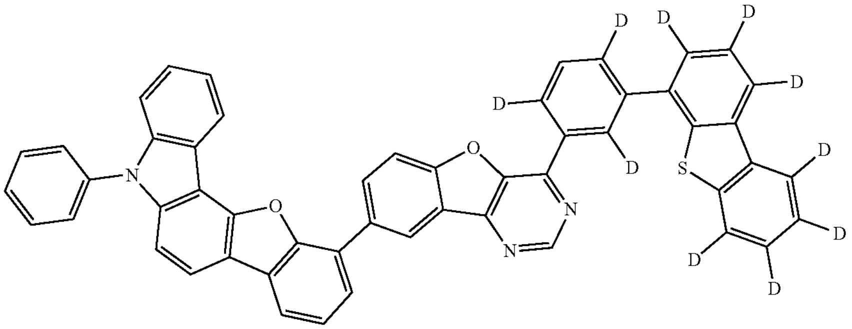
(585)
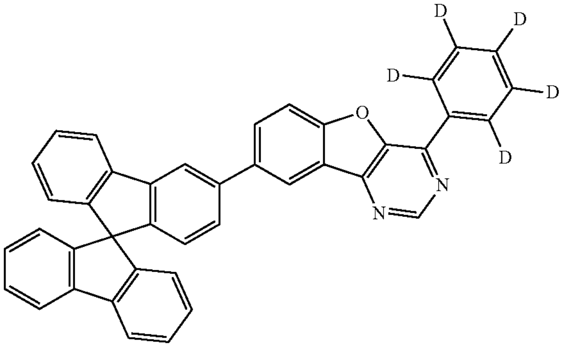
(586)
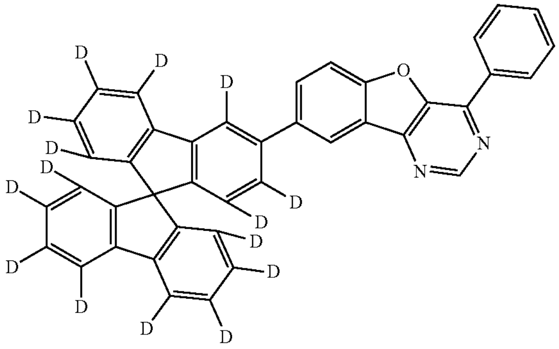
(587)
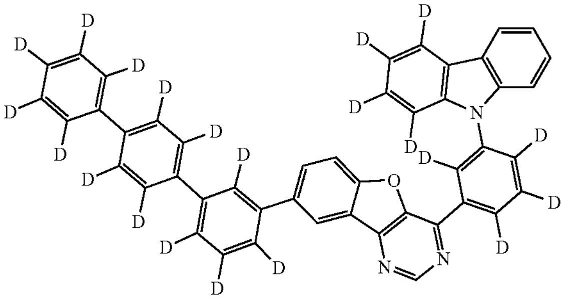
(588)
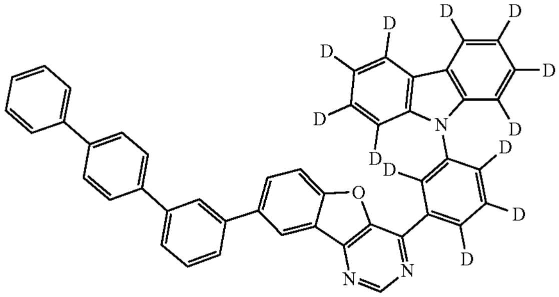
(589)
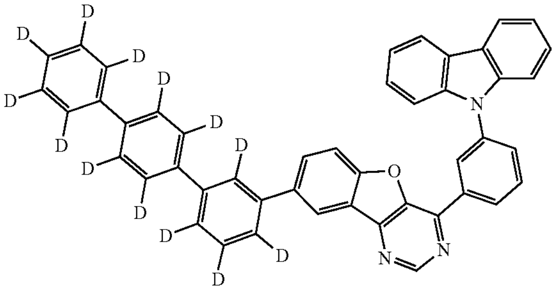
(590)
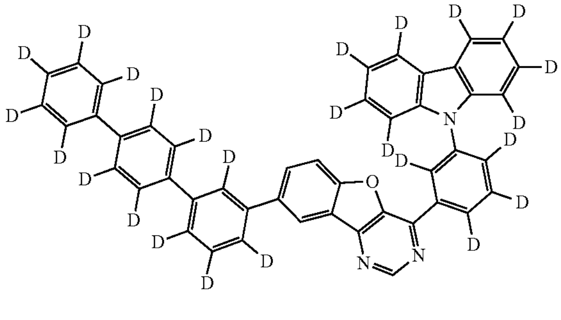

-continued
(591)
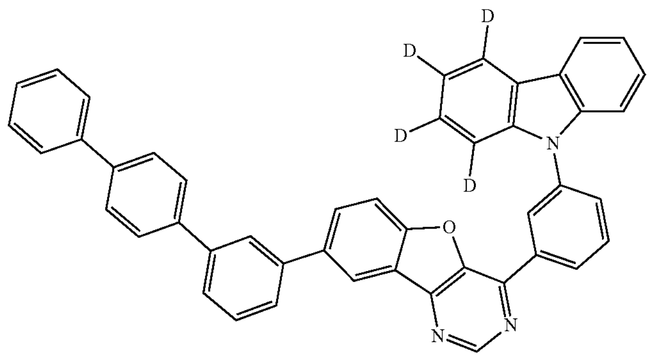
[Chemical Formula 41]
(592)
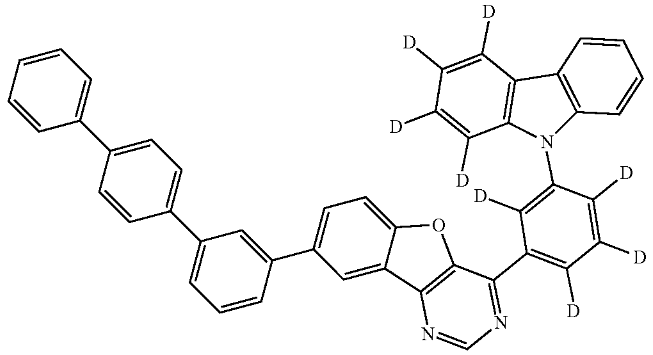
(593)
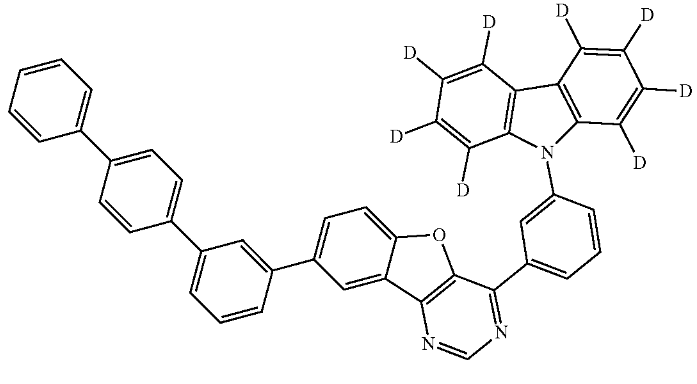

-continued
(594)
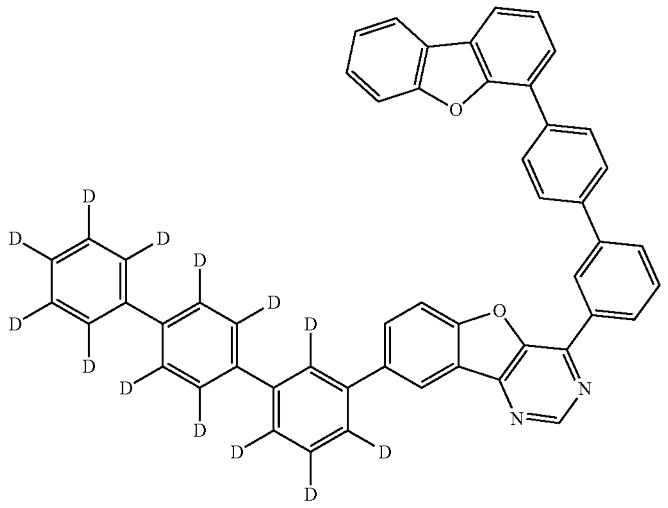
(595)
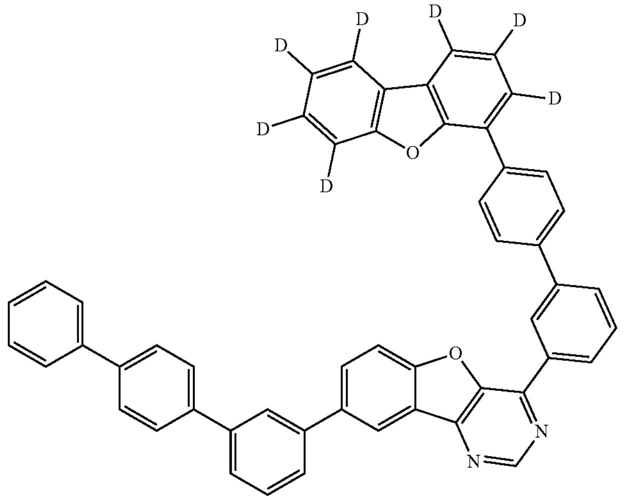
(596)
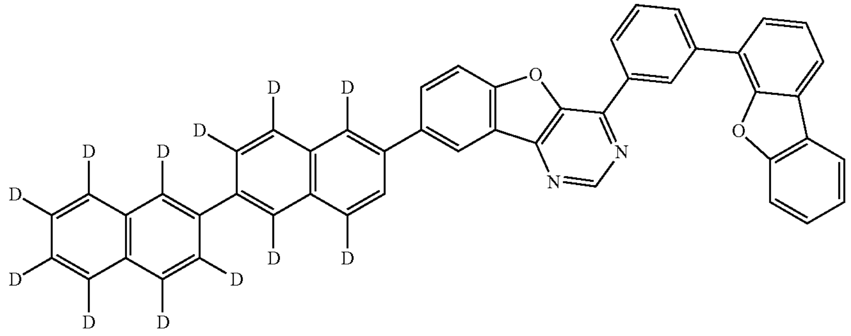

-continued
(597)
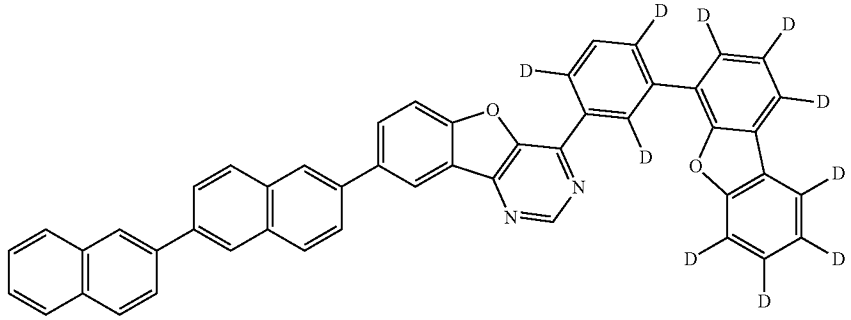
(598)
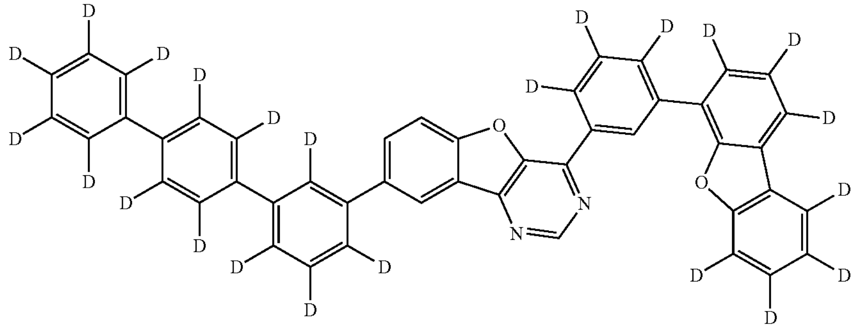
(599)
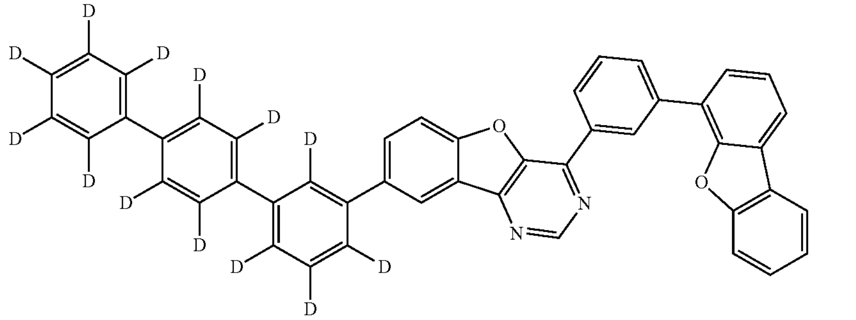
(600)
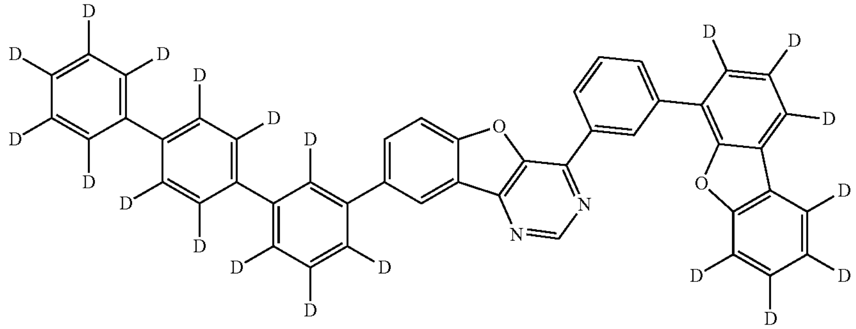
(601)
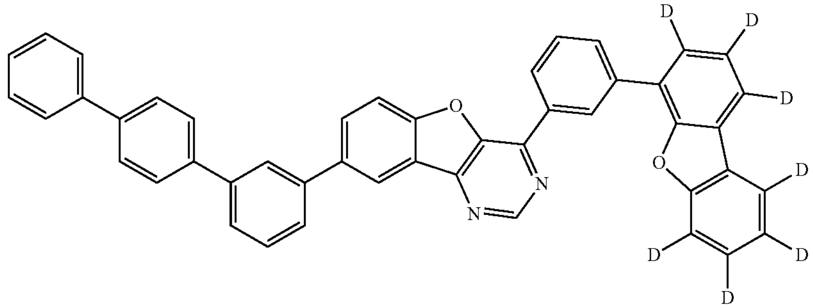

The organic compounds represented by Structural Formulae (100) to (195) and Structural Formulae (501) to (601) above are examples of the organic compounds represented by General Formulae (G1) to (G4). The organic compound of one embodiment of the present invention is not limited thereto.

Specific Example 2

The following are specific examples of the organic compounds of one embodiment of the present invention having the structures represented by General Formulae (G1) to (G4) above. Note that in the following examples, $Q^1$ and $Q^2$ each independently represent oxygen or sulfur.

[Chemical Formula 42]

(200)

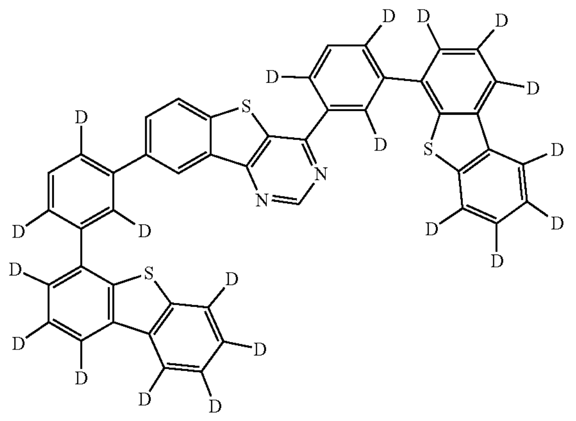

(201)

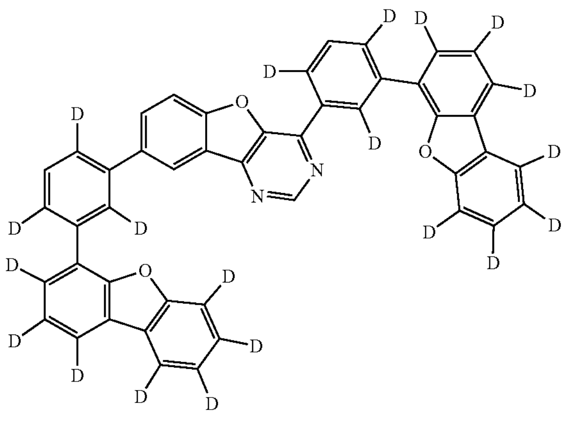

(202)

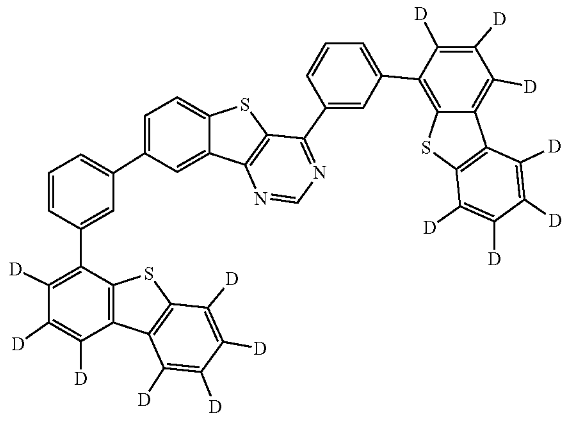

(203)

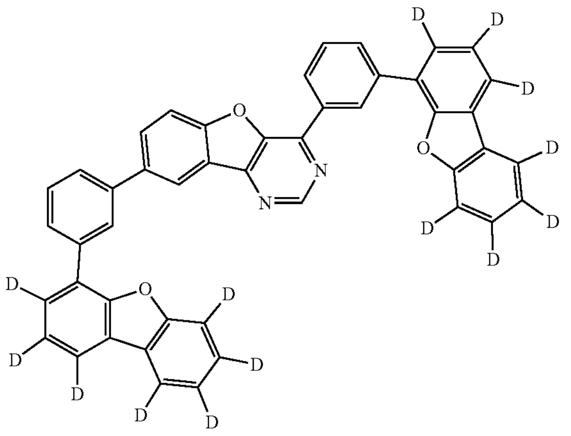

(204)

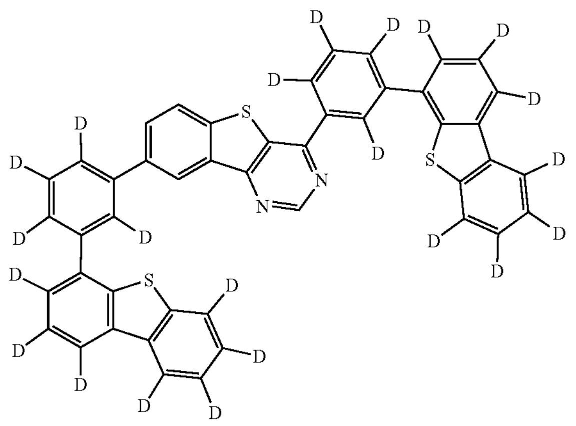

(205)

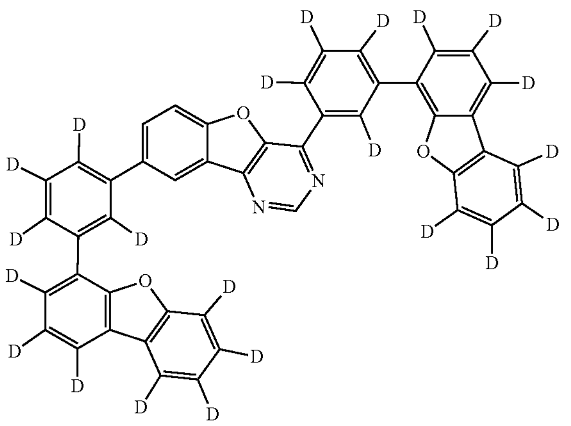

-continued
(206)
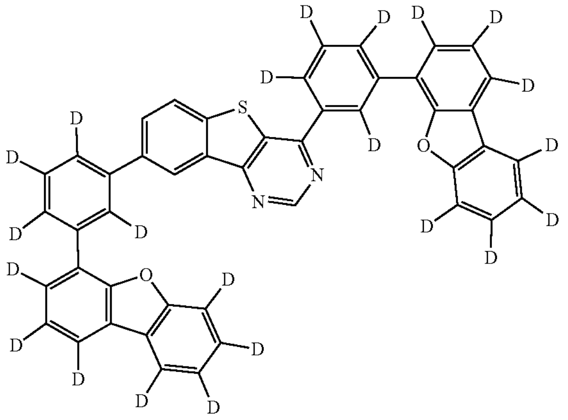
(207)
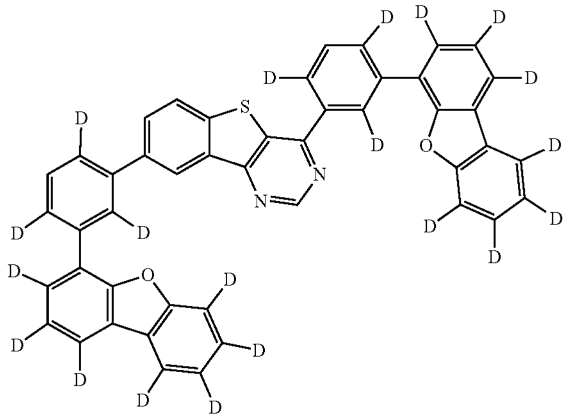
(208)
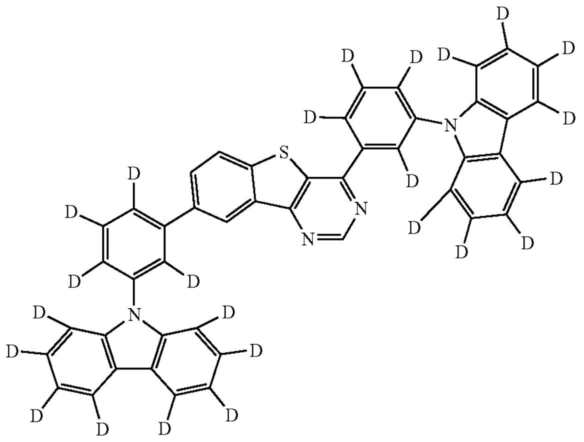
(209)
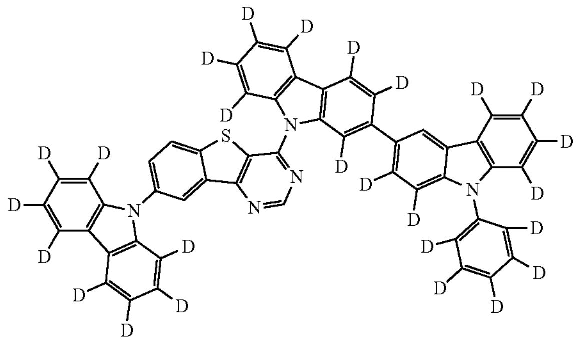
[Chemical Formula 43]
(210)
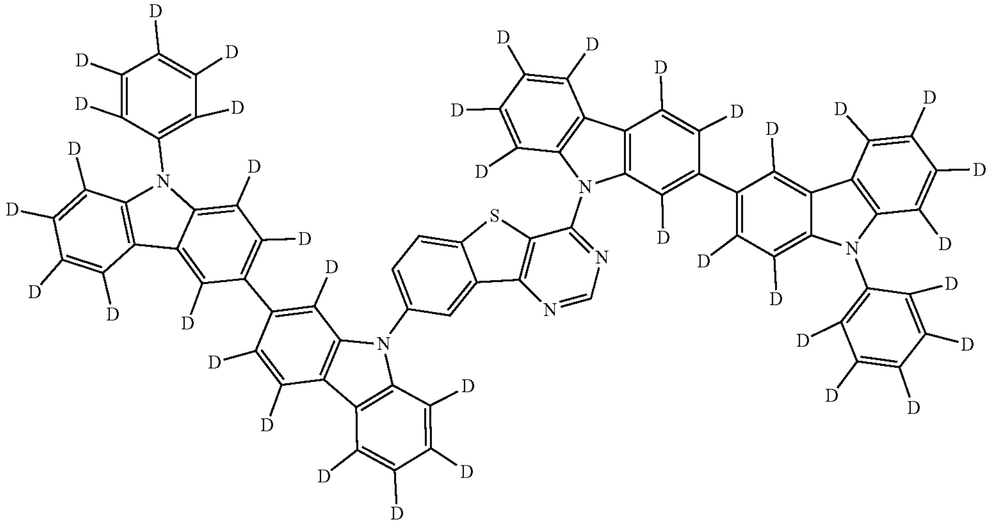

-continued
(211)
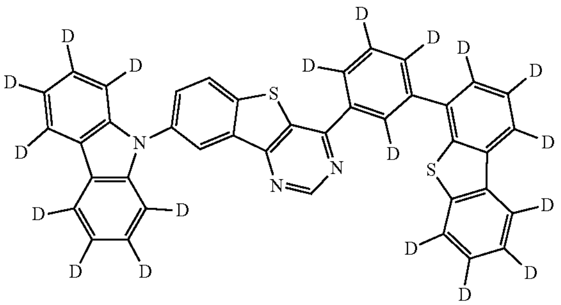
(212)
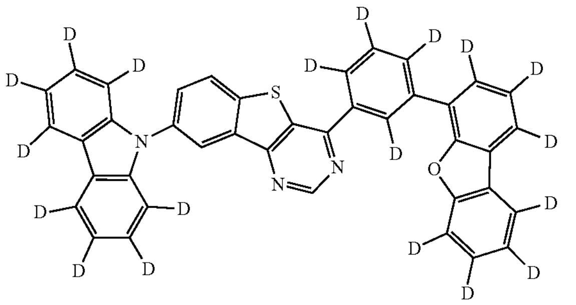
(213)
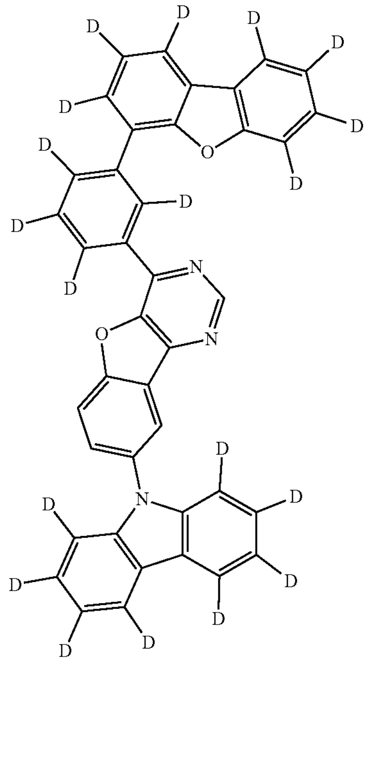
(214)
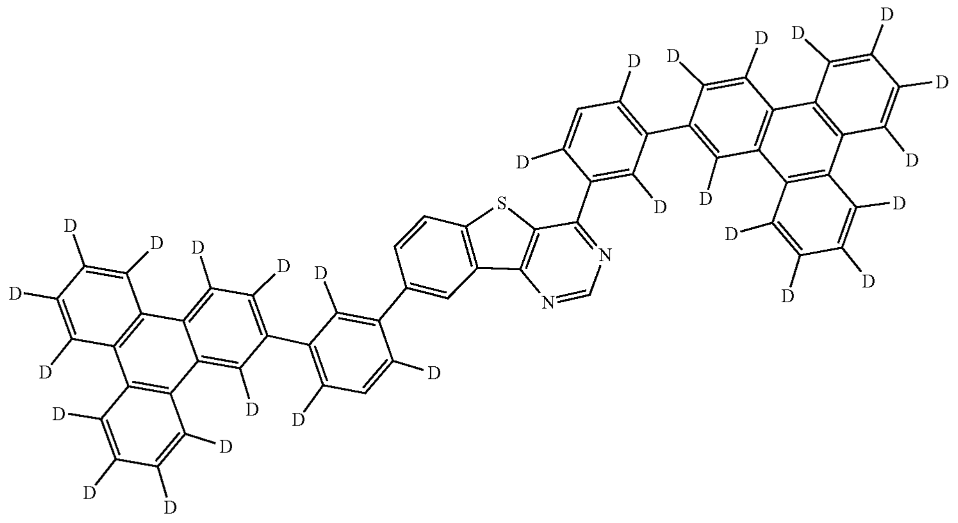

-continued
(215)
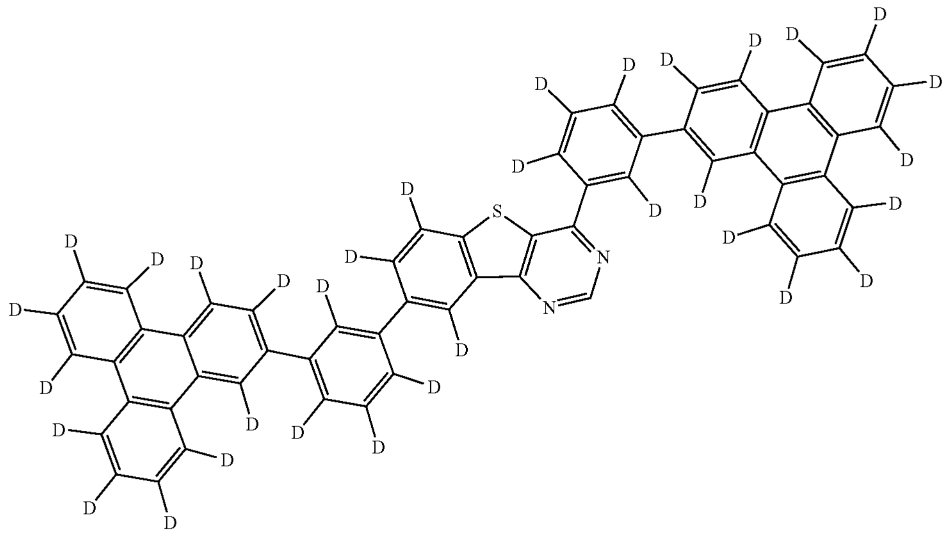
(216)
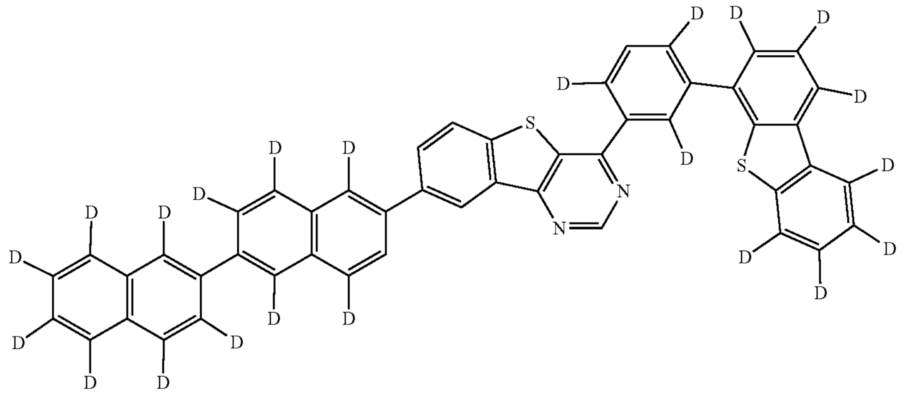
(217)
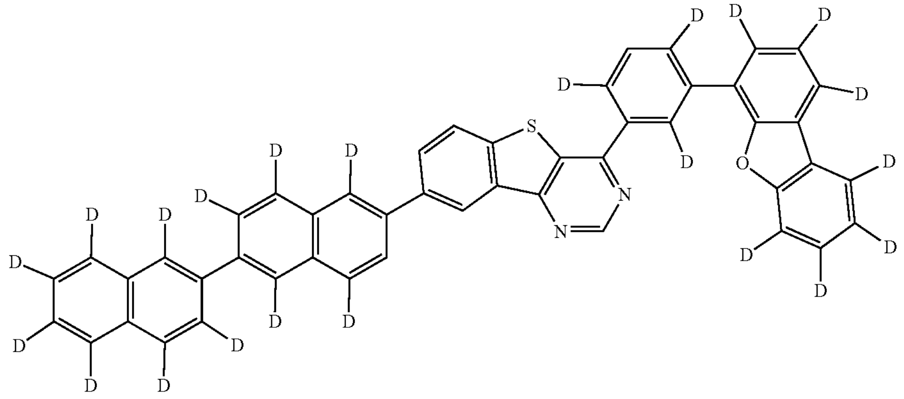

-continued
(218)
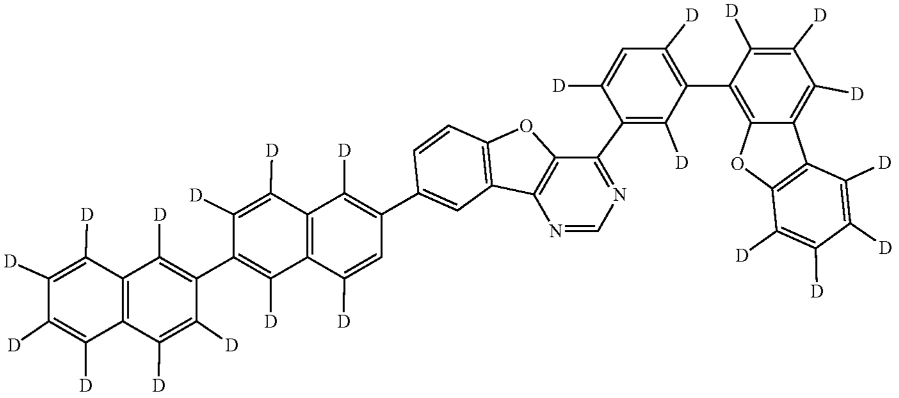
(219)
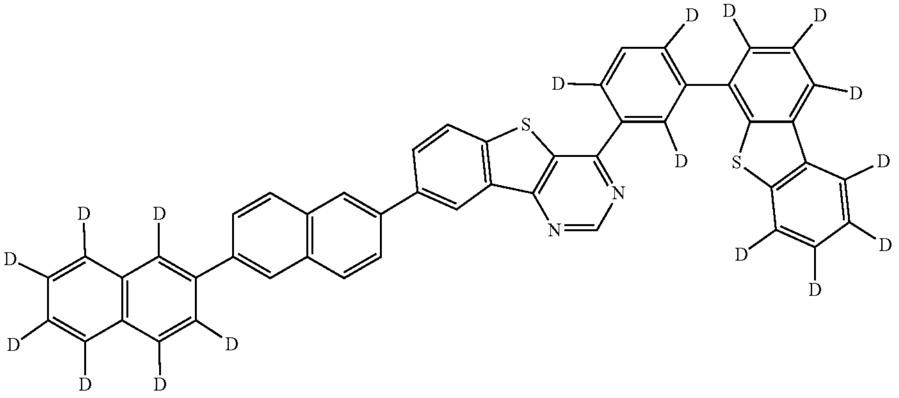
(220)
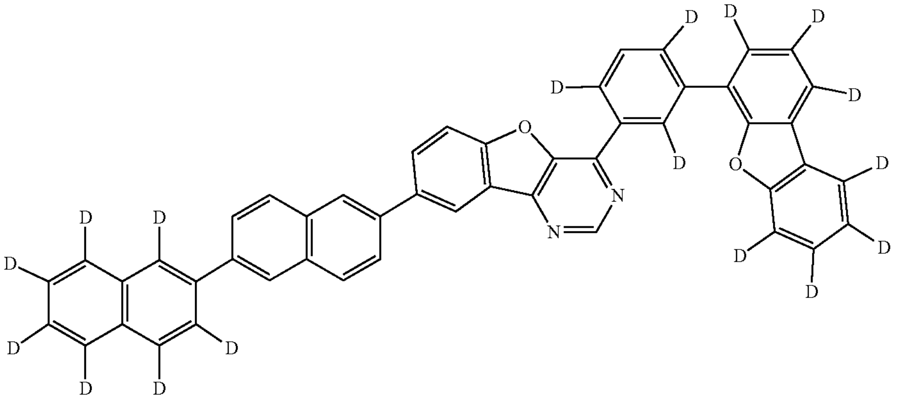
(221)
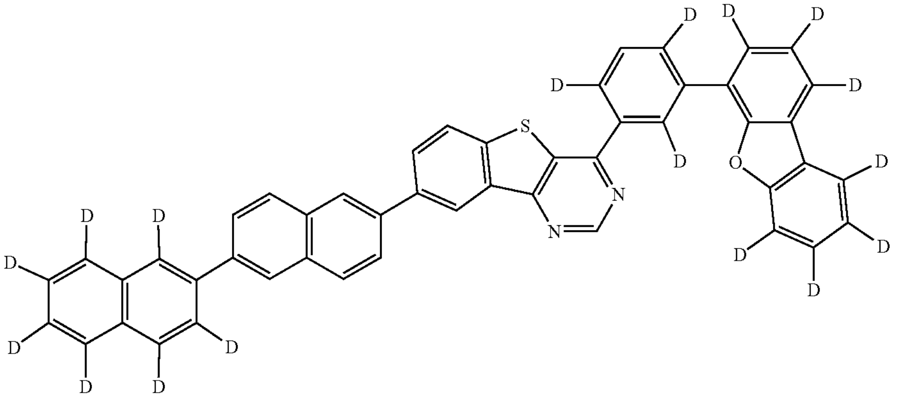

-continued
(222)
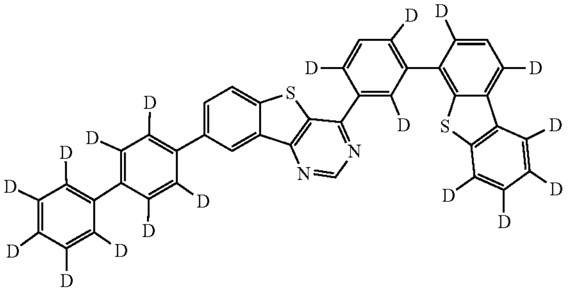
(223)
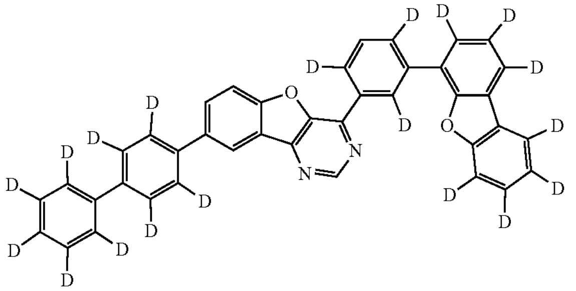
(224)
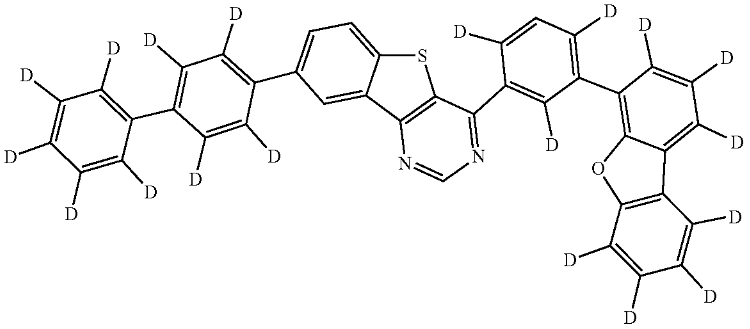
(225)
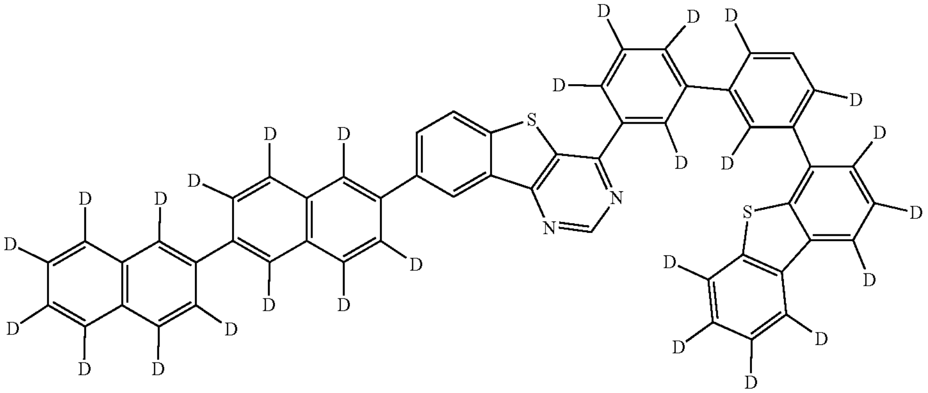
[Chemical Formula 45]
(226)
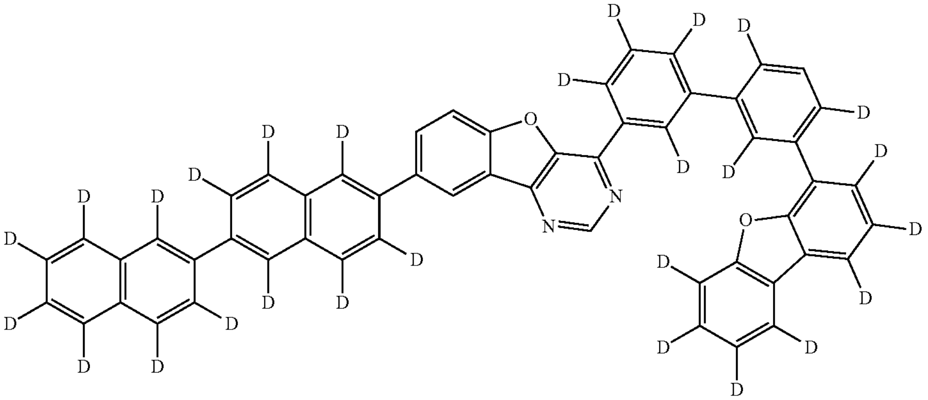

-continued
(224)
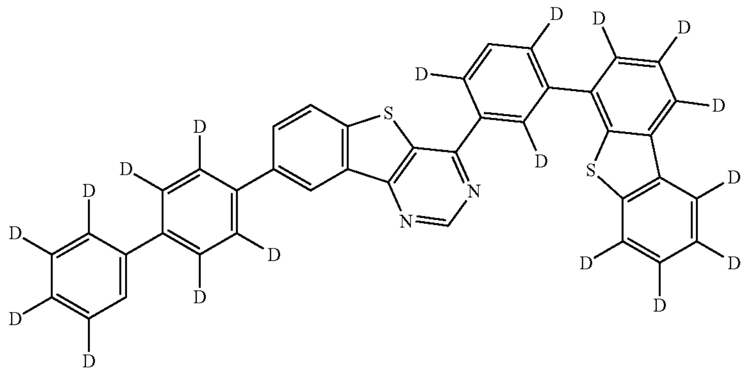
(227)
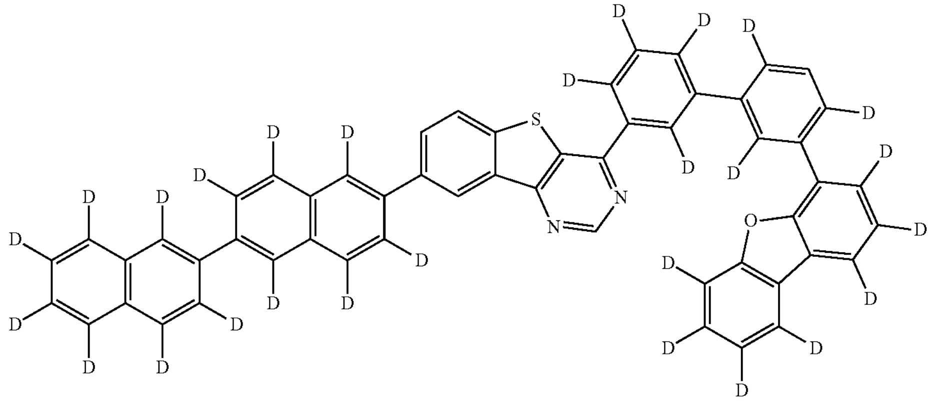
(228)
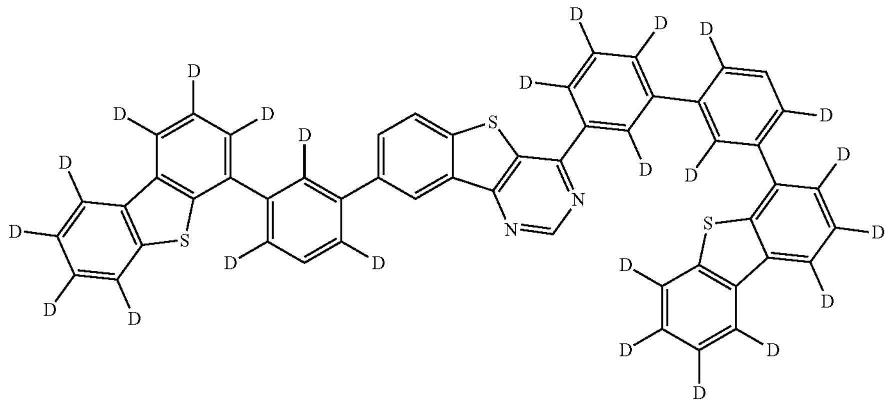
(229)
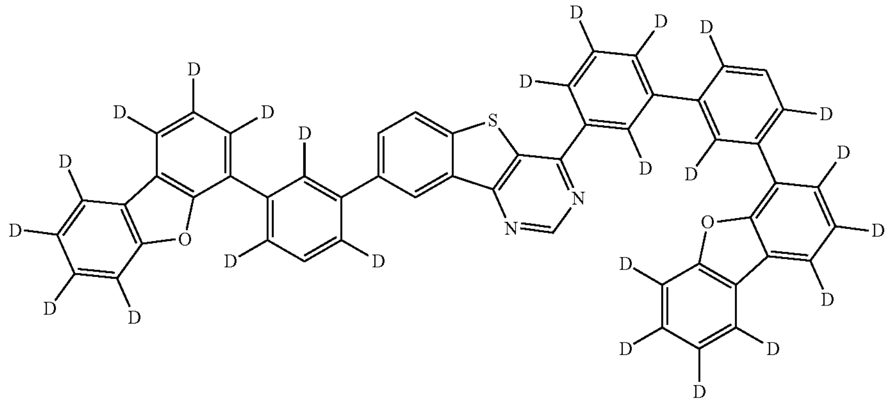

-continued
(230)
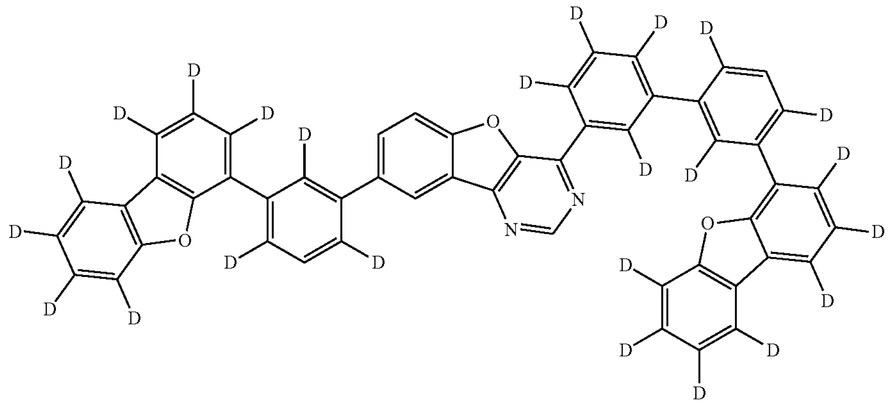
(231)
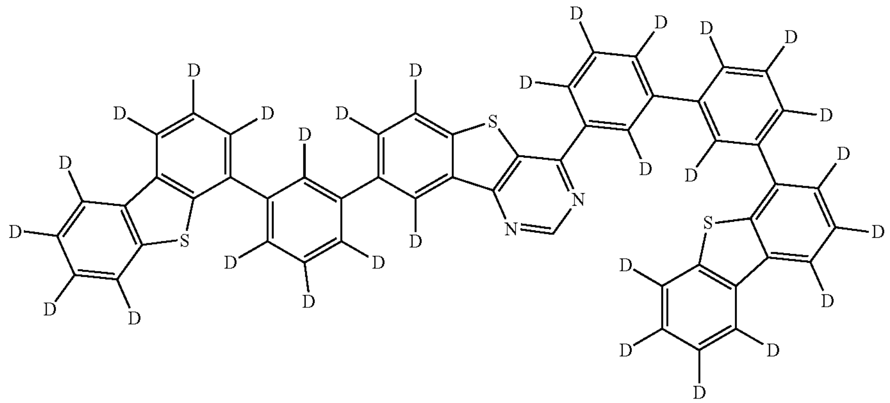
(232)
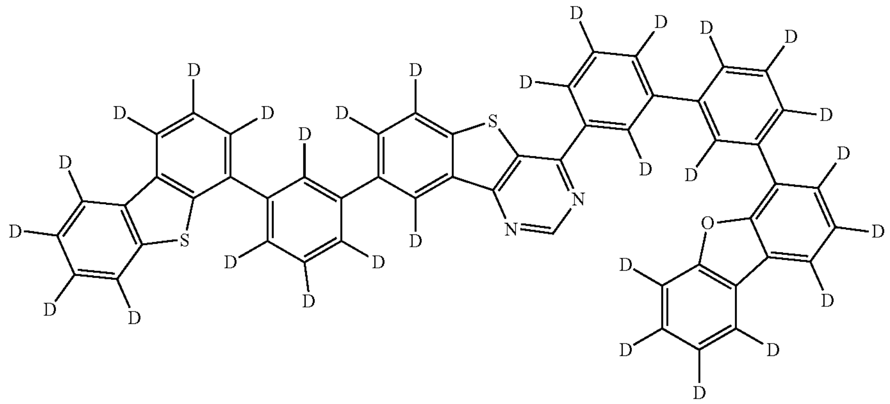
[Chemical Formula 46]
(234)
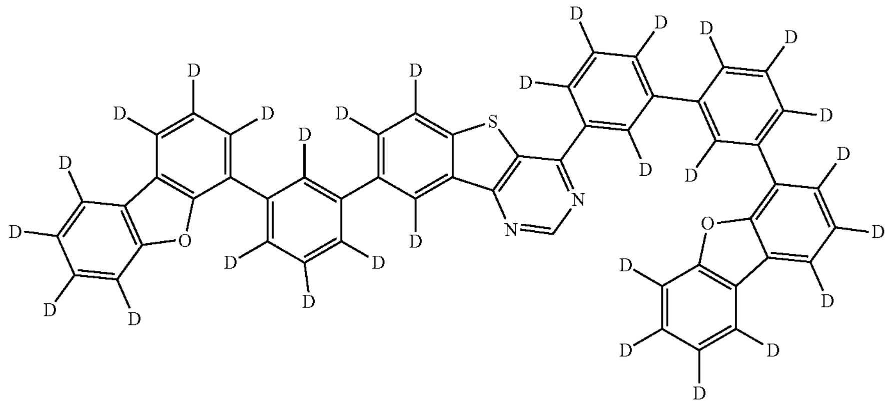

-continued
(235)
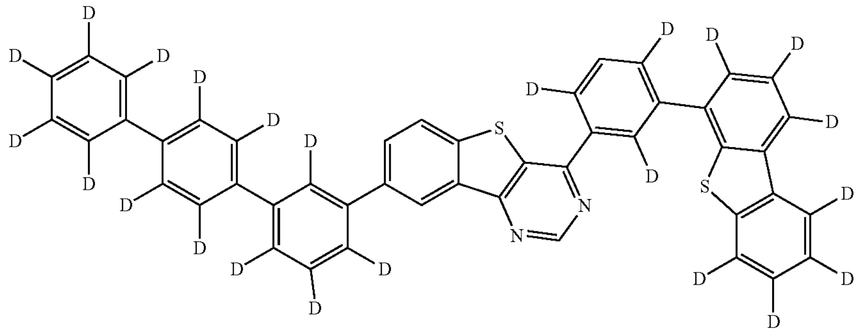
(236)
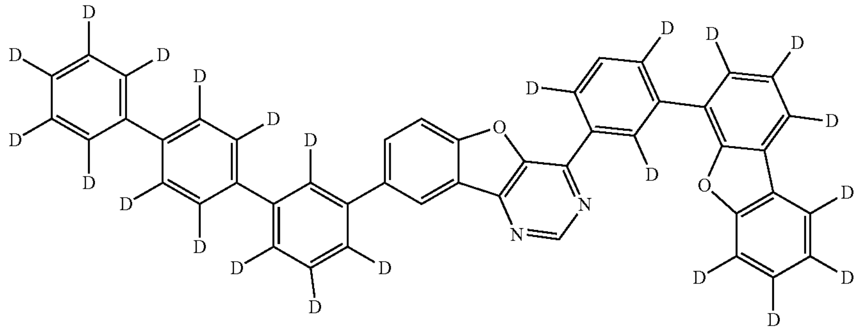
(237)
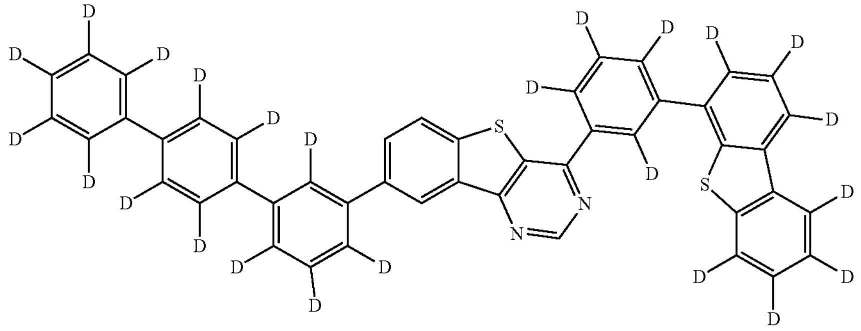
(238)
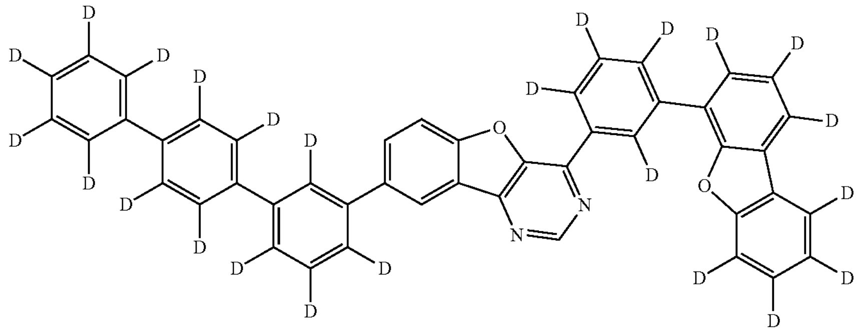

-continued
(239)
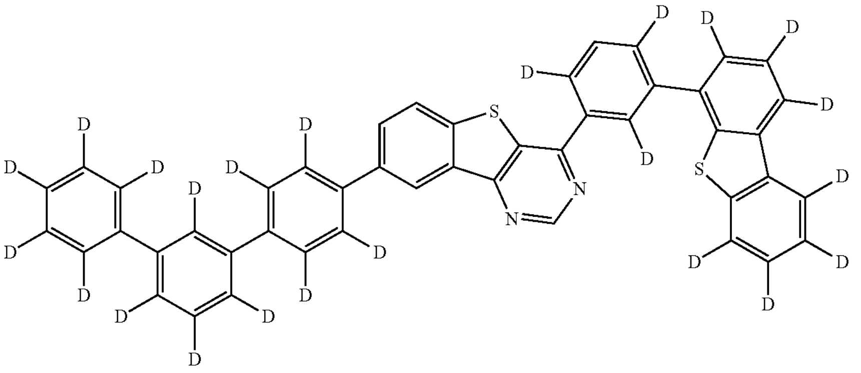
(240)
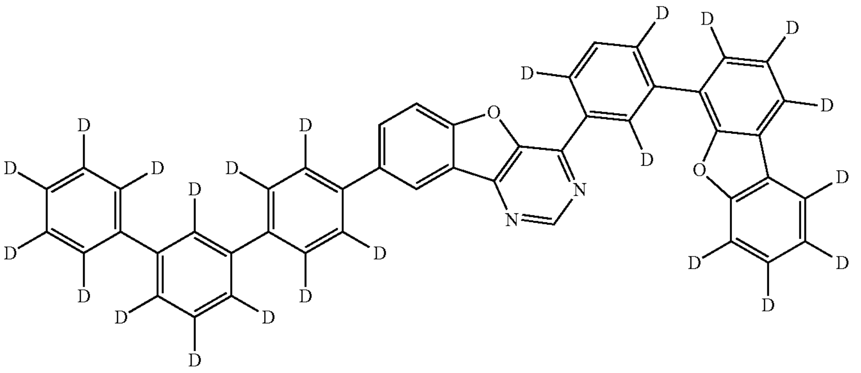
[0150]
[Chemical Formula 47]
(241)
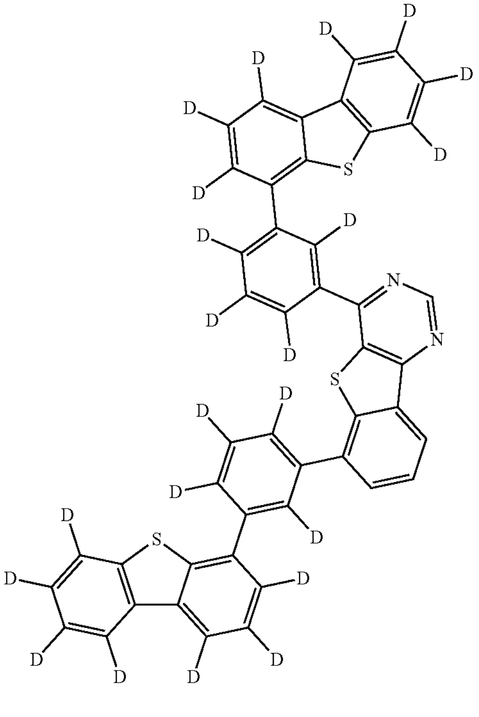
(242)
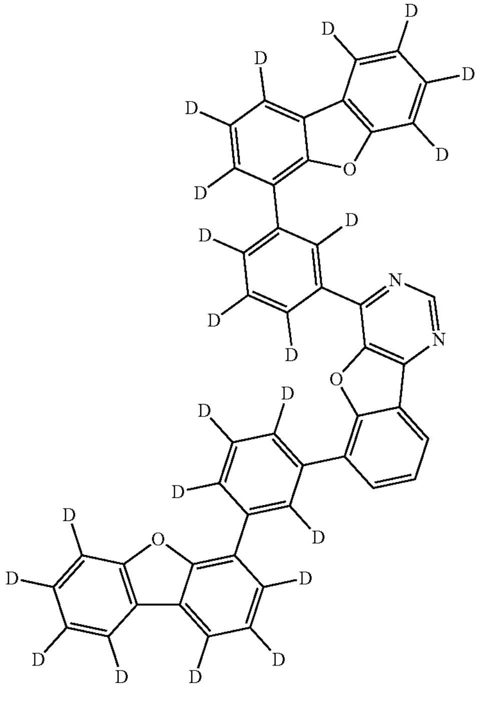

-continued
(243)
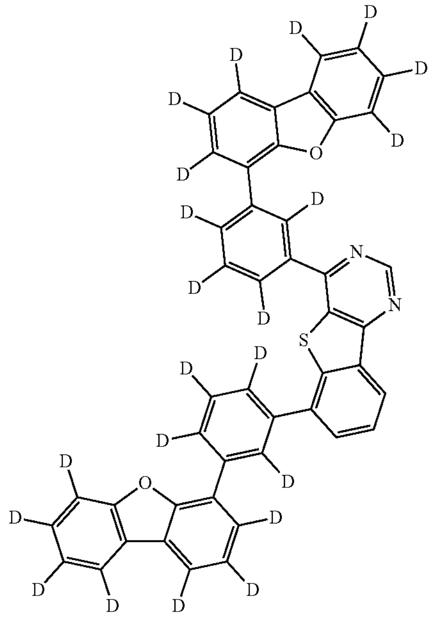
(244)
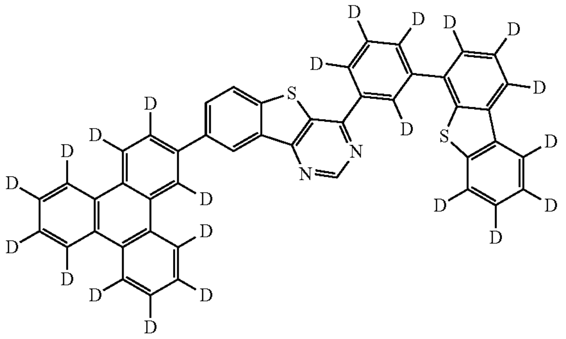
(245)
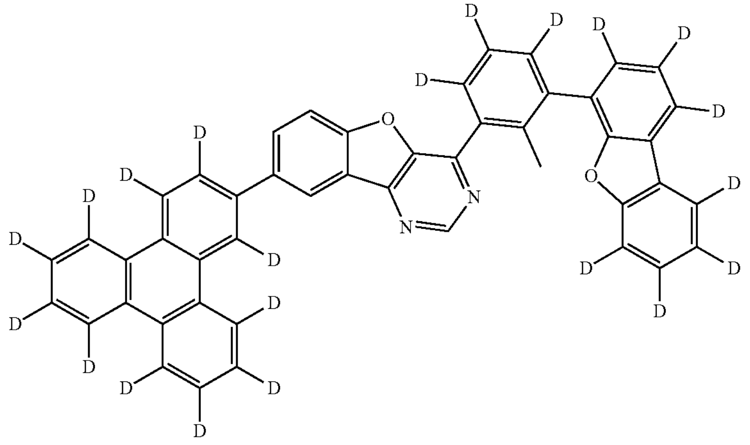

-continued
(246)
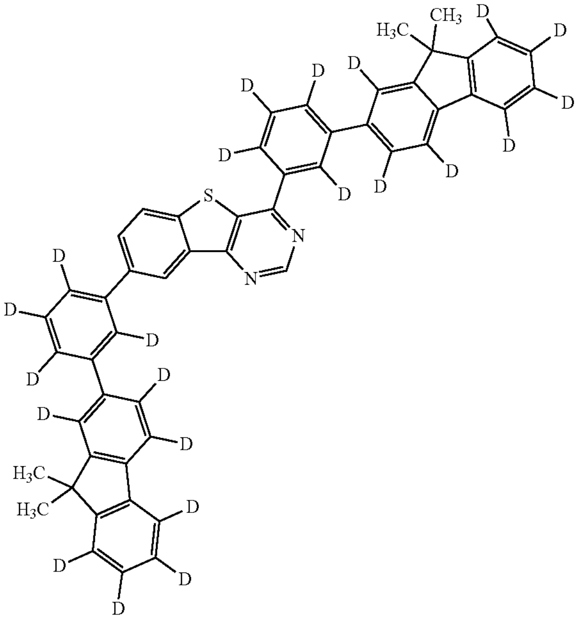
(247)
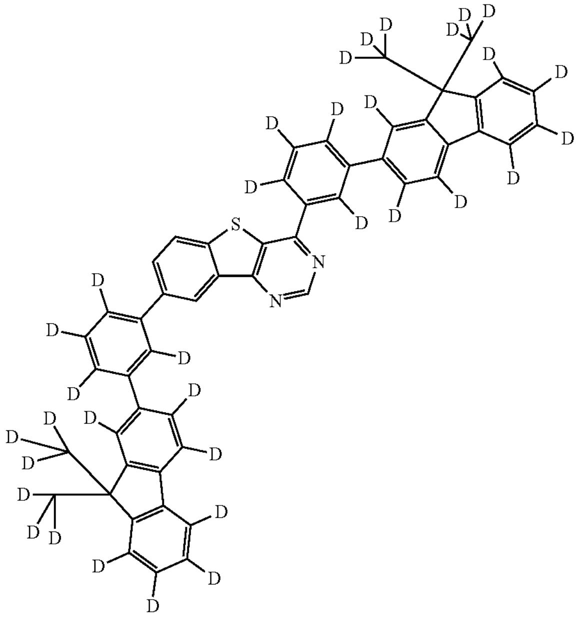
[Chemical Formula 48]
248
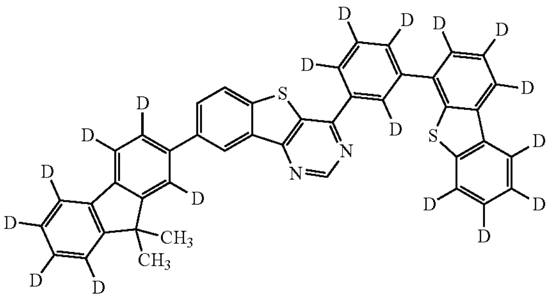
-continued
249
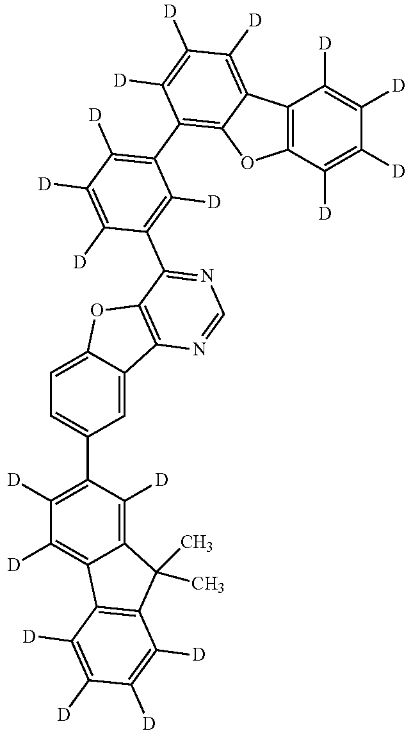

-continued
250
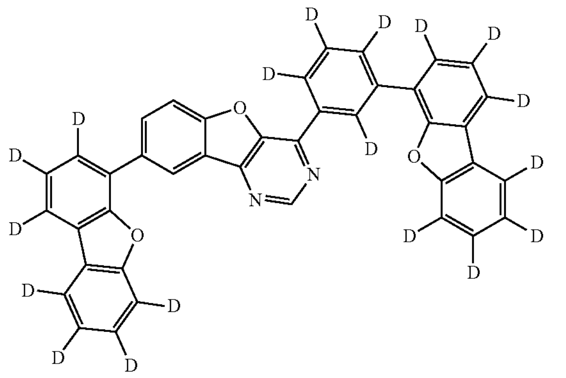
251
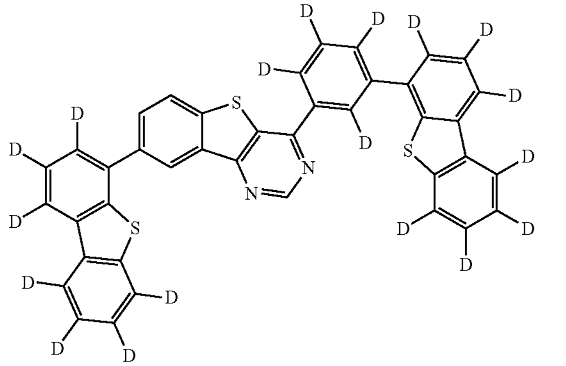
252
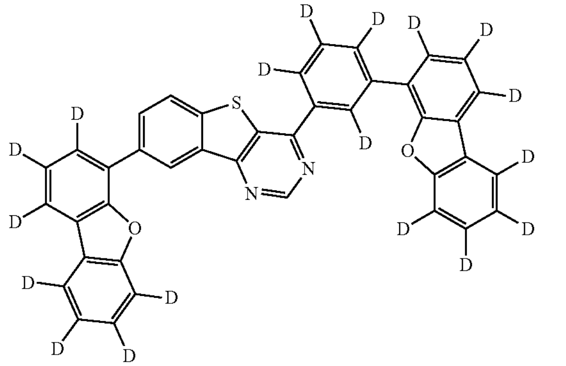
253
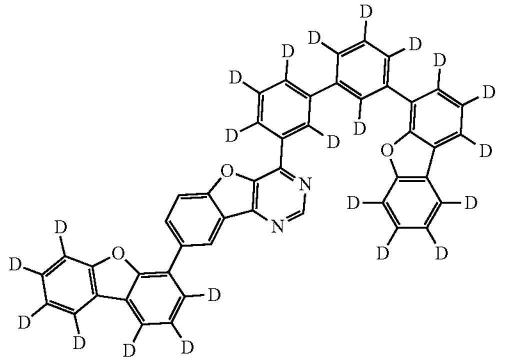
-continued
254
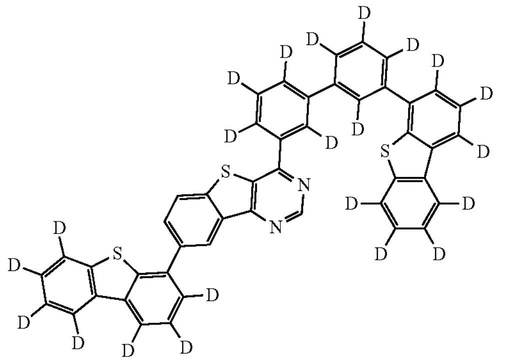
255
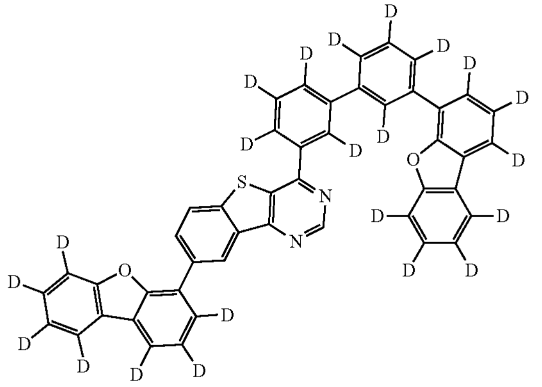
256
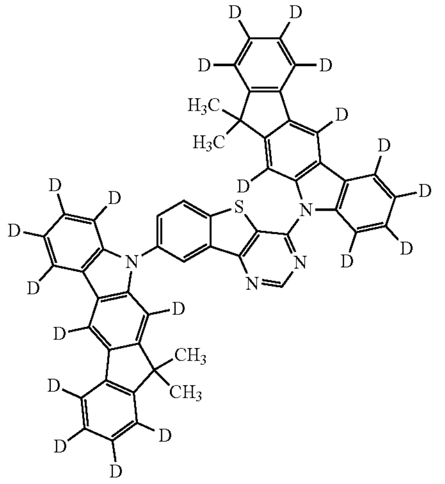

[Chemical Formula 49]
257
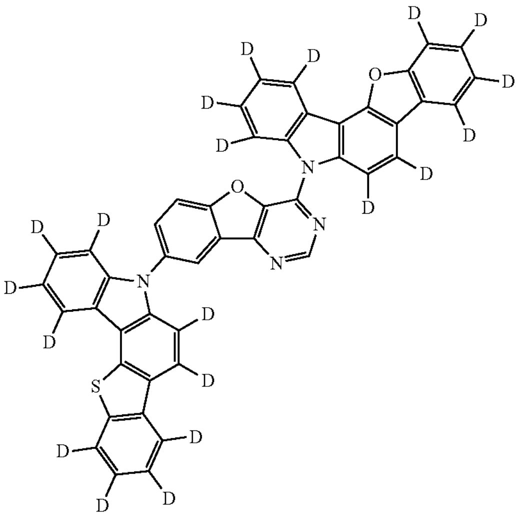
258
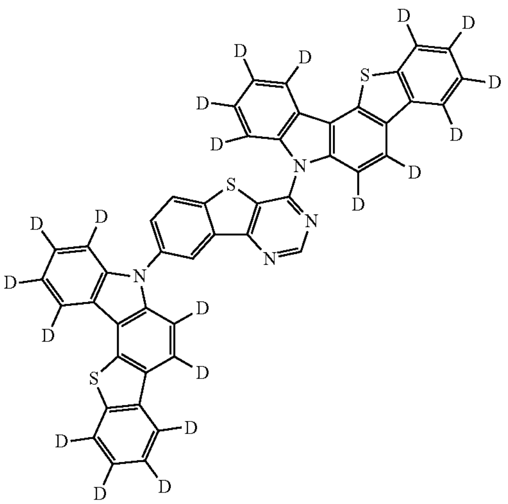
259
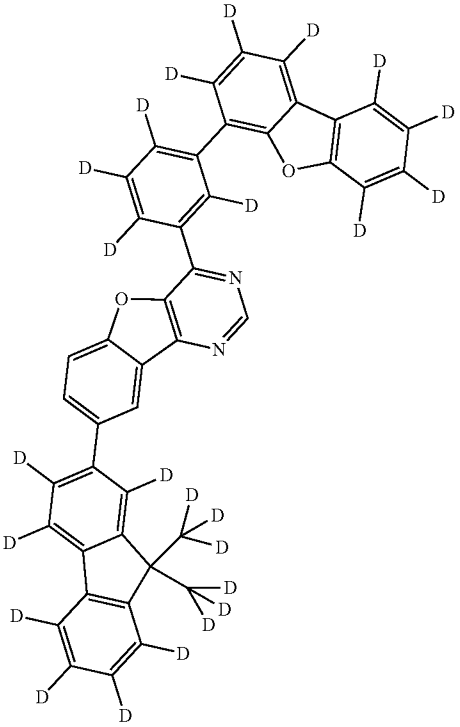
260
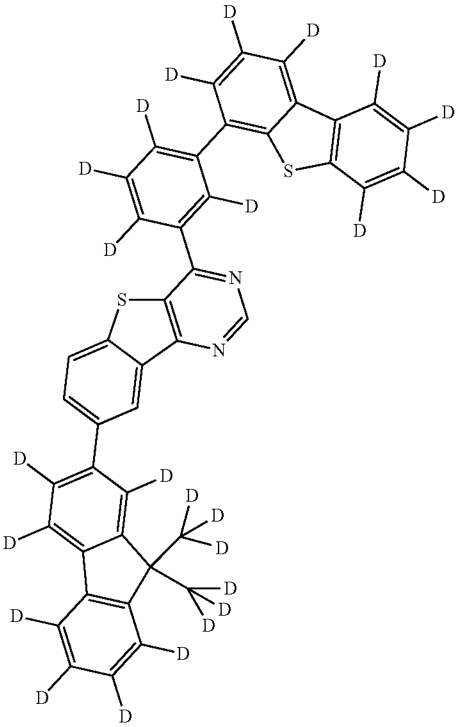

-continued
261
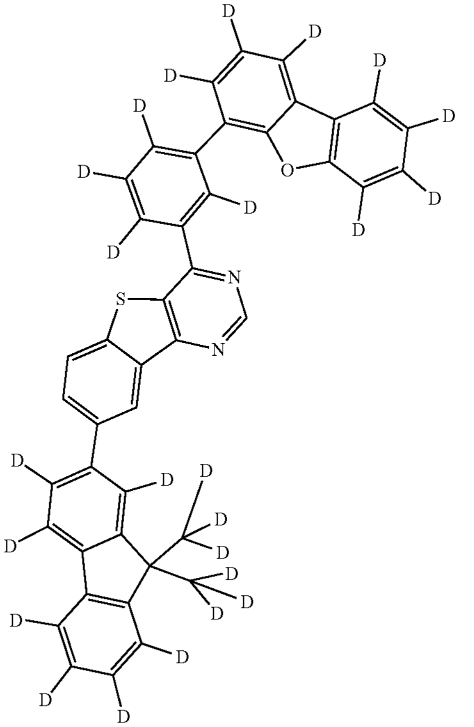
262
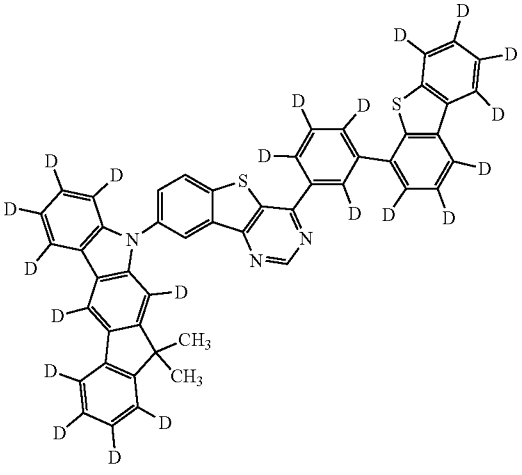
-continued
263
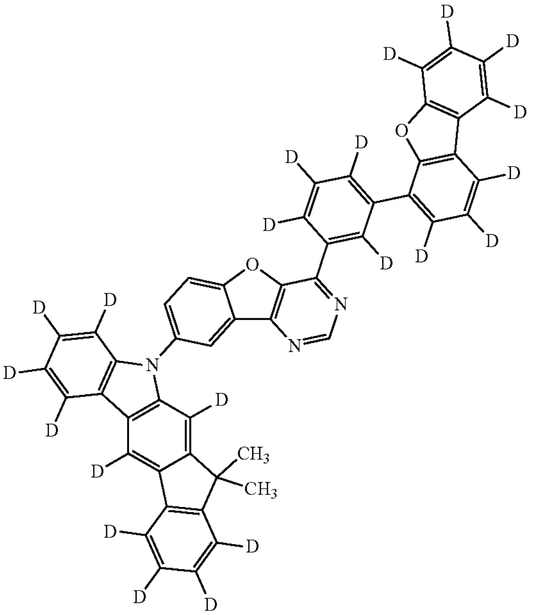
264
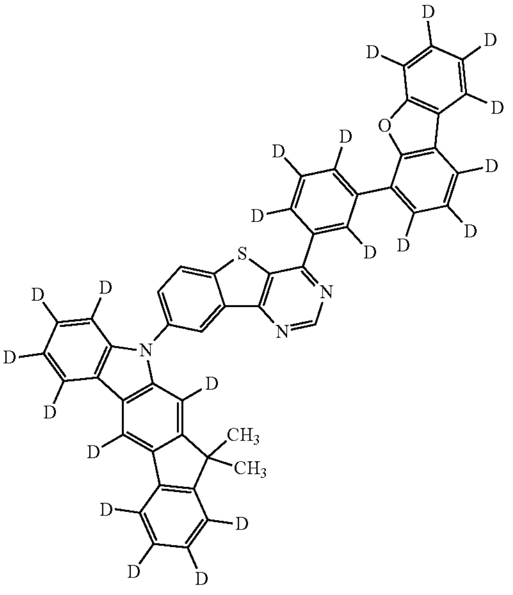
[Chemical Formula 50]
265
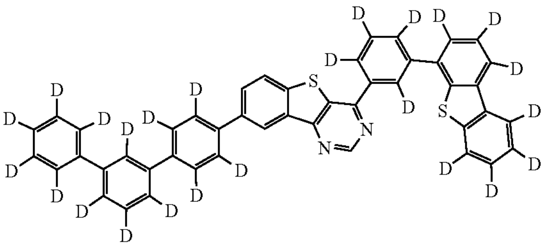

-continued
266
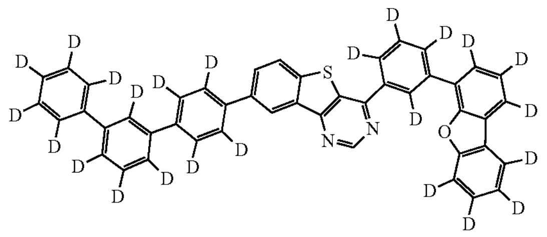
267
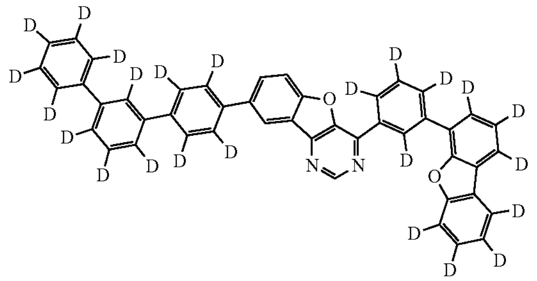
268
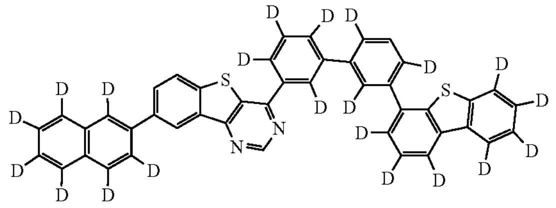
269
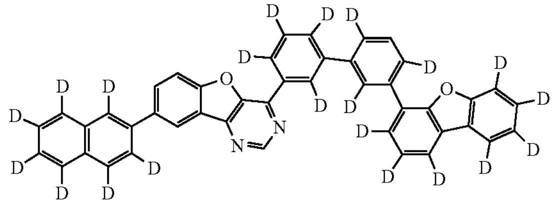
-continued
270
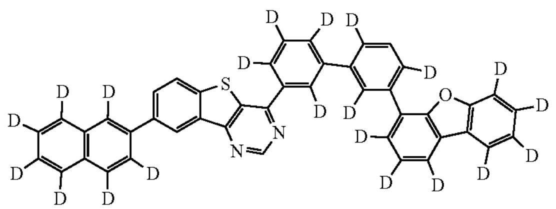
271
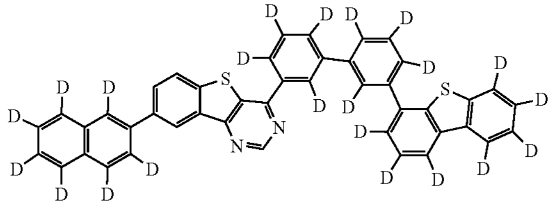
272
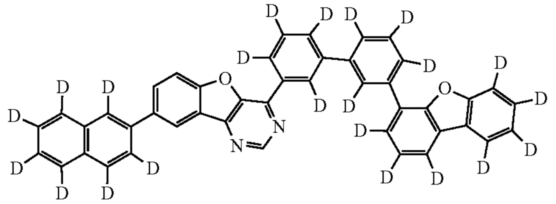
[Chemical Formula 51]
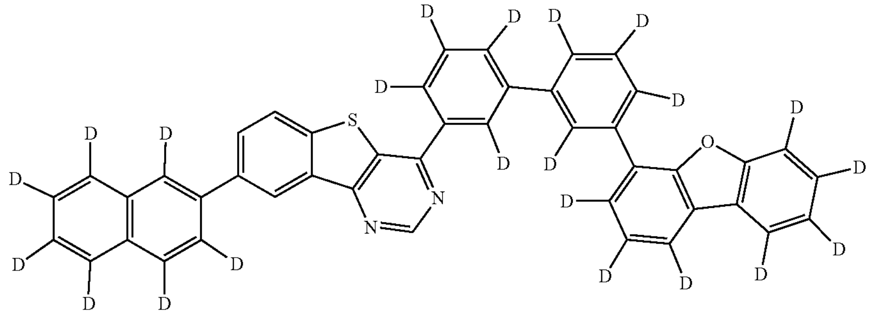

-continued
(274)
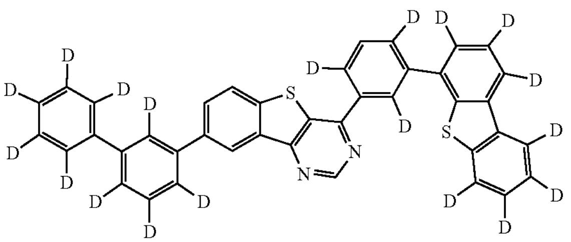
(275)
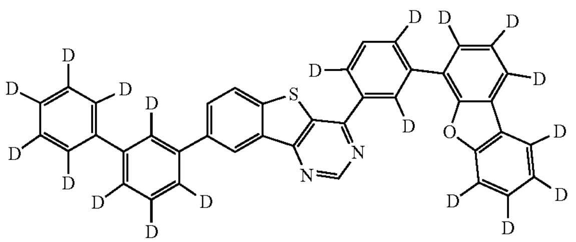
(276)
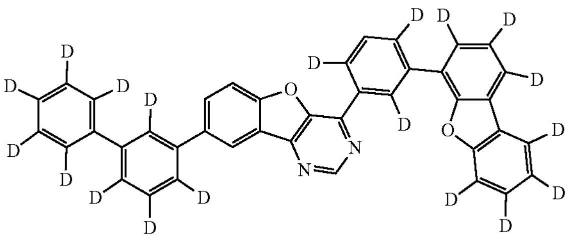
(277)
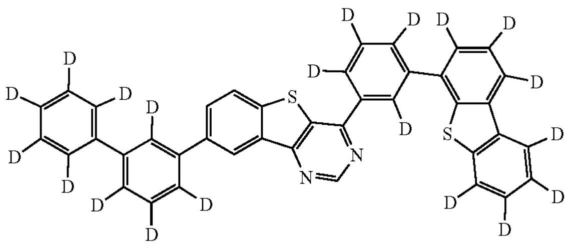
(278)
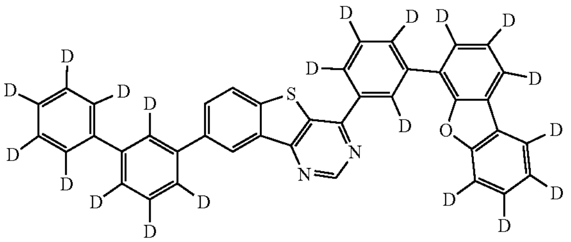
(279)
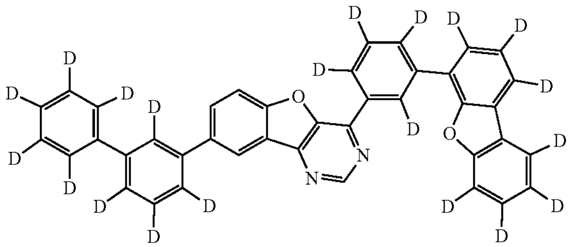
(280)
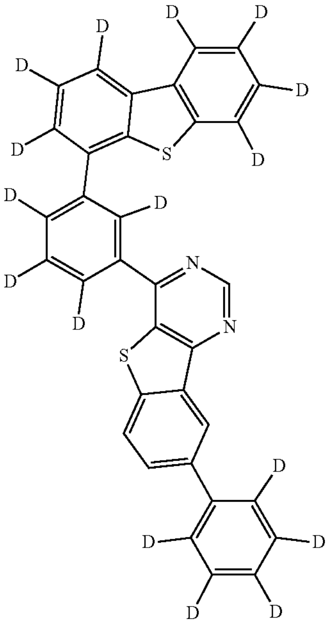
(281)
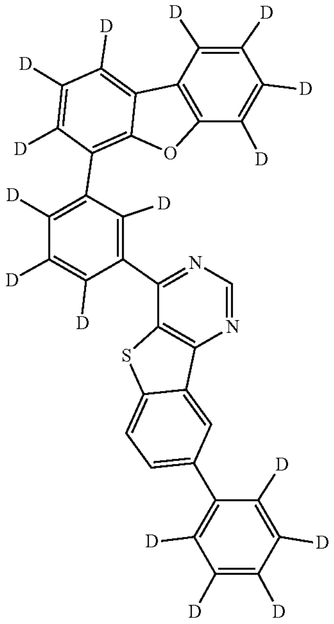

-continued
(282)
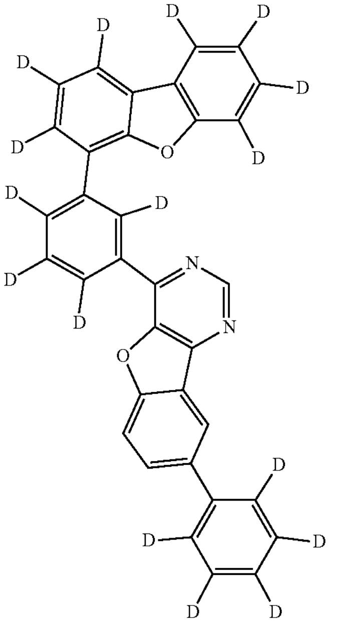
(283)
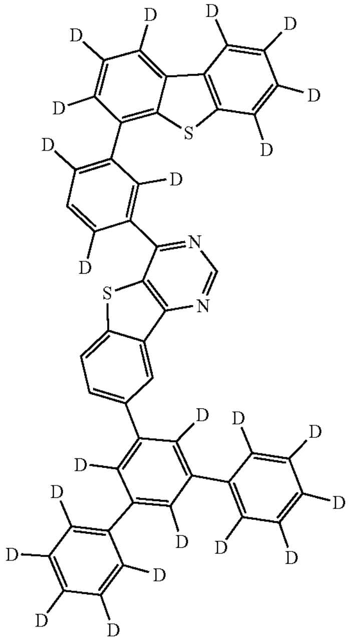
[Chemical Formula 52]
(284)
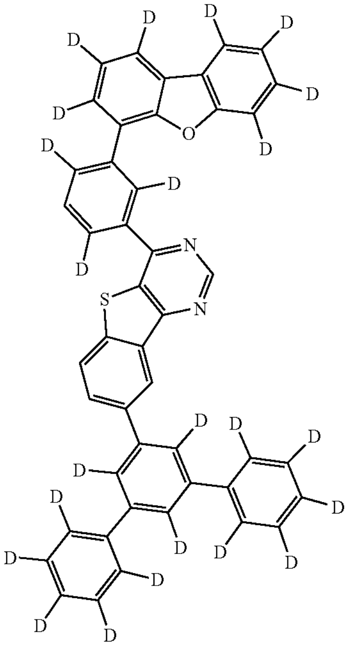
(285)
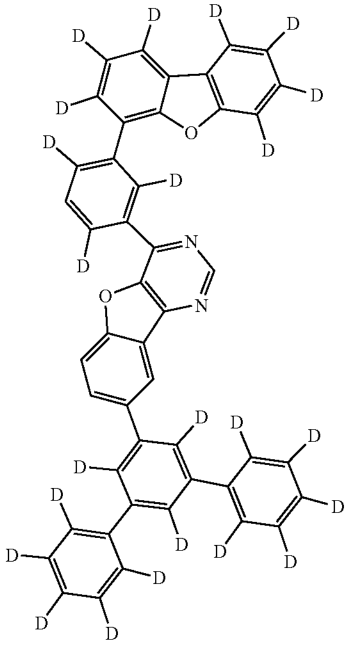
(286)
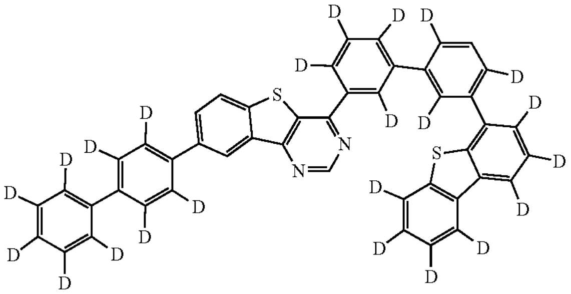
(287)
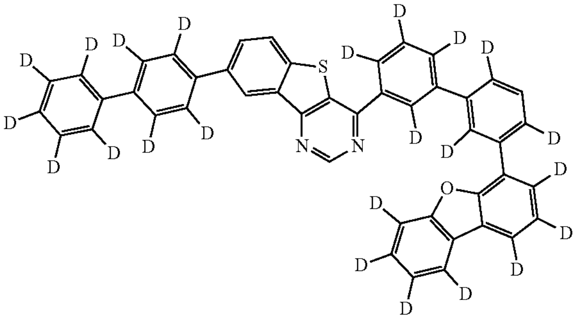

-continued
(288)
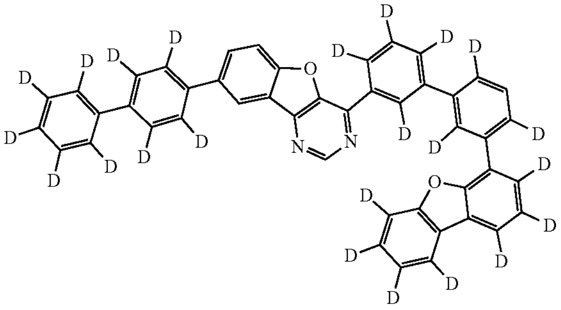
(289)
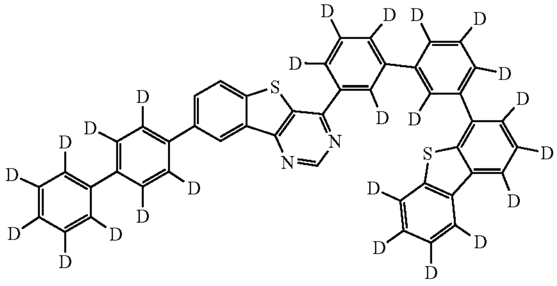
(290)
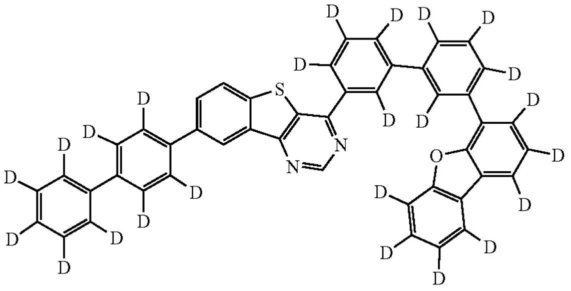
(291)
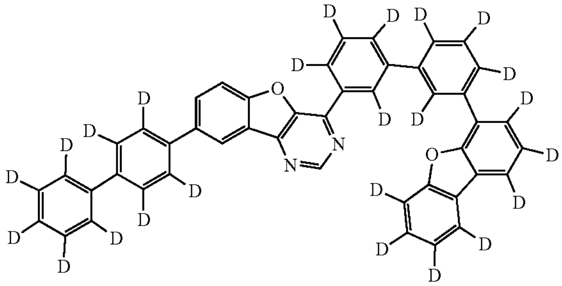
[Chemical Formula 53]
(292)
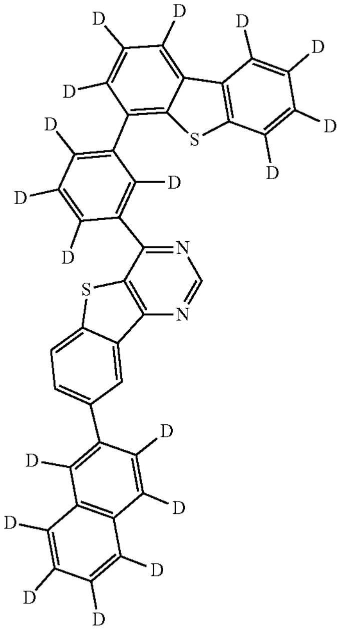
(293)
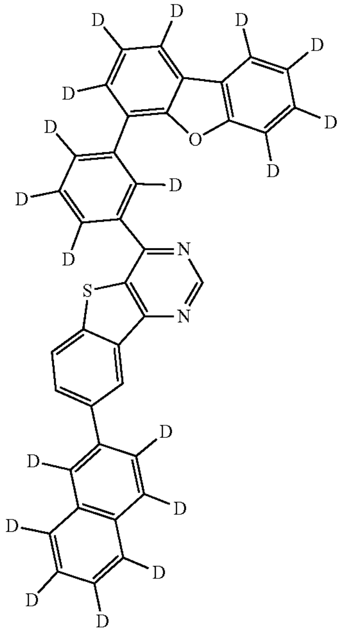

-continued
(294)
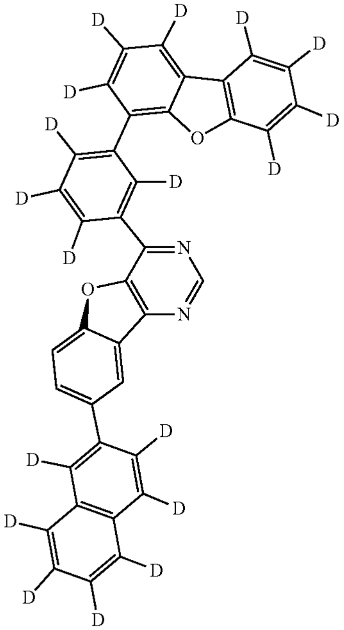
(295)
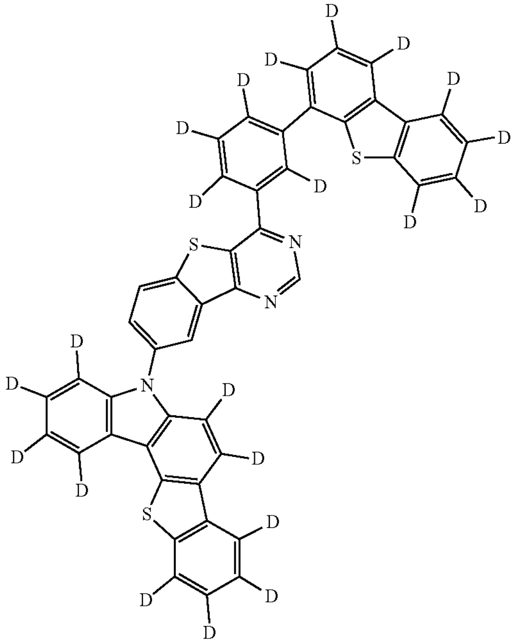
(296)
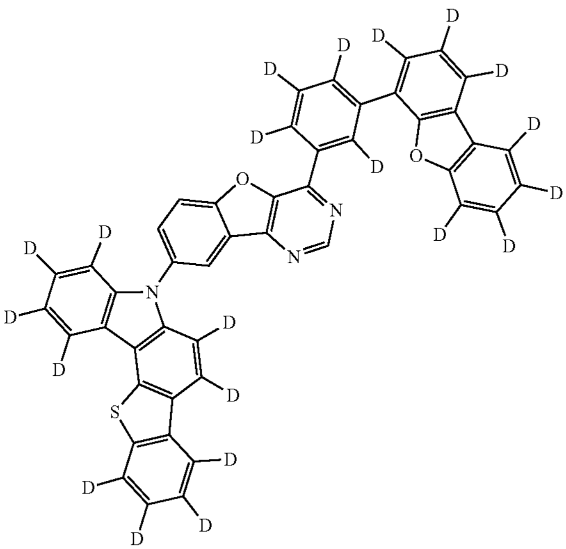
(297)
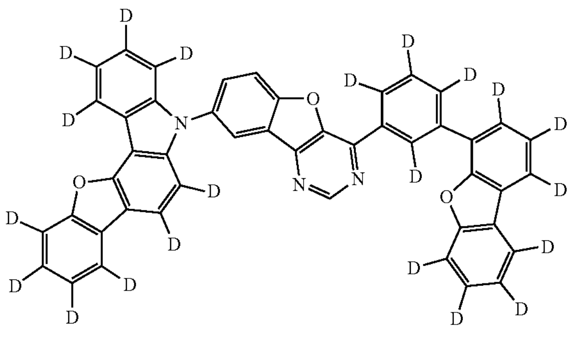

-continued
(298)
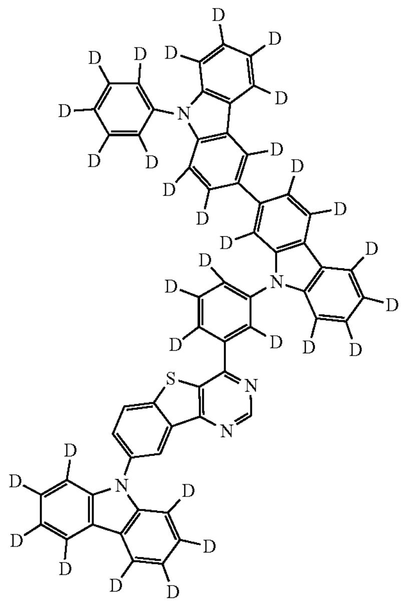
(299)
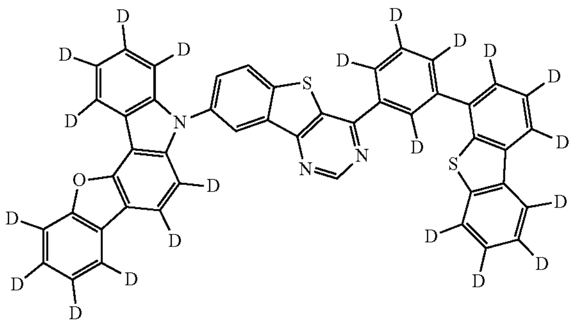
(300)
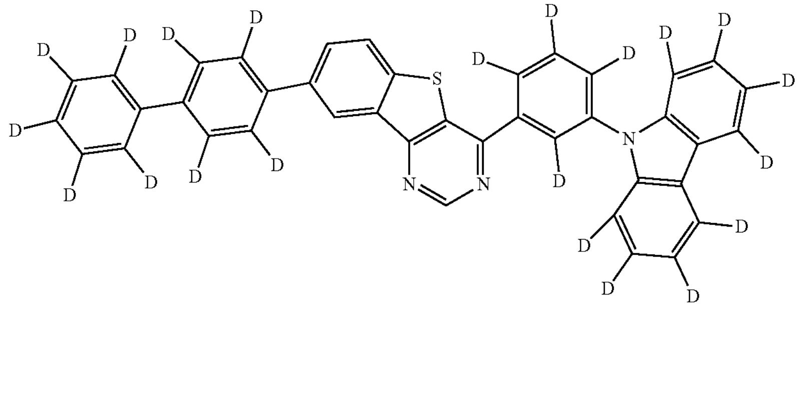

[Chemical Formula 54]
(301)
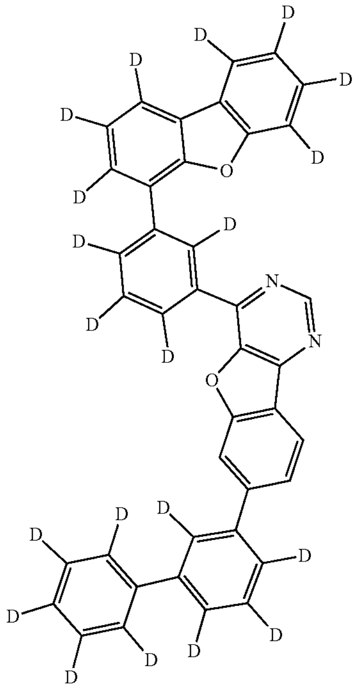
(302)
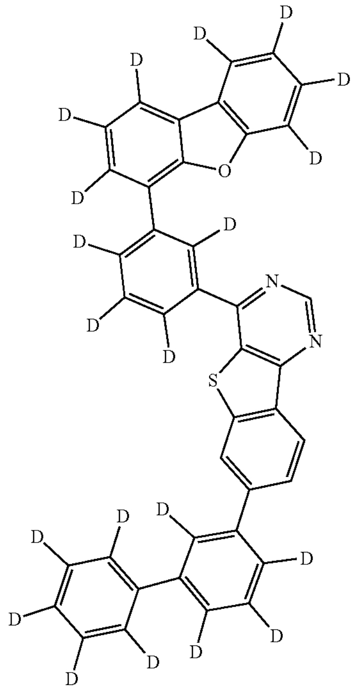
-continued
(303)
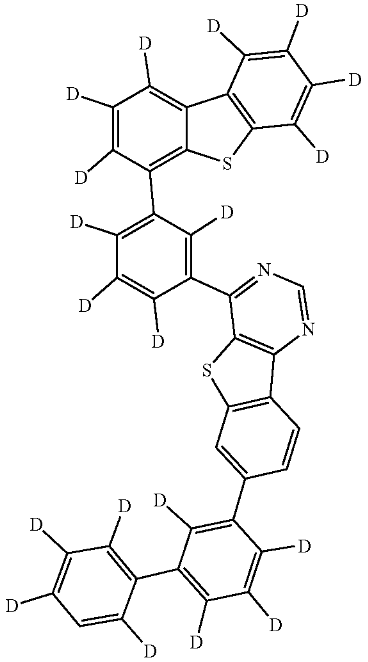
(304)
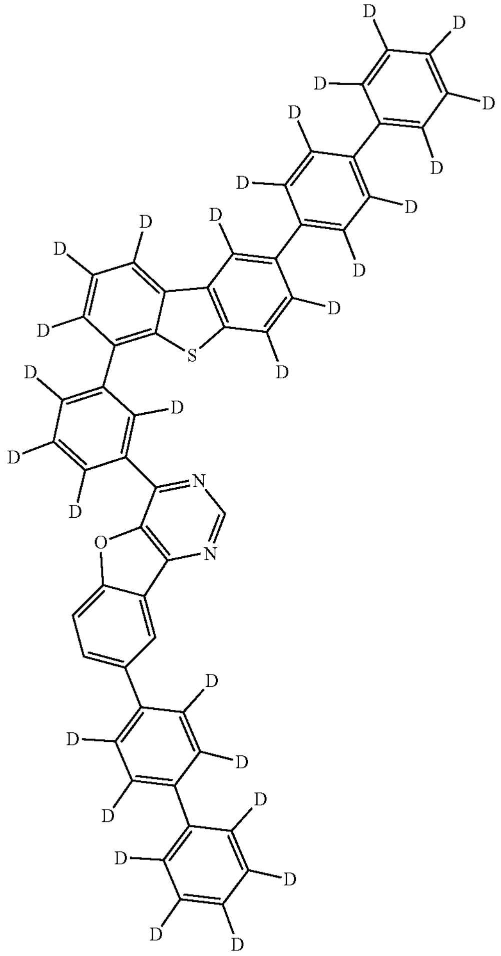

-continued
(305)
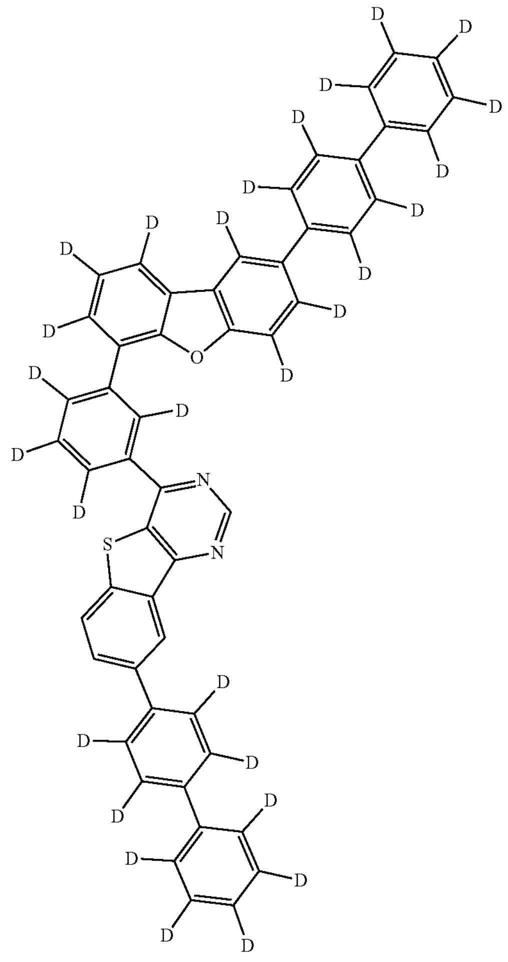
-continued
(306)
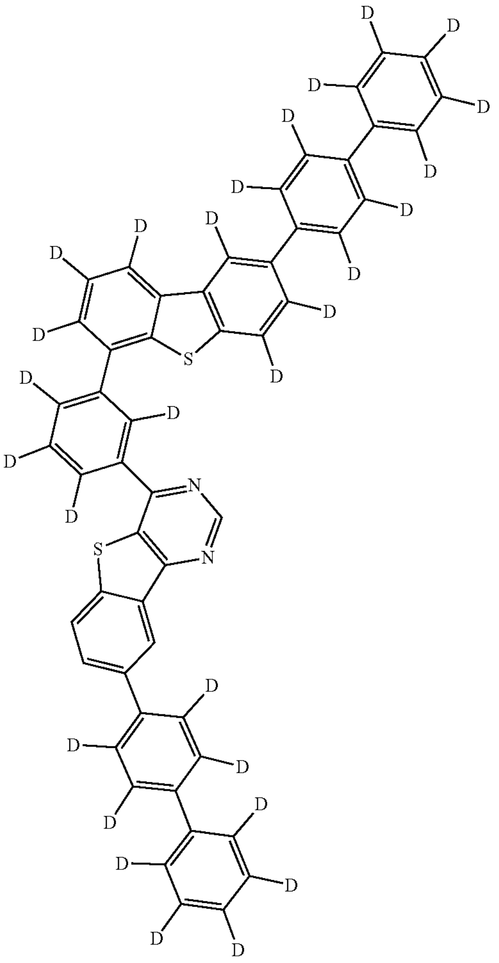

-continued
(306)
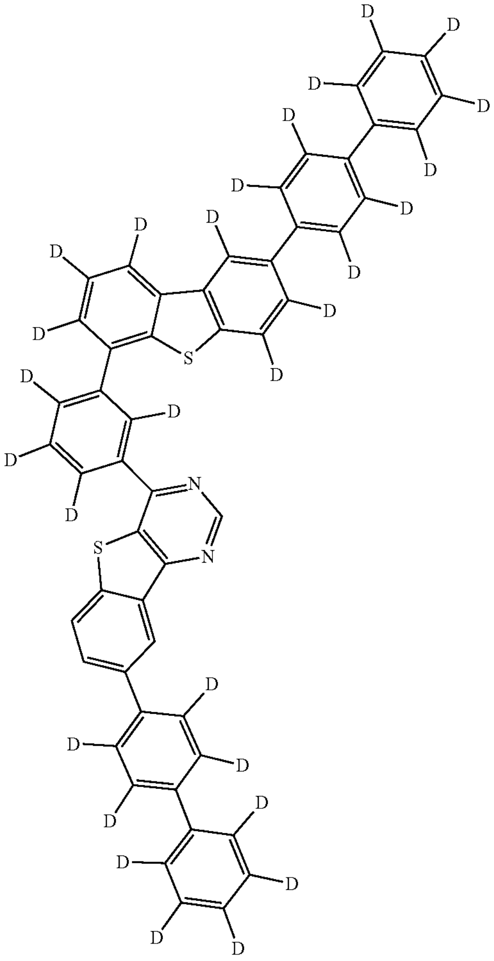
(307)
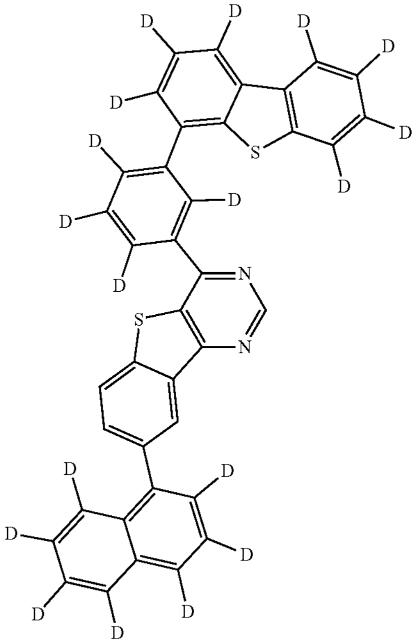
(308)
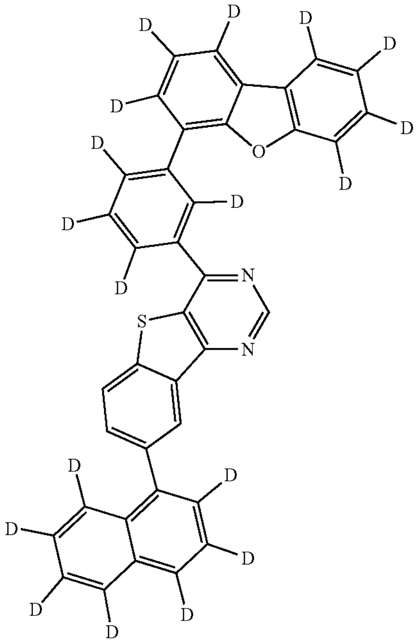
(309)
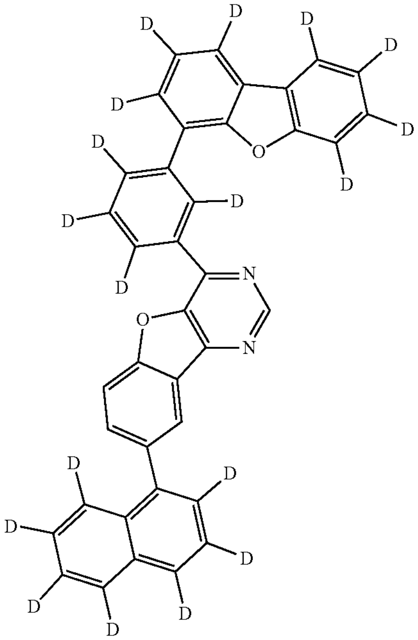

-continued
[Chemical Formula 55]
(310)
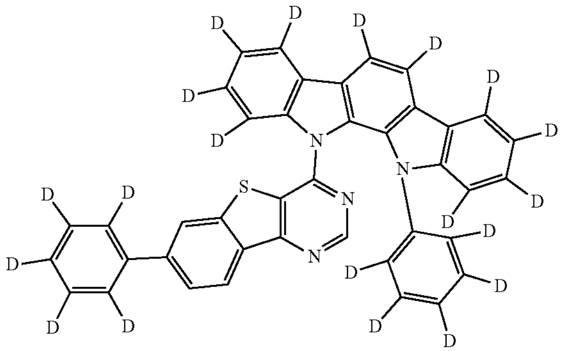
(311)
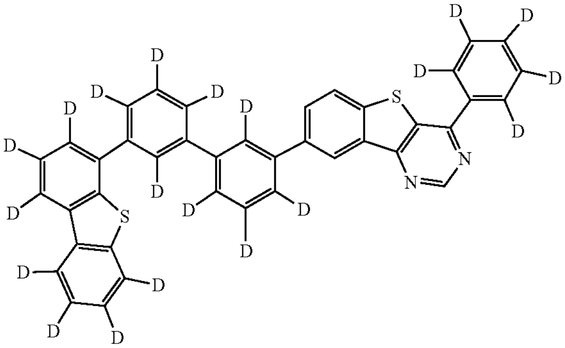
(312)
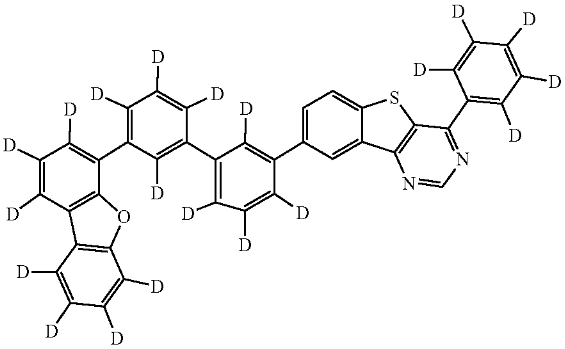
(313)
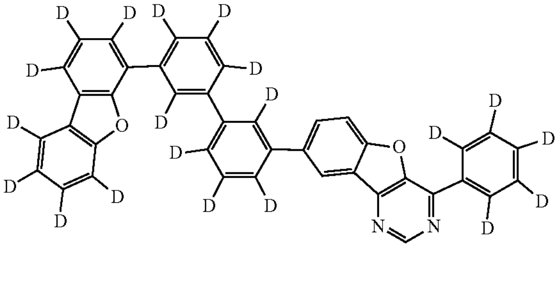
-continued
(314)
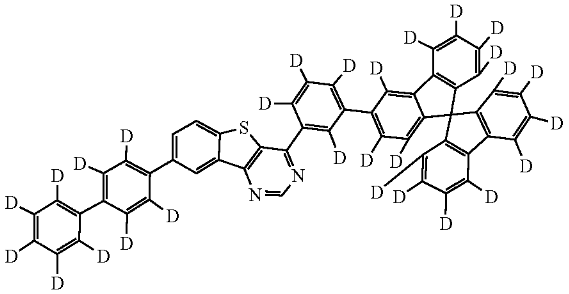
(315)
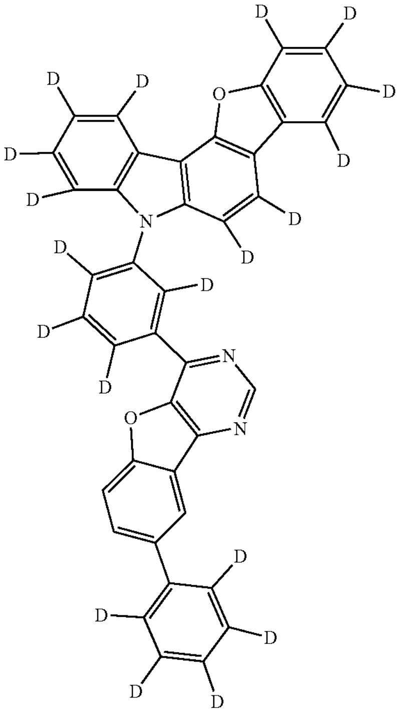

-continued
(316)
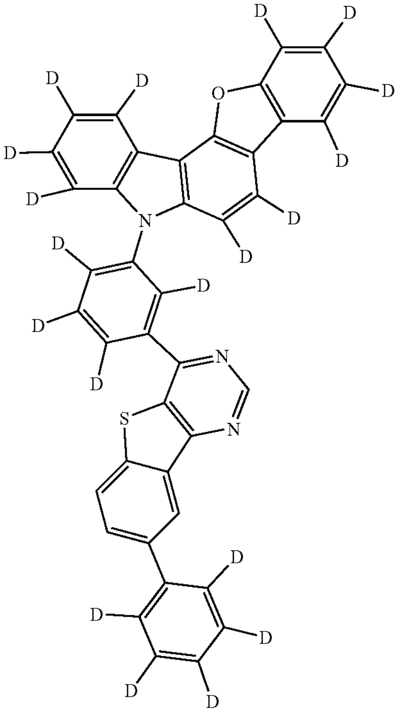
(317)
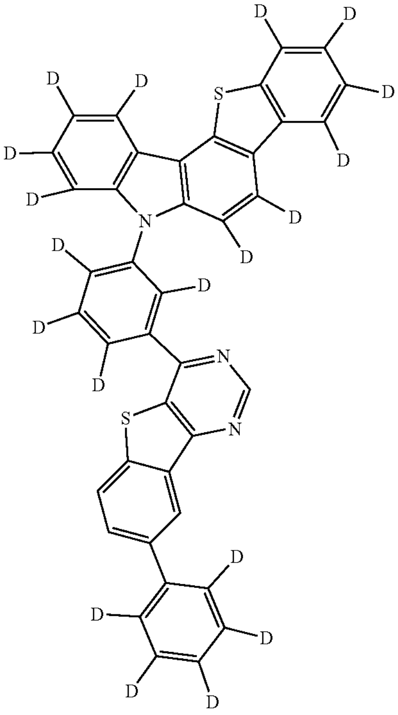
-continued
[Chemical Formula 56]
(318)
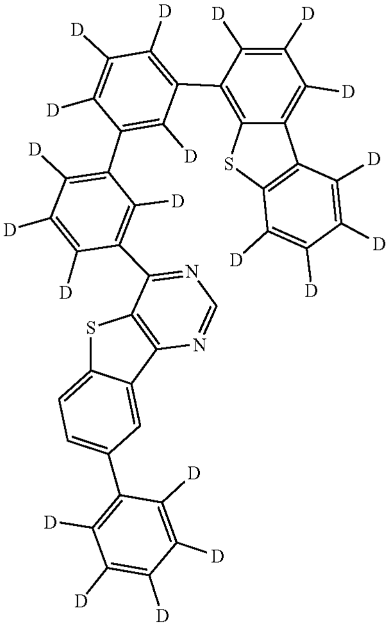
(319)
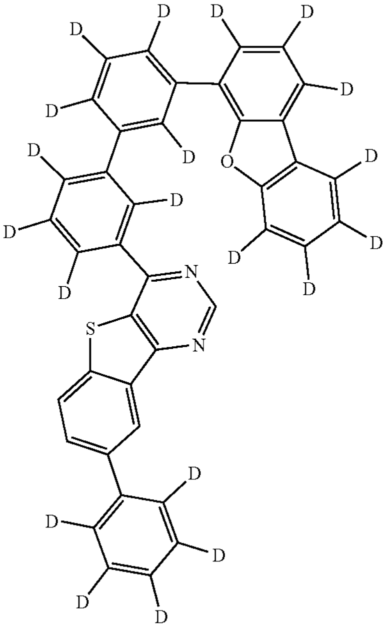

-continued
(320)
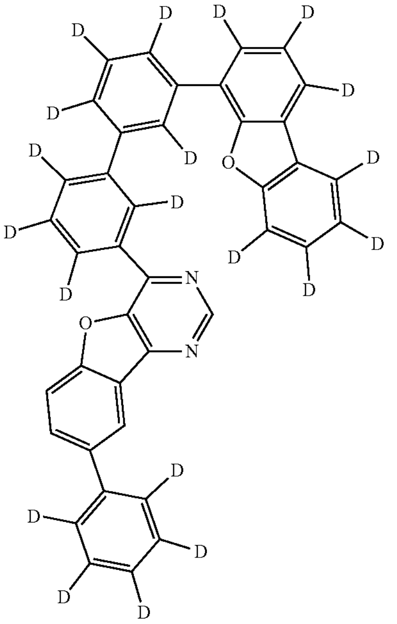
(321)
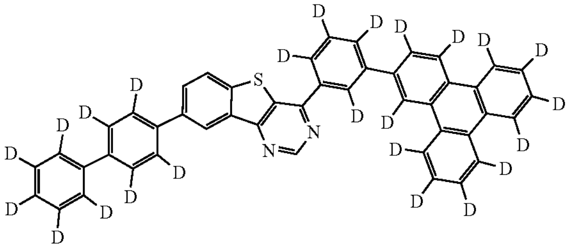
(322)
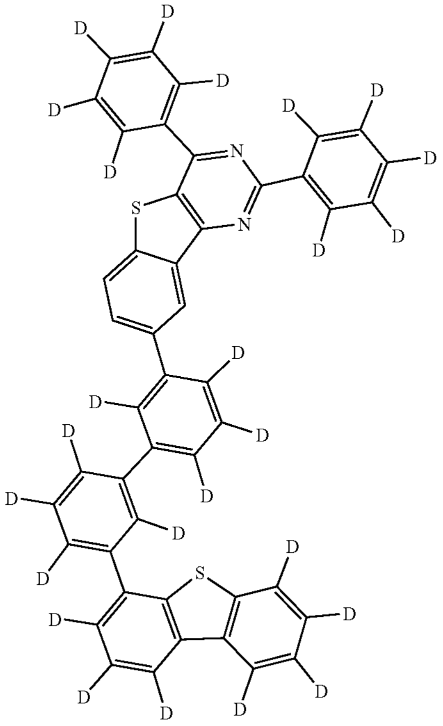
-continued
(323)
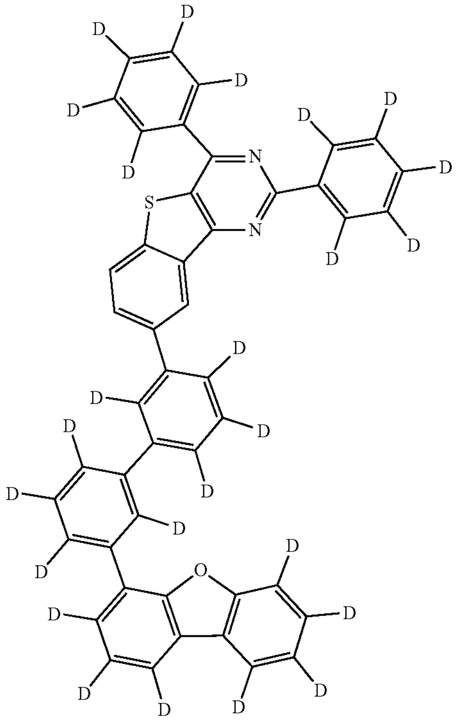
(324)
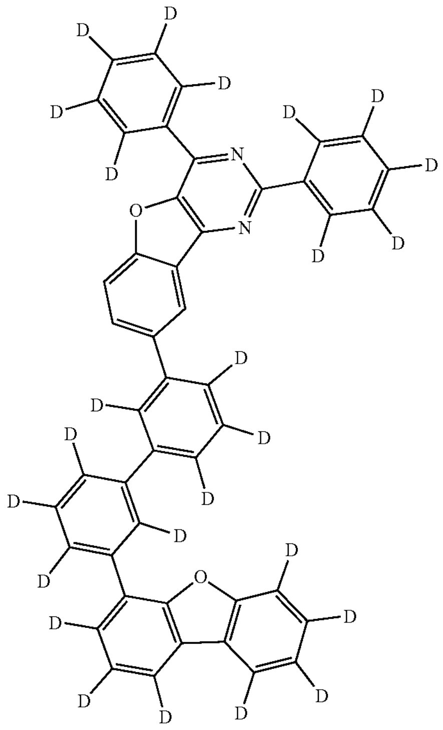

[chemical Formula 57]
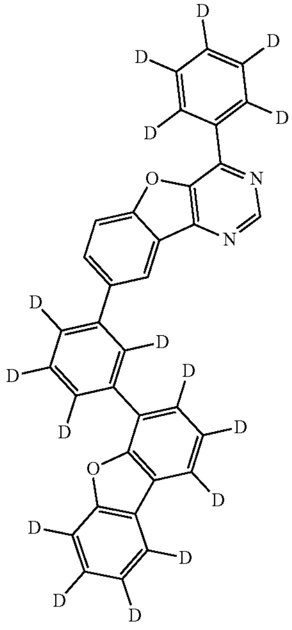
(325)
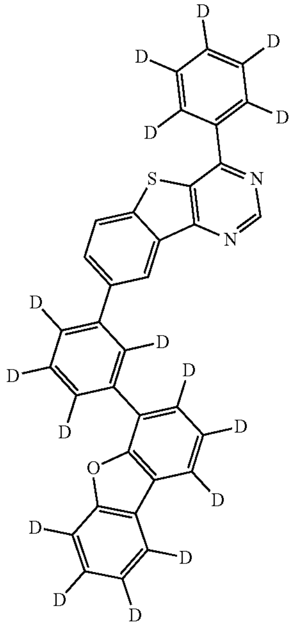
(326)
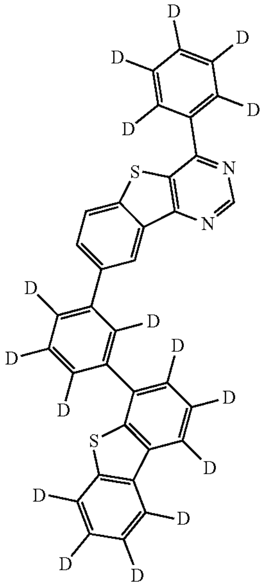
(327)
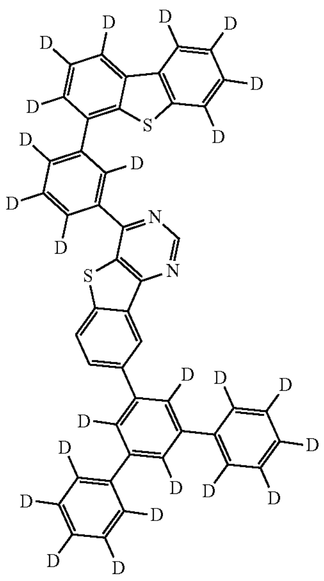
(328)

-continued
(329)
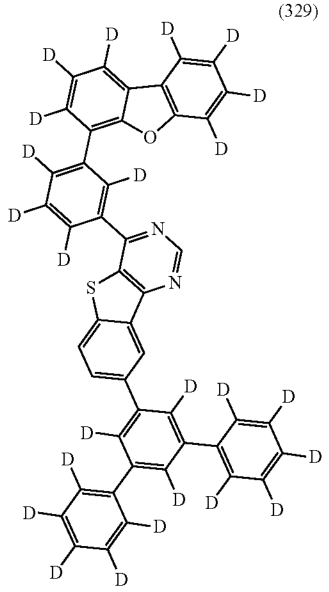
(330)
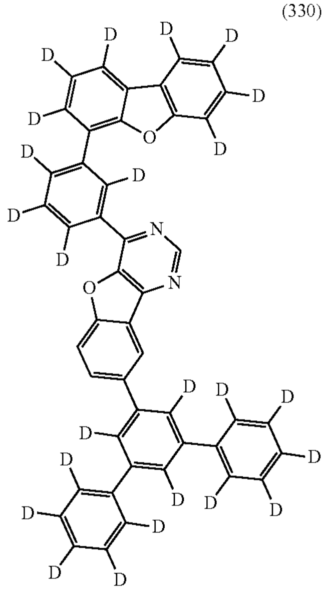
(331)
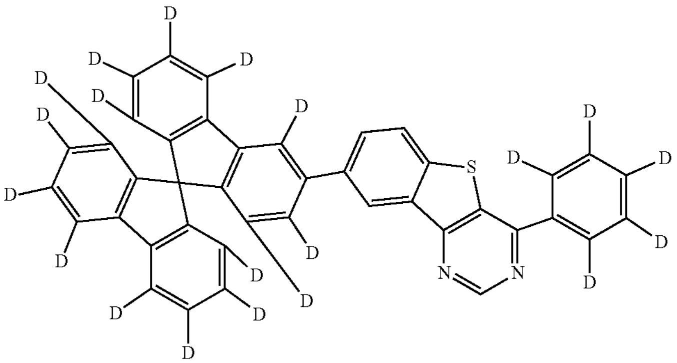
[Chemical Formula 58]
(332)
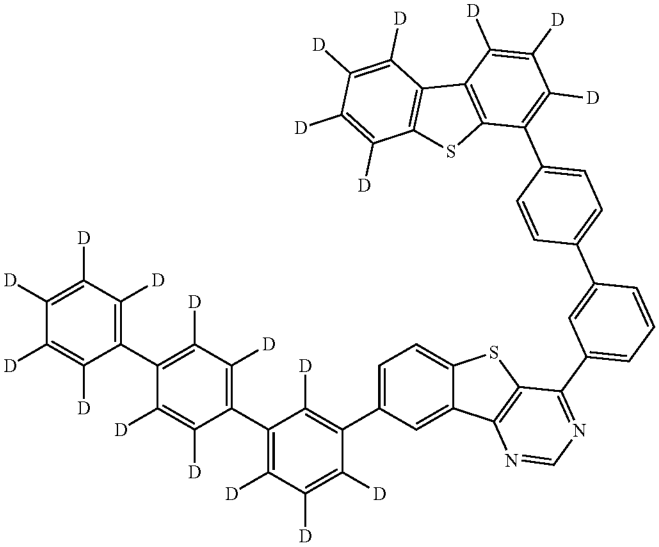

-continued
(333)
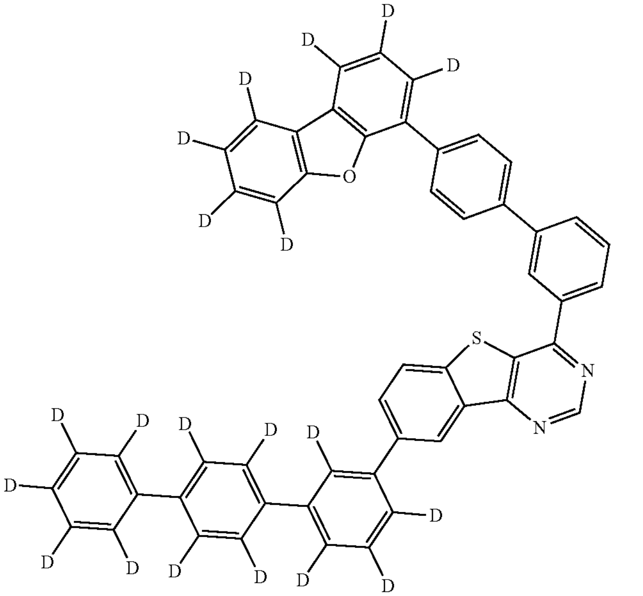
(334)
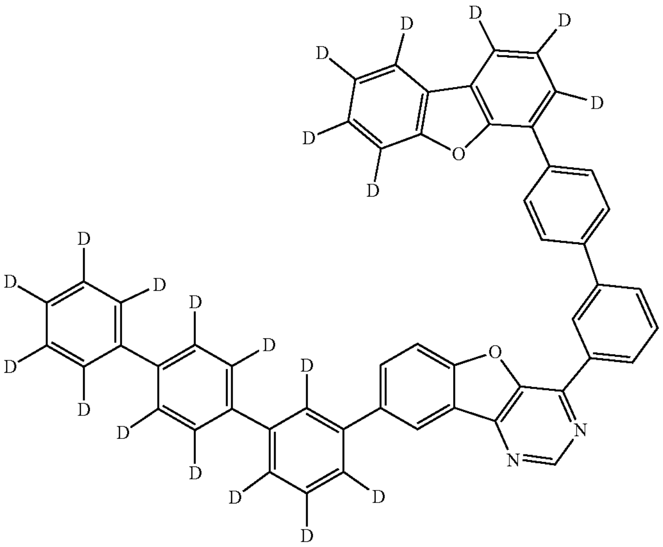

-continued
(335)
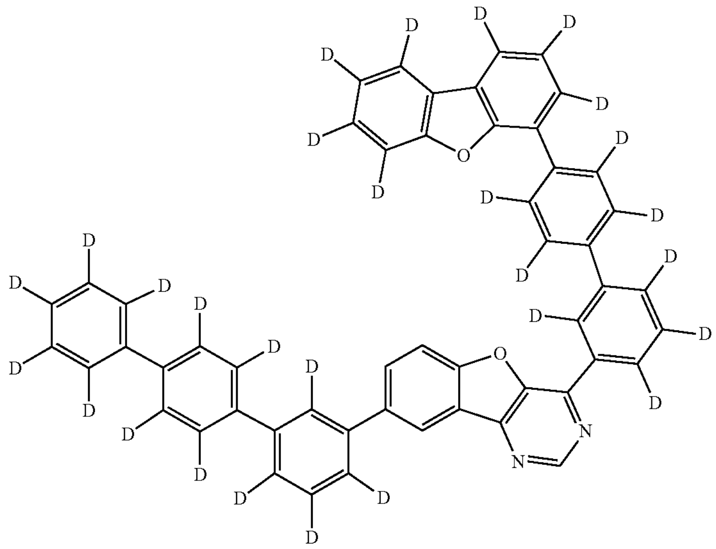
(336)
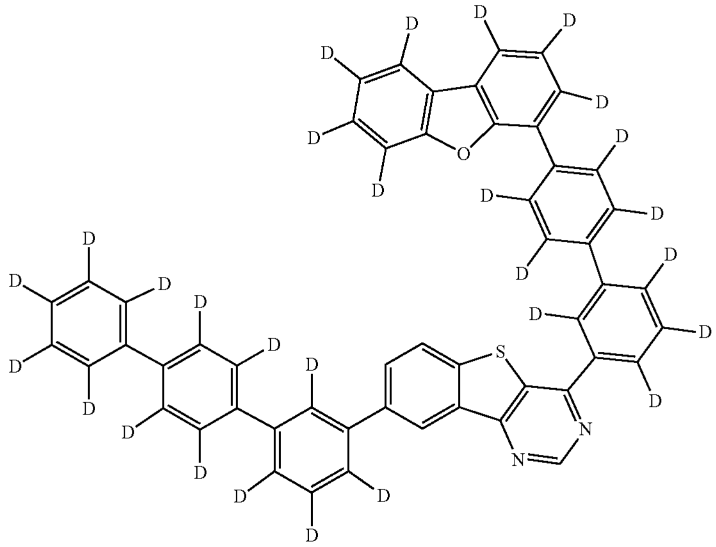
(337)
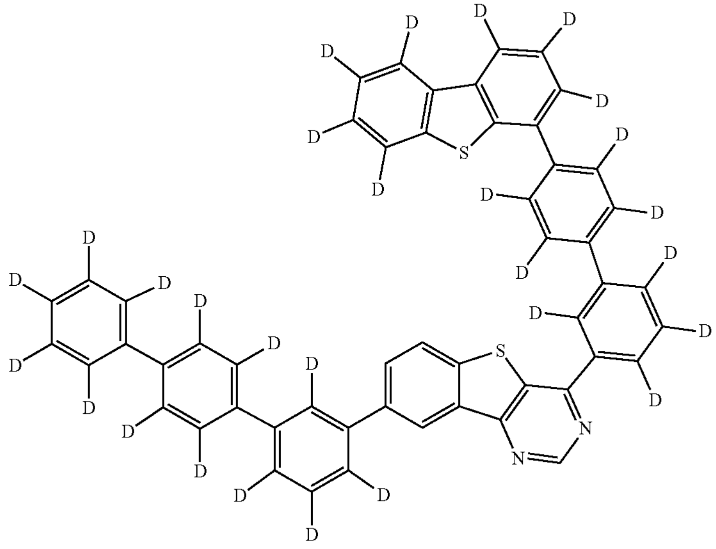

-continued
[Chemical Formula 59]
(700)
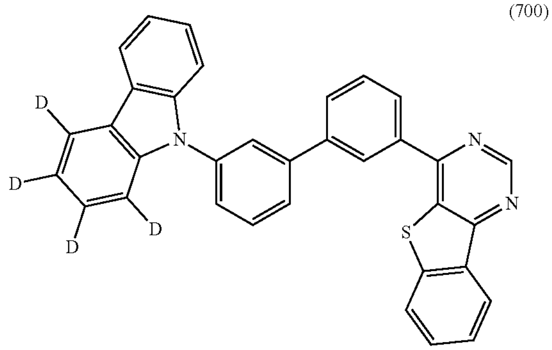
(701)
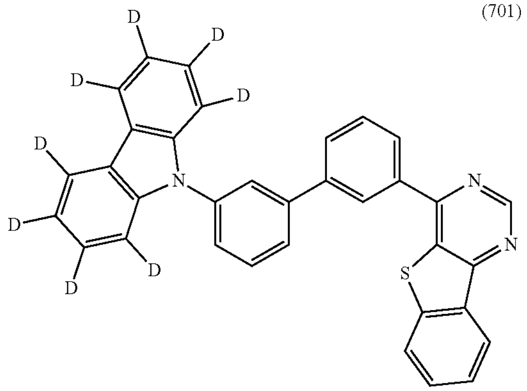
(702)
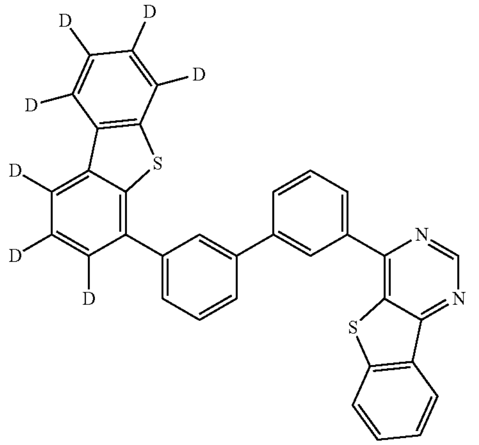
(703)
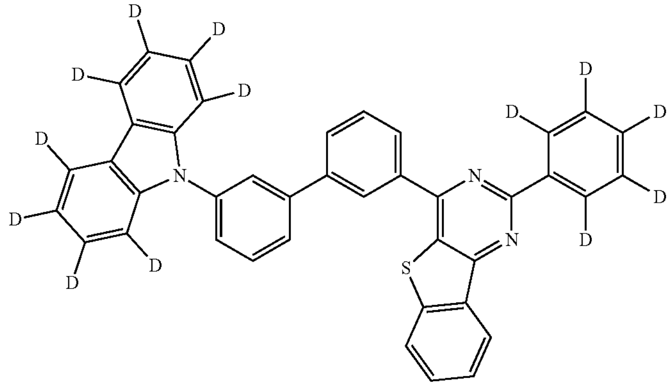
(704)
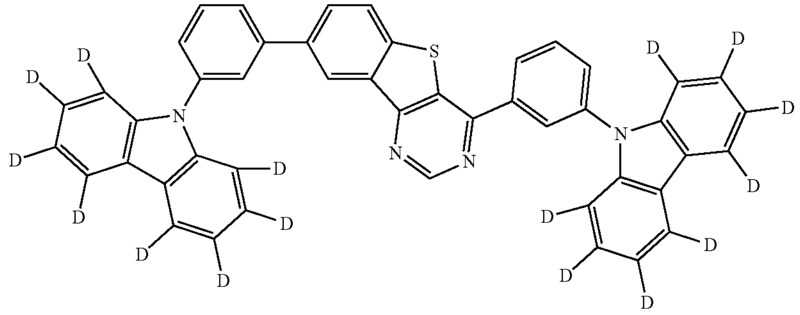

-continued
(705)
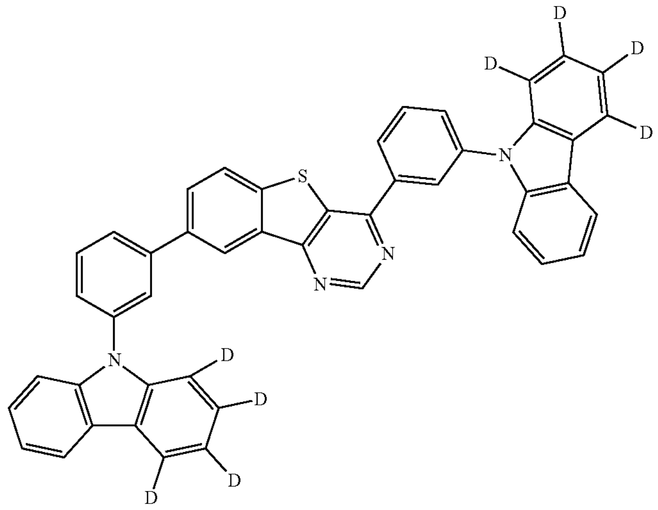
(706)
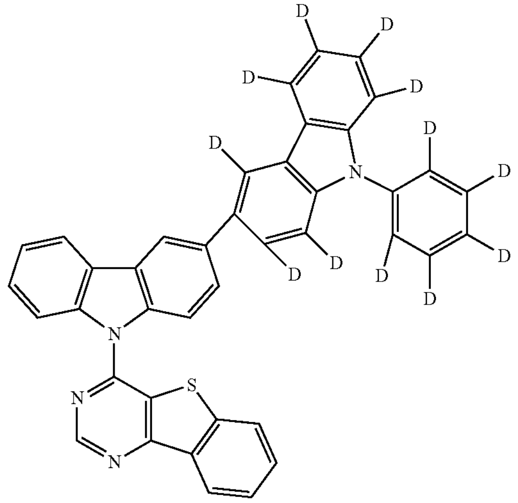
(707)
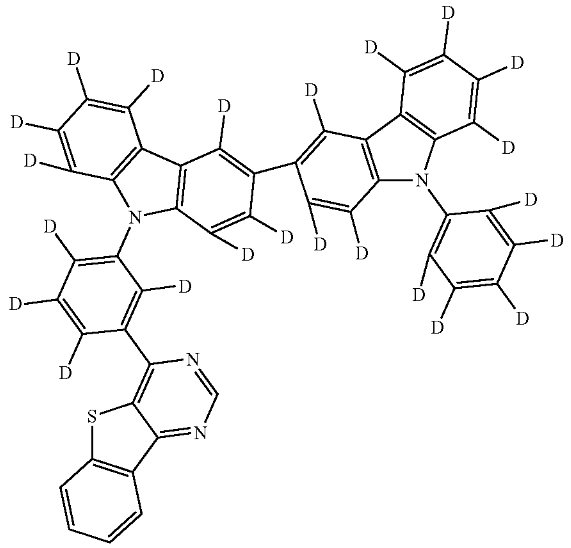

-continued
(708)
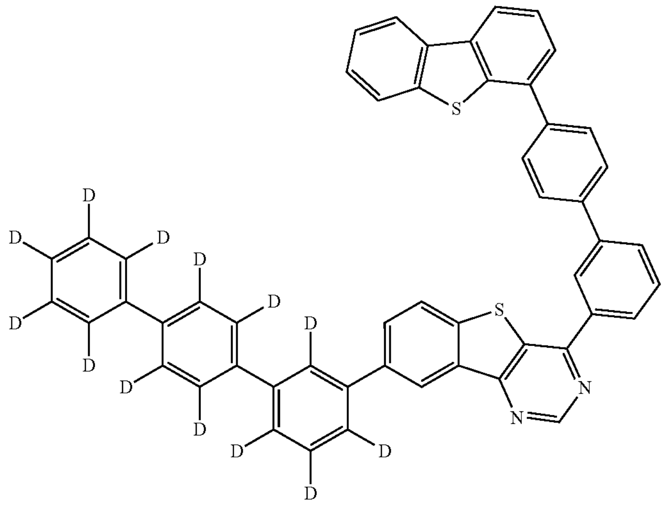
(709)
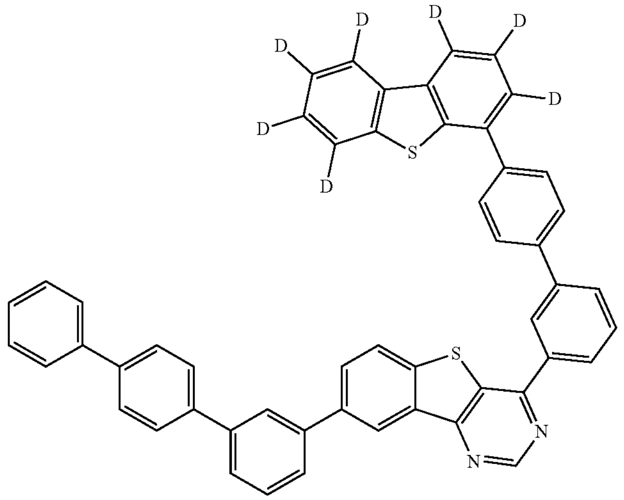
(710)
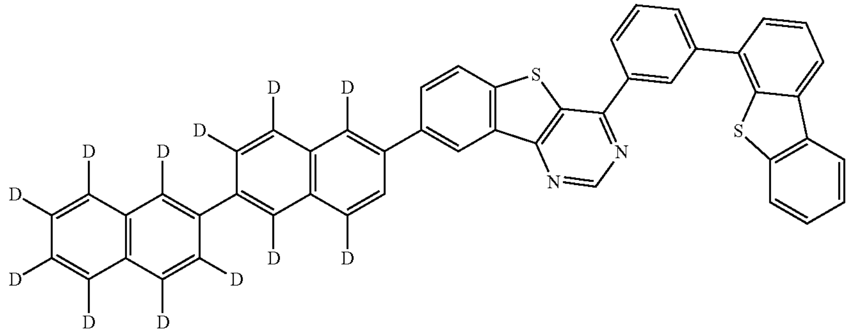

-continued
(711)
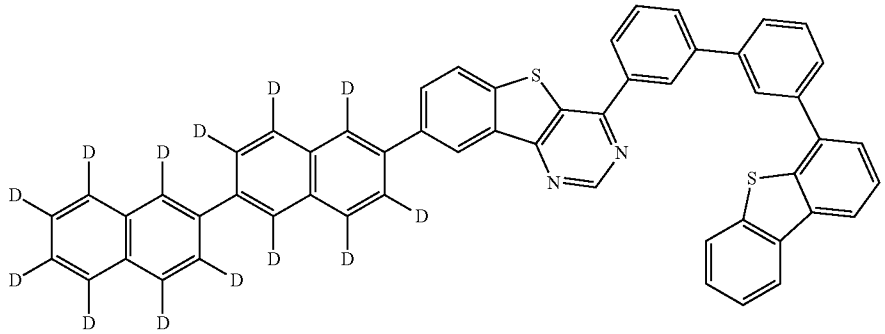
[Chemical Formula 60]
(712)
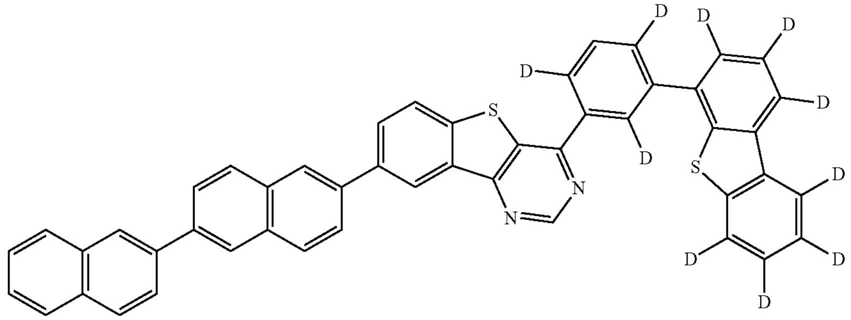
(713)
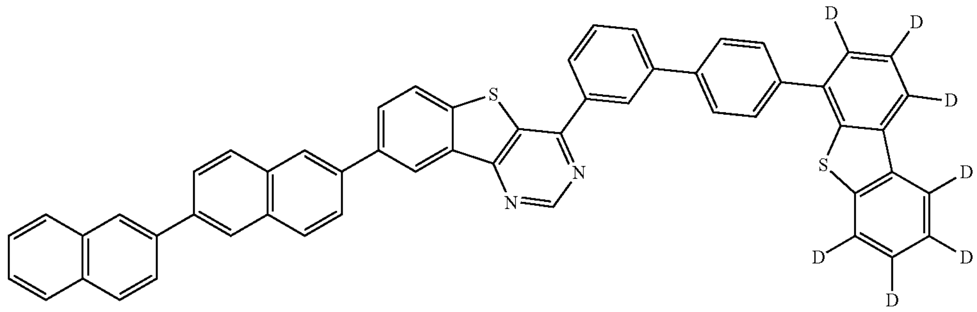
(714)
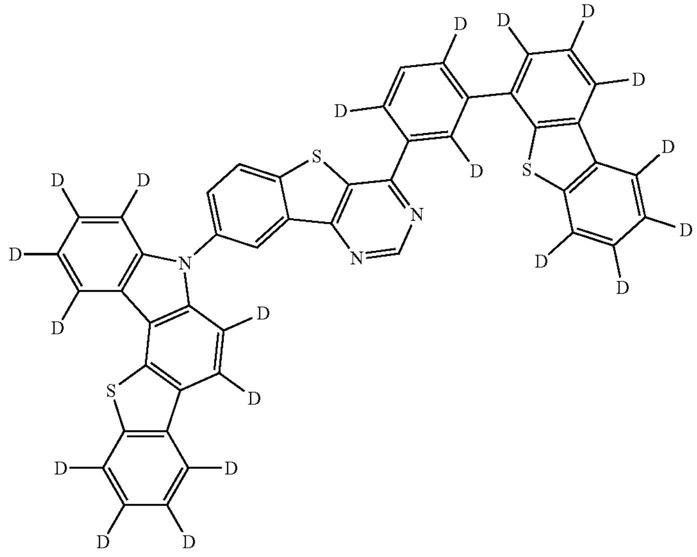

-continued
(715)
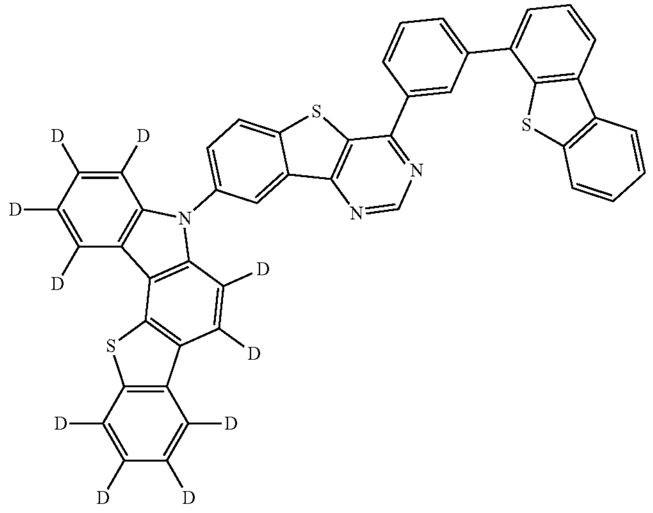
(716)
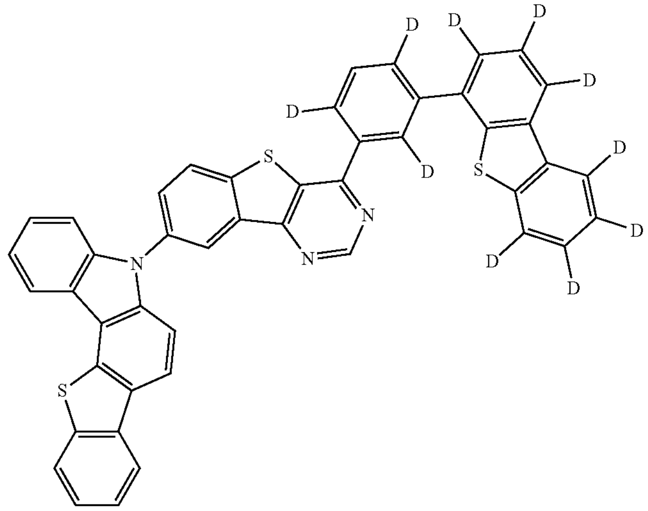
(717)
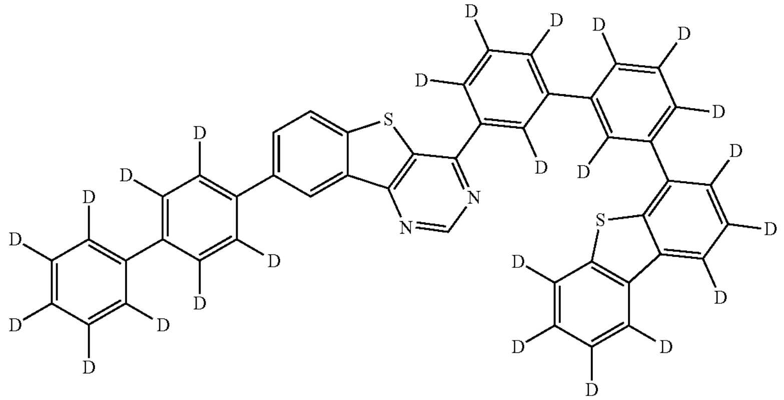

-continued
(718)
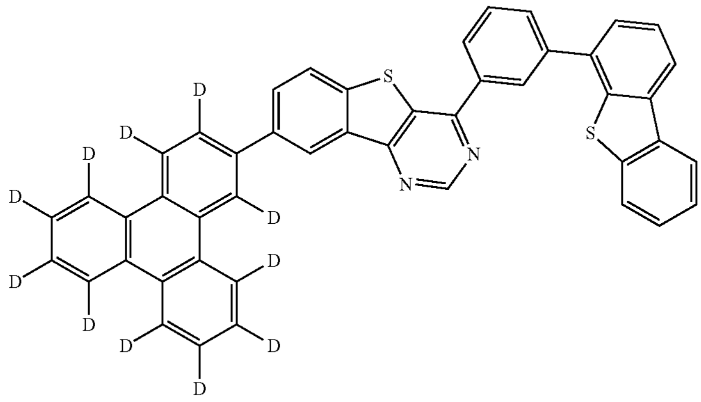
(719)
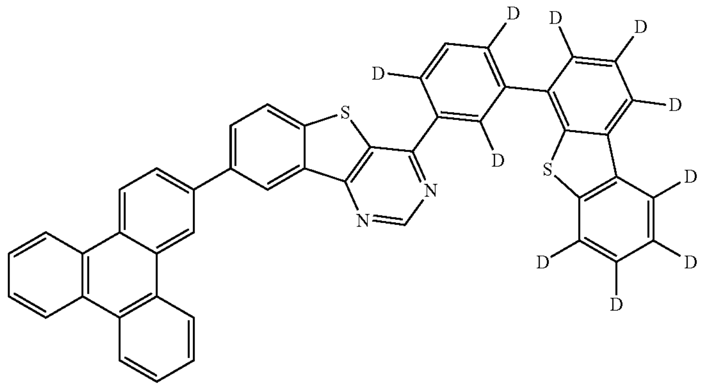
(720)
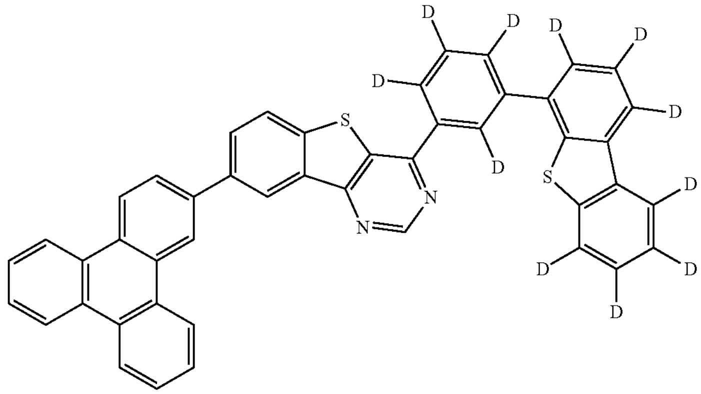
(721)
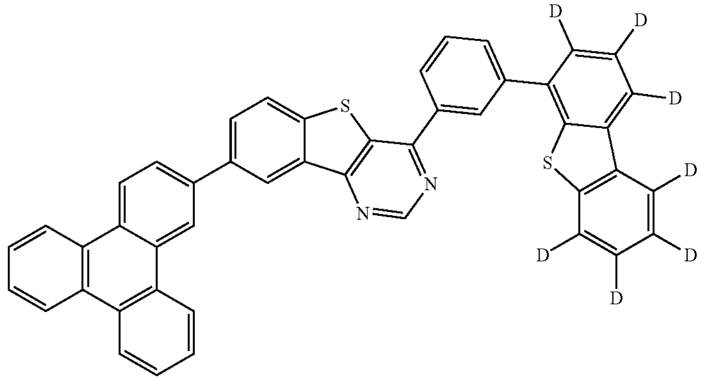

-continued
[Chemical Formula 61]
(722)
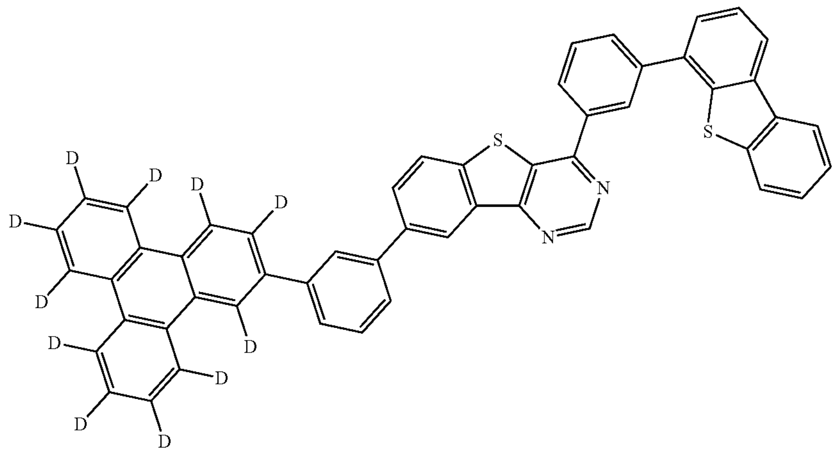
(723)
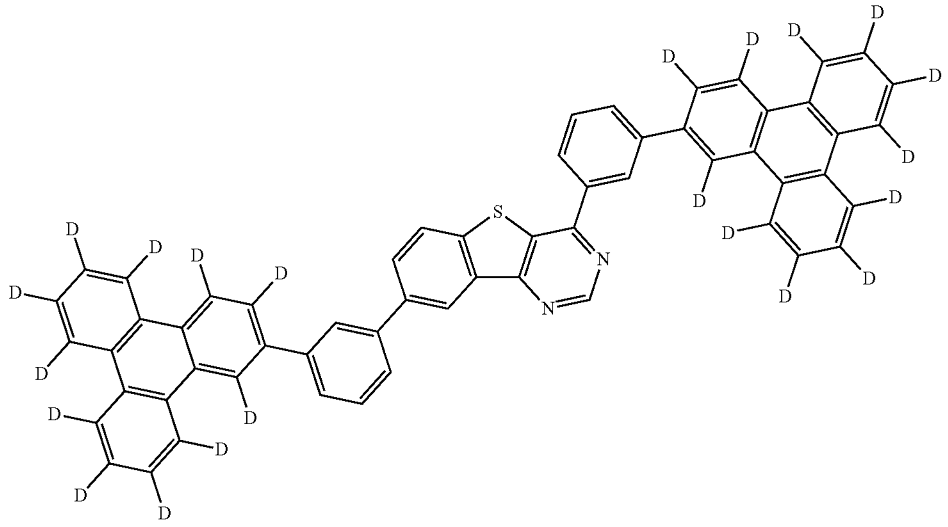
(724)
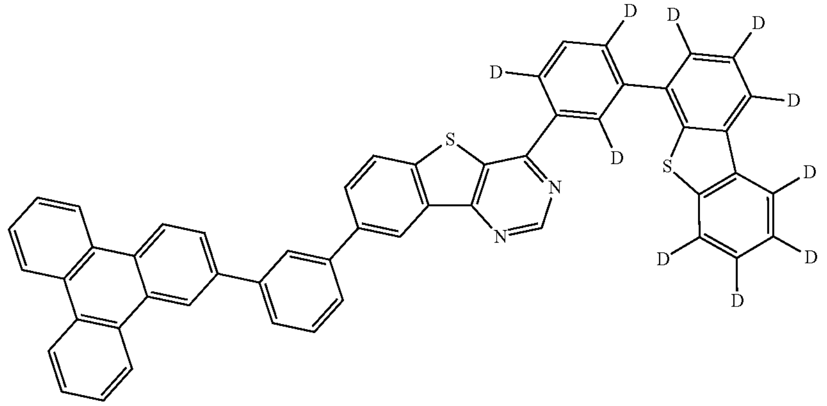

-continued
(725)
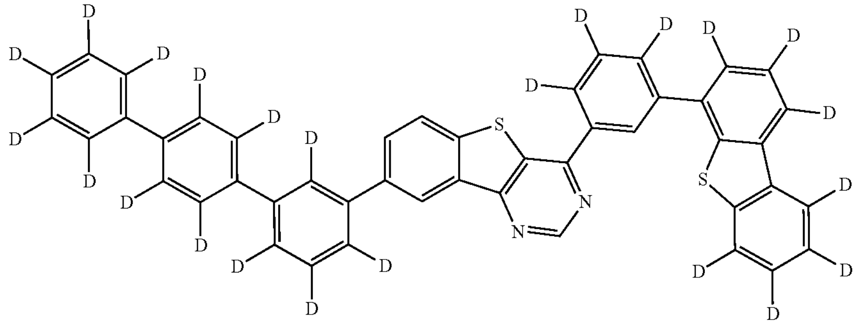
(726)
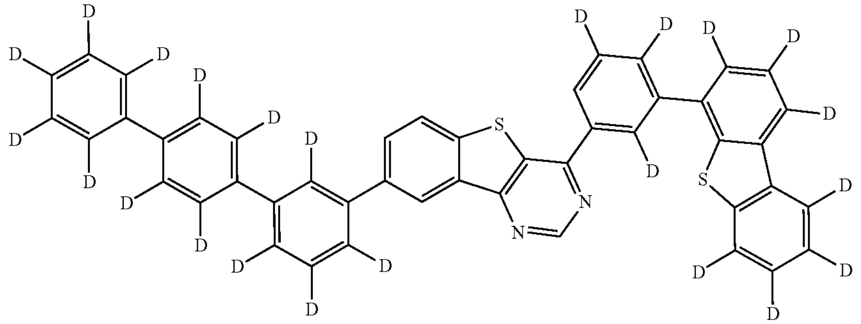
(727)
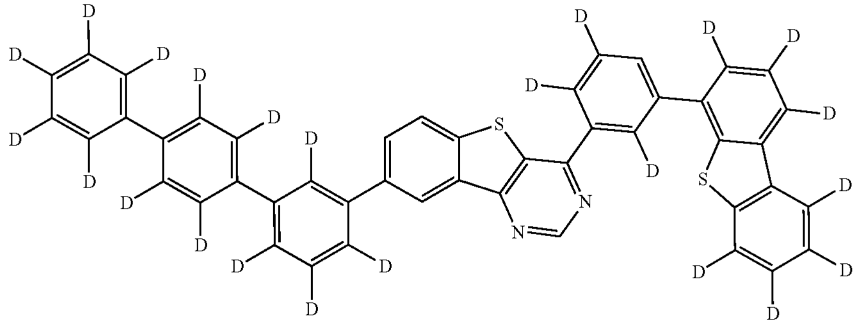
(728)
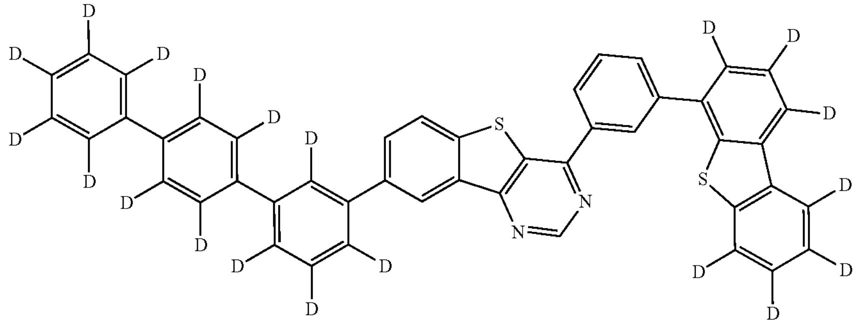
(729)
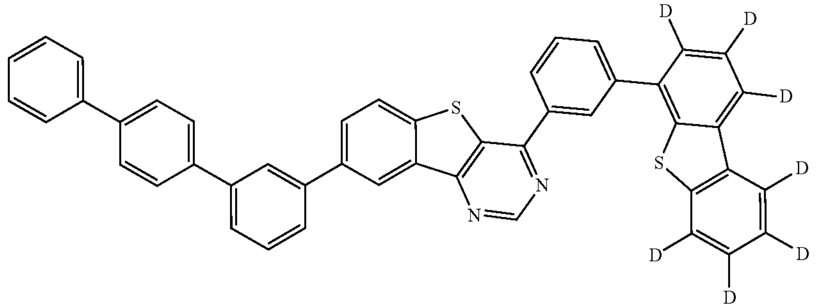

-continued
[Chemical Formula 62]
(730)
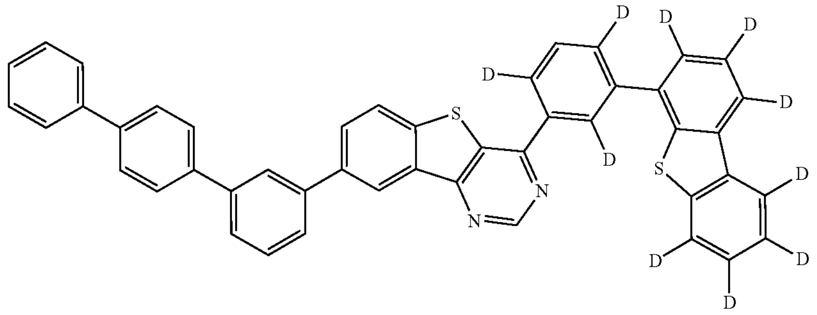
(731)
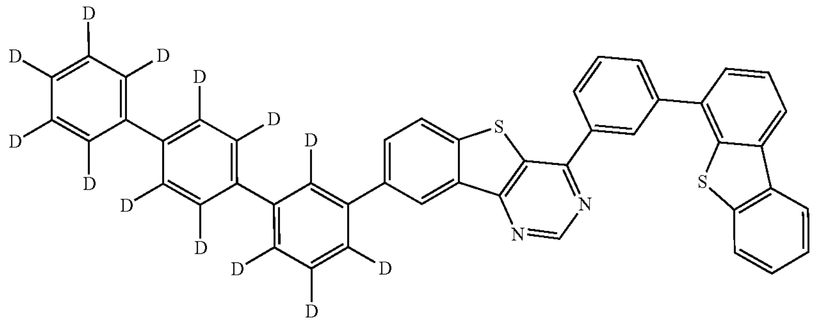
(732)
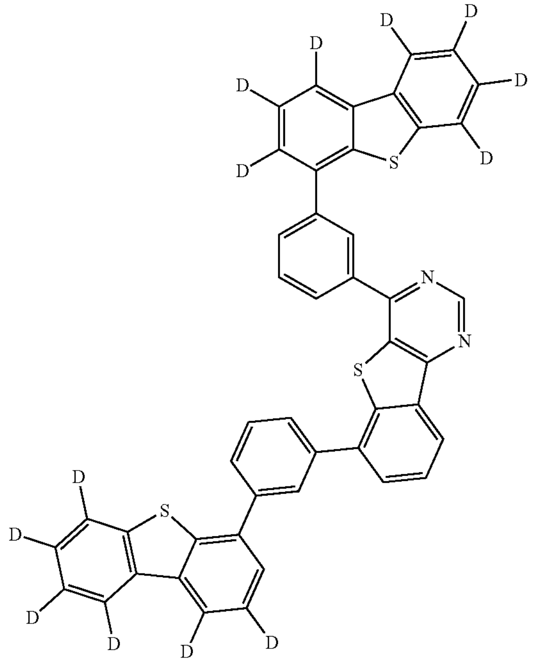

-continued
(733)
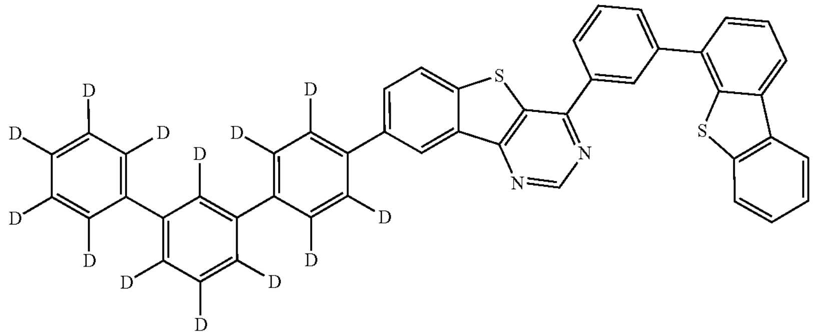
(734)
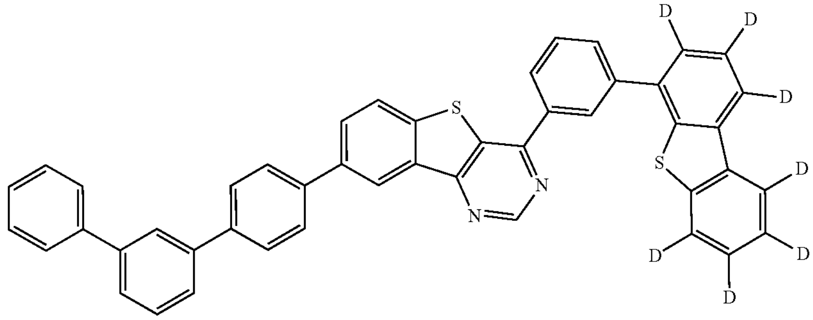
(735)
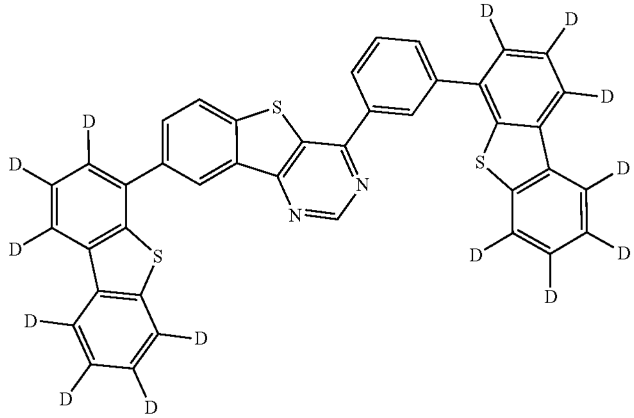
(736)
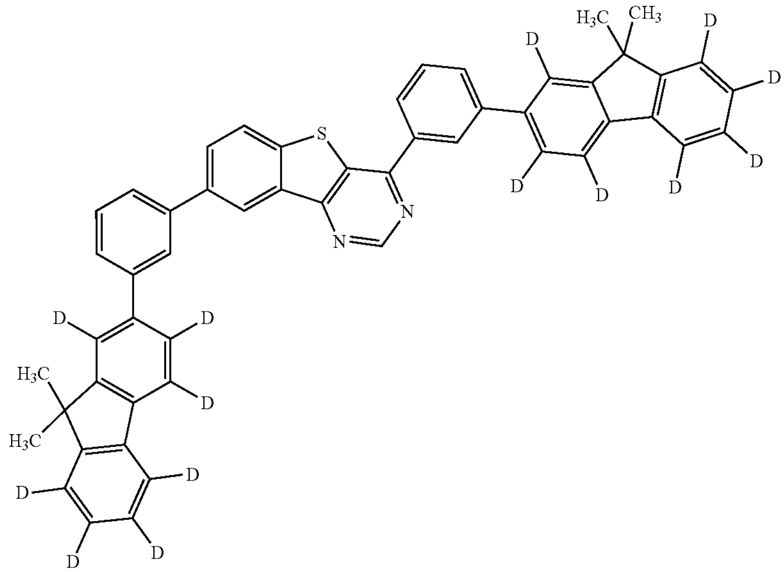

-continued
(737)
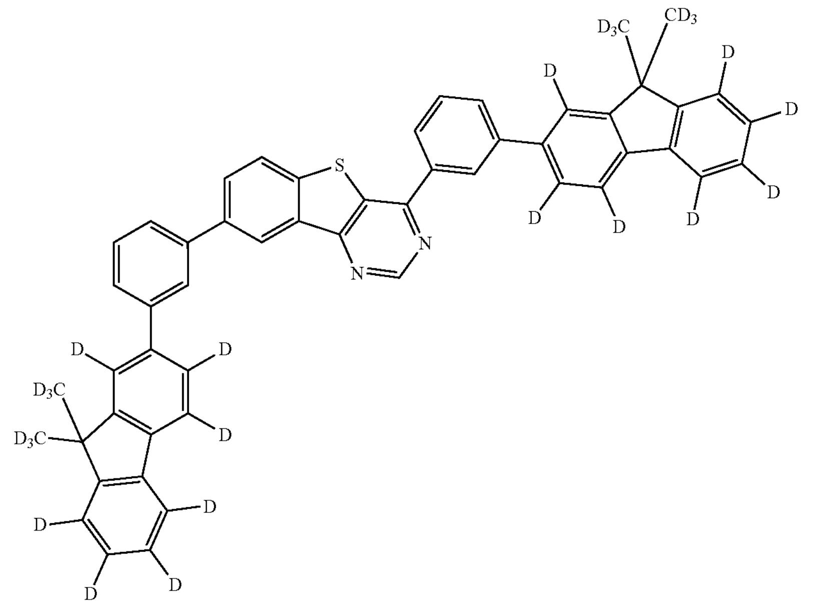
(738)
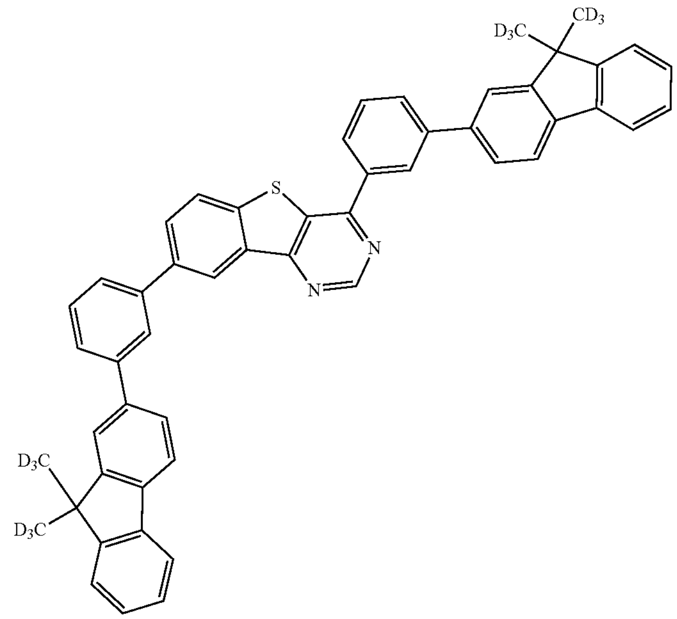

-continued
(739)
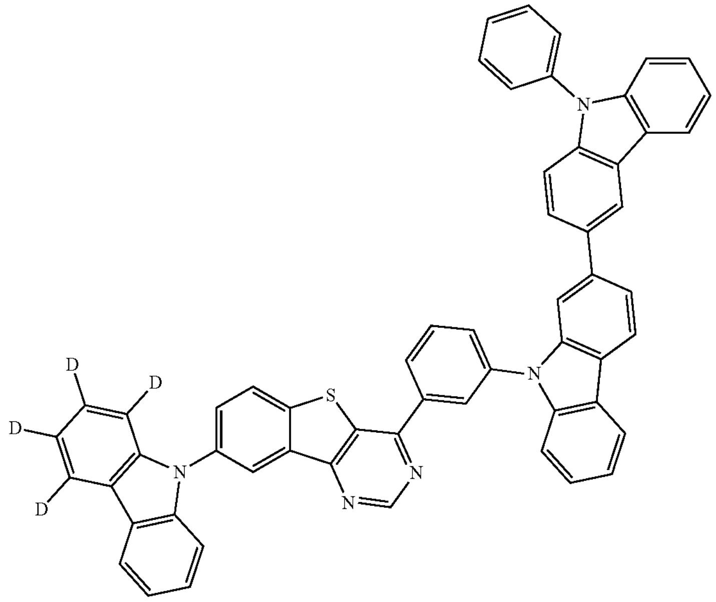
(740)
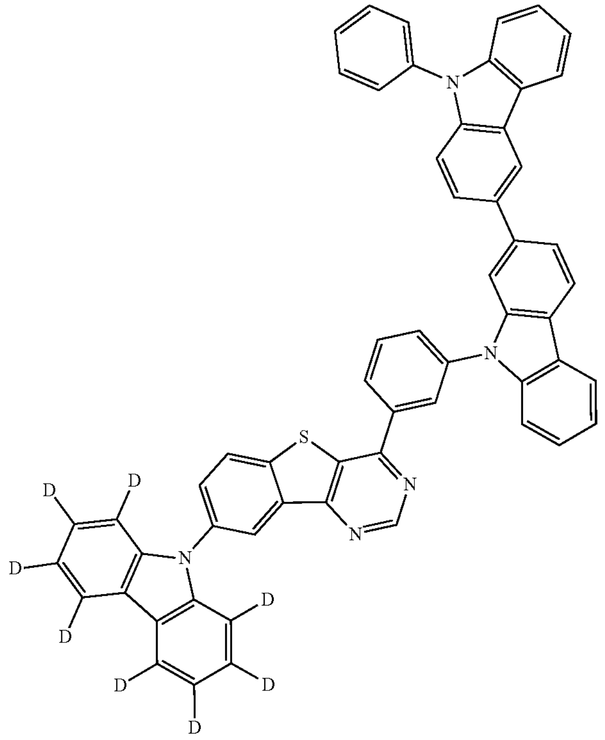

[Chemical Formula 63]
(741)
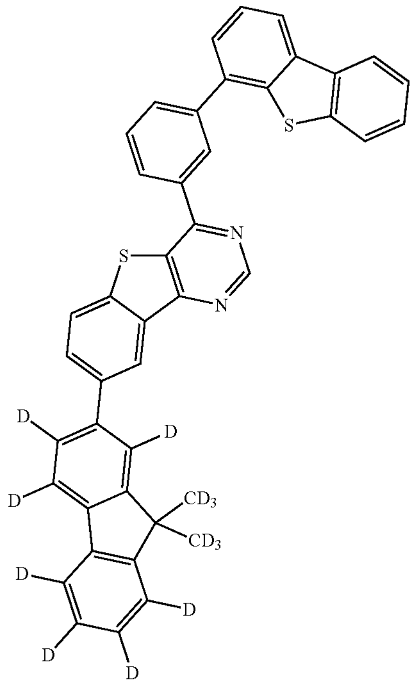
(742)
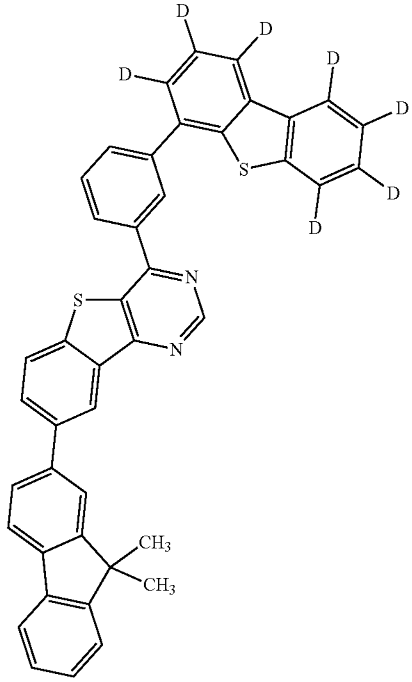
-continued
(743)
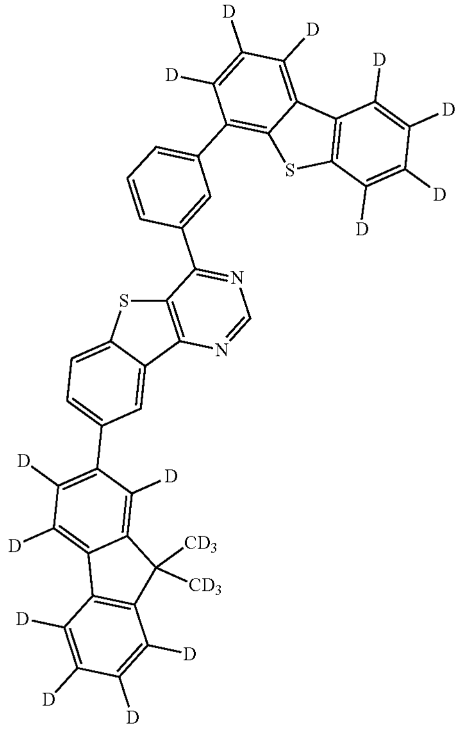
(745)
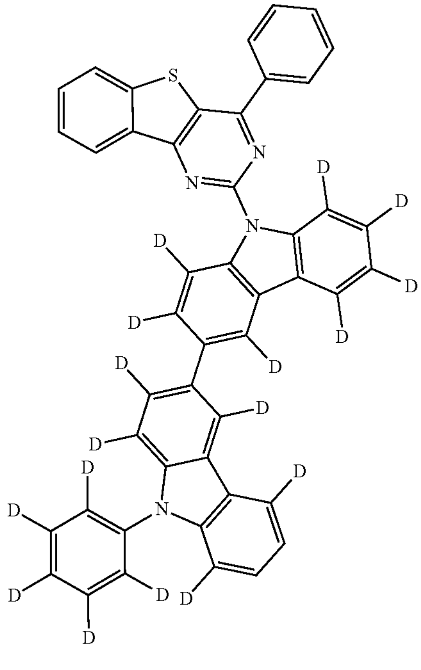

-continued
(744)
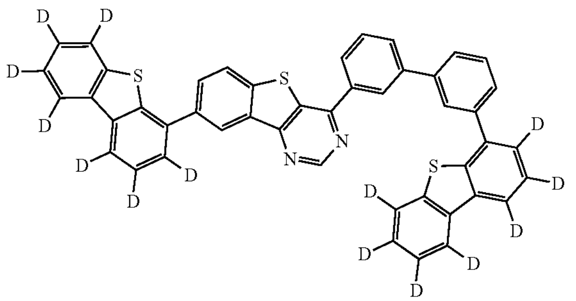
(746)
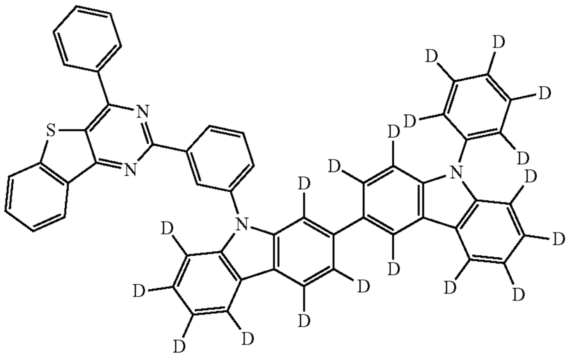
(747)
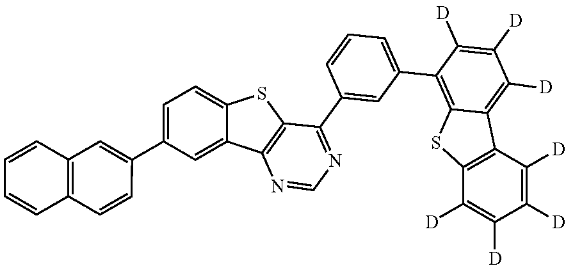
(749)
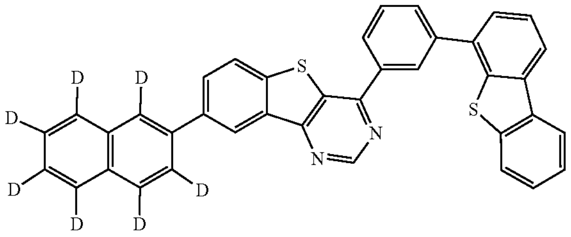
-continued
(748)
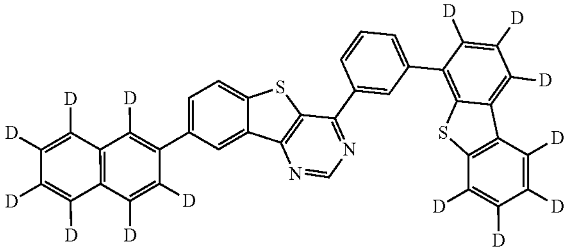
(750)
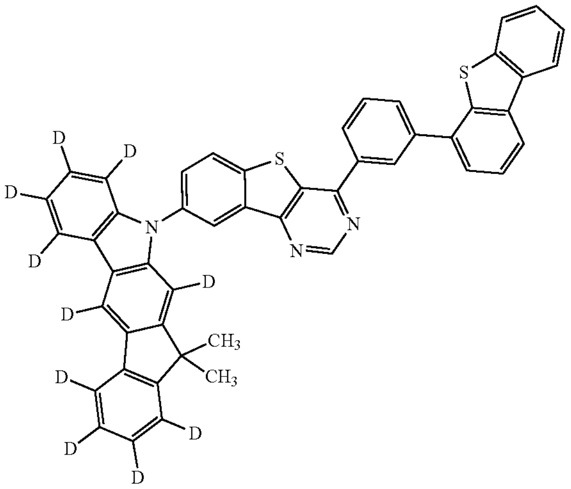
(751)
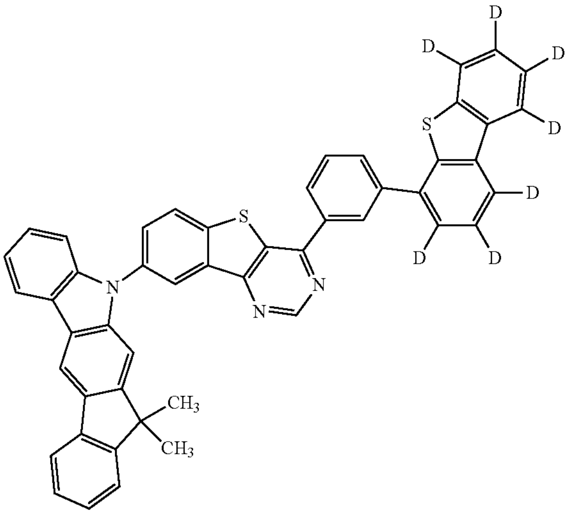

-continued
[Chemical Formula 64]
(741)
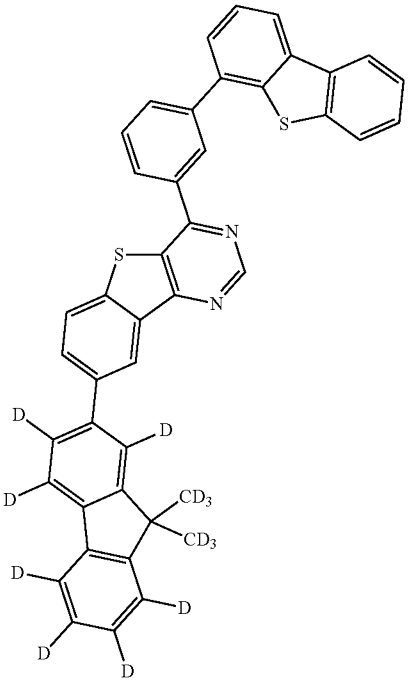
(742)
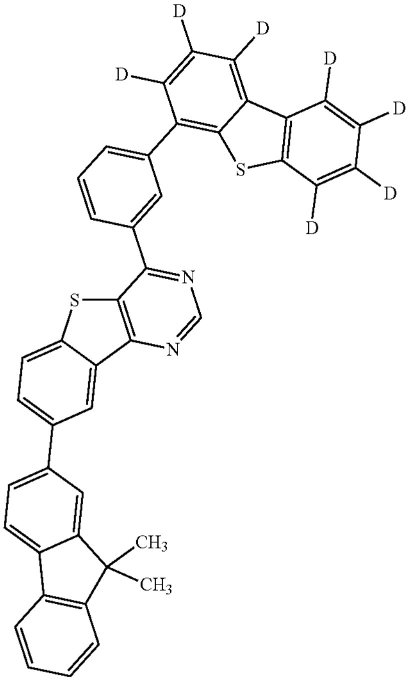
-continued
(743)
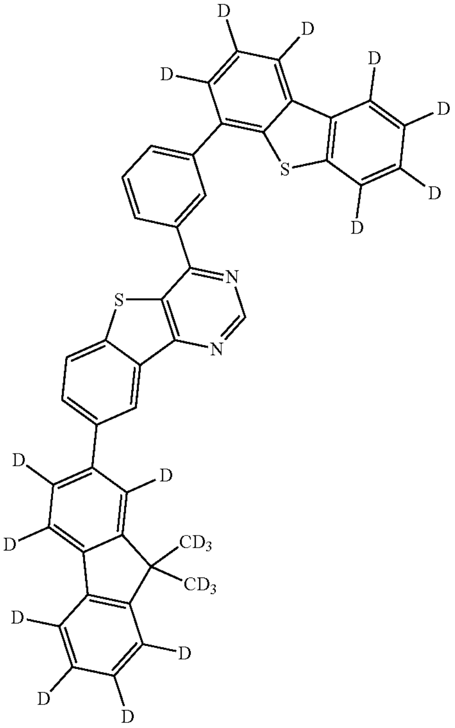
(745)
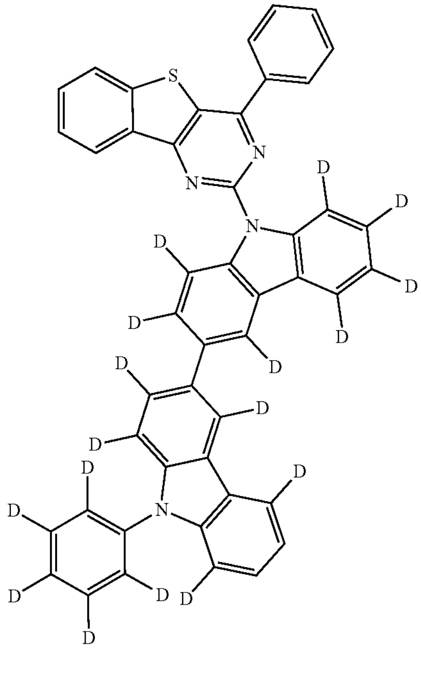

-continued
(744)
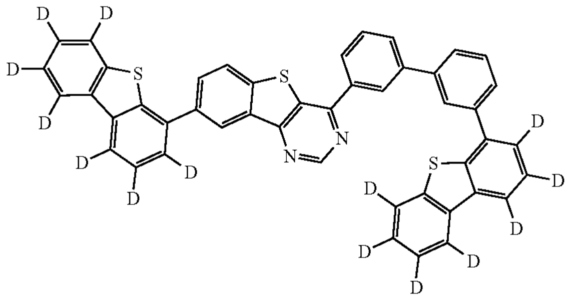
(746)
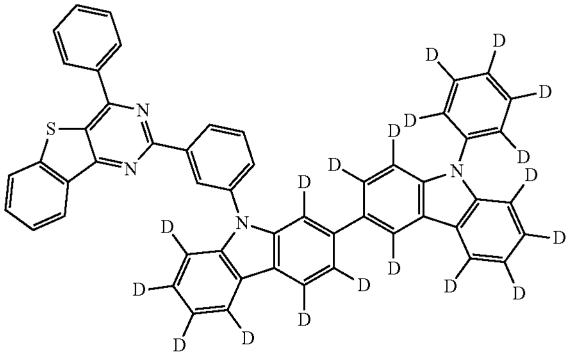
(747)
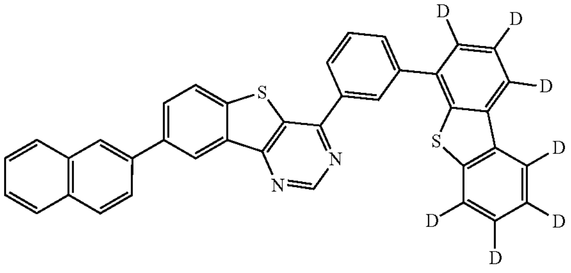
(749)
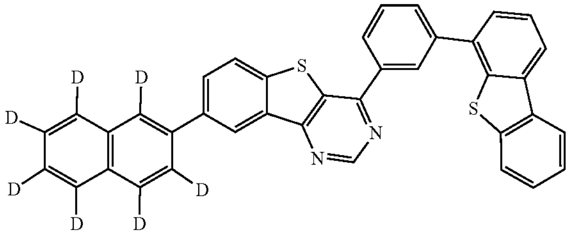
-continued
(748)
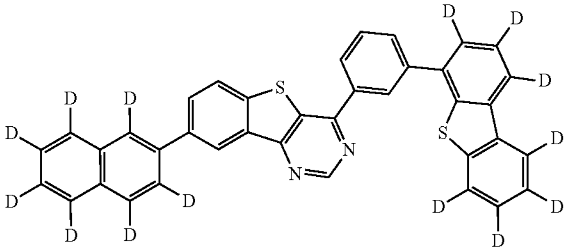
(750)
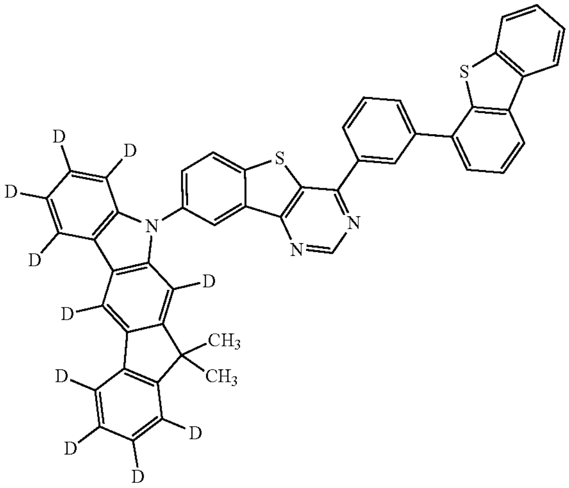
(751)
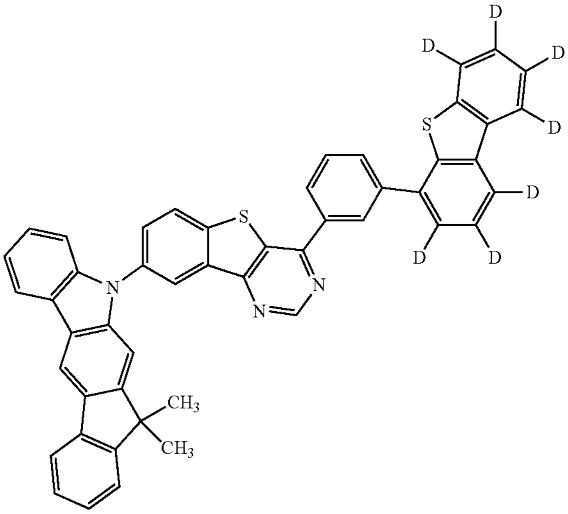

-continued
[Chemical Formula 65]
(765)
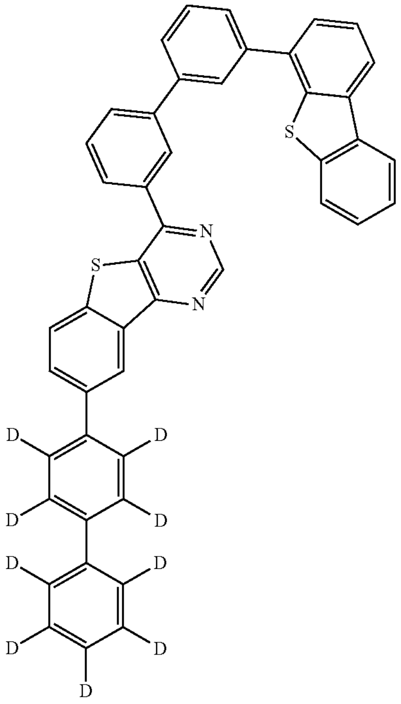
(767)
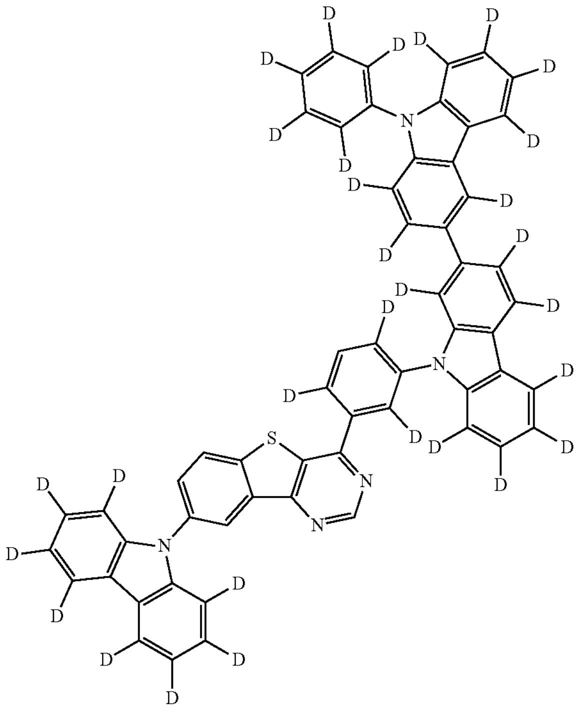
-continued
(766)
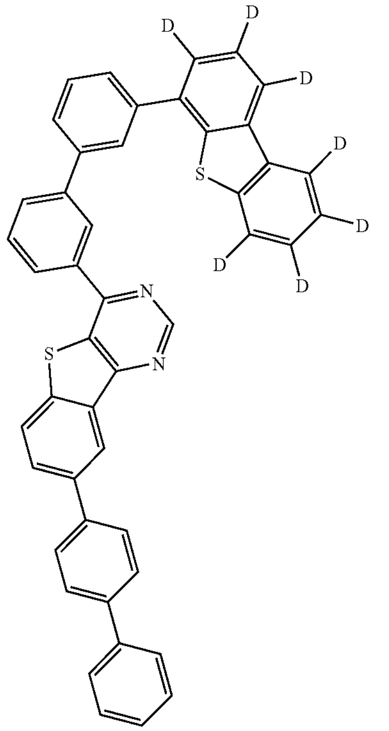
(769)
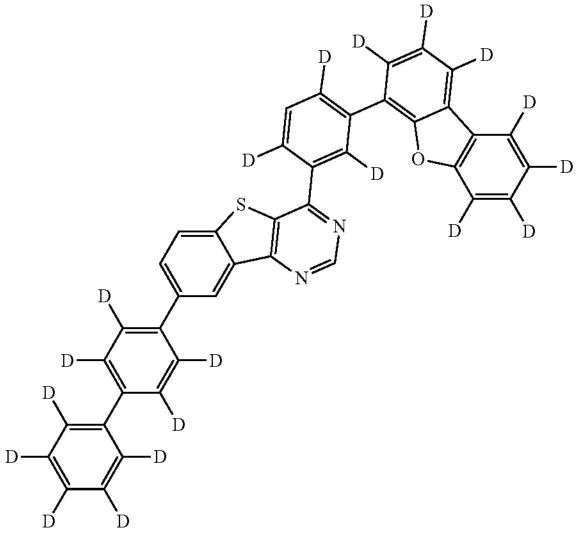

-continued
(768)
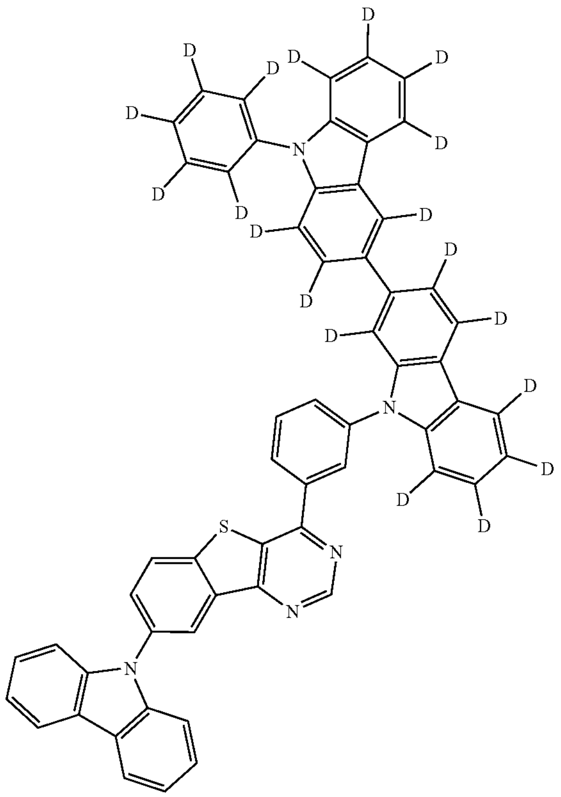
(770)
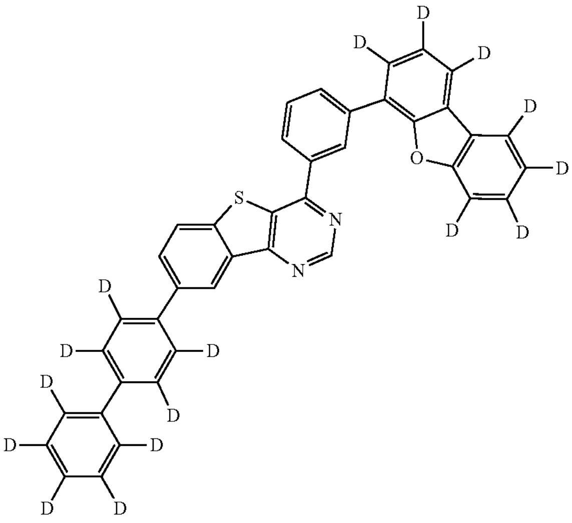
-continued
(771)
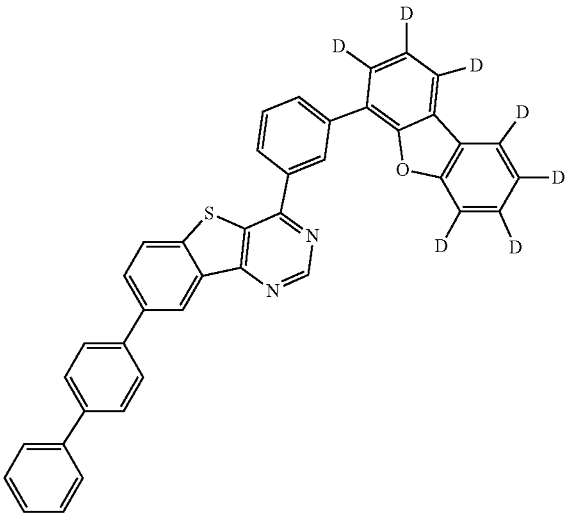
(773)
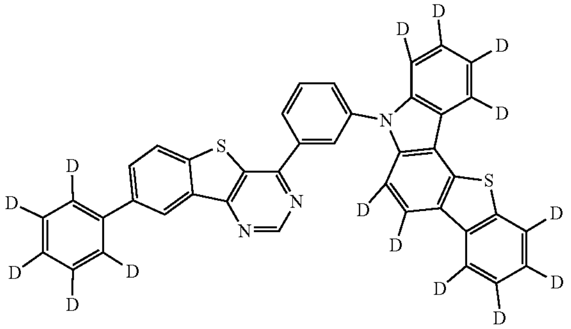
(772)
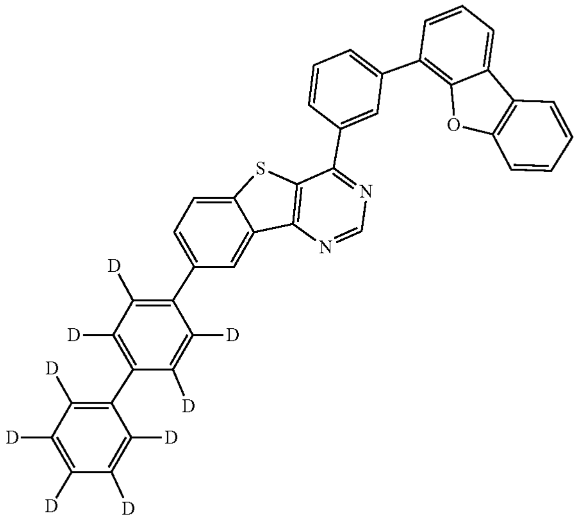

-continued
(774)
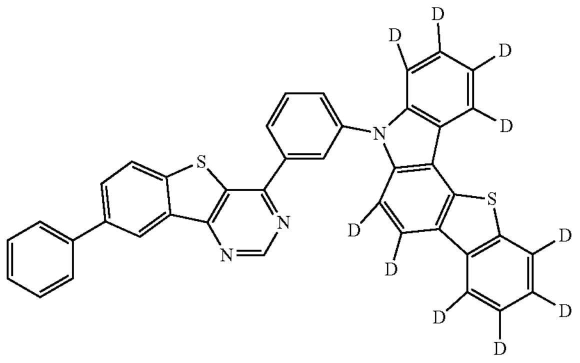
[Chemical Formula 66]
775
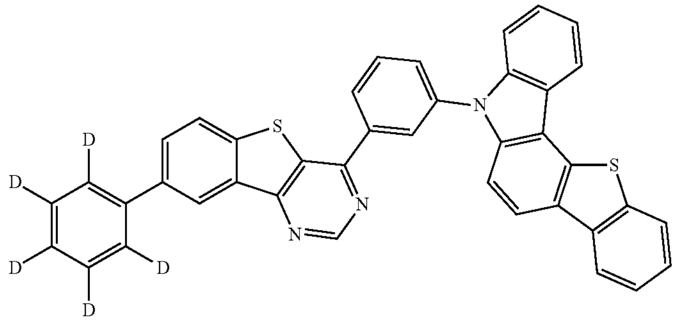
776
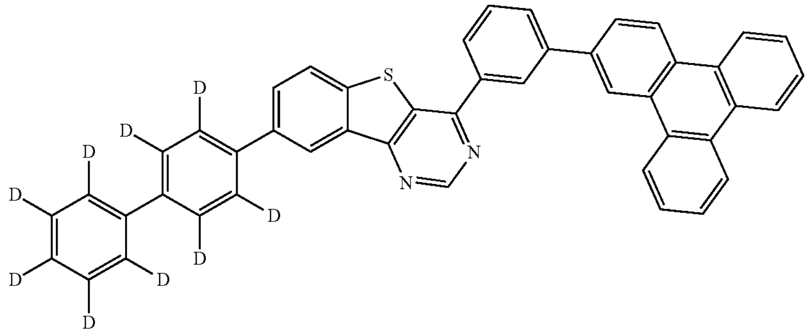
777
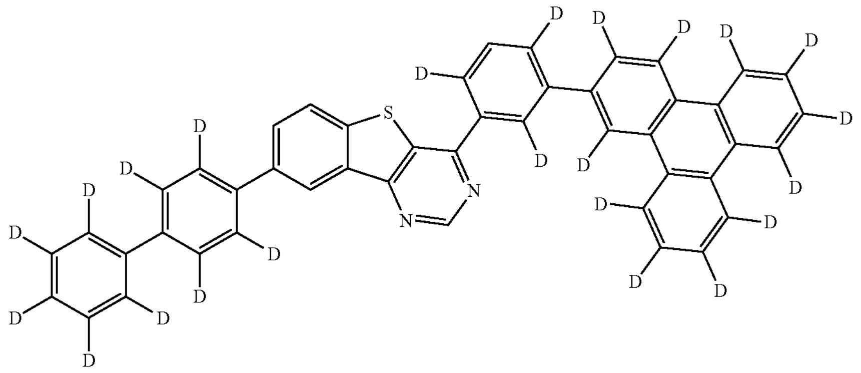

-continued
778
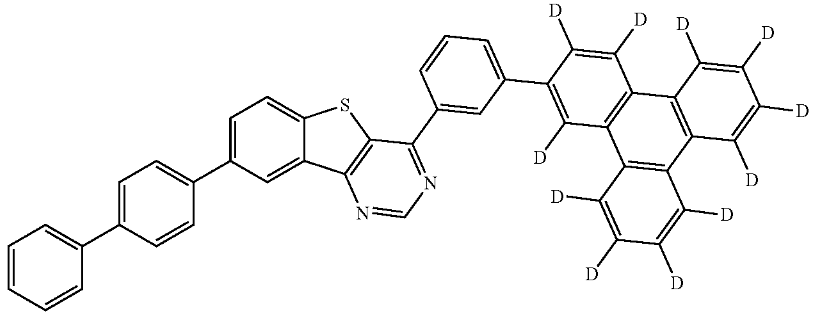
779
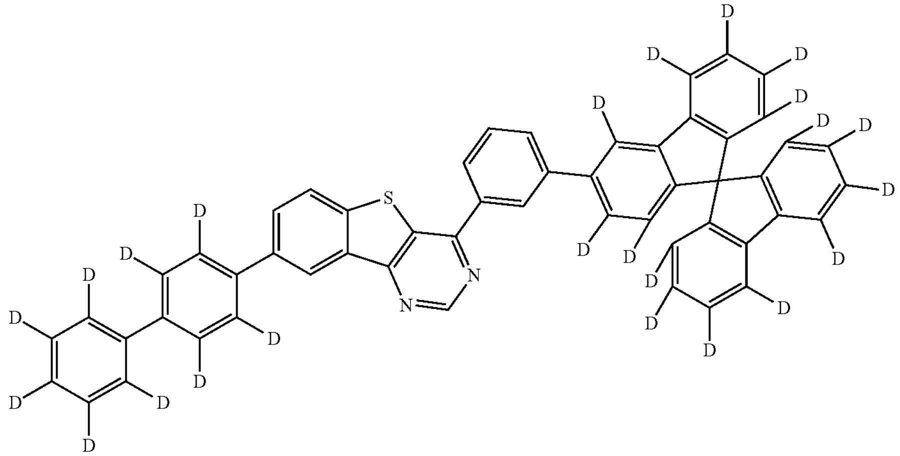
780
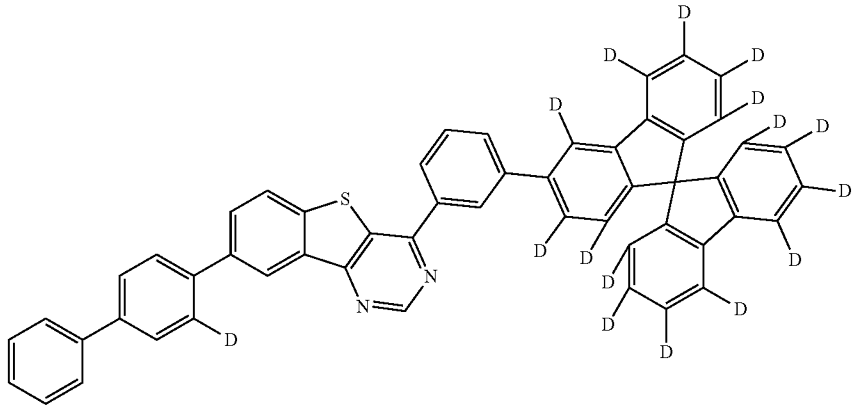
781
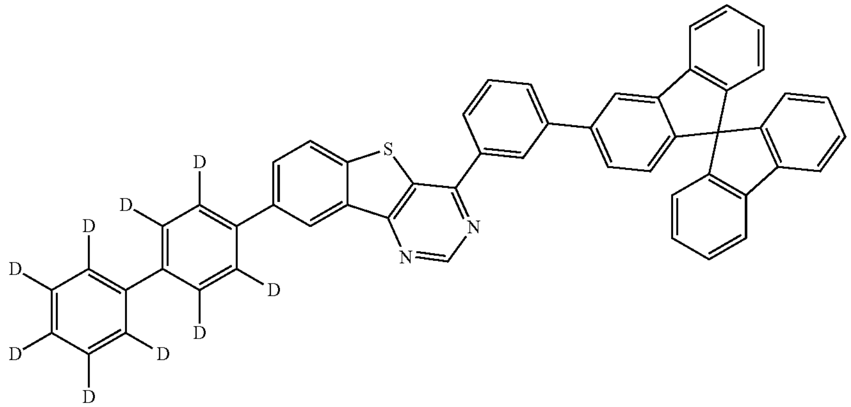

-continued
782
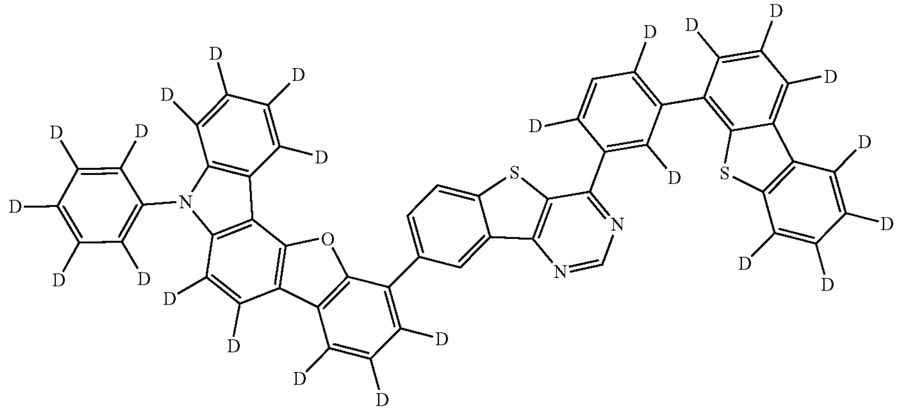
783
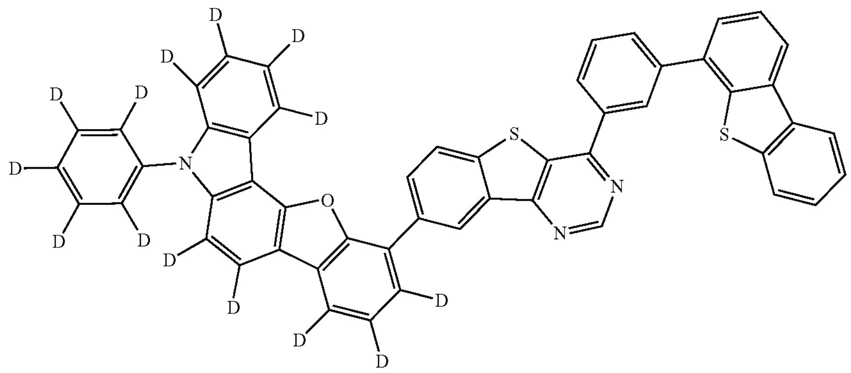
784
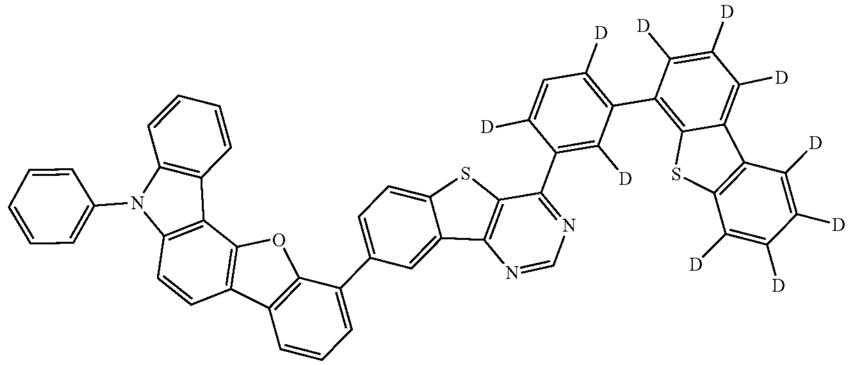
[Chemical Formula 67]
785
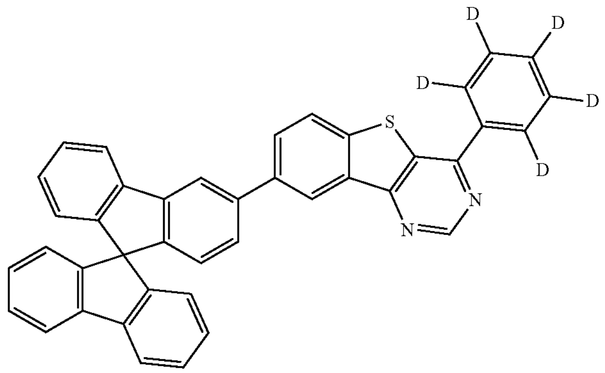

-continued
786
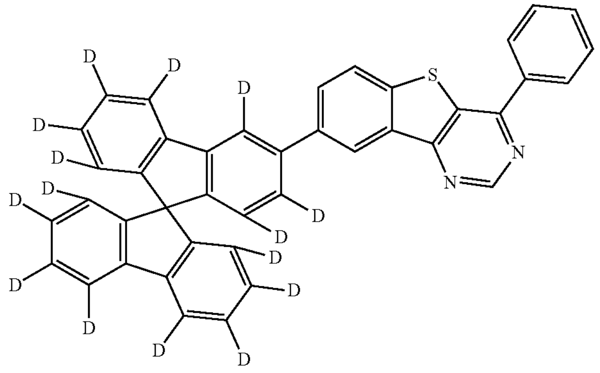
787
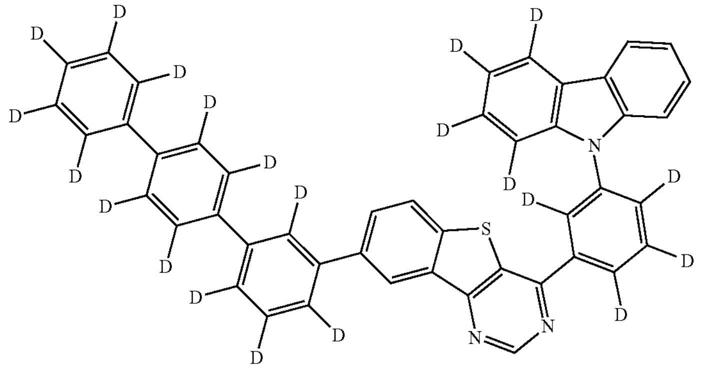
788
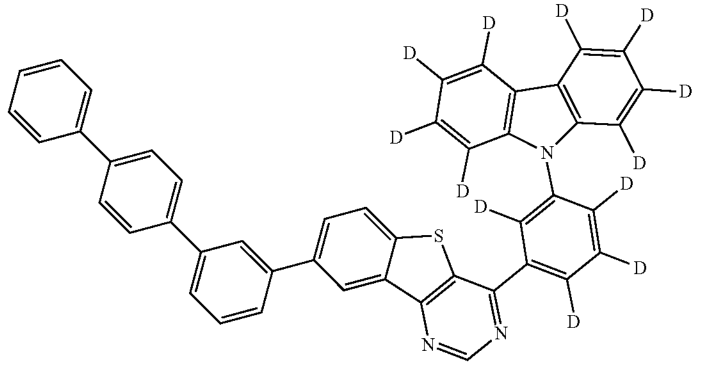
789
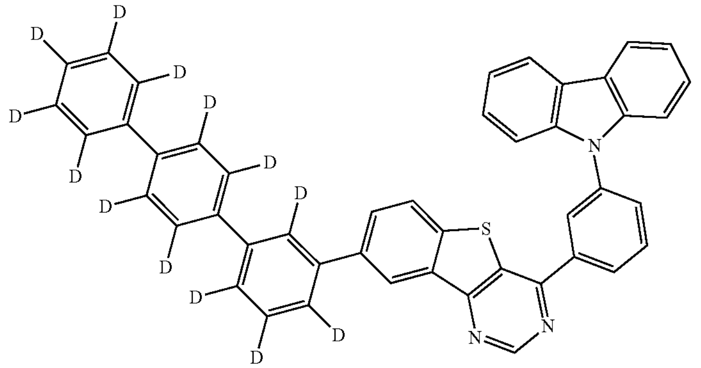

-continued
790
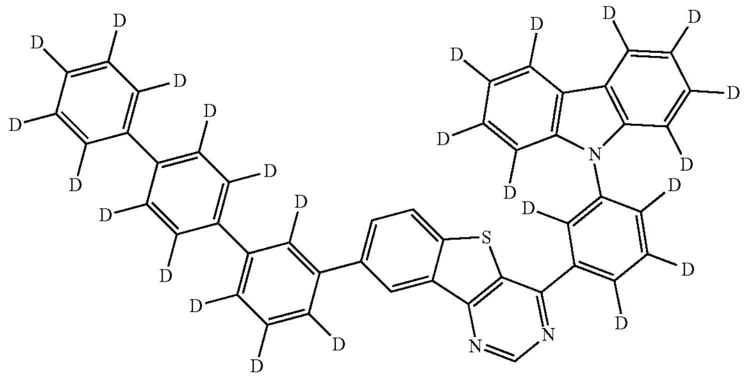
791
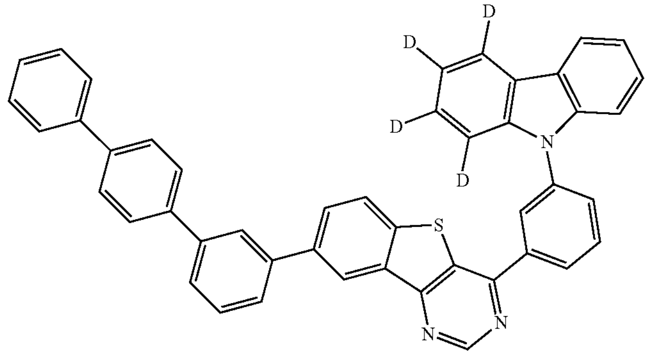
792
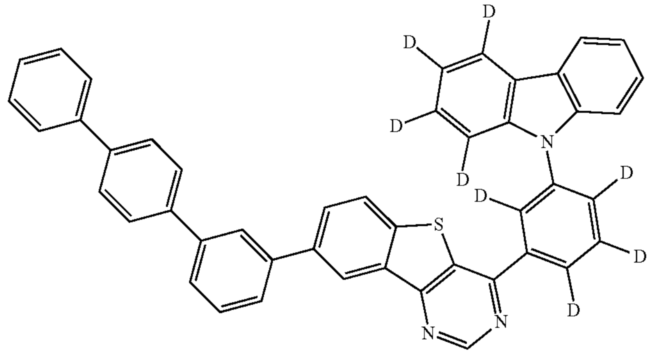
793
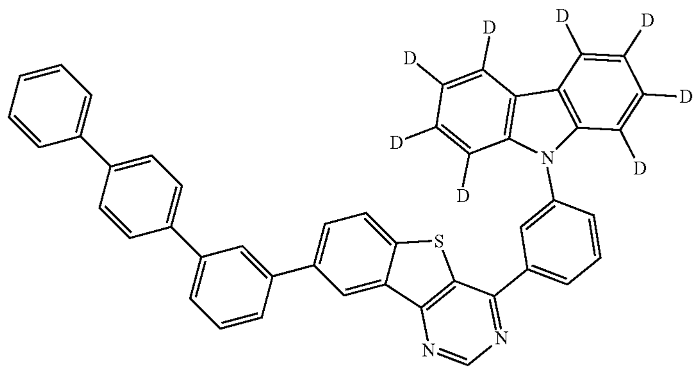

-continued
794
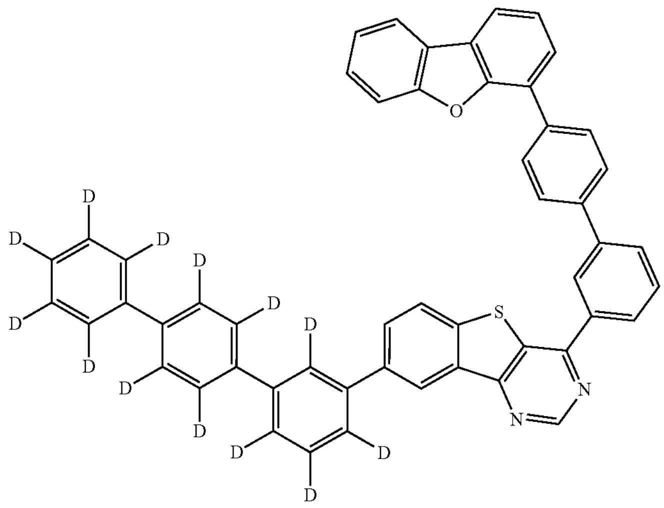
795
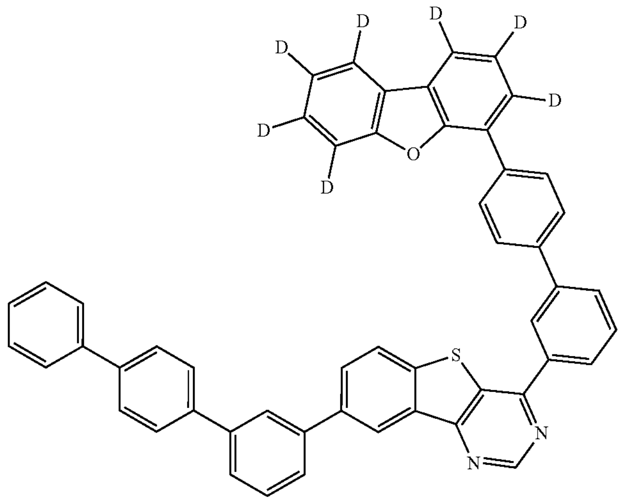
[Chemical Formula 68]
796
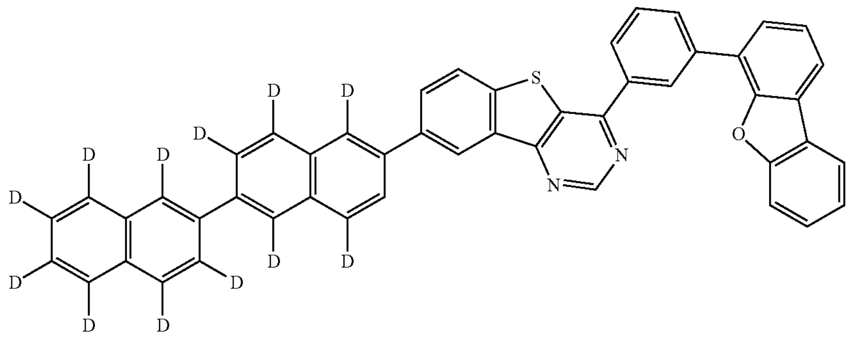

-continued
797
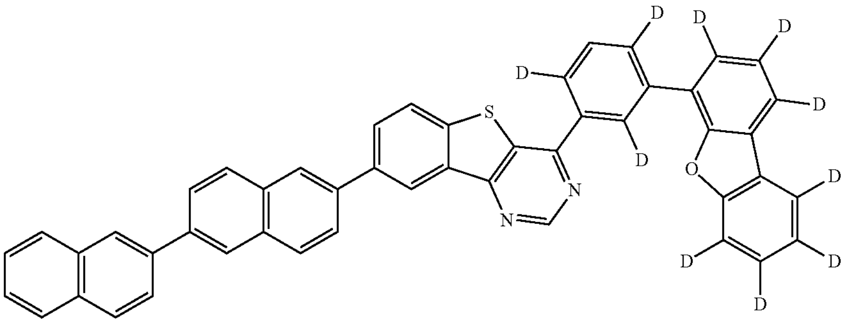
798
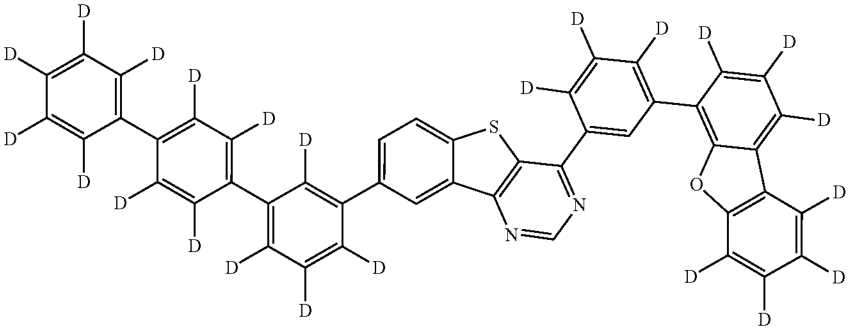
799
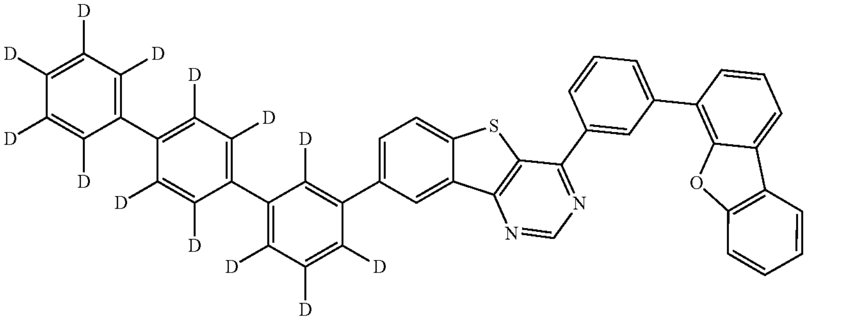
800
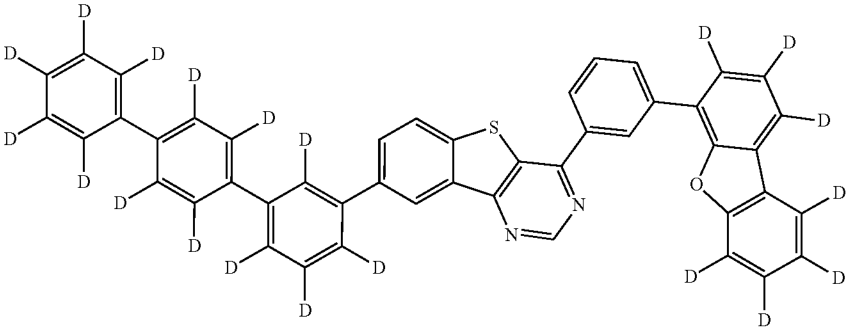
801
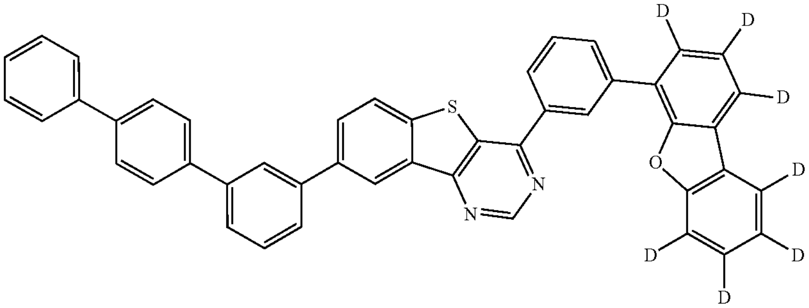

The organic compounds represented by Structural Formulae (201) to (337) and Structural Formulae (700) to (801) above are examples of the organic compounds represented by General Formulae (G1) to (G4). The organic compound of one embodiment of the present invention is not limited thereto.

<Synthesis Method of Organic Compound>

In this embodiment, a method for synthesizing the organic compound represented by General Formula (G1) below is described.

[Chemical Formula 69]

(G1)

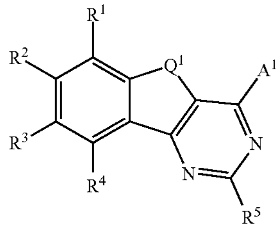

In General Formula (G1), $Q^1$ represents sulfur or oxygen, $R^1$ to $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, $A^1$ represents an aryl group having 6 to 100 carbon atoms and including a substituted or unsubstituted substituent, or a heteroaryl group having 2 to 100 carbon atoms and including a substituted or unsubstituted substituent, and deuterium is substituted for at least one of hydrogen contained in $R^1$ to $R^5$ and $A^1$.

The organic compound of the present invention represented by General Formula (G1) can be synthesized by Synthesis Schemes (s-1) to (s-5) shown below.

The organic compound represented by General Formula (G1) can be obtained by coupling due to Suzuki-Miyaura reaction between a halogen compound having a benzofuropyrimidine skeleton or a benzothienopyrimidine skeleton and a deuterated organic boron compound or boronic acid, for example. Alternatively, the organic compound represented by General Formula (G1) can be obtained by coupling due to Suzuki-Miyaura reaction between an organic boron compound or a boronic acid having a benzofuropyrimidine skeleton or a benzothienopyrimidine skeleton and a deuterated halogen compound.

[Chemical Formula 70]

(s-1)

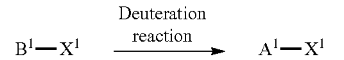

Compound 1 Compound 2

[Chemical Formula 71]

(s-2)

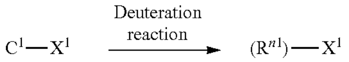

Compound 3 Compound 4

-continued

[Chemical Formula 72]

(s-3)

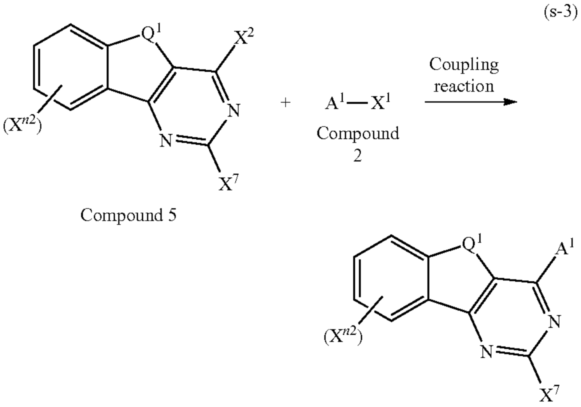

Compound 5 Compound 2 Compound 6

[Chemical Formula 73]

(s-4)

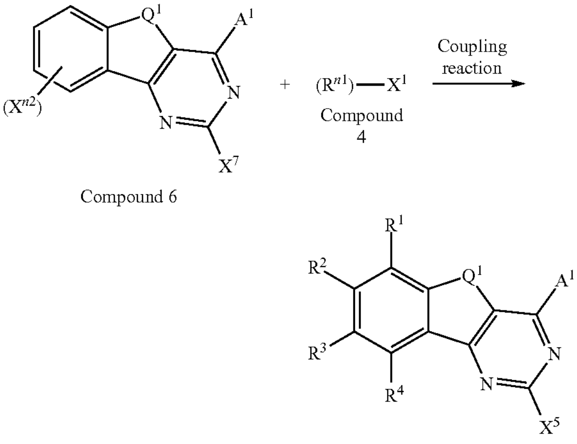

Compound 6 Compound 4

(G1)

In the above synthesis schemes, $Q^1$ represents sulfur or oxygen, $R^1$ to $R^5$ (also referred to as $(R^{n1})$ (n1 is an integer of 1 to 5)) each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, $A^1$ represents an aryl group having 6 to 100 carbon atoms and including a substituted or unsubstituted substituent, or a heteroaryl group having 2 to 100 carbon atoms and including a substituted or unsubstituted substituent, and deuterium is substituted for at least one of hydrogen contained in $R^1$ to $R^5$ and $A^1$.

Furthermore, $X^1$ to $X^7$ (note that $X^3$ to $X^6$ are each also referred to as $(X^{n2})$ (n2 is an integer of 3 to 6)) each independently represent a halogen or a triflate group, and when $X^1$ to $X^7$ each represent a halogen, chlorine, bromine, or iodine is especially preferred. However, $X^1$ to $X^7$ are not limited thereto and may each independently represent an organic boron group or a boronic acid. $X^3$ to $X^7$ each independently represent any one of hydrogen and deuterium.

Examples of a palladium catalyst that can be used for the coupling reaction represented by the above synthesis scheme include palladium(II) acetate, tetrakis(triphenylphosphine) palladium(0), and bis(triphenylphosphine)palladium(II) dichloride.

Examples of a ligand in the above palladium catalyst include tri(ortho-tolyl)phosphine, triphenylphosphine, and tricyclohexylphosphine.

Examples of a base that can be used for the coupling reaction represented by the above synthesis scheme include an organic base such as sodium tert-butoxide and an inorganic base such as potassium carbonate or sodium carbonate.

Examples of a solvent that can be used for the coupling reaction represented by the above synthesis scheme include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as diethylene glycol dimethyl ether. However, the solvent that can be used is not limited to these solvents. In particular, a mixed solvent of toluene and water, a mixed solvent of toluene, ethanol, and water, or a mixed solvent of water and an ether such as diethylene glycol dimethyl ether is preferred.

The reaction employed in the above synthesis scheme is not limited to the Suzuki-Miyaura coupling reaction. A Migita-Kosugi-Stille coupling reaction using an organotin compound, a coupling reaction using a Grignard reagent, or the like can be employed.

In Synthesis Scheme (s-1) above, $B^1$ in Compound 1 represents a precursor of a compound not containing deuterium of $A^1$ in Compound 2, and in Synthesis Scheme (s-2) above, $C^1$ in Compound 3 represents a precursor of a compound not containing deuterium of $R^{n1}$ (n1 is 1 to 5) in Compound 4. A deuterated material can be obtained owing to a deuteration reaction of a desired unit.

The organic compound represented by General Formula (G1) can be synthesized in such a manner: as shown in Synthesis Scheme (s-5) below, Compound 7 not containing deuterium for any of $R^1$ to $R^5$ and $A^1$ in General Formula (G1) is a precursor of General Formula (G1), and the precursor is deuterated. However, in this case, it is sometimes difficult that all hydrogen is deuterated, and thus deuteration rate might be lowered. Accordingly, a synthesis method in which each partial structure is deuterated and then a coupling reaction is performed is preferable for improved deuteration rate.

[Chemical Formula 74]

(s-5)

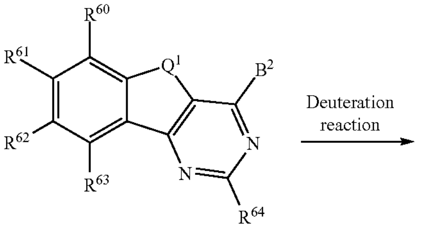

Compound 7

-continued

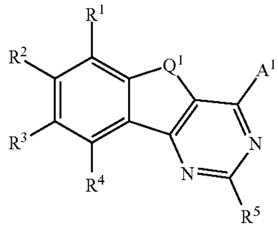

(G1)

$R^{60}$ to $R^{64}$ each independently represent hydrogen, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms.

Examples of a solvent that can be used for the deuteration reaction include benzene-d6, toluene-d8, xylene-d10, DMSO-d6, acetonitrile-d3, and heavy water. However, the solvent that can be used is not limited to these solvents.

Examples of a catalyst that can be used for the deuteration reaction include molybdenum(V) chloride, tungsten(VI) chloride, niobium(V) chloride, tantalum(V) chloride, aluminum(III) chloride, titanium(IV) chloride, and tin(IV) chloride. However, the catalyst that can be used is not limited to these catalysts.

The deuteration reaction may be performed after Synthesis Scheme (s-3) or Synthesis Scheme (s-4).

In the above scheme, in the case where $A^1$ and one of $R^1$ to $R^5$ are the same substituent, when Compound 2 is 2 equivalents with respect to Compound 5 in Synthesis Scheme (s-3), the target organic compound represented by General Formula (G1) can be synthesized by one step. Therefore, Synthesis Scheme (s-4) can be omitted and synthesis cost can be reduced.

In the case where $A^1$ and 2 to 4 of $R^1$ to $R^5$ are the same substituents, when Compound 2 is 3 to 5 equivalents with respect to Compound 5 in Synthesis Scheme (s-3), the target organic compound represented by General Formula (G1) can be synthesized by one step.

Described above is an example of the method for synthesizing the benzofuropyrimidine derivative or the benzothienopyrimidine derivative, which is a compound of one embodiment of the present invention. The present invention is not limited to this example and any other synthesis methods may be employed.

The structures described in this embodiment can be used in combination with any of the structures described in the other embodiments as appropriate.

Embodiment 2

In this embodiment, structures of the light-emitting devices including any of the organic compounds described in Embodiment 1 are described with reference to FIGS. 1A to 1E.

<<Basic Structure of Light-Emitting Device<<

A basic structure of a light-emitting device is described. FIG. 1A illustrates a light-emitting device including, between a pair of electrodes, an EL layer including a light-emitting layer. Specifically, an EL layer 103 is positioned between a first electrode 101 and a second electrode 102.

Figure 1B:
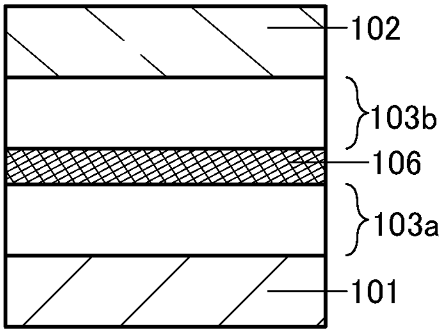

FIG. 1B illustrates a light-emitting device that has a stacked-layer structure (tandem structure) in which a plurality of EL layers (two EL layers 103*a* and 103*b* in FIG. 1B) are provided between a pair of electrodes and a charge-generation layer 106 is provided between the EL layers. A light-emitting device having a tandem structure enables fabrication of a light-emitting apparatus that has high efficiency without changing the amount of current.

The charge-generation layer 106 has a function of injecting electrons into one of the EL layers 103*a* and 103*b* and injecting holes into the other of the EL layers 103*a* and 103*b* when a potential difference is caused between the first electrode 101 and the second electrode 102. Thus, when voltage is applied in FIG. 1B such that the potential of the first electrode 101 is higher than that of the second electrode 102, the charge-generation layer 106 injects electrons into the EL layer 103*a* and injects holes into the EL layer 103*b*.

Note that in terms of light extraction efficiency, the charge-generation layer 106 preferably has a property of transmitting visible light (specifically, the charge-generation layer 106 preferably has a visible light transmittance of 40% or more). The charge-generation layer 106 functions even if it has lower conductivity than the first electrode 101 or the second electrode 102.

Figure 1C:
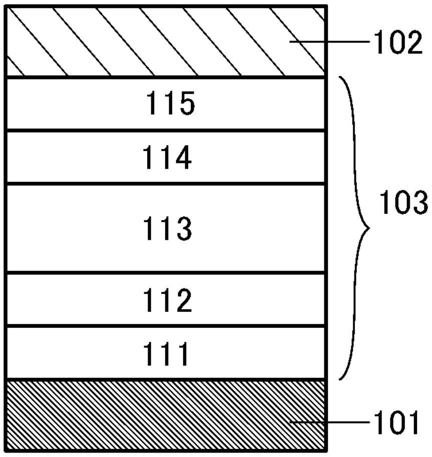

FIG. 1C illustrates a stacked-layer structure of the EL layer 103 in the light-emitting device of one embodiment of the present invention. In this case, the first electrode 101 is regarded as functioning as an anode and the second electrode 102 is regarded as functioning as a cathode. The EL layer 103 has a structure in which a hole-injection layer 111, a hole-transport layer 112, the light-emitting layer 113, an electron-transport layer 114, and an electron-injection layer 115 are stacked in this order over the first electrode 101. Note that the light-emitting layer 113 may have a stacked-layer structure of a plurality of light-emitting layers that emit light of different colors. For example, a light-emitting layer containing a light-emitting substance that emits red light, a light-emitting layer containing a light-emitting substance that emits green light, and a light-emitting layer containing a light-emitting substance that emits blue light may be stacked with or without a layer containing a carrier-transport material therebetween. Alternatively, a light-emitting layer containing a light-emitting substance that emits yellow light and a light-emitting layer containing a light-emitting substance that emits blue light may be used in combination. Note that the stacked-layer structure of the light-emitting layer 113 is not limited to the above. For example, the light-emitting layer 113 may have a stacked-layer structure of a plurality of light-emitting layers that emit light of the same color. For example, a first light-emitting layer containing a light-emitting substance that emits blue light and a second light-emitting layer containing a light-emitting substance that emits blue light may be stacked with or without a layer containing a carrier-transport material therebetween. The structure in which a plurality of light-emitting layers that emit light of the same color are stacked can achieve higher reliability than a single-layer structure in some cases. In the case where a plurality of EL layers are provided as in the tandem structure illustrated in FIG. 1B, the layers in each EL layer are sequentially stacked from the anode side as described above. When the first electrode 101 is the cathode and the second electrode 102 is the anode, the stacking order of the layers in the EL layer 103 is reversed. Specifically, the layer 111 over the first electrode 101 serving as the cathode is an electron-injection layer; the layer 112 is an electron-transport layer; the layer 113 is a light-emitting layer; the layer 114 is a hole-transport layer; and the layer 115 is a hole-injection layer.

The light-emitting layer 113 included in the EL layers (103, 103*a*, and 103*b*) contains an appropriate combination of a light-emitting substance and a plurality of substances, so that fluorescent light of a desired color or phosphorescent light of a desired color can be obtained. The light-emitting layer 113 may have a stacked-layer structure having different emission colors. In that case, light-emitting substances and other substances are different between the stacked light-emitting layers. Alternatively, the plurality of EL layers (103*a* and 103*b*) in FIG. 1B may exhibit their respective emission colors. Also in that case, the light-emitting substances and other substances are different between the stacked light-emitting layers.

The light-emitting device of one embodiment of the present invention can have a micro optical resonator (microcavity) structure when, for example, the first electrode 101 is a reflective electrode and the second electrode 102 is a transflective electrode in FIG. 1C. Thus, light from the light-emitting layer 113 in the EL layer 103 can be resonated between the electrodes and light emitted through the second electrode 102 can be intensified.

Note that when the first electrode 101 of the light-emitting device is a reflective electrode having a stacked-layer structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is λ, the optical path length between the first electrode 101 and the second electrode 102 (the product of the thickness and the refractive index) is preferably adjusted to be $m\lambda/2$ (m is an integer of 1 or more) or close to $m\lambda/2$.

To amplify desired light (wavelength: λ) obtained from the light-emitting layer 113, it is preferable to adjust each of the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) to be $(2m'+1)\lambda/4$ (m' is an integer of 1 or more) or close to $(2m'+1)\lambda/4$. Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer that emits the desired light is, to be exact, the optical path length between the reflective region in the first electrode 101 and the light-emitting region in the light-emitting layer that emits the desired light. However, it is difficult to precisely determine the reflective region in the first electrode 101 and the light-emitting region in the light-emitting layer that emits the desired light; thus, it is assumed that the above effect can be sufficiently obtained wherever the reflective region and the light-emitting region may be set in the first electrode 101 and the light-emitting layer that emits the desired light, respectively.

Figure 1D:
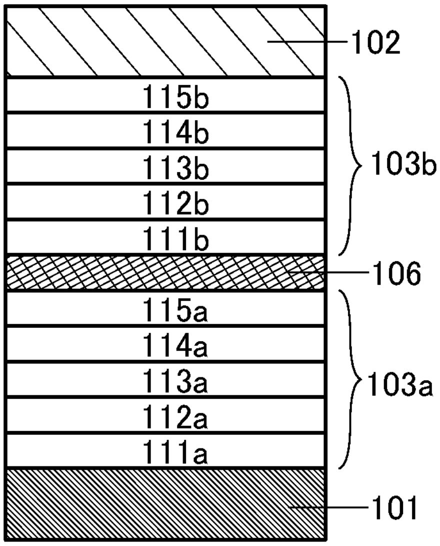

The light-emitting device illustrated in FIG. 1D is a light-emitting device having a tandem structure. Owing to a microcavity structure of the light-emitting device, light (monochromatic light) with different wavelengths from the EL layers (103*a* and 103*b*) can be extracted. Thus, it is unnecessary to separately form EL layers for obtaining a plurality of emission colors (e.g., R, G, and B). Therefore, high resolution can be easily achieved. A combination with coloring layers (color filters) is also possible. Furthermore, the emission intensity of light with a specific wavelength in the front direction can be increased, whereby power consumption can be reduced.

Figure 1E:
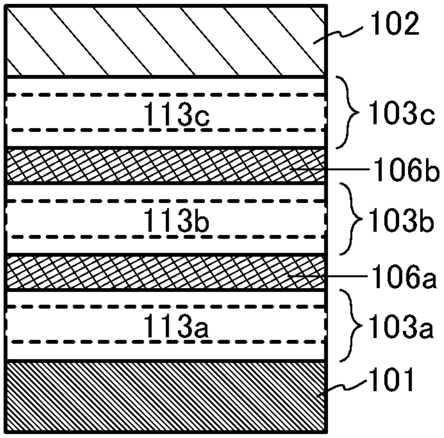

The light-emitting device illustrated in FIG. 1E is an example of the light-emitting device having the tandem structure illustrated in FIG. 1B, and includes three EL layers (103*a*, 103*b*, and 103*c*) stacked with charge-generation layers (106*a* and 106*b*) positioned therebetween, as illustrated in FIG. 1E. The three EL layers (103*a*, 103*b*, and 103*c*) include respective light-emitting layers (113*a*, 113*b*, and 113*c*), and the emission colors of the light-emitting layers can be selected freely. For example, the light-emitting layer 113*a* can emit blue light, the light-emitting layer 113*b* can emit red light, green light, or yellow light, and the light-emitting layer 113*c* can emit blue light, or the light-emitting layer 113*a* can emit red light, the light-emitting layer 113*b* can emit blue light, green light, or yellow light, and the light-emitting layer 113*c* can emit red light.

In the light-emitting device of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance higher than or equal to 40%. In the case where the light-transmitting electrode is a transflective electrode, the transflective electrode has a visible light reflectance higher than or equal to 20% and lower than or equal to 80%, preferably higher than or equal to 40% and lower than or equal to 70%. These electrodes preferably have a resistivity of $1\times10^{-2}$ Ωcm or less.

When one of the first electrode 101 and the second electrode 102 is a reflective electrode in the light-emitting device of one embodiment of the present invention, the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ Ωcm or less.

<<Specific Structure of Light-Emitting Device>>

Next, a specific structure of the light-emitting device of one embodiment of the present invention will be described. Here, the description is made using FIG. 1D illustrating the tandem structure. Note that the structure of the EL layer applies also to the structure of the light-emitting devices having a single structure in FIGS. 1A and 1C. When the light-emitting device in FIG. 1D has a microcavity structure, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103*b*, with the use of a material selected as appropriate.

<First Electrode and Second Electrode>

As materials for the first electrode 101 and the second electrode 102, any of the following materials can be used in an appropriate combination as long as the above functions of the electrodes can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), magnesium (Mg), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table that is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

In the light-emitting device in FIG. 1D, when the first electrode 101 is the anode, a hole-injection layer 111*a* and a hole-transport layer 112*a* of the EL layer 103*a* are sequentially stacked over the first electrode 101 by a vacuum evaporation method. After the EL layer 103*a* and the charge-generation layer 106 are formed, a hole-injection layer 111*b* and a hole-transport layer 112*b* of the EL layer 103*b* are sequentially stacked over the charge-generation layer 106 in a similar manner.

<Hole-Injection Layer>

The hole-injection layers (111, 111*a*, and 111*b*) inject holes from the first electrode 101 serving as the anode and the charge-generation layers (106, 106*a*, and 106*b*) to the EL layers (103, 103*a*, and 103*b*) and contain an organic acceptor material or a material having a high hole-injection property.

The organic acceptor material allows holes to be generated in another organic compound whose HOMO level is close to the LUMO level of the organic acceptor material when charge separation is caused between the organic acceptor material and the organic compound. Thus, as the organic acceptor material, a compound having an electron-withdrawing group (e.g., a halogen group or a cyano group), such as a quinodimethane derivative, a chloranil derivative, and a hexaazatriphenylene derivative, can be used. Examples of the organic acceptor material include 7,7,8,8-tetracyano-2,3,5,6-tetrafluoroquinodimethane (abbreviation: $F_4$-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), and 2-(7-dicyanomethylene-1,3,4,5,6,8,9,10-octafluoro-7H-pyren-2-ylidene)malononitrile. Note that among organic acceptor materials, a compound in which electron-withdrawing groups are bonded to fused aromatic rings each having a plurality of heteroatoms, such as HAT-CN, is particularly preferred because it has a high acceptor property and stable film quality against heat. Besides, a [3]radialene derivative having an electron-withdrawing group (particularly a cyano group or a halogen group such as a fluoro group), which has a very high electron-accepting property, is preferred; specific examples include α,α',α"-1,2,3-cyclopropanetriylidenetris[4-cyano-2, 3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile].

As the material having a high hole-injection property, an oxide of a metal belonging to Group 4 to Group 8 in the periodic table (e.g., a transition metal oxide such as molybdenum oxide, vanadium oxide, ruthenium oxide, tungsten oxide, or manganese oxide) can be used. Specific examples include molybdenum oxide, vanadium oxide, niobium oxide, tantalum oxide, chromium oxide, tungsten oxide, manganese oxide, and rhenium oxide. Among these oxides, molybdenum oxide is preferable because it is stable in the air, has a low hygroscopic property, and is easily handled. Other examples are phthalocyanine (abbreviation: $H_2Pc$), a phthalocyanine-based compound such as copper phthalocyanine (abbreviation: CuPc), and the like.

Other examples are aromatic amine compounds, which are low-molecular compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples are high-molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl) methacrylamide] (abbreviation: PTPDMA), and poly[N,N'-bis(4-butylphenyl)-N,N'-bis(phenyl)benzidine] (abbreviation: Poly-TPD). Alternatively, it is possible to use a high-molecular compound to which acid is added, such as poly(3,4-ethylenedioxythiophene)/polystyrenesulfonic acid (abbreviation: PEDOT/PSS) or polyaniline/polystyrenesulfonic acid (abbreviation: PAni/PSS), for example.

As the material having a high hole-injection property, a mixed material containing a hole-transport material and the above-described organic acceptor material (electron-accepting material) can be used. In that case, the organic acceptor material extracts electrons from the hole-transport material, so that holes are generated in the hole-injection layer 111 and the holes are injected into the light-emitting layer 113 through the hole-transport layer 112. Note that the hole-injection layer 111 may be formed to have a single-layer structure using a mixed material containing a hole-transport material and an organic acceptor material (electron-accepting material), or a stacked-layer structure of a layer containing a hole-transport material and a layer containing an organic acceptor material (electron-accepting material).

The hole-transport material preferably has a hole mobility higher than or equal to $1\times10^{-6}$ $cm^2/Vs$ in the case where the square root of the electric field strength [V/cm] is 600. Note that other substances can also be used as long as the substances have hole-transport properties higher than electron-transport properties.

As the hole-transport material, materials having a high hole-transport property, such as a compound having a π-electron rich heteroaromatic ring (e.g., a carbazole derivative, a furan derivative, and a thiophene derivative) and an aromatic amine (an organic compound having an aromatic amine skeleton), are preferable. The compound in Embodiment 1 has a hole-transport property and thus can be used as a hole-transport material.

Examples of the carbazole derivative (an organic compound having a carbazole ring) include a bicarbazole derivative (e.g., a 3,3'-bicarbazole derivative) and an aromatic amine having a carbazolyl group.

Specific examples of the bicarbazole derivative (e.g., a 3,3'-bicarbazole derivative) include 3,3'-bis(9-phenyl-9H-carbazole) (abbreviation: PCCP), 9,9'-bis(biphenyl-4-yl)-3,3'-bi-9H-carbazole (abbreviation: BisBPCz), 9,9'-bis(1,1'-biphenyl-3-yl)-3,3'-bi-9H-carbazole (abbreviation: BismBPCz), 9-(1,1'-biphenyl-3-yl)-9'-(1,1'-biphenyl-4-yl)-9H,9'H-3,3'-bicarbazole (abbreviation: mBPCCBP), and 9-(2-naphthyl)-9'-phenyl-9H,9'H-3,3'-bicarbazole (abbreviation: PNCCP).

Specific examples of the aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), N-[4-(9-phenyl-9H-carbazol-3-yl)phenyl]-bis(9,9-dimethyl-9H-fluoren-2-yl)amine (abbreviation: PCBFF), N-(1,1'-biphenyl-4-yl)-N-[4-(9-phenyl-9H-carbazol-3-yl)phenyl]-9,9-dimethyl-9H-fluoren-4-amine, N-[4-(9-phenyl-9H-carbazol-3-yl)phenyl]-(9,9-dimethyl-9H-fluoren-2-yl)-9,9-dimethyl-9H-fluoren-4-amine, N-(1,1'-biphenyl-4-yl)-N-[4-(9-phenyl-9H-carbazol-3-yl)phenyl]-9,9-diphenyl-9H-fluoren-2-amine, N-(1,1'-biphenyl-4-yl)-N-[4-(9-phenyl-9H-carbazol-3-yl)phenyl]-9,9-diphenyl-9H-fluoren-4-amine, N-(1,1'-biphenyl-4-yl)-N-[4-(9-phenyl-9H-carbazol-3-yl)phenyl]-9,9'-spirobi(9H-fluoren)-2-amine, N-(1,1'-biphenyl-4-yl)-N-[4-(9-phenyl-9H-carbazol-3-yl)phenyl]-9,9'-spirobi(9H-fluoren)-4-amine, N-[4-(9-phenyl-9H-carbazol-3-yl)phenyl]-N-[1,1':3',1"-terphenyl-4-yl]-9,9-dimethyl-9H-fluoren-2-amine, N-[4-(9-phenyl-9H-carbazol-3-yl)phenyl]-N-[1,1': 4,1"-terphenyl-4-yl]-9,9-dimethyl-9H-fluoren-2-amine, N-[4-(9-phenyl-9H-carbazol-3-yl)phenyl]-N-[1,1':3',1"-terphenyl-4-yl]-9,9-dimethyl-9H-fluoren-4-amine, N-[4-(9-phenyl-9H-carbazol-3-yl)phenyl]-N-[1,1:4',1"-terphenyl-4-yl]-9,9-dimethyl-9H-fluoren-4-amine, 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl) triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N,N"-triphenyl-N,N',N"-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenylcarbazole (abbreviation: PCzPCAT), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl) amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4"-tris(carbazol-9-yl)triphenylamine (abbreviation: TCTA).

Other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the furan derivative (an organic compound having a furan ring) include 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Specific examples of the thiophene derivative (an organic compound having a thiophene ring) include 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV).

Specific examples of the aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[V-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]spiro-9,9'-bifluorene (abbreviation: DPA2SF), 4,4',4"-tris[N-(1-naphthyl)-N-phenylamino]triphenylamine (abbreviation: 1'-TNATA), 4,4',4"-tris(N,N'-diphenylamino)triphenylamine (abbreviation: TDATA), 4,4',4"-tris[N-(3-methylphenyl)-N-phenylamino]triphenylamine (abbreviation: m-MTDATA), N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), N-(4-biphenyl)-6,N-diphenylbenzo[b]naphtho[1,2-d]furan-8-amine (abbreviation: BnfABP), N,N'-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N'-bis(4-biphenyl)benzo[b]naphtho[1,2-d]furan-6-amine (abbreviation: BBABnf(6)), N,N'-bis(4-biphenyl)benzo[b]naphtho[1,2-d]furan-8-amine (abbreviation: BBABnf(8)), N,N'-bis(4-biphenyl)benzo[b]naphtho[2,3-d]furan-4-amine (abbreviation: BBABnf(II)(4)), N,N'-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6; 1'-binaphthyl-2-yl)triphenylamine (abbreviation: BBAαNβNB), 4,4'-diphenyl-4"-(7; 1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6; 2'-binaphthyl-2-yl)triphenylamine (abbreviation: BBA(βN2)B), 4,4'-diphenyl-4"-(7; 2'-binaphthyl-2-yl)triphenylamine (abbreviation: BBA(βN2)B-03), 4,4'-diphenyl-4"-(4; 2'-binaphthyl-1-yl)triphenylamine (abbreviation: BBAβNαNB), 4,4'-diphenyl-4"-(5; 2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)-triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazol-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N'-bis([1,1'-biphenyl]-4-yl)-9,9'-spirobi[9H-fluoren]-2-amine (abbreviation: BBASF), N,N'-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-[4-(9-phenylfluoren-9-yl)phenyl]triphenylamine (abbreviation: BPAFLBi), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)-9,9'-spirobi-9H-fluoren-2-amine, and N,N-bis(9,9-dimethyl-9H-fluoren-2-yl)-9,9'-spirobi-9H-fluoren-1-amine.

Other examples of the hole-transport material include high-molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide](abbreviation: PTPDMA), and poly[N,N'-bis(4-butylphenyl)-N,N'-bis(phenyl)benzidine](abbreviation: Poly-TPD). Alternatively, it is possible to use a high-molecular compound to which acid is added, such as poly(3,4-ethylenedioxythiophene)/polystyrenesulfonic acid (abbreviation: PEDOT/PSS) or polyaniline/polystyrenesulfonic acid (abbreviation: PAni/PSS), for example.

Note that the hole-transport material is not limited to the above examples, and any of a variety of known materials may be used alone or in combination as the hole-transport material.

The hole-injection layers (111, 111*a*, and 11*b*) can be formed by any of known film formation methods such as a vacuum evaporation method.

<Hole-Transport Layer>

The hole-transport layers (112, 112*a*, and 112*b*) transport the holes, which are injected from the first electrodes 101 by the hole-injection layers (111, 111*a*, and 111*b*), to the light-emitting layers (113, 113*a*, and 113*b*). Note that the hole-transport layers (112, 112*a*, and 112*b*) each contain a hole-transport material. Thus, the hole-transport layers (112, 112*a*, and 112*b*) can be formed using hole-transport materials that can be used for the hole-injection layers (111, 111*a*, and 111*b*).

Note that in the light-emitting device of one embodiment of the present invention, the organic compound used for the hole-transport layers (112, 112*a*, and 112*b*) can also be used for the light-emitting layers (113, 113*a*, and 113*b*). The use of the same organic compound for the hole-transport layers (112, 112*a*, and 112*b*) and the light-emitting layers (113, 113*a*, and 113*b*) is preferable, in which case holes can be efficiently transported from the hole-transport layers (112, 112*a*, and 112*b*) to the light-emitting layers (113, 113*a*, and 113*b*).

<Light-Emitting Layer>

The light-emitting layers (113, 113*a*, and 113*b*) contain a light-emitting substance. Note that as a light-emitting substance that can be used in the light-emitting layers (113, 113*a*, and 113*b*), a substance whose emission color is blue, violet, bluish violet, green, yellowish green, yellow, orange, red, or the like can be used as appropriate. When a plurality of light-emitting layers are provided, the use of different light-emitting substances for the light-emitting layers enables a structure that exhibits different emission colors (e.g., white light emission obtained by a combination of complementary emission colors). Furthermore, one light-emitting layer may have a stacked-layer structure including different light-emitting substances.

The light-emitting layers (113, 113*a*, and 113*b*) may each contain one or more kinds of organic compounds (e.g., a host material) in addition to a light-emitting substance (a guest material).

In the case where a plurality of host materials are used in the light-emitting layers (113, 113*a*, and 113*b*), a second host material that is additionally used is preferably a substance having a larger energy gap than those of a known guest material and a first host material. Preferably, the lowest singlet excitation level (S1 level) of the second host material is higher than that of the first host material, and the lowest triplet excitation level (T1 level) of the second host material is higher than that of the guest material. Preferably, the lowest triplet excitation level (T1 level) of the second host material is higher than that of the first host material. With such a structure, an exciplex can be formed by the two kinds of host materials. To form an exciplex efficiently, it is particularly preferable to combine a compound that easily accepts holes (hole-transport material) and a compound that easily accepts electrons (electron-transport material). With the above structure, high efficiency, low voltage, and a long lifetime can be achieved at the same time.

As an organic compound used as the host material (including the first host material and the second host material), organic compounds such as the hole-transport materials usable for the hole-transport layers (112, 112*a*, and 112*b*) described above and electron-transport materials usable for electron-transport layers (114, 114*a*, and 114*b*) described later can be used as long as they satisfy requirements for the host material used in the light-emitting layer. Another example is an exciplex formed by two or more kinds of organic compounds (the first host material and the second host material). An exciplex whose excited state is formed by two or more kinds of organic compounds has an extremely small difference between the S1 level and the T1 level and functions as a TADF material capable of converting triplet excitation energy into singlet excitation energy. In an example of a preferred combination of two or more kinds of organic compounds forming an exciplex, one compound of the two or more kinds of organic compounds has a π-electron deficient heteroaromatic ring and the other compound has a π-electron rich heteroaromatic ring. A phosphorescent substance such as an iridium-, rhodium-, or platinum-based organometallic complex or a metal complex may be used as one compound of the combination for forming an exciplex. The organic compound described in Embodiment 1 has an electron-transport property and thus can be efficiently used as the first host material. Furthermore, since the organic compound has a hole-transport property, it can be used as the second host material.

There is no particular limitation on the light-emitting substances that can be used for the light-emitting layers (113, 113*a*, and 113*b*), and a light-emitting substance that converts singlet excitation energy into light in the visible light range or a light-emitting substance that converts triplet excitation energy into light in the visible light range can be used.

<<Light-Emitting Substance that Converts Singlet Excitation Energy into Light>>

The following substances that emit fluorescent light (fluorescent substances) can be given as examples of the light-emitting substance that converts singlet excitation energy into light and can be used in the light-emitting layers (113, 113*a*, and 113*b*): a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPrn), N,N'-(pyrene-1,6-diyl)bis[(N-phenylbenzo[b]naphtho[1,2-d]furan)-8-amine](abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use, for example, 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra-tert-butylperylene (abbreviation: TBP), N,N'-(2-tert-butylanthracene-9,10-diyldi-4,1-phenylene)bis[N,N',N''-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), and N-[4-(9,10-diphenyl-2-anthryl)phenyl]-N,N',N''-triphenyl-1,4-phenylenediamine (abbreviation: 2DPAPPA).

It is also possible to use, for example, N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), 1,6BnfAPm-03, 3,10-bis[N-(9-phenyl-9H-carbazol-2-yl)-N-phenylamino]naphtho[2,3-b; 6,7-b']bisbenzofuran (abbreviation: 3,10PCA2Nbf(IV)-02), and 3,10-bis[N-(dibenzofuran-3-yl)-N-phenylamino]naphtho[2,3-b; 6,7-b']bisbenzofuran (abbreviation: 3,10FrA2Nbf(IV)-02). In particular, pyrenediamine compounds such as 1,6FLPAPrn, 1,6mMemFLPAPrn, and 1,6BnfAPrn-03 can be used, for example.

<<Light-Emitting Substance that Converts Triplet Excitation Energy into Light>>

Examples of the light-emitting substance that converts triplet excitation energy into light and can be used in the light-emitting layer 113 include substances that emit phosphorescent light (phosphorescent substances) and thermally activated delayed fluorescent (TADF) materials that exhibit thermally activated delayed fluorescence.

A phosphorescent substance is a compound that emits phosphorescent light but does not emit fluorescent light at a temperature higher than or equal to a low temperature (e.g., 77 K) and lower than or equal to room temperature (i.e., higher than or equal to 77 K and lower than or equal to 313 K). The phosphorescent substance preferably contains a metal element with large spin-orbit interaction, and can be an organometallic complex, a metal complex (platinum complex), or a rare earth metal complex, for example. Specifically, the phosphorescent substance preferably contains a transition metal element. It is preferable that the phosphorescent substance contain a platinum group element (ruthenium (Ru), rhodium (Rh), palladium (Pd), osmium (Os), iridium (Ir), or platinum (Pt)), especially iridium, in which case the probability of direct transition between the singlet ground state and the triplet excited state can be increased.

<<Phosphorescent Substance (from 450 nm to 570 nm: Blue or Green)>>

As examples of a phosphorescent substance which emits blue or green light and whose emission spectrum has a peak wavelength of greater than or equal to 450 nm and less than or equal to 570 nm, the following substances can be given.

Examples include organometallic complexes having a 4H-triazole ring, such as tris{2-[5-(2-methylphenyl)-4-(2,6-dimethylphenyl)-4H-1,2,4-triazol-3-yl-κ$N^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole ring, such as tris[3-methyl-1-(2-methylphenyl)-5-phenyl-TH-1,2,4-triazolato]iridium(III) (abbreviation: [Ir(Mptzl-mp)$_3$]) and tris(1-methyl-5-phenyl-3-propyl-TH-1,2,4-triazolato)iridium(III) (abbreviation: [Ir(Prptzl-Me)$_3$]); organometallic complexes having an imidazole ring, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: [Ir($CF_3$ppy)$_2$(pic)]), and bis[2-(4',6'-difluorophenyl)pyridinato-N,$C^{2'}$]iridium(III) acetylacetonate (abbreviation: FIr(acac)).

<<Phosphorescent Substance (from 495 nm to 590 nm: Green or Yellow)>>

As examples of a phosphorescent substance which emits green or yellow light and whose emission spectrum has a peak wavelength of greater than or equal to 495 nm and less than or equal to 590 nm, the following substances can be given.

Examples of the phosphorescent substance include organometallic iridium complexes having a pyrimidine ring, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), (acetylacetonato) bis{4,6-dimethyl-2-[6-(2,6-dimethylphenyl)-4-pyrimidinyl-κ$N^3$]phenyl-κC}iridium(III) (abbreviation: $[Ir(dmppm\text{-}dmp)_2(acac)]$), and (acetylacetonato)bis(4,6-diphenylpyrimidinato)iridium(III) (abbreviation: $[Ir(dppm)_2(acac)]$); organometallic iridium complexes having a pyrazine ring, such as (acetylacetonato)bis(3,5-dimethyl-2-phenylpyrazinato)iridium(III) (abbreviation: $[Ir(mppr\text{-}Me)_2(acac)]$) and (acetylacetonato)bis(5-isopropyl-3-methyl-2-phenylpyrazinato)iridium(III) (abbreviation: $[Ir(mppr\text{-}iPr)_2(acac)]$); organometallic iridium complexes having a pyridine ring, such as tris(2-phenylpyridinato-N,$C^{2'}$)iridium (III) (abbreviation: $[Ir(ppy)_3]$), bis(2-phenylpyridinato-N,$C^{2'}$)iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), tris(2-phenylquinolinato-N,$C^{2'}$)iridium(III) (abbreviation: $[Ir(pq)_3]$), bis(2-phenylquinolinato-N,$C^{2'}$)iridium(III) acetylacetonate (abbreviation: $[Ir(pq)_2(acac)]$), bis[2-(2-pyridinyl-κN)phenyl-κC][2-(4-phenyl-2-pyridinyl-κN)phenyl-κC]iridium(III) (abbreviation: $[Ir(ppy)_2(4dppy)]$), bis[2-(2-pyridinyl-κN)phenyl-κC][2-(4-methyl-5-phenyl-2-pyridinyl-κN)phenyl-κC], [2-d3-methyl-8-(2-pyridinyl-κN)benzofuro[2,3-b]pyridine-κC]bis[2-(5-d3-methyl-2-pyridinyl-κ$N^2$)phenyl-κC]iridium(III) (abbreviation: $[Ir(5mppy\text{-}d3)_2(mbfpypy\text{-}d3)]$), [2-(methyl-d3)-8-[4-(1-methylethyl-1-d)-2-pyridinyl-MN]benzofuro[2,3-b]pyridin-7-yl-κC]bis[5-(methyl-d3)-2-[5-(methyl-d3)-2-pyridinyl-κN]phenyl-κC]iridium(III) (abbreviation: $Ir(5mtpy\text{-}d6)_2(mbfpypy\text{-}iPr\text{-}d4)$), [2-d3-methyl-(2-pyridinyl-κN) benzofuro[2,3-b]pyridine-κC]bis[2-(2-pyridinyl-N)phenyl-κC]iridium(III) (abbreviation: $Ir(ppy)_2(mbfpypy\text{-}d3)$), and [2-(4-methyl-5-phenyl-2-pyridinyl-κN)phenyl-κC]bis[2-(2-pyridinyl-κN)phenyl-κC]iridium(III) (abbreviation: $Ir(ppy)_2(mdppy)$); organometallic complexes such as bis(2,4-diphenyl-1,3-oxazolato-N,$C^{2'}$)iridium(III) acetylacetonate (abbreviation: $[Ir(dpo)_2(acac)]$), bis{2-[4'-(perfluorophenyl) phenyl]pyridinato-N,$C^{2'}$}iridium(III) acetylacetonate (abbreviation: $[Ir(p\text{-}PF\text{-}ph)_2(acac)]$), and bis(2-phenylbenzothiazolato-N,$C^{2'}$)iridium(III) acetylacetonate (abbreviation: $[Ir(bt)_2(acac)]$); and a rare earth metal complex such as tris (acetylacetonato) (monophenanthroline)terbium(III) (abbreviation: $[Tb(acac)_3(Phen)]$).

<<Phosphorescent Substance (from 570 nm to 750 nm: Yellow or Red)>>

As examples of a phosphorescent substance which emits yellow or red light and whose emission spectrum has a peak wavelength of greater than or equal to 570 nm and less than or equal to 750 nm, the following substances can be given.

Examples of a phosphorescent substance include organometallic complexes having a pyrimidine ring, such as (diisobutyrylmethanato)bis[4,6-bis(3-methylphenyl)pyrimidinato]iridium(III) (abbreviation: $[Ir(5mdppm)_2(dibm)]$), bis[4,6-bis(3-methylphenyl)pyrimidinato](dipivaloylmethanato)iridium(III) (abbreviation: $[Ir(5mdppm)_2(dpm)]$), and (dipivaloylmethanato)bis[4,6-di(naphthalen-1-yl)pyrimidinato]iridium(III) (abbreviation: $[Ir(dlnpm)_2(dpm)]$); organometallic complexes having a pyrazine ring, such as (acetylacetonato)bis(2,3,5-triphenylpyrazinato)iridium(III) (abbreviation: $[Ir(tppr)_2(acac)]$), bis(2,3,5-triphenylpyrazinato)(dipivaloylmethanato)iridium (III) (abbreviation: $[Ir(tppr)_2(dpm)]$), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: $[Ir(dmdppr\text{-}P)_2(dibm)]$), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: $[Ir(dmdppr\text{-}dmCP)_2(dpm)]$), bis[2-(5-(2,6-dimethylphenyl)-3-(3,5-dimethylphenyl)-2-pyrazinyl-κN)-4,6-dimethylphenyl-κC](2,2',6,6'-tetramethyl-3,5-heptanedionato-κ$^2$O,O')iridium (III) (abbreviation: $[Ir(dmdppr\text{-}dmp)_2(dpm)]$), (acetylacetonato)bis[2-methyl-3-phenylquinoxalinato-N,$C^{2'}$]iridium(III) (abbreviation: $[Ir(mpq)_2(acac)]$), (acetylacetonato)bis(2,3-diphenylquinoxalinato-N,$C^{2'}$)iridium(III) (abbreviation: $[Ir(dpq)_2(acac)]$), and (acetylacetonato)bis[2,3-bis(4-fluorophenyl)quinoxalinato]iridium(III) (abbreviation: $[Ir(Fdpq)_2(acac)]$); organometallic complexes having a pyridine ring, such as tris(1-phenylisoquinolinato-N,$C^{2'}$) iridium(III) (abbreviation: $[Ir(piq)_3]$), bis(1-phenylisoquinolinato-N,$C^{2'}$)iridium(III) acetylacetonate (abbreviation: $[Ir(piq)_2(acac)]$), and bis[4,6-dimethyl-2-(2-quinolinyl-κN) phenyl-κC](2,4-pentanedionato-κ$^2$O,O')iridium(III) (abbreviation: $[Ir(dmpqn)_2(acac)]$); a platinum complex such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato) (monophenanthroline)europium(III) (abbreviation: $[Eu(DBM)_3(Phen)]$) and tris[1-(2-thenoyl)-3,3,3-trifluoroacetonato](monophenanthroline)europium(III) (abbreviation: $[Eu(TTA)_3(Phen)]$).

<<TADF Material>>

Any of materials described below can be used as the TADF material. The TADF material is a material that has a small difference between its S1 and T1 levels (preferably less than or equal to 0.2 eV), enables up-conversion of a triplet excited state into a singlet excited state (i.e., reverse intersystem crossing) using a little thermal energy, and efficiently exhibits light (fluorescent light) from the singlet excited state. The thermally activated delayed fluorescence is efficiently obtained under the condition where the difference in energy between the triplet excitation level and the singlet excitation level is greater than or equal to 0 eV and less than or equal to 0.2 eV, preferably greater than or equal to 0 eV and less than or equal to 0.1 eV. Note that delayed fluorescent light by the TADF material refers to light emission having a spectrum similar to that of normal fluorescent light and an extremely long lifetime. The lifetime is longer than or equal to $1\times10^{-6}$ seconds, or longer than or equal to $1\times10^{-3}$ seconds. In addition, the organic compound described in Embodiment 1 can be used.

Note that the TADF material can be also used as an electron-transport material, a hole-transport material, or a host material.

Examples of the TADF material include fullerene, a derivative thereof, an acridine derivative such as proflavine, and eosin. Other examples thereof include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

[Chemical Formula 75]

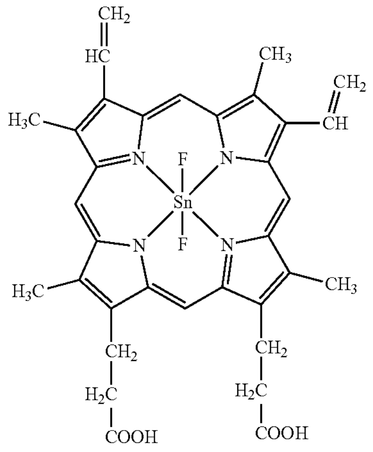

$SnF_2$(Proto IX)

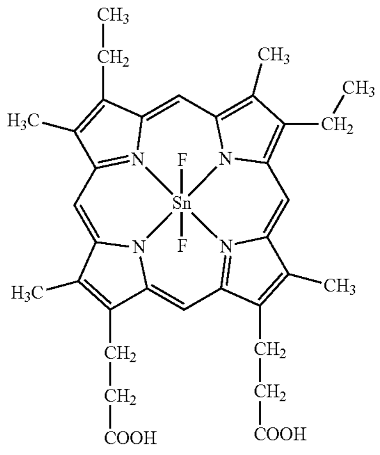

$SnF_2$(Meso IX)

-continued

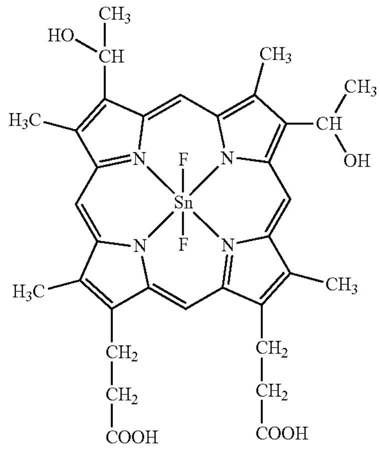

$SnF_2$(Hemato IX)

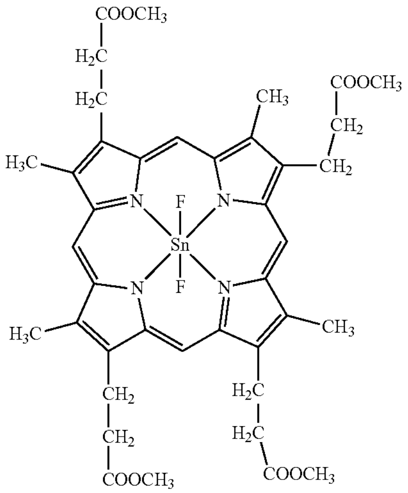

$SnF_2$(Copro III-4Me)

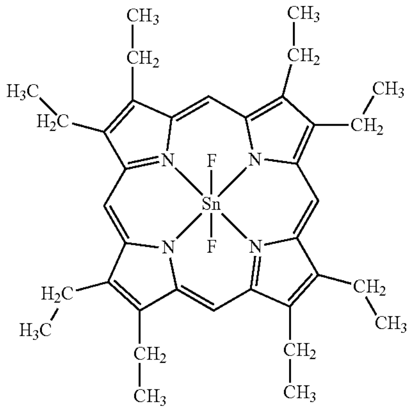

$SnF_2$(OEP)

-continued

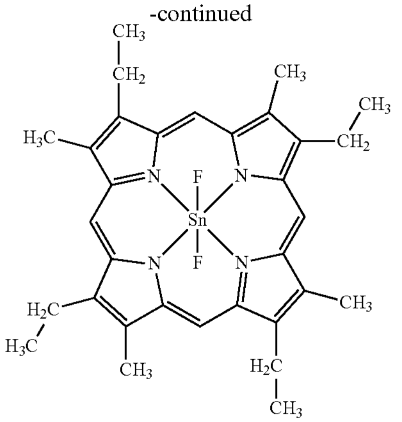

$SnF_2$(Etio I)

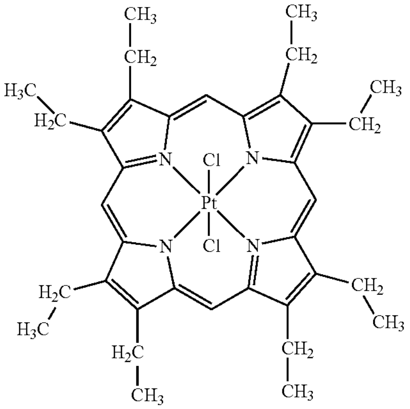

$PtCl_2OEP$

Additionally, a heteroaromatic compound having a π-electron rich heteroaromatic compound and a π-electron deficient heteroaromatic compound, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), or 9-[3-(4,6-diphenyl-1,3,5-triazin-2-yl)phenyl]-9'-phenyl-2,3'-bi-9H-carbazole (abbreviation: mPCCzPTzn-02) may be used.

Note that a substance in which a π-electron rich heteroaromatic compound is directly bonded to a π-electron deficient heteroaromatic compound is particularly preferable because both the donor property of the π-electron rich heteroaromatic compound and the acceptor property of the π-electron deficient heteroaromatic compound are improved and the energy difference between the singlet excited state and the triplet excited state becomes small. As the TADF material, a TADF material in which the singlet and triplet excited states are in thermal equilibrium (TADF100) may be used. Since such a TADF material enables a short emission lifetime (excitation lifetime), the efficiency of a light-emitting device in a high-luminance region can be less likely to decrease.

[Chemical Formula 76]

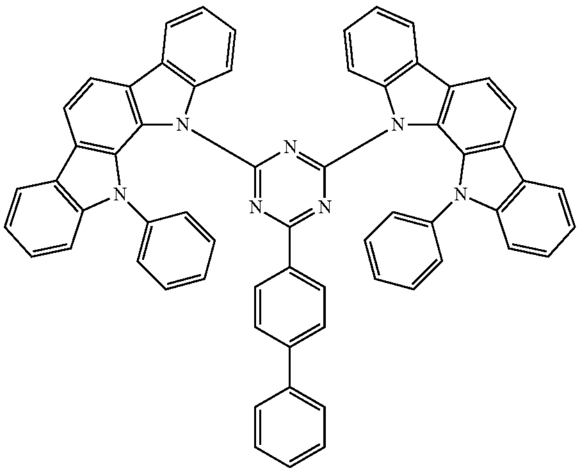

PIC-TRZ

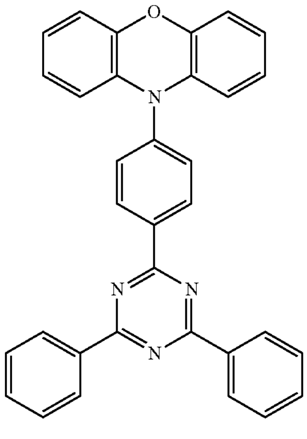

PXZ-TRZ

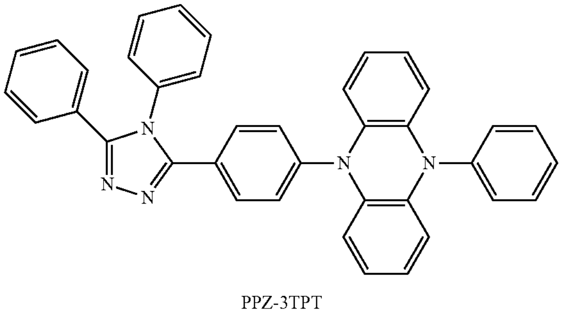

PPZ-3TPT

-continued

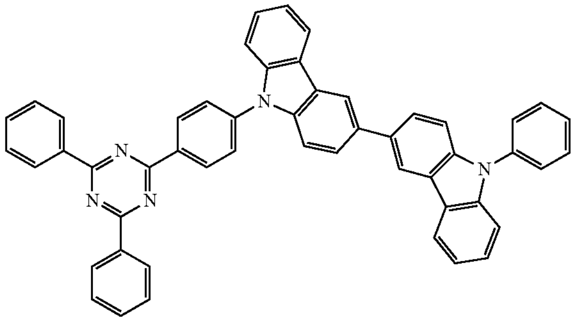

PCCzPTzn

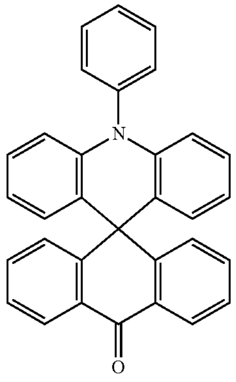

ACRSA

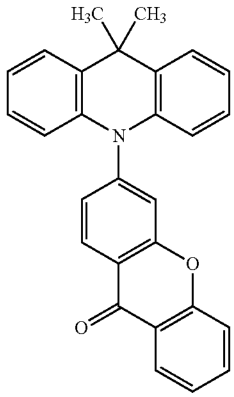

ACRXTN

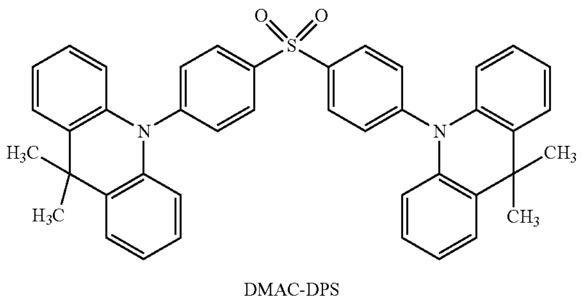

DMAC-DPS

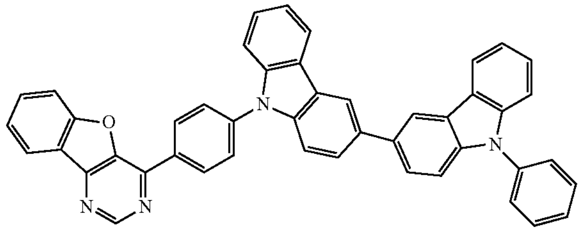

4PCCzPBfpm

-continued

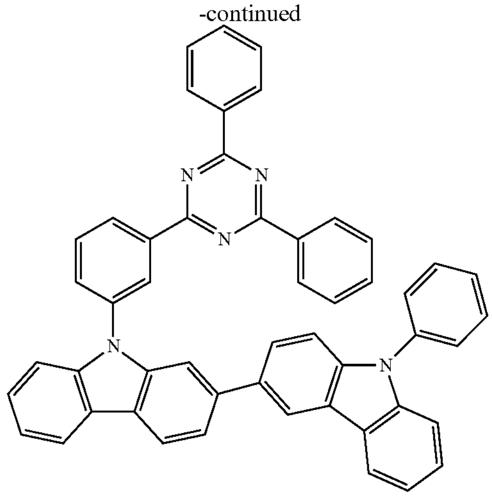

mPCCzPTzn-02

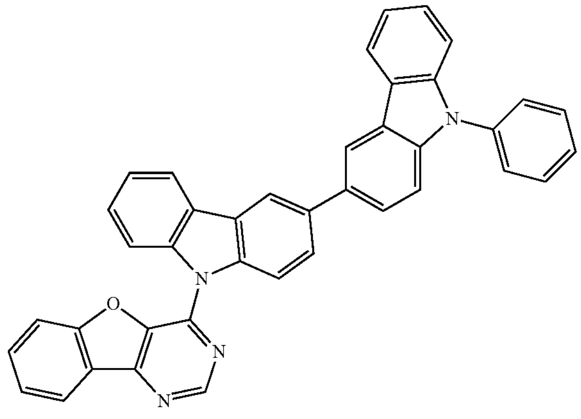

4PCCzBfpm

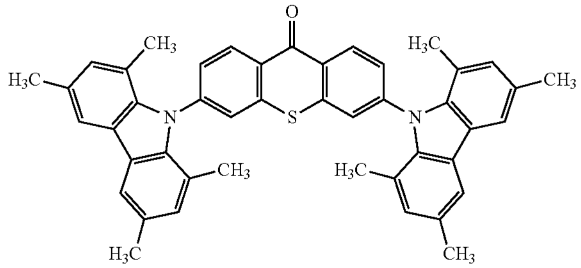

TADF100

In addition to the above, another example of a material having a function of converting triplet excitation energy into light is a nano-structure of a transition metal compound having a perovskite structure. In particular, a nano-structure of a metal halide perovskite material is preferable. The nano-structure is preferably a nanoparticle or a nanorod.

As the organic compound (e.g., the host material) used in combination with the above-described light-emitting substance (guest material) in the light-emitting layers (113, 113*a*, 113*b*, and 113*c*), one or more kinds selected from substances having a larger energy gap than the light-emitting substance (guest material) can be used.

<<Host Material for Fluorescent Light>>

In the case where the light-emitting substance used in the light-emitting layers (113, 113*a*, 113*b*, and 113*c*) is a fluorescent substance, an organic compound (host material) used in combination with the fluorescent substance is preferably an organic compound that has a high energy level in a singlet excited state and has a low energy level in a triplet excited state or an organic compound having a high fluorescence quantum yield. Therefore, the hole-transport material (described above) and the electron-transport material (described below) shown in this embodiment, for example, can be used as long as they are organic compounds that satisfy such a condition. In addition, the organic compound described in Embodiment 1 can be used.

In terms of a preferred combination with the light-emitting substance (fluorescent substance), examples of the organic compound (host material), some of which overlap the above specific examples, include fused polycyclic aromatic compounds such as an anthracene derivative, a tetracene derivative, a phenanthrene derivative, a pyrene derivative, a chrysene derivative, and a dibenzo[g,p] chrysene derivative.

Specific examples of the organic compound (host material) that is preferably used in combination with the fluorescent substance include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N,N'-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N,N,N,",N",N",N"-octaphenyldibenzo[g,p] chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d] furan (abbreviation: 2mBnfPPA), 9-phenyl-10-{4-(9-phenyl-9H-fluoren-9-yl)biphenyl-4'-yl}anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9-(1-naphthyl)-10-(2-naphthyl)anthracene (abbreviation: α,β-ADN), 2-(10-phenylanthracen-9-yl)dibenzofuran, 2-(10-phenyl-9-anthracenyl)-benzo[b]naphtho[2,3-d]furan (abbreviation: Bnf(II)PhA), 9-(1-naphthyl)-10-[4-(2-naphthyl)phenyl]anthracene (abbreviation: αN-PNPAnth), 2,9-di(1-naphthyl)-10-phenylanthracene (abbreviation: 2αN-αNPhA), 9-(1-naphthyl)-10-[3-(1-naphthyl)phenyl]anthracene (abbreviation: αN-mαNPAnth), 9-(2-naphthyl)-10-[3-(1-naphthyl)phenyl]anthracene (abbreviation: PN-mαNPAnth), 9-(1-naphthyl)-10-[4-(1-naphthyl)phenyl] anthracene (abbreviation: αN-αNPAnth), 9-(2-naphthyl)-10-[4-(2-naphthyl)phenyl]anthracene (abbreviation: PN-PNPAnth), 2-(1-naphthyl)-9-(2-naphthyl)-10-phenylanthracene (abbreviation: 2αN-PNPhA), 9-(2-naphthyl)-10-[3-(2-naphthyl)phenyl]anthracene (abbreviation: PN-mPNPAnth), 1-[4-(10-[1,1'-biphenyl]-4-yl-9-anthracenyl) phenyl]-2-ethyl-TH-benzimidazole (abbreviation: EtBImPBPhA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

<<Host Material for Phosphorescent Light>>

In the case where the light-emitting substance used in the light-emitting layers (113, 113*a*, 113*b*, and 113*c*) is a phosphorescent substance, an organic compound having triplet excitation energy (an energy difference between a ground state and a triplet excited state) which is higher than that of the light-emitting substance is preferably selected as the organic compound (host material) used in combination with the phosphorescent substance. Note that when a plurality of organic compounds (e.g., a first host material and a second host material (or an assist material)) are used in combination with a light-emitting substance so that an exciplex is formed, the plurality of organic compounds are preferably mixed with the phosphorescent substance. In addition, the organic compound described in Embodiment 1 can be used.

With such a structure, light emission can be efficiently obtained by exciplex-triplet energy transfer (ExTET), which is energy transfer from an exciplex to a light-emitting substance. Note that a combination of the plurality of organic compounds that easily forms an exciplex is preferred, and it is particularly preferable to combine a compound that easily accepts holes (hole-transport material) and a compound that easily accepts electrons (electron-transport material).

In terms of a preferred combination with the light-emitting substance (phosphorescent substance), examples of the organic compounds (the host material and the assist material), some of which overlap the above specific examples, include an aromatic amine (an organic compound having an aromatic amine skeleton), a carbazole derivative (an organic compound having a carbazole ring), a dibenzothiophene derivative (an organic compound having a dibenzothiophene ring), a dibenzofuran derivative (an organic compound having a dibenzofuran ring), an oxadiazole derivative (an organic compound having an oxadiazole ring), a triazole derivative (an organic compound having an triazole ring), a benzimidazole derivative (an organic compound having an benzimidazole ring), a quinoxaline derivative (an organic compound having a quinoxaline ring), a dibenzoquinoxaline derivative (an organic compound having a dibenzoquinoxaline ring), a pyrimidine derivative (an organic compound having a pyrimidine ring), a triazine derivative (an organic compound having a triazine ring), a pyndine derivative (an organic compound having a pyridine ring), a bipyridine derivative (an organic compound having a bipyridine ring), a phenanthroline derivative (an organic compound having a phenanthroline ring), a furodiazine derivative (an organic compound having a furodiazine ring), and zinc- or aluminum-based metal complexes.

Among the above organic compounds, specific examples of the aromatic amine and the carbazole derivative, which are organic compounds having a high hole-transport property, are the same as the specific examples of the hole-transport materials described above, and those materials are preferable as the host material.

Among the above organic compounds, specific examples of the dibenzothiophene derivative and the dibenzofuran derivative, which are organic compounds having a high hole-transport property, include 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl] dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)

phenyl]dibenzothiophene (abbreviation: mDBTPTp-II). Such derivatives are preferable as the host material.

Other examples of preferred host materials include metal complexes having an oxazole-based or thiazole-based ligand, such as bis[2-(2-benzoxazolyl)phenolato]zinc(II) (abbreviation: ZnPBO) and bis[2-(2-benzothiazolyl)phenolato]zinc(II) (abbreviation: ZnBTZ).

Among the above organic compounds, specific examples of the oxadiazole derivative, the triazole derivative, the benzimidazole derivative, the quinoxaline derivative, the dibenzoquinoxaline derivative, the quinazoline derivative, and the phenanthroline derivative, which are organic compounds having a high electron-transport property, include: an organic compound including a heteroaromatic ring having a polyazole ring such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), or 4,4'-bis(5-methylbenzoxazol-2-yl)stilbene (abbreviation: BzOs); an organic compound including a heteroaromatic ring having a pyridine ring such as bathophenanthroline (abbreviation: BPhen), bathocuproine (abbreviation: BCP), 2,9-di(naphthalen-2-yl)-4,7-diphenyl-1,10-phenanthroline (abbreviation: NBPhen); 2-[3-(dibenzothiophen-4-yl)phenyl]dibenzo[f,h]quinoxaline (abbreviation: 2mDBTPDBq-II); 2-[3'-(dibenzothiophen-4-yl)biphenyl-3-yl]dibenzo[f,h]quinoxaline (abbreviation: 2mDBTBPDBq-II); 2-[3'-(9H-carbazol-9-yl)biphenyl-3-yl]dibenzo[f,h]quinoxaline (abbreviation: 2mCzBPDBq); 2-[4-(3,6-diphenyl-9H-carbazol-9-yl)phenyl]dibenzo[f,h]quinoxaline (abbreviation: 2CzPDBq-III); 7-[3-(dibenzothiophen-4-yl)phenyl]dibenzo[f,h]quinoxaline (abbreviation: 7mDBTPDBq-II); 6-[3-(dibenzothiophen-4-yl)phenyl]dibenzo[f,h]quinoxaline (abbreviation: 6mDBTPDBq-II); 2-{4-[9,10-di(2-naphthyl)-2-anthryl]phenyl}-1-phenyl-1H-benzimidazole (abbreviation: ZADN); and 2-4'-(9-phenyl-9H-carbazol-3-yl)-3,1'-biphenyl-1-yl]dibenzo[f,h]quinoxaline (abbreviation: 2mpPCBPDBq). Such organic compounds are preferable as the host material.

Among the above organic compounds, specific examples of the pyridine derivative, the diazine derivative (e.g., the pyrimidine derivative, the pyrazine derivative, and the pyridazine derivative), the triazine derivative, the furodiazine derivative, which are organic compounds having a high electron-transport property, include organic compounds including a heteroaromatic ring having a diazine ring such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 3,5-bis[3-(9H-carbazol-9-yl)phenyl]pyridine (abbreviation: 35DCzPPy), 1,3,5-tri[3-(3-pyridyl)phenyl]benzene (abbreviation: TmPyPB), 9,9'-[pyrimidine-4,6-diylbis(biphenyl-3,3'-diyl)]bis(9H-carbazole) (abbreviation: 4,6mCzBP2Pm), 2-[3'-(9,9-dimethyl-9H-fluoren-2-yl)-1,1'-biphenyl-3-yl]-4,6-diphenyl-1,3,5-triazine (abbreviation: mFBPTzn), 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm), 9-[3'-(dibenzothiophen-4-yl)biphenyl-3-yl]naphtho[1',2': 4,5]furo[2,3-b]pyrazine (abbreviation: 9mDBtBPNfpr), 9-[3'-(dibenzothiophen-4-yl)biphenyl-4-yl]naphtho[1',2': 4,5]furo[2,3-b]pyrazine (abbreviation: 9pmDBtBPNfpr), 11-[3'-(dibenzothiophen-4-yl)biphenyl-3-yl]phenanthro[9',10': 4,5]furo[2,3-b]pyrazine (abbreviation: 11mDBtBPPnfpr), 11-[3'-(dibenzothiophen-4-yl)biphenyl-4-yl]phenanthro[9',10': 4,5]furo[2,3-b]pyrazine, 11-[3'-(9H-carbazol-9-yl)biphenyl-3-yl]phenanthro[9',10': 4,5]furo[2,3-b]pyrazine, 12-(9'-phenyl-3,3'-bi-9H-carbazol-9-yl)phenanthro[9',10': 4,5]furo[2,3-b]pyrazine (abbreviation: 12PCCzPnfpr), 9-[(3'-9-phenyl-9H-carbazol-3-yl)biphenyl-4-yl]naphtho[1',2': 4,5]furo[2,3-b]pyrazine (abbreviation: 9pmPCBPNfpr), 9-(9'-phenyl-3,3'-bi-9H-carbazol-9-yl)naphtho[1',2': 4,5]furo[2,3-b]pyrazine (abbreviation: 9PCCzNfpr), 10-(9'-phenyl-3,3'-bi-9H-carbazol-9-yl)naphtho[1',2': 4,5]furo[2,3-b]pyrazine (abbreviation: 10PCCzNfpr), 9-[3'-(6-phenylbenzo[b]naphtho[1,2-d]furan-8-yl)biphenyl-3-yl]naphtho[1',2': 4,5]furo[2,3-b]pyrazine (abbreviation: 9mBnfBPNfpr), 9-{3-[6-(9,9-dimethylfluoren-2-yl)dibenzothiophen-4-yl]phenyl}naphtho[1',2': 4,5]furo[2,3-b]pyrazine (abbreviation: 9mFDBtPNfpr), 9-[3'-(6-phenyldibenzothiophen-4-yl)biphenyl-3-yl]naphtho[1',2': 4,5]furo[2,3-b]pyrazine (abbreviation: 9mDBtBPNfpr-02), 9-[3-(9'-phenyl-3,3'-bi-9H-carbazol-9-yl)phenyl]naphtho[1',2': 4,5]furo[2,3-b]pyrazine (abbreviation: 9mPCCzPNfpr), 9-{(3'-[2,8-diphenyldibenzothiophen-4-yl)biphenyl-3-yl}naphtho[1',2': 4,5]furo[2,3-b]pyrazine, 11-{(3'-[2,8-diphenyldibenzothiophen-4-yl)biphenyl-3-yl]phenanthro[9',10': 4,5]furo[2,3-b]pyrazine, 5-[3-(4,6-diphenyl-1,3,5-triazin-2-yl)phenyl]-7,7-dimethyl-5H,7H-indeno[2,1-b]carbazole (abbreviation: mINc(II)PTzn), 2-[3'-(triphenylen-2-yl)-1,1'-biphenyl-3-yl]-4,6-diphenyl-1,3,5-triazine (abbreviation: mTpBPTzn), 2-[(1,1'-biphenyl)-4-yl]-4-phenyl-6-[9,9'-spirobi(9H-fluoren)-2-yl]-1,3,5-triazine (abbreviation: BP-SFTzn), 2,6-bis(4-naphthalen-1-ylphenyl)-4-[4-(3-pyridyl)phenyl]pyrimidine (abbreviation: 2,4NP-6PyPPm), 3-[9-(4,6-diphenyl-1,3,5-triazin-2-yl)-2-dibenzofuranyl]-9-phenyl-9H-carbazole (abbreviation: PCDBfTzn), 2-[1,1'-biphenyl]-3-yl-4-phenyl-6-(8-[1,1':4',1''-terphenyl]-4-yl-1-dibenzofuranyl)-1,3,5-triazine (abbreviation: mBP-TPDBfTzn), 6-(1,1'-biphenyl-3-yl)-4-[3,5-bis(9H-carbazol-9-yl)phenyl)-2-phenylpyrimidine (abbreviation: 6mBP-4Cz2PPm), and 4-[3,5-bis(9H-carbazol-9-yl)phenyl]-2-phenyl-6-(1,1'-biphenyl-4-yl)pyrimidine (abbreviation: 6BP-4Cz2PPm), and those materials are preferable as the host material.

Among the above organic compounds, specific examples of metal complexes that are organic compounds having a high electron-transport property include zinc- or aluminum-based metal complexes, such as tris(8-quinolinolato)aluminum(III) (abbreviation: Alq), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), and bis(8-quinolinolato)zinc(II) (abbreviation: Znq), and metal complexes having a quinoline ring or a benzoquinoline ring. Such metal complexes are preferable as the host material.

Moreover, high-molecular compounds such as poly(2,5-pyridinediyl) (abbreviation: PPy), poly[(9,9-dihexylfluorene-2,7-diyl)-co-(pyridine-3,5-diyl)](abbreviation: PF-Py), and poly[(9,9-dioctylfluorene-2,7-diyl)-co-(2,2'-bipyridine-6,6'-diyl)] (abbreviation: PF-BPy) are preferable as the host material.

Furthermore, the following organic compounds having a diazine ring, which have bipolar properties, a high hole-transport property, and a high electron-transport property, can be used as the host material: 9-phenyl-9'-(4-phenyl-2-quinazolinyl)-3,3'-bi-9H-carbazole (abbreviation: PCCzQz), 2-[4'-(9-phenyl-9H-carbazol-3-yl)-3,1'-biphenyl-1-yl]dibenzo[f,h]quinoxaline (abbreviation: 2mpPCBPDBq), 5-[3-(4,6-diphenyl-1,3,5-triazin-2-yl)phenyl]-7,7-dimethyl-5H,7H-indeno[2,1-b]carbazole (abbreviation: mINc(II)PTzn), 11-(4-[1,1'-biphenyl]-4-yl-6-phenyl-1,3,5-triazin-2-yl)-11,12-dihydro-12-phenyl-indolo[2,3-a]carbazole (abbreviation: BP-Icz(II)Tzn), and 7-[4-(9-phenyl-9H-carbazol-2-yl)quinazolin-2-yl]-7H-dibenzo[c,g] carbazole (abbreviation: PC-cgDBCzQz).

<Electron-Transport Layer>

The electron-transport layers (114, 114*a*, and 114*b*) transport the electrons, which are injected from the second electrode 102 and the charge-generation layers (106, 106*a*, and 106*b*) by electron-injection layers (115, 115*a*, and 115*b*) described later, to the light-emitting layers (113, 113*a*, and 113*b*). The heat resistance of the light-emitting device of one embodiment of the present invention can be improved by including the stacked electron-transport layers. The electron-transport material used in the electron-transport layers (114, 114*a*, and 114*b*) is preferably a substance having an electron mobility of $1\times10^{-6}$ $cm^2/Vs$ or higher in the case where the square root of the electric field strength [V/cm] is 600. Note that any other substance can also be used as long as the substance has an electron-transport property higher than a hole-transport property. The electron-transport layers (114, 114*a*, and 114*b*) can function even with a single-layer structure and may have a stacked-layer structure including two or more layers. When a photolithography process is performed over the electron-transport layer including the above-described mixed material, which has heat resistance, an adverse effect of the thermal process on the device characteristics can be reduced.

<<Electron-Transport Material>>

As the electron-transport material that can be used for the electron-transport layers (114, 114*a*, and 114*b*), an organic compound having a high electron-transport property can be used, and for example, a heteroaromatic compound can be used. The term heteroaromatic compound refers to a cyclic compound including at least two different kinds of elements in a ring. Examples of cyclic structures include a three-membered ring, a four-membered ring, a five-membered ring, a six-membered ring, and the like, among which a five-membered ring and a six-membered ring are particularly preferred. The elements included in the heteroaromatic compound are preferably one or more of nitrogen, oxygen, and sulfur, in addition to carbon. In particular, a heteroaromatic compound containing nitrogen (a nitrogen-containing heteroaromatic compound) is preferred, and any of materials having a high electron-transport property (electron-transport materials), such as a nitrogen-containing heteroaromatic compound and a π-electron deficient heteroaromatic compound including the nitrogen-containing heteroaromatic compound, is preferably used. The compound in Embodiment 1 has an electron-transport property and thus can be used as an electron-transport material.

Note that the electron-transport material can be different from the materials used in the light-emitting layer. Not all excitons formed by recombination of carriers in the light-emitting layer can contribute to light emission and some excitons are diffused into a layer in contact with the light-emitting layer or a layer in the vicinity of the light-emitting layer. In order to avoid this phenomenon, the energy level (the lowest singlet excitation level or the lowest triplet excitation level) of a material used for the layer in contact with the light-emitting layer or the layer in the vicinity of the light-emitting layer is preferably higher than that of a material used for the light-emitting layer. Therefore, when a material different from the material of the light-emitting layer is used as the electron-transport material, an element with high efficiency can be obtained.

The heteroaromatic compound is an organic compound including at least one heteroaromatic ring.

The heteroaromatic ring includes any one of a pyridine ring, a diazine ring, a triazine ring, a polyazole ring, an oxazole ring, a thiazole ring, and the like. A heteroaromatic ring having a diazine ring includes a heteroaromatic ring having a pyrimidine ring, a pyrazine ring, a pyridazine ring, or the like. A heteroaromatic ring having a polyazole ring includes a heteroaromatic ring having an imidazole ring, a triazole ring, or an oxadiazole ring.

The heteroaromatic ring includes a fused heteroaromatic ring having a fused ring structure. Examples of the fused heteroaromatic ring include a quinoline ring, a benzoquinoline ring, a quinoxaline ring, a dibenzoquinoxaline ring, a quinazoline ring, a benzoquinazoline ring, a dibenzoquinazoline ring, a phenanthroline ring, a furodiazine ring, and a benzimidazole ring.

Examples of the heteroaromatic compound having a five-membered ring structure, which is a heteroaromatic compound containing carbon and one or more of nitrogen, oxygen, and sulfur, include a heteroaromatic compound having an imidazole ring, a heteroaromatic compound having a triazole ring, a heteroaromatic compound having an oxazole ring, a heteroaromatic compound having an oxadiazole ring, a heteroaromatic compound having a thiazole ring, and a heteroaromatic compound having a benzimidazole ring.

Examples of the heteroaromatic compound having a six-membered ring structure, which is a heteroaromatic compound containing carbon and one or more of nitrogen, oxygen, and sulfur, include a heteroaromatic compound having a heteroaromatic ring, such as a pyridine ring, a diazine ring (a pyrimidine ring, a pyrazine ring, a pyridazine ring, or the like), a triazine ring, or a polyazole ring. Other examples include a heteroaromatic compound having a bipyridine structure, a heteroaromatic compound having a terpyridine structure, and the like, which are included in examples of a heteroaromatic compound in which pyridine rings are connected.

Examples of the heteroaromatic compound having a fused ring structure partly including the above six-membered ring structure include a heteroaromatic compound having a fused heteroaromatic ring such as a quinoline ring, a benzoquinoline ring, a quinoxaline ring, a dibenzoquinoxaline ring, a phenanthroline ring, a furodiazine ring (including a structure in which an aromatic ring is fused to a furan ring of a furodiazine ring), or a benzimidazole ring.

Specific examples of the above-described heteroaromatic compound having a five-membered ring structure (a polyazole ring (including an imidazole ring, a triazole ring, or an oxadiazole ring), an oxazole ring, a thiazole ring, or a benzimidazole ring) include 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl]benzene (abbreviation: OXD-7), 9-[4-(5-phenyl-1,3,4-oxadiazol-2-yl) phenyl]-9H-carbazole (abbreviation: CO11), 3-(4-biphenylyl)-4-phenyl-5-(4-tert-butylphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), and 4,4'-bis(5-methylbenzoxazol-2-yl)stilbene (abbreviation: BzOs).

Specific examples of the above-described heteroaromatic compound having a six-membered ring structure (including a heteroaromatic ring having a pyridine ring, a diazine ring, a triazine ring, or the like) include: a heteroaromatic compound including a heteroaromatic ring having a pyridine ring, such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB); a heteroaromatic compound including a heteroaromatic ring having a triazine ring, such as 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 5-[3-(4,6-diphenyl-1,3,5-triazin-2-yl)phenyl]-7,7-dimethyl-5H,7H-indeno[2,1-b]carbazole (abbreviation: mINc(II)PTzn), 2-[3'-(triphenylen-2-yl)-1,1'-biphenyl-3-yl]-4,6-diphenyl-1,3,5-triazine (abbreviation: mTpBPTzn), 2-[(1,1'-biphenyl)-4-yl]-4-phenyl-6-[9,9'-spirobi(9H-fluoren)-2-yl]-1,3,5-triazine (abbreviation: BP-SFTzn), 2,6-bis(4-naphthalen-1-ylphenyl)-4-[4-(3-pyridyl)phenyl]pyrimidine (abbreviation: 2,4NP-6PyPPm), 3-[9-(4,6-diphenyl-1,3,5-triazin-2-yl)-2-dibenzofuranyl]-9-phenyl-9H-carbazole (abbreviation: PCDBfTzn), 2-[1,1'-biphenyl]-3-yl-4-phenyl-6-(8-[1,1':4',1"-terphenyl]-4-yl-1-dibenzofuranyl)-1,3,5-triazine (abbreviation: mBP-TPDBfTzn), 2-{3-[3-(dibenzothiophen-4-yl)phenyl]phenyl}-4,6-diphenyl-1,3,5-triazine (abbreviation: mDBtBPTzn), or mFBPTzn; and a heteroaromatic compound including a heteroaromatic ring having a diazine (pyrimidine) ring, such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 4,6mCzBP2Pm, 6-(1,1'-biphenyl-3-yl)-4-[3,5-bis(9H-carbazol-9-yl)phenyl]-2-phenylpyrimidine (abbreviation: 6mBP-4Cz2PPm), 4-[3,5-bis(9H-carbazol-9-yl)phenyl]-2-phenyl-6-(1,1'-biphenyl-4-yl)pyrimidine (abbreviation: 6BP-4Cz2PPm), 4-[3-(dibenzothiophen-4-yl)phenyl]-8-(naphthalen-2-yl)-[1]benzofuro[3,2-d]pyrimidine (abbreviation: 8PN-4mDBtPBfpm), 8BP-4mDBtPBfpm, 9mDBtBPNfpr, 9pmDBtBPNfpr, 3,8-bis[3-(dibenzothiophen-4-yl)phenyl]benzofuro[2,3-b]pyrazine (abbreviation: 3,8mDBtP2Bfpr), 4,8-bis[3-(dibenzothiophen-4-yl)phenyl]-[1]benzofuro[3,2-d]pyrimidine (abbreviation: 4,8mDBtP2Bfpm), 8-[3'-(dibenzothiophen-4-yl)(1,1'-biphenyl-3-yl)]naphtho[1',2': 4,5]furo[3,2-d]pyrimidine (abbreviation: 8mDBtBPNfpm), or 8-[(2,2'-binaphthalen)-6-yl]-4-[3-(dibenzothiophen-4-yl)phenyl]-[1]benzofuro[3,2-d]pyrimidine (abbreviation: 8(βN2)-4mDBtPBfpm). Note that the above aromatic compounds including a heteroaromatic ring include a heteroaromatic compound having a fused heteroaromatic ring.

Other examples include heteroaromatic compounds including a heteroaromatic ring having a diazine (pyrimidine) ring, such as 2,2'-(pyridine-2,6-diyl)bis(4-phenylbenzo[h]quinazoline) (abbreviation: 2,6(P-Bqn)$_2$Py), 2,2'-(2,2'-bipyridine-6,6'-diyl)bis(4-phenylbenzo[h]quinazoline) (abbreviation: 6,6'(P-Bqn)$_2$BPy), 2,2'-(pyridine-2,6-diyl)bis{4-[4-(2-naphthyl)phenyl]-6-phenylpyrimidine} (abbreviation: 2,6(NP-PPm)$_2$Py), or 6-(1,1'-biphenyl-3-yl)-4-[3,5-bis(9H-carbazol-9-yl)phenyl]-2-phenylpyrimidine (abbreviation: 6mBP-4Cz2PPm), and a heteroaromatic compound including a heteroaromatic ring having a triazine ring, such as 2,4,6-tris[3'-(pyridin-3-yl)biphenyl-3-yl]-1,3,5-triazine (abbreviation: TmPPPyTz), 2,4,6-tris(2-pyridyl)-1,3,5-triazine (abbreviation: 2Py3Tz), or 2-[3-(2,6-dimethyl-3-pyridinyl)-5-(9-phenanthrenyl)phenyl]-4,6-diphenyl-1,3,5-triazine (abbreviation: mPn-mDMePyPTzn).

Specific examples of the above-described heteroaromatic compound having a fused ring structure partly including a six-membered ring structure (the heteroaromatic compound having a fused ring structure) include a heteroaromatic compound having a quinoxaline ring, such as bathophenanthroline (abbreviation: BPhen), bathocuproine (abbreviation: BCP), 2,9-di(naphthalen-2-yl)-4,7-diphenyl-1,10-phenanthroline (abbreviation: NBPhen), 2,2'-(pyridin-2,6-diyl)bis(4-phenylbenzo[h]quinazoline) (abbreviation: 2,6(P-Bqn)$_2$Py), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), or 2mpPCBPDBq.

For the electron-transport layers (114, 114*a*, and 114*b*), any of the metal complexes given below can be used as well as the heteroaromatic compounds described above. Examples of the metal complexes include a metal complex having a quinoline ring or a benzoquinoline ring, such as tris(8-quinolinolato)aluminum(III) (abbreviation: $Alq_3$), $Almq_3$, 8-quinolinolatolithium(I) (abbreviation: Liq), $BeBq_2$, bis(2-methyl-8-quinolinolato)(4-phenylphenolato)aluminum(III) (abbreviation: BAlq), or bis(8-quinolinolato)zinc(II) (abbreviation: Znq), and a metal complex having an oxazole ring or a thiazole ring, such as bis[2-(2-benzoxazolyl)phenolato]zinc(II) (abbreviation: ZnPBO), or bis[2-(2-benzothiazolyl)phenolato]zinc(II) (abbreviation: ZnBTZ).

High-molecular compounds such as poly(2,5-pyridinediyl) (abbreviation: PPy), poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can be used as the electron-transport material.

Each of the electron-transport layers (114, 114*a*, and 114*b*) is not limited to a single layer and may be a stack of two or more layers each containing any of the above substances.

<Electron-Injection Layer>

The electron-injection layers (115, 115*a*, and 115*b*) contain a substance having a high electron-injection property. The electron-injection layers (115, 115*a*, and 115*b*) are layers for increasing the efficiency of electron injection from the second electrode 102 and are preferably formed using a material whose value of the LUMO level has a small difference (0.5 eV or less) from the work function of a material used for the second electrode 102. Thus, the electron-injection layer 115 can be formed using an alkali metal, an alkaline earth metal, or a compound thereof, such as lithium, cesium, lithium fluoride (LiF), cesium fluoride (CsF), calcium fluoride ($CaF_2$), 8-quinolinolato lithium(I) (abbreviation: Liq), 2-(2-pyridyl)phenolatolithium (abbreviation: LiPP), 2-(2-pyridyl)-3-pyridinolatolithium (abbreviation: LiPPy), 4-phenyl-2-(2-pyridyl)phenolatolithium (abbreviation: LiPPP), an oxide of lithium ($LiO_x$), or cesium carbonate. A rare earth metal or a compound of a rare earth metal, such as erbium fluoride ($ErF_3$) or ytterbium (Yb), can also be used. For the electron-injection layers (115, 115*a*, and 115*b*), a plurality of kinds of materials given above may be mixed or stacked as films. Electride may also be used for the electron-injection layers (115, 115*a*, and 115*b*). Examples of the electride include a substance in which electrons are added at high concentration to calcium oxide-aluminum oxide. Any of the substances used for the electron-transport layers (114, 114*a*, and 114*b*), which are given above, can also be used.

A mixed material in which an organic compound and an electron donor (donor) are mixed may also be used for the electron-injection layers (115, 115*a*, and 115*b*). Such a mixed material is excellent in an electron-injection property and an electron-transport property because electrons are generated in the organic compound by the electron donor. The organic compound here is preferably a material excellent in transporting the generated electrons; specifically, for example, the above-described electron-transport materials used for the electron-transport layers (114, 114*a*, and 114*b*), such as a metal complex and a heteroaromatic compound, can be used. As the electron donor, a substance showing an electron-donating property with respect to an organic compound is preferably used. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. Alternatively, a Lewis base such as magnesium oxide can be used. Further alternatively, an organic compound such as tetrathiafulvalene (abbreviation: TTF) can be used. Alternatively, a stack of two or more of these materials may be used.

A mixed material in which an organic compound and a metal are mixed may also be used for the electron-injection layers (115, 115*a*, and 115*b*). The organic compound used here preferably has a lowest unoccupied molecular orbital (LUMO) level higher than or equal to −3.6 eV and lower than or equal to −2.3 eV. Moreover, a material having an unshared electron pair is preferable.

Thus, as the organic compound used in the above mixed material, a mixed material obtained by mixing a metal and the heteroaromatic compound given above as the material that can be used for the electron-transport layer may be used. Preferred examples of the heteroaromatic compound include materials having an unshared electron pair, such as a heteroaromatic compound having a five-membered ring structure (e.g., an imidazole ring, a triazole ring, an oxazole ring, an oxadiazole ring, a thiazole ring, or a benzimidazole ring), a heteroaromatic compound having a six-membered ring structure (e.g., a pyridine ring, a diazine ring (including a pyrimidine ring, a pyrazine ring, a pyridazine ring, or the like), a triazine ring, a bipyridine ring, or a terpyridine ring), and a heteroaromatic compound having a fused ring structure partly including a six-membered ring structure (e.g., a quinoline ring, a benzoquinoline ring, a quinoxaline ring, a dibenzoquinoxaline ring, or a phenanthroline ring). Since the materials are specifically described above, description thereof is omitted here.

As a metal used for the above mixed material, a transition metal that belongs to Group 5, Group 7, Group 9, or Group 11 or a material that belongs to Group 13 in the periodic table is preferably used, and examples include Ag, Cu, Al, and In. Here, the organic compound forms a singly occupied molecular orbital (SOMO) with the transition metal.

To amplify light obtained from the light-emitting layer 113*b*, for example, the optical path length between the second electrode 102 and the light-emitting layer 113*b* is preferably less than one fourth of the wavelength λ of light emitted from the light-emitting layer 113*b*. In that case, the optical path length can be adjusted by changing the thickness of the electron-transport layer 114*b* or the electron-injection layer 115*b*.

When the charge-generation layer 106 is provided between the two EL layers (103*a* and 103*b*) as in the light-emitting device in FIG. 1D, a structure in which a plurality of EL layers are stacked between the pair of electrodes (the structure is also referred to as a tandem structure) can be obtained.

<Charge-Generation Layer>

The charge-generation layer 106 has a function of injecting electrons into the EL layer 103*a* and injecting holes into the EL layer 103*b* when voltage is applied between the first electrode (anode) 101 and the second electrode (cathode) 102. The charge-generation layer 106 may be either a p-type layer in which an electron acceptor (acceptor) is added to a hole-transport material or an electron-injection buffer layer in which an electron donor (donor) is added to an electron-transport material. Alternatively, both of these structures may be stacked. Furthermore, an electron-relay layer may be provided between the p-type layer and the electron-injection buffer layer. Note that forming the charge-generation layer 106 with the use of any of the above materials can inhibit an increase in driving voltage caused by the stack of the EL layers.

In the case where the charge-generation layer 106 is a p-type layer in which an electron acceptor is added to a hole-transport material, which is an organic compound, any of the materials described in this embodiment can be used as the hole-transport material. Examples of the electron acceptor include 7,7,8,8-tetracyano-2,3,5,6-tetrafluoroquinodimethane (abbreviation: $F_4$-TCNQ) and chloranil. Other examples include oxides of metals that belong to Group 4 to Group 8 of the periodic table. Specific examples include vanadium oxide, niobium oxide, tantalum oxide, chromium oxide, molybdenum oxide, tungsten oxide, manganese oxide, and rhenium oxide. Any of the above-described acceptor materials may be used. Furthermore, a mixed film obtained by mixing materials of a p-type layer or a stack of films containing the respective materials may be used.

In the case where the charge-generation layer 106 is an electron-injection buffer layer in which an electron donor is added to an electron-transport material, any of the materials described in this embodiment can be used as the electron-transport material. As the electron donor, it is possible to use an alkali metal, an alkaline earth metal, a rare earth metal, a metal belonging to Group 2 or Group 13 of the periodic table, or an oxide or a carbonate thereof. Specifically, lithium (Li), cesium (Cs), magnesium (Mg), calcium (Ca), ytterbium (Yb), indium (In), lithium oxide ($Li_2O$), cesium carbonate, or the like is preferably used. An organic compound such as tetrathianaphthacene may be used as the electron donor.

When an electron-relay layer is provided between a p-type layer and an electron-injection buffer layer in the charge-generation layer 106, the electron-relay layer contains at least a substance having an electron-transport property and has a function of preventing an interaction between the electron-injection buffer layer and the p-type layer and transferring electrons smoothly. The LUMO level of the substance having an electron-transport property in the electron-relay layer is preferably between the LUMO level of the acceptor substance in the p-type layer and the LUMO level of the substance having an electron-transport property in the electron-transport layer in contact with the charge-generation layer. Specifically, the LUMO level of the substance having an electron-transport property in the electron-relay layer is preferably higher than or equal to −5.0 eV, further preferably higher than or equal to −5.0 eV and lower than or equal to −3.0 eV. Note that as the substance having an electron-transport property in the electron-relay layer, a phthalocyanine-based material or a metal complex having a metal-oxygen bond and an aromatic ligand is preferably used.

Although FIG. 1D illustrates the structure in which two EL layers 103 are stacked, three or more EL layers may be stacked with charge-generation layers each provided between two adjacent EL layers.

<Cap Layer>

Although not illustrated in FIGS. 1A to 1E, a cap layer may be provided over the second electrode 102 of the light-emitting device. For example, a material with high refractive index can be used for the cap layer. When the cap layer is provided over the second electrode 102, extraction efficiency of light emitted from the second electrode 102 can be improved.

Specific examples of a material that can be used for the cap layer include 5,5'-diphenyl-2,2'-di-5H-[1]benzothieno[3,2-c]carbazole (abbreviation: BisBTc), and 4,4',4"-(benzene-1,3,5-triyl)tri(dibenzothiophene) (abbreviation: DBT3P-II). In addition, the organic compound described in Embodiment 1 can be used.

<Substrate>

The light-emitting device described in this embodiment can be formed over a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES), a synthetic resin such as acrylic resin, polypropylene, polyester, polyvinyl fluoride, polyvinyl chloride, polyamide, polyimide, aramid, epoxy resin, an inorganic vapor deposition film, and paper.

For fabrication of the light-emitting device in this embodiment, a gas phase method such as an evaporation method or a liquid phase method such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the layers having various functions (the hole-injection layer 111, the hole-transport layer 112, the light-emitting layer 113, the electron-transport layer 114, and the electron-injection layer 115) included in the EL layers of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

In the case where a film formation method such as the coating method or the printing method is employed, a high-molecular compound (e.g., an oligomer, a dendrimer, or a polymer), a middle-molecular compound (a compound between a low-molecular compound and a high-molecular compound with a molecular weight of 400 to 4000), an inorganic compound (e.g., a quantum dot material), or the like can be used. The quantum dot material can be a colloidal quantum dot material, an alloyed quantum dot material, a core-shell quantum dot material, a core quantum dot material, or the like.

Materials that can be used for the layers (the hole-injection layer 111, the hole-transport layer 112, the light-emitting layer 113, the electron-transport layer 114, and the electron-injection layer 115) included in the EL layer 103 of the light-emitting device described in this embodiment are not limited to the materials described in this embodiment, and other materials can be used in combination as long as the functions of the layers are fulfilled.

Note that in this specification and the like, the terms "layer" and "film" can be interchanged with each other as appropriate.

The structures described in this embodiment can be used in combination with any of the structures described in the other embodiments as appropriate.

Embodiment 3

In this embodiment, specific structure examples of a light-emitting and light-receiving apparatus of one embodiment of the present invention and an example of the manufacturing method will be described.

<Structure Example of Light-Emitting and Light-Receiving Apparatus 700>

Figure 2A:
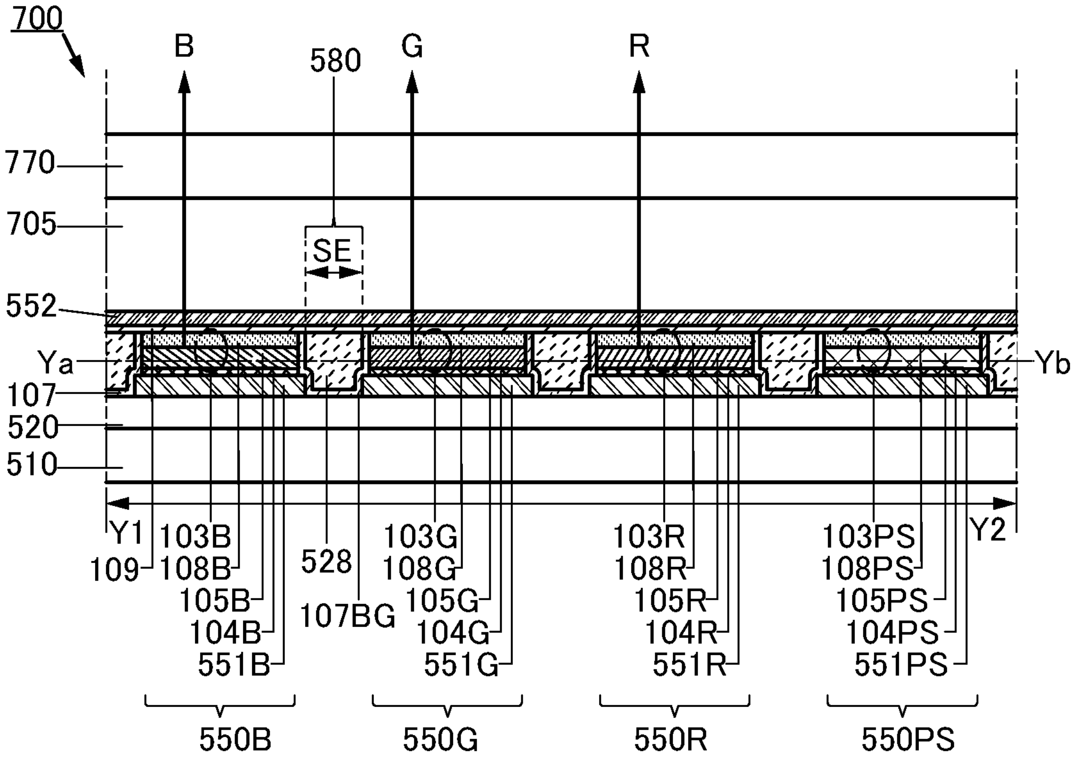
FIGS. 2A to 2D illustrate a light-emitting apparatus of an embodiment.

A light-emitting and light-receiving apparatus 700 illustrated in FIG. 2A includes a light-emitting device 550B, a light-emitting device 550G, a light-emitting device 550R, and a light-receiving device 550PS. The light-emitting device 550B, the light-emitting device 550G, the light-emitting device 550R, and the light-receiving device 550PS are formed over a functional layer 520 provided over a first substrate 510. The functional layer 520 includes, for example, driver circuits such as a gate driver and a source driver that are composed of a plurality of transistors, and wirings that electrically connect these circuits. Note that these driver circuits are electrically connected to the light-emitting device 550B, the light-emitting device 550G, the light-emitting device 550R, and the light-receiving device 550PS, for example, to drive them. The light-emitting and light-receiving apparatus 700 includes an insulating layer 705 over the functional layer 520 and the devices (the light-emitting devices and the light-receiving device), and the insulating layer 705 has a function of attaching a second substrate 770 and the functional layer 520.

The light-emitting device 550B, the light-emitting device 550G, and the light-emitting device 550R each have the device structure described in Embodiment 2. In other words, the EL layer 103 illustrated in FIG. 2A is different in each light-emitting device. Note that although in this embodiment, the case where the devices (a plurality of light-emitting devices and a light-receiving device) are formed separately is described, part of an EL layer of a light-emitting device (a hole-injection layer, a hole-transport layer, or an electron-transport layer) and part of an active layer of a light-receiving device (a first transport layer or a second transport layer) may be formed using the same material at the same time in the manufacturing process. The detailed description will be made in Embodiment 8.

In this specification and the like, a structure in which light-emitting layers in light-emitting devices of different colors (for example, blue (B), green (G), and red (R)) and a light-receiving layer in a light-receiving device are separately formed or separately patterned is sometimes referred to as a side-by-side (SBS) structure. Although the light-emitting device 550B, the light-emitting device 550G, the light-emitting device 550R, and the light-receiving device 550PS are arranged in this order in the light-emitting and light-receiving apparatus 700 illustrated in FIG. 2A, one embodiment of the present invention is not limited to this structure. For example, in the light-emitting and light-receiving apparatus 700, these devices may be arranged in the order of the light-emitting device 550R, the light-emitting device 550G, the light-emitting device 550B, and the light-receiving device 550PS.

In FIG. 2A, the light-emitting device 550B includes an electrode 551B, the electrode 552, and an EL layer 103B. The light-emitting device 550G includes an electrode 551G, the electrode 552, and an EL layer 103G. The light-emitting device 550R includes an electrode 551R, the electrode 552, and an EL layer 103R. The light-receiving device 550PS includes an electrode 551PS, the electrode 552, and a light-receiving layer 103PS. Note that a specific structure of each layer of the light-receiving device is as described in Embodiment 2. In addition, a specific structure of each layer of the light-emitting device is as described in Embodiment 2. The EL layer 103B, the EL layer 103G, and the EL layer 103R each have a stacked-layer structure of layers having different functions including their respective light-emitting layers (105B, 105G, and 105R). The light-receiving layer 103PS has a stacked-layer structure of layers having different functions including an active layer 105PS. FIG. 2A illustrates a case where the EL layer 103B includes a hole-injection/transport layer 104B, a light-emitting layer 105B, an electron-transport layer 108B, and an electron-injection layer 109; the EL layer 103G includes a hole-injection/transport layer 104G, a light-emitting layer 105G, an electron-transport layer 108G, and the electron-injection layer 109; the EL layer 103R includes a hole-injection/transport layer 104R, a light-emitting layer 105R, an electron-transport layer 108R, and the electron-injection layer 109; and the light-receiving layer 103PS includes a first transport layer 104PS, the active layer 105PS, a second transport layer 108PS, and the electron-injection layer 109. However, the present invention is not limited thereto. Note that each of the hole-injection/transport layers (104B, 104G, and 104R) represents a layer having the functions of the hole-injection layer and the hole-transport layer described in Embodiment 2, and may have a stacked-layer structure.

Note that the electron-transport layers (108B, 108G, and 108R) and the second transport layer 108PS may have a function of blocking holes moving from the anode side to the cathode side through the EL layers (103B, 103G, and 103R). The electron-injection layer 109 may have a stacked-layer structure in which some or all of layers are formed using different materials.

As illustrated in FIG. 2A, insulating layers 107 may be formed on side surfaces (or end portions) of the hole-injection/transport layers (104B, 104G, and 104R), the light-emitting layers (105B, 105G, and 105R), and the electron-transport layers (108B, 108G, and 108R) included in the EL layers (103B, 103G, and 103R), and side surfaces (or end portions) of the first transport layer 104PS, the active layer 105PS, and the second transport layer 108PS included in the light-receiving layer 103PS. The insulating layers 107 are formed in contact with the side surfaces (or the end portions) of the EL layers (103B, 103G, and 103R) and the light-receiving layer 103PS. This can inhibit entry of oxygen, moisture, or constituent elements thereof into the inside through the side surfaces of the EL layers (103B, 103G, and 103R) and the light-receiving layer 103PS. For the insulating layers 107, aluminum oxide, magnesium oxide, hafnium oxide, gallium oxide, indium gallium zinc oxide, silicon nitride, or silicon nitride oxide can be used, for example. Some of the above-described materials may be stacked to form the insulating layers 107. The insulating layers 107 can be formed by a sputtering method, a CVD method, an MBE method, a PLD method, an ALD method, or the like and is formed preferably by an ALD method, which achieves favorable coverage. Note that the insulating layer 107 continuously covers the side surfaces (or the end portions) of parts of the EL layers (103B, 103G, and 103R) and parts of the light-receiving layer 103PS of adjacent devices. For example, in FIG. 2A, the side surfaces of parts of the EL layer 103B of the light-emitting device 550B and the EL layer 103G of the light-emitting device 550G are covered with the insulating layer 107BG. In regions covered with the insulating layer 107BG, partition walls 528 formed using an insulating material are preferably formed, as illustrated in FIG. 2A.

In addition, the electron-injection layer 109 is formed over the electron-transport layers (108B, 108G, and 108R) that are parts of the EL layers (103B, 103G, and 103R) and the insulating layers 107. Note that the electron-injection layer 109 may have a stacked-layer structure of two or more layers (for example, stacked layers having different electric resistances).

The electrode 552 is formed over the electron-injection layer 109. Note that the electrodes (551B, 551G, and 551R) and the electrode 552 include overlap regions. The light-emitting layer 105B is provided between the electrode 551B and the electrode 552, the light-emitting layer 105G is provided between the electrode 551G and the electrode 552, the light-emitting layer 105R is provided between the electrode 551R and the electrode 552, and the light-receiving layer 103PS is provided between the electrode 551PS and the electrode 552.

The EL layers (103B, 103G, and 103R) illustrated in FIG. 2A each have a structure similar to that of the EL layer 103 described in Embodiment 2. The light-emitting layer 105B can emit blue light, the light-emitting layer 105G can emit green light, and the light-emitting layer 105R can emit red light, for example.

The partition walls 528 are provided between the electrodes (551B, 551G, 551R, and 551PS), parts of the EL layers (103B, 103G, and 103R), and parts of the light-receiving layer 103PS. As illustrated in FIG. 2A, the partition walls 528 are in contact with the side surfaces (or the end portions) of the electrodes (551B, 551G, 551R, and 551PS), parts of the EL layers (103B, 103G, and 103R), and part of the light-receiving layer 103PS in the devices with the insulating layers 107 therebetween.

In each of the EL layers and the light-receiving layer, particularly the hole-injection layer, which is included in the hole-transport region between the anode and the light-emitting layer and between the anode and the active layer, often has high conductivity; thus, a hole-injection layer formed as a layer shared by adjacent devices might cause crosstalk. Thus, as described in this structure example, the partition walls 528 formed using an insulating material are provided between the EL layers and between the EL layer and the light-receiving layer, which can inhibit occurrence of crosstalk between adjacent devices (between the light-receiving device and the light-emitting device, between the light-emitting devices, or between the light-receiving devices).

In the manufacturing method described in this embodiment, side surfaces (or end portions) of the EL layer and the light-receiving layer are exposed in the patterning step. This may promote deterioration of the EL layer and the light-receiving layer by allowing the entry of oxygen, water, or the like through the side surfaces (or the end portions) of the EL layer and the light-receiving layer. Hence, providing the partition wall 528 can inhibit the deterioration of the EL layer and the light-receiving layer in the manufacturing process.

Providing the partition wall 528 can flatten the surface by reducing a depressed portion formed between adjacent devices (between the light-receiving device and the light-emitting device, between the light-emitting devices, or between the light-receiving devices). When the depressed portion is reduced, disconnection of the electrode 552 formed over the EL layers and the light-receiving layer can be inhibited. Examples of an insulating material used to form the partition wall 528 include organic materials such as an acrylic resin, a polyimide resin, an epoxy resin, an imide resin, a polyamide resin, a polyimide-amide resin, a silicone resin, a siloxane resin, a benzocyclobutene-based resin, a phenol resin, and precursors of these resins. Other examples include organic materials such as polyvinyl alcohol (PVA), polyvinyl butyral, polyvinyl pyrrolidone, polyethylene glycol, polyglycerin, pullulan, water-soluble cellulose, and alcohol-soluble polyamide resin. A photosensitive resin such as a photoresist can also be used. Examples of the photosensitive resin include positive-type materials and negative-type materials.

With the use of the photosensitive resin, the partition wall 528 can be fabricated by only light exposure and developing steps. The partition wall 528 may be fabricated using a negative photosensitive resin (e.g., a resist material). In the case where an insulating layer containing an organic material is used as the partition wall 528, a material absorbing visible light is suitably used. When such a material absorbing visible light is used for the partition wall 528, light emission from the EL layer can be absorbed by the partition wall 528, leading to a reduction in light leakage (stray light) to an adjacent EL layer or light-receiving layer. Accordingly, a display panel with high display quality can be provided.

For example, the difference between the top-surface level of the partition wall 528 and the top-surface level of any of the EL layer 103B, the EL layer 103G, the EL layer 103R, and the light-receiving layer 103PS is preferably 0.5 times or less, further preferably 0.3 times or less the thickness of the partition wall 528. The partition wall 528 may be provided such that the top-surface level of any of the EL layer 103B, the EL layer 103G, the EL layer 103R, and the light-receiving layer 103PS is higher than the top-surface level of the partition wall 528, for example. Alternatively, the partition wall 528 may be provided such that the top-surface level of the partition wall 528 is higher than the top-surface level of any of the EL layer 103B, the EL layer 103G, the EL layer 103R, and the light-receiving layer 103PS, for example.

When electrical continuity is established between the EL layer 103B, the EL layer 103G, the EL layer 103R, and the light-receiving layer 103PS in a light-emitting and light-receiving apparatus (display panel) with a high resolution more than 1000 ppi, crosstalk occurs, resulting in a narrower color gamut that the light-emitting and light-receiving apparatus is capable of reproducing. Providing the partition wall 528 in a high-resolution display panel with more than 1000 ppi, preferably more than 2000 ppi, or further preferably in an ultrahigh-resolution display panel with more than 5000 ppi allows the display panel to express vivid colors.

Figure 2B:
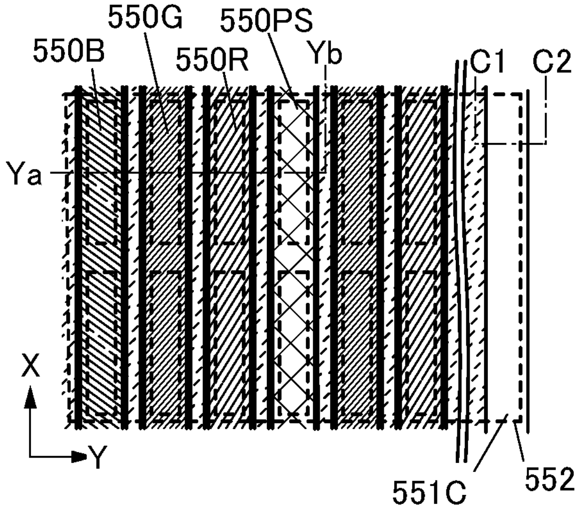
Figure 2C:
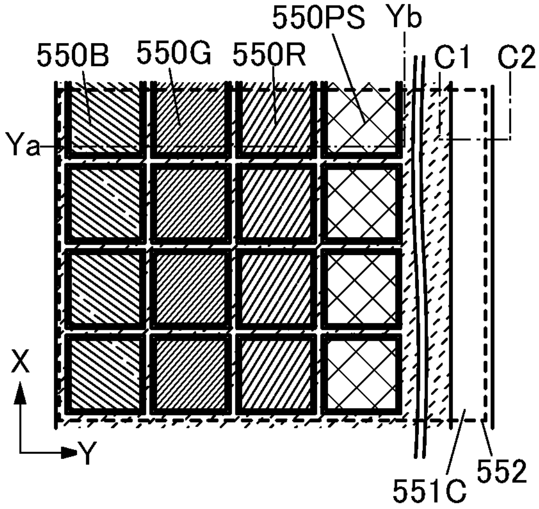

FIGS. 2B and 2C are each a schematic top view of the light-emitting and light-receiving apparatus 700 taken along the dashed-dotted line Ya-Yb in the cross-sectional view of FIG. 2A. Specifically, the light-emitting device 550B, the light-emitting device 550G, and the light-emitting device 550R are arranged in a matrix. Note that FIG. 2B illustrates what is called a stripe arrangement, in which the light-emitting devices of the same color are arranged in the X-direction. FIG. 2C illustrates a structure in which the light-emitting devices of the same color are arranged in the X-direction and separated by patterning for each pixel. Note that the arrangement method of the light-emitting devices is not limited thereto; another method such as a delta, zigzag, PenTile, or diamond arrangement may also be used.

The EL layers (the EL layer 103B, the EL layer 103G, and the EL layer 103R) and the light-receiving layer 103PS are processed to be separated by patterning using a photolithography method; hence, a light-emitting and light-receiving apparatus (display panel) with a high resolution can be fabricated. End portions (side surfaces) of the EL layer processed by patterning using a photolithography method have substantially one surface (or are positioned on substantially the same plane). In this case, the widths (SE) of spaces 580 between the EL layers and between the EL layer and the light-receiving layer are each preferably 5 μm or less, further preferably 1 μm or less.

In the EL layer, particularly the hole-injection layer, which is included in the hole-transport region between the anode and the light-emitting layer, often has high conductivity; thus, a hole-injection layer formed as a layer shared by adjacent light-emitting devices might cause crosstalk. Therefore, processing the EL layers to be separated by patterning using a photolithography method as described in this structure example can suppress occurrence of crosstalk between adjacent light-emitting devices.

Figure 2D:
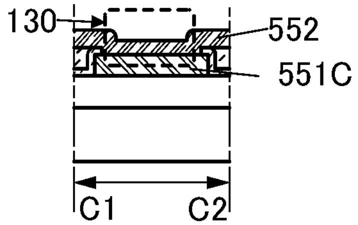

FIG. 2D is a schematic cross-sectional view taken along the dashed-dotted line C1-C2 in FIGS. 2B and 2C. FIG. 2D illustrates a connection portion 130 where a connection electrode 551C and the electrode 552 are electrically connected to each other. In the connection portion 130, the electrode 552 is provided over and in contact with the connection electrode 551C. The partition wall 528 is provided to cover an end portion of the connection electrode 551C.

<Example of Method for Manufacturing Light-Emitting and Light-Receiving Apparatus>

Figure 3A:
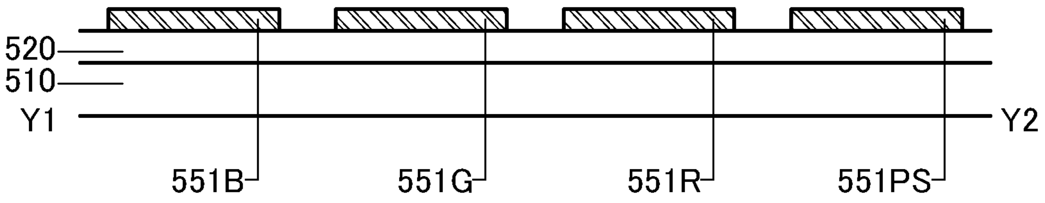
FIGS. 3A to 3C illustrate a method for manufacturing a light-emitting apparatus of an embodiment.

The electrode 551B, the electrode 551G, the electrode 551R, and the electrode 551PS are formed as illustrated in FIG. 3A. For example, a conductive film is formed over the functional layer 520 over the first substrate 510 and processed into predetermined shapes by a photolithography method.

The conductive film can be formed by any of a sputtering method, a chemical vapor deposition (CVD) method, a molecular beam epitaxy (MBE) method, a vacuum evaporation method, a pulsed laser deposition (PLD) method, an atomic layer deposition (ALD) method, and the like. Examples of the CVD method include a plasma-enhanced chemical vapor deposition (PECVD) method and a thermal CVD method. An example of a thermal CVD method is a metal organic CVD (MOCVD) method.

The conductive film may be processed by a nanoimprinting method, a sandblasting method, a lift-off method, or the like as well as a photolithography method described above. Alternatively, island-shaped thin films may be directly formed by a film formation method using a shielding mask such as a metal mask.

There are two typical examples of photolithography methods. In one of the methods, a resist mask is formed over a thin film that is to be processed, the thin film is processed by etching or the like, and then the resist mask is removed. In the other method, a photosensitive thin film is formed and then processed into a desired shape by light exposure and development. The former method involves heat treatment steps such as pre-applied bake (PAB) after resist application and post-exposure bake (PEB) after light exposure. In one embodiment of the present invention, a lithography method is used not only for processing of a conductive film but also for processing of a thin film used for formation of an EL layer (a film made of an organic compound or a film partly containing an organic compound).

As light for exposure in a photolithography method, it is possible to use light with the i-line (wavelength: 365 nm), light with the g-line (wavelength: 436 nm), light with the h-line (wavelength: 405 nm), or light in which the i-line, the g-line, and the h-line are mixed. Alternatively, ultraviolet light, KrF laser light, ArF laser light, or the like can be used. Exposure may be performed by liquid immersion exposure technique. As the light for exposure, extreme ultraviolet (EUV) light or X-rays may also be used. Instead of the light for exposure, an electron beam can be used. It is preferable to use EUV, X-rays, or an electron beam because extremely minute processing can be performed. Note that a photomask is not needed when light exposure is performed by scanning with a beam such as an electron beam.

For etching of a thin film using a resist mask, a dry etching method, a wet etching method, a sandblast method, or the like can be used.

Figure 3B:
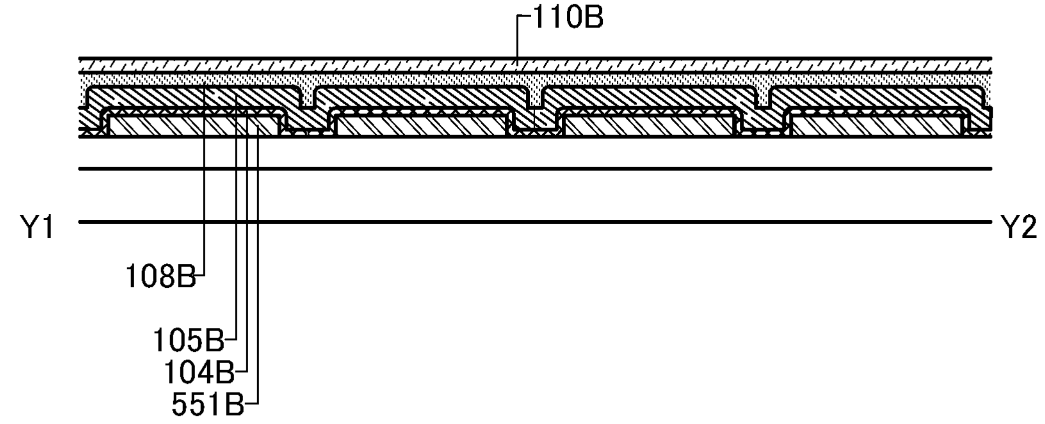

Subsequently, as illustrated in FIG. 3B, the hole-injection/transport layer 104B, the light-emitting layer 105B, and the electron-transport layer 108B are formed over the electrode 551B, the electrode 551G, the electrode 551R, and the electrode 551PS. Note that the hole-injection/transport layer 104B, the light-emitting layer 105B, and the electron-transport layer 108B can be formed using a vacuum evaporation method, for example. Furthermore, a sacrifice layer 1101B is formed over the electron-transport layer 108B. For the formation of the hole-injection/transport layer 104B, the light-emitting layer 105B, and the electron-transport layer 108B, any of the materials described in Embodiment 2 can be used.

For the sacrifice layer 1101B, it is preferable to use a film highly resistant to etching treatment performed on the hole-injection/transport layer 104B, the light-emitting layer 105B, and the electron-transport layer 108B, i.e., a film having high etching selectivity with respective to the hole-injection/transport layer 104B, the light-emitting layer 105B, and the electron-transport layer 108B. The sacrifice layer 1101B preferably has a stacked-layer structure of a first sacrifice layer and a second sacrifice layer which have different etching selectivities. For the sacrifice layer 110B, it is possible to use a film that can be removed by a wet etching method, which causes less damage to the EL layer 103B. In wet etching, oxalic acid or the like can be used as an etching material.

For the sacrifice layer 110B, an inorganic film such as a metal film, an alloy film, a metal oxide film, a semiconductor film, or an inorganic insulating film can be used, for example. The sacrifice layer 110B can be formed by any of a variety of film formation methods such as a sputtering method, an evaporation method, a CVD method, and an ALD method.

For the sacrifice layer 110B, a metal material such as gold, silver, platinum, magnesium, nickel, tungsten, chromium, molybdenum, iron, cobalt, copper, palladium, titanium, aluminum, yttrium, zirconium, or tantalum or an alloy material containing the metal material can be used, for example. It is particularly preferable to use a low-melting-point material such as aluminum or silver.

A metal oxide such as indium gallium zinc oxide (also referred to as In—Ga—Zn oxide or IGZO) can be used for the sacrifice layer 110B. It is also possible to use indium oxide, indium zinc oxide (In—Zn oxide), indium tin oxide (In—Sn oxide), indium titanium oxide (In—Ti oxide), indium tin zinc oxide (In—Sn—Zn oxide), indium titanium zinc oxide (In—Ti—Zn oxide), indium gallium tin zinc oxide (In—Ga—Sn—Zn oxide), or the like. Alternatively, indium tin oxide containing silicon can also be used, for example.

An element M (M is one or more of aluminum, silicon, boron, yttrium, copper, vanadium, beryllium, titanium, iron, nickel, germanium, zirconium, molybdenum, lanthanum, cerium, neodymium, hafnium, tantalum, tungsten, and magnesium) may be used instead of gallium.

For the sacrifice layer 110B, an inorganic insulating material such as aluminum oxide, hafnium oxide, or silicon oxide can be used.

The sacrifice layer 1101B is preferably formed using a material that can be dissolved in a solvent chemically stable with respect to at least the electron-transport layer 108B that is in the uppermost position. Specifically, a material that can be dissolved in water or alcohol can be suitably used for the sacrifice layer 1101B. In formation of the sacrifice layer 1101B, it is preferable that application of such a material dissolved in a solvent such as water or alcohol be performed by a wet process and followed by heat treatment for evaporating the solvent. At this time, the heat treatment is preferably performed under a reduced-pressure atmosphere, in which case the solvent can be removed at a low temperature in a short time and thermal damage to the hole-injection/transport layer 104B, the light-emitting layer 105B, and the electron-transport layer 108B can be accordingly reduced.

In the case where the sacrifice layer 110B having a stacked-layer structure is formed, the stacked-layer structure can include the first sacrifice layer formed using any of the above-described materials and the second sacrifice layer thereover.

The second sacrifice layer in that case is a film used as a hard mask for etching of the first sacrifice layer. In processing the second sacrifice layer, the first sacrifice layer is exposed. Thus, a combination of films having greatly different etching rates is selected for the first sacrifice layer and the second sacrifice layer. Thus, a film that can be used for the second sacrifice layer can be selected in accordance with the etching conditions of the first sacrifice layer and those of the second sacrifice layer.

For example, in the case where the second sacrifice layer is etched by dry etching involving a fluorine-containing gas (also referred to as a fluorine-based gas), the second sacrifice layer can be formed using silicon, silicon nitride, silicon oxide, tungsten, titanium, molybdenum, tantalum, tantalum nitride, an alloy containing molybdenum and niobium, an alloy containing molybdenum and tungsten, or the like. Here, a film of a metal oxide such as IGZO or ITO can be given as an example of a film having a high etching selectivity to the second sacrifice layer (i.e., a film with a low etching rate) in the dry etching involving the fluorine-based gas, and can be used for the first sacrifice layer.

Note that the material for the second sacrifice layer is not limited to the above and can be selected from a variety of materials in accordance with the etching conditions of the first sacrifice layer and those of the second sacrifice layer. For example, any of the films that can be used for the first sacrifice layer can be used for the second sacrifice layer.

For the second sacrifice layer, a nitride film can be used, for example. Specifically, it is possible to use a nitride such as silicon nitride, aluminum nitride, hafnium nitride, titanium nitride, tantalum nitride, tungsten nitride, gallium nitride, or germanium nitride.

Alternatively, an oxide film can be used for the second sacrifice layer. Typically, it is possible to use a film of an oxide or an oxynitride such as silicon oxide, silicon oxynitride, aluminum oxide, aluminum oxynitride, hafnium oxide, or hafnium oxynitride.

Figure 3C:
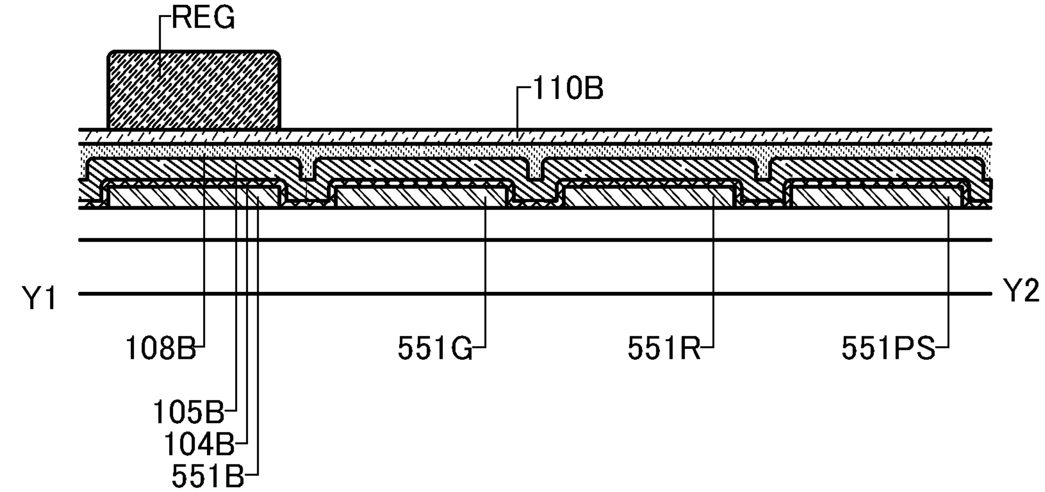

Next, as illustrated in FIG. 3C, a resist is applied onto the sacrifice layer 1101B, and the resist having a desired shape (a resist mask REG) is formed by a photolithography method. Such a method involves heat treatment steps such as pre-applied bake (PAB) after the resist application and post-exposure bake (PEB) after light exposure. The temperature reaches approximately 100° C. during the PAB, and approximately 120° C. during the PEB, for example. Therefore, the light-emitting device should be resistant to such high treatment temperatures.

Figure 4A:
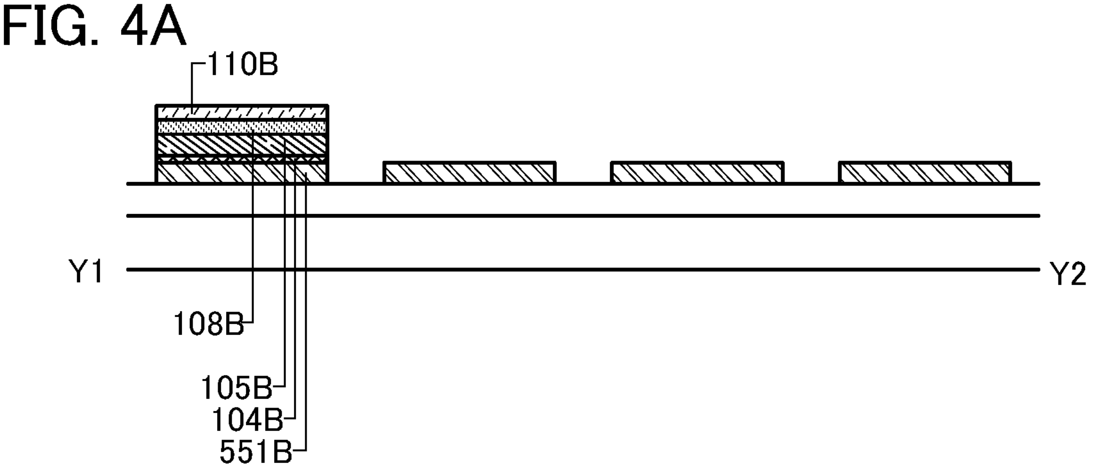
FIGS. 4A to 4C illustrate a method for manufacturing a light-emitting apparatus of an embodiment.

Next, part of the sacrifice layer 1101B that is not covered with the resist mask REG is removed by etching using the resist mask REG, the resist mask REG is removed, and then the hole-injection/transport layer 104B, the light-emitting layer 105B, and the electron-transport layer 108B that are not covered with the sacrifice layer 110B are removed by etching, so that the hole-injection/transport layer 104B, the light-emitting layer 105B, and the electron-transport layer 108B are processed to have side surfaces (or have their side surfaces exposed) over the electrode 551B or have belt-like shapes extending in the direction intersecting the sheet of the diagram. Note that dry etching is preferably employed for the etching. Note that in the case where the sacrifice layer 1101B has the aforementioned stacked-layer structure of the first sacrifice layer and the second sacrifice layer, the hole-injection/transport layer 104B, the light-emitting layer 105B, and the electron-transport layer 108B may be processed into a predetermined shape in the following manner: part of the second sacrifice layer is etched using the resist mask REG, the resist mask REG is then removed, and part of the first sacrifice layer is etched using the second sacrifice layer as a mask. The structure illustrated in FIG. 4A is obtained through these etching steps.

Figure 4B:
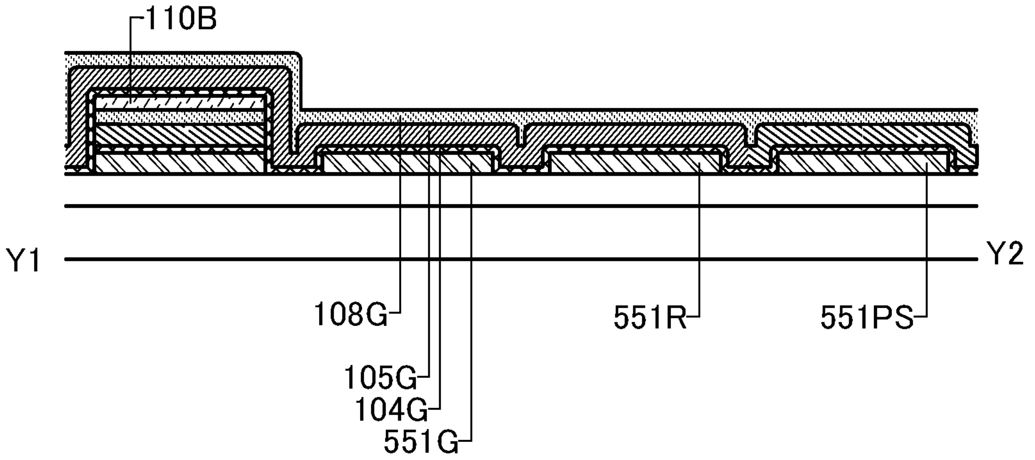

Subsequently, as illustrated in FIG. 4B, the hole-injection/transport layer 104G, the light-emitting layer 105G, and the electron-transport layer 108G are formed over the sacrifice layer 110B, the electrode 551G, the electrode 551R, and the electrode 551PS. The hole-injection/transport layer 104G, the light-emitting layer 105G, and the electron-transport layer 108G can be formed using any of the materials described in Embodiment 2. Note that the hole-injection/transport layer 104G, the light-emitting layer 105G, and the electron-transport layer 108G can be formed by a vacuum evaporation method, for example.

Figure 4C:
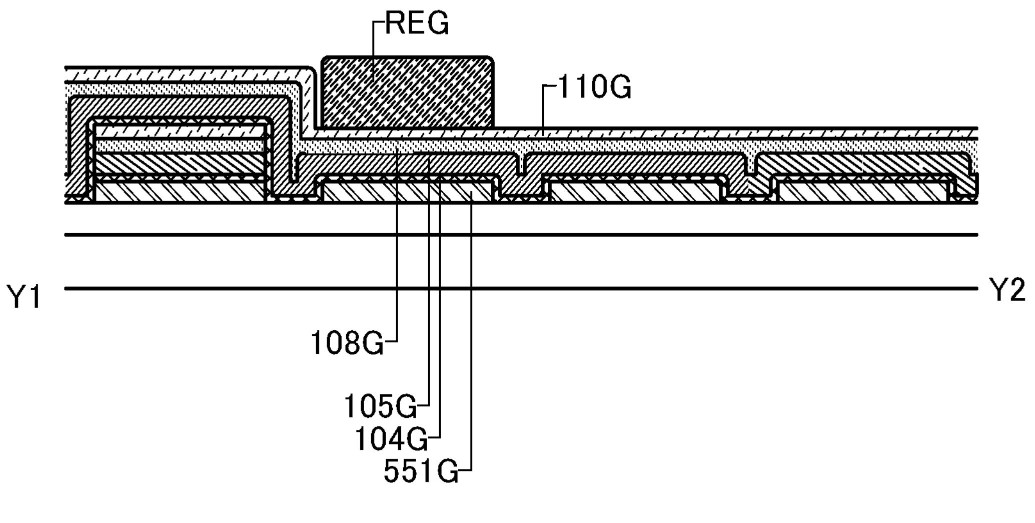
Figure 5A:
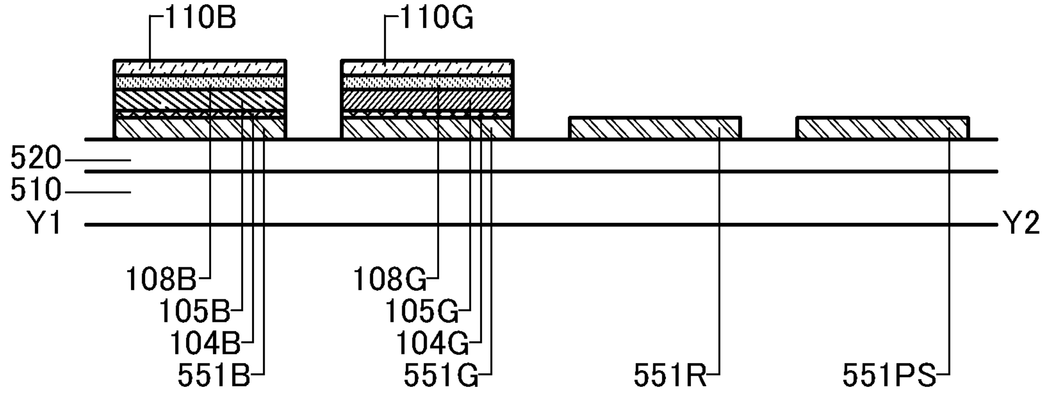
FIGS. 5A to 5C illustrate a method for manufacturing a light-emitting apparatus of an embodiment.

Next, as illustrated in FIG. 4C, the sacrifice layer 110G is formed over the electron-transport layer 108G, a resist is applied onto the sacrifice layer 110G, and the resist having a desired shape (the resist mask REG) is formed by a lithography method. Part of the sacrifice layer 110G that is not covered with the obtained resist mask REG is removed by etching, the resist mask REG is removed, and then parts of the hole-injection/transport layer 104G, the light-emitting layer 105G, and the electron-transport layer 108G that are not covered with the sacrifice layer 110G are removed by etching. Thus, the hole-injection/transport layer 104G, the light-emitting layer 105G, and the electron-transport layer 108G are processed to have side surfaces (or have their side surfaces exposed) over the electrode 551G or have belt-like shapes extending in the direction intersecting the sheet of the diagram. Note that dry etching is preferably employed for the etching. Note that the sacrifice layer 110G can be formed using a material similar to that for the sacrifice layer 1101B. In the case where the sacrifice layer 110G has the aforementioned stacked-layer structure of the first sacrifice layer and the second sacrifice layer, the hole-injection/transport layer 104G, the light-emitting layer 105G, and the electron-transport layer 108G may be processed into a predetermined shape in the following manner: part of the second sacrifice layer is etched using the resist mask REG, the resist mask REG is then removed, and part of the first sacrifice layer is etched using the second sacrifice layer as a mask. The structure illustrated in FIG. 5A is obtained through these etching steps.

Figure 5B:
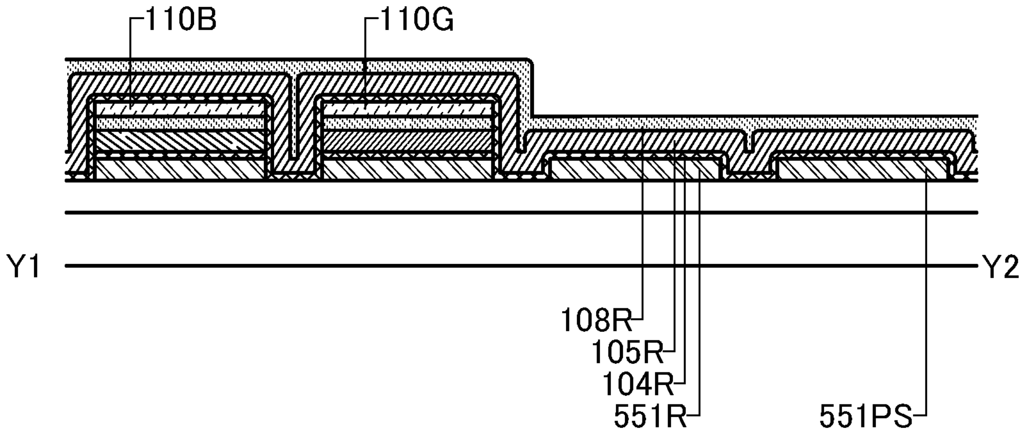

Next, as illustrated in FIG. 5B, the hole-injection/transport layer 104R, the light-emitting layer 105R, and the electron-transport layer 108R are formed over the sacrifice layer 110B, the sacrifice layer 110G, the electrode 551R, and the electrode 551PS. The hole-injection/transport layer 104R, the light-emitting layer 105R, and the electron-transport layer 108R can be formed using any of the materials described in Embodiment 2. The hole-injection/transport layer 104R, the light-emitting layer 105R, and the electron-transport layer 108R can be formed by a vacuum evaporation method, for example.

Figure 5C:
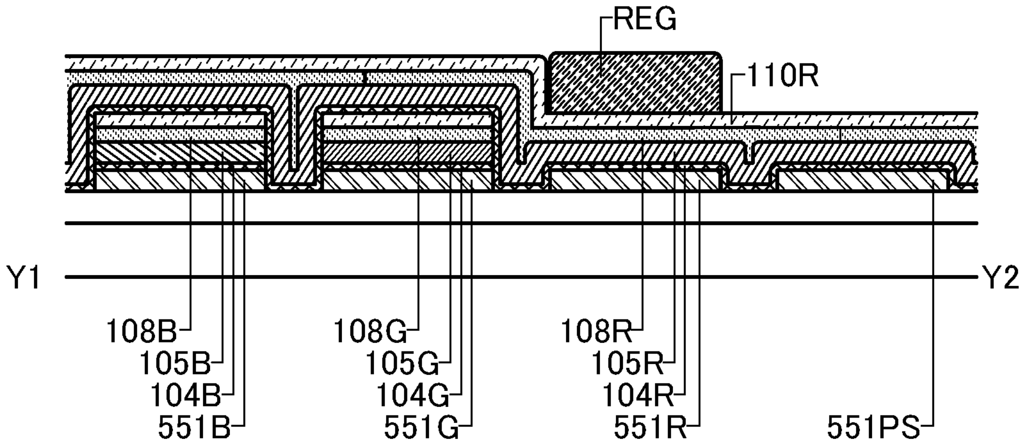
Figure 6A:
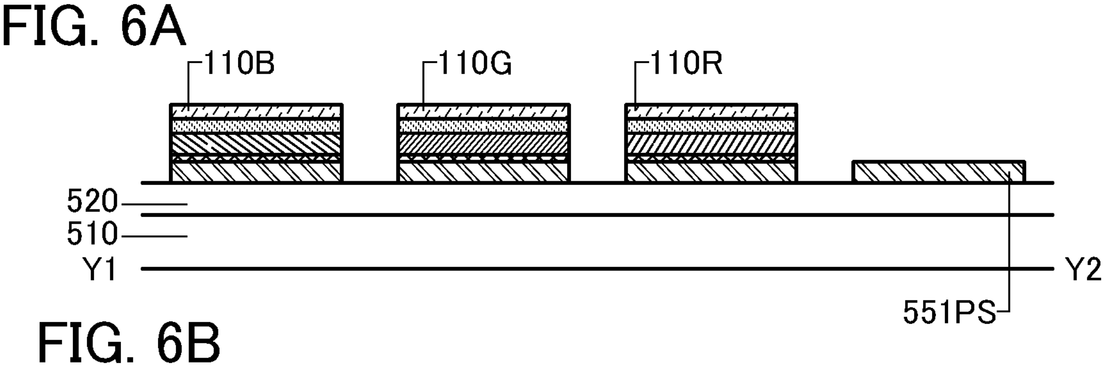
FIGS. 6A to 6D illustrate a method for manufacturing a light-emitting apparatus of an embodiment.

Next, as illustrated in FIG. 5C, the sacrifice layer 110R is formed over the electron-transport layer 108R, a resist is applied onto the sacrifice layer 110R, and the resist having a desired shape (the resist mask REG) is formed by a photolithography method. Part of the sacrifice layer 110R that is not covered with the obtained resist mask REG is removed by etching, the resist mask REG is removed, and then parts of the hole-injection/transport layer 104R, the light-emitting layer 105R, and the electron-transport layer 108R that are not covered with the sacrifice layer 110R are removed by etching. Thus, the hole-injection/transport layer 104R, the light-emitting layer 105R, and the electron-transport layer 108R are processed to have side surfaces (or have their side surfaces exposed) over the electrode 551R or have belt-like shapes extending in the direction intersecting the sheet of the diagram. Note that dry etching is preferably employed for the etching. Note that the sacrifice layer 110R can be formed using a material similar to that for the sacrifice layer 1101B. In the case where the sacrifice layer 110R has the aforementioned stacked-layer structure of the first sacrifice layer and the second sacrifice layer, the hole-injection/transport layer 104R, the light-emitting layer 105R, and the electron-transport layer 108R may be processed into a predetermined shape in the following manner: part of the second sacrifice layer is etched using the resist mask REG, the resist mask REG is then removed, and part of the first sacrifice layer is etched using the second sacrifice layer as a mask. The structure illustrated in FIG. 6A is obtained through these etching steps.

Figure 6B:
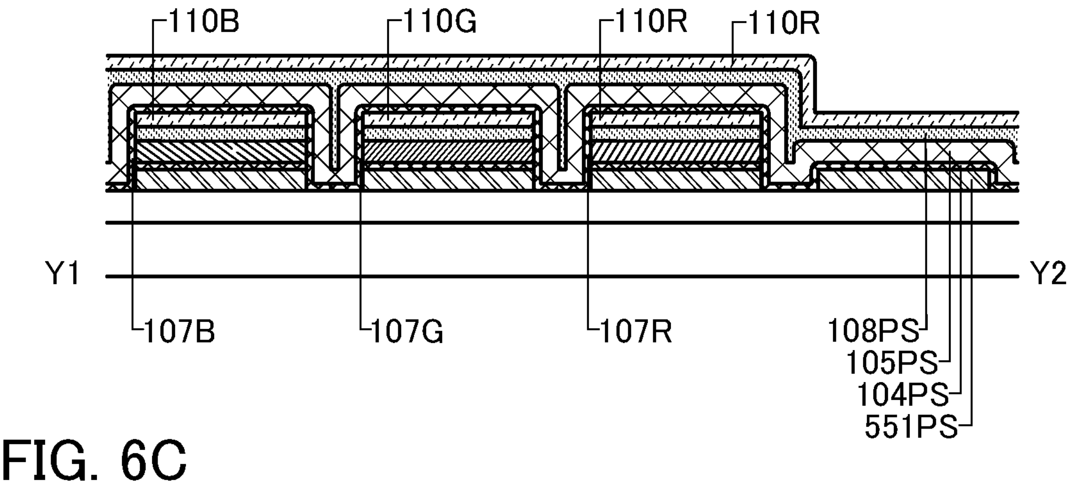

Next, as illustrated in FIG. 6B, the first transport layer 104PS, the active layer 105PS, and the second transport layer 108PS are formed over the sacrifice layer 110B, the sacrifice layer 110G, the sacrifice layer 110R, and the electrode 551PS. As a material for forming the first transport layer 104PS, for example, the material for the hole-injection layer and the hole-transport layer described in Embodiment 2 can be used. As a material for the active layer 105PS, a material described in Embodiment 2 can be used. Furthermore, as a material for forming the second transport layer 108PS, for example, the material for the electron-transport layer and the electron-injection layer described in Embodiment 2 can be used. Note that the first transport layer 104PS, the active layer 105PS, and the second transport layer 108PS can be formed by a vacuum evaporation method, for example.

Figure 6C:
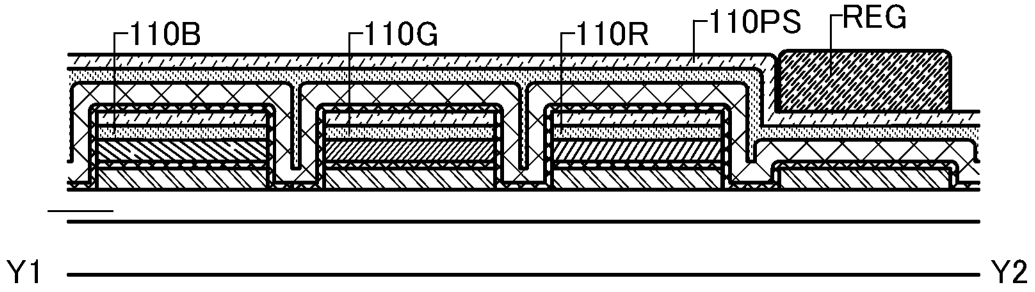
Figure 6D:
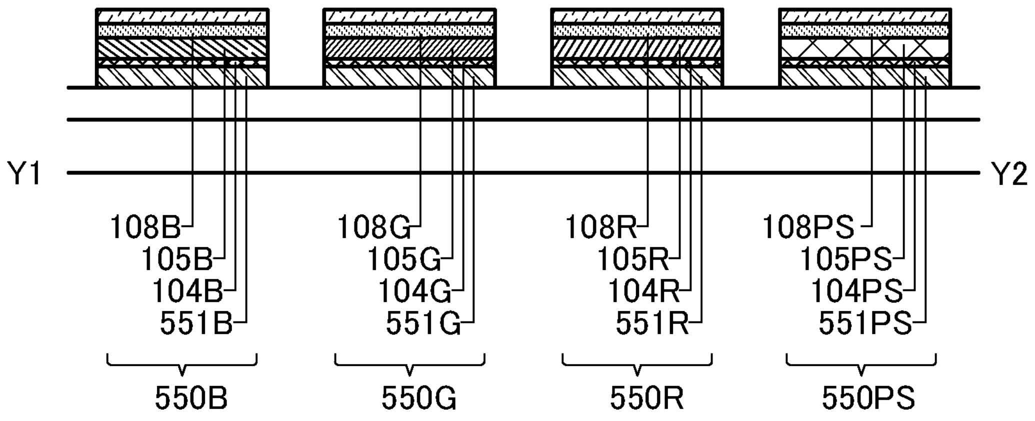

Next, as illustrated in FIG. 6C, a sacrifice layer 110PS is formed over the second transport layer 108PS, a resist is applied onto the sacrifice layer 110PS, and the resist having a desired shape (the resist mask REG) is formed by a photolithography method. Part of the sacrifice layer 110PS that is not covered with the obtained resist mask REG is removed by etching, the resist mask REG is removed, and then parts of the first transport layer 104PS, the active layer 105PS, and the second transport layer 108PS that are not covered with the sacrifice layer 110PS are removed by etching. Thus, the first transport layer 104PS, the active layer 105PS, and the second transport layer 108PS are processed to have side surfaces (or have their side surfaces exposed) over the electrode 551PS or have belt-like shapes extending in the direction intersecting the sheet of the diagram. Note that dry etching is preferably employed for the etching. Note that the sacrifice layer 110PS can be formed using a material similar to that for the sacrifice layer 1101B. In the case where the sacrifice layer 110PS has the aforementioned stacked-layer structure of the first sacrifice layer and the second sacrifice layer, the first transport layer 104PS, the active layer 105PS, and the second transport layer 108PS may be processed into a predetermined shape in the following manner: part of the second sacrifice layer is etched using the resist mask REG, the resist mask REG is then removed, and part of the first sacrifice layer is etched using the second sacrifice layer as a mask. The structure illustrated in FIG. 6D is obtained through these etching steps.

Figure 7A:
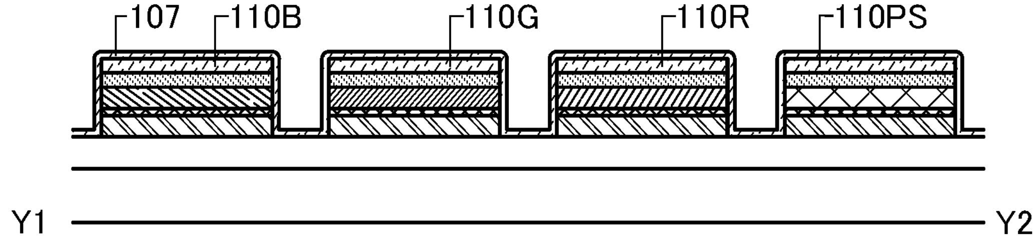
FIGS. 7A to 7E illustrate a light-emitting apparatus of an embodiment.

Next, as illustrated in FIG. 7A, the insulating layer 107 is formed over the sacrifice layer 110B, the sacrifice layer 110G, the sacrifice layer 110R, and the sacrifice layer 110PS.

Note that the insulating layer 107 can be formed by an ALD method, for example. In this case, as illustrated in FIG. 7A, the insulating layer 107 is formed to be in contact with the side surfaces (end portions) of the hole-injection/transport layers (104B, 104G, and 104R), the light-emitting layers (105B, 105G, and 105R), and the electron-transport layers (108B, 108G, and 108R) of the light-emitting devices and the first transport layer 104PS, the active layer 105PS, and the second transport layer 108PS of the light-receiving device. This can inhibit entry of oxygen, moisture, or constituent elements thereof into the inside through the side surfaces of the layers. Examples of the material used for the insulating layer 107 include aluminum oxide, magnesium oxide, hafnium oxide, gallium oxide, indium gallium zinc oxide, silicon nitride, and silicon nitride oxide.

Figure 7B:
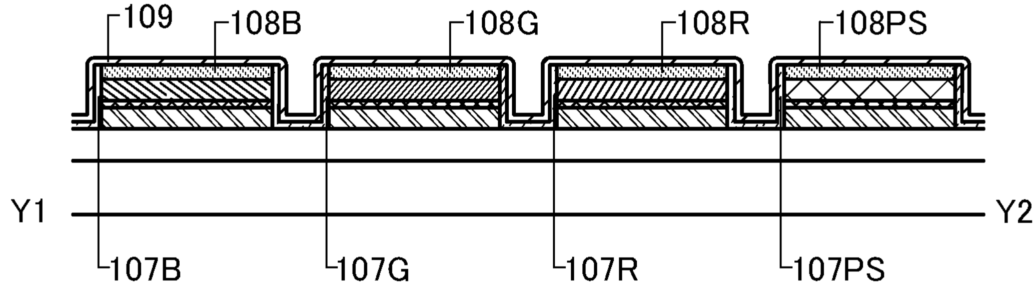

Then, as illustrated in FIG. 7B, after the sacrifice layers (110B, 110G, 110R, and 110PS) are removed, the electron-injection layer 109 is formed over the insulating layers (107B, 107G, 107R, and 107PS), the electron-transport layers (108B, 108G, and 108R), and the second transport layer 108PS. Note that parts of the insulating layers 107 are removed at the same time when the sacrificial layers (110B, 110G, 110R, and 110PS) are removed, whereby the insulating layers (107B, 107G, 107R, and 107PS) are formed. The electron-injection layer 109 can be formed using any of the materials described in Embodiment 2. The electron-injection layer 109 is formed by a vacuum evaporation method, for example. Note that the electron-injection layer 109 is formed over the electron-transport layers (108B, 108G, and 108R) and the second transport layer 108PS. Note that the electron-injection layer 109 is in contact with the side surfaces (end portions) of the hole-injection/transport layers (104B, 104G, and 104R), the light-emitting layers (105B, 105G, and 105R), and the electron-transport layers (108B, 108G, and 108R) of the light-emitting devices and the first transport layer 104PS, the active layer 105PS, and the second transport layer 108PS of the light-receiving device with the insulating layers (107B, 107G, 107R, and 107PS) therebetween.

Figure 7C:
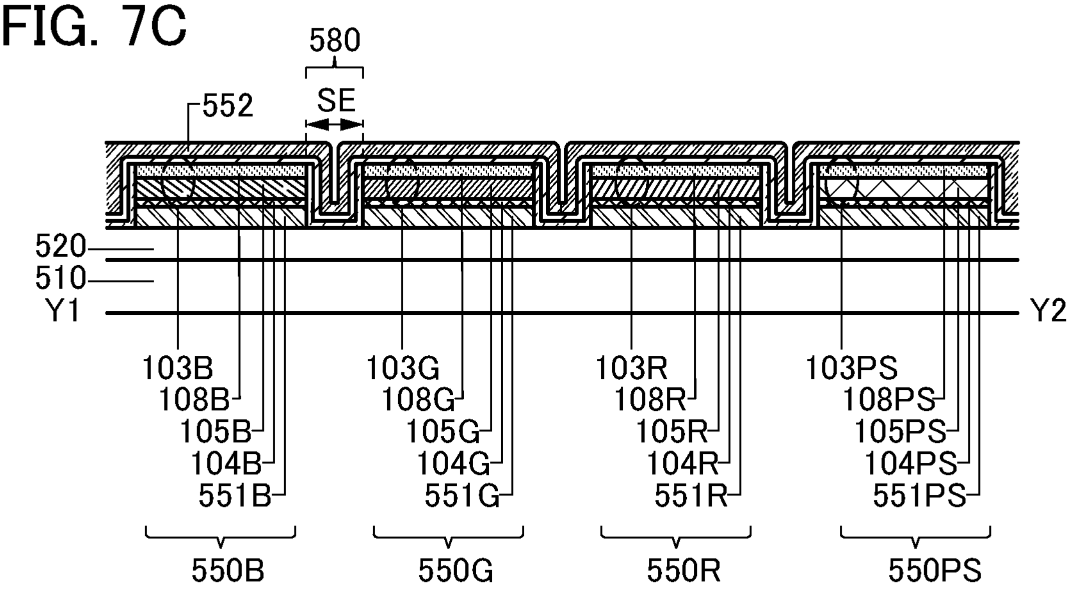

Next, as illustrated in FIG. 7C, the electrode 552 is formed. The electrode 552 is formed by a vacuum evaporation method, for example. The electrode 552 is formed over the electron-injection layer 109. Note that the electrode 552 is in contact with the side surfaces (end portions) of the hole-injection/transport layers (104B, 104G, and 104R), the light-emitting layers (105B, 105G, and 105R), and the electron-transport layers (108B, 108G, and 108R) of the light-emitting devices and the first transport layer 104PS, the active layer 105PS, and the second transport layer 108PS of the light-receiving device with the electron-injection layer 109 and the insulating layers (107B, 107G, and 107R) therebetween. This can prevent electrical short circuits between the electrode 552 and each of the following layers: the hole-injection/transport layers (104B, 104G, and 104R), the light-emitting layers (105B, 105G, and 105R), and the electron-transport layers (108B, 108G, and 108R) of the light-emitting devices and the first transport layer 104PS, the active layer 105PS, and the second transport layer 108PS of the light-receiving device.

Through the above steps, the EL layer 103B, the EL layer 103G, the EL layer 103R, and the light-receiving layer 103PS in the light-emitting device 550B, the light-emitting device 550G, the light-emitting device 550R, and the light-receiving device 550PS can be processed to be separated from each other.

The EL layers (the EL layer 103B, the EL layer 103G, and the EL layer 103R) and the light-receiving layer 103PS are processed to be separated by patterning using a photolithography method; hence, a light-emitting and light-receiving apparatus (display panel) with a high resolution can be fabricated. End portions (side surfaces) of the EL layer processed by patterning using a photolithography method have substantially the same surface (or are positioned on substantially the same plane).

Each of the hole-injection/transport layers (104B, 104G, and 104R) of the EL layers and the first transport layer 104PS of the light-receiving layer often has high conductivity, and thus might cause crosstalk when formed as a layer shared by adjacent devices. Therefore, processing the EL layers to be separated by patterning using a photolithography method as described in this structure example can inhibit occurrence of crosstalk between adjacent devices.

In this structure example, the hole-injection/transport layers (104B, 104G, and 104R), the light-emitting layers (105B, 105G, and 105R), and the electron-transport layers (108B, 108G, and 108R) of the EL layers (the EL layer 103B, the EL layer 103G, and the EL layer 103R) included in the light-emitting devices and the first transport layer 104PS, the active layer 105PS, and the second transport layer 108PS of the light-receiving layer 103PS included in the light-receiving device are processed to be separated by patterning using a photolithography method; thus, the side surfaces (end portions) of the layers of the processed EL layer have substantially the same surface (or are positioned on substantially the same plane).

In addition, the hole-injection/transport layers (104B, 104G, and 104R), the light-emitting layers (105R, 105G, and 105B), and the electron-transport layers (108B, 108G, and 108R) of the EL layers (the EL layer 103B, the EL layer 103G, and the EL layer 103R) included in the light-emitting devices and the first transport layer 104PS, the active layer 105PS, and the second transport layer 108PS of the light-receiving layer 103PS included in the light-receiving device are processed to be separated by patterning using a photolithography method. Thus, the space 580 is provided between the processed end portions (side surfaces) of adjacent devices. In FIG. 7C, when the space 580 is denoted by a distance SE between the EL layers of adjacent devices, decreasing the distance SE increases the aperture ratio and the resolution. By contrast, as the distance SE is increased, the effect of the difference in the fabrication process between the adjacent devices becomes permissible, which leads to an increase in manufacturing yield. Since the light-emitting device fabricated according to this specification is suitable for a miniaturization process, the distance SE between the EL layers or the light-emitting layers in the adjacent devices can be longer than or equal to 0.5 μm and shorter than or equal to 5 μm, preferably longer than or equal to 1 μm and shorter than or equal to 3 μm, further preferably longer than or equal to 1 μm and shorter than or equal to 2.5 m, and still further preferably longer than or equal to 1 μm and shorter than or equal to 2 m. Typically, the distance SE is preferably longer than or equal to 1 μm and shorter than or equal to 2 μm (e.g., 1.5 μm or a neighborhood thereof).

In this specification and the like, a device formed using a metal mask or a fine metal mask (FMM) is sometimes referred to as a device having a metal mask (MM) structure. In this specification and the like, a device formed without using a metal mask or an FMM is sometimes referred to as a device having a metal maskless (MML) structure.

Note that the island-shaped EL layers of the light-emitting and light-receiving apparatus having the MML structure are formed by not using a fine metal mask but processing after formation of an EL layer. Thus, a light-emitting and light-receiving apparatus with a higher resolution or a higher aperture ratio than a conventional one can be achieved. Moreover, EL layers can be formed separately for each color, which enables extremely clear images; thus, a light-emitting and light-receiving apparatus with a high contrast and high display quality can be achieved. Furthermore, provision of a sacrifice layer over an EL layer can reduce damage on the EL layer during the manufacturing process and increase the reliability of the light-emitting device.

In FIG. 2A and FIG. 7C, the widths of the EL layers (103B, 103G, and 103R) are substantially equal to those of the electrodes (551B, 551G, and 551R) in the light-emitting device 550B, the light-emitting device 550G, and the light-emitting device 550R, and the width of the light-receiving layer 103PS is substantially equal to that of the electrode 551PS in the light-receiving device 550PS; however, one embodiment of the present invention is not limited thereto.

Figure 7D:
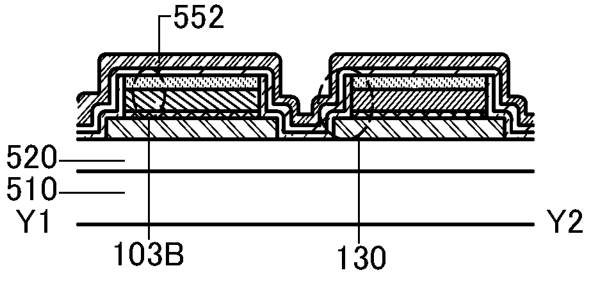

In the light-emitting device 550B, the light-emitting device 550G, and the light-emitting device 550R, the widths of the EL layers (103B, 103G, and 103R) may be smaller than those of the electrodes (551B, 551G, and 551R). In the light-receiving device 550PS, the width of the light-receiving layer 103PS may be smaller than that of the electrode 551PS. FIG. 7D illustrates an example in which the widths of the EL layers (103B and 103G) are smaller than those of the electrodes (551B and 551G) in the light-emitting device 550B and the light-emitting device 550G.

Figure 7E:
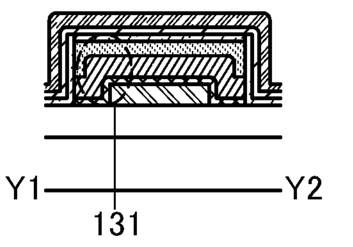

In the light-emitting device 550B, the light-emitting device 550G, and the light-emitting device 550R, the widths of the EL layers (103B, 103G, and 103R) may be larger than those of the electrodes (551B, 551G, and 551R). In the light-receiving device 550PS, the width of the light-receiving layer 103PS may be larger than that of the electrode 551PS. FIG. 7E illustrates an example in which the width of the EL layer 103R is larger than that of the electrode 551R in a connection portion 131 of the light-emitting device 550R.

The structures described in this embodiment can be used in combination with any of the structures described in the other embodiments as appropriate.

Embodiment 4

In this embodiment, an apparatus 720 is described with reference to FIGS. 8A to 8F, FIGS. 9A to 9C, and FIG. 10. The apparatus 720 illustrated in FIGS. 8A to 8F, FIGS. 9A to 9C, and FIG. 10 includes the light-emitting device described in Embodiment 2 and therefore is a light-emitting apparatus. Furthermore, the apparatus 720 described in this embodiment can be used in a display unit of an electronic appliance or the like and therefore can also be referred to as a display panel or a display device. Moreover, when the apparatus 720 includes the light-emitting device as a light source and a light-receiving device that can receive light from the light-emitting device, the apparatus 720 can be referred to as a light-emitting and light-receiving apparatus. Note that the light-emitting apparatus, the display panel, the display device, and the light-emitting and light-receiving apparatus each include at least a light-emitting device.

Furthermore, the light-emitting apparatus, the display panel, the display device, and the light-emitting and light-receiving apparatus of this embodiment can have high definition or large size. Therefore, the light-emitting apparatus, the display panel, the display device, and the light-emitting and light-receiving apparatus of this embodiment can be used, for example, in display units of electronic appliances such as a digital camera, a digital video camera, a digital photo frame, a mobile phone, a portable game console, a smart phone, a wristwatch terminal, a tablet terminal, a portable information terminal, and an audio reproducing apparatus, in addition to display units of electronic appliances with a relatively large screen, such as a television device, a desktop or laptop personal computer, a monitor of a computer or the like, digital signage, and a large game machine such as a pachinko machine.

Figure 8A:
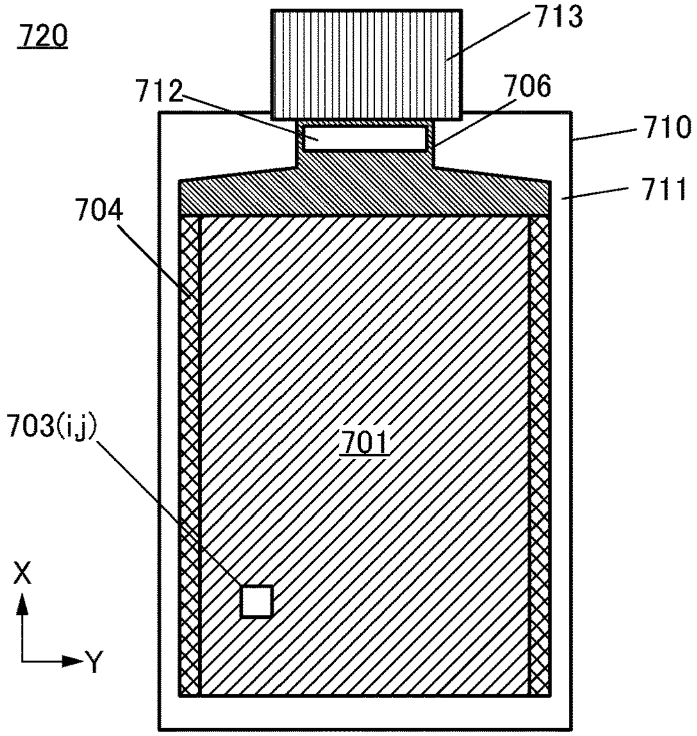
FIGS. 8A to 8F illustrate an apparatus of an embodiment and pixel arrangements.

FIG. 8A is a top view of the apparatus 720 (e.g., the light-emitting apparatus, the display panel, the display device, and the light-emitting and light-receiving apparatus).

Figure 8B:
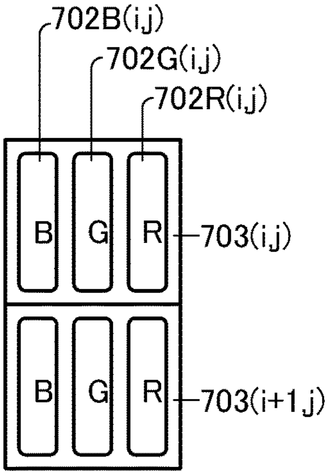

In FIG. 8A, the apparatus 720 has a structure in which a substrate 710 and a substrate 711 are attached to each other. In addition, the apparatus 720 includes a display region 701, a circuit 704, a wiring 706, and the like. Note that the display region 701 includes a plurality of pixels. As illustrated in FIG. 8B, a pixel 703(*i,j*) illustrated in FIG. 8A and a pixel 703(*i*+1, j) are adjacent to each other.

Furthermore, in the example of the apparatus 720 illustrated in FIG. 8A, the substrate 710 is provided with an integrated circuit (IC) 712 by a chip on glass (COG) method, a chip on film (COF) method, or the like. As the IC 712, an IC including a scan line driver circuit, a signal line driver circuit, or the like can be used, for example. In the example illustrated in FIG. 8A, an IC including a signal line driver circuit is used as the IC 712, and a scan line driver circuit is used as the circuit 704.

The wiring 706 has a function of supplying signals and power to the display region 701 and the circuit 704. The signals and power are input to the wiring 706 from the outside through a flexible printed circuit (FPC) 713 or to the wiring 706 from the IC 712. Note that the apparatus 720 is not necessarily provided with the IC. The IC may be mounted on the FPC by a COF method or the like.

FIG. 8B illustrates the pixel 703(*i, j*) and the pixel 703(*i*+1, j) of the display region 701. A plurality of kinds of subpixels including light-emitting devices that emit different color light from each other can be included in the pixel 703(*i,j*). Alternatively, a plurality of subpixels including light-emitting devices that emit the same color light may be included in addition to those described above. For example, the pixel can include three kinds of subpixels. The three subpixels can be of three colors of red (R), green (G), and blue (B) or of three colors of yellow (Y), cyan (C), and magenta (M), for example. Alternatively, the pixel can include four kinds of subpixels. The four subpixels can be of four colors of R, G, B, and white (W) or of four colors of R, G, B, and Y, for example. Specifically, the pixel 703(*i,j*) can consist of a subpixel 702B(i,j) for blue display, a subpixel 702G(i, j) for green display, and a subpixel 702R(i,j) for red display.

Other than the subpixels including the light-emitting devices, a subpixel including a light-receiving device may also be provided. In the case where the subpixel includes a light-receiving device, the apparatus 720 is also referred to as a light-emitting and light-receiving apparatus.

Figure 8C:
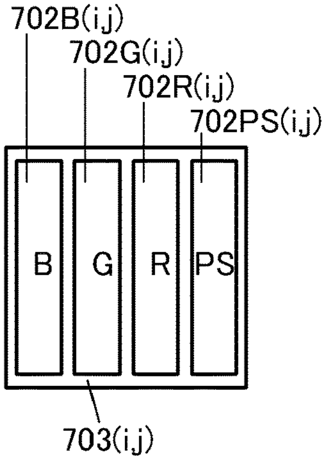
Figure 8D:
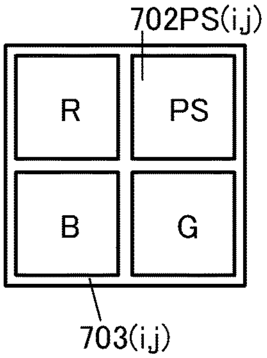
Figure 8E:
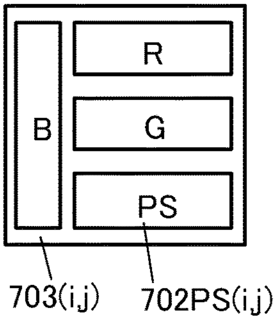

FIGS. 8C to 8F illustrate various layout examples of the pixel 703(*i,j*) including a subpixel 702PS(i, j) including alight-receiving device. The pixel arrangement in FIG. 8C is stripe arrangement, and the pixel arrangement in FIG. 8D is matrix arrangement. The pixel arrangement in FIG. 8E has a structure where three subpixels (the subpixels R, G, and PS) are vertically arranged next to one subpixel (the subpixel B). In the pixel arrangement in FIG. 8F, the vertically oriented three subpixels G, B, and R are arranged laterally, and the subpixel PS and the horizontally oriented subpixel IR are arranged laterally below the three subpixels. Note that the wavelength of light detected by the subpixel 702PS(i, j) is not particularly limited; however, the light-receiving device included in the subpixel 702PS(i, j) preferably has sensitivity to light emitted by the light-emitting device included in the subpixel 702R(i, j), the subpixel 702G(i, j), the subpixel 702B(i, j), or a subpixel 702IR(i, j). For example, the light-receiving device preferably detects one or more kinds of light in blue, violet, bluish violet, green, yellowish green, yellow, orange, red, and infrared wavelength ranges, for example.

Figure 8F:
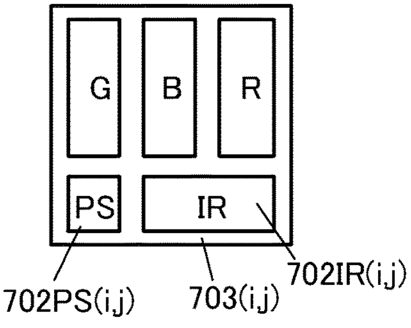

Furthermore, as illustrated in FIG. 8F, the subpixel 702IR (i, j) that emits infrared rays may be added to any of the above-described sets of subpixels in the pixel 703(*i, j*). Specifically, a subpixel that emits light including light with a wavelength higher than or equal to 650 nm and lower than or equal to 1000 nm may be used in the pixel 703(*i,j*).

Note that the arrangement of subpixels is not limited to the structures illustrated in FIGS. 8B to 8F and a variety of arrangement methods can be employed. The arrangement of subpixels may be stripe arrangement, S stripe arrangement, matrix arrangement, delta arrangement, Bayer arrangement, or pentile arrangement, for example.

Furthermore, top surfaces of the subpixels may have a triangular shape, a quadrangular shape (including a rectangular shape and a square shape), a polygonal shape such as a pentagonal shape, a polygonal shape with rounded corners, an elliptical shape, or a circular shape, for example. The top surface shape of a subpixel herein refers to a top surface shape of a light-emitting region of a light-emitting device.

Furthermore, in the case where not only a light-emitting device but also a light-receiving device is included in a pixel, the pixel has a light-receiving function and thus can detect a contact or approach of an object while displaying an image. For example, an image can be displayed by using all the subpixels included in a light-emitting apparatus; or light can be emitted by some of the subpixels as a light source and an image can be displayed by using the remaining subpixels.

Note that the light-receiving area of the subpixel 702PS(i, j) is preferably smaller than the light-emitting areas of the other subpixels. A smaller light-receiving area leads to a narrower image-capturing range, inhibits a blur in a captured image, and improves the definition. Thus, by using the subpixel 702PS(i, j), high-resolution or high-definition image capturing is possible. For example, image capturing for personal authentication with the use of a fingerprint, a palm print, the iris, the shape of a blood vessel (including the shape of a vein and the shape of an artery), a face, or the like is possible by using the subpixel 702PS(i, j).

Moreover, the subpixel 702PS(i, j) can be used in a touch sensor (also referred to as a direct touch sensor), a near touch sensor (also referred to as a hover sensor, a hover touch sensor, a contactless sensor, or a touchless sensor), or the like. For example, the subpixel 702PS(i, j) preferably detects infrared light. Thus, touch sensing is possible even in a dark place.

Here, the touch sensor or the near touch sensor can detect an approach or contact of an object (e.g., a finger, a hand, or a pen). The touch sensor can detect the object when the light-emitting and light-receiving apparatus and the object come in direct contact with each other. Furthermore, the near touch sensor can detect the object even when the object is not in contact with the light-emitting and light-receiving apparatus. For example, the light-emitting and light-receiving apparatus can preferably detect the object when the distance between the light-emitting and light-receiving apparatus and the object is more than or equal to 0.1 mm and less than or equal to 300 mm, preferably more than or equal to 3 mm and less than or equal to 50 mm. With this structure, the light-emitting and light-receiving apparatus can be controlled without the object directly contacting with the light-emitting and light-receiving apparatus. In other words, the light-emitting and light-receiving apparatus can be controlled in a contactless (touchless) manner. With the above-described structure, the light-emitting and light-receiving apparatus can be controlled with a reduced risk of making the light-emitting and light-receiving apparatus dirty or damaging the light-emitting and light-receiving apparatus or without the object directly touching a dirt (e.g., dust, bacteria, or a virus) attached to the light-emitting and light-receiving apparatus.

For high-resolution image capturing, the subpixel 702PS (i, j) is preferably provided in every pixel included in the light-emitting and light-receiving apparatus. Meanwhile, in the case where the subpixel 702PS(i, j) is used in a touch sensor, a near touch sensor, or the like, high accuracy is not required as compared to the case of capturing an image of a fingerprint or the like; accordingly, the subpixel 702PS(i, j) is provided in some subpixels in the light-emitting and light-receiving apparatus. When the number of subpixels 702PS(i, j) included in the light-emitting and light-receiving apparatus is smaller than the number of subpixels 702R(i, j) or the like, higher detection speed can be achieved.

Next, an example of a pixel circuit of a subpixel included in the light-emitting device is described with reference to FIG. 9A. A pixel circuit 530 illustrated in FIG. 9A includes a light-emitting device (EL) 550, a transistor M15, a transistor M16, a transistor M17, and a capacitor C3. Note that a light-emitting diode can be used as the light-emitting device 550. In particular, the light-emitting device described in Embodiment 2 is preferably used as the light-emitting device 550.

Figure 9A:
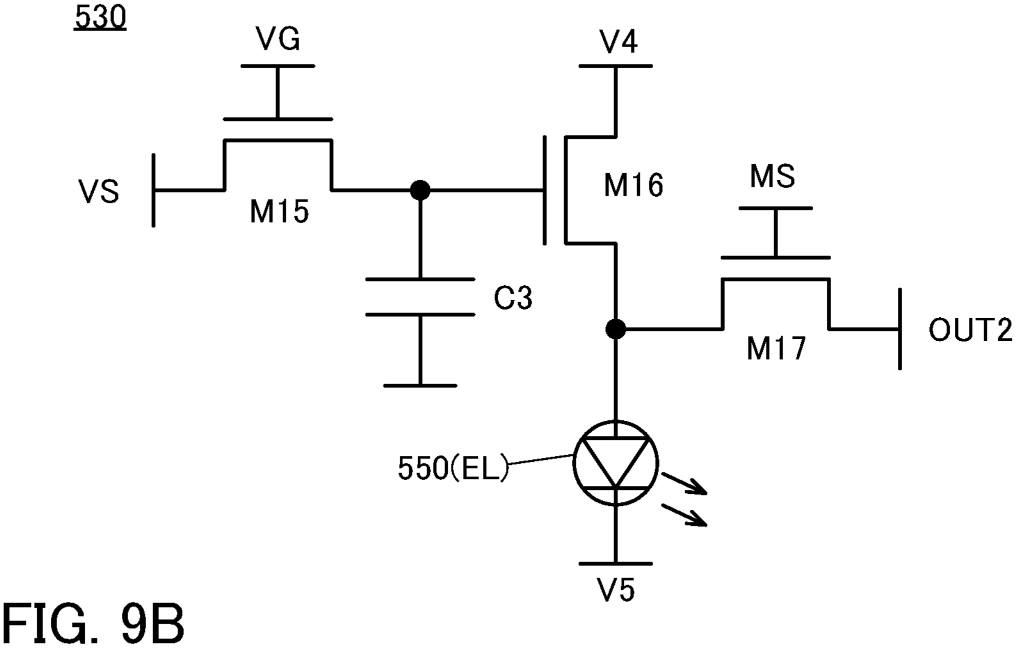
FIGS. 9A to 9C illustrate pixel circuits of an embodiment.

In FIG. 9A, a gate of the transistor M15 is electrically connected to a wiring VG, one of a source and a drain of the transistor M15 is electrically connected to a wiring VS, and the other of the source and the drain of the transistor M15 is electrically connected to one electrode of the capacitor C3 and a gate of the transistor M16. One of a source and a drain of the transistor M16 is electrically connected to a wiring V4, and the other is electrically connected to an anode of the light-emitting device 550 and one of a source and a drain of the transistor M17. A gate of the transistor M17 is electrically connected to a wiring MS, and the other of the source and the drain of the transistor M17 is electrically connected to a wiring OUT2. A cathode of the light-emitting device 550 is electrically connected to a wiring V5.

A constant potential is supplied to the wiring V4 and the wiring V5. In the light-emitting device 550, the anode side can have a high potential and the cathode side can have a lower potential than the anode side. The transistor M15 is controlled by a signal supplied to the wiring VG and functions as a selection transistor for controlling a selection state of the pixel circuit 530. The transistor M16 functions as a driving transistor that controls a current flowing through the light-emitting device 550 in accordance with a potential supplied to the gate of the transistor M16. When the transistor M15 is on, a potential supplied to the wiring VS is supplied to the gate of the transistor M16, and the luminance of the light-emitting device 550 can be controlled in accordance with the potential. The transistor M17 is controlled by a signal supplied to the wiring MS and has a function of outputting a potential between the transistor M16 and the light-emitting device 550 to the outside through the wiring OUT2.

Figure 9B:
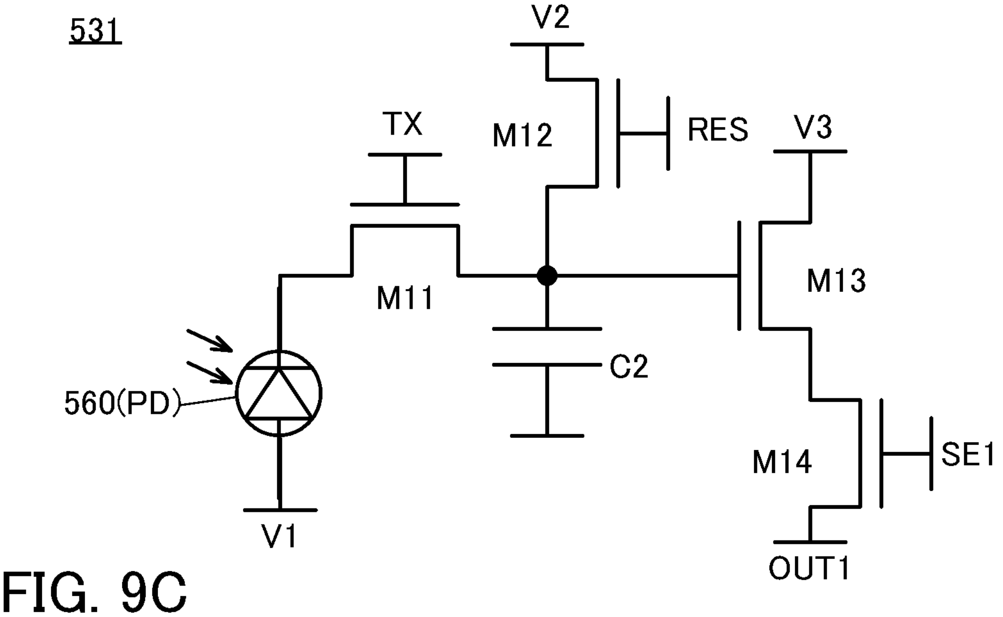

Here, a transistor in which a metal oxide (an oxide semiconductor) is used in a semiconductor layer where a channel is formed is preferably used as the transistors M15, M16, and M17 included in a pixel circuit 530 in FIG. 9A and transistors M11, M12, M13, and M14 included in a pixel circuit 531 in FIG. 9B.

A transistor using a metal oxide having a wider band gap and a lower carrier density than silicon can achieve an extremely low off-state current. Such a low off-state current enables retention of charges accumulated in a capacitor that is connected in series to the transistor for a long time. Therefore, it is particularly preferable to use a transistor including an oxide semiconductor as the transistors M11, M12, and M15 each of which is connected in series to a capacitor C2 or the capacitor C3. When each of the other transistors also includes an oxide semiconductor, manufacturing cost can be reduced.

Alternatively, transistors using silicon as a semiconductor in which a channel is formed can be used as the transistors M11 to M17. It is particularly preferable to use silicon with high crystallinity such as single crystal silicon or polycrystalline silicon because high field-effect mobility can be achieved and higher-speed operation can be performed.

Alternatively, a transistor including an oxide semiconductor may be used as at least one of the transistors M11 to M17, and transistors including silicon may be used as the other transistors.

Next, an example of a pixel circuit of a subpixel including a light-receiving device is described with reference to FIG. 9B. The pixel circuit 531 illustrated in FIG. 9B includes a light-receiving device (PD) 560, the transistor M11, the transistor M12, the transistor M13, the transistor M14, and the capacitor C2. In the example illustrated here, a photodiode is used as the light-receiving device (PD) 560.

In FIG. 9B, an anode of the light-receiving device (PD) 560 is electrically connected to a wiring V1, and a cathode of the light-receiving device (PD) 560 is electrically connected to one of a source and a drain of the transistor M11. A gate of the transistor M11 is electrically connected to a wiring TX, and the other of the source and the drain of the transistor M11 is electrically connected to one electrode of the capacitor C2, one of a source and a drain of the transistor M12, and a gate of the transistor M13. A gate of the transistor M12 is electrically connected to a wiring RES, and the other of the source and the drain of the transistor M12 is electrically connected to a wiring V2. One of a source and a drain of the transistor M13 is electrically connected to a wiring V3, and the other of the source and the drain of the transistor M13 is electrically connected to one of a source and a drain of the transistor M14. A gate of the transistor M14 is electrically connected to a wiring SET, and the other of the source and the drain of the transistor M14 is electrically connected to a wiring OUT1.

A constant potential is supplied to the wiring VI, the wiring V2, and the wiring V3. When the light-receiving device (PD) 560 is driven with a reverse bias, the wiring V2 is supplied with a potential higher than the potential of the wiring VI. The transistor M12 is controlled by a signal supplied to the wiring RES and has a function of resetting the potential of a node connected to the gate of the transistor M13 to a potential supplied to the wiring V2. The transistor M11 is controlled by a signal supplied to the wiring TX and has a function of controlling the timing at which the potential of the node changes, in accordance with a current flowing through the light-receiving device (PD) 560. The transistor M13 functions as an amplifier transistor for outputting a signal corresponding to the potential of the node. The transistor M14 is controlled by a signal supplied to the wiring SE1 and functions as a selection transistor for reading an output corresponding to the potential of the node by an external circuit connected to the wiring OUT1.

Although n-channel transistors are illustrated in FIGS. 9A and 9B, p-channel transistors can alternatively be used.

The transistors included in the pixel circuit 530 and the transistors included in the pixel circuit 531 are preferably formed side by side over the same substrate. It is particularly preferable that the transistors included in the pixel circuit 530 and the transistors included in the pixel circuit 531 be periodically arranged in one region.

One or more layers including the transistor and/or the capacitor are preferably provided to overlap with the light-receiving device (PD) 560 or the light-emitting device (EL)

550. Thus, the effective area of each pixel circuit can be reduced, and a high-resolution light-receiving unit or display unit can be achieved.

Figure 9C:
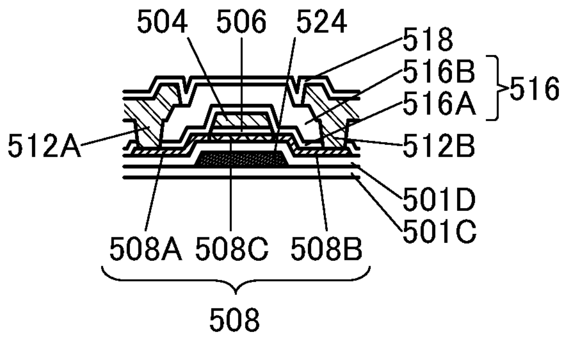

FIG. 9C illustrates an example of a specific structure of a transistor that can be used in the pixel circuit described with reference to FIGS. 9A and 9B. As the transistor, a bottom-gate transistor, a top-gate transistor, or the like can be used as appropriate.

The transistor illustrated in FIG. 9C includes a semiconductor film 508, a conductive film 504, an insulating film 506, a conductive film 512A, and a conductive film 512B. The transistor is formed over an insulating film 501C, for example. The transistor also includes an insulating film 516 (an insulating film 516A and an insulating film 516B) and an insulating film 518.

The semiconductor film 508 includes a region 508A electrically connected to the conductive film 512A and a region 508B electrically connected to the conductive film 512B. The semiconductor film 508 includes a region 508C between the region 508A and the region 508B.

The conductive film 504 includes a region overlapping with the region 508C and has a function of a gate electrode.

The insulating film 506 includes a region positioned between the semiconductor film 508 and the conductive film 504. The insulating film 506 has a function of a first gate insulating film.

The conductive film 512A has one of a function of a source electrode and a function of a drain electrode, and the conductive film 512B has the other.

A conductive film 524 can be used in the transistor. The semiconductor film 508 is sandwiched between the conductive film 504 and a region included in the conductive film 524. The conductive film 524 has a function of a second gate electrode. An insulating film 501D is positioned between the semiconductor film 508 and the conductive film 524 and has a function of a second gate insulating film.

The insulating film 516 functions as, for example, a protective film covering the semiconductor film 508. Specifically, a film including a silicon oxide film, a silicon oxynitride film, a silicon nitride oxide film, a silicon nitride film, an aluminum oxide film, a hafnium oxide film, an yttrium oxide film, a zirconium oxide film, a gallium oxide film, a tantalum oxide film, a magnesium oxide film, a lanthanum oxide film, a cerium oxide film, or a neodymium oxide film can be used as the insulating film 516, for example.

For the insulating film 518, a material that has a function of inhibiting diffusion of oxygen, hydrogen, water, an alkali metal, an alkaline earth metal, and the like is preferably used. Specifically, the insulating film 518 can be formed using silicon nitride, silicon oxynitride, aluminum nitride, or aluminum oxynitride, for example. In each of silicon oxynitride and aluminum oxynitride, the number of nitrogen atoms contained is preferably larger than the number of oxygen atoms contained.

Note that in a step of forming the semiconductor film used in the transistor of the pixel circuit, the semiconductor film used in the transistor of the driver circuit can be formed. A semiconductor film having the same composition as the semiconductor film used in the transistor of the pixel circuit can be used in the driver circuit, for example.

The semiconductor film 508 preferably contains indium, M (M is one or more of gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more of aluminum, gallium, yttrium, and tin.

It is particularly preferable that an oxide containing indium (In), gallium (Ga), and zinc (Zn) (also referred to as IGZO) be used as the semiconductor film 508. Alternatively, it is preferable to use an oxide containing indium, tin, and zinc. Further alternatively, it is preferable to use an oxide containing indium, gallium, tin, and zinc. Further alternatively, it is preferable to use an oxide containing indium (In), aluminum (Al), and zinc (Zn) (also referred to as IAZO). Further alternatively, it is preferable to use an oxide containing indium (In), aluminum (Al), gallium (Ga), and zinc (Zn) (also referred to as IAGZO).

When the semiconductor film is an In-M-Zn oxide, the atomic ratio of In is preferably greater than or equal to the atomic ratio of Min the In-M-Zn oxide. Examples of the atomic ratio of the metal elements in such an In-M-Zn oxide are In:M:Zn=1:1:1, 1:1:1.2, 1:3:2, 1:3:4, 2:1:3, 3:1:2, 4:2:3, 4:2:4.1, 5:1:3, 5:1:6, 5:1:7, 5:1:8, 6:1:6, and 5:2:5 and a composition in the vicinity of any of the above atomic ratios. Note that the vicinity of the atomic ratio includes ±30% of an intended atomic ratio.

For example, when the atomic ratio is described as In:Ga:Zn=4:2:3 or a composition in the vicinity thereof, the case is included where the atomic ratio of Ga is greater than or equal to 1 and less than or equal to 3 and the atomic ratio of Zn is greater than or equal to 2 and less than or equal to 4 with the atomic ratio of In being 4. In addition, when the atomic ratio is described as In:Ga:Zn=5:1:6 or a composition in the vicinity thereof, the case is included where the atomic ratio of Ga is greater than 0.1 and less than or equal to 2 and the atomic ratio of Zn is greater than or equal to 5 and less than or equal to 7 with the atomic ratio of In being 5. Furthermore, when the atomic ratio is described as In:Ga:Zn=1:1:1 or a composition in the vicinity thereof, the case is included where the atomic ratio of Ga is greater than 0.1 and less than or equal to 2 and the atomic ratio of Zn is greater than 0.1 and less than or equal to 2 with the atomic ratio of In being 1.

There is no particular limitation on the crystallinity of a semiconductor material used in the transistor, and an amorphous semiconductor or a semiconductor having crystallinity (a microcrystalline semiconductor, a polycrystalline semiconductor, a single crystal semiconductor, or a semiconductor partly including crystal regions) can be used. It is preferable to use a semiconductor having crystallinity, in which case deterioration of transistor characteristics can be suppressed.

It is preferable that a semiconductor layer of a transistor contain a metal oxide (also referred to as an oxide semiconductor). As an oxide semiconductor having crystallinity, a c-axis aligned crystalline oxide semiconductor (CAAC-OS), a nanocrystalline oxide semiconductor (nc-OS), and the like are given.

Alternatively, a transistor using silicon in its channel formation region (a Si transistor) may be used. Examples of silicon include single crystal silicon (single crystal Si), polycrystalline silicon, and amorphous silicon. In particular, a transistor containing low-temperature polysilicon (LTPS) in its semiconductor layer (hereinafter also referred to as an LTPS transistor) can be used. The LTPS transistor has high field-effect mobility and excellent frequency characteristics.

With the use of Si transistors such as LTPS transistors, a circuit required to drive at a high frequency (e.g., a source driver circuit) can be formed on the same substrate as the display unit. This allows simplification of an external circuit mounted on the light-emitting apparatus and a reduction in costs of parts and mounting costs.

The OS transistor has much higher field-effect mobility than a transistor containing amorphous silicon. In addition, the OS transistor has an extremely low leakage current between a source and a drain in an off state (hereinafter also referred to as off-state current), and charge accumulated in a capacitor that is connected in series to the transistor can be held for a long period. Furthermore, the power consumption of the light-emitting apparatus can be reduced with the OS transistor.

The off-state current per micrometer of channel width of the OS transistor at room temperature can be lower than or equal to 1 aA ($1\times10^{-18}$ A), lower than or equal to 1 zA ($1\times10^{-21}$ A), or lower than or equal to 1 yA ($1\times10^{-24}$ A). Note that the off-state current per micrometer of channel width of a Si transistor at room temperature is higher than or equal to 1 fA ($1\times10^{-15}$ A) and lower than or equal to 1 pA ($1\times10^{-12}$ A). In other words, the off-state current of the OS transistor is lower than that of the Si transistor by approximately ten orders of magnitude.

To increase the luminance of the light-emitting device included in the pixel circuit, the amount of current fed through the light-emitting device needs to be increased. To increase the current amount, the source-drain voltage of a driving transistor included in the pixel circuit needs to be increased. An OS transistor has a higher withstand voltage between a source and a drain than a Si transistor; hence, high voltage can be applied between the source and the drain of the OS transistor. Thus, with use of an OS transistor as a driving transistor included in the pixel circuit, the amount of current flowing through the light-emitting device can be increased, resulting in an increase in emission luminance of the light-emitting device.

When transistors operate in a saturation region, a change in source-drain current relative to a change in gate-source voltage can be smaller in an OS transistor than in a Si transistor. Accordingly, when an OS transistor is used as the driving transistor in the pixel circuit, a current flowing between the source and the drain can be set minutely by a change in gate-source voltage; hence, the amount of current flowing through the light-emitting device can be controlled. Accordingly, the gray level in the pixel circuit can be increased.

Regarding saturation characteristics of current flowing when transistors operates in a saturation region, even in the case where the source-drain voltage of an OS transistor increases gradually, a more stable current (saturation current) can be fed through the OS transistor than through a Si transistor. Thus, by using an OS transistor as the driving transistor, a stable current can be fed through light-emitting devices even when the current-voltage characteristics of the light-emitting devices vary, for example. In other words, when the OS transistor operates in the saturation region, the source-drain current hardly changes with an increase in the source-drain voltage; hence, the luminance of the light-emitting device can be stable.

As described above, with use of an OS transistor as a driving transistor included in the pixel circuit, it is possible to achieve "inhibition of black floating", "increase in emission luminance", "increase in gray level", "inhibition of variation in light-emitting devices", and the like.

The semiconductor film used in the transistor of the driver circuit can be formed in the same step as the semiconductor film used in the transistor of the pixel circuit. The driver circuit can be formed over a substrate where the pixel circuit is formed. The number of components of an electronic appliance can be reduced.

When an LTPS transistor is used as one or more of the transistors included in the pixel circuit and an OS transistor is used as the rest, the light-emitting apparatus can have low power consumption and high driving capability. As a favorable example, it is preferable that an OS transistor be used as a transistor functioning as a switch for controlling electrical continuity between wirings and an LTPS transistor be used as a transistor for controlling current, for instance. A structure where an LTPS transistor and an OS transistor are used in combination may be referred to as LTPO. The use of LTPO enables the display panel to have low power consumption and high drive capability.

For example, one of the transistors included in the pixel circuit functions as a transistor for controlling a current flowing through the light-emitting device and can be referred to as a driving transistor. One of a source and a drain of the driving transistor is electrically connected to the pixel electrode of the light-emitting device. An LTPS transistor is preferably used as the driving transistor. Accordingly, the amount of current flowing through the light-emitting device can be increased in the pixel circuit.

Another transistor included in the pixel circuit functions as a switch for controlling selection and non-selection of the pixel and can be referred to as a selection transistor. A gate of the selection transistor is electrically connected to a gate line, and one of a source and a drain thereof is electrically connected to a source line (signal line). An OS transistor is preferably used as the selection transistor. Accordingly, the gray level of the pixel can be maintained even with an extremely low frame frequency (e.g., 1 fps or less); thus, power consumption can be reduced by stopping the driver in displaying a still image.

In the case of using an oxide semiconductor in a semiconductor film, the apparatus 720 includes a light-emitting device including an oxide semiconductor in its semiconductor film and having a metal maskless (MML) structure. With this structure, the leakage current that might flow through the transistor and the leakage current that might flow between adjacent light-emitting devices (also referred to as a lateral leakage current, a side leakage current, or the like) can become extremely low. With the structure, a viewer can observe any one or more of the image crispness, the image sharpness, a high chroma, and a high contrast ratio in an image displayed on the display device. When the leakage current that might flow through the transistor and the lateral leakage current that might flow between light-emitting devices are extremely low, display with little leakage of light at the time of black display (what is called black floating) (such display is also referred to as deep black display) can be achieved.

In particular, in the case where a light-emitting device having an MML structure employs the above-described SBS structure, a layer provided between light-emitting devices (for example, also referred to as an organic layer or a common layer which is shared by the light-emitting devices) is disconnected; accordingly, display with no or extremely small lateral leakage can be achieved.

The structure of the transistors used in the display panel may be selected as appropriate depending on the size of the screen of the display panel. For example, single crystal Si transistors can be used in the display panel with a screen diagonal greater than or equal to 0.1 inches and less than or equal to 3 inches. In addition, LTPS transistors can be used in the display panel with a screen diagonal greater than or equal to 0.1 inches and less than or equal to 30 inches, preferably greater than or equal to 1 inch and less than or equal to 30 inches. In addition, an LTPO structure (where an LTPS transistor and an OS transistor are used in combination) can be used for the display panel with a screen diagonal greater than or equal to 0.1 inches and less than or equal to 50 inches, preferably greater than or equal to 1 inch and less than or equal to 50 inches. In addition, OS transistors can be used in the display panel with a screen diagonal greater than or equal to 0.1 inches and less than or equal to 200 inches, preferably greater than or equal to 50 inches and less than or equal to 100 inches.

With the use of single crystal Si transistors, an increase in screen size is extremely difficult due to the size of a single crystal Si substrate. Furthermore, since a laser crystallization apparatus is used in the fabrication process, LTPS transistors are unlikely to respond to an increase in screen size (typically to a screen diagonal greater than 30 inches). By contrast, since the fabrication process does not necessarily require a laser crystallization apparatus or the like or can be performed at a relatively low temperature (typically, lower than or equal to 450° C.), OS transistors can be applied to a display panel with a relatively large area (typically, a screen diagonal greater than or equal to 50 inches and less than or equal to 100 inches). In addition, LTPO can be applied to a display panel with a size (typically, a screen diagonal greater than or equal to 1 inch and less than or equal to 50 inches) midway between the structure using LTPS transistors and the structure using OS transistors.

Figure 10:
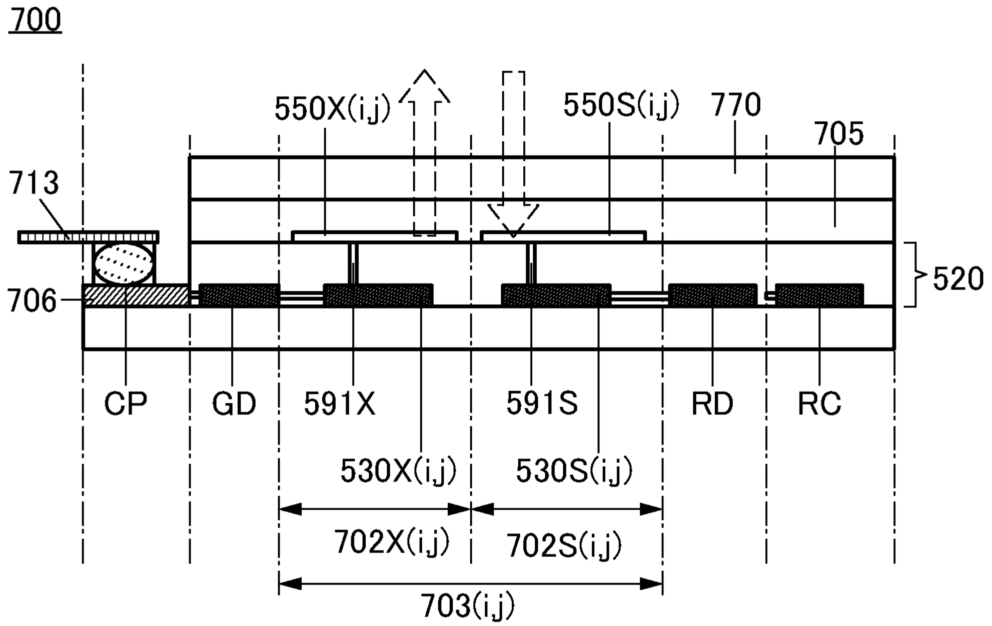
FIG. 10 illustrates a light-emitting apparatus of an embodiment.

Next, a cross-sectional view of a light-emitting and light-receiving apparatus is shown. FIG. 10 is a cross-sectional view of the light-emitting and light-receiving apparatus illustrated in FIG. 8A.

FIG. 10 is a cross-sectional view of part of a region including the FPC 713 and the wiring 706 and part of the display region 701 including the pixel 703(*i,j*).

In FIG. 10, the light-emitting and light-receiving apparatus 700 includes the functional layer 520 between the first substrate 510 and the second substrate 770. The functional layer 520 includes, as well as the above-described transistors (M11, M12, M13, M14, M15, M16, and M17), the capacitor (C2 and C3), and the like described in FIGS. 9A, 9B, and 9C, wirings (VS, VG, V1, V2, V3, V4, and V5) electrically connected to these components, for example. FIG. 10 illustrates a non-limiting example of the functional layer 520 that includes a pixel circuit 530X(i, j), a pixel circuit 530S(i, j), and a circuit GD.

Furthermore, the pixel circuits (e.g., the pixel circuit 530X(i, j) and the pixel circuit 530S(i, j) in FIG. 10) formed over the functional layer 520 are electrically connected to a light-emitting device and a light-receiving device (e.g., a light-emitting device 550X(i, j) and a light-receiving device 550S(i, j) in FIG. 10) formed over the functional layer 520. Specifically, the light-emitting device 550X(i, j) is electrically connected to the pixel circuit 530X(i, j) through a wiring 591X, and the light-receiving device 550S(i, j) is electrically connected to the pixel circuit 530S(i, j) through a wiring 591S. The insulating layer 705 is provided over the functional layer 520, the light-emitting devices, and the light-receiving device, and has a function of attaching the second substrate 770 and the functional layer 520.

As the second substrate 770, a substrate where touch sensors are arranged in a matrix can be used. For example, a substrate provided with capacitive touch sensors or optical touch sensors can be used as the second substrate 770. Thus, the light-emitting and light-receiving apparatus of one embodiment of the present invention can be used as a touch panel.

The structures described in this embodiment can be used in appropriate combination with any of the structures described in the other embodiments.

Embodiment 5

In this embodiment, structures of electronic appliances of embodiments of the present invention will be described with reference to FIGS. 11A to 11E, FIGS. 12A to 12E, and FIGS. 13A and 13B.

Figure 11A:
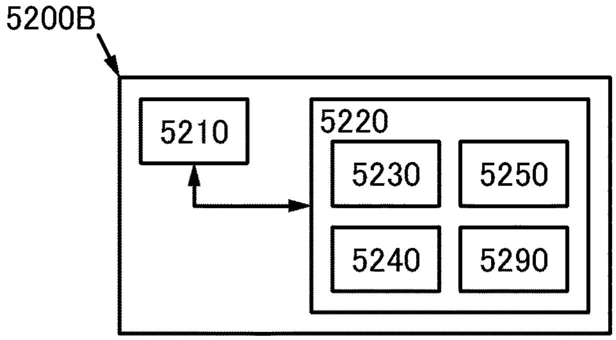
FIGS. 11A to 11E illustrate electronic appliances of an embodiment.
Figure 11B:
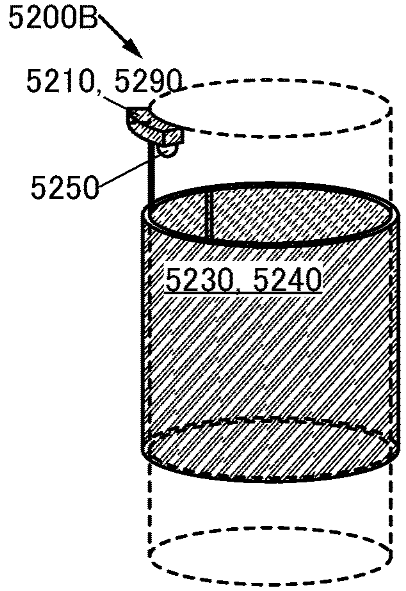
Figure 11C:
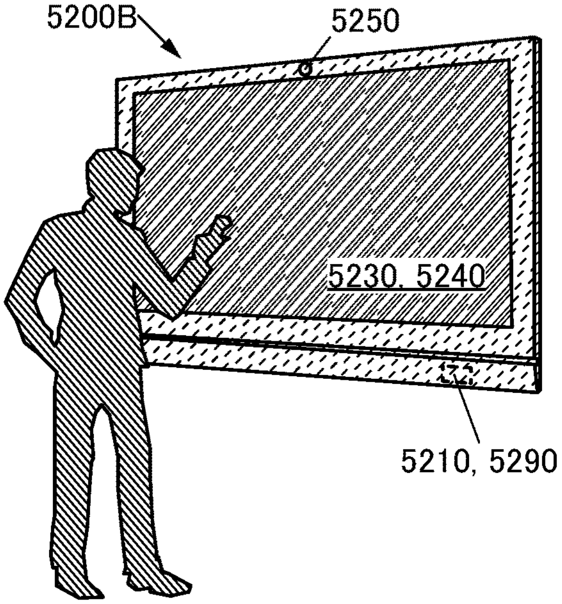
Figure 11D:
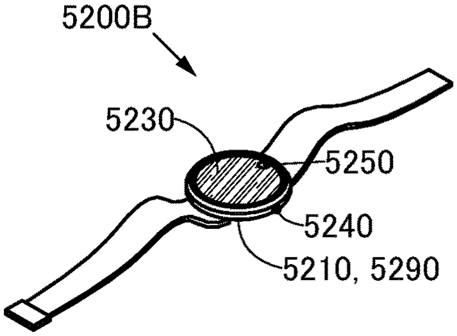
Figure 11E:
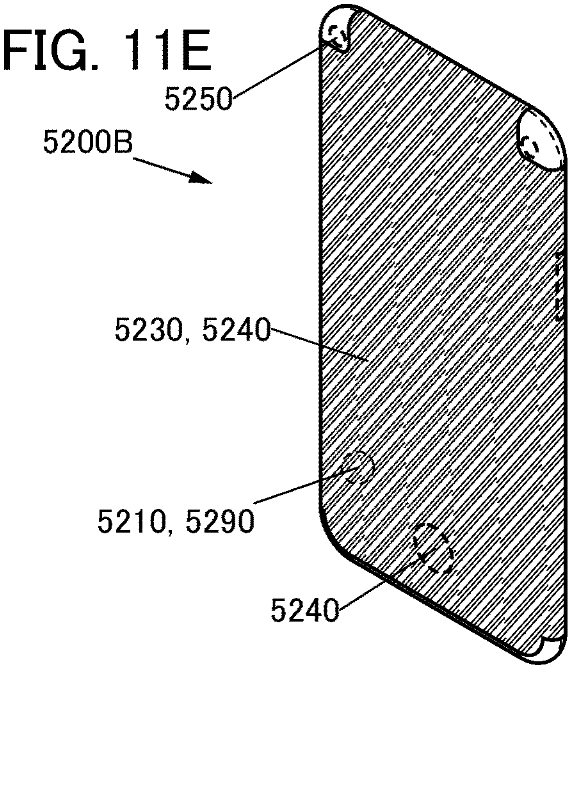
Figure 12A:
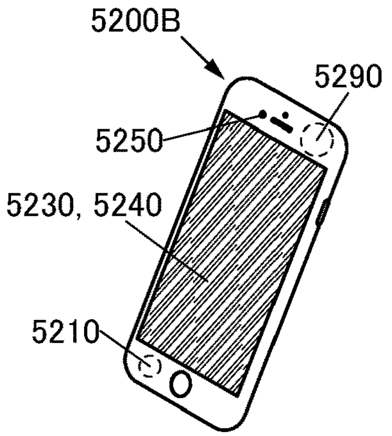
FIGS. 12A to 12E illustrate electronic appliances of an embodiment.
Figure 12B:
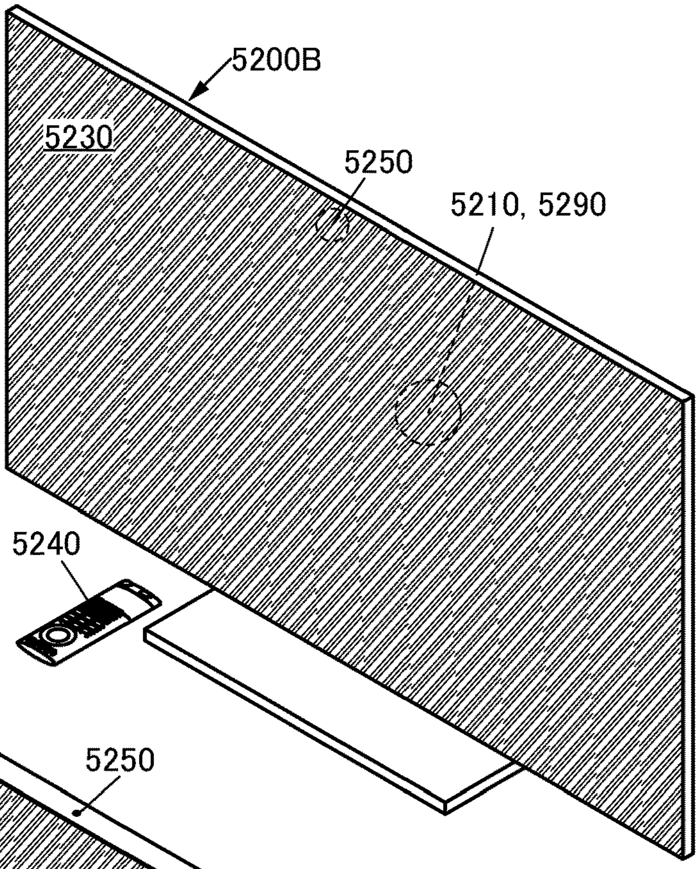
Figure 12C:
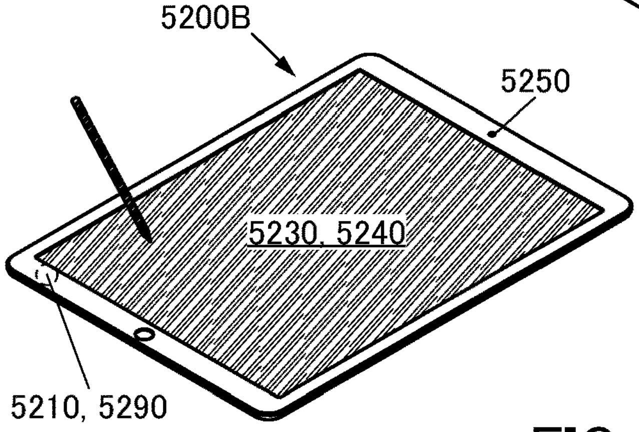
Figure 12D:
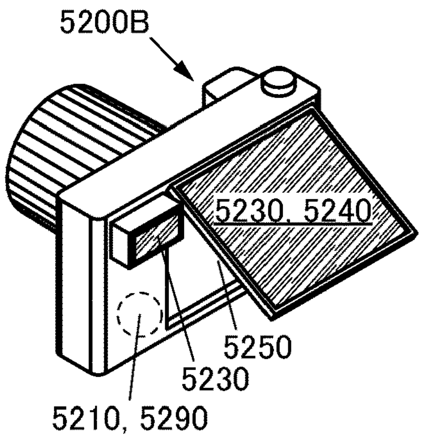
Figure 12E:
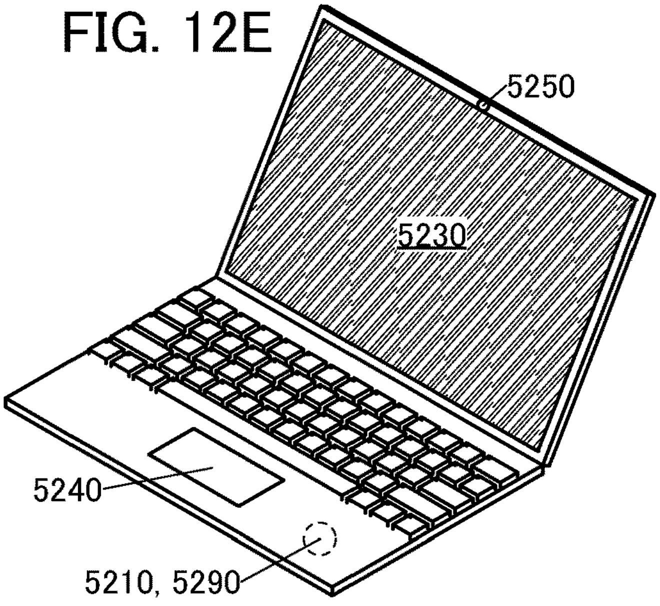
Figure 13A:
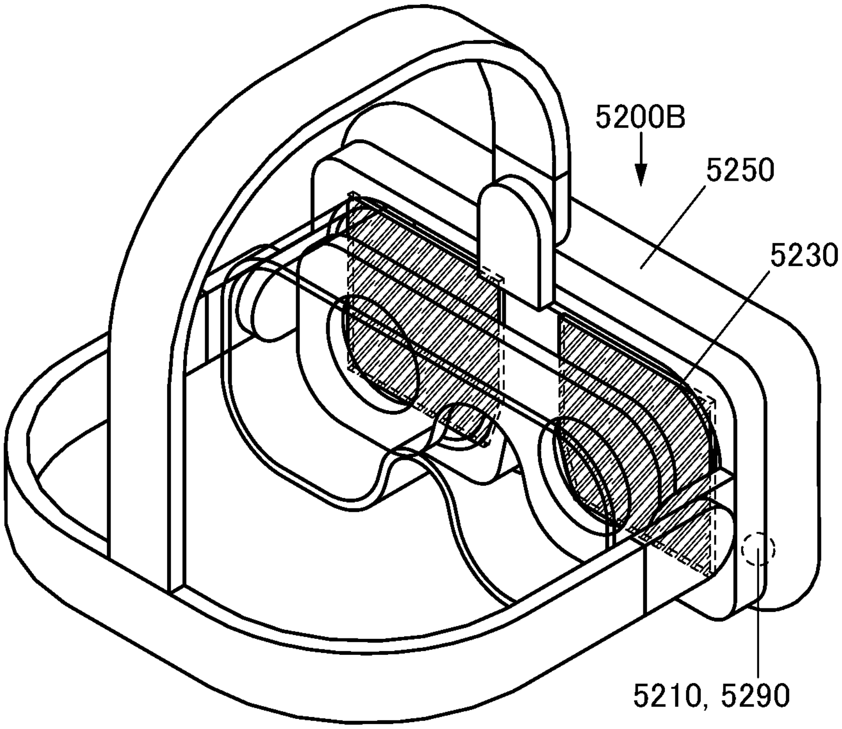
FIGS. 13A and 13B illustrate electronic appliances of an embodiment.
Figure 13B:
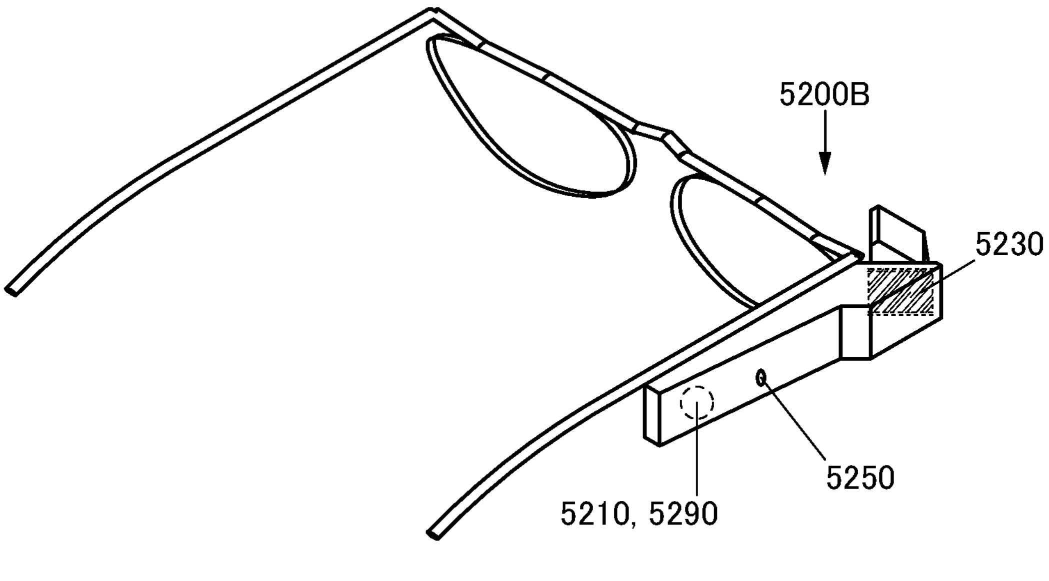

FIG. 11A to FIG. 13B each illustrate a structure of an electronic appliance of one embodiment of the present invention. FIG. 11A is a block diagram of an electronic appliance and FIGS. 11B to 11E are perspective views illustrating structures of electronic appliances. FIGS. 12A to 12E are perspective views illustrating structures of electronic appliances. FIGS. 13A and 13B are perspective views illustrating structures of electronic appliances.

An electronic appliance 5200B described in this embodiment includes an arithmetic device 5210 and an input/output device 5220 (see FIG. 11A).

The arithmetic device 5210 has a function of receiving handling data and a function of supplying image data on the basis of the handling data.

The input/output device 5220 includes a display unit 5230, an input unit 5240, a sensor unit 5250, and a communication unit 5290, and has a function of supplying handling data and a function of receiving image data. The input/output device 5220 also has a function of supplying sensing data, a function of supplying communication data, and a function of receiving communication data.

The input unit 5240 has a function of supplying handling data. For example, the input unit 5240 supplies handling data on the basis of handling by a user of the electronic appliance 5200B.

Specifically, a keyboard, a hardware button, a pointing device, a touch sensor, an illuminance sensor, an imaging device, an audio input device, an eye-gaze input device, an attitude sensing device, or the like can be used as the input unit 5240.

The display unit 5230 includes a display panel and has a function of displaying image data. For example, the display panel described in Embodiment 3 can be used for the display unit 5230.

The sensor unit 5250 has a function of supplying sensing data. For example, the sensor unit 5250 has a function of sensing a surrounding environment where the electronic appliance is used and supplying the sensing data.

Specifically, an illuminance sensor, an imaging device, an attitude sensing device, a pressure sensor, a human motion sensor, or the like can be used as the sensor unit 5250.

The communication unit 5290 has a function of receiving and supplying communication data. For example, the communication unit 5290 has a function of being connected to another electronic appliance or a communication network by wireless communication or wired communication. Specifically, the communication unit 5290 has a function of wireless local area network communication, telephone communication, near field communication, or the like.

FIG. 11B illustrates an electronic appliance having an outer shape along a cylindrical column or the like. An example of such an electronic appliance is digital signage. The display panel of one embodiment of the present invention can be used for the display unit 5230. The electronic appliance may have a function of changing its display method in accordance with the illuminance of a usage environment. The electronic appliance has a function of changing the displayed content when sensing the existence of a person. Thus, for example, the electronic appliance can be provided on a column of a building. The electronic appliance can display advertising, guidance, or the like.

FIG. 11C illustrates an electronic appliance having a function of generating image data on the basis of the path of a pointer used by the user. Examples of such an electronic appliance include an electronic blackboard, an electronic bulletin board, and digital signage. Specifically, a display panel with a diagonal size of 20 inches or longer, preferably 40 inches or longer, further preferably 55 inches or longer can be used. A plurality of display panels can be arranged and used as one display region. Alternatively, a plurality of display panels can be arranged and used as a multiscreen.

FIG. 11D illustrates an electronic appliance that is capable of receiving data from another device and displaying the data on the display unit 5230. An example of such an electronic appliance is a wearable electronic appliance. Specifically, the electronic appliance can display several options, and the user can choose some from the options and send a reply to the data transmitter. As another example, the electronic appliance has a function of changing its display method in accordance with the illuminance of a usage environment. Thus, for example, power consumption of the wearable electronic appliance can be reduced. As another example, the wearable electronic appliance can display an image so as to be suitably used even in an environment under strong external light, e.g., outdoors in fine weather.

FIG. 11E illustrates an electronic appliance including the display unit 5230 having a surface gently curved along a side surface of a housing. An example of such an electronic appliance is a mobile phone. The display unit 5230 includes a display panel that has a function of displaying images on the front surface, the side surfaces, the top surface, and the rear surface, for example. Thus, a mobile phone can display data on not only its front surface but also its side surfaces, top surface, and rear surface, for example.

FIG. 12A illustrates an electronic appliance that is capable of receiving data via the Internet and displaying the data on the display unit 5230. An example of such an electronic appliance is a smartphone. For example, the user can check a created message on the display unit 5230 and send the created message to another device. As another example, the electronic appliance has a function of changing its display method in accordance with the illuminance of a usage environment. Thus, power consumption of the smartphone can be reduced. As another example, it is possible to obtain a smartphone which can display an image such that the smartphone can be suitably used in an environment under strong external light, e.g., outdoors in fine weather.

FIG. 12B illustrates an electronic appliance that can use a remote controller as the input unit 5240. An example of such an electronic appliance is a television system. For example, data received from a broadcast station or via the Internet can be displayed on the display unit 5230. The electronic appliance can take an image of the user with the sensor unit 5250 and transmit the image of the user. The electronic appliance can acquire a viewing history of the user and provide it to a cloud service. The electronic appliance can acquire recommendation data from a cloud service and display the data on the display unit 5230. A program or a moving image can be displayed on the basis of the recommendation data. As another example, the electronic appliance has a function of changing its display method in accordance with the illuminance of a usage environment. Accordingly, for example, it is possible to obtain a television system which can display an image such that the television system can be suitably used even under strong external light entering the room from the outside in fine weather.

FIG. 12C illustrates an electronic appliance that is capable of receiving an educational material via the Internet and displaying it on the display unit 5230. An example of such an electronic appliance is a tablet computer. The user can input an assignment with the input unit 5240 and send it via the Internet. The user can obtain a corrected assignment or the evaluation from a cloud service and have it displayed on the display unit 5230. The user can select a suitable educational material on the basis of the evaluation and have it displayed.

For example, an image signal can be received from another electronic appliance and displayed on the display unit 5230. When the electronic appliance is placed on a stand or the like, the display unit 5230 can be used as a sub-display. Thus, for example, it is possible to obtain a tablet computer which can display an image such that the tablet computer is favorably used even in an environment under strong external light, e.g., outdoors in fine weather.

FIG. 12D illustrates an electronic appliance including a plurality of display units 5230. An example of such an electronic appliance is a digital camera. For example, the display unit 5230 can display an image that the sensor unit 5250 is capturing. A captured image can be displayed on the sensor unit. A captured image can be decorated using the input unit 5240. A message can be attached to a captured image. A captured image can be transmitted via the Internet. The electronic appliance has a function of changing shooting conditions in accordance with the illuminance of a usage environment. Accordingly, for example, it is possible to obtain a digital camera that can display a subject such that an image is favorably viewed even in an environment under strong external light, e.g., outdoors in fine weather.

FIG. 12E illustrates an electronic appliance in which the electronic appliance of this embodiment is used as a master to control another electronic appliance used as a slave. An example of such an electronic appliance is a portable personal computer. For example, part of image data can be displayed on the display unit 5230 and another part of the image data can be displayed on a display unit of another electronic appliance. Image signals can be supplied. Data written from an input unit of another electronic appliance can be obtained with the communication unit 5290. Thus, a large display region can be utilized in the case of using a portable personal computer, for example.

FIG. 13A illustrates an electronic appliance including the sensor unit 5250 that senses an acceleration or a direction. An example of such an electronic appliance is a goggles-type electronic appliance. The sensor unit 5250 can supply data on the position of the user or the direction in which the user faces. The electronic appliance can generate image data for the right eye and image data for the left eye in accordance with the position of the user or the direction in which the user faces. The display unit 5230 includes a display region for the right eye and a display region for the left eye. Thus, a virtual reality image that gives the user a sense of immersion can be displayed on the goggles-type electronic appliance, for example.

FIG. 13B illustrates an electronic appliance including an imaging device and the sensor unit 5250 that senses an acceleration or a direction. An example of such an electronic appliance is a glasses-type electronic appliance. The sensor unit 5250 can supply data on the position of the user or the direction in which the user faces. The electronic appliance can generate image data in accordance with the position of the user or the direction in which the user faces. Accordingly, the data can be shown together with a real-world scene, for example. Alternatively, an augmented reality image can be displayed on the glasses-type electronic appliance.

Note that this embodiment can be combined with any of the other embodiments in this specification as appropriate.

Embodiment 6

Figure 14A:
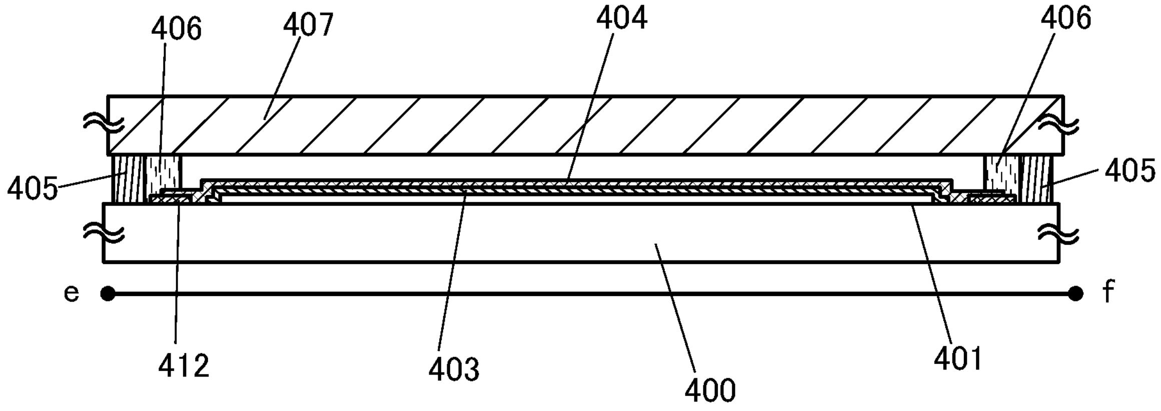
FIGS. 14A and 14B illustrate a lighting device of an embodiment.
Figure 14B:
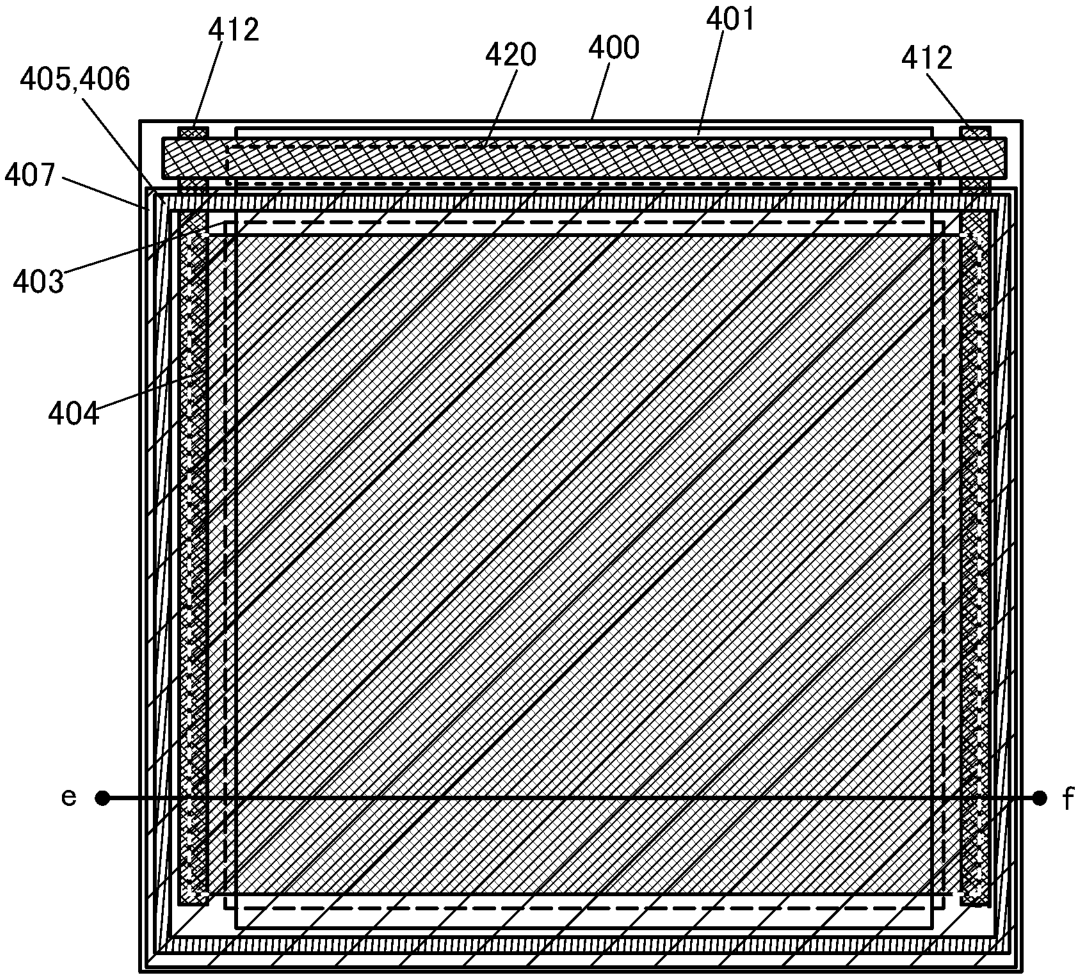

In this embodiment, a structure in which the light-emitting device described in Embodiment 2 is used as a lighting device will be described with reference to FIGS. 14A and 14B. FIG. 14A shows a cross section taken along the line e-f in a top view of the lighting device in FIG. 14B.

In the lighting device in this embodiment, a first electrode 401 is formed over a substrate 400 that is a support and has a light-transmitting property. The first electrode 401 corresponds to the first electrode 101 in Embodiment 2. When light is extracted from the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to the structure of the EL layer 103 in Embodiment 2. Refer to the corresponding description for these structures.

The second electrode 404 is formed to cover the EL layer 403. The second electrode 404 corresponds to the second electrode 102 in Embodiment 2. The second electrode 404 is formed using a material having high reflectance when light is extracted from the first electrode 401 side. The second electrode 404 is connected to the pad 412 so that voltage is applied to the second electrode 404.

As described above, the lighting device described in this embodiment includes a light-emitting device including the first electrode 401, the EL layer 403, and the second electrode 404. Since the light-emitting device has high emission efficiency, the lighting device in this embodiment can have low power consumption.

The substrate 400 provided with the light-emitting device having the above structure and a sealing substrate 407 are fixed and sealed with sealing materials 405 and 406, whereby the lighting device is completed. It is possible to use only either the sealing material 405 or the sealing material 406. In addition, the inner sealing material 406 (not illustrated in FIG. 14B) can be mixed with a desiccant that enables moisture to be adsorbed, increasing the reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

Embodiment 7

Figure 15:
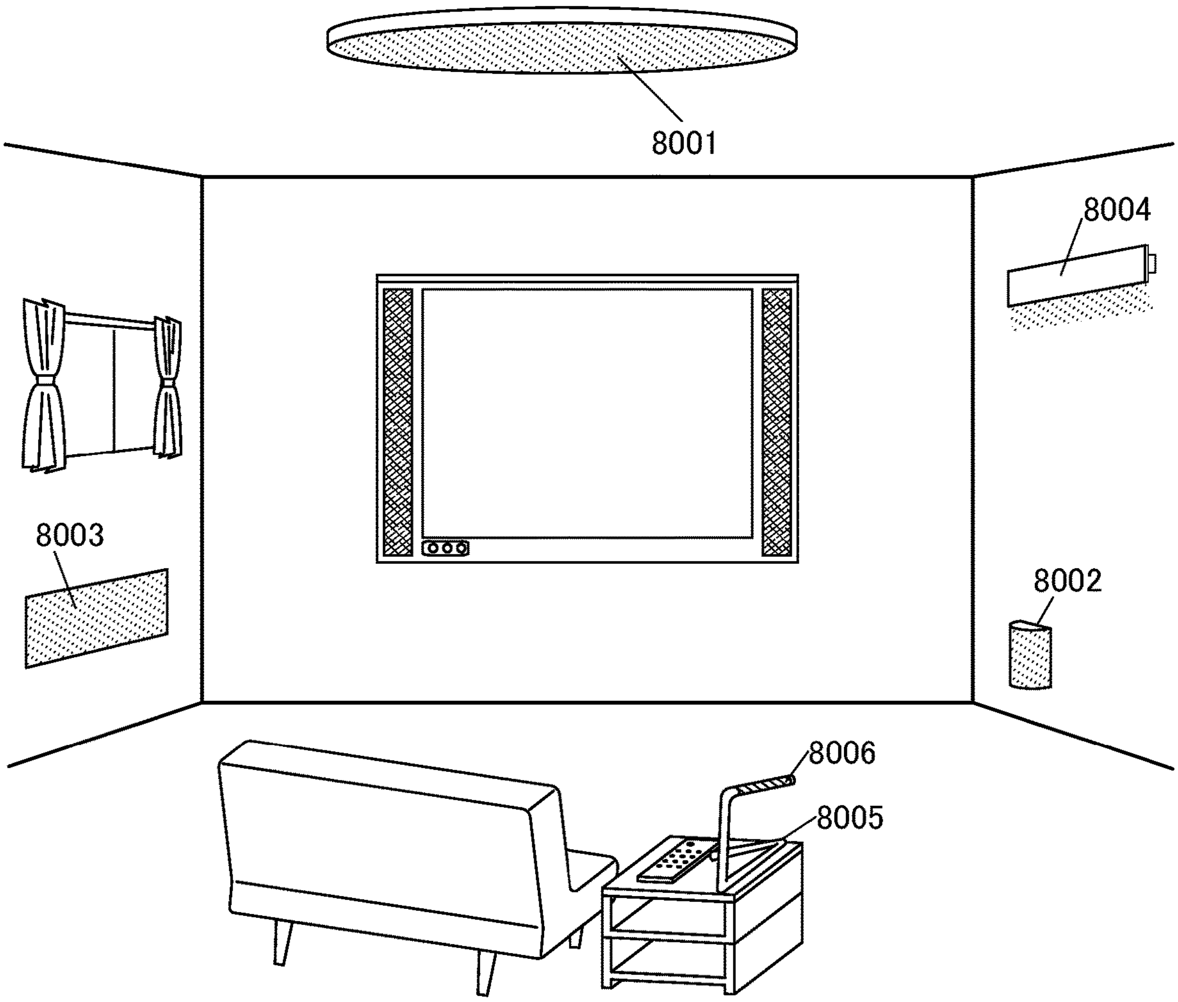
FIG. 15 illustrates lighting devices of an embodiment.

In this embodiment, application examples of lighting devices fabricated using the light-emitting apparatus of one embodiment of the present invention or the light-emitting device, which is part of the light-emitting apparatus, will be described with reference to FIG. 15.

A ceiling light 8001 can be used as an indoor lighting device. Examples of the ceiling light 8001 include a direct-mount light and an embedded light. Such lighting devices are fabricated using the light-emitting apparatus and a housing and a cover in combination. Application to a cord pendant light (light that is suspended from a ceiling by a cord) is also possible.

Afoot light 8002 lights a floor so that safety on the floor can be improved. For example, it can be effectively used in a bedroom, on a staircase, and on a passage. In such cases, the size and shape of the foot light can be changed in accordance with the dimensions and structure of a room. The foot light can be a stationary lighting device using the light-emitting apparatus and a support in combination.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be easily increased. The sheet-like lighting can also be used on a wall or a housing that has a curved surface.

A lighting device 8004 in which the direction of light from a light source is controlled to be only a desired direction can be used.

A desk lamp 8005 includes a light source 8006. As the light source 8006, the light-emitting apparatus of one embodiment of the present invention or the light-emitting device, which is part of the light-emitting apparatus, can be used.

Besides the above examples, when the light-emitting apparatus of one embodiment of the present invention or the light-emitting device, which is part of the light-emitting apparatus, is used as part of furniture in a room, a lighting device that functions as the furniture can be obtained.

As described above, a variety of lighting devices that include the light-emitting apparatus can be obtained. Note that these lighting devices are also embodiments of the present invention.

The structures described in this embodiment can be used in appropriate combination with any of the structures described in the other embodiments.

Embodiment 8

In this embodiment, a light-emitting device and a light-receiving device that can be used in the light-emitting and light-receiving apparatus of one embodiment of the present invention will be described with reference to FIGS. 16A to 16C.

Figure 16A:
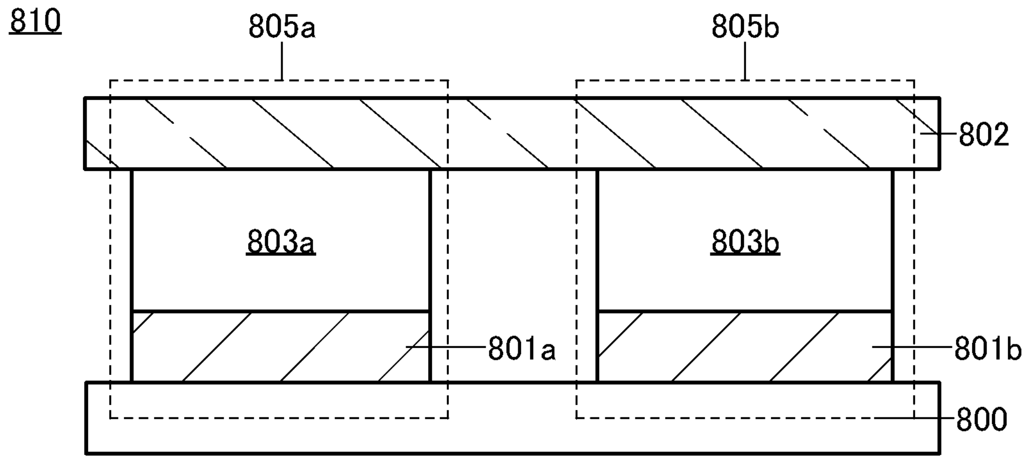
FIGS. 16A to 16C illustrate a light-emitting device and a light-receiving device of an embodiment.

FIG. 16A is a schematic cross-sectional view of a light-emitting device **805*a* and a light-receiving device 805*b* included in a light-emitting and light-receiving apparatus 810** of one embodiment of the present invention.

The light-emitting device **805*a* has a function of emitting light (hereinafter, also referred to as a light-emitting function). The light-emitting device 805*a* includes an electrode 801*a*, an EL layer 803*a*, and an electrode 802. The light-emitting device 805*a* is preferably a light-emitting device utilizing organic EL (an organic EL device) described in Embodiment 2. Thus, the EL layer 803*a* interposed between the electrode 801*a* and the electrode 802 includes at least a light-emitting layer. The light-emitting layer includes a light-emitting substance. The EL layer 803*a* emits light when voltage is applied between the electrode 801*a* and the electrode 802. The EL layer 803*a*** may include any of a variety of layers such as a hole-injection layer, a hole-transport layer, an electron-transport layer, an electron-injection layer, a carrier-blocking (hole-blocking or electron-blocking) layer, and a charge-generation layer, in addition to the light-emitting layer.

The light-receiving device 805*b* has a function of sensing light (hereinafter, also referred to as a light-receiving function). As the light-receiving device 805*b*, a PN photodiode or a PIN photodiode can be used, for example. The light-receiving device 805*b* includes an electrode 801*b*, a light-receiving layer 803*b*, and the electrode 802. Thus, the light-receiving layer 803*b* interposed between the electrode 801*b* and the electrode 802 includes at least an active layer. Note that for the light-receiving layer 803*b*, any of materials that are used for the variety of layers (e.g., the hole-injection layer, the hole-transport layer, the light-emitting layer, the electron-transport layer, the electron-injection layer, the carrier-blocking (hole-blocking or electron-blocking) layer, and the charge-generation layer) included in the above-described EL layer 803*a* can be used. The light-receiving device 805*b* functions as a photoelectric conversion device. When light is incident on the light-receiving layer 803*b*, electric charge can be generated and extracted as a current. At this time, voltage may be applied between the electrode 801*b* and the electrode 802. The amount of generated electric charge depends on the amount of the light incident on the light-receiving layer 803*b*.

The light-receiving device 805*b* has a function of sensing visible light. The light-receiving device 805*b* has sensitivity to visible light. The light-receiving device 805*b* further preferably has a function of sensing visible light and infrared light. The light-receiving device 805*b* preferably has sensitivity to visible light and infrared light.

In this specification and the like, a blue (B) wavelength region ranges from 400 nm to less than 490 nm, and blue (B) light has at least one emission spectrum peak in the wavelength region. A green (G) wavelength region ranges from 490 nm to less than 580 nm, and green (G) light has at least one emission spectrum peak in the wavelength region. A red (R) wavelength region ranges from 580 nm to less than 700 nm, and red (R) light has at least one emission spectrum peak in the wavelength region. In this specification and the like, a visible wavelength region ranges from 400 nm to less than 700 nm, and visible light has at least one emission spectrum peak in the wavelength region. An infrared (IR) wavelength region ranges from 700 nm to less than 900 nm, and infrared (IR) light has at least one emission spectrum peak in the wavelength region.

The active layer in the light-receiving device 805*b* includes a semiconductor. Examples of the semiconductor are inorganic semiconductors such as silicon and organic semiconductors such as organic compounds. As the light-receiving device 805*b*, an organic semiconductor device (or an organic photodiode) including an organic semiconductor in the active layer is preferably used. An organic photodiode, which is easily made thin, lightweight, and large in area and has a high degree of freedom for shape and design, can be used in a variety of display devices. An organic semiconductor is preferably used, in which case the EL layer 803*a* included in the light-emitting device 805*a* and the light-receiving layer 803*b* included in the light-receiving device 805*b* can be formed by the same method (e.g., a vacuum evaporation method) with the same manufacturing apparatus. Note that any of the organic compounds of one embodiment of the present invention can be used for the light-receiving layer 803*b* in the light-receiving device 805*b*.

In the display device of one embodiment of the present invention, an organic EL device and an organic photodiode can be suitably used as the light-emitting device 805*a* and the light-receiving device 805*b*, respectively. The organic EL device and the organic photodiode can be formed over one substrate. Thus, the organic photodiode can be incorporated into the display device including the organic EL device. A display device of one embodiment of the present invention has one or both of an image capturing function and a sensing function in addition to a function of displaying an image.

The electrode 801*a* and the electrode 801*b* are provided on the same plane. In FIG. 16A, the electrodes 801*a* and 801*b* are provided over a substrate 800. The electrodes 801*a* and 801*b* can be formed by processing a conductive film formed over the substrate 800 into island shapes, for example. In other words, the electrodes 801*a* and 801*b* can be formed through the same process.

As the substrate 800, a substrate having heat resistance high enough to withstand the formation of the light-emitting device 805*a* and the light-receiving device 805*b* can be used. When an insulating substrate is used, a glass substrate, a quartz substrate, a sapphire substrate, a ceramic substrate, an organic resin substrate or the like can be used as the substrate 800. Alternatively, a semiconductor substrate can be used. For example, a single crystal semiconductor substrate or a polycrystalline semiconductor substrate of silicon, silicon carbide, or the like; a compound semiconductor substrate of silicon germanium or the like; an SOI substrate; or the like can be used.

As the substrate 800, it is particularly preferable to use the insulating substrate or the semiconductor substrate over which a semiconductor circuit including a semiconductor element such as a transistor is formed. The semiconductor circuit preferably forms a pixel circuit, a gate line driver circuit (a gate driver), a source line driver circuit (a source driver), or the like. In addition to the above, an arithmetic circuit, a memory circuit, or the like may be formed.

The electrode 802 is formed of a layer shared by the light-emitting device 805*a* and the light-receiving device 805*b*. As the electrode through which light enters or exits, a conductive film that transmits visible light and infrared light is used. As the electrode through which light neither enters nor exits, a conductive film that reflects visible light and infrared light is preferably used.

The electrode 802 in the display device of one embodiment of the present invention functions as one of the electrodes in each of the light-emitting device 805*a* and the light-receiving device 805*b*.

Figure 16B:
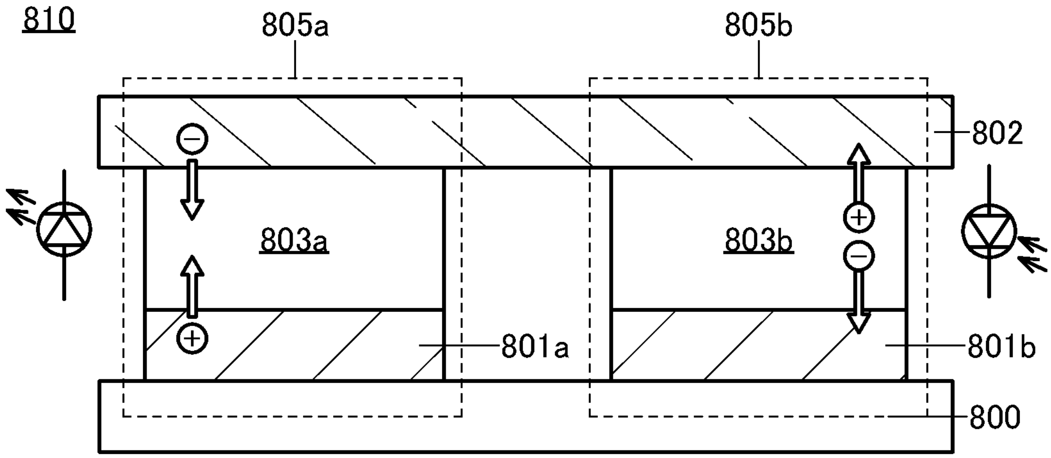

In FIG. 16B, the electrode 801*a* of the light-emitting device 805*a* has a potential higher than the electrode 802. In this case, the electrode 801*a* and the electrode 802 function as an anode and a cathode, respectively, in the light-emitting device 805*a*. The electrode 801*b* of the light-receiving device 805*b* has a potential lower than the electrode 802. For easy understanding of the direction of current flow, FIG. 16B illustrates a circuit symbol of a light-emitting diode on the left of the light-emitting device 805*a* and a circuit symbol of a photodiode on the right of the light-receiving device 805*b*. The flow directions of carriers (electrons and holes) in each device are also schematically indicated by arrows.

In the structure illustrated in FIG. 16B, when a first potential is supplied to the electrode 801*a* through a first wiring, a second potential is supplied to the electrode 802 through a second wiring, and a third potential is supplied to the electrode 801*b* through a third wiring, the following relationship is satisfied: the first potential> the second potential> the third potential.

Figure 16C:
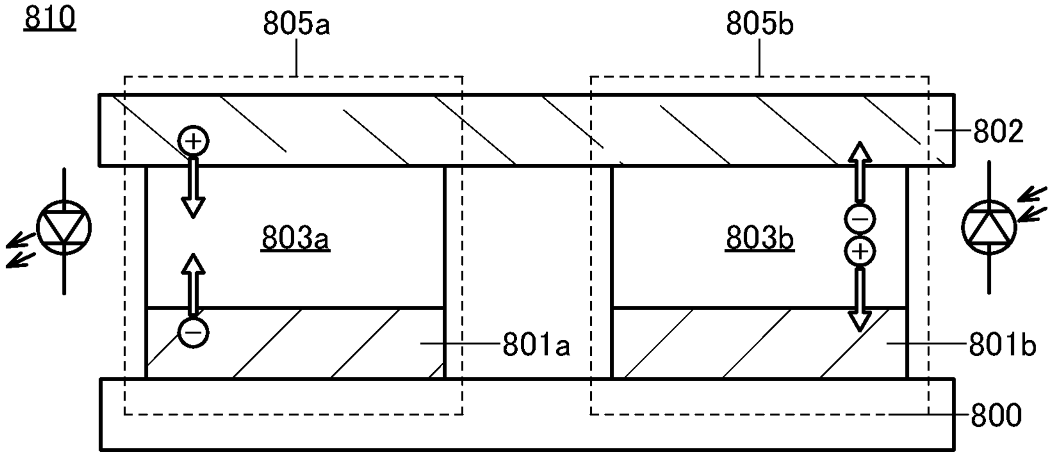

In FIG. 16C, the electrode 801*a* of the light-emitting device 805*a* has a potential lower than the electrode 802. In this case, the electrode 801*a* and the electrode 802 function as a cathode and an anode, respectively, in the light-emitting device 805*a*. The electrode 801*b* of the light-receiving device 805*b* has a potential lower than the potential of the electrode 802 and a potential higher than the potential of the electrode 801*a*. For easy understanding of the direction of current flow, FIG. 16C illustrates a circuit symbol of a light-emitting diode on the left of the light-emitting device 805*a* and a circuit symbol of a photodiode on the right of the light-receiving device 805*b*. The flow directions of carriers (electrons and holes) in each device are also schematically indicated by arrows.

In the structure illustrated in FIG. 16C, when a first potential is supplied to the electrode 801*a* through a first wiring, a second potential is supplied to the electrode 802 through a second wiring, and a third potential is supplied to the electrode 801*b* through a third wiring, the following relationship is satisfied: the second potential> the third potential> the first potential.

Figure 17A:
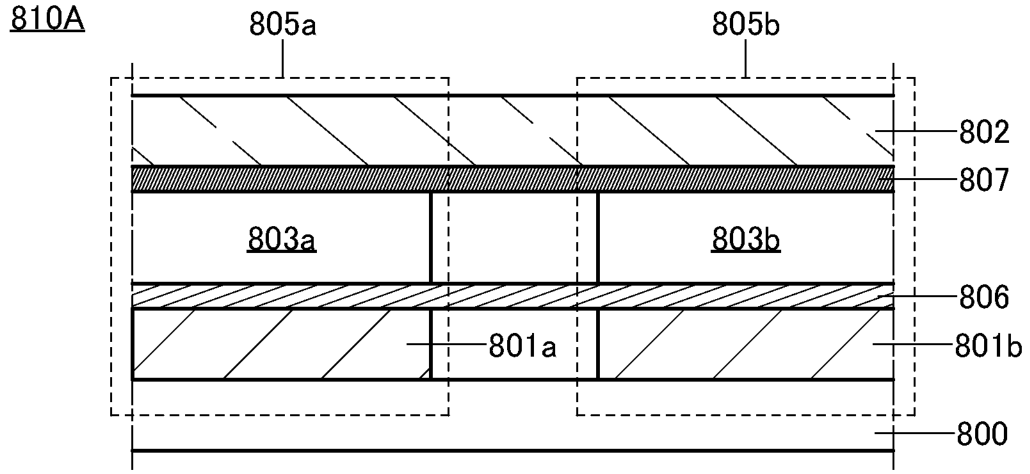
FIGS. 17A and 17B illustrate a light-emitting device and a light-receiving device of an embodiment.

FIG. 17A illustrates a light-emitting and light-receiving apparatus 810A that is a variation example of the light-emitting and light-receiving apparatus 810. The light-emitting and light-receiving apparatus 810A is different from the light-emitting and light-receiving apparatus 810 in including a common layer 806 and a common layer 807. In the light-emitting device 805*a*, the common layers 806 and 807 function as part of the EL layer 803*a*. In the light-receiving device 805*b*, the common layers 806 and 807 function as part of the light-receiving layer 803*b*. The common layer 806 includes a hole-injection layer and a hole-transport layer, for example. The common layer 807 includes an electron-transport layer and an electron-injection layer, for example.

With the common layers 806 and 807, a light-receiving device can be incorporated without a significant increase in the number of times of separate coloring, whereby the light-emitting and light-receiving apparatus 810A can be manufactured with a high throughput.

Figure 17B:
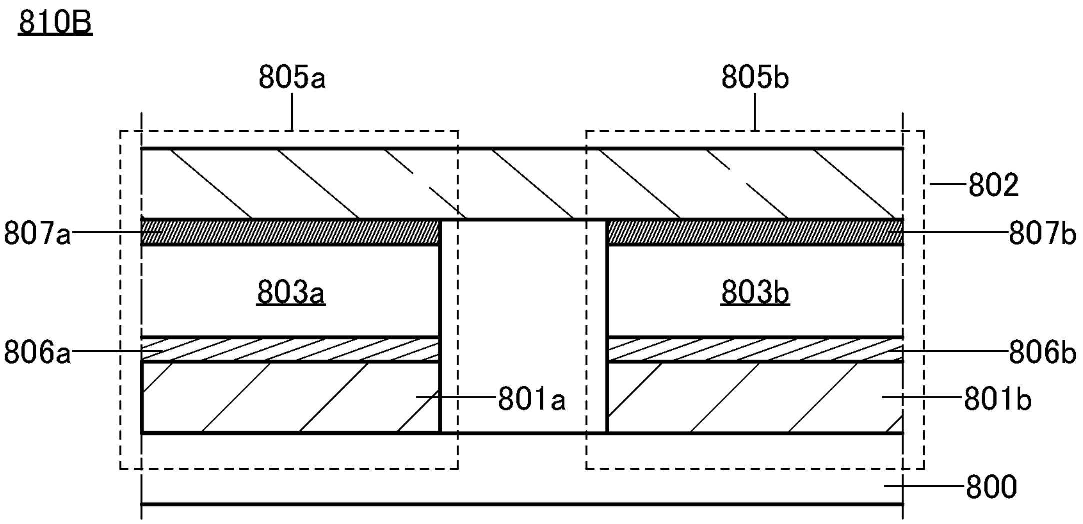

FIG. 17B illustrates a light-emitting and light-receiving apparatus 810B that is a variation example of the light-emitting and light-receiving apparatus 810A. The light-emitting and light-receiving apparatus 810B is different from the light-emitting and light-receiving apparatus 810A in that the EL layer 803*a* includes a layer 806*a* and a layer 807*a* and the light-receiving layer 803*b* includes a layer 806*b* and a layer 807*b*. The layers 806*a* and 806*b* are formed using different materials, and each include a hole-injection layer and a hole-transport layer, for example. Note that the layers 806*a* and 806*b* may be formed using the same material. The layers 807*a* and 807*b* are formed using different materials, and each include an electron-transport layer and an electron-injection layer, for example. Note that the layers 807*a* and 807*b* may be formed using the same material.

An optimum material for forming the light-emitting device 805*a* is selected for the layers 806*a* and 807*a* and an optimum material for forming the light-receiving device 805*b* is selected for the layers 806*b* and 807*b*, whereby the light-emitting device 805*a* and the light-receiving device 805*b* can have higher performance in the light-emitting and light-receiving apparatus 810B.

The resolution of the light-receiving device 805*b* described in this embodiment can be 100 ppi or higher, preferably 200 ppi or higher, further preferably 300 ppi or higher, still further preferably 400 ppi or higher, and still further preferably 500 ppi or higher, and 2000 ppi or lower, 1000 ppi or lower, or 600 ppi or lower, for example. In particular, when the resolution of the light-receiving device 805*b* is 200 ppi or higher and 600 ppi or lower, preferably 300 ppi or higher and 600 ppi or lower, the display device of one embodiment of the present invention can be suitably applied to image capturing of fingerprints. In fingerprint authentication with the display device of one embodiment of the present invention, the increased resolution of the light-receiving device 805*b* enables, for example, high accuracy extraction of the minutiae of fingerprints; thus, the accuracy of the fingerprint authentication can be increased. The resolution is preferably 500 ppi or higher, in which case the authentication conforms to the standard by the National Institute of Standards and Technology (NIST) or the like. On the assumption that the resolution of the light-receiving device is 500 ppi, the size of each pixel is 50.8 μm, which is adequate for image capturing of a fingerprint ridge distance (typically, greater than or equal to 300 μm and less than or equal to 500 μm).

The structures described in this embodiment can be used in appropriate combination with any of the structures described in the other embodiments.

Example 1

Synthesis Example 1

In this example, a method for synthesizing 4,8-bis[3-(dibenzothiophen-4-yl-1,2,3,6,7,8,9-$d_7$)phenyl-2,4,6-$d_3$]-[1]benzofuro[3,2-d]pyrimidine (abbreviation: 4,8mDBtP2Bfpm-$d_{20}$) shown as Structural Formula (100) in Embodiment 1 is specifically described.

[Chemical Formula 77]

(100

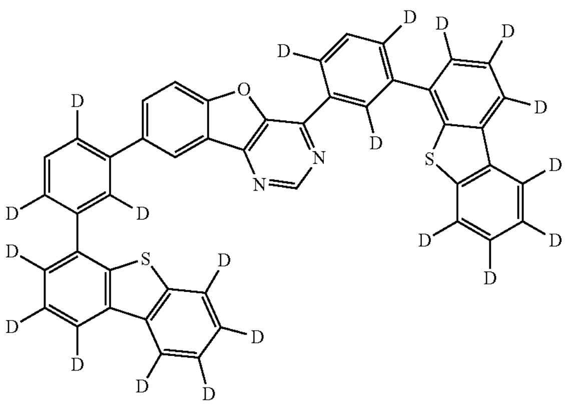

4,8mDBtP2Bfpm-d20

Step 1-1; Synthesis of 4-(3-bromophenyl-2,4,6-$d_3$)dibenzothiophene-1,2,3,6,7,8,9-$d_7$ Into a 200 mL three-neck flask were put 1.4 g (5.0 mmol) of molybdenum(V) pentachloride (abbreviation: $MoCl_5$), 20 g of deuterated toluene (abbreviation: toluene-$d_8$), and 3.4 g (10 mmol) of 4-(3-bromophenyl)dibenzothiophene, and the mixture was stirred under a nitrogen stream at 100° C. for 8 hours. After the reaction, toluene and 1.0 mol/L hydrochloric acid was added to the mixture in the flask, and the precipitated solid was removed by suction filtration. The filtrate was subjected to extraction with toluene, and the obtained organic layer was washed with a saturated aqueous solution of sodium hydrogen carbonate and saturated saline, and then was dried with magnesium sulfate. This mixture was separated by gravity filtration, and the filtrate was concentrated to give a brown oily substance. The obtained oily substance was purified by silica gel column chromatography (hexane), so that 2.3 g of the target 4-(3-bromophenyl-2,4,6-$d_3$)dibenzothiophene-1,2,3,6,7,8,9-$d_7$ (transparent oily substance) was obtained in a yield of 67%. The synthesis scheme of Step 1-1 is shown in (a-1) below.

[Chemical Formula 78]

(a-1)

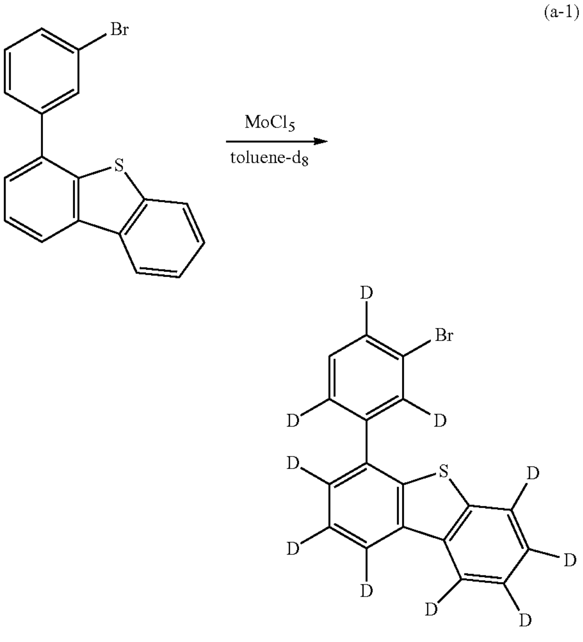

Figure 18A:
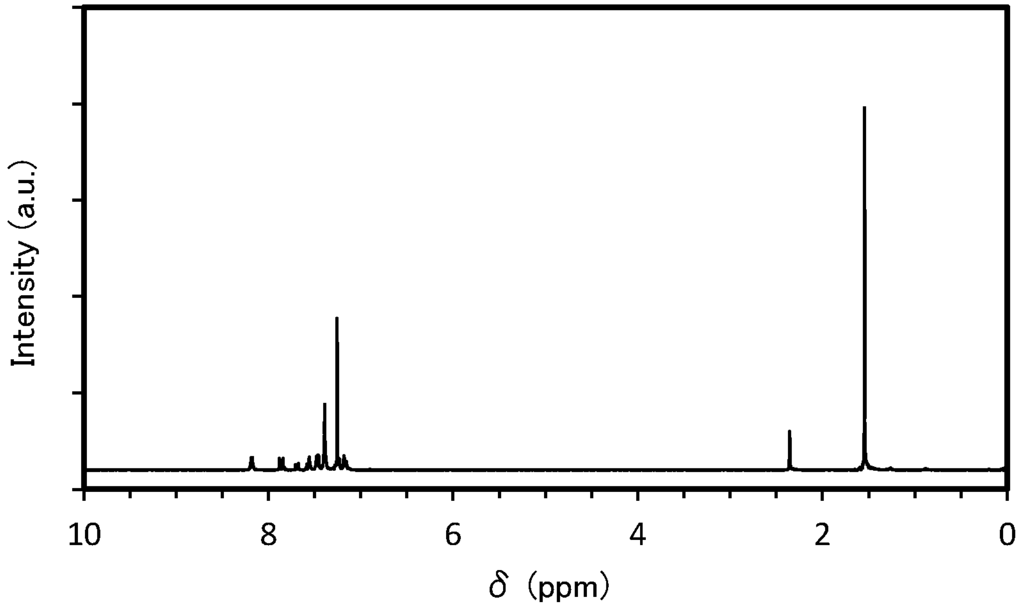
FIGS. 18A and 18B show $^1$H NMR spectra of an organic compound obtained in Example 1.

Analysis results by nuclear magnetic resonance ($^1$H-NMR) spectroscopy of 4-(3-bromophenyl-2,4,6-$d_3$)dibenzothiophene-1,2,3,6,7,8,9-$d_7$ obtained in Step 1-1 are shown below. In addition, FIGS. 18A and 18B show $^1$H-NMR charts.

$^1$H-NMR. δ ($CDCl_3$, 300 MHz): 7.38-7.40 (m, 1H).

Figure 18B:
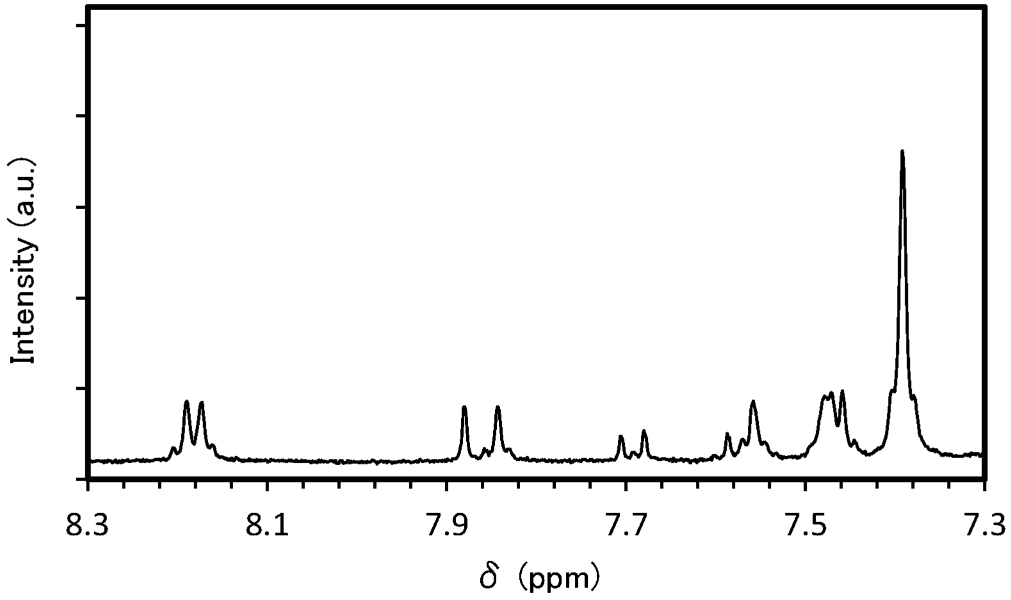
Figure 19A:
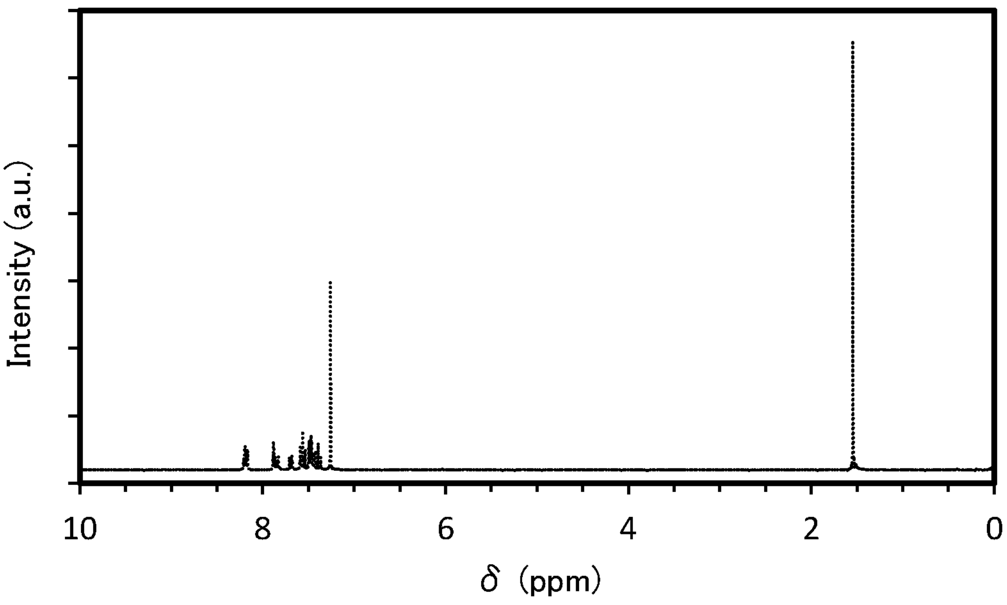
FIG. 19A shows a $^1$H NMR spectrum of 4-(3-bromophenyl)dibenzothiophene.
Figure 19B:
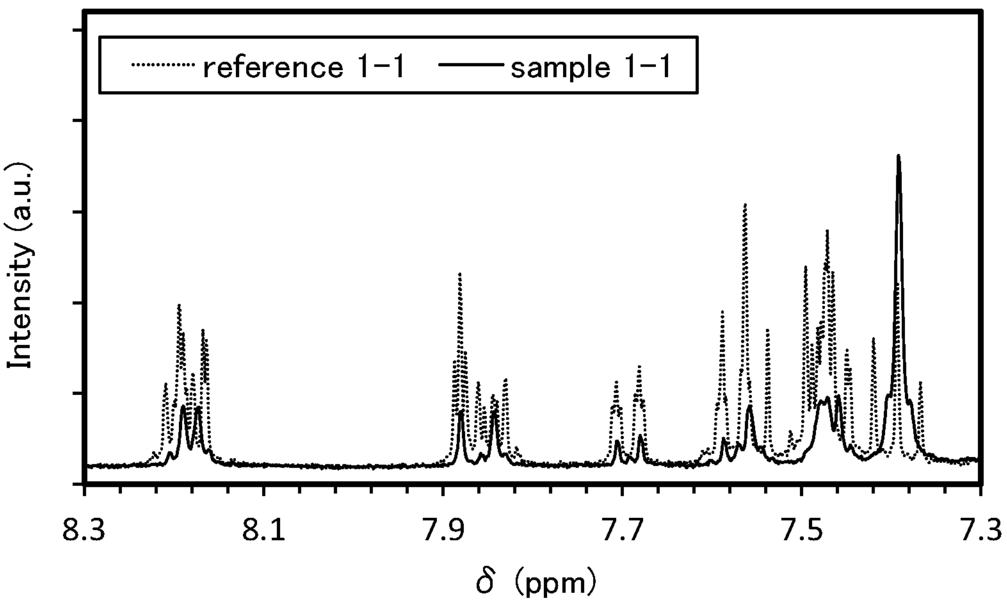
FIG. 19B shows $^1$H NMR spectra of the organic compound obtained in Example 1 and 4-(3-bromophenyl)dibenzothiophene.

In FIG. 18B, signals that appear around δ=7.68 ppm to 7.71 ppm, δ=8.17 ppm to 8.21 ppm, or the like are assumed to be protium in which deuteration did not proceed in Synthesis Scheme (a-1). The deuteration rate was estimated in the following manner: the peak of 7.38-7.40 ppm (m, 1H) in which deuteration did not proceed was used as the reference, and the number of protons of 4-(3-bromophenyl) dibenzothiophene that was a non-deuterated substance of 4-(3-bromophenyl-2,4,6-$d_3$)dibenzothiophene-1,2,3,6,7,8,9-$d_7$ was referred to. FIG. 19A shows the $^1$H-NMR chart of 4-(3-bromophenyl)dibenzothiophene, and FIG. 19B is an enlarged view of δ=7.30 ppm to 8.30 ppm, which compares 4-(3-bromophenyl-2,4,6-$d_3$)dibenzothiophene-1,2,3,6,7,8,9-$d_7$ (sample 1-1) and 4-(3-bromophenyl)dibenzothiophene (reference 1-1). From the above, the deuteration rate of 4-(3-bromophenyl-2,4,6-$d_3$)dibenzothiophene-1,2,3,6,7,8,9-$d_7$ was estimated to be approximately 86%.

Step 1-2; Synthesis of 2-[3-(dibenzo[b,d]thiophen-4-yl-1,2,3,6,7,8,9-$d_7$)phenyl-2,4,6-$d_3$]-4,4,5,5-tetramethyl-1,3,2-dioxaborolane Into a 200 mL three-neck flask were put 2.3 g (6.7 mmol) of 4-(3-bromophenyl-2,4,6-$d_3$)dibenzothiophene-1,2,3,6,7,8,9-$d_7$ obtained in Step 1-1, 1.9 g (7.4 mmol) of bis(pinacolato)diboron, 2.2 g (22 mmol) of potassium acetate, and 35 mL of N,N'-dimethylformamide (DMF). The mixture in the flask was stirred under reduced pressure and degassed. After that, the mixture was heated at 60° C. under a nitrogen stream, 0.32 g (0.39 mmol) of [1,1'-bis(diphenylphosphino) ferrocene]dichloropalladium(II) dichloromethane adduct (abbreviation: $Pd(dppf)_2Cl_2{\cdot}CH_2Cl_2$) was added thereto, and then the temperature was raised to 100° C. and the mixture was stirred for 5 hours. After the reaction, extraction was performed with toluene and the obtained organic layer was washed with saturated saline and dried with magnesium sulfate. This mixture was separated by gravity filtration, and the filtrate was concentrated to give a black oily substance. The obtained oily substance was purified by silica gel column chromatography (toluene:hexane=1:1 to toluene: hexane=1:0), so that 1.7 g of the target light-blue oily substance of 2-[3-(dibenzo[b,d]thiophen-4-yl-1,2,3,6,7,8,9-$d_7$)phenyl-2,4,6-$d_3$]-4,4,5,5-tetramethyl-1,3,2-dioxaborolane was obtained in a yield of 65%. The synthesis scheme of Step 1-2 is shown in (a-2) below.

[Chemical Formula 79]

(a-2)

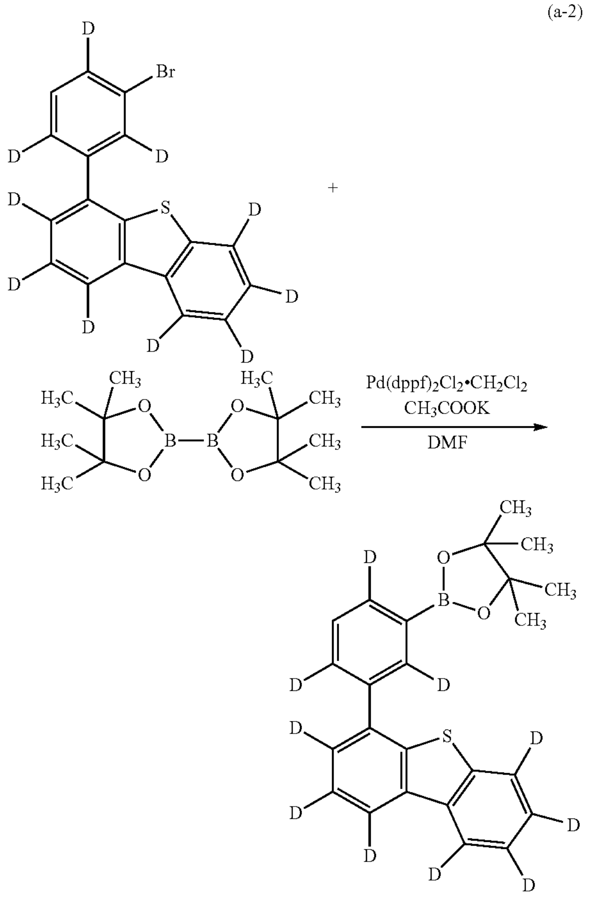

Figure 20A:
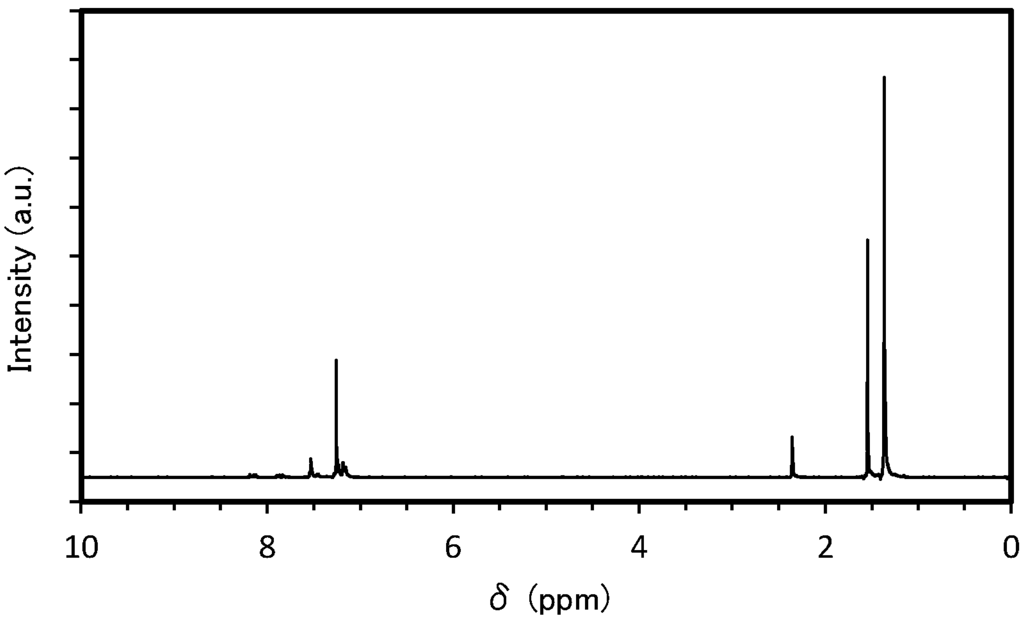
FIGS. 20A and 20B show $^1$H NMR spectra of the organic compound obtained in Example 1.

Analysis results by nuclear magnetic resonance ($^1$H-NMR) spectroscopy of 2-[3-(dibenzo[b,d]thiophen-4-yl-1,2,3,6,7,8,9-$d_7$)phenyl-2,4,6-$d_3$]-4,4,5,5-tetramethyl-1,3,2-dioxaborolane obtained in Step 1-2 are shown below. In addition, FIGS. 20A and 20B show $^1$H-NMR charts.

$^1$H-NMR. δ ($CDCl_3$, 300 MHz): 1.37 (s, 12H), 7.52-7.54 (m, 1H).

Figure 20B:
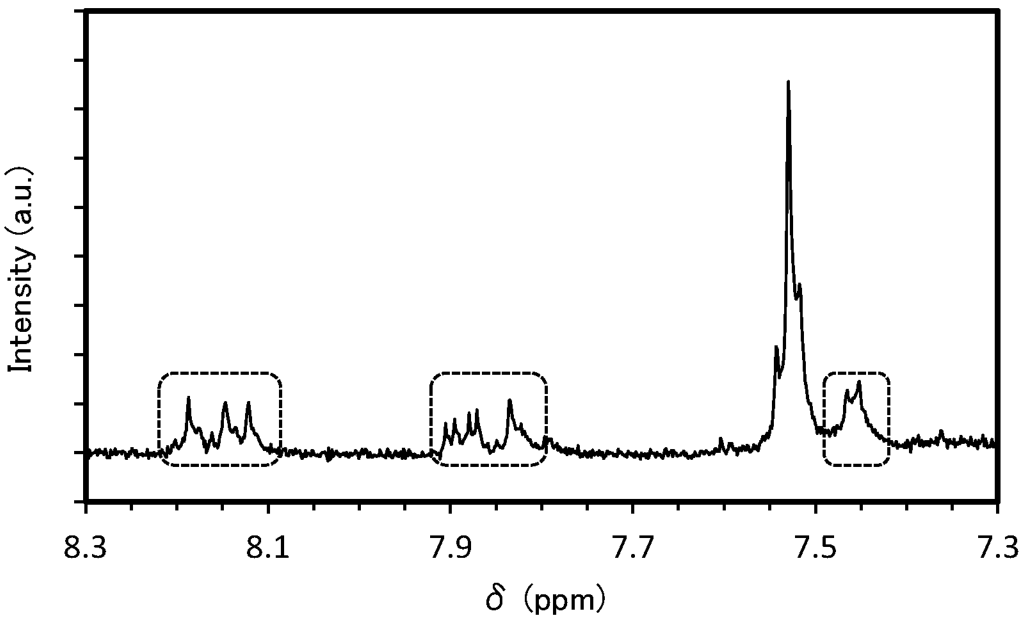

In FIG. 20B, signals that appear around δ=7.4 ppm to 7.5 ppm, δ=8.1 ppm to 8.2 ppm, or other regions surrounded with dashed lines are assumed to be peaks derived from protium that were not deuterated and remained in Synthesis Scheme (a-2).

Step 1-3: Synthesis of 4,8-bis[3-(dibenzothiophen-4-yl-1,2,3,6,7,8,9-$d_7$)phenyl-2,4,6-$d_3$]-[1]benzofuro[3,2-d]pyrimidine (abbreviation: 4,8mDBtP2Bfpm-$d_{20}$)

Into a 200 mL three-neck flask were put 1.7 g (4.3 mmol) of 2-[3-(dibenzo[b,d]thiophen-4-yl-1,2,3,6,7,8,9-$d_7$)phenyl-2,4,6-$d_3$]-4,4,5,5-tetramethyl-1,3,2-dioxaborolane obtained in Step 1-2, 0.47 g (2.0 mmol) of 4,8-dichloro[1]benzofuro[3,2-d]pyrimidine, 2.5 g (12 mmol) of tripotassium phosphate, 0.89 g (12 mmol) of tert-butylalcohol (abbreviation: tBuOH), and 30 mL of diethyleneglycoldimethylether (abbreviation: diglyme). The mixture in the flask was stirred under reduced pressure and degassed. After that, the mixture was heated at 60° C. under a nitrogen stream, 90 g (0.40 mmol) of palladium(II) acetate (abbreviation: $Pd(OAc)_2$) and 0.29 g (0.81 mmol) of di(1-adamantyl)-N-butylphosphine (abbreviation: cataCxiumA) were added thereto, and then the temperature was raised to 110° C. and the mixture was stirred for 3.5 hours. Furthermore, the temperature was raised to 130° C. and the mixture was stirred for 4.5 hours. Moreover, the temperature was raised to 150° C. and the mixture was stirred for 1.5 hours. After the reaction, water was added to the mixture and suction filtration was performed, and the obtained residue was washed with water and ethanol. The obtained residue was dissolved in toluene by heating, followed by filtration through a filter medium in which Celite, alumina, and Celite were stacked in this order. The filtrate was concentrated and then recrystallized with toluene to give 0.70 g of a white solid in a yield of 51%. By a train sublimation method, 0.70 g of the obtained white solid was purified by sublimation. The sublimation purification was conducted under the conditions where the pressure was 3.2 Pa, the flow rate of an argon gas was 7 mL/min, and the solid was heated at 355° C. After the sublimation purification, 0.54 g of a target pale yellow solid was obtained at a collection rate of 77%. The synthesis scheme of Step 1-3 is shown in (a-3) below.

[Chemical Formula 80]

(a-3)

2 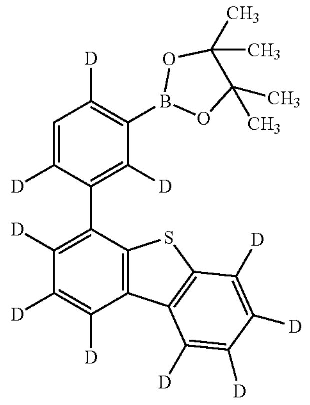 +

-continued

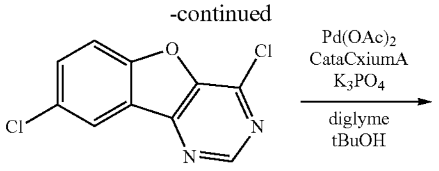

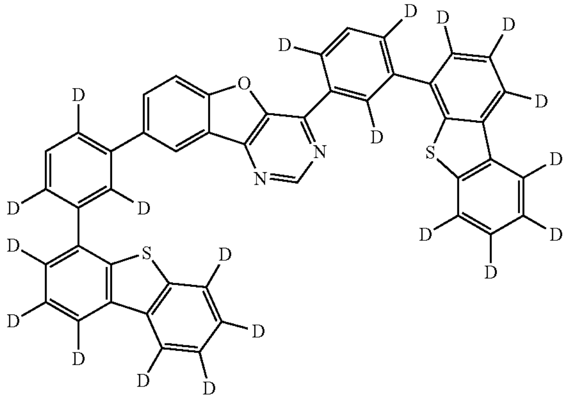

(100)

Figure 21A:
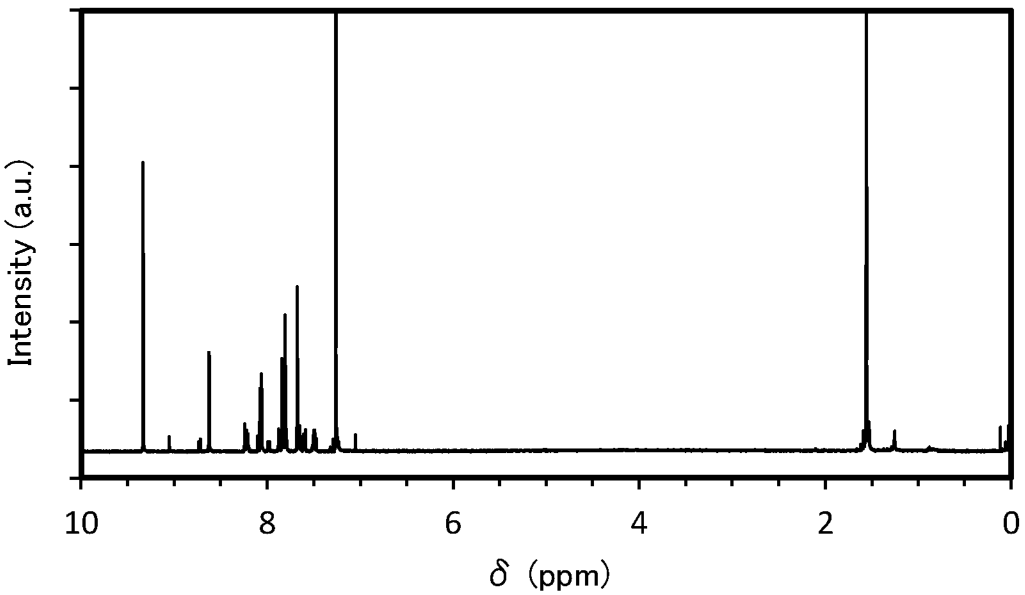
FIGS. 21A and 21B show $^1$H NMR spectra of 4,8mDBtP2Bfpm-$d_{20}$.

Analysis results by nuclear magnetic resonance ($^1$H-NMR) spectroscopy of the pale yellow solid obtained in the above step are described below. FIG. 21A shows the $^1$H-NMR chart. From this result, it was found that 4,8mDBtP2Bfpm-$d_{20}$, which is represented by the structural formula (100) and is one embodiment of the present invention, was obtained in Synthesis example 1.

$^1$H-NMR. δ ($CDCl_3$, 500 MHz): 7.67-7.68 (m, 1H), 7.79-7.81 (m, 1H), 7.83 (d, J=8.59 Hz, 1H), 8.07 (dd, J1=8.59 Hz, J2=1.72 Hz, 1H), 8.63 (sd, J=1.72 Hz, 1H), 9.33 (s, 1H).

Figure 21B:
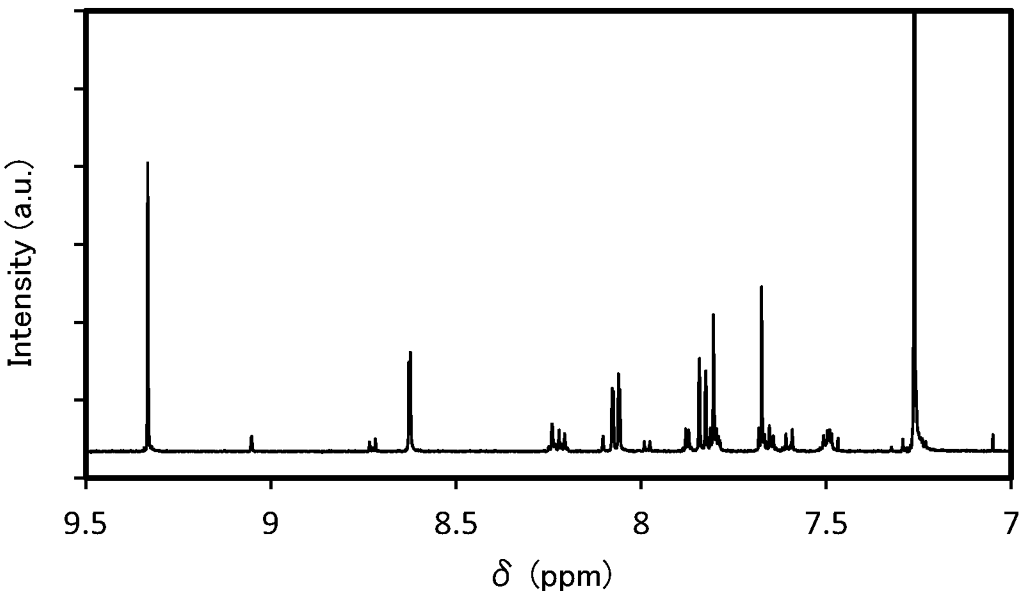

In FIG. 21B, fine signals are observed around δ=7.45 ppm to 7.55 ppm, 9.50 ppm, or the like. They are assumed to be protium that was not deuterated and remained in Synthesis Scheme (a-1).

Figure 22A:
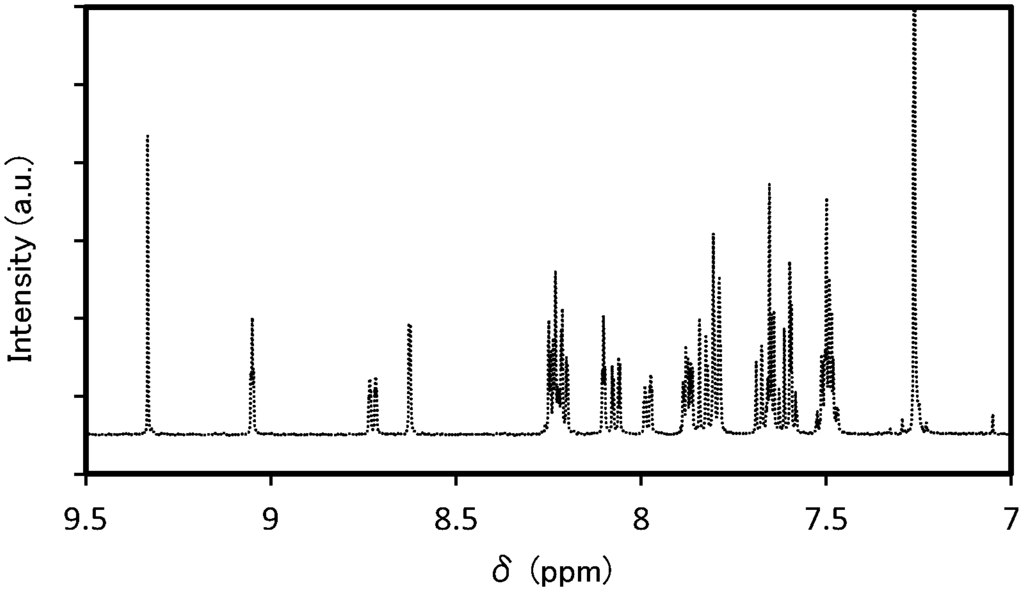
FIG. 22A shows a $^1$H NMR spectrum of 4,8mDBtP2Bfpm that is non-deuterated substance.
Figure 22B:
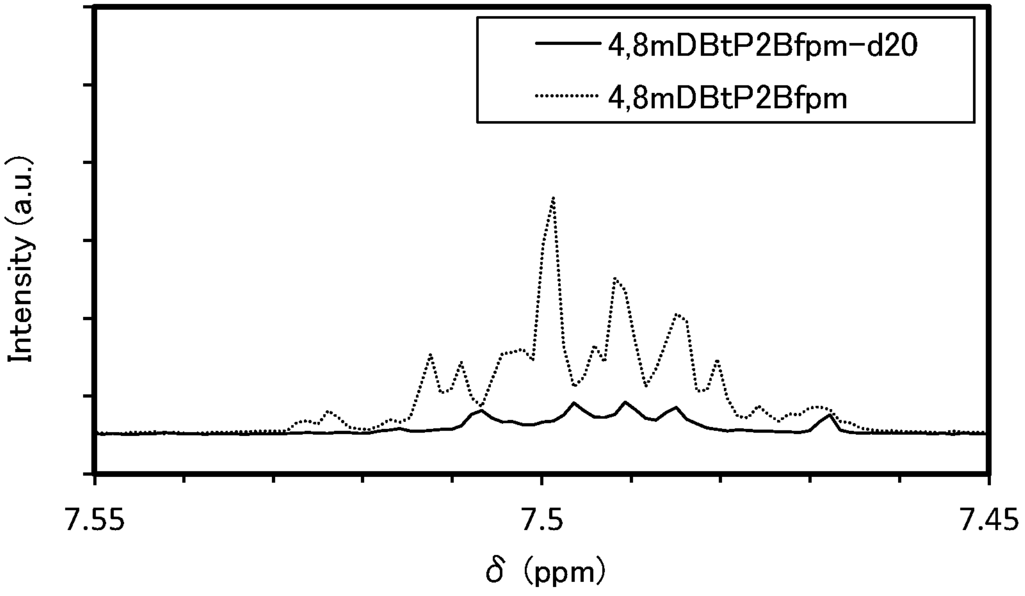
FIG. 22B shows $^1$H NMR spectra of 4,8mDBtP2Bfpm-$d_{20}$ and 4,8mDBtP2Bfpm.

FIG. 22A shows the $^1$H-NMR chart of 4,8mDBtP2Bfpm that is a non-deuterated substance of 4,8mDBtP2Bfpm-$d_{20}$. FIG. 22B is an enlarged view of δ=7.45 ppm to 7.55 ppm, which compares 4,8mDBtP2Bfpm-$d_{20}$ and 4,8mDBtP2Bfpm. Signals around 7.45 ppm to 7.55 ppm are derived from a dibenzothiophene skeleton, and the deuteration rate is estimated to be approximately 88%. The deuteration rate of a partial structure derived from 4-(3-bromophenyl-2,4,6-$d_3$)dibenzothiophene-1,2,3,6,7,8,9-$d_7$ of 4,8mDBtP2Bfpm-$d_{20}$ synthesized using 4-(3-bromophenyl-2,4,6-$d_3$)dibenzothiophene-1,2,3,6,7,8,9-$d_7$ whose deuteration rate was approximately 86% was kept after the synthesis of the target 4,8mDBtP2Bfpm-$d_{20}$.

<Characteristics of 4,8mDBtP2Bfpm-$d_{20}$>

Figure 23:
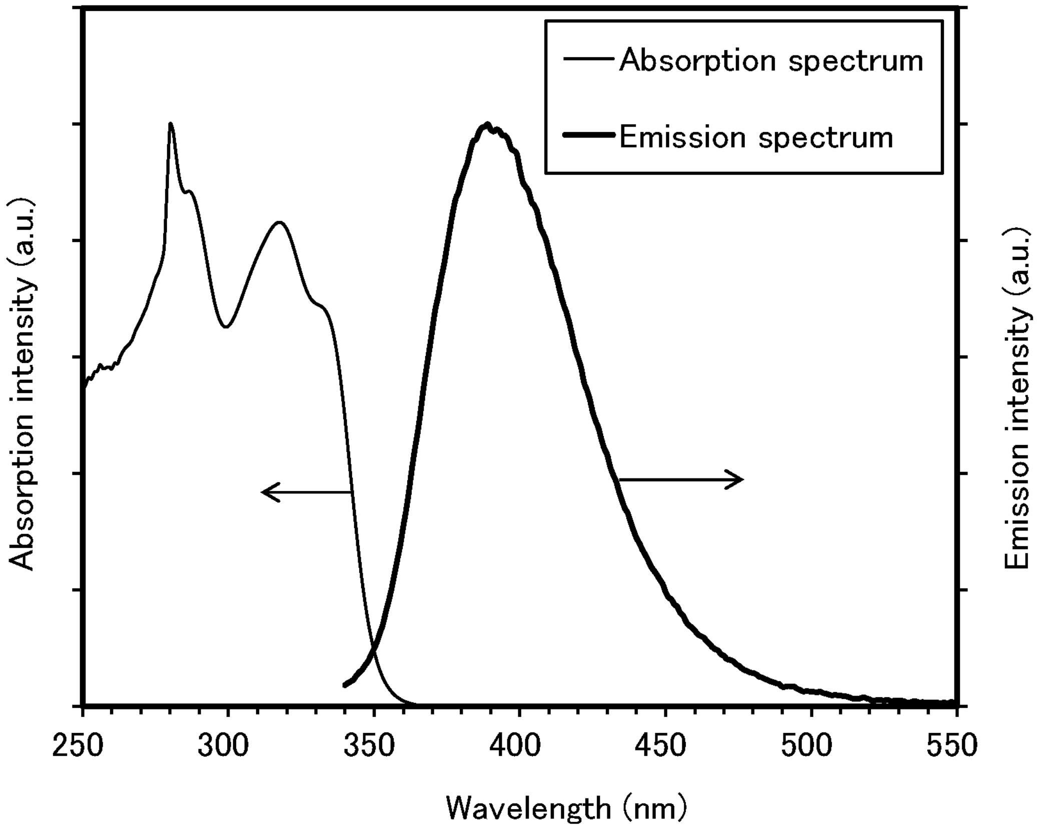
FIG. 23 shows an absorption spectrum and an emission spectrum of 4,8mDBtP2Bfpm-$d_{20}$ in a toluene solution.

Then, the ultraviolet-visible absorption spectrum (hereinafter, simply referred to as "absorption spectrum") and emission spectrum of a toluene solution of 4,8mDBtP2Bfpm-$d_{20}$ were measured. The absorption spectrum was measured at room temperature with an ultraviolet-visible light spectrophotometer (V-770DS, manufactured by JASCO Corporation) in a state where the toluene solution was put in a quartz cell. The emission spectrum was measured at room temperature with a spectrofluorometer (FP-8600DS, manufactured by JASCO Corporation) in a state where the toluene solution was put in a quartz cell. FIG. 23 shows obtained measurement results of the absorption spectrum and the emission spectrum. The horizontal axis represents the wavelength and the vertical axes represent the absorption intensity and the emission intensity. The absorption spectrum shown in FIG. 23 is a result obtained by subtraction of an absorption spectrum of only toluene in a quartz cell from the measured absorption spectrum of the toluene solution in the quartz cell.

As shown in FIG. 23, in the toluene solution of 4,8mDBtP2Bfpm-$d_{20}$, absorption peaks were observed around 286 nm, 317 nm, and 331 nm, and an emission peak was observed around 389 nm (excitation wavelength: 300 nm).

Figure 24:
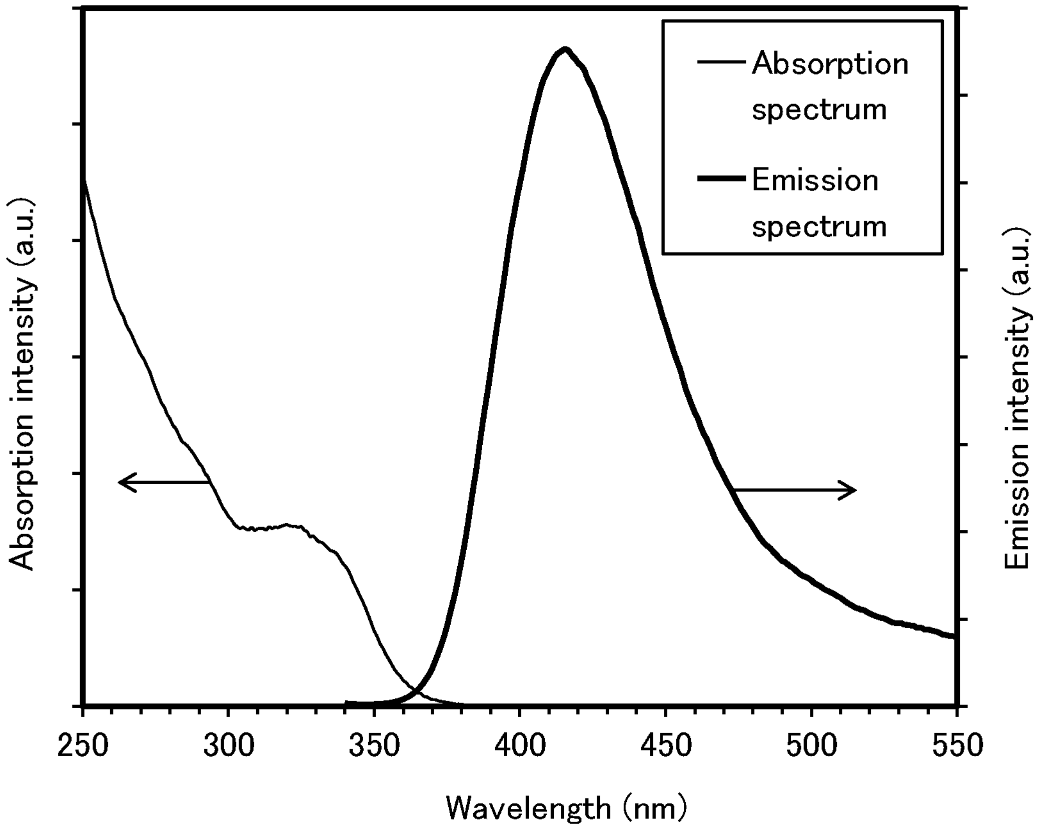
FIG. 24 shows an absorption spectrum and an emission spectrum of a thin film of 4,8mDBtP2Bfpm-$d_{20}$.

Next, the absorption spectrum and emission spectrum of a solid thin film of 4,8mDBtP2Bfpm-$d_{20}$ were measured. The solid thin film was fabricated over a quartz substrate by a vacuum evaporation method. The absorption spectrum of the thin film was calculated using an absorbance ($-\log_{10}$ [% T/(100−% R)]) obtained from the transmittance and reflectance of the thin film including the substrate. Note that % T represents transmittance and % R represents reflectance. The absorption spectrum was measured with an ultraviolet-visible spectrophotometer (U-4100, manufactured by Hitachi High-Technologies Corporation). The emission spectrum was measured using a spectrofluorometer (FP-8600DS, manufactured by JASCO Corporation). FIG. 24 shows the measurement results of the obtained absorption and emission spectra of the solid thin film. The horizontal axis represents the wavelength and the vertical axes represent the absorption intensity and the emission intensity.

From the results in FIG. 24, in the solid thin film of 4,8mDBtP2Bfpm-$d_{20}$, absorption peaks were observed around 287 nm, 325 nm, and 338 nm, and an emission peak was observed around 416 nm (excitation wavelength: 326 nm).

The ionization potential value of a thin film of 4,8mDBtP2Bfpm-$d_{20}$ was measured in the air with a photoelectron spectrometer (AC-3, manufactured by Riken Keiki Co., Ltd.). The obtained ionization potential value was converted into a negative value, so that the HOMO level of 4,8mDBtP2Bfpm-$d_{20}$ was −6.25 eV. From the data of the absorption spectrum of the thin film, the absorption edge of 4,8mDBtP2Bfpm-$d_{20}$, which was obtained from Tauc plot with an assumption of direct transition, was 3.45 eV. Thus, the optical energy gap of 4,8mDBtP2Bfpm-$d_{20}$ in the solid state was estimated at 3.45 eV; from the values of the HOMO level obtained above and this energy gap, the LUMO level of 4,8mDBtP2Bfpm-$d_{20}$ can be estimated at −2.80 eV. This reveals that 4,8mDBtP2Bfpm-$d_{20}$ in the solid state has an energy gap as wide as 3.45 eV.

The glass transition temperature (Tg) of 4,8mDBtP2Bfpm-$d_{20}$ was measured. Note that Tg was measured with a differential scanning calorimeter (DSC8500, manufactured by PerkinElmer Japan Co., Ltd.) in a state where a powder was put on an aluminum cell. As a result, Tg of 4,8mDBtP2Bfpm-$d_{20}$ was 136° C.

Furthermore, the electrochemical characteristics (oxidation reaction characteristics and reduction reaction characteristics) of 4,8mDBtP2Bfpm-$d_{20}$ were measured by cyclic voltammetry (CV). An electrochemical analyzer (ALS model 600A, manufactured by BAS Inc.) was used for the measurement. The solution for the measurement was prepared by using dehydrated N,N-dimethylformamide (DMF) (produced by Aldrich Corp., 99.8%, catalog number: 22705-6) as a solvent, dissolving a supporting electrolyte, tetra-n-butylammonium perchlorate ($n\text{-}Bu_4NClO_4$) (produced by Tokyo Chemical Industry Co., Ltd., catalog number: T0836), at a concentration of 100 mmol/L, and then dissolving the object of measurement at a concentration of 2 mmol/L.

A platinum electrode (PTE platinum electrode, manufactured by BAS Inc.) was used as a working electrode, another platinum electrode (Pt counter electrode (5 cm), manufactured by BAS Inc.) was used as an auxiliary electrode, and an $Ag/Ag^+$ electrode (RE7 reference electrode for nonaqueous solvent, manufactured by BAS Inc.) was used as a reference electrode. Note that the measurement was performed at room temperature (20° C. to 25° C.).

In addition, the scan speed in the CV measurement was fixed to 0.1 V/sec, and an oxidation potential Ea[V] and a reduction potential Ec[V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a measurement result of the oxidation potential Ea [V] of 4,8mDBtP2Bfpm-$d_{20}$, the HOMO level is around −6.2 eV. In contrast, the LUMO level was found to be −3.02 eV from the measurement result of the reduction potential Ec [V]. These results reveal that 4,8mDBtP2Bfpm-$d_{20}$ has a low LUMO level and a low HOMO level. In addition, the results of repetitive measurement of the oxidation-reduction wave showed that when the waveform of the first cycle was compared with that of the hundredth cycle, 89% of the peak intensity were maintained in the Ec measurement, which confirmed that 4,8mDBtP2Bfpm-$d_{20}$ had extremely high resistance to reduction.

Example 2

Synthesis Example 2

In this example, a method for synthesizing 4,8-bis[3-(dibenzothiophen-4-yl-1,2,3,6,7,8,9-$d_7$)phenyl]-[1]benzofuro[3,2-d]pyrimidine (abbreviation: 4,8mDBtP2Bfpm-$d_{14}$) shown as Structural Formula (101) in Embodiment 1 is specifically described.

[Chemical Formula 81]

(101)

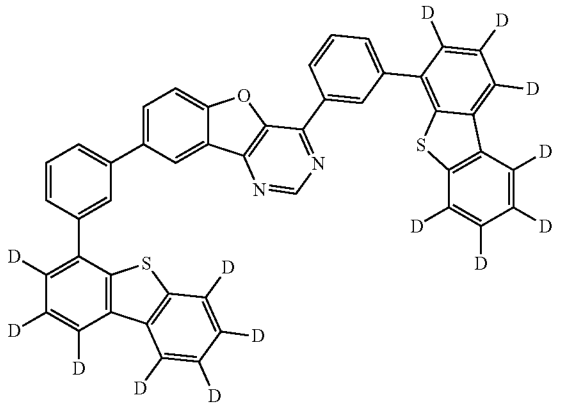

4,8mDBtP2Bfpm-d14

Step 2-1; Synthesis of 4-(3-bromophenyl)dibenzothiophene-1,2,3,6,7,8,9-$d_7$

Into a 200 mL three-neck flask were put 25 mL of deuterated toluene (abbreviation: toluene-$d_8$) and 16 g (46 mmol) of 4-(3-bromophenyl)dibenzothiophene, dissolving was performed, and the air in the flask was replaced with nitrogen. Into the flask was added 6.4 g (23 mmol) of molybdenum(V) pentachloride (abbreviation: $MoCl_5$), and the mixture was refluxed under a nitrogen stream at 100° C. for 6 hours. After the reaction, 1.0 mol/L hydrochloric acid was added to the mixture, and the precipitated solid was removed by suction filtration. The filtrate was subjected to extraction with toluene, and the obtained organic layer was washed with a saturated aqueous solution of sodium hydrogen carbonate and saturated saline, and then was dried with magnesium sulfate. This mixture was separated by gravity filtration, and the filtrate was concentrated to give a brown oily substance. The obtained oily substance was purified by silica gel column chromatography (hexane), so that 8.00 g of the target 4-(3-bromophenyl)dibenzothiophene-1,2,3,6,7,8,9-$d_7$ was obtained in a yield of 50%. The synthesis scheme of Step 2-1 is shown in (b-1) below.

[Chemical Formula 82]

(b-1)

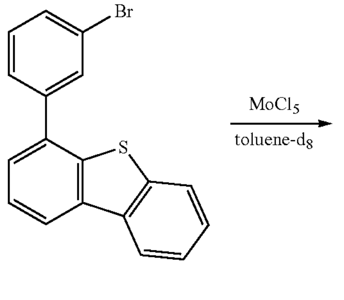

-continued

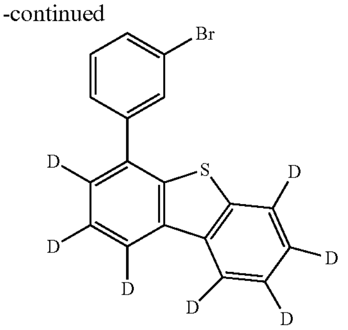

Figure 25A:
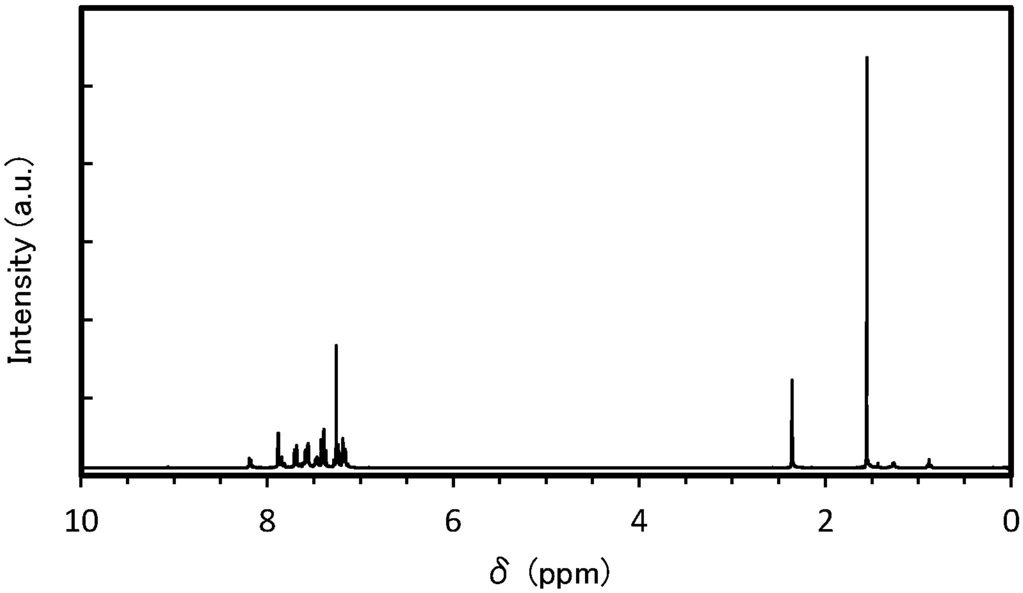
FIGS. 25A and 25B show $^1$H NMR spectra of an organic compound obtained in Example 2.

Analysis results by nuclear magnetic resonance ($^1$H-NMR) spectroscopy of 4-(3-bromophenyl)dibenzothiophene-1,2,3,6,7,8,9-$d_7$ obtained in Step 2-1 are shown below. In addition, FIGS. 25A and 25B show $^1$H-NMR charts.

$^1$H-NMR. δ ($CDCl_3$, 300 MHz): 7.34-7.42 (m, 1H), 7.56-7.61 (m, 1H), 7.68-7.71 (m, 1H), 7.88-7.89 (m, 1H).

As can be seen from (a-1) shown in Example 1 and (b-1) in this example, protium that is replaced with deuterium can be controlled by changing heating time in Step 2-1. For example, when heating is performed at 100° C. for 6 hours, a substitution reaction of deuterium for protium bonded to a dibenzothiophene skeleton proceeds. When the heating is further performed, the substitution of deuterium for protium of a phenyl group bonded to a dibenzothiophene skeleton also proceeds.

Figure 25B:
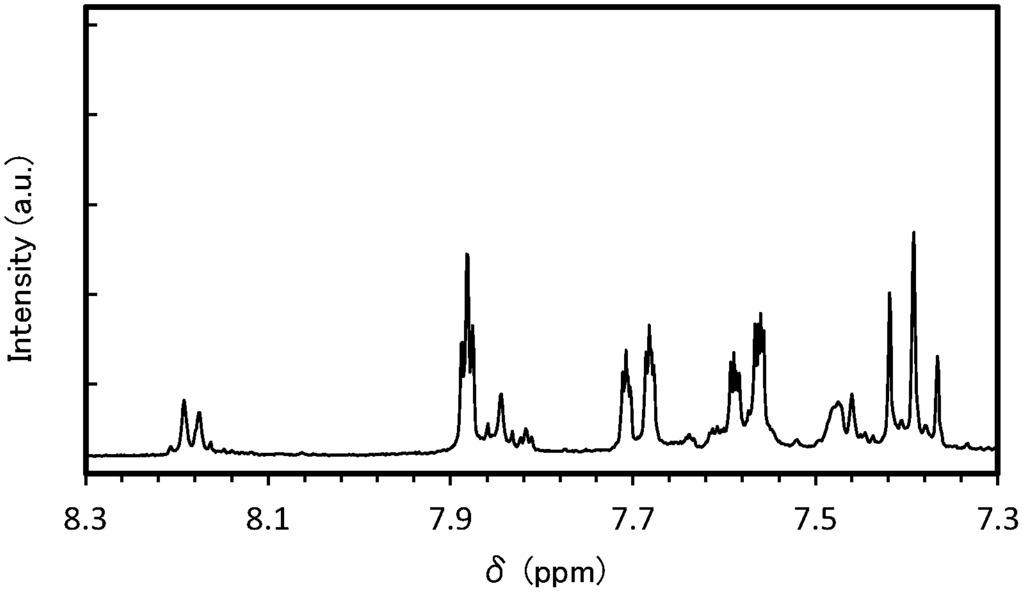
Figure 26A:
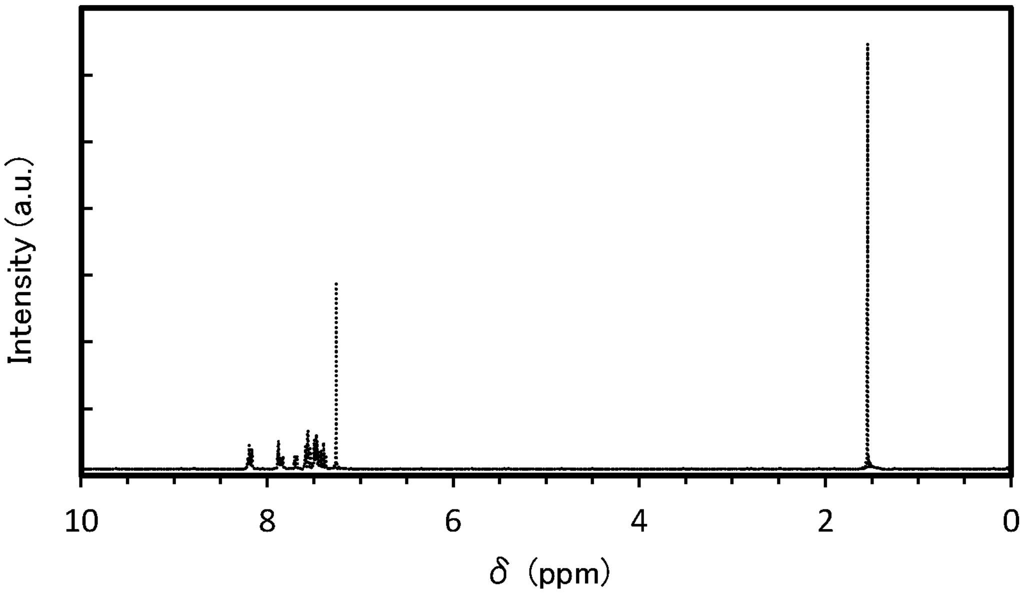
FIG. 26A shows a $^1$H NMR spectrum of 4-(3-bromophenyl)dibenzothiophene.
Figure 26B:
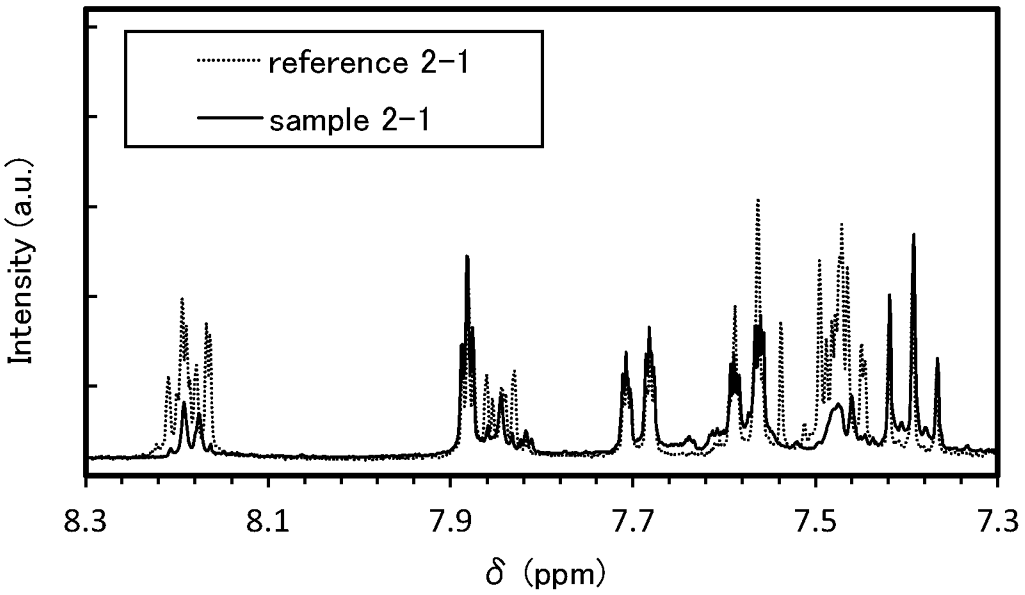
FIG. 26B shows $^1$H NMR spectra of the organic compound obtained in Example 2 and 4-(3-bromophenyl)dibenzothiophene.

In FIG. 25B, signals that appear around δ=7.81 ppm to 7.86 ppm, δ=8.16 ppm to 8.21 ppm, or the like are assumed to be protium that was not deuterated and remained in Synthesis Scheme (b-1). The deuteration rate was estimated in the following manner: the peak of 7.34-7.42 ppm (m, 1H) in which deuteration did not proceed was used as the reference, and the number of protons of 4-(3-bromophenyl)dibenzothiophene that was a non-deuterated substance of 4-(3-bromophenyl)dibenzothiophene-1,2,3,6,7,8,9-$d_7$ was referred to. FIG. 26A shows the $^1$H-NMR chart of 4-(3-bromophenyl)dibenzothiophene, and FIG. 26B is an enlarged view of δ=7.30 ppm to 8.30 ppm, which compares 4-(3-bromophenyl)dibenzothiophene-1,2,3,6,7,8,9-$d_7$ (sample 2-1) and 4-(3-bromophenyl)dibenzothiophene (reference 2-1). From the above, the deuteration rate of 4-(3-bromophenyl)dibenzothiophene-1,2,3,6,7,8,9-$d_7$ was estimated to be approximately 78%.

Step 2-2; Synthesis of 2-[3-(dibenzo[b,d]thiophen-4-yl-1,2,3,6,7,8,9-$d_7$)phenyl]-4,4,5,5-tetramethyl-1,3,2-dioxaborolane Into a 200 mL three-neck flask were put 8.0 g (23 mmol) of 4-(3-bromophenyl)dibenzothiophene-1,2,3,6,7,8,9-$d_7$ obtained in Step 2-1, 7.4 g (29 mmol) of bis(pinacolato)diboron, 8.9 g (90 mmol) of potassium acetate, and 116 mL of N,N-dimethylformamide (DMF). The mixture in the flask was stirred under reduced pressure and degassed. After that, the mixture was heated at 60° C. under a nitrogen stream, 0.98 g (1.2 mmol) of [1,1'-bis(diphenylphosphino)ferrocene]dichloropalladium(II) dichloromethane adduct (abbreviation: $Pd(dppf)_2Cl_2·CH_2Cl_2$) was added thereto, and then the temperature was raised to 100° C. and the mixture was stirred for 5 hours. After the reaction, extraction was performed with toluene and the obtained organic layer was washed with saturated saline and dried with magnesium sulfate to give the mixture. This mixture was separated by gravity filtration, and the filtrate was concentrated to give a black oily substance. The obtained oily substance was purified by silica gel column chromatography (toluene: hexane=1:1 to toluene:hexane=1:0), so that 7.2 g of the target yellow-green oily substance of 2-[3-(dibenzo[b,d]thiophen-4-yl-1,2,3,6,7,8,9-$d_7$)phenyl]-4,4,5,5-tetramethyl-1,3,2-dioxaborolane was obtained in a yield of 79%. The synthesis scheme of Step 2-2 is shown in (b-2) below.

[Chemical Formula 83]

(b-2)

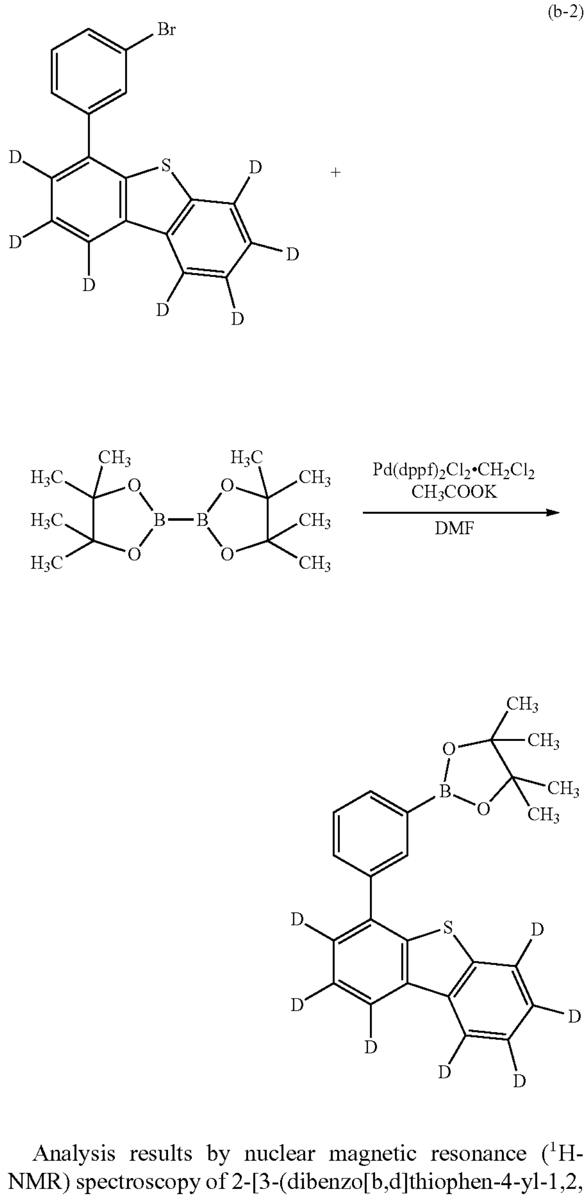

Figure 27A:
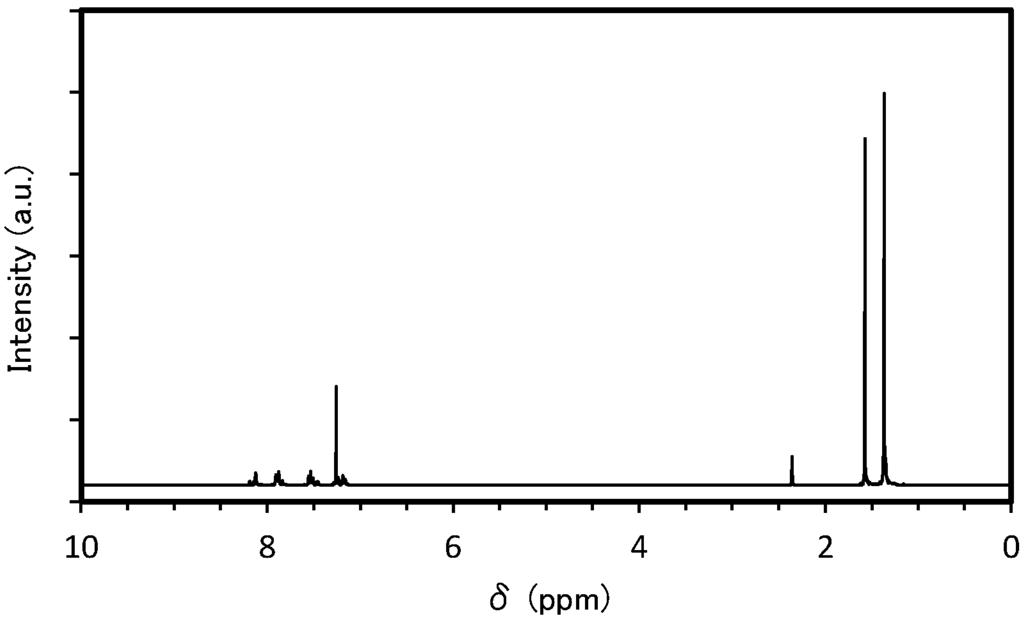
FIGS. 27A and 27B are $^1$H NMR spectra of the organic compound obtained in Example 2.

Analysis results by nuclear magnetic resonance ($^1$H-NMR) spectroscopy of 2-[3-(dibenzo[b,d]thiophen-4-yl-1,2,3,6,7,8,9-$d_7$)phenyl]-4,4,5,5-tetramethyl-1,3,2-dioxaborolane obtained in Step 2-2 are shown below. In addition, FIGS. 27A and 27B show $^1$H-NMR charts.

$^1$H-NMR. δ ($CDCl_3$, 300 MHz): 1.37 (s, 12H), 7.51-7.56 (m, 1H), 7.87-7.91 (m, 2H), 8.12 (s, 1H).

Figure 27B:
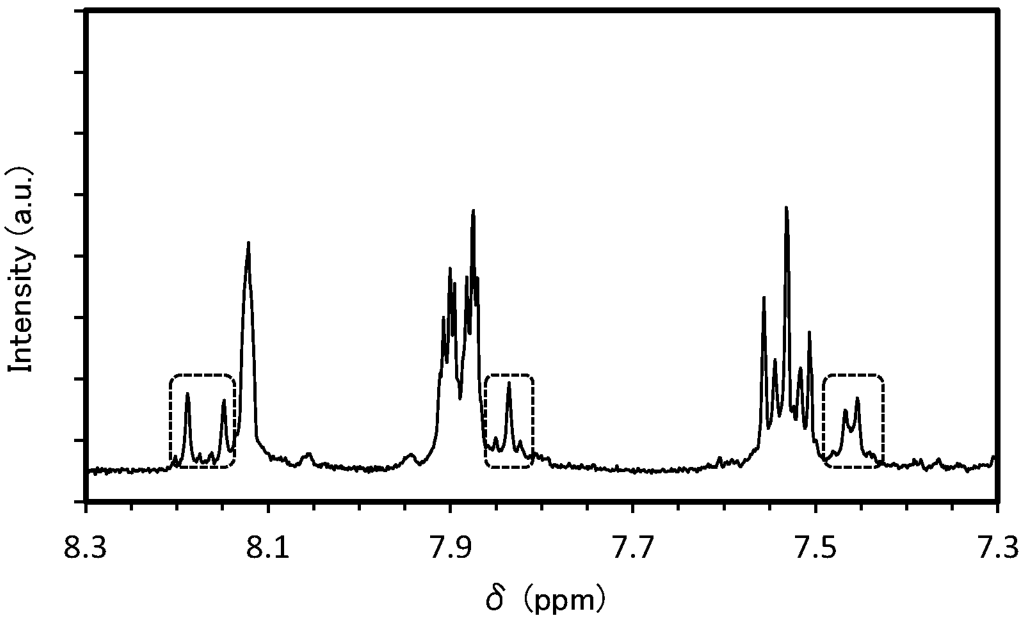

In FIG. 27B, signals that appear around δ=7.4 ppm to 7.5 ppm and other regions surrounded with dashed lines are assumed to be peaks derived from protium that were not deuterated and remained in Synthesis Scheme (b-2) above.

Step 2-3: Synthesis of 4,8mDBtP2Bfpm-$d_{14}$)

Into a 200 mL three-neck flask were put 7.2 g (18 mmol) of 2-[3-(dibenzo[b,d]thiophen-4-yl-1,2,3,6,7,8,9-$d_7$)phenyl]-4,4,5,5-tetramethyl-1,3,2-dioxaborolane obtained in Step 2-2, 2.0 g (8.2 mmol) of 4,8-dichloro[1]benzofuro[3,2-d]pyrimidine, 11 g (50 mmol) of tripotassium phosphate, 3.9 g (53 mmol) of tert-butylalcohol (abbreviation: tBuOH), and 85 mL of diethyleneglycoldimethylether (abbreviation: diglyme). The mixture in the flask was stirred under reduced pressure and degassed. After that, the mixture was heated at 60° C. under a nitrogen stream, 0.33 g (1.5 mmol) of palladium(II) acetate (abbreviation: $Pd(OAc)_2$) and 1.0 g (2.8 mmol) of di(1-adamantyl)-N-butylphosphine (abbreviation: cataCxiumA) were added thereto, and then the temperature was raised to 110° C. and the mixture was stirred at the same temperature for 2 hours. Furthermore, the temperature was raised to 130° C. and the mixture was stirred at the same temperature for 4 hours. Moreover, the temperature was raised to 155° C. and the mixture was stirred at the same temperature for 3.5 hours. After the reaction, water was added to the mixture in the flask and suction filtration was performed, and the obtained residue was washed with water and ethanol. The obtained residue was dissolved in toluene by heating, followed by filtration through a filter medium in which Celite, alumina, and Celite were stacked in this order. The filtrate was concentrated and then recrystallized with toluene to give 2.4 g of the target yellow-white solid in a yield of 41%. By a train sublimation method, 2.4 g of the obtained yellow-white solid was purified by sublimation. The sublimation purification was conducted under the conditions where the pressure was 2.9 Pa, the flow rate of an argon gas was 15 mL/min, and the solid was heated at 355° C. After the sublimation purification, 1.4 g of a target pale yellow solid was obtained at a collection rate of 58%. The synthesis scheme of Step 2-3 is shown in (b-3) below.

[Chemical Formula 84]

(b-3)

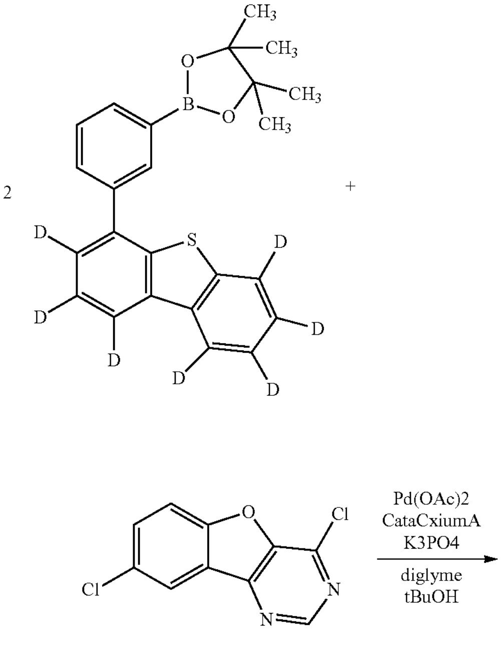

-continued

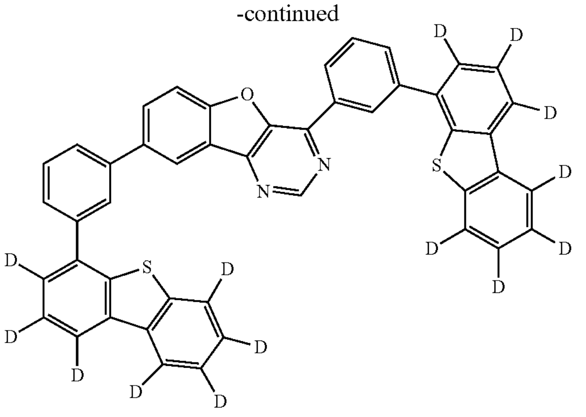

(101)

Figure 28A:
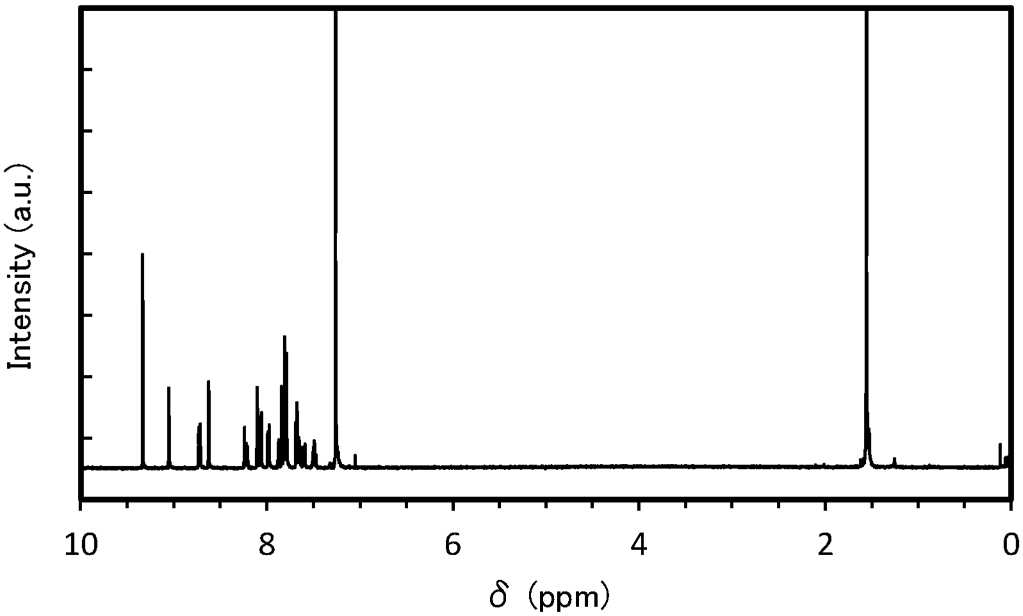
FIGS. 28A and 28B show $^1$H NMR spectra of 4,8mDBtP2Bfpm-$d_{14}$.

Analysis results by nuclear magnetic resonance ($^1$H-NMR) spectroscopy of the pale yellow solid obtained in the above step are described below. FIG. 28A is the $^1$H-NMR chart. From this result, it was found that 4,8mDBtP2Bfpm-$d_{14}$, which is represented by the structural formula (101) and is one embodiment of the present invention, was obtained in Synthesis example 2.

$^1$H-NMR. δ ($CDCl_3$, 500 MHz): 7.64-7.69 (m, 1H), 7.79-7.84 (m, 4H), 7.98 (d, J=7.45 Hz, 1H), 8.07 (dd, J1=8.59 Hz, J2=1.72 Hz, 1H), 8.10 (s, 1H), 8.63 (sd, J=1.72 Hz, 1H), 8.72 (d, J=8.02 Hz, 1H), 9.05 (s, 1H), 9.33 (s, 1H).

Figure 28B:
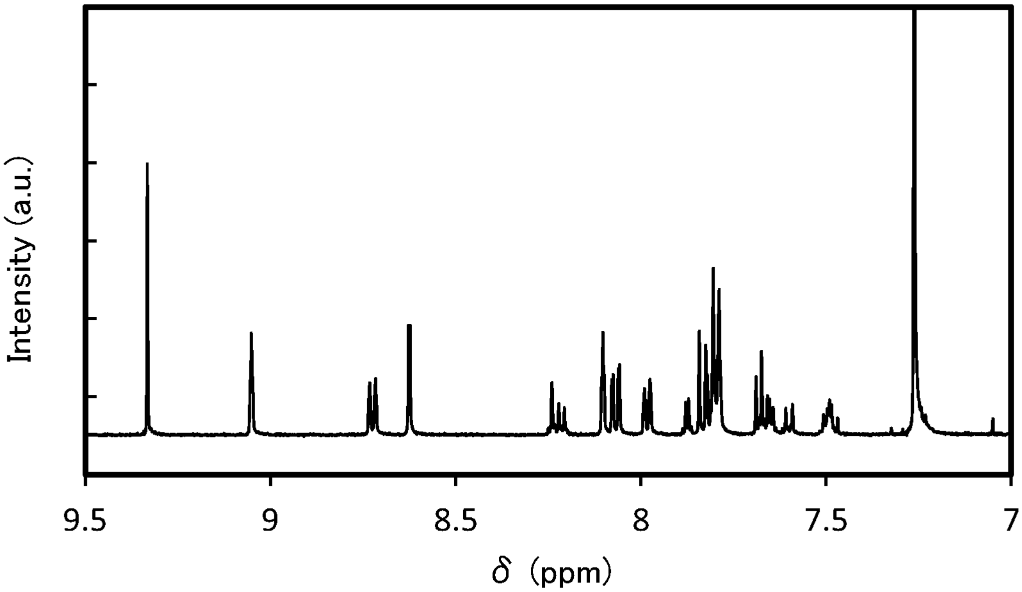

In FIG. 28B, fine signals are observed around δ=7.45 ppm to 7.55 ppm, 8.20 ppm to 8.25 ppm, or the like. They are assumed to be protium that were not deuterated and remained in Synthesis Scheme (b-1).

Figure 29A:
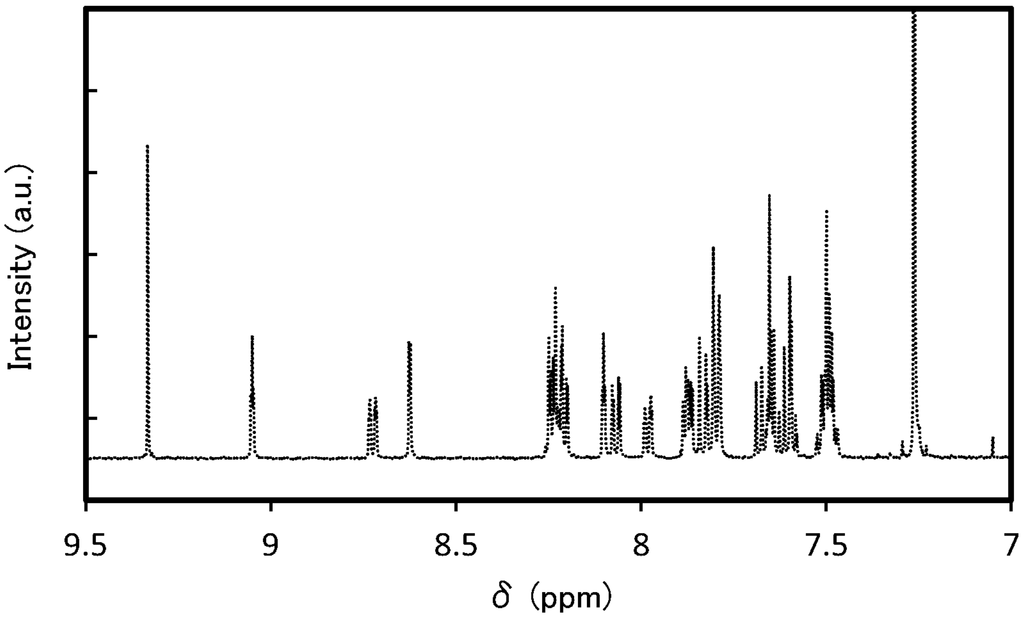
FIG. 29A shows a $^1$H NMR spectrum of 4,8mDBtP2Bfpm-$d_{14}$ that is a non-deuterated substance.
Figure 29B:
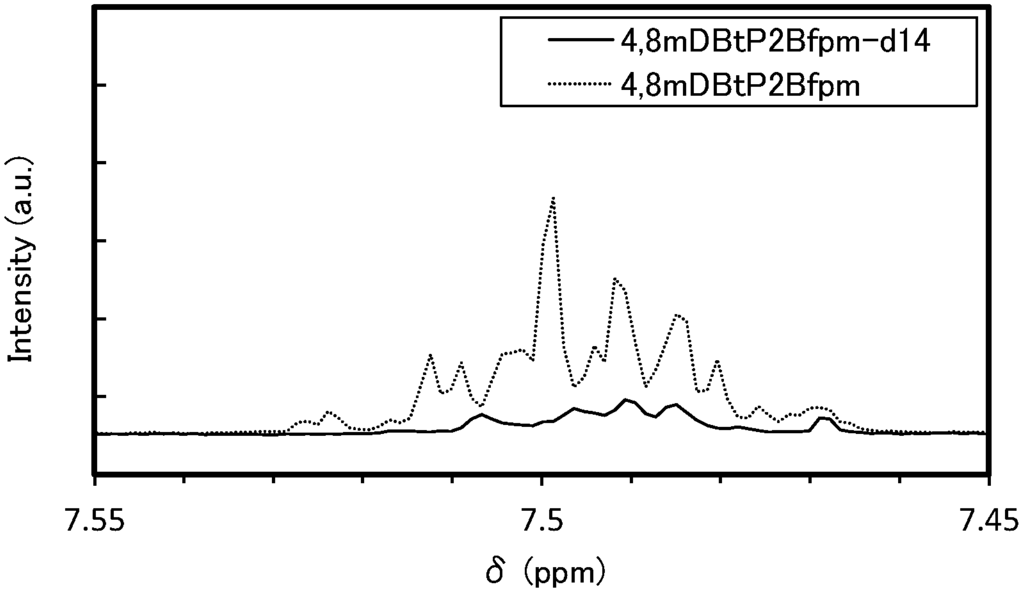
FIG. 29B shows $^1$H NMR spectra of 4,8mDBtP2Bfpm-$d_{14}$ and 4,8mDBtP2Bfpm.

FIG. 29A shows the $^1$H-NMR chart of 4,8mDBtP2Bfpm that is a non-deuterated substance of 4,8mDBtP2Bfpm-$d_{14}$. FIG. 29B is an enlarged view of δ=7.45 ppm to 7.55 ppm, which compares 4,8mDBtP2Bfpm-$d_{14}$ and 4,8mDBtP2Bfpm. Signals around 7.45 ppm to 7.55 ppm are signals derived from a dibenzothiophene skeleton, and the deuteration rate is estimated to be approximately 75%. The deuteration rate of a partial structure derived from 4-(3-bromophenyl)dibenzothiophene-1,2,3,6,7,8,9-$d_7$ of 4,8mDBtP2Bfpm-$d_{14}$ synthesized using 4-(3-bromophenyl) dibenzothiophene-1,2,3,6,7,8,9-$d_7$ whose deuteration rate was 78% was kept until the synthesis of a final product.

<Characteristics of 4,8mDBtP2Bfpm-$d_{14}$>

Figure 30:
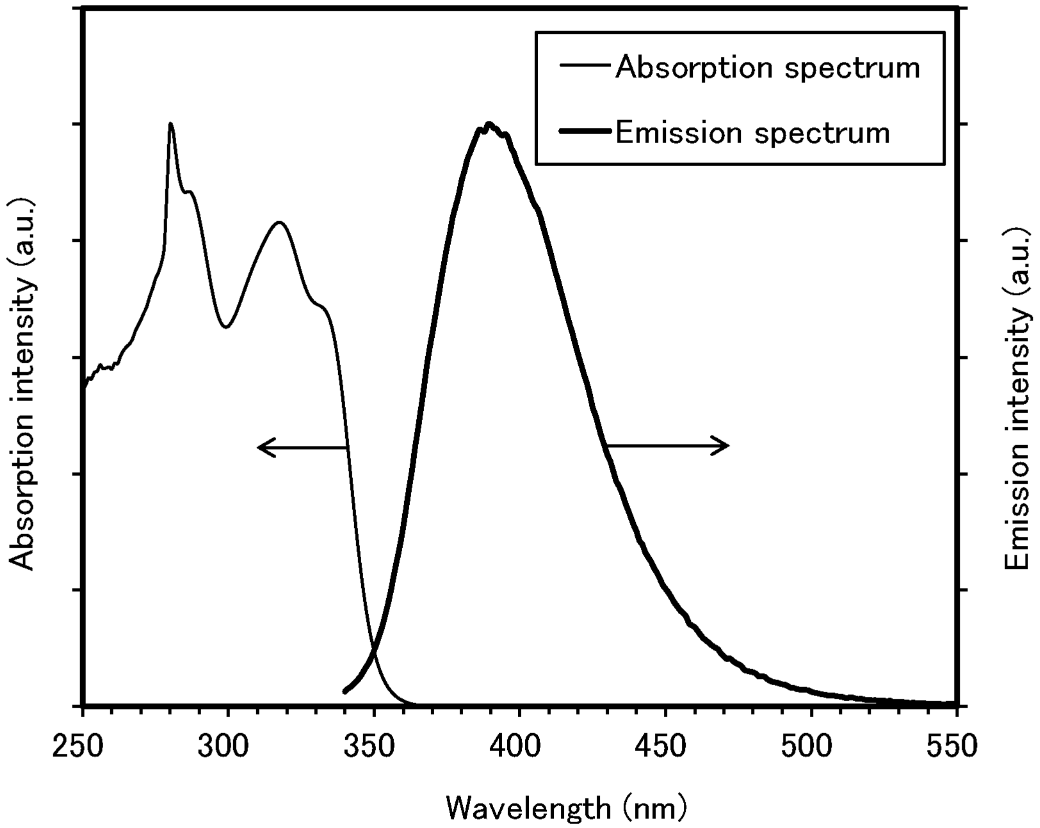
FIG. 30 shows an absorption spectrum and an emission spectrum of 4,8mDBtP2Bfpm-$d_{14}$ in a toluene solution.

Then, the ultraviolet-visible absorption spectrum (hereinafter, simply referred to as "absorption spectrum") and emission spectrum of a toluene solution of 4,8mDBtP2Bfpm-$d_{14}$ were measured. The absorption spectrum was measured at room temperature with an ultraviolet-visible light spectrophotometer (V-770DS, produced by JASCO Corporation) in a state where the toluene solution was put in a quartz cell. The emission spectrum was measured at room temperature with a fluorescence spectrophotometer (FP-8600DS, produced by JASCO Corporation) in a state where the toluene solution was put in a quartz cell. FIG. 30 shows obtained measurement results of the absorption spectrum and the emission spectrum. The horizontal axis represents the wavelength and the vertical axes represent the absorption intensity and the emission intensity. The absorption spectrum shown in FIG. 30 is a result obtained by subtraction of an absorption spectrum of only toluene in a quartz cell from the measured absorption spectrum of the toluene solution in the quartz cell.

As shown in FIG. 30, in the toluene solution of 4,8mDBtP2Bfpm-$d_{14}$, absorption peaks were observed around 286 nm, 317 nm, and 331 nm, and an emission peak was observed around 390 nm (excitation wavelength: 300 nm).

The glass transition temperature (Tg) of 4,8mDBtP2Bfpm-$d_{14}$ was measured. Note that Tg was measured with a differential scanning calorimeter (DSC8500 produced by PerkinElmer Japan Co., Ltd.) in a state where a powder was put on an aluminum cell. As a result, Tg of 4,8mDBtP2Bfpm-$d_{14}$ was 136° C.

Furthermore, the electrochemical characteristics (oxidation reaction characteristics and reduction reaction characteristics) of 4,8mDBtP2Bfpm-$d_{14}$ were measured by cyclic voltammetry (CV). An electrochemical analyzer (ALS model 600A, manufactured by BAS Inc.) was used for the measurement. The solution for the measurement was prepared by using dehydrated N,N-dimethylformamide (DMF) (produced by Aldrich Corp., 99.8%, catalog number: 22705-6) as a solvent, dissolving a supporting electrolyte, tetra-n-butylammonium perchlorate ($n-Bu_4NClO_4$) (produced by Tokyo Chemical Industry Co., Ltd., catalog number: T0836), at a concentration of 100 mmol/L, and then dissolving the object of measurement at a concentration of 2 mmol/L.

A platinum electrode (PTE platinum electrode, manufactured by BAS Inc.) was used as a working electrode, another platinum electrode (Pt counter electrode (5 cm), manufactured by BAS Inc.) was used as an auxiliary electrode, and an $Ag/Ag^+$ electrode (RE7 reference electrode for nonaqueous solvent, manufactured by BAS Inc.) was used as a reference electrode. Note that the measurement was performed at room temperature (20° C. to 25° C.).

In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a measurement result of the oxidation potential Ea [V] of 4,8mDBtP2Bfpm-$d_{14}$, the HOMO level is around −6.2 eV. In contrast, the LUMO level was found to be −3.02 eV from the measurement result of the reduction potential Ec [V]. These results reveal that 4,8mDBtP2Bfpm-$d_{14}$ has a low LUMO level and a low HOMO level. In addition, the results of repetitive measurement of the oxidation-reduction wave showed that when the waveform of the first cycle was compared with that of the hundredth cycle, 84% of the peak intensity were maintained in the Ec measurement, which confirmed that 4,8mDBtP2Bfpm-$d_{14}$ had extremely high resistance to reduction.

Example 3

Synthesis Example 3

In this example, a method for synthesizing 8-(1,1': 4',1"-terphenyl-3-yl-2,4,5,6,2',3',5',6,2",3",4",5",6"-$d_{13}$)-4-[3-(dibenzothiophen-4-yl-1,2,3,6,7,8,9-d)phenyl-2,4,6-$d_3$]-[1]benzofuro[3,2-d]pyrimidine (abbreviation: 8mpTP-4mDBtPBfpm-$d_{23}$) shown as Structural Formula (128) in Embodiment 1 is specifically described.

[Chemical Formula 85]

(128)

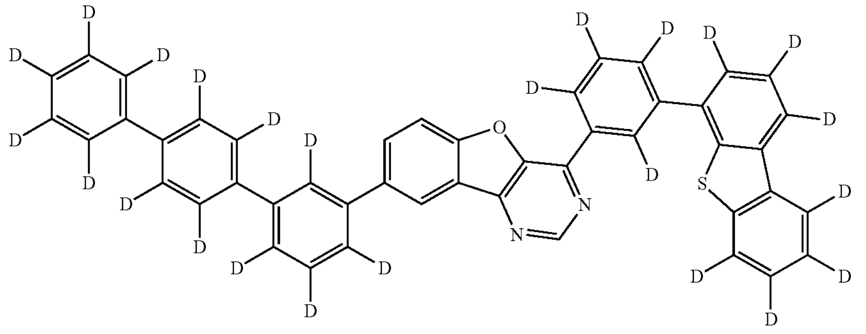

8mpTP-4mDBtPBfpm-d23

Step 3-1; Synthesis of 4-(3-bromophenyl-2,4,6-$d_3$)dibenzothiophene-1,2,3,6,7,8,9-$d_7$ Into a 300 mL three-neck flask were put 1.0 g (3.8 mmol) of molybdenum(V) pentachloride (abbreviation: $MoCl_5$), and the air in the flask was replaced with nitrogen. Then, 60 mL of deuterated toluene (abbreviation: toluene-$d_8$) was added thereto, and the solution was stirred. To this solution, 10 g (30 mmol) of 4-(3-bromophenyl)dibenzothiophene was added, and the solution was stirred under a nitrogen stream at room temperature for 15 hours. By nuclear magnetic resonance ($^1$H-NMR) spectroscopy and mass spectrometry, the reaction was confirmed not to be completed, and thus 3.1 g (11 mmol) of $MoCl_5$ was added to the reaction solution and the reaction solution was stirred at 80° C. for 21 hours. To the obtained reaction solution, 20 mL of 1.0 mol/L hydrochloric acid was added, and after one-hour stirring, suction filtration was performed to remove an insoluble matter. The obtained filtrate was subjected to extraction with toluene. The obtained organic layer was dried with magnesium sulfate, and this mixture was gravity-filtered to give filtrate. The obtained filtrate was concentrated to give a black oily substance. The obtained oily substance was purified by silica gel column chromatography (developing solvent: hexane). The obtained fraction was concentrated, so that 7.5 g of 4-(3-bromophenyl-2,4,6-$d_3$)dibenzothiophene-1,2,3,6,7,8,9-$d_7$ that is a white solid was obtained in a yield of 72%. It was confirmed from $^1$H-NMR and mass spectrometry that the obtained substance was 4-(3-bromophenyl-2,4,6-$d_3$)dibenzothiophene-1,2,3,6,7,8,9-$d_7$. The synthesis scheme of Step 3-1 is shown in (c-1) below.

[Chemical Formula 86]

(c-1)

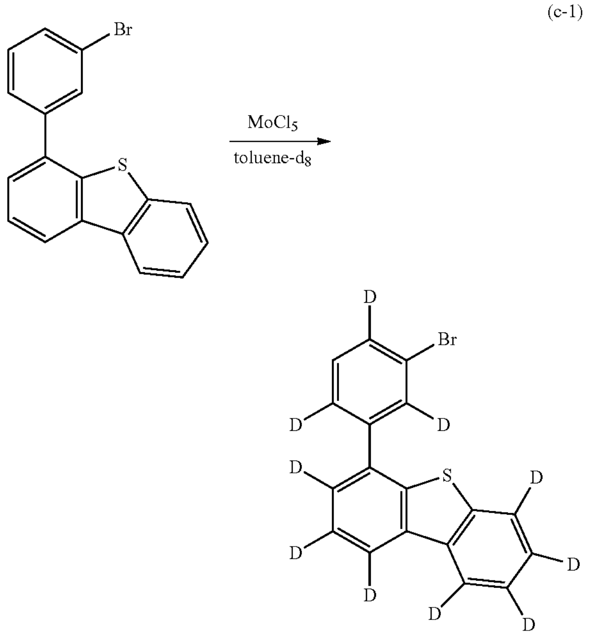

Figure 31A:
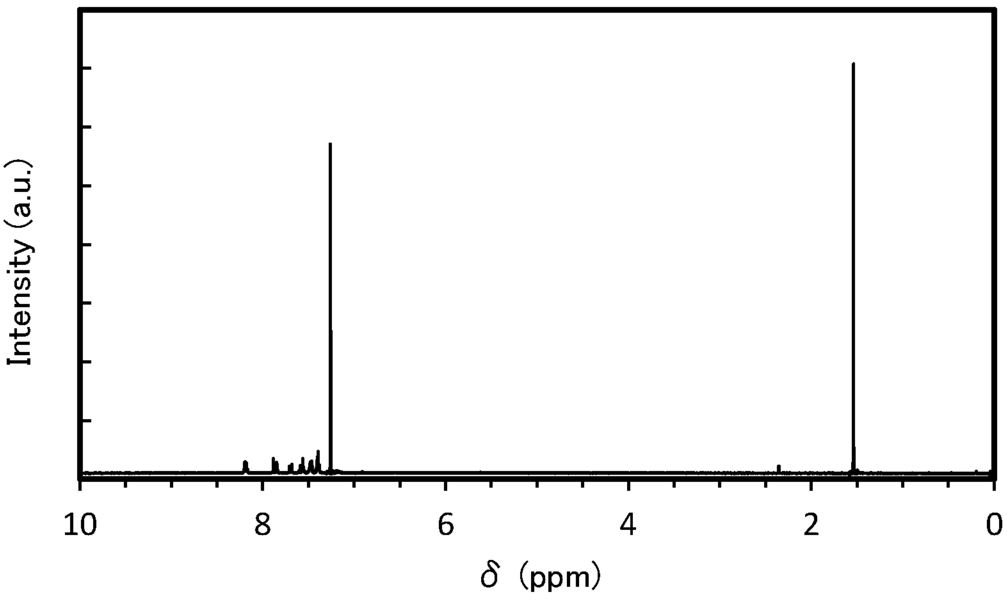
FIGS. 31A and 31B are $^1$H NMR spectra of the organic compound obtained in Example 3.

Analysis results by nuclear magnetic resonance ($^1$H-NMR) spectroscopy of 4-(3-bromophenyl-2,4,6-$d_3$)dibenzothiophene-1,2,3,6,7,8,9-$d_7$ obtained in Step 3-1 are shown below. In addition, FIGS. 31A and 31B show $^1$H-NMR charts.

$^1$H-NMR. δ ($CDCl_3$, 300 MHz): 7.38-7.42 (s, 1H).

As described in Example 3, in the case where the heating temperature in Step 3-1 is 80° C., when the heating time is 21 hours, 4-(3-bromophenyl-2,4,6-$d_3$)dibenzothiophene-1,2,3,6,7,8,9-$d_7$ that is the same deuterated substance as (a-1) described in Example 1 can be obtained. The result shows that protium that is replaced with deuterium can be controlled by changing heating temperature and heating time.

Figure 31B:
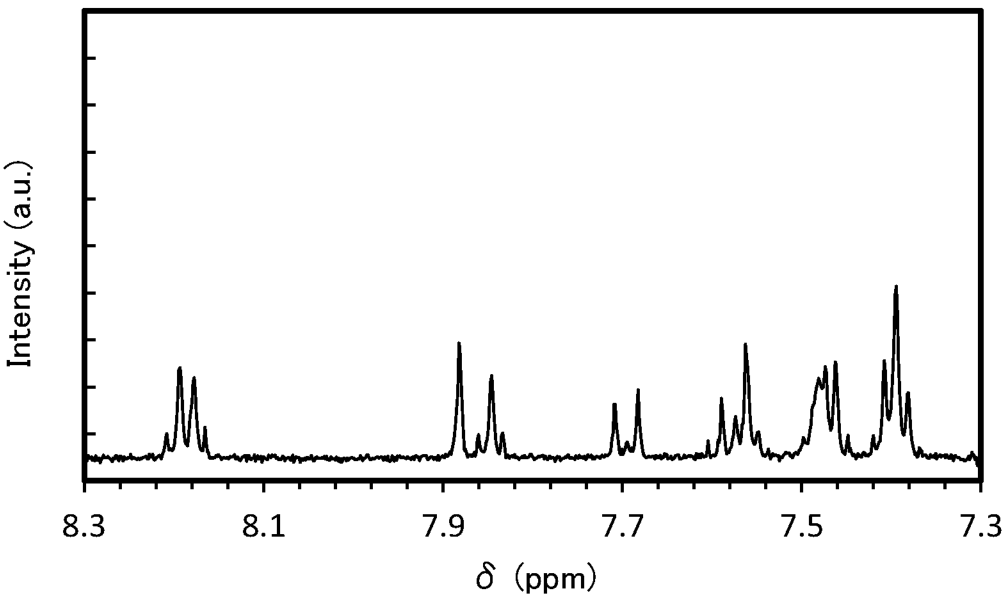
Figure 32A:
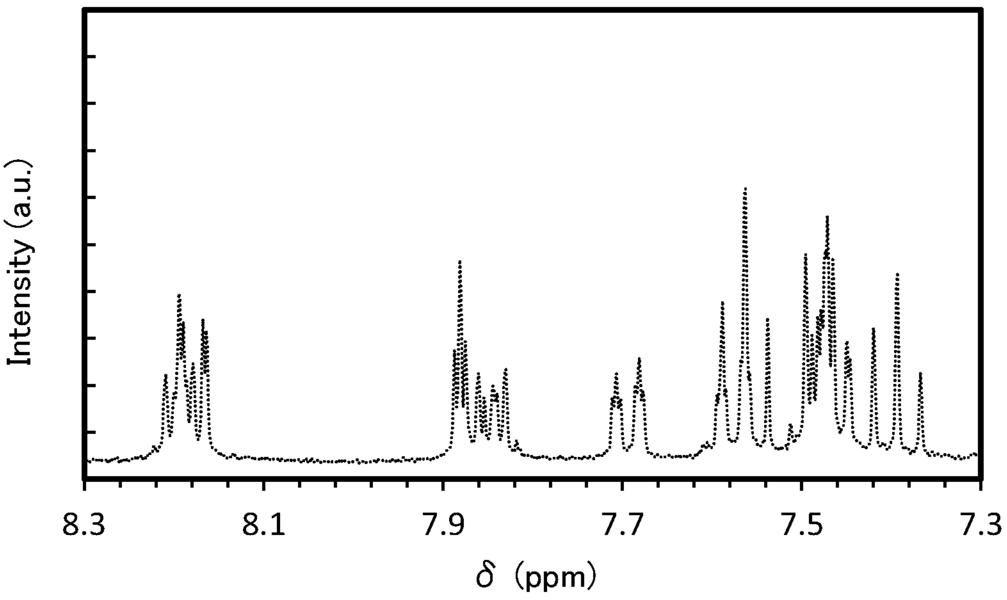
FIG. 32A shows a $^1$H NMR spectrum of reference 3-1.
Figure 32B:
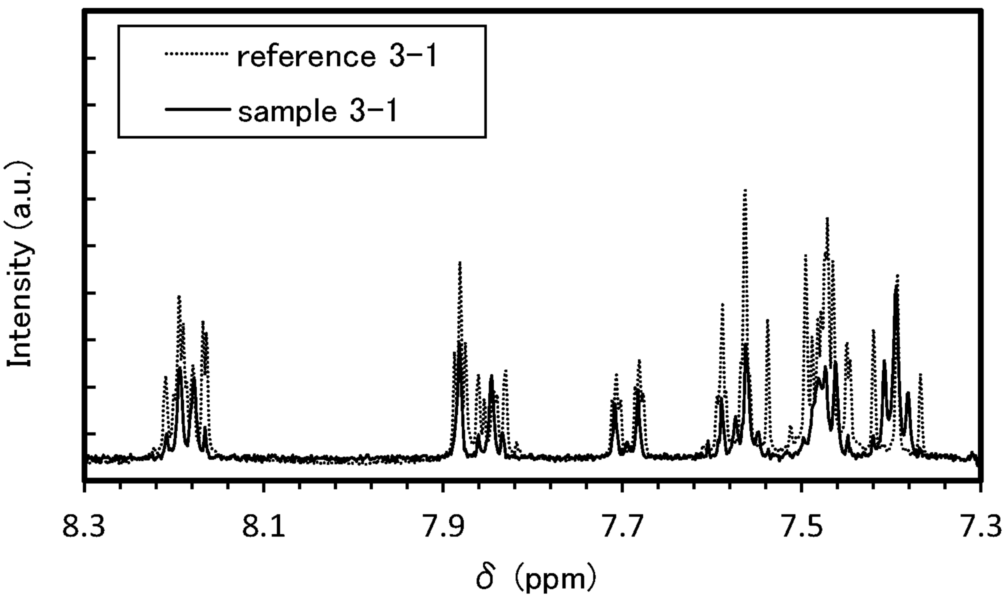
FIG. 32B shows $^1$H NMR spectra of an organic compound obtained in Example 3 and reference 3-1.

In FIG. 31B, signals that appear around δ=7.68 ppm to 7.71 ppm, δ=8.17 ppm to 8.21 ppm, or the like are assumed to be protium that was not deuterated and remained in Synthesis Scheme (c-1). The deuteration rate was estimated by $^1$H NMR. FIG. 32A shows the $^1$H-NMR chart of 4-(3-bromophenyl)dibenzothiophene, and FIG. 32B is an enlarged view of δ=7.30 ppm to 8.30 ppm, which compares 4-(3-bromophenyl-2,4,6-$d_3$)dibenzothiophene-1,2,3,6,7,8,9-$d_7$ (sample 3-1) and 4-(3-bromophenyl)dibenzothiophene (reference 3-1). From the above, the deuteration rate of 4-(3-bromophenyl-2,4,6-$d_3$)dibenzothiophene-1,2,3,6,7,8,9-$d_7$ was estimated to be approximately 65%.

Step 3-2; Synthesis of 2-[3-(dibenzo[b,d]thiophen-4-yl-1,2,3,6,7,8,9-$d_7$)phenyl-2,4,6-$d_3$]-4,4,5,5-tetramethyl-1,3,2-dioxaborolane Into a 200 mL three-neck flask were put 7.5 g (22 mmol) of 4-(3-bromophenyl-2,4,6-$d_3$)dibenzothiophene-1,2,3,6,7,8,9-$d_7$ obtained in Step 3-1, 7.1 g (28 mmol) of bis(pinacolato)diboron, 8.3 g (84 mmol) of potassium acetate, and 110 mL of N,N-dimethylformamide (DMF). The mixture in the flask was stirred under reduced pressure and degassed. After that, the mixture was heated at 60° C. under a nitrogen stream, 0.91 g (1.1 mmol) of [1,1'-bis(diphenylphosphino)ferrocene]dichloropalladium(II) dichloromethane adduct (abbreviation: $Pd(dppf)_2Cl_2 \cdot CH_2Cl_2$) was added thereto, and then the mixture was stirred at 100° C. for 3 hours. After the stirring, the obtained mixture was subjected to extraction with toluene and the obtained solution was washed with saturated saline and dried with magnesium sulfate. This mixture was separated by gravity filtration, and the obtained filtrate was concentrated to give a brown oily substance. The obtained oily substance was purified by silica gel column chromatography (hexane:ethyl acetate=10:1), so that 8.2 g of the target light-green oily substance of 2-[3-(dibenzo[b,d]thiophen-4-yl-1,2,3,6,7,8,9-$d_7$)phenyl-2,4,6-$d_3$]-4,4,5,5-tetramethyl-1,3,2-dioxaborolane was obtained in a yield of 96%. The synthesis scheme of Step 3-2 is shown in (c-2) below.

[Chemical Formula 87]

(c-2)

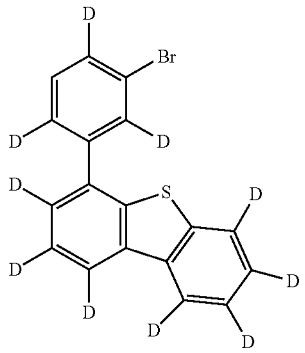

+

-continued

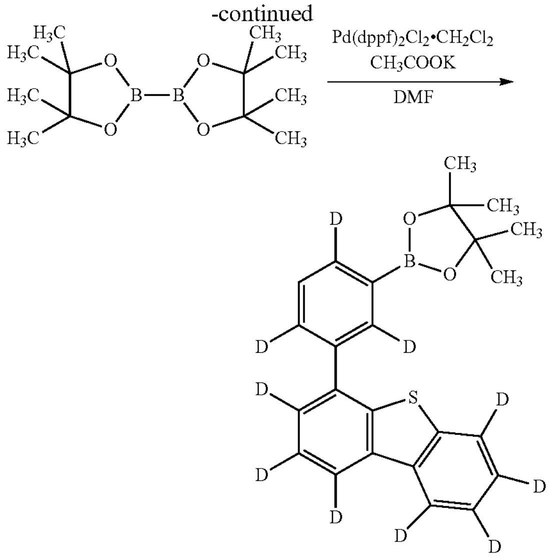

Figure 33A:
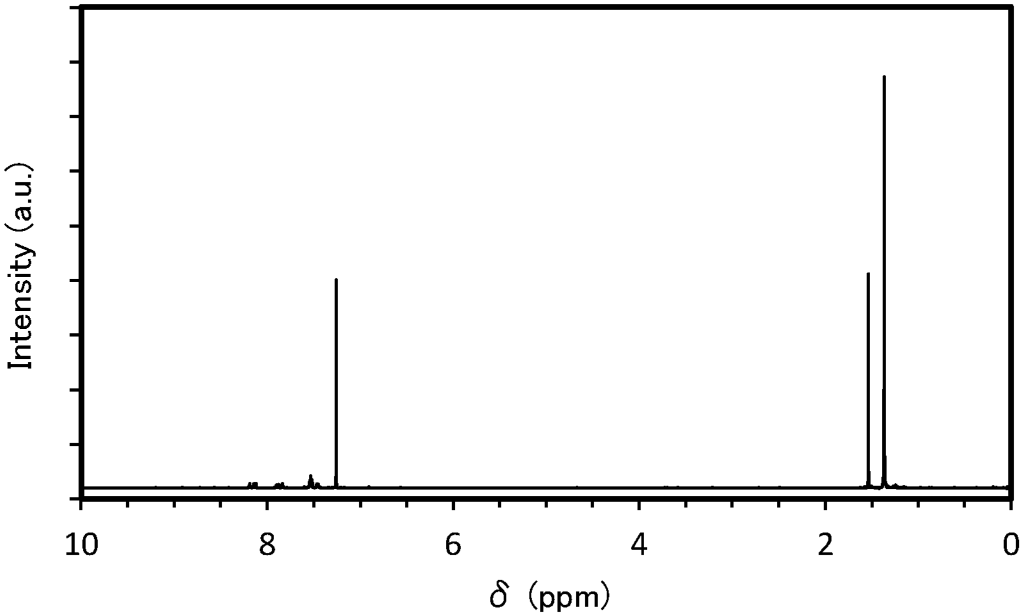
FIGS. 33A and 33B show $^1$H NMR spectra of the organic compound obtained in Example 3.

Analysis results by nuclear magnetic resonance ($^1$H-NMR) spectroscopy of 2-[3-(dibenzo[b,d]thiophen-4-yl-1,2,3,6,7,8,9-$d_7$)phenyl-2,4,6-$d_3$]-4,4,5,5-tetramethyl-1,3,2-dioxaborolane obtained in Step 3-2 are shown below. In addition, FIGS. 33A and 33B show $^1$H-NMR charts.

$^1$H-NMR. δ ($CDCl_3$, 300 MHz): 1.37 (s, 12H), 7.52-7.54 (m, 1H).

Figure 33B:
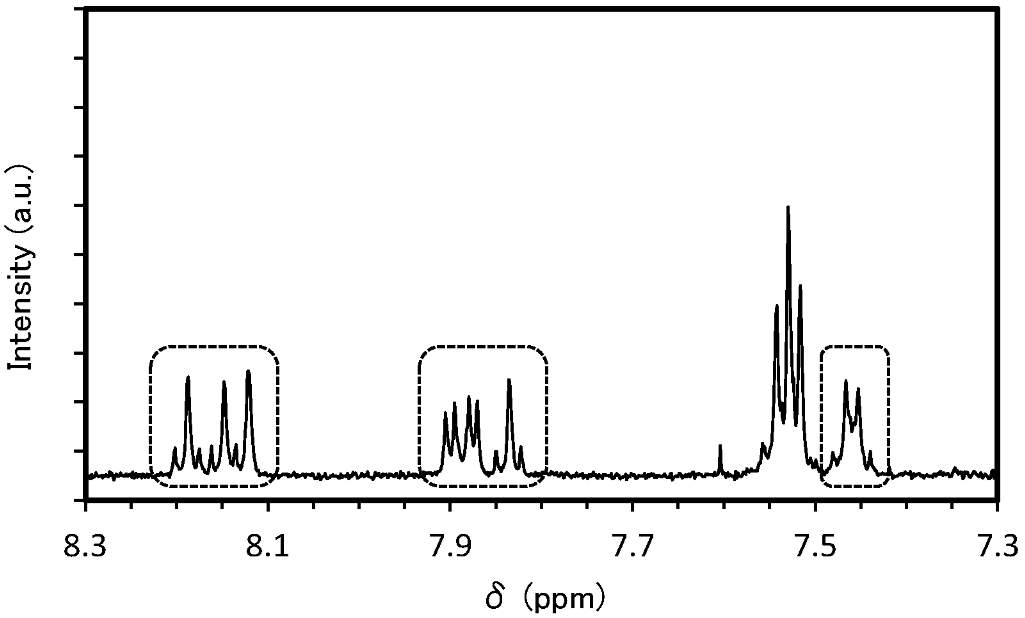

In FIG. 33B, signals that appear around δ=7.4 ppm to 7.5 ppm, δ=8.1 ppm to 8.2 ppm, or other regions surrounded with dashed lines are assumed to be peaks derived from protium that were not deuterated and remained in Synthesis Scheme (c-2) above.

Step 3-3; 3-bromo-1,1': 4',1"-terphenyl-2,4,5,6,2',3',5',6',2",3",4",5",6"-$d_{13}$ Into a 200 mL three-neck flask were put 5.1 g (16.5 mmol) of 3-bromo-1,1':4',1"-terphenyl and 30 g of deuterated toluene (abbreviation: toluene-$d_8$), and the mixture in the flask was stirred under reduced pressure and degassed. Then, 0.90 g (3.3 mmol) of molybdenum(V) pentachloride (abbreviation: $MoCl_5$) was added thereto, and the mixture was stirred at room temperature under a nitrogen stream for 20 hours. By nuclear magnetic resonance ($^1$H-NMR) spectroscopy, the reaction was confirmed not to be completed, and thus 1.8 g (6.5 mmol) of $MoCl_5$ was added to the reaction solution and the reaction solution was stirred at 80° C. for 11 hours. Furthermore, 0.91 g (3.3 mmol) of $MoCl_5$ was added, and the reaction solution was stirred at 100° C. for 7 hours. After the stirring, 50 mL of 1.0 mol/L hydrochloric acid was added to the mixture, and the mixture was stirred at room temperature. Then, the precipitated solid was removed by suction filtration. The filtrate was subjected to extraction with toluene, and the obtained solution was washed with a saturated aqueous solution of sodium hydrogen carbonate and saturated saline, and then was dried with magnesium sulfate. This mixture was separated by gravity filtration, and the filtrate was concentrated to give a brown solid. The obtained solid was purified by silica gel column chromatography (hexane:dichloromethane=5:1). The obtained solid was further purified by high performance liquid chromatography (HPLC), so that 4.3 g of the target white solid of 3-bromo-1,1':4',1"-terphenyl-2,4,5,6,2',3',5',6',2",3",4",5", 6"-$d_{13}$ was obtained in a yield of 81%. The synthesis scheme of Step 3-3 is shown in (c-3) below.

[Chemical Formula 88]

(c-3)

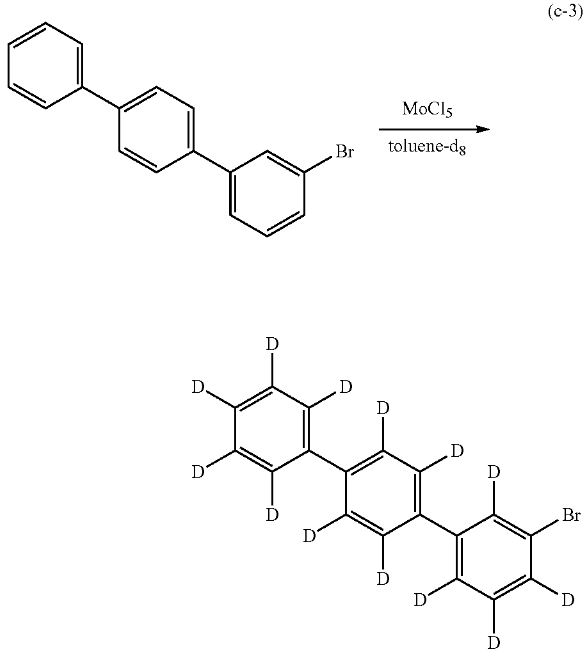

Step 3-4; Synthesis of 4,4,5,5-tetramethyl-2-(1,1':4',1"-terphenyl-2,4,5,6,2,3',5',6',2",3",4",5",6"-$d_{13}$)-3-yl-1,3,2-dioxaborolane Into a 200 mL three-neck flask were put 4.3 g (13 mmol) of 3-bromo-1,1':4',1"-terphenyl-2,4,5,6,2',3',5',6',2",3",4",5",6"-$d_{13}$ obtained in Step 3-3, 4.1 g (16 mmol) of bis(pinacolato)diboron, 3.9 g (40 mmol) of potassium acetate, and 67 mL of N,N-dimethylformamide (DMF). The mixture in the flask was stirred under reduced pressure and degassed. After that, the mixture was heated at 60° C. under a nitrogen stream, 0.55 g (0.67 mmol) of [1,1'-bis(diphenylphosphino)ferrocene]dichloropalladium(II) dichloromethane adduct (abbreviation: $Pd(dppf)_2Cl_2 \cdot CH_2Cl_2$) was added thereto, and then the temperature was raised to 100° C. and the mixture was stirred for 6 hours. After the stirring, the obtained mixture was subjected to extraction with toluene and the obtained organic layer was washed with saturated saline and dried with magnesium sulfate. This mixture was separated by gravity filtration, and the filtrate was concentrated to give a brown solid. The obtained solid was purified by silica gel column chromatography (the ratio was changed from toluene:hexane=1:1 to 100% toluene to perform a gradient), so that 3.4 g of the target light-blue oily substance of 4,4,5,5-tetramethyl-2-(1,1':4',1"-terphenyl-2,4,5,6,2',3',5',6,2",3",4",5",6"-$d_{13}$)-3-yl-1,3,2-dioxaborolane was obtained in a yield of 69%. The synthesis scheme of Step 3-4 is shown in (c-4) below.

[Chemical Formula 89]

(c-4)

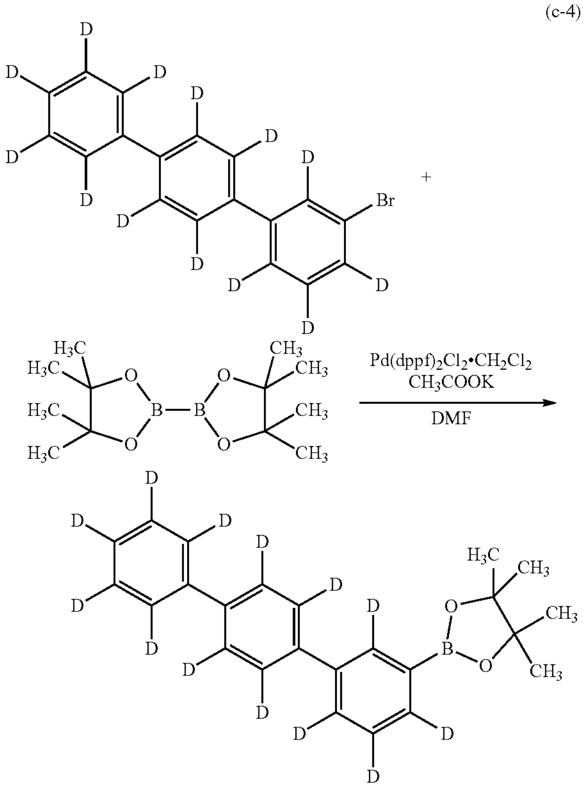

Figure 34A:
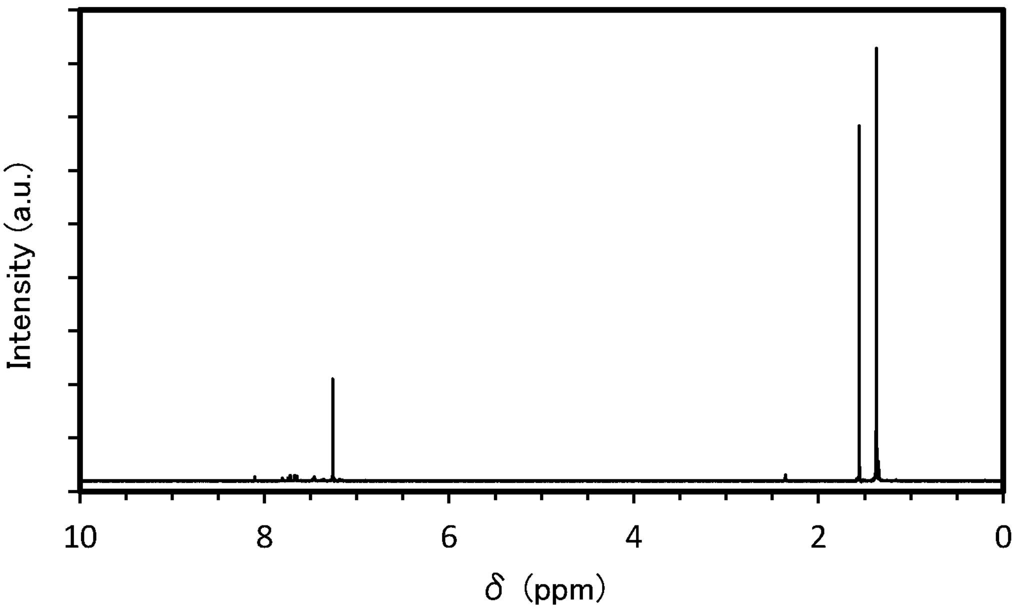
FIGS. 34A and 34B show $^1$H NMR spectra of the organic compound obtained in Example 3.

Analysis results by nuclear magnetic resonance ($^1$H-NMR) spectroscopy of 4,4,5,5-tetramethyl-2-(1,1':4',1"-terphenyl-2,4,5,6,2',3',5',6',2",3",4",5",6"-$d_{13}$)-3-yl-1,3,2-dioxaborolane obtained in Step 3-4 are shown below. In addition, FIGS. 34A and 34B show $^1$H-NMR charts.

$^1$H-NMR. δ ($CDCl_3$, 300 MHz): 1.37 (s, 12H).

Figure 34B:
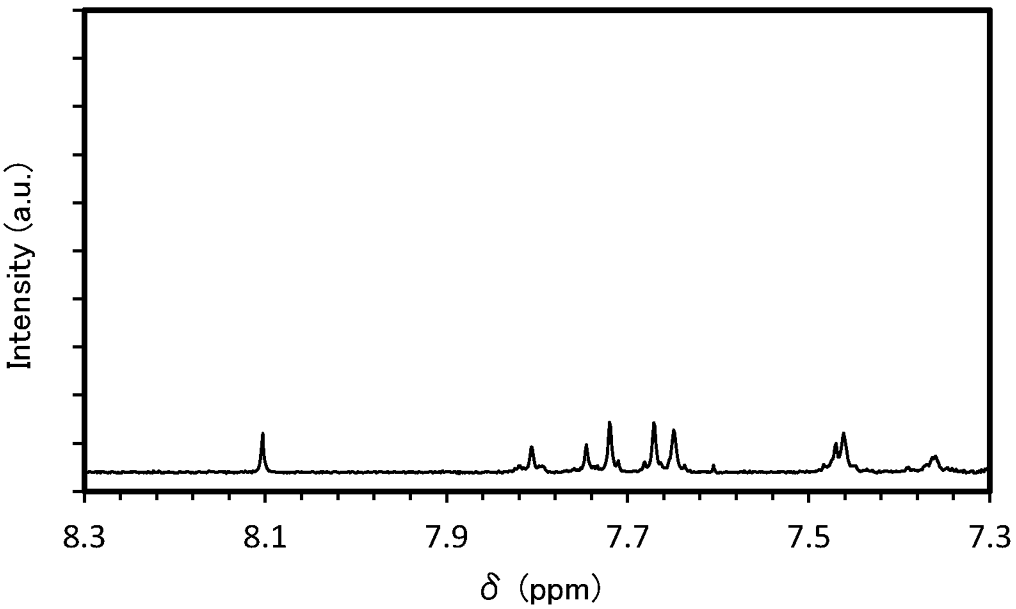
Figure 35A:
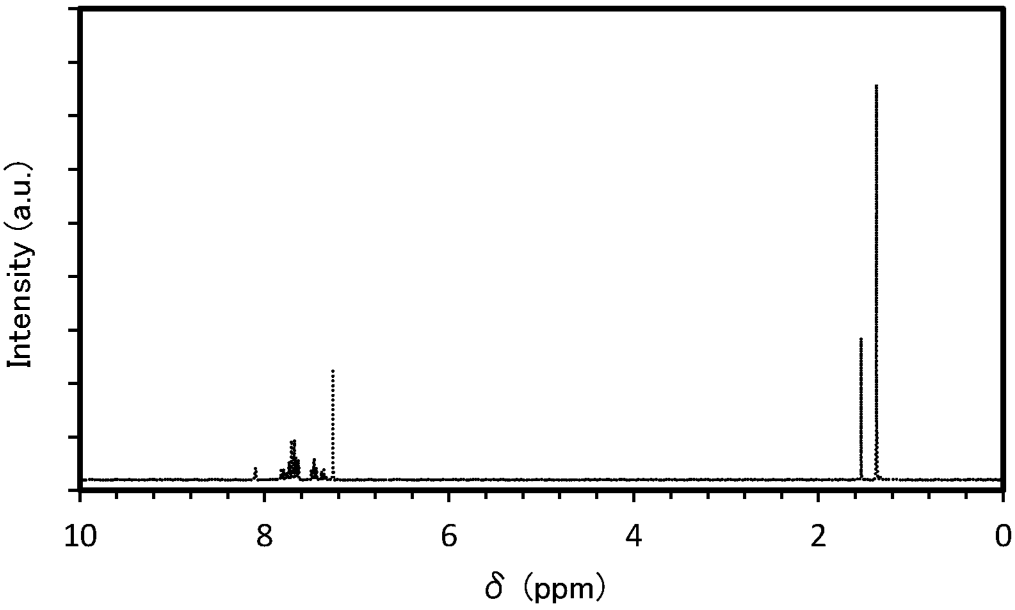
FIG. 35A shows a $^1$H NMR spectrum of reference 3-2.
Figure 35B:
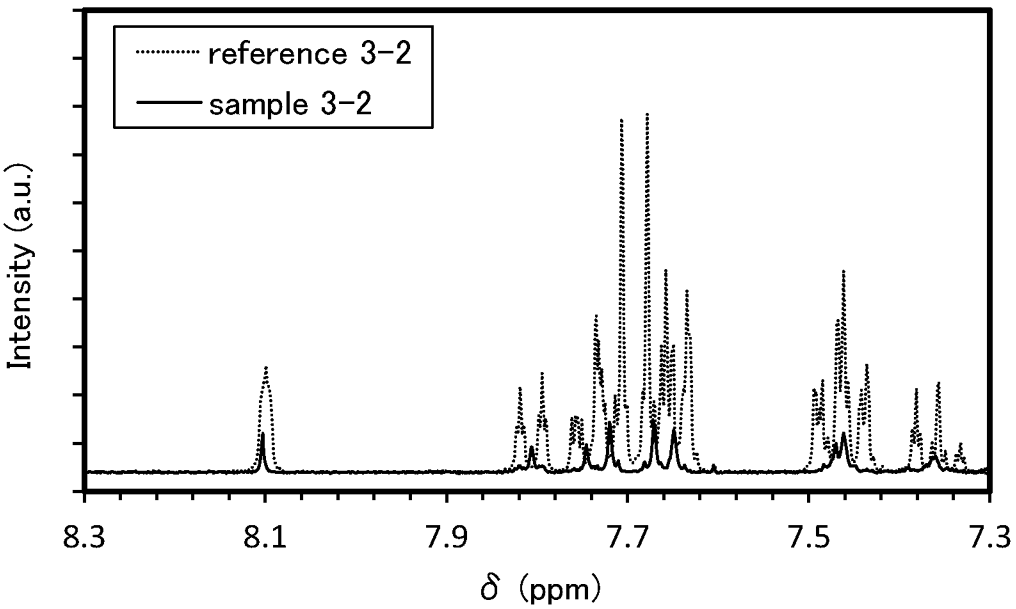
FIG. 35B shows $^1$H NMR spectra of the organic compound obtained in Example 3 and reference 3-2.

In FIG. 34B, signals that appear around δ=7.30 ppm to 8.30 ppm are assumed to be protium that was not deuterated and remained in Synthesis Scheme (c-1). The deuteration rate of 4,4,5,5-tetramethyl-2-(1,1':4',1"-terphenyl)-3-yl-1,3,2-dioxaborolane was estimated. FIG. 35A shows the $^1$H-NMR chart of 4,4,5,5-tetramethyl-2-(1,1':4',1"-terphenyl)-3-yl-1,3,2-dioxaborolane, and FIG. 35B is an enlarged view of δ=7.30 ppm to 8.30 ppm, which compares 4,4,5,5-tetramethyl-2-(1,1':4',1"-terphenyl-2,4,5,6,2',3',5',6,2",3",4",5",6"-$d_{13}$)-3-yl-1,3,2-dioxaborolane (sample 3-2) and 4,4,5,5-tetramethyl-2-(1,1':4',1"-terphenyl)-3-yl-1,3,2-dioxaborolane (reference 3-2). The deuteration rate of 4,4,5,5-tetramethyl-2-(1,1':4',1"-terphenyl-2,4,5,6,2',3',5',6',2",3",4",5",6"-$d_{13}$)-3-yl-1,3,2-dioxaborolane was estimated to be approximately 83%.

Step 3-5; Synthesis of 8-chloro-4[3-(dibenzothiophen-4-yl-1,2,3,6,7,8,9-$d_7$)phenyl-2,4,6-$d_3$]-[1]benzofuro[3,2-d]pyrimidine Into a 200 mL three-neck flask were put 1.6 g (4.1 mmol) of 2-[3-(dibenzo[b,d]thiophen-4-yl-1,2,3,6,7,8,9-d)phenyl-2,4,6-$d_3$]-4,4,5,5-tetramethyl-1,3,2-dioxaborolane obtained in Step 3-2, 0.81 g (3.4 mmol) of 4,8-dichloro[1]benzofuro[3,2-d]pyrimidine, 0.95 g (6.9 mmol) of potassium carbonate, 14 mL of toluene, 3.5 mL of ethanol, and 3.5 mL of water. The mixture in the flask was stirred under reduced pressure and degassed. After that, the mixture was heated at 60° C. under a nitrogen stream, 0.80 g (0.70 mmol) of tetrakis(triphenylphosphine)palladium(0) (abbreviation: (Pd $(PPh_3)_4$) was added thereto; then, the temperature was raised to 90° C. and the mixture was stirred for 19 hours. After the stirring, this mixture was suction-filtered, and the obtained residue was washed with water and ethanol. The obtained residue was dissolved in toluene by heating, followed by filtration through a filter aid in which Celite, alumina, and Celite were stacked in this order. The filtrate was concentrated and then the obtained solid was recrystallized with toluene, so that 1.4 g of the target gray solid of 8-chloro-4[3-(dibenzothiophen-4-yl-1,2,3,6,7,8,9-$d_7$)phenyl-2,4,6-$d_3$]-[1]benzofuro[3,2-d]pyrimidine in a yield of 89%. The synthesis scheme of Step 3-5 is shown in (c-5) below.

Note that 8-chloro-4[3-(dibenzothiophen-4-yl-1,2,3,6,7,8,9-$d_4$)phenyl-2,4,6-$d_3$]-[1]benzofuro[3,2-d]pyrimidine is one of the specific examples of Compound 6 in <Synthesis method of organic compound> described in Embodiment 1.

[Chemical Formula 90]

(c-5)

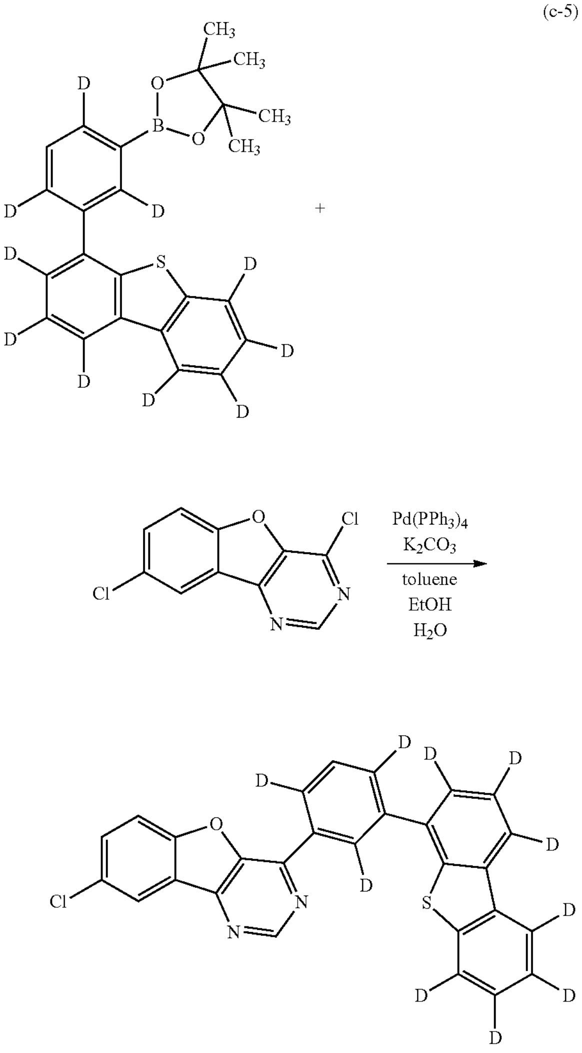

Figure 36A:
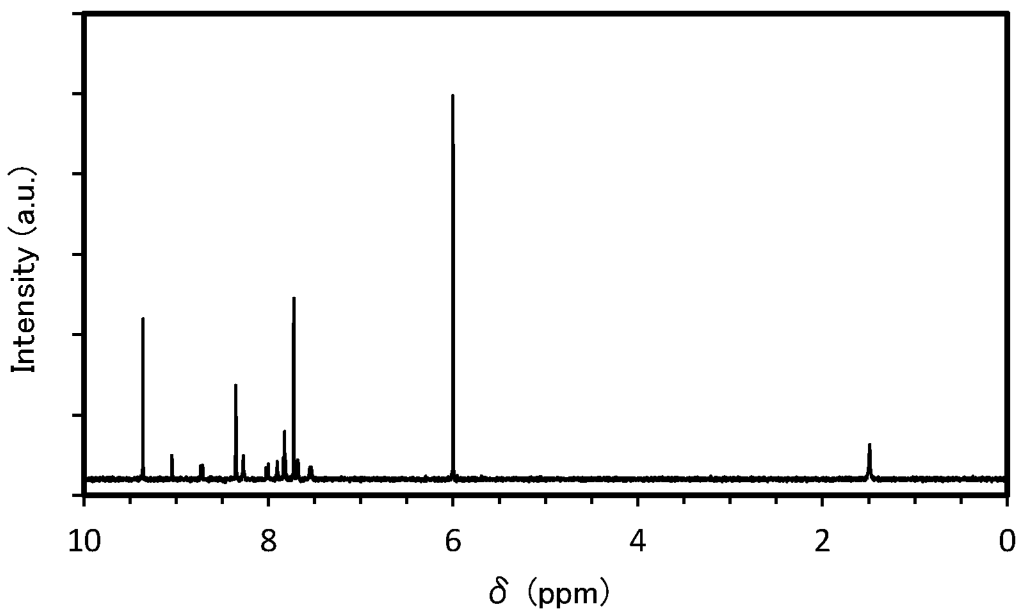
FIGS. 36A and 36B show $^1$H NMR spectra of the organic compound obtained in Example 3.

Analysis results by nuclear magnetic resonance ($^1$H-NMR) spectroscopy of 8-chloro-4[3-(dibenzothiophen-4-yl-1,2,3,6,7,8,9-$d_7$)phenyl-2,4,6-$d_3$]-[1]benzofuro[3,2-d]pyrimidine obtained in Step 3-5 are shown below. In addition, FIGS. 36A and 36B show $^1$H-NMR charts.

$^1$H-NMR. δ (C2D2Cl4, 300 MHz): 7.73 (d, J=1.5 Hz, 2H), 7.83 (t, J=3.8 Hz, 1H), 8.35 (t, J=1.5 Hz, 1H), 9.36 (s, 1H).

Figure 36B:
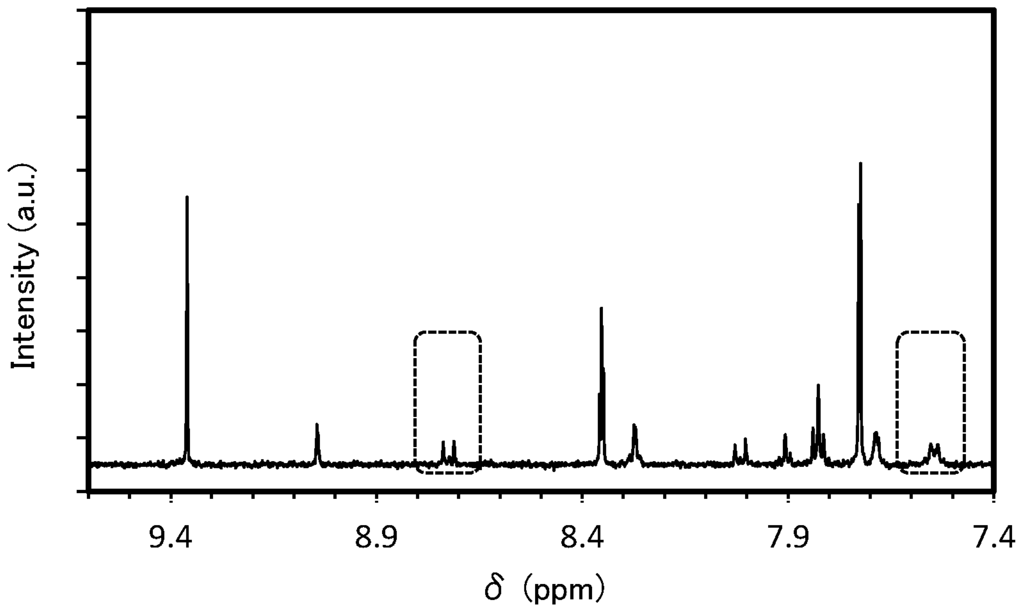

In FIG. 36B, signals that appear around δ=7.5 ppm to 7.6 ppm and δ=8.6 ppm to 8.8 ppm (regions surrounded with dashed lines) are assumed to be peaks derived from protium that were not deuterated and remained in Synthesis Scheme (c-1) above.

Figure 37A:
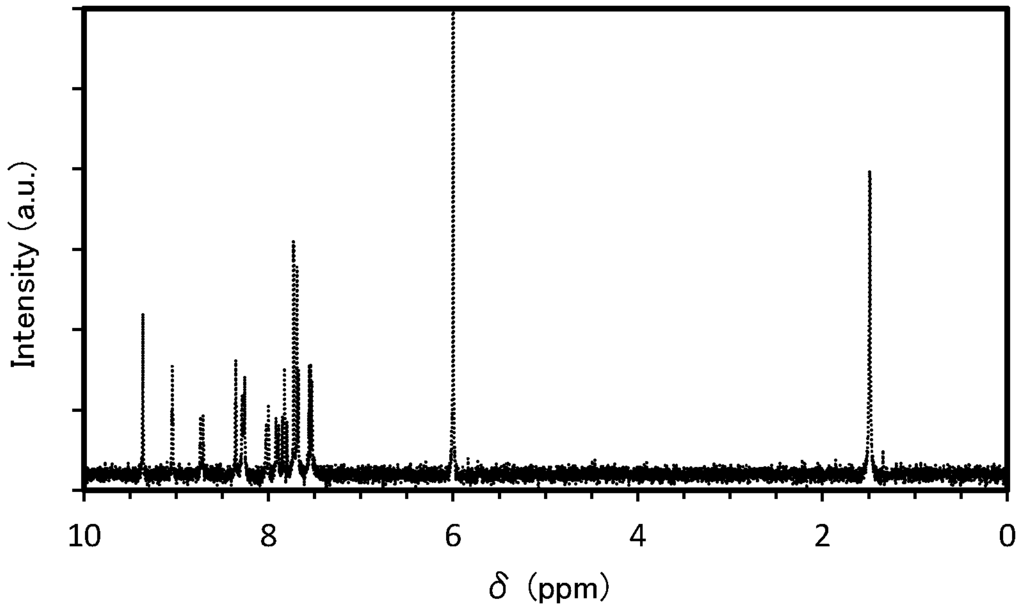
FIG. 37A shows a $^1$H NMR spectrum of reference 3-3.
Figure 37B:
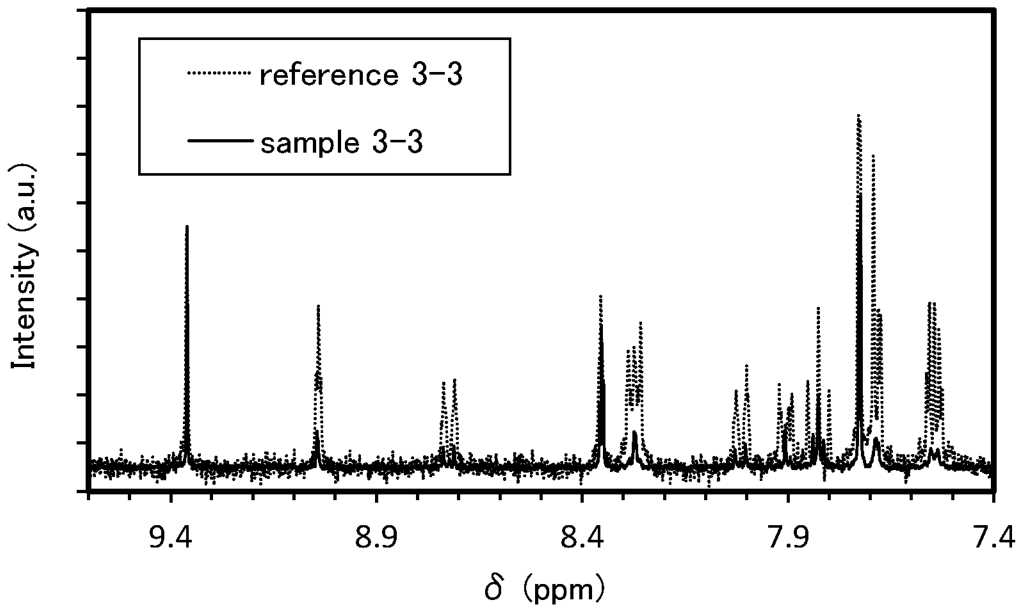
FIG. 37B shows $^1$H NMR spectra of the organic compound obtained in Example 3 and reference 3-3.

Here, the deuteration rate was estimated from $^1$H-NMR. FIG. 37A shows the $^1$H-NMR chart of 8-chloro-4[3-(dibenzothiophen-4-yl)phenyl]-[1]benzofuro[3,2-d]pyrimidine, and FIG. 37B is an enlarged view of δ=7.40 ppm to 9.60 ppm, which compares 8-chloro-4[3-(dibenzothiophen-4-yl-1,2,3,6,7,8,9-$d_7$)phenyl-2,4,6-$d_3$]-[1]benzofuro[3,2-d]pyrimidine (sample 3-3) and 8-chloro-4[3-(dibenzothiophen-4-yl)phenyl]-[1]benzofuro[3,2-d]pyrimidine (reference 3-3). Here, in sample 3-3 and reference 3-3, the peak appearing in δ=9.36 ppm is a peak derived from [1]benzofuro[3,2-d]pyrimidine. The deuteration rate of sample 3-3 was calculated using the peak as the reference (100%). As a result, the deuteration rate of 8-chloro-4[3-(dibenzothiophen-4-yl-1,2,3,6,7,8,9-$d_7$)phenyl-2,4,6-$d_3$]-[1]benzofuro[3,2-d]pyrimidine was estimated to be approximately 69%.

Step 3-6; Synthesis of 8-(1,1':4',1"-terphenyl-3-yl-2,4,5,6,2',3',5',6',2",3",4",5",6"-$d_{13}$)-4-[3-(dibenzothiophen-4-yl-1,2,3,6,7,8,9-$d_7$)phenyl-2,4,6-$d_3$]-[1]benzofuro[3,2-d]pyrimidine (abbreviation: 8mpTP-4mDBtPBfpm-$d_{23}$)

Into a 200 mL three-neck flask were put 1.3 g (2.7 mmol) of 8-chloro-4[3-(dibenzothiophen-4-yl-1,2,3,6,7,8,9-$d_7$)phenyl-2,4,6-$d_3$]-[1]benzofuro[3,2-d]pyrimidine obtained in Step 3-5, 1.1 g (3.0 mmol) of 4,4,5,5-tetramethyl-2-(1,1':4',1"-terphenyl-2,4,5,6,2',3',5',6,2",3",4",5",6"-$d_{13}$)-3-yl-1,3,2-dioxaborolane obtained in Step 3-4, 1.7 g (8.1 mmol) of tripotassium phosphate, 0.67 g (9.0 mmol) of tert-butylalcohol (abbreviation: tBuOH), and 27 mL of diethylene glycol dimethyl ether (abbreviation: diglyme), and the mixture in the flask was stirred under reduced pressure and degassed. After that, the mixture was heated at 60° C. under a nitrogen stream, 0.060 g (0.27 mmol) of palladium(II) acetate (abbreviation: $Pd(OAc)_2$) and 0.20 g (0.56 mmol) of di(1-adamantyl)-N-butylphosphine (abbreviation: cataCXiumA) were added to the flask, and then the mixture was stirred at 130° C. for 15 hours. After the stirring, water was added to the mixture, suction filtration was performed, and the residue was washed with water and ethanol. The obtained residue was dissolved in toluene by heating, and the obtained solution was filtered. The filtrate was filtered through a filter medium in which Celite, alumina, and Celite were stacked in this order. The filtrate was concentrated and purified by silica gel column chromatography (the ratio was changed from toluene 100% to toluene:ethyl acetate=30:1 to perform a gradient). The resulting solid was recrystallized with toluene to give 1.2 g of a white solid in a yield of 68%. By a train sublimation method, 1.2 g of the obtained white solid was purified by sublimation. The sublimation purification was conducted under the conditions where the pressure was 2.9 Pa, the flow rate of an argon gas was 15 mL/min, and the solid was heated at 350° C. for 18 hours. After the sublimation purification by sublimation, 1.0 g of a target pale yellow solid was obtained at a collection rate of 83%. The synthesis scheme of Step 3-6 is shown in (c-6) below.

[Chemical Formula 91]

(c-6)

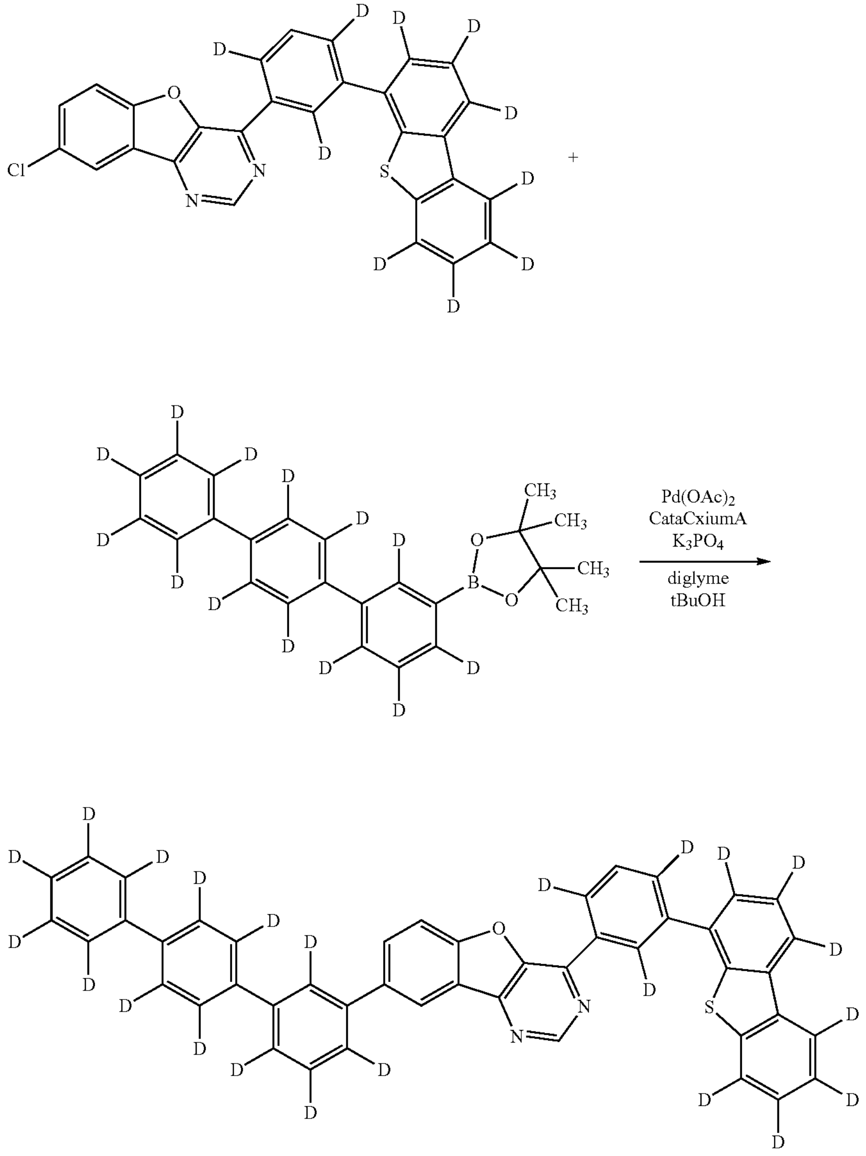

(128)

Figure 38A:
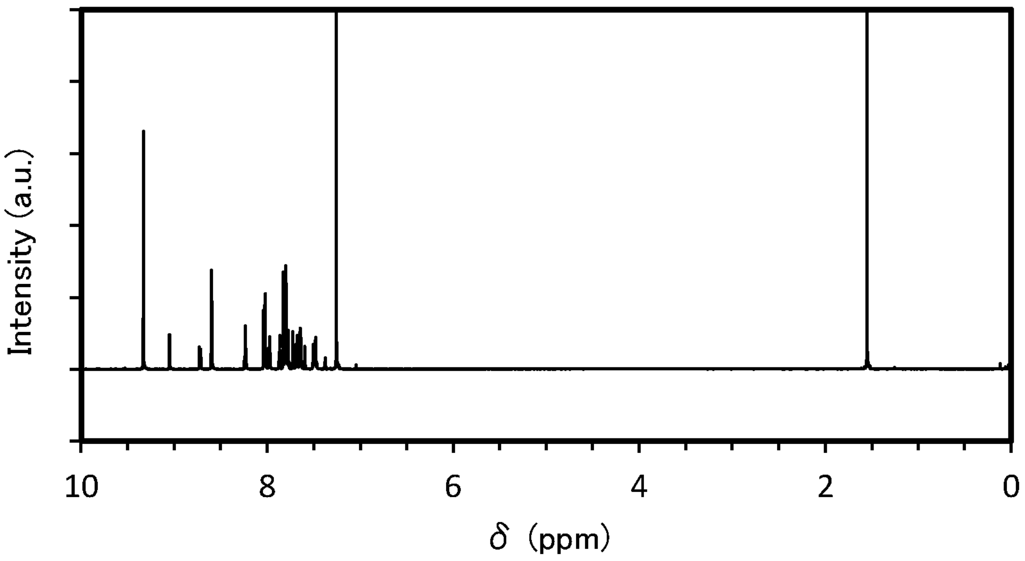
FIGS. 38A and 38B show $^1$H NMR spectra of 8mpTP-4mDBtPBfpm-$d_{23}$.

Measurement results obtained by nuclear magnetic resonance ($^1$H-NMR) spectroscopy of the pale yellow solid obtained in the above step are shown below. FIG. 38A shows the $^1$H-NMR chart. The measurement results reveal that 8mpTP-4mDBtPBfpm-$d_{23}$, which is represented by the structural formula (128) and is one embodiment of the present invention, was obtained in Synthesis example 3.

$^1$H-NMR. δ ($CDCl_3$, 500 MHz): 7.77-7.68 (m, 2H), 8.03 (dd, J1=8.59 Hz, J2=2.29 Hz, 1H), 8.60 (sd, J=1.72 Hz, 1H), 9.33 (s, 1H).

Figure 38B:
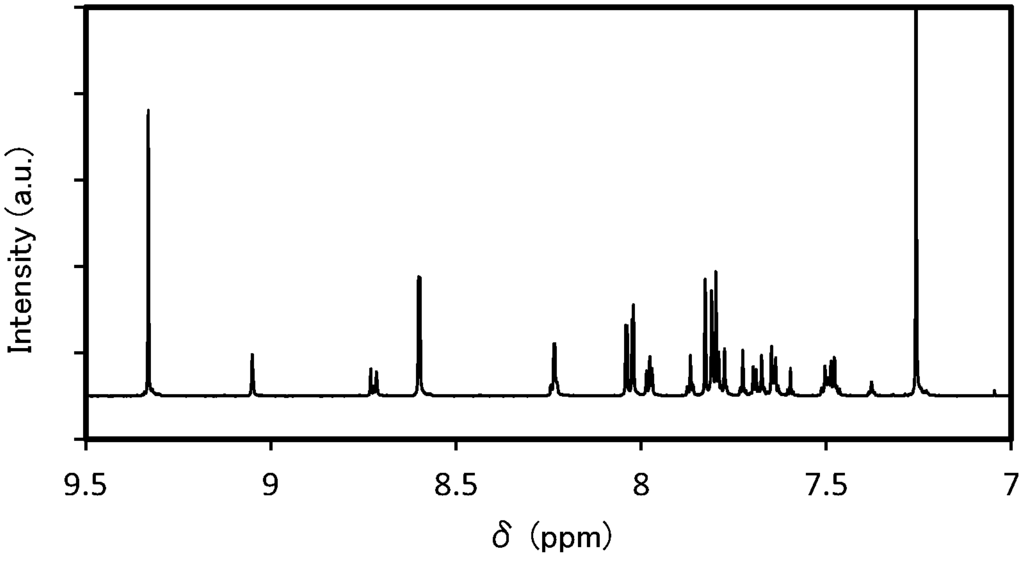
Figure 39A:
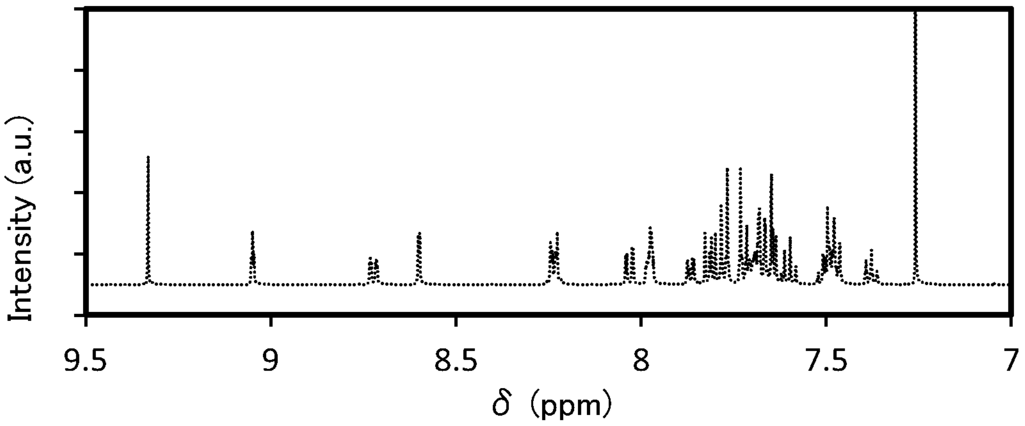
FIG. 39A shows a $^1$H NMR spectrum of 8mpTP-4mDBtPBfpm.
Figure 39B:
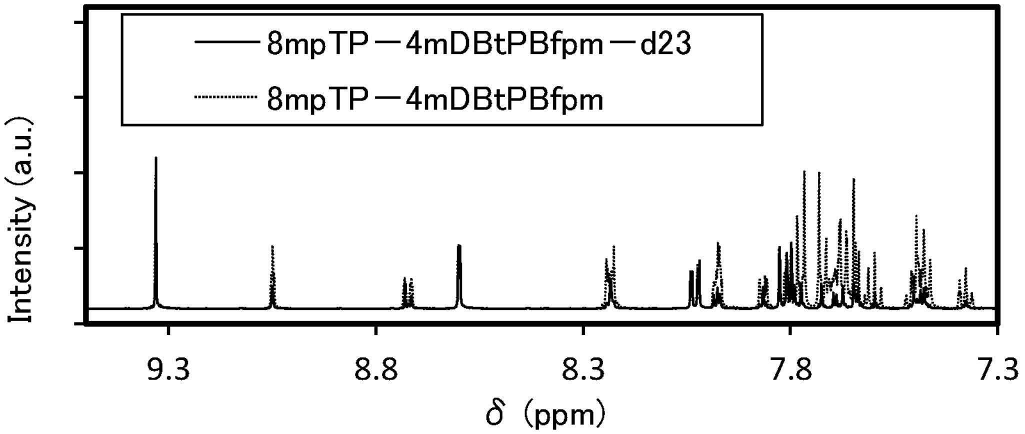
FIGS. 39B and 39C show $^1$H NMR spectra of 8mpTP-4mDBtPBfpm-$d_{23}$ and 8mpTP-4mDBtPBfpm.
Figure 39C:
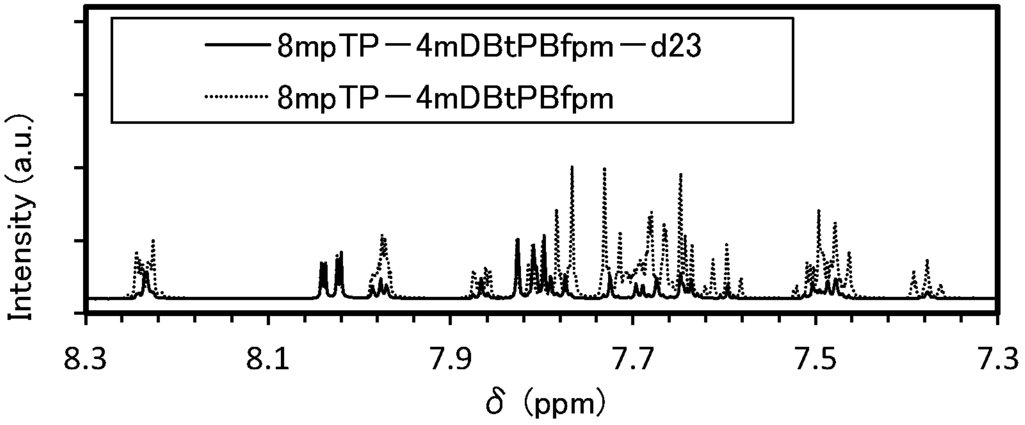

In FIG. 38B, fine signals are observed around δ=7.46 ppm to 7.51 ppm, 9.05 ppm, or the like. The deuteration rate of 8mpTP-4mDBtPBfpm-$d_{23}$ was estimated. FIG. 39A shows the $^1$H-NMR chart of 8mpTP-4mDBtPBfpm that is a non-deuterated substance of 8mpTP-4mDBtPBfpm-$d_{23}$. FIG. 39B is a diagram of δ=7.30 ppm to 9.50 ppm, which compares 8mpTP-4mDBtPBfpm-$d_{23}$ and 8mpTP-4mDBtPBfpm that are normalized with a signal in δ=9.33 ppm. FIG. 39C is an enlarged view of δ=7.30 ppm to 8.30 ppm in FIG. 39B. In FIG. 39C, peaks having low intensity around δ=7.46 ppm to 7.51 ppm or the like are assumed to be signals derived from protium that was not deuterated and remained in Synthesis Schemes (c-1) and (c-3). The deuteration rate of 8mpTP-4mDBtPBfpm-$d_{23}$ was estimated to be approximately 78%.

<Characteristics of 8mpTP-4mDBtPBfpm-$d_{23}$>

Figure 40:
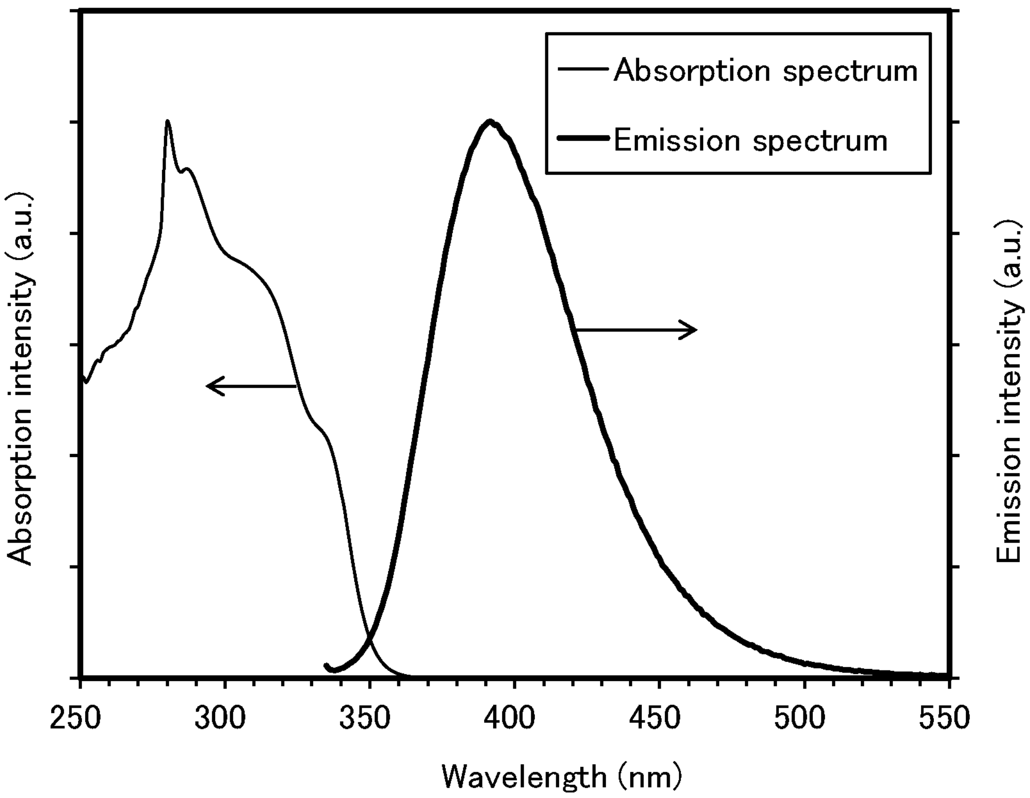
FIG. 40 shows an absorption spectrum and an emission spectrum of 8mpTP-4mDBtPBfpm-$d_{23}$ in a toluene solution.

Then, the ultraviolet-visible absorption spectrum (hereinafter, simply referred to as "absorption spectrum") and emission spectrum of a toluene solution of 8mpTP-4mDBtPBfpm-$d_{23}$ were measured. The absorption spectrum was measured at room temperature with an ultraviolet-visible light spectrophotometer (V-770DS, produced by JASCO Corporation) in a state where the toluene solution was put in a quartz cell. The emission spectrum was measured at room temperature with a fluorescence spectrophotometer (FP-8600DS, produced by JASCO Corporation) in a state where the toluene solution was put in a quartz cell. FIG. 40 shows obtained measurement results of the absorption spectrum and the emission spectrum. The horizontal axis represents the wavelength and the vertical axes represent the absorption intensity and the emission intensity. The absorption spectrum shown in FIG. 40 is a result obtained by subtraction of an absorption spectrum of only toluene in a quartz cell from the measured absorption spectrum of the toluene solution in the quartz cell.

As shown in FIG. 40, in the toluene solution of 8mpTP-4mDBtPBfpm-$d_{23}$, absorption peaks were observed around 305 nm and 332 nm, and an emission peak was observed around 392 nm (excitation wavelength: 300 nm).

Figure 41:
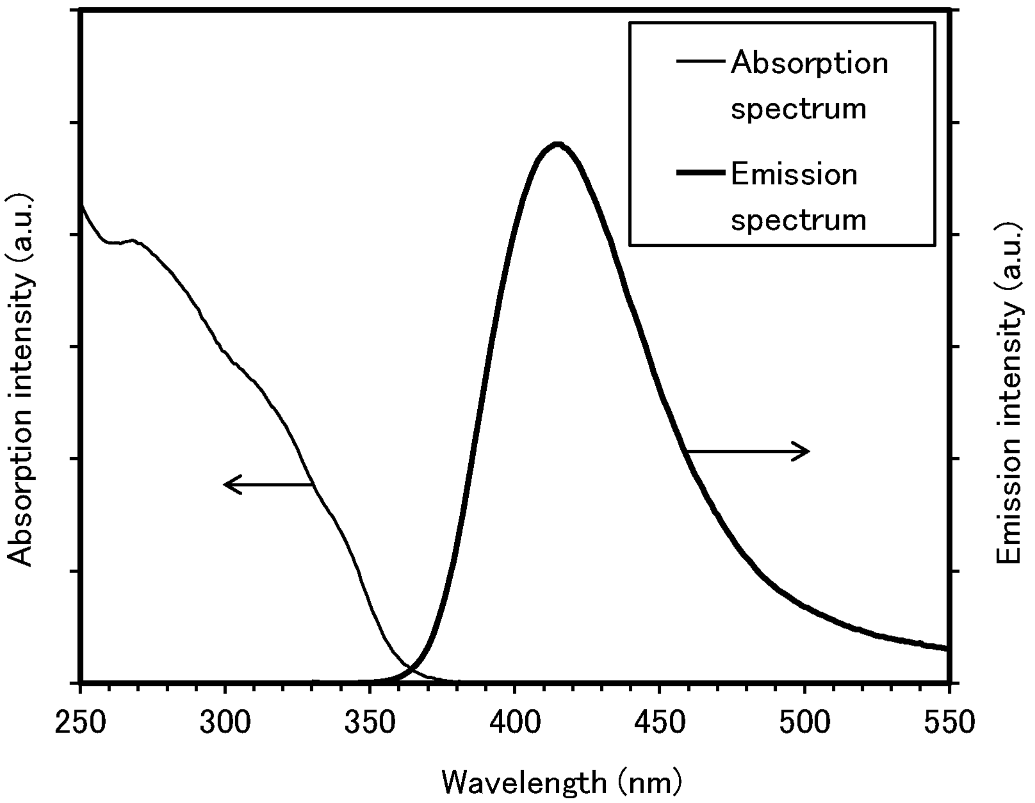
FIG. 41 shows an absorption spectrum and an emission spectrum of a thin film of 8mpTP-4mDBtPBfpm-$d_{23}$.

Next, the absorption spectrum and emission spectrum of a solid thin film of 8mpTP-4mDBtPBfpm-$d_{23}$ were measured. The solid thin film was fabricated over a quartz substrate by a vacuum evaporation method. The absorption spectrum of the thin film was calculated using an absorbance ($-\log_{10}$ [% T/(100−% R)]) obtained from the transmittance and reflectance of the thin film including the substrate. Note that % T represents transmittance and % R represents reflectance. The absorption spectrum was measured with a UV-visible spectrophotometer (U-4100 manufactured by Hitachi High-Technologies Corporation). The emission spectrum was measured using a spectrofluorometer (FP-8600DS manufactured by JASCO Corporation). FIG. 41 shows the measurement results of the obtained absorption and emission spectra of the solid thin film. The horizontal axis represents the wavelength and the vertical axes represent the absorption intensity and the emission intensity.

From the results in FIG. 41, in the solid thin film of 8mpTP-4mDBtPBfpm-$d_{23}$, absorption peaks were observed around 273 nm, 317 nm, and 338 nm, and an emission peak was observed around 414 nm (excitation wavelength: 320 nm).

The ionization potential value of a thin film of 8mpTP-4mDBtPBfpm-$d_{23}$ was measured in the air with a photoelectron spectrometer (AC-3, produced by Riken Keiki Co., Ltd.). The obtained ionization potential value was converted into a negative value, so that the HOMO level of 8mpTP-4mDBtPBfpm-$d_{23}$ was −6.13 eV. From the data of the absorption spectrum of the thin film, the absorption edge of 8mpTP-4mDBtPBfpm-$d_{23}$, which was obtained from Tauc plot with an assumption of direct transition, was 3.51 eV. Thus, the optical energy gap of 8mpTP-4mDBtPBfpm-$d_{23}$ in the solid state was estimated at 3.51 eV; from the values of the HOMO level obtained above and this energy gap, the LUMO level of 8mpTP-4mDBtPBfpm-$d_{23}$ can be estimated at −2.62 eV. This reveals that 8mpTP-4mDBtPBfpm-$d_{23}$ in the solid state has an energy gap as wide as 3.51 eV.

The glass transition temperature (Tg) of 8mpTP-4mDBtPBfpm-$d_{23}$ was measured. Note that Tg was measured with a differential scanning calorimeter (DSC8500 produced by PerkinElmer Japan Co., Ltd.) in a state where a powder was put on an aluminum cell. The result showed that the Tg of 8mpTP-4mDBtPBfpm-$d_{23}$ was 121° C.

Furthermore, the electrochemical characteristics (oxidation reaction characteristics and reduction reaction characteristics) of 8mpTP-4mDBtPBfpm-$d_{23}$ were measured by cyclic voltammetry (CV). An electrochemical analyzer (ALS model 600B, manufactured by BAS Inc.) was used for the measurement. The solution for the measurement was prepared by using dehydrated N,N-dimethylformamide (DMF) (produced by Aldrich Corp., 99.8%, catalog number: 22705-6) as a solvent, dissolving a supporting electrolyte, tetra-n-butylammonium perchlorate ($n\text{-}Bu_4NClO_4$) (produced by Tokyo Chemical Industry Co., Ltd., catalog number: T0836), at a concentration of 100 mmol/L, and then dissolving the object of measurement at a concentration of 2 mmol/L.

A platinum electrode (PTE platinum electrode, manufactured by BAS Inc.) was used as a working electrode, another platinum electrode (Pt counter electrode (5 cm), manufactured by BAS Inc.) was used as an auxiliary electrode, and an $Ag/Ag^+$ electrode (RE7 reference electrode for nonaqueous solvent, manufactured by BAS Inc.) was used as a reference electrode. Note that the measurement was performed at room temperature (20° C. to 25° C.).

In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the oxidation potential Ea[V] of 8mpTP-4mDBtPBfpm-$d_{23}$ was not observed. Therefore, the HOMO level is estimated to be lower than −6.2 eV. In contrast, the LUMO level was found to be −3.01 eV from the measurement result of the reduction potential Ec [V]. In addition, the results of repetitive measurement of the oxidation-reduction wave showed that when the waveform of the first cycle was compared with that of the hundredth cycle, 83% of the peak intensity were maintained in the Ec measurement, which confirmed that 8mpTP-4mDBtPBfpm-$d_{23}$ had high resistance to reduction.

Example 4

In this example, light-emitting devices (light-emitting devices 4A to 4C) of one embodiment of the present invention described in the above embodiments and a comparative light-emitting device 4 are fabricated and the measurement results of the characteristics are described.

Structural formulae of organic compounds used for the comparative light-emitting device 4 and the light-emitting devices 4A to 4C are shown below.

[Chemical Formula 92]
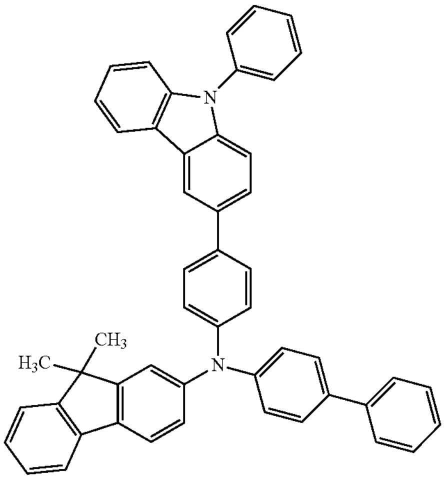
PCBBif
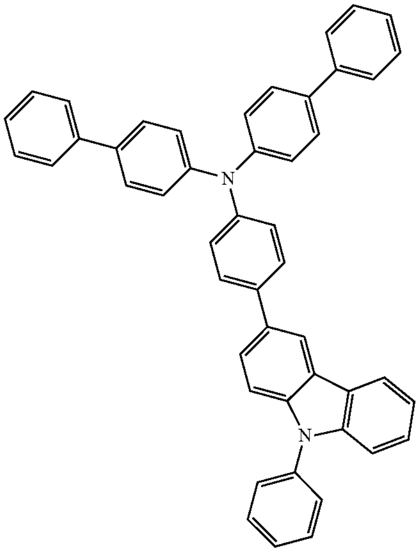
PCBBi1BP
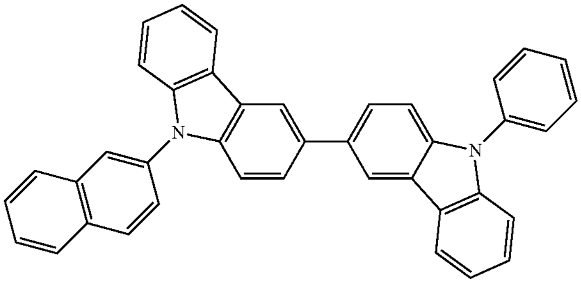
β NCCP
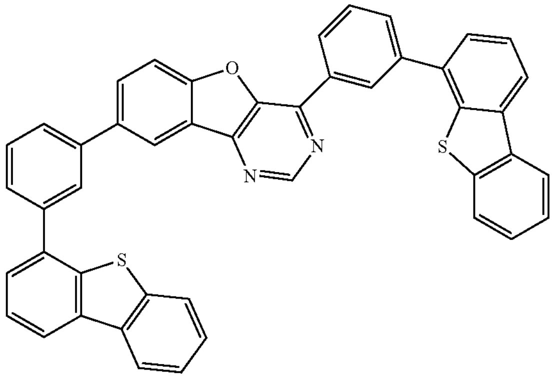
4,8mDBtP2Bfpm
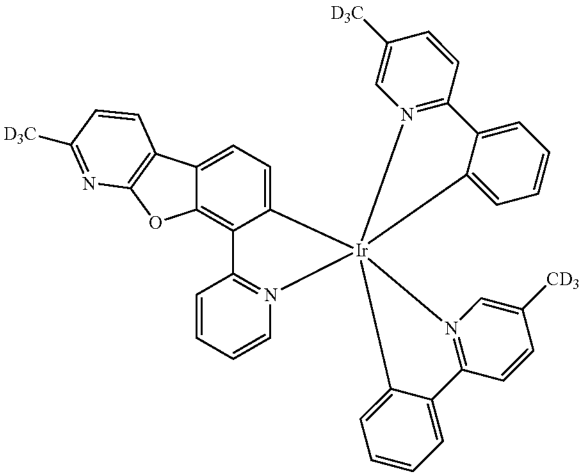
$Ir(5mppy\text{-}d3)_2(mbfpypy\text{-}d3)$ -continued

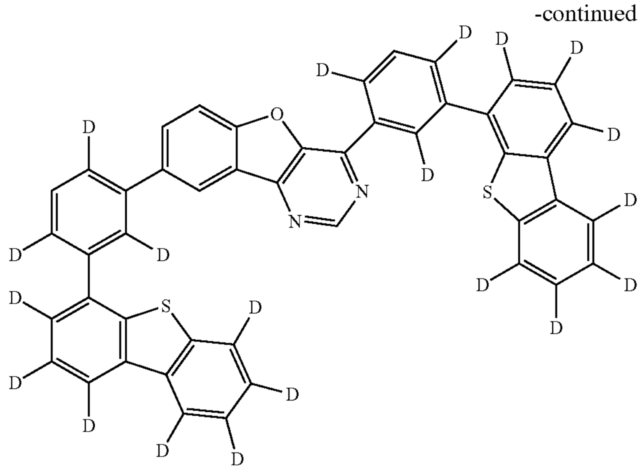

4,8mDBtP2Bfpm-d20

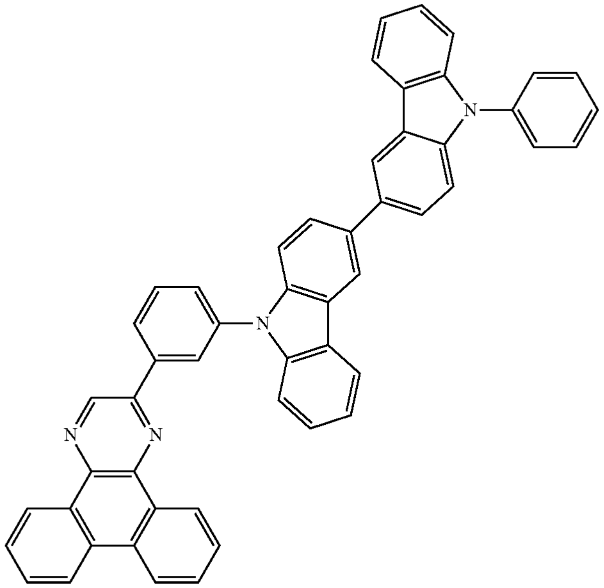

2mPCCzPDBq

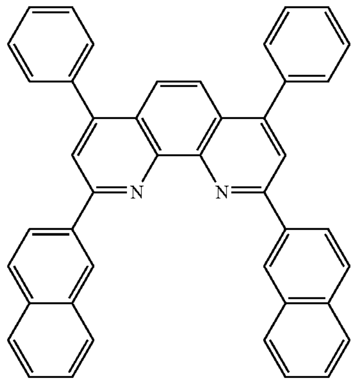

NBphen

<Method for Fabricating Comparative Light-Emitting Device 4>

Figure 42:
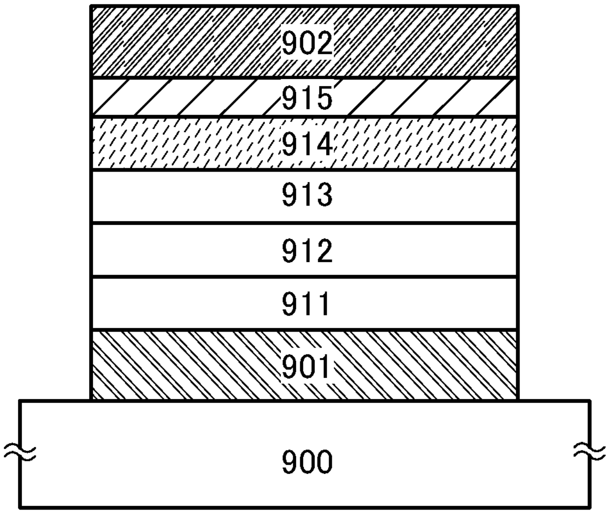
FIG. 42 illustrates a structure of a light-emitting device of an example.

In the comparative light-emitting device 4, as illustrated in FIG. 42, a hole-injection layer 911, a hole-transport layer 912, a light-emitting layer 913, an electron-transport layer 914, and an electron-injection layer 915 are stacked in this order over a first electrode 901 formed over a glass substrate 900, and a second electrode 902 is stacked over the electron-injection layer 915.

First, indium oxide-tin oxide containing silicon or silicon oxide (abbreviation: ITSO) was deposited by a sputtering method over the glass substrate 900, whereby the first electrode 901 was formed. The thickness of the first electrode 901 was 70 nm and the electrode area was 4 $mm^2$ (2 mm×2 mm).

Next, in pretreatment for forming the light-emitting device over the substrate, a surface of the substrate was washed with water and baking was performed at 200° C. for 1 hour. Then, the substrate was transferred into a vacuum evaporation apparatus where the pressure was reduced to approximately 10-4 Pa, and vacuum baking was performed at 180° C. for 60 minutes in a heating chamber of the vacuum evaporation apparatus. After that, natural cooling was performed to 30° C. or lower.

Then, the substrate provided with the first electrode 901 was fixed to a substrate holder provided in the vacuum evaporation apparatus such that the surface on which the first electrode 901 was formed faced downward. Over the first electrode 901, N-(1,1'-biphenyl-4-yl)-N-[4-(9-phenyl-9H-carbazol-3-yl)phenyl]-9,9-dimethyl-9H-fluoren-2-amine (abbreviation: PCBBiF) and a fluorine-containing electron acceptor material with a molecular weight of 672 (OCHD-003) were deposited by co-evaporation to a thickness of 10 nm such that the weight ratio of PCBBiF to OCHD-003 was 1:0.03 using a resistance-heating method, whereby the hole-injection layer 911 was formed.

Next, PCBBiF was deposited over the hole-injection layer 911 to a thickness of 40 nm, and then PCBBi1BP was deposited to a thickness of 10 nm, whereby the hole-transport layer 912 was formed.

Next, over the hole-transport layer 912, 4,8-bis[3-(dibenzothiophen-4-yl)phenyl]-[1]benzofuro[3,2-d]pyrimidine (abbreviation: 4,8mDBtP2Bfpm), 9-(2-naphthyl)-9'-phenyl-9H,9'H-3,3'-bicarbazole (abbreviation: PNCCP), and [2-$d_3$-methyl-8-(2-pyridinyl-κN)benzofuro[2,3-b]pyridine-κC]bis[2-(5-$d_3$-methyl-2-pyridinyl-$κN^2$)phenyl-κC]iridium(III) (abbreviation: Ir(5mppy-$d_3$)$_2$(mbfpypy-$d_3$)) were deposited by co-evaporation to a thickness of 40 nm such that the weight ratio of 4,8mDBtP2Bfpm to PNCCP and Ir(5mppy-$d_3$)$_2$(mbfpypy-$d_3$) was 0.5:0.5:0.1 using a resistance-heating method, whereby the light-emitting layer 913 was formed.

Next, over the light-emitting layer 913, 2-{3-[3-(N-phenyl-9H-carbazol-3-yl)-9H-carbazol-9-yl]phenyl}dibenzo[f,h]quinoxaline (abbreviation: 2mPCCzPDBq) was deposited by evaporation to a thickness of 10 nm, and then 2,9-di(2-naphthyl)-4,7-diphenyl-1,10-phenanthroline (abbreviation: NBPhen) was deposited by evaporation to a thickness of 25 nm to form the electron-transport layer 914.

Next, lithium fluoride (LiF) was deposited by evaporation to a thickness of 1 nm over the electron-transport layer 914, whereby the electron-injection layer 915 was formed.

Next, 200 nm of aluminum (abbreviation: Al) was deposited by evaporation over the electron-injection layer 915 using a resistance-heating method to form the second electrode 902, so that the comparative light-emitting device 4 was fabricated.

<Method for Fabricating Light-Emitting Device 4A>

Next, a method for fabricating the light-emitting device 4A is described.

The light-emitting device 4A is different from the comparative light-emitting device 4 in the structure of the light-emitting layer 913. That is, in the light-emitting device 4A, over the hole-transport layer 912, 4,8-bis[3-(dibenzothiophen-4-yl-1,2,3,6,7,8,9-$d_7$)phenyl-2,4,6-$d_3$]-[1]benzofuro[3,2-d]pyrimidine (abbreviation: 4,8mDBtP2Bfpm-$d_{20}$), 9-(2-naphthyl)-9'-phenyl-9H,9'H-3,3'-bicarbazole (abbreviation: PNCCP), and [2-$d_3$-methyl-8-(2-pyridinyl-κN)benzofuro[2,3-b]pyridine-κC]bis[2-(5-$d_3$-methyl-2-pyridinyl-$κN^2$)phenyl-κC]iridium(III) (abbreviation: Ir(5mppy-$d_3$)$_2$(mbfpypy-$d_3$)) were deposited by co-evaporation to a thickness of 40 nm such that the weight ratio of 4,8mDBtP2Bfpm-$d_{20}$ to PNCCP and Ir(5mppy-$d_3$)$_2$(mbfpypy-$d_3$) was 0.4:0.6:0.1 using a resistance-heating method, whereby the light-emitting layer 913 was formed.

Other components are the same as the comparative light-emitting device 4.

<Method for Fabricating Light-Emitting Device 4B>

Next, a method for fabricating the light-emitting device 4B is described.

The light-emitting device 4B is different from the comparative light-emitting device 4 in the structure of the light-emitting layer 913. That is, in the light-emitting device 4B, over the hole-transport layer 912, 4,8mDBtP2Bfpm-$d_{20}$, 9-(2-naphthyl)-9'-phenyl-9H,9'H-3,3'-bicarbazole (abbreviation: PNCCP), and [2-$d_3$-methyl-8-(2-pyridinyl-κN)benzofuro[2,3-b]pyridine-κC]bis[2-(5-$d_3$-methyl-2-pyridinyl-$κN^2$)phenyl-κC]iridium(III) (abbreviation: Ir(5mppy-$d_3$)$_2$(mbfpypy-$d_3$)) were deposited by co-evaporation to a thickness of 40 nm such that the weight ratio of 4,8mDBtP2Bfpm-$d_{20}$ to PNCCP and Ir(5mppy-$d_3$)$_2$(mbfpypy-$d_3$) was 0.5:0.5:0.1 using a resistance-heating method, whereby the light-emitting layer 913 was formed.

Other components are the same as the comparative light-emitting device 4.

<Method for Fabricating Light-Emitting Device 4C>

Next, a method for fabricating the light-emitting device 4C is described. The light-emitting device 4C is different from the comparative light-emitting device 4 in the structure of the light-emitting layer 913. That is, in the light-emitting device 4C, over the hole-transport layer 912, 4,8mDBtP2Bfpm-$d_{20}$, 9-(2-naphthyl)-9'-phenyl-9H,9'H-3,3'-bicarbazole (abbreviation: PNCCP), and [2-$d_3$-methyl-8-(2-pyridinyl-κN)benzofuro[2,3-b]pyridine-κC]bis[2-(5-$d_3$-methyl-2-pyridinyl-$κN^2$)phenyl-κC]iridium(III) (abbreviation: Ir(5mppy-$d_3$)$_2$(mbfpypy-$d_3$)) were deposited by co-evaporation to a thickness of 40 nm such that the weight ratio of 4,8mDBtP2Bfpm-$d_{20}$ to PNCCP and Ir(5mppy-$d_3$)$_2$(mbfpypy-$d_3$) was 0.6:0.4:0.1 using a resistance-heating method, whereby the light-emitting layer 913 was formed.

Other components are the same as the comparative light-emitting device 4.

The structures of the light-emitting devices 4A to 4C and the comparative light-emitting device 4 are listed in the following table. Note that X in the table refers to 4,8mDBtP2Bfpm or 4,8mDBtP2Bfpm-$d_{20}$.

TABLE 1

| | Thickness [nm] | Comparative light-emitting device 4 | Light-emitting device 4A | Light-emitting device 4B | Light-emitting device 4C |
|---|---|---|---|---|---|
| Second electrode | 200 | Al | | | |
| Electron-injection layer | 1 | LiF | | | |
| Electron-transport | 25 | NBPhen | | | |
| layer | 10 | 2mPCCzPDBq | | | |
| Light-emitting | 40 | X:βNCCP:Ir(5mppy-d3)$_2$(mbfpypy-d3) | | | |
| layer | | 4,8mDBtP2Bfpm | 4,8mDBtP2Bfpm-d20 | | |
| | | (0.5:0.5:0.1) | (0.4:0.6:0.1) | (0.5:0.5:0.1) | (0.6:0.4:0.1) |
| Hole-transport | 10 | PCBBi1BP | | | |
| layer | 40 | PCBBiF | | | |
| Hole-injection layer | 10 | PCBBiF:OCHD-003 (1:0.03) | | | |
| First electrode | 70 | ITSO | | | |

In the above manner, the light-emitting devices 4A to 4C and the comparative light-emitting device 4 were fabricated.

<Device Characteristics>

The above light-emitting devices 4A to 4C and the above comparative light-emitting device 4 were sealed using a glass substrate in a glove box containing a nitrogen atmosphere so as not to be exposed to the atmosphere (a sealing material was applied to surround the devices and UV treatment and heat treatment at 80° C. for 1 hour were performed at the time of sealing). Then, the initial characteristics of the light-emitting devices were measured.

Figure 43:
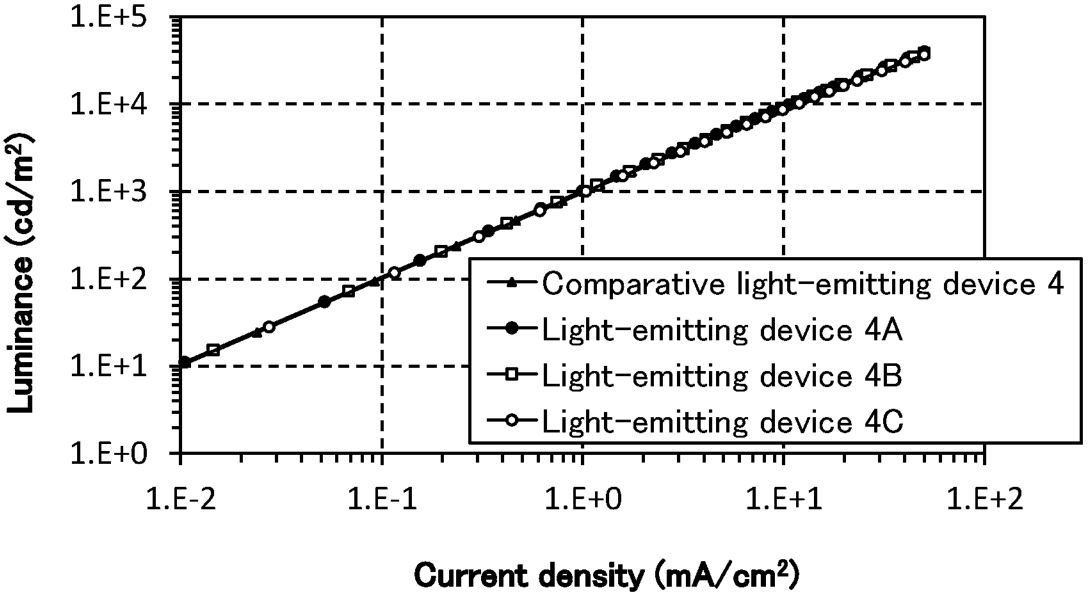
FIG. 43 shows luminance-current density characteristics of light-emitting devices of an example.
Figure 44:
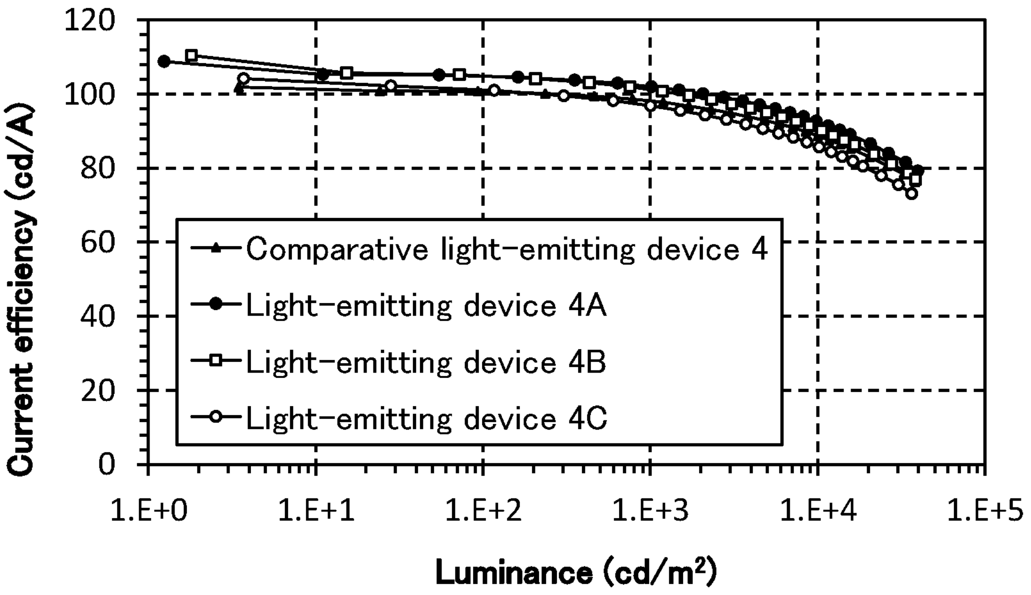
FIG. 44 shows current efficiency-luminance characteristics of light-emitting devices of an example.
Figure 45:
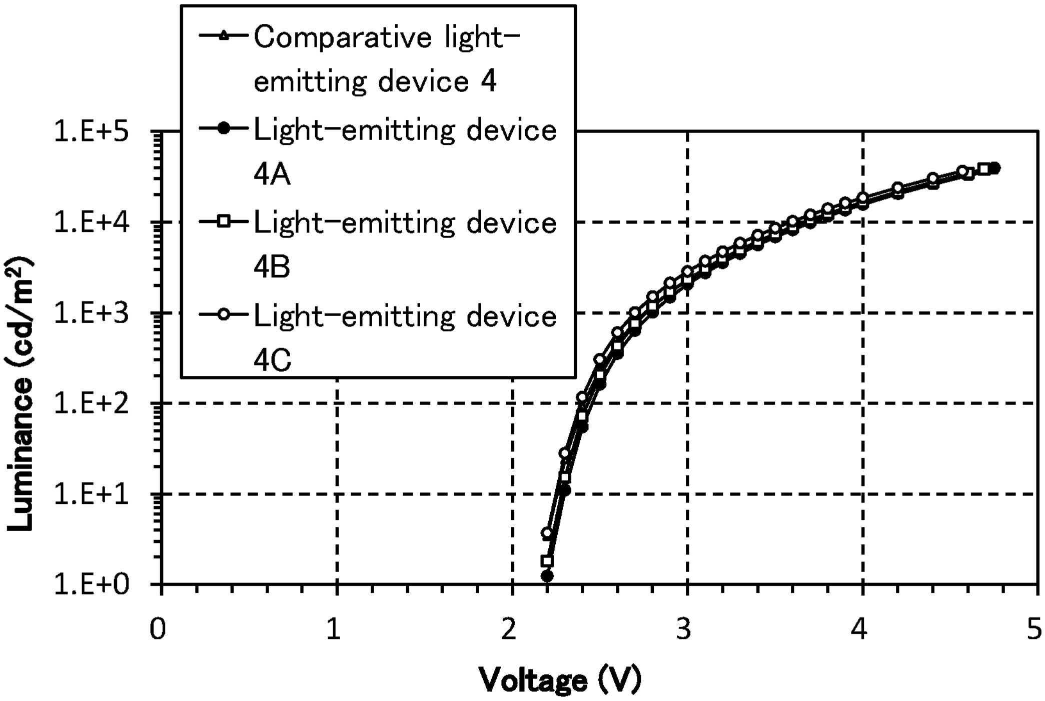
FIG. 45 shows luminance-voltage characteristics of light-emitting devices of an example.
Figure 46:
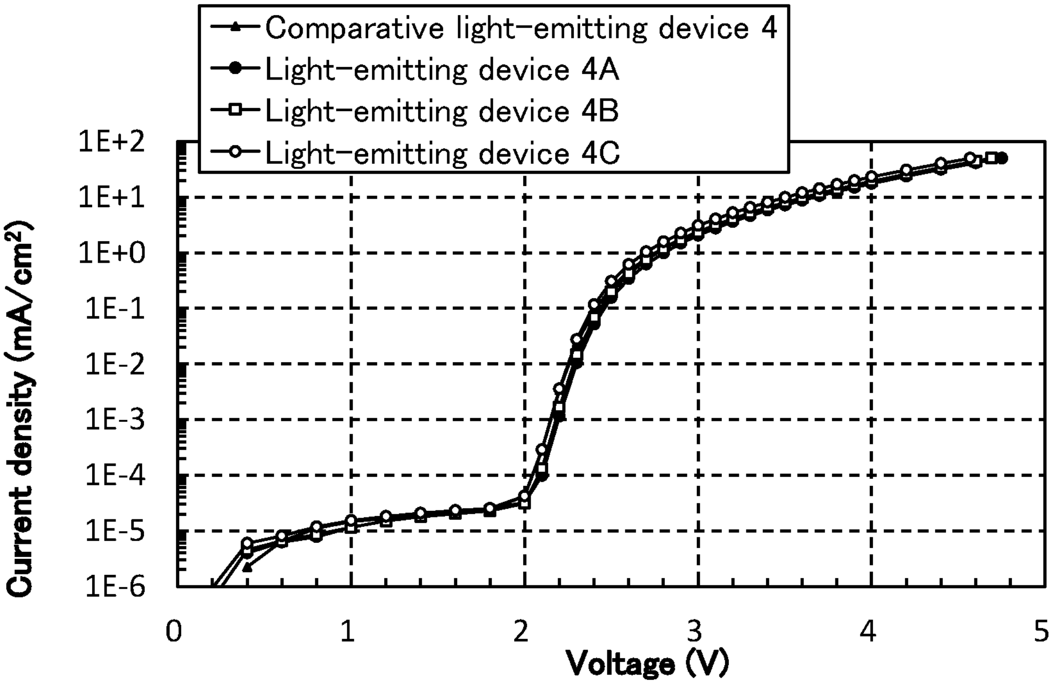
FIG. 46 shows current density-voltage characteristics of light-emitting devices of an example.
Figure 47:
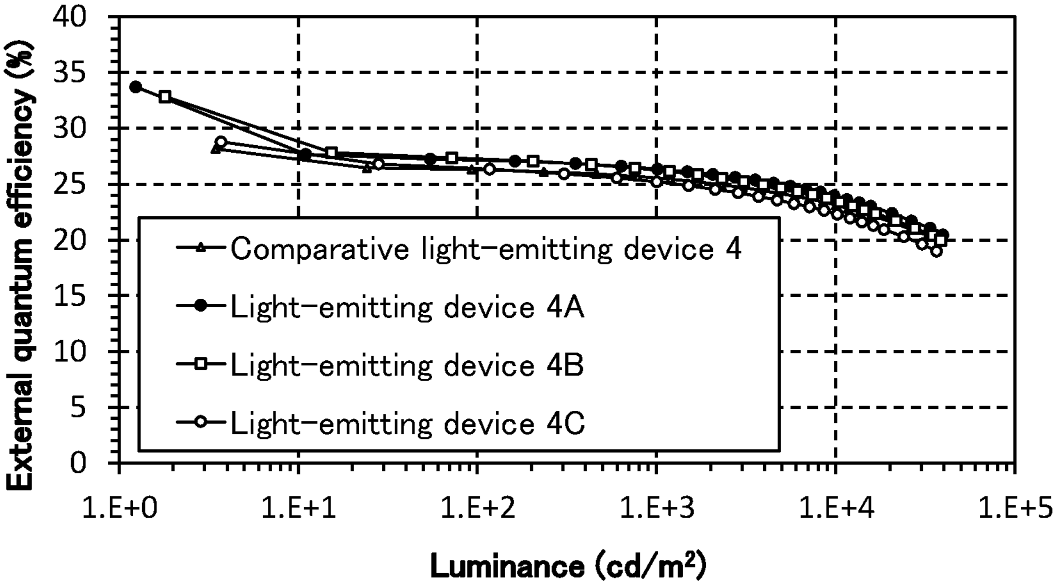
FIG. 47 shows external quantum efficiency-luminance characteristics of light-emitting devices of an example.

FIG. 43 shows the luminance-current density characteristics; FIG. 44, the current efficiency-luminance characteristics; FIG. 45, the luminance-voltage characteristics; FIG. 46, the current density-voltage characteristics; FIG. 47, the external quantum efficiency-luminance characteristics; and FIG. 48, the emission spectrum of the light-emitting devices 4A to 4C and the comparative light-emitting device 4. The following table shows the main characteristics of the light-emitting devices at a luminance of approximately 1000 cd/m$^2$. Note that luminance, CIE chromaticity, and emission spectra were measured with a spectroradiometer (SR-UL1R, manufactured by TOPCON TECHNOHOUSE CORPORATION). The external quantum efficiency was calculated from the luminance and the emission spectra measured with the spectroradiometer, on the assumption that the light-emitting devices had Lambertian light-distribution characteristics.

<Results of Reliability Test>

Figure 49:
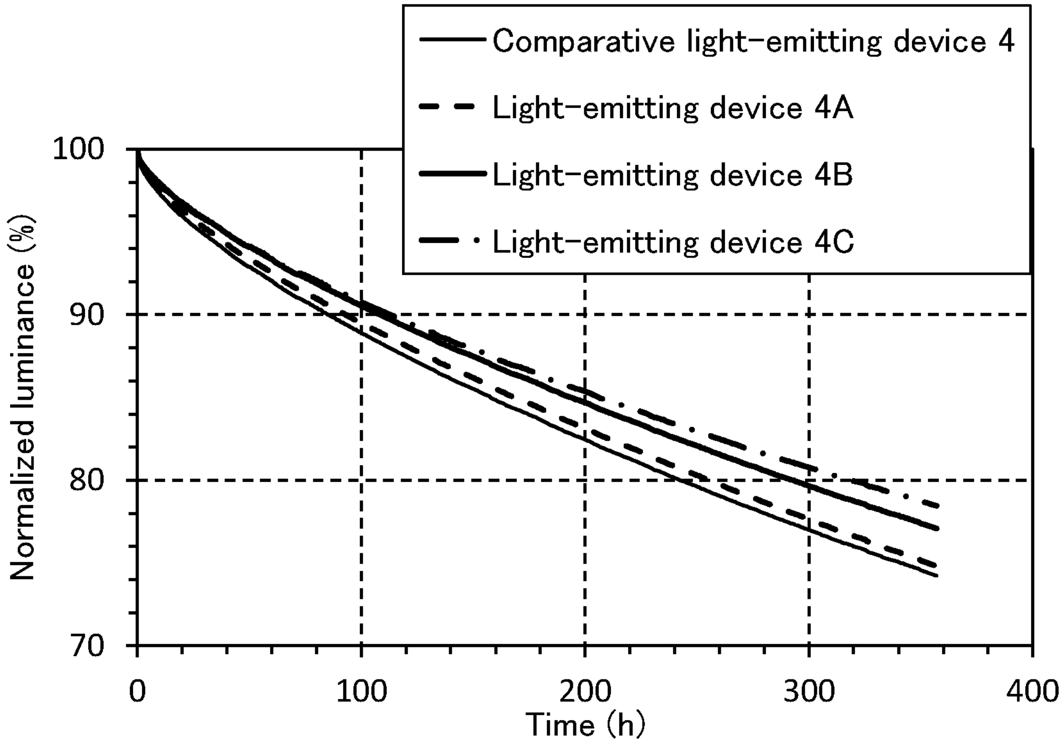
FIG. 49 shows a driving time-dependent change in luminance of light-emitting devices of an example.

Furthermore, a reliability test was performed on the light-emitting devices 4A to 4C and the comparative light-emitting device 4. FIG. 49 shows a time-dependent change in normalized luminance at the time of constant current density driving (50 [mA/cm$^2$]). In FIG. 49, the vertical axis represents normalized luminance (%), and the horizontal axis represents time (h). The value of LT80 (h) that is elapsed time until the measurement luminance reduces to 80% of the initial luminance was 243 hours, 256 hours, 293 hours, and 320 hours in the comparative light-emitting device 4 and the light-emitting devices 4A to 4C, respectively.

From the results of the comparative light-emitting device 4 containing 4,8mDBtP2Bfpm and the light-emitting device 4B containing 4,8mDBtP2Bfpm-$d_{20}$ with deuterium, it was found that, in the light-emitting layer 913, in the case where the weight ratio of (4,8mDBtP2Bfpm or 4,8mDBtP2Bfpm-$d_{20}$) to PNCCP and Ir(5mppy-$d_3$)$_2$(mbfpypy-$d_3$) was 0.5:0.5:0.1, the light-emitting device 4B containing deuterium had high reliability.

A carbon-deuterium bond has higher bond dissociation energy than a carbon-hydrogen bond. That is, deuteration of a hole-transport unit included in 4,8mDBtP2Bfpm can inhibit dissociation of a carbon-hydrogen bond, leading to higher stability of a molecular structure. That is, an excited state was stabilized, whereby a light-emitting device containing 4,8mDBtP2Bfpm-$d_{20}$ exhibited excellent lifetime characteristics.

TABLE 2

| | Voltage (V) | Current density (mA/cm$^2$) | Chromaticity x | Chromaticity y | Current efficiency (cd/A) | External quantum efficiency (%) |
|---|---|---|---|---|---|---|
| Comparative light-emitting device 4 | 2.80 | 1.22 | 0.370 | 0.609 | 97.8 | 25.4 |
| Light-emitting device 4A | 2.80 | 1.00 | 0.360 | 0.617 | 102.0 | 26.4 |
| Light-emitting device 4B | 2.80 | 1.17 | 0.362 | 0.615 | 100.8 | 26.1 |
| Light-emitting device 4C | 2.70 | 1.04 | 0.365 | 0.613 | 96.9 | 25.2 |

Figure 48:
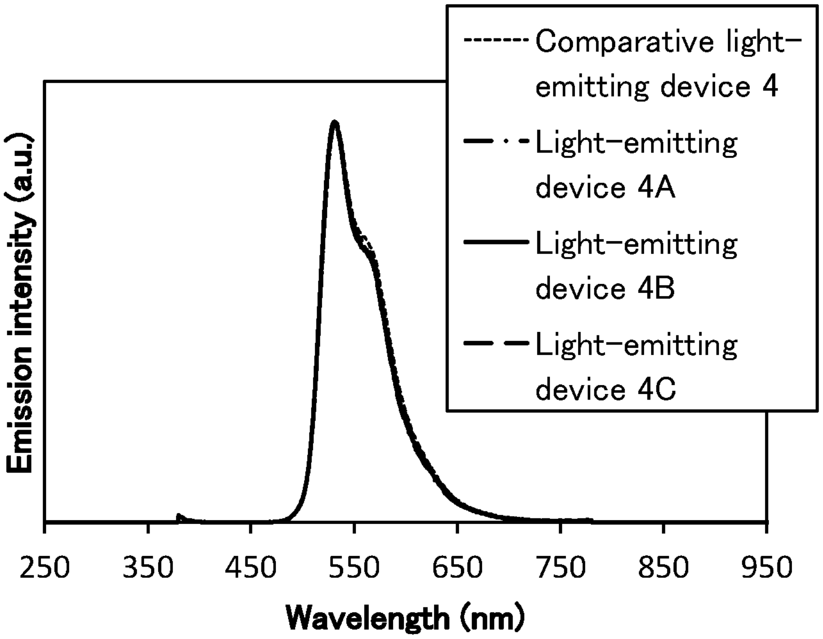
FIG. 48 shows emission spectra of light-emitting devices of an example.

In FIG. 46, the comparative light-emitting device 4 and the light-emitting device 4B showed the similar current density-voltage characteristics, whereby the carrier-transport properties of 4,8mDBtP2Bfpm and 4,8mDBtP2Bfpm-$d_{20}$ were found to be similar. In FIG. 47 and FIG. 48, the comparative light-emitting device 4 and the light-emitting device 4B show the similar external quantum efficiency and emission spectra. It can be said from the above that an organic compound 4,8mDBtP2Bfpm-$d_{20}$ obtained by substituting deuterium for hydrogen bonded to carbon of an organic compound 4,8mDBtP2Bfpm does not affect the driving characteristics and emission characteristics of a light-emitting device containing 4,8mDBtP2Bfpm-$d_{20}$.

It was found from FIG. 43 to FIG. 48 that the light-emitting devices 4A to 4C that were light-emitting devices of one embodiment of the present invention had device characteristics similar to that of the comparative light-emitting device 4.

Furthermore, from the results of the light-emitting devices 4A to 4C, it was found that, in the light-emitting layer 913, in the case where 4,8mDBtP2Bfpm-$d_{20}$ with deuterium was used, the reliability increased when the ratio of 4,8mDBtP2Bfpm-$d_{20}$ was large.

Example 5

Synthesis Example 4

In this example, a method for synthesizing 8-(1,1': 4',1"-terphenyl-3-yl-2,4,5,6,2',3',5',6,2",3",4",5",6"-$d_{13}$)-4-[3-(dibenzothiophen-4-yl)phenyl]-[1]benzofuro[3,2-d]pyrimidine (abbreviation: 8mpTP-4mDBtPBfpm-$d_{13}$) shown as Structural Formula (512) in Embodiment 1 is specifically described.

[Chemical Formula 93]

(512)

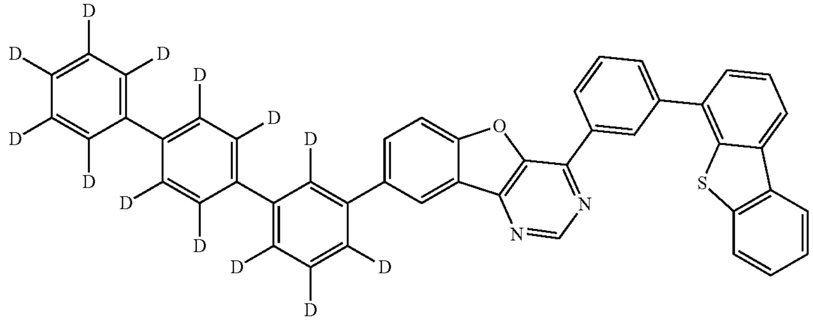

Step 4-1; Synthesis of (3-bromo-1,1':4',1"-terphenyl-2,4,5,6,2',3',5',6',2",3",4",5",6'-$d_{13}$)

By the same synthesis method as <Step 3-3> in Example 3, 9.3 g of the target pale yellow solid was obtained in a yield of 85%. The synthesis scheme of Step 4-1 is shown in (d-1) below.

[Chemical Formula 94]

(d-1)

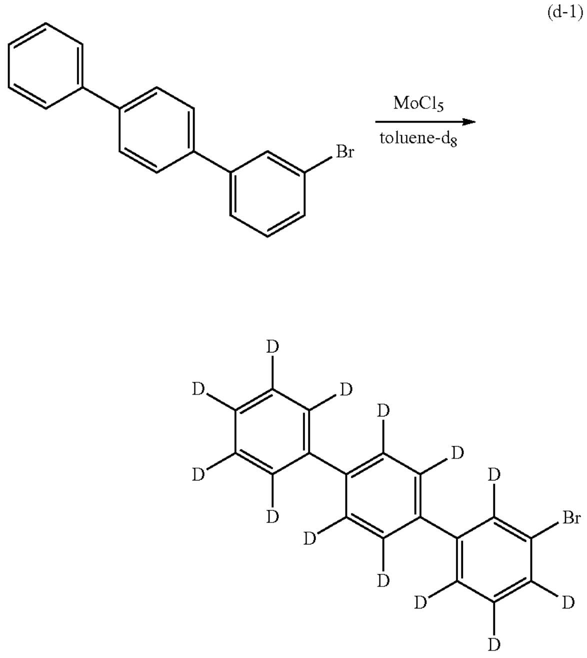

Step 4-2; Synthesis of 4,4,5,5-tetramethyl-2-(1,1':4',1"-terphenyl-2,4,5,6,2',3',5',6',2",3",4",5",6"-$d_{13}$)-3-yl-1,3,2-dioxaborolane By the same synthesis method as <Step 3-4> in Example 3, the target light-blue solid was obtained. The light-blue solid was washed with ethanol and hexane to give 7.7 g of a white solid in a yield of 73%. The synthesis scheme of Step 4-2 is shown in (d-2) below.

[Chemical Formula 95]

(d-2)

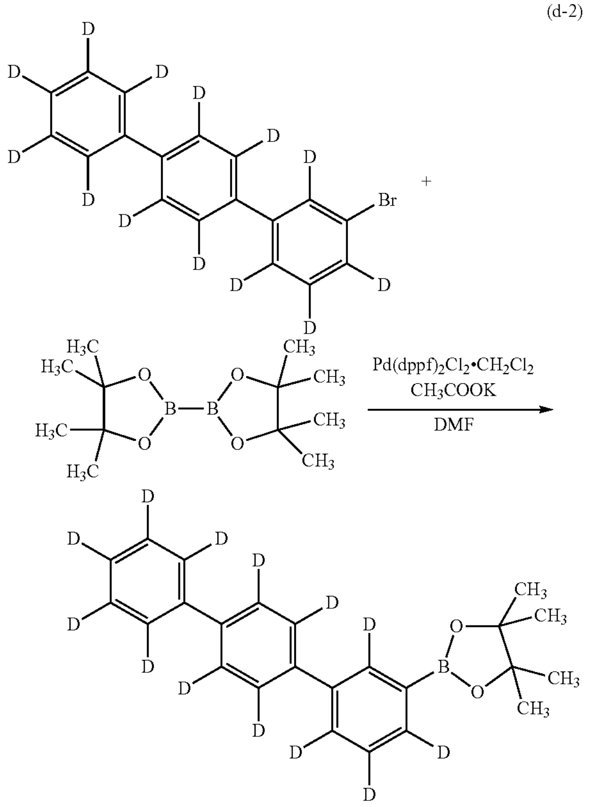

Figure 50A:
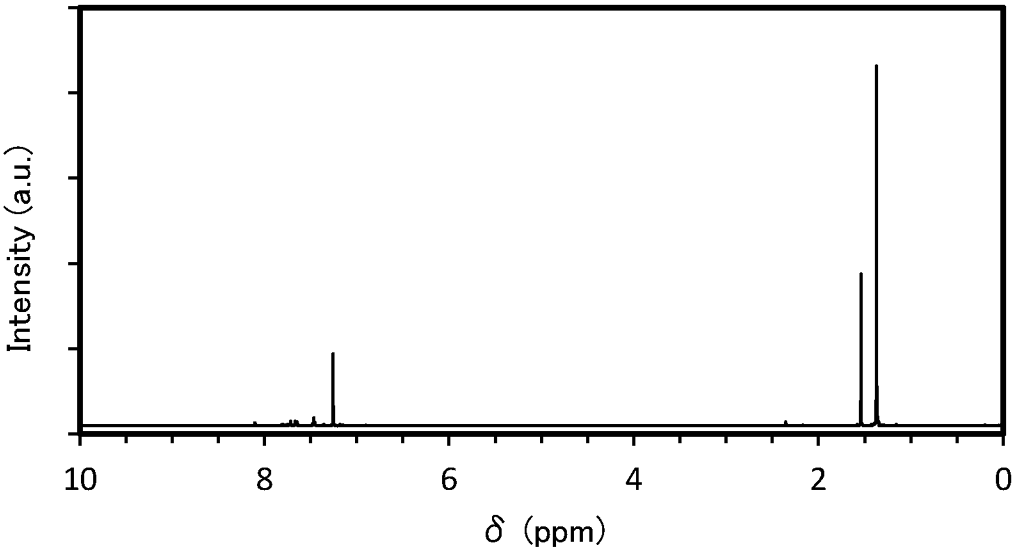
FIGS. 50A and 50B are $^1$H NMR spectra of an organic compound obtained in Example 5.

Analysis results by nuclear magnetic resonance ($^1$H-NMR) spectroscopy of 4,4,5,5-tetramethyl-2-(1,1':4',1"-terphenyl-2,4,5,6,2',3',5',6',2",3",4",5",6"-$d_{13}$)-3-yl-1,3,2-dioxaborolane obtained in Step 4-2 are shown below. In addition, FIGS. 50A and 50B show $^1$H-NMR charts.

$^1$H-NMR. δ ($CDCl_3$, 300 MHz): 1.37 (s, 12H).

Figure 50B:
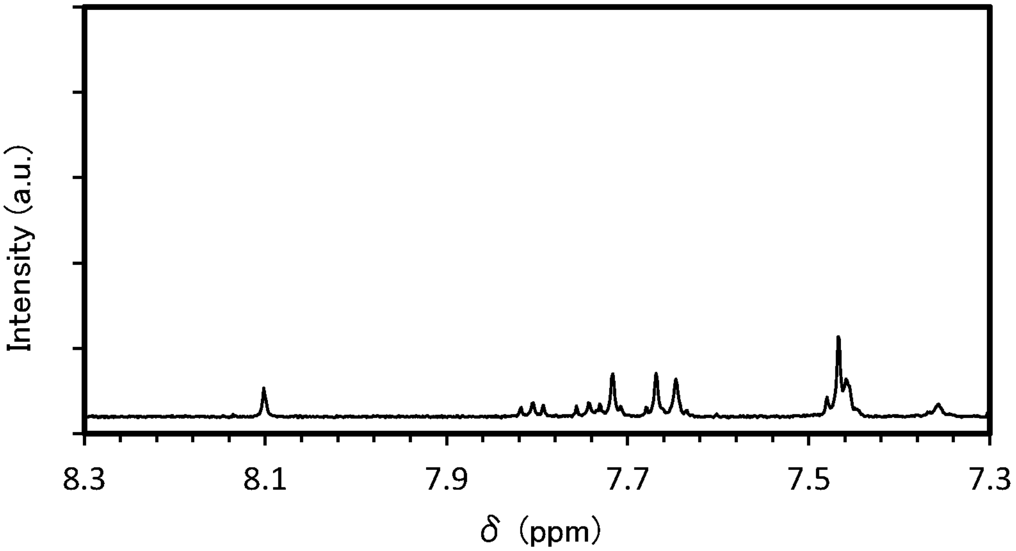
Figure 51A:
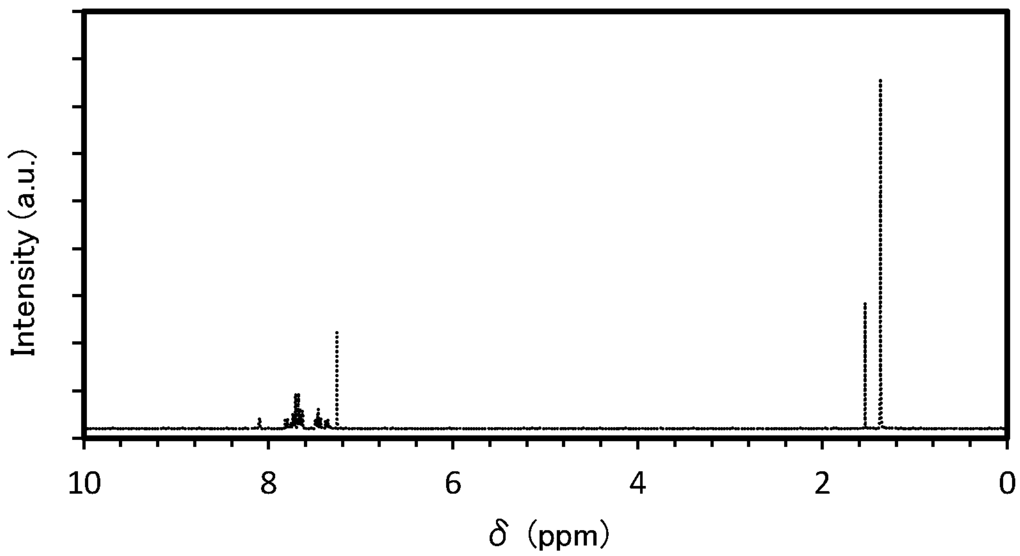
FIG. 51A shows a $^1$H NMR spectrum of the organic compound obtained in Example 5.
Figure 51B:
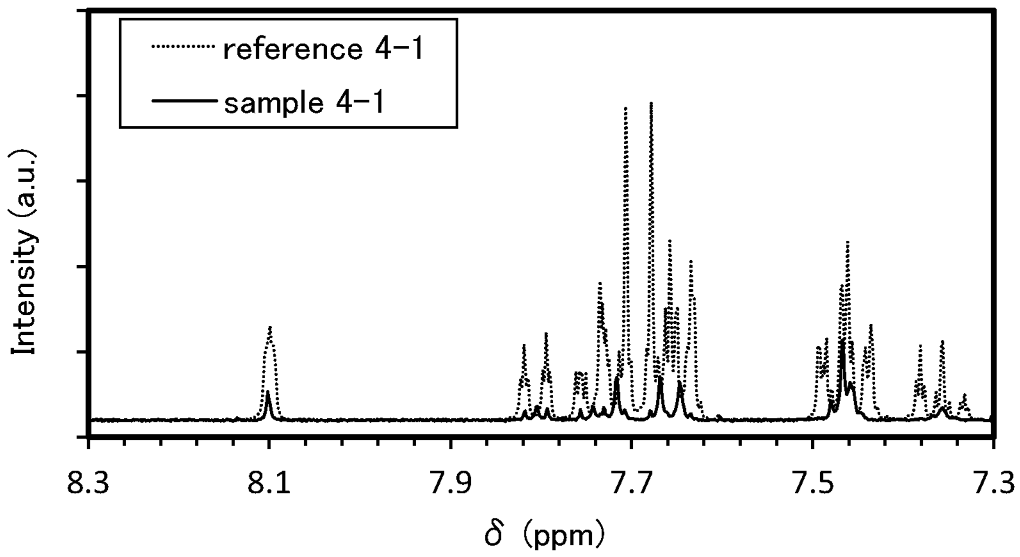
FIG. 51B shows $^1$H NMR spectra of the organic compound obtained in Example 5 and reference 4-1.

In FIG. 50B, signals that appear around δ=7.30 ppm to 8.30 ppm are assumed to be protium that was not deuterated and remained in Synthesis Scheme (d-1). The deuteration rate was estimated in the following manner: the peak of 1.37 ppm (s, 12H) was used as the reference, and the number of protons of 4,4,5,5-tetramethyl-2-(1,1':4',1"-terphenyl)-3-yl-1,3,2-dioxaborolane that was a non-deuterated substance of 4,4,5,5-tetramethyl-2-(1,1':4',1"-terphenyl-2,4,5,6,2',3',5',6,2",3",4",5",6"-$d_{13}$)-3-yl-1,3,2-dioxaborolane was referredto. FIG. 51A shows the $^1$H-NMR chart of 4,4,5,5-tetramethyl-2-(1,1':4',1"-terphenyl)-3-yl-1,3,2-dioxaborolane, and FIG. 51B is an enlarged view of δ=7.30 ppm to 8.30 ppm, which compares 4,4,5,5-tetramethyl-2-(1,1':4',1"-terphenyl-2,4,5,6,2',3',5',6',2",3",4",5",6"-$d_{13}$)-3-yl-1,3,2-dioxaborolane (sample 4-1) and 4,4,5,5-tetramethyl-2-(1,1':4',1"-terphenyl)-3-yl-1,3,2-dioxaborolane (reference 4-1). From the above, the deuteration rate of 4,4,5,5-tetramethyl-2-(1,1':4',1"-terphenyl-2,4,5,6,2',3',5',6',2",3",4",5",6"-$d_{13}$)-3-yl-1,3,2-dioxaborolane was estimated to be approximately 87%.

Step 4-3; Synthesis of 8-(1,1':4',1"-terphenyl-3-yl-2,4,5,6,2',3',5',6',2",3",4",5",6"-$d_{13}$)-4-[3-(dibenzothiophen-4-yl)phenyl]-[1]benzofuro[3,2-d]pyrimidine (abbreviation: 8mpTP-4mDBtPBfpm-$d_3$)

Into a 200 mL three-neck flask were put 2.9 g (6.2 mmol) of 8-chloro-4[3-(dibenzothiophen-4-yl)phenyl]-[1]benzofuro[3,2-d]pyrimidine, 2.8 g (7.5 mmol) of 4,4,5,5-tetramethyl-2-(1,1':4',1"-terphenyl-2,4,5,6,2',3',5',6',2",3",4",5",6"-$d_{13}$)-3-yl-1,3,2-dioxaborolane obtained in Step 4-2, 4.0 g (19 mmol) of tripotassium phosphate, 1.4 g (19 mmol) of tert-butylalcohol (abbreviation: tBuOH), and 62 mL of diethylene glycol dimethyl ether (abbreviation: diglyme), and the mixture in the flask was stirred under reduced pressure and degassed. After that, the mixture was heated at 60° C. under a nitrogen stream, 0.15 g (0.65 mmol) of palladium(II) acetate (abbreviation: $Pd(OAc)_2$) and 0.45 g (1.3 mmol) of di(1-adamantyl)-N-butylphosphine (abbreviation: cataCxiumA) were added to the mixture, and then the mixture was stirred at 130° C. for 12 hours. After the stirring, water was added to the obtained mixture, suction filtration was performed, and the residue was washed with water and ethanol. The obtained residue was dissolved in toluene by heating, and the obtained solution was filtered through a filter aid in which Celite, alumina, and Celite were stacked in this order, and the filtrate was concentrated to give a solid. The obtained solid was purified by silica gel column chromatography (the ratio was changed from toluene 100% to toluene:ethyl acetate=30:1 to perform a gradient). The resulting solid was recrystallized with toluene to give 3.0 g of a white solid in a yield of 72%. By a train sublimation method, 2.5 g of the obtained white solid was purified by sublimation. The sublimation purification was conducted under the conditions where the pressure was 3.0 Pa, the flow rate of an argon gas was 12 mL/min, the solid was heated at 355° C. for 5 hours, and the temperature was raised to 358° C. to further heat the solid for 1 hour. After the sublimation purification by sublimation, 1.7 g of a target pale yellow solid was obtained at a collection rate of 68%. The synthesis scheme of Step 4-3 is shown in (d-3) below.

[Chemical Formula 96]

(d-3)

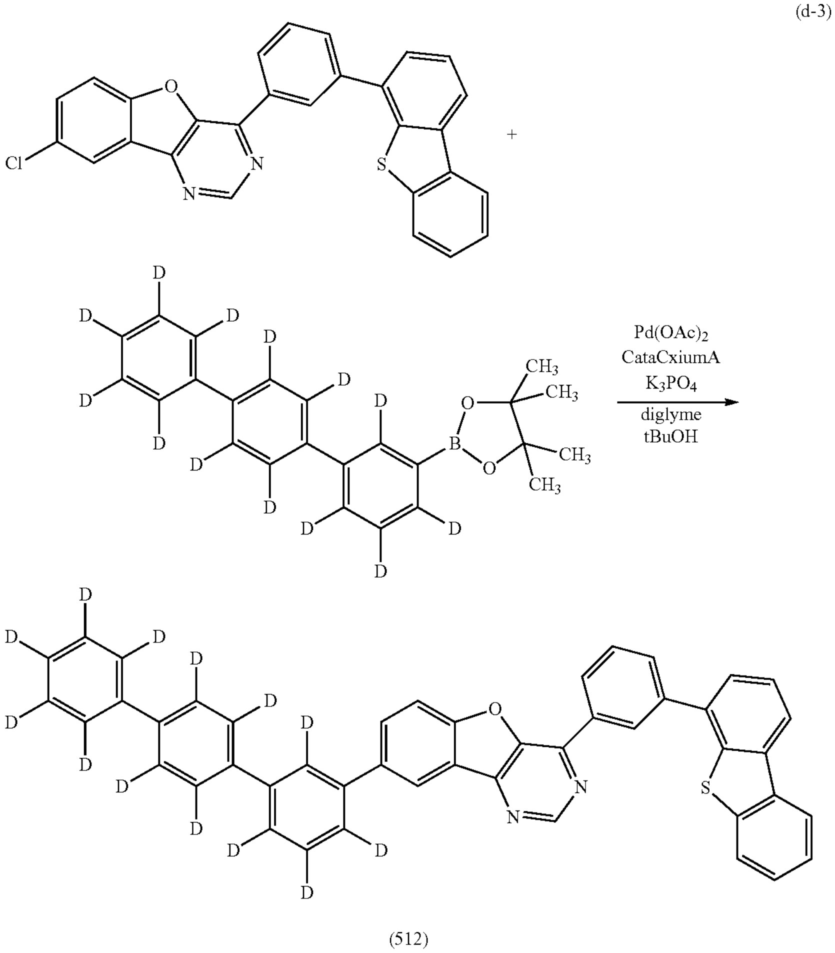

(512)

Figure 52A:
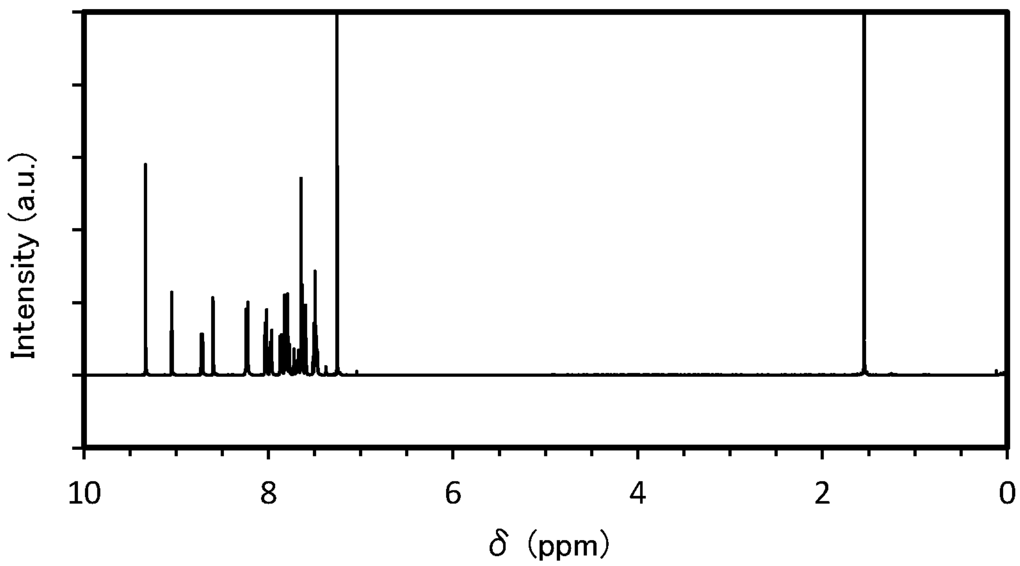
FIGS. 52A and 52B show $^1$H NMR spectra of 8mpTP-4mDBtPBfpm-$d_{13}$.

Measurement results obtained by nuclear magnetic resonance ($^1$H-NMR) spectroscopy of the pale yellow solid obtained in the above step are shown below. FIG. 52A shows the $^1$H-NMR chart. The measurement results reveal that 8mpTP-4mDBtPBfpm-$d_{13}$, which is represented by the structural formula (512) and is one embodiment of the present invention, was obtained in Synthesis example 4.

$^1$H-NMR. δ ($CDCl_3$, 500 MHz): 7.46-7.52 (m, 2H), 7.63-7.66 (m, 2H), 7.77-7.83 (m, 2H), 7.85-7.88 (m, 1H), 7.97-7.98 (m, 1H), 8.03 (dd, J1=8.59 Hz, J2=1.72 Hz, 1H), 8.21-8.25 (m, 2H), 8.60 (sd, J=1.72 Hz, 1H), 8.72 (td, J1=8.59 Hz, J2=1.72 Hz, 1H), 9.05 (t, J=1.72 Hz, 1H), 9.33 (s, 1H).

Figure 52B:
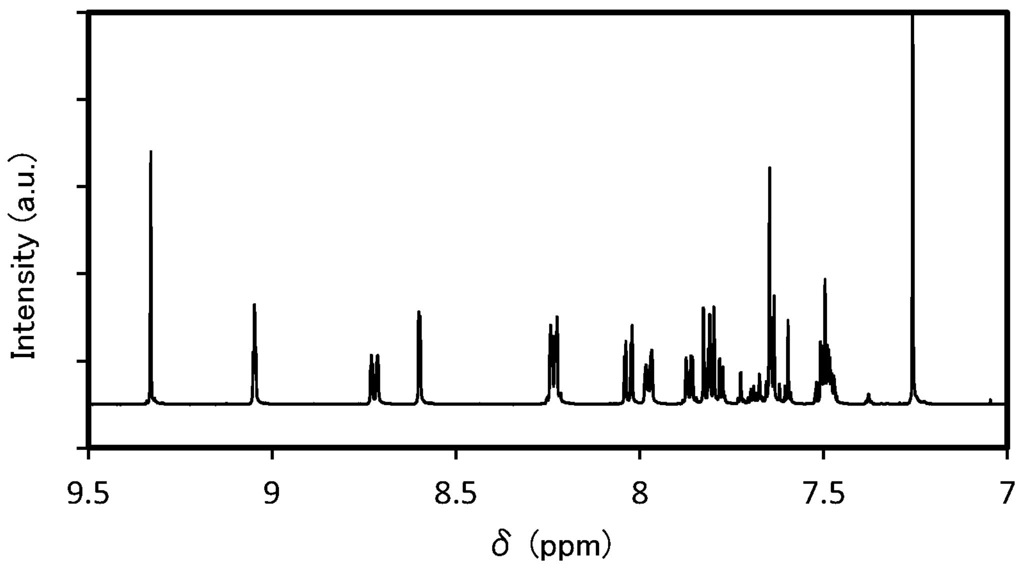
Figure 53A:
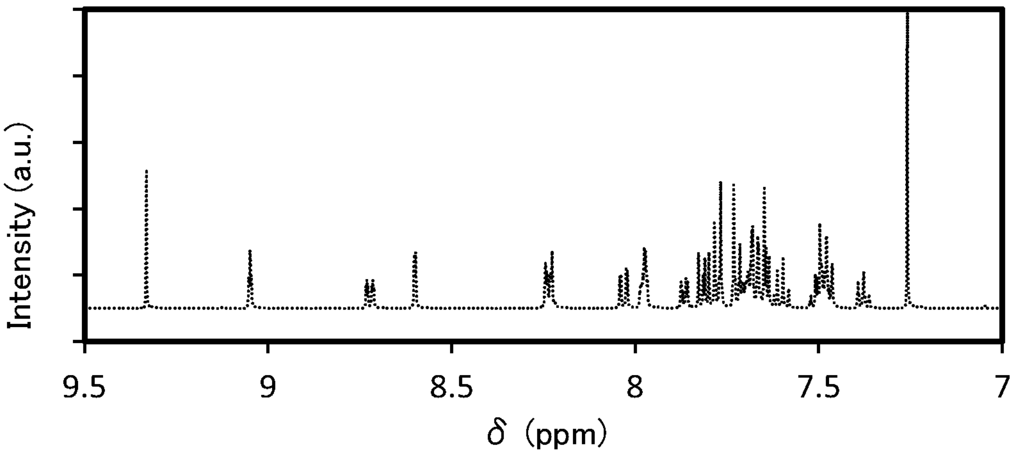
FIG. 53A shows a $^1$H NMR spectrum of 8mpTP-4mDBtPBfpm.
Figure 53B:
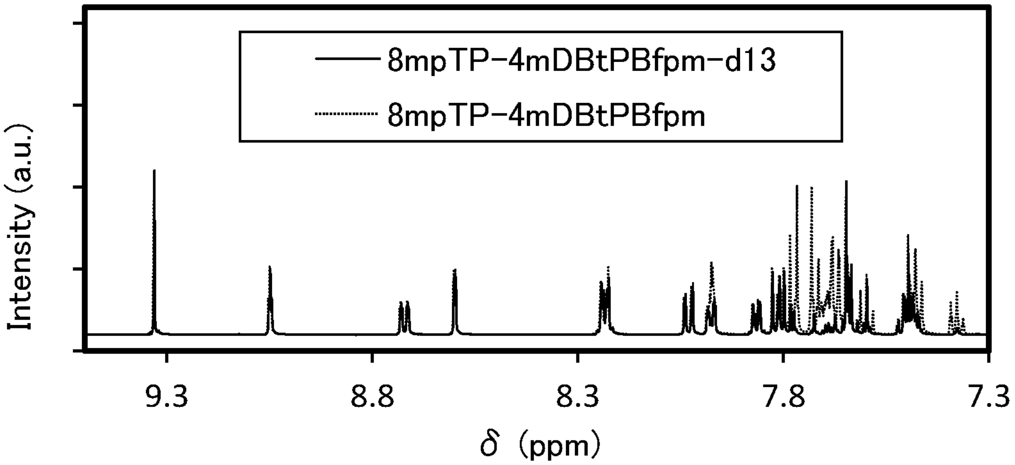
FIGS. 53B and 53C show $^1$H NMR spectra of 8mpTP-4mDBtPBfpm-$d_{13}$ and 8mpTP-4mDBtPBfpm.
Figure 53C:
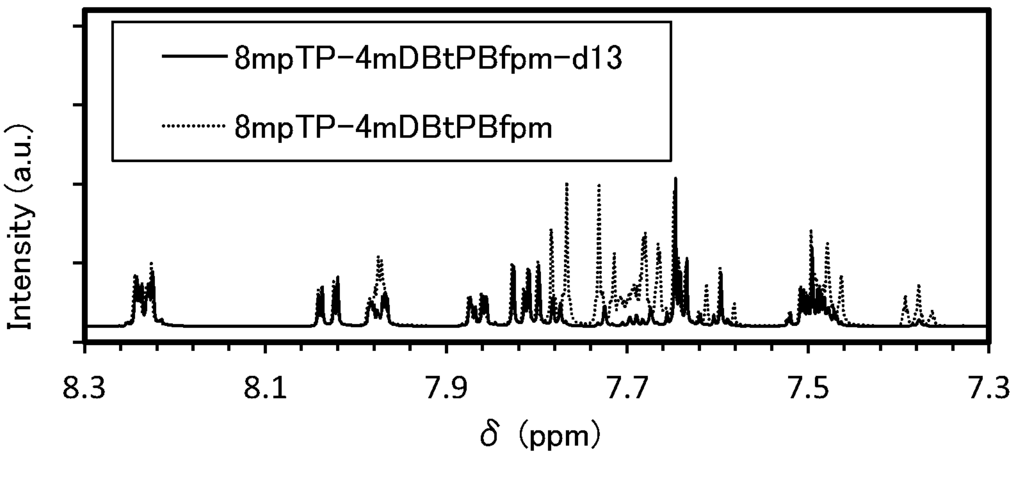

In FIG. 52B, peaks having low intensity were observed around δ=7.34 ppm to 7.38 ppm, 7.67 ppm to 7.73 ppm, or the like. They are assumed to be protium that was not deuterated and remained in Synthesis Scheme (d-2). The deuteration rate of 8mpTP-4mDBtPBfpm-$d_{13}$ was estimated using a signal at δ=9.33 ppm (s, 1H) as the reference. FIG. 53A shows the $^1$H-NMR chart of 8mpTP-4mDBtPBfpm that is a non-deuterated substance of 8mpTP-4mDBtPBfpm-$d_{13}$. FIG. 53B is a diagram of δ=7.30 ppm to 9.50 ppm, which compares 8mpTP-4mDBtPBfpm-$d_{13}$ and 8mpTP-4mDBtPBfpm that are normalized with the signal in δ=9.33 ppm. FIG. 53C is an enlarged view of δ=7.30 ppm to 8.30 ppm in FIG. 53B. In FIG. 53C, peaks having low intensity around δ=7.34 ppm to 7.38 ppm and 7.67 ppm to 7.73 ppm are peaks derived from protium that was not deuterated and remained in Synthesis Scheme (d-2). Based on the peaks, the deuteration rate of 8mpTP-4mDBtPBfpm-$d_{13}$ was estimated to be approximately 77%.

<Characteristics of 8mpTP-4mDBtPBfpm-$d_{13}$>

Figure 54:
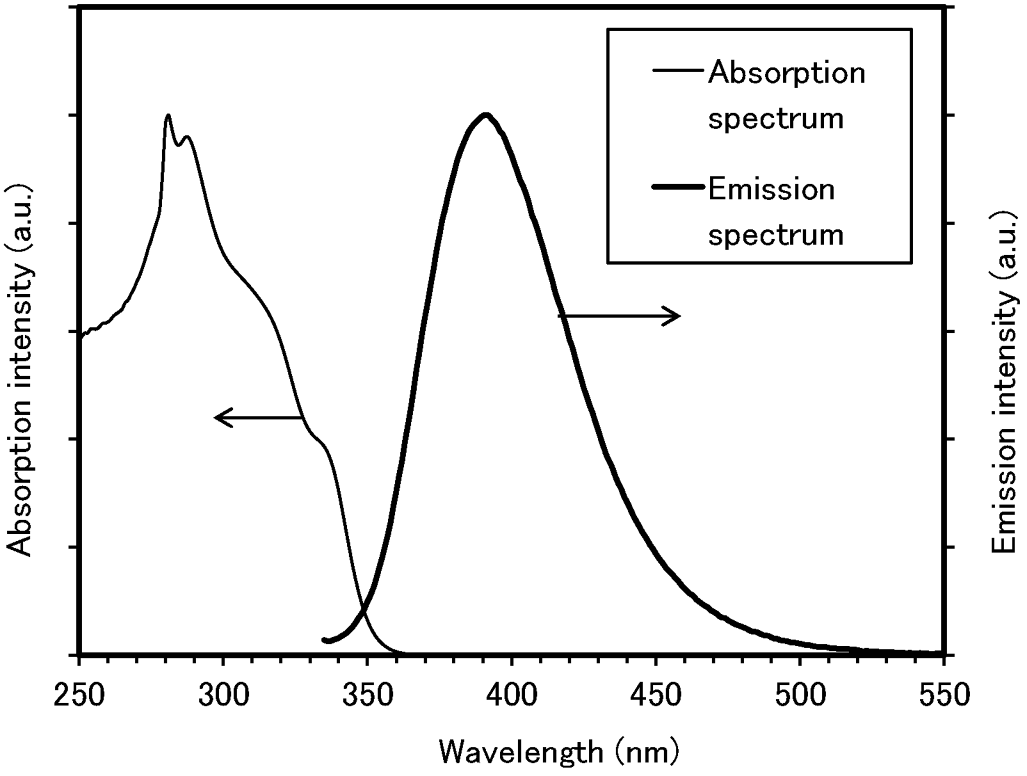
FIG. 54 shows an absorption spectrum and an emission spectrum of 8mpTP-4mDBtPBfpm-$d_{13}$ in a toluene solution.

Then, the ultraviolet-visible absorption spectrum (hereinafter, simply referred to as "absorption spectrum") and emission spectrum of a toluene solution of 8mpTP-4mDBtPBfpm-$d_{13}$ were measured. The absorption spectrum was measured at room temperature with an ultraviolet-visible light spectrophotometer (V-770DS, produced by JASCO Corporation) in a state where the toluene solution was put in a quartz cell. The emission spectrum was measured at room temperature with a fluorescence spectrophotometer (FP-8600DS, produced by JASCO Corporation) in a state where the toluene solution was put in a quartz cell. FIG. 54 shows results of the measured absorption spectrum and emission spectrum. The horizontal axis represents the wavelength and the vertical axes represent the absorption intensity and the emission intensity. The absorption spectrum shown in FIG. 54 is a result obtained by subtraction of an absorption spectrum of only toluene in a quartz cell from the measured absorption spectrum of the toluene solution in the quartz cell.

As shown in FIG. 54, in the toluene solution of 8mpTP-4mDBtPBfpm-$d_{13}$, absorption peaks were observed around 310 nm and 333 nm, and an emission peak was observed around 391 nm (excitation wavelength: 300 nm).

Figure 55:
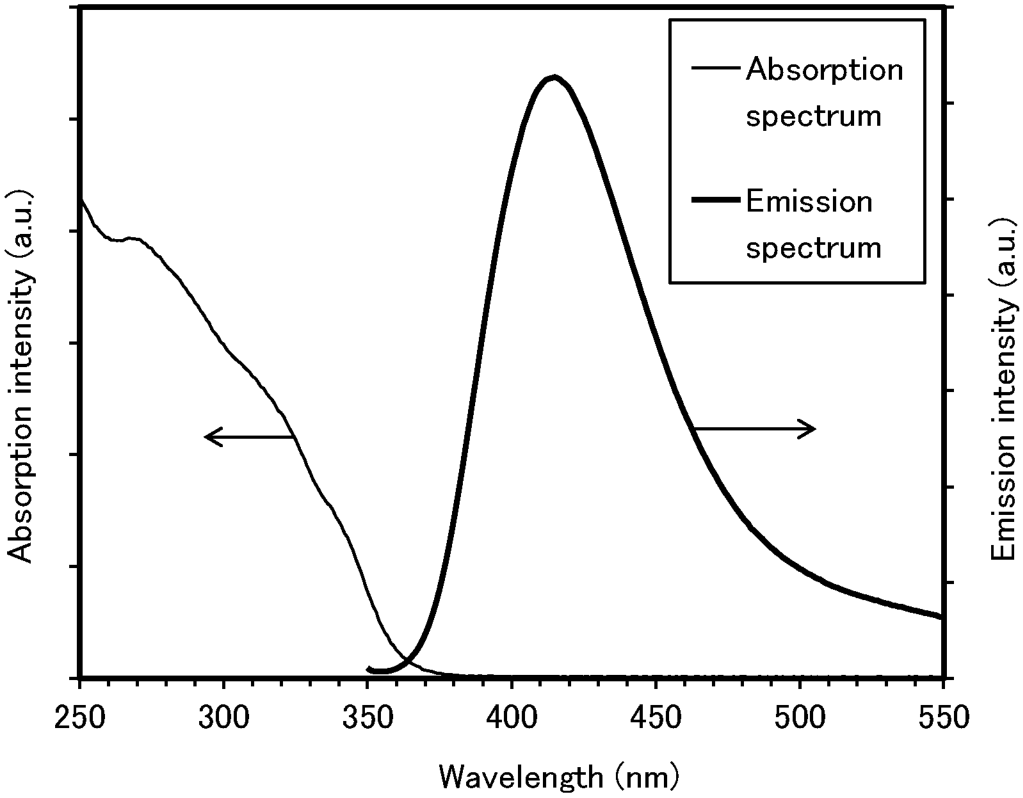
FIG. 55 shows an absorption spectrum and an emission spectrum of a thin film of 8mpTP-4mDBtPBfpm-$d_{13}$.

Next, the absorption spectrum and emission spectrum of a solid thin film of 8mpTP-4mDBtPBfpm-$d_{13}$ were measured. The solid thin film was fabricated over a quartz substrate by a vacuum evaporation method. The absorption spectrum of the thin film was calculated using an absorbance ($-\log_{10}$ [% T/(100−% R)]) obtained from the transmittance and reflectance of the thin film including the substrate. Note that % T represents transmittance and % R represents reflectance. The absorption spectrum was measured with a UV-visible spectrophotometer (U-4100 manufactured by Hitachi High-Technologies Corporation). The emission spectrum was measured using a spectrofluorometer (FP-8600DS manufactured by JASCO Corporation). FIG. 55 shows the measurement results of the obtained absorption and emission spectra of the solid thin film. The horizontal axis represents the wavelength and the vertical axes represent the absorption intensity and the emission intensity.

From the results in FIG. 55, in the solid thin film of 8mpTP-4mDBtPBfpm-$d_{13}$, absorption peaks were observed around 273 nm, 320 nm, and 339 nm, and an emission peak was observed around 415 nm (excitation wavelength: 340 nm).

The ionization potential value of a thin film of 8mpTP-4mDBtPBfpm-$d_{13}$ was measured in the air with a photoelectron spectrometer (AC-3, produced by Riken Keiki Co., Ltd.). The obtained ionization potential value was converted into a negative value, so that the HOMO level of 8mpTP-4mDBtPBfpm-$d_{13}$ was −6.26 eV. From the data of the absorption spectrum of the thin film, the absorption edge of 8mpTP-4mDBtPBfpm-$d_{13}$, which was obtained from Tauc plot with an assumption of direct transition, was 3.50 eV. Thus, the optical energy gap of 8mpTP-4mDBtPBfpm-$d_{13}$ in the solid state was estimated at 3.50 eV; from the values of the HOMO level obtained above and this energy gap, the LUMO level of 8mpTP-4mDBtPBfpm-$d_{13}$ can be estimated at −2.76 eV. This reveals that 8mpTP-4mDBtPBfpm-$d_{13}$ in the solid state has an energy gap as wide as 3.50 eV.

The glass transition temperature (Tg) of 8mpTP-4mDBtPBfpm-$d_{13}$ was measured. Note that Tg was measured with a differential scanning calorimeter (DSC8500 produced by PerkinElmer Japan Co., Ltd.) in a state where a powder was put on an aluminum cell. The result showed that the Tg of 8mpTP-4mDBtPBfpm-$d_{13}$ was 120° C.

Next, the electrochemical characteristics (oxidation reaction characteristics and reduction reaction characteristics) of 8mpTP-4mDBtPBfpm-$d_{13}$ were measured by cyclic voltammetry (CV) measurement. An electrochemical analyzer (ALS model 600A and ALS model 600B, manufactured by BAS Inc.) was used for the measurement. The solution for the CV measurement was prepared by using dehydrated N,N-dimethylformamide (DMF) (produced by Aldrich Corp., 99.8%, catalog number: 22705-6) as a solvent, dissolving a supporting electrolyte of tetra-n-butylammonium perchlorate ($n\text{-}Bu_4NClO_4$) (produced by Tokyo Chemical Industry Co., Ltd., catalog number: T0836) at a concentration of 100 mmol/L, and then dissolving the object of measurement at a concentration of 2 mmol/L.

A platinum electrode (PTE platinum electrode, manufactured by BAS Inc.) was used as a working electrode, another platinum electrode (Pt counter electrode (5 cm), manufactured by BAS Inc.) was used as an auxiliary electrode, and an $Ag/Ag^+$ electrode (RE7 reference electrode for nonaqueous solvent, manufactured by BAS Inc.) was used as a reference electrode. Note that the measurement was performed at room temperature (20° C. to 25° C.).

In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the oxidation potential Ea[V] of 8mpTP-4mDBtPBfpm-$d_{13}$ was not observed. Therefore, the HOMO level is estimated to be lower than −6.2 eV. In contrast, the LUMO level was found to be −3.01 eV from the measurement result of the reduction potential Ec [V]. In addition, the results of repetitive measurement of the oxidation-reduction wave showed that when the waveform of the first cycle was compared with that of the hundredth cycle, 84% of the peak intensity were maintained in the Ec measurement, which confirmed that 8mpTP-4mDBtPBfpm-$d_{13}$ had high resistance to reduction.

Example 6

Synthesis Example 5

In this example, a method for synthesizing 8-(1,1':4',1"-terphenyl-3-yl)-4-[3-(dibenzothiophen-4-yl-1,2,3,6,7,8,9-$d_7$)phenyl-2,4,6-$d_3$]-[1]benzofuro[3,2-d]pyrimidine (abbreviation: 8mpTP-4mDBtPBfpm-$d_{10}$) shown as Structural Formula (530) in Embodiment 1 is specifically described.

[Chemical Formula 97]

(530)

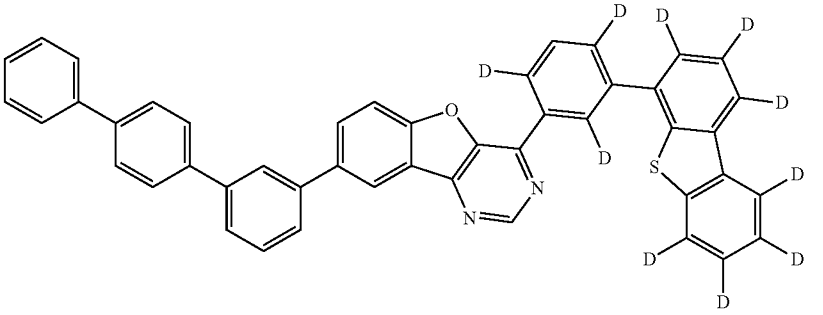

Step 5-1; Synthesis of 8-chloro-4[3-(dibenzothiophen-4-yl-1,2,3,6,7,8,9-$d_7$)phenyl-2,4,6-$d_3$]-[1]benzofuro[3,2-d]pyrimidine Into a 200 mL three-neck flask were put 4.3 g (11 mmol) of 2-[3-(dibenzo[b,d]thiophen-4-yl-1,2,3,6,7,8,9-d)phenyl-2,4,6-$d_3$]-4,4,5,5-tetramethyl-1,3,2-dioxaborolane obtained in Step 3-2 in Example 3, 2.6 g (10.8 mmol) of 4,8-dichloro[1]benzofuro[3,2-d]pyrimidine, 3.0 g (22 mmol) of potassium carbonate, 45 mL of toluene, 11 mL of ethanol, and 11 mL of water. The mixture in the flask was stirred under reduced pressure and degassed. After that, the mixture was heated at 60° C. under a nitrogen stream, 1.3 g (1.1 mmol) of tetrakis(triphenylphosphine)palladium(0) (abbreviation: $(Pd(PPh_3)_4)$ was added thereto; then, the temperature was raised to 90° C. and the mixture was stirred for 7 hours. After the reaction, this mixture was suction-filtered, and the obtained residue was washed with water and ethanol. Then, 4.9 g of the target gray solid of 8-chloro-4[3-(dibenzothiophen-4-yl-1,2,3,6,7,8,9-$d_7$)phenyl-2,4,6-$d_3$]-[1]benzofuro[3,2-d]pyrimidine was obtained in a yield of 96%.

The obtained 2.9 g of 8-chloro-4[3-(dibenzothiophen-4-yl-1,2,3,6,7,8,9-$d_7$)phenyl-2,4,6-$d_3$]-[1]benzofuro[3,2-d]pyrimidine was dissolved in toluene by heating, followed by filtration through a filter aid in which Celite, alumina, and Celite were stacked in this order. The filtrate was concentrated and then recrystallized with toluene, so that 1.8 g of the target white solid of 8-chloro-4[3-(dibenzothiophen-4-yl-1,2,3,6,7,8,9-$d_7$)phenyl-2,4,6-$d_3$]-[1]benzofuro[3,2-d]pyrimidine was obtained in a yield of 62%.

The synthesis scheme of Step 5-1 is shown in (e-1) below.

[Chemical Formula 98]

(e-1)

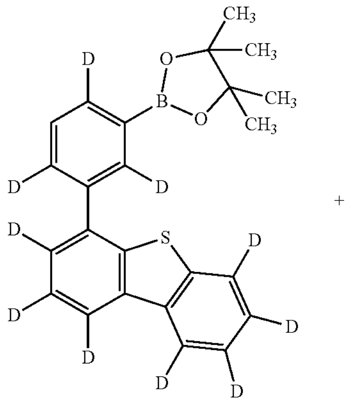

-continued

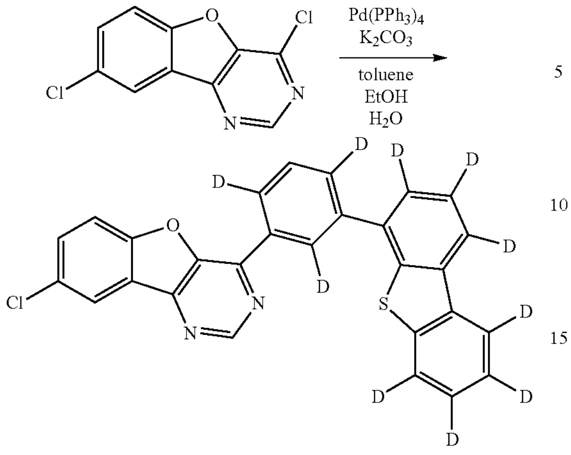

Step 5-2; Synthesis of 8-(1,1':4',1"-terphenyl-3-yl)-4-[3-(dibenzothiophen-4-yl-1,2,3,6,7,8,9-$d_7$)phenyl-2,4,6-$d_3$]-[1]benzofuro[3,2-d]pyrimidine (abbreviation: 8mpTP-4mDBtPBfpm-$d_{10}$)

Into a 200 mL three-neck flask were put 1.8 g (3.8 mmol) of 8-chloro-4[3-(dibenzothiophen-4-yl-1,2,3,6,7,8,9-$d_7$)phenyl-2,4,6-$d_3$]-[1]benzofuro[3,2-d]pyrimidine obtained in Step 5-1, 1.6 g (4.6 mmol) of 4,4,5,5-tetramethyl-2-(1,1':4',1"-terphenyl)-3-yl-1,3,2-dioxaborolane, 2.4 g (11 mmol) of tripotassium phosphate, 0.86 g (12 mmol) of tert-butylalcohol (abbreviation: tBuOH), and 40 mL of diethylene glycol dimethyl ether (abbreviation: diglyme), and the mixture in the flask was stirred under reduced pressure and degassed. After that, the mixture was heated at 60° C. under a nitrogen stream, 0.11 g (0.47 mmol) of palladium(II) acetate (abbreviation: $Pd(OAc)_2$) and 0.28 g (0.77 mmol) of di(1-adamantyl)-N-butylphosphine (abbreviation: cataCxiumA) were added to the flask, and then the mixture was stirred at 130° C. for 10 hours. After the reaction, water was added to the mixture and suction filtration was performed, and the obtained residue was washed with water and ethanol. The obtained residue was dissolved in toluene by heating, followed by filtration. The filtrate was concentrated and purified by silica gel column chromatography (the ratio was changed from toluene 100% to toluene:ethyl acetate=30:1 to perform a gradient). The resulting solid was recrystallized with toluene to give 1.9 g of a white solid in a yield of 77%. Then, by a train sublimation method, 1.7 g of the obtained white solid was purified by sublimation. The sublimation purification was conducted under the conditions where the pressure of 2.9 Pa, the flow rate of an argon gas of 15 mL/min, and the solid was heated at 355° C. for 6 hours. After the sublimation purification by sublimation, 1.41 g of a target pale yellow solid was obtained at a collection rate of 83%. The synthesis scheme of Step 5-2 is shown in (e-2) below.

[Chemical Formula 99]

(e-2)

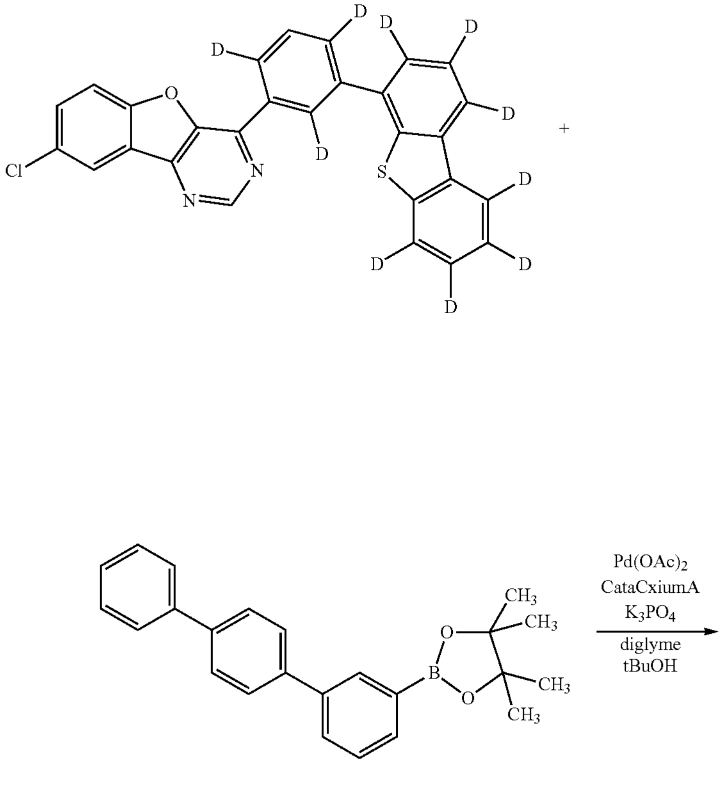

-continued

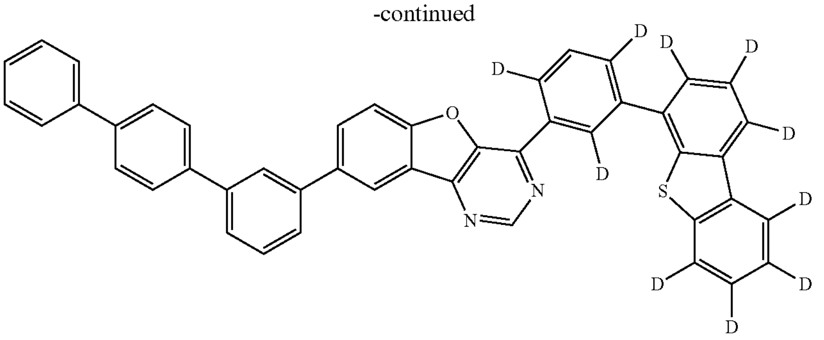

(530)

Figure 56A:
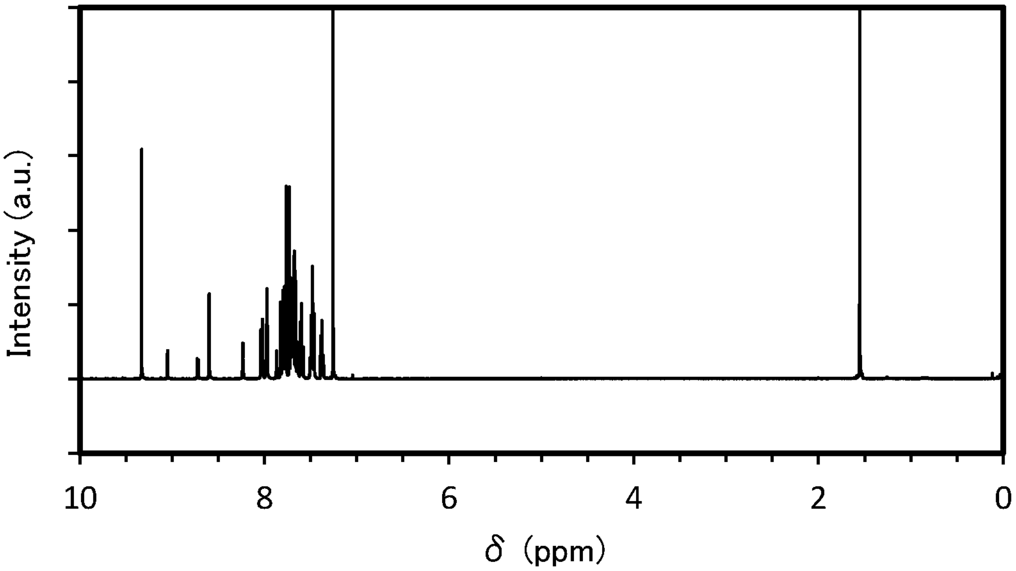
FIGS. 56A and 56B show $^1$H NMR spectra of 8mpTP-4mDBtPBfpm-$d_{10}$.

Measurement results obtained by nuclear magnetic resonance ($^1$H-NMR) spectroscopy of the pale yellow solid obtained in the above step are shown below. FIG. 56A shows the $^1$H-NMR chart. The results reveal that 8mpTP-4mDBtPBfpm-$d_{10}$, which is represented by the structural formula (530) and is one embodiment of the present invention, was obtained in Synthesis example 5.

$^1$H-NMR. δ ($CDCl_3$, 500 MHz): 7.36-7.39 (m, 1H), 7.46-7.51 (m, 2H), 7.60 (t, J=7.45 Hz, 1H), 7.66-7.74 (m, 6H), 7.77-7.83 (m, 4H), 7.97-7.99 (m, 1H), 8.03 (dd, J1=8.59 Hz, J2=1.72 Hz, 1H), 8.60 (sd, J=1.72 Hz, 1H), 9.33 (s, 1H).

Figure 56B:
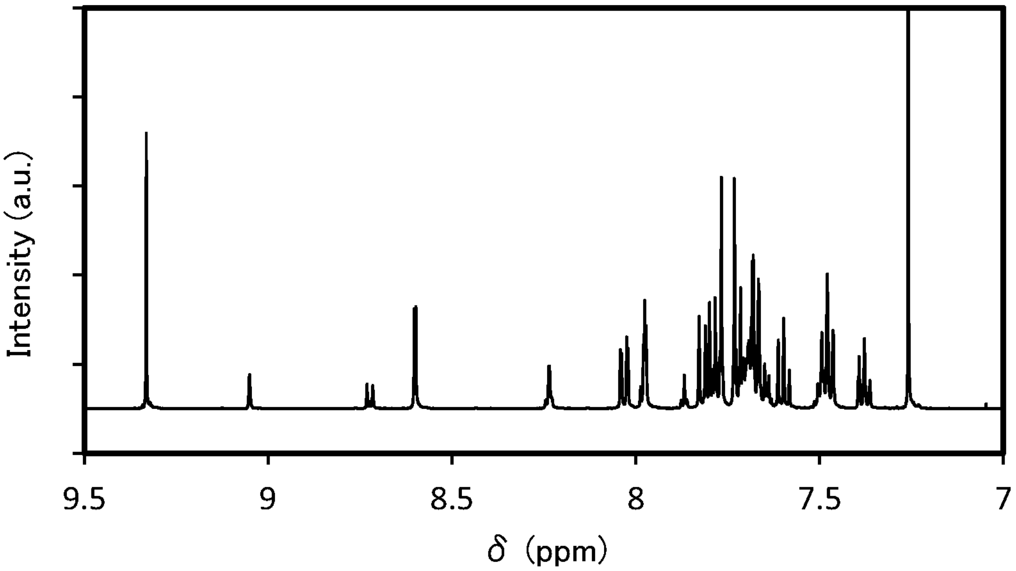
Figure 57A:
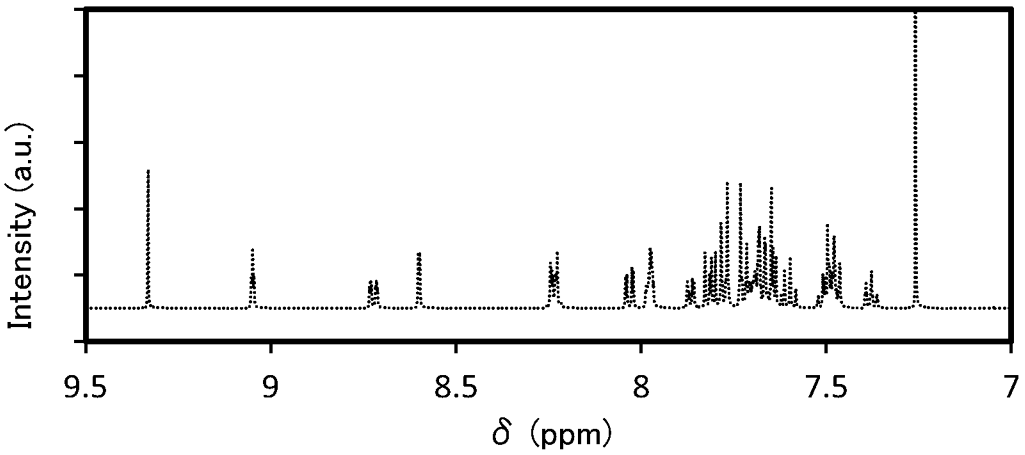
FIG. 57A shows a $^1$H NMR spectrum of 8mpTP-4mDBtPBfpm.
Figure 57B:
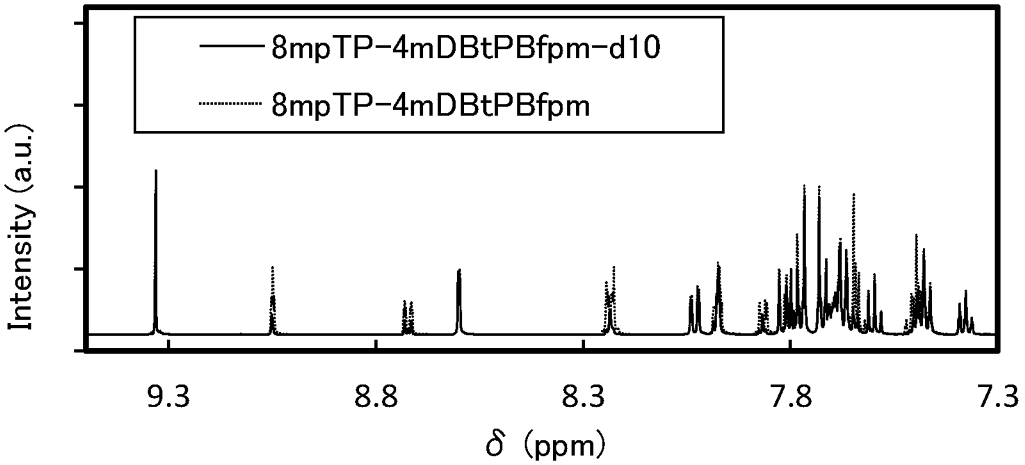
FIGS. 57B and 57C show $^1$H NMR spectra of 8mpTP-4mDBtPBfpm-$d_{10}$ and 8mpTP-4mDBtPBfpm.
Figure 57C:
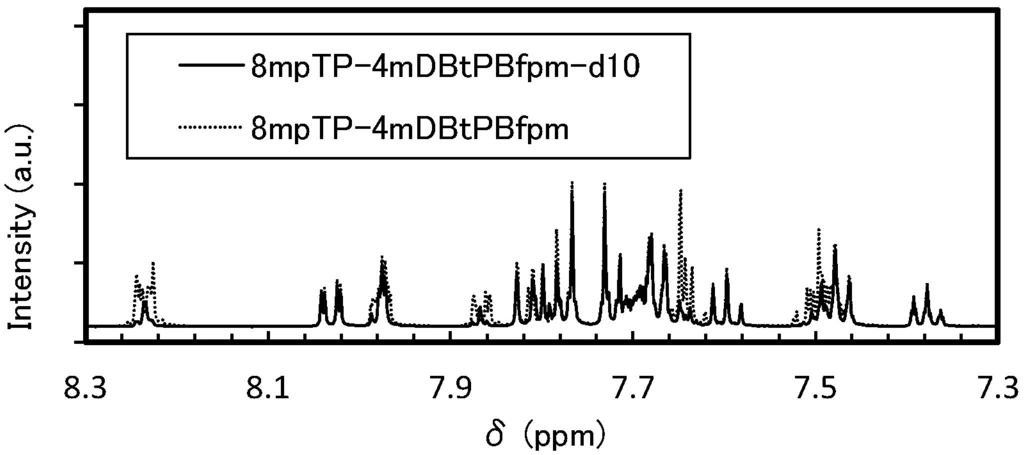

In FIG. 56B, peaks having low intensity were observed around δ=8.23 ppm to 8.24 ppm, 8.72 ppm to 8.73 ppm, or the like. They are assumed to be protium that was not deuterated and remained in Synthesis Scheme (e-1). The deuteration rate of 8mpTP-4mDBtPBfpm-$d_{10}$ was estimated. FIG. 57A shows the $^1$H-NMR chart of 8mpTP-4mDBtPBfpm that is a non-deuterated substance of 8mpTP-4mDBtPBfpm-$d_{10}$. FIG. 57B is a diagram of δ=7.30 ppm to 9.50 ppm, which compares 8mpTP-4mDBtPBfpm-$d_{10}$ and 8mpTP-4mDBtPBfpm that are normalized with a signal in δ=9.33 ppm. FIG. 57C is an enlarged view of δ=7.30 ppm to 8.30 ppm in FIG. 57B. In FIG. 57B, peaks having low intensity around δ=8.23 ppm to 8.24 ppm, 8.72 ppm to 8.73 ppm, or the like are peaks derived from protium that was not deuterated and remained in Synthesis Scheme (e-1). With the use of the peaks, the deuteration rate of 8mpTP-4mDBtPBfpm-$d_{10}$ was estimated to be approximately 75%.

<Characteristics of 8mpTP-4mDBtPBfpm-$d_{10}$>

Figure 58:
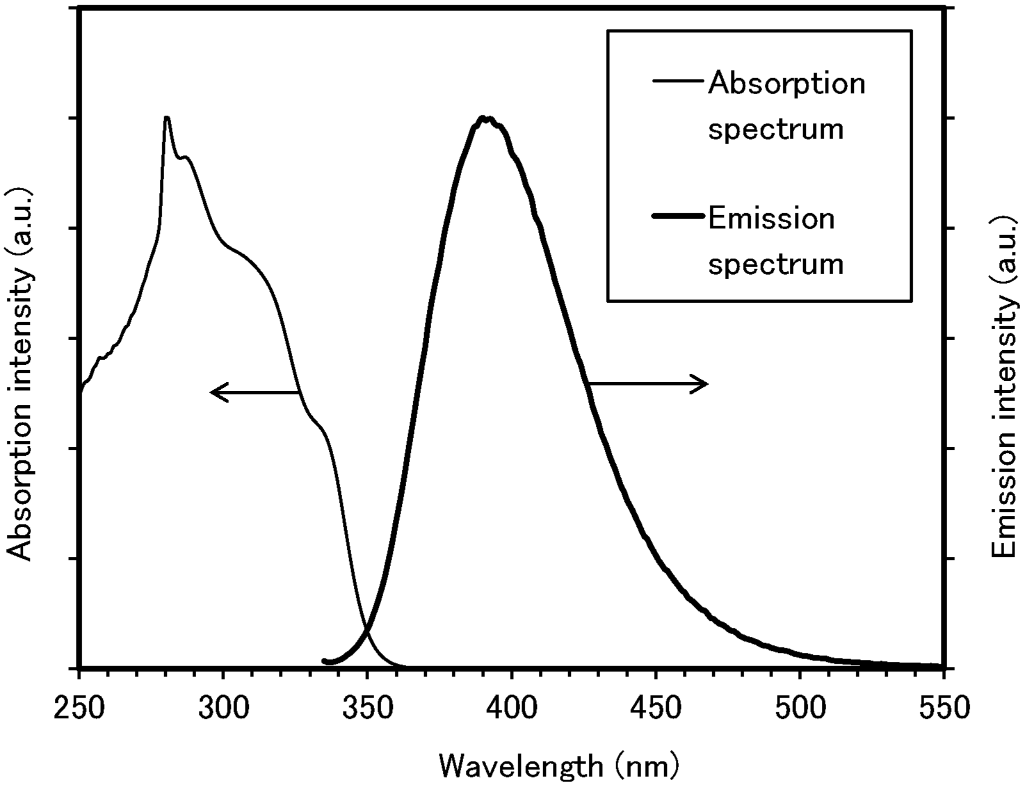
FIG. 58 shows an absorption spectrum and an emission spectrum of 8mpTP-4mDBtPBfpm-$d_{10}$ in a toluene solution.

Then, the ultraviolet-visible absorption spectrum (hereinafter, simply referred to as "absorption spectrum") and emission spectrum of a toluene solution of 8mpTP-4mDBtPBfpm-$d_{10}$ were measured. The absorption spectrum was measured at room temperature with an ultraviolet-visible light spectrophotometer (V-770DS, produced by JASCO Corporation) in a state where the toluene solution was put in a quartz cell. The emission spectrum was measured at room temperature with a fluorescence spectrophotometer (FP-8600DS, produced by JASCO Corporation) in a state where the toluene solution was put in a quartz cell. FIG. 58 shows results of the measured absorption spectrum and emission spectrum. The horizontal axis represents the wavelength and the vertical axes represent the absorption intensity and the emission intensity. The absorption spectrum shown in FIG. 58 is a result obtained by subtraction of an absorption spectrum of only toluene in a quartz cell from the measured absorption spectrum of the toluene solution in the quartz cell.

As shown in FIG. 58, in the toluene solution of 8mpTP-4mDBtPBfpm-$d_{10}$, absorption peaks were observed around 307 nm and 333 nm, and an emission peak was observed around 390 nm (excitation wavelength: 300 nm).

Figure 59:
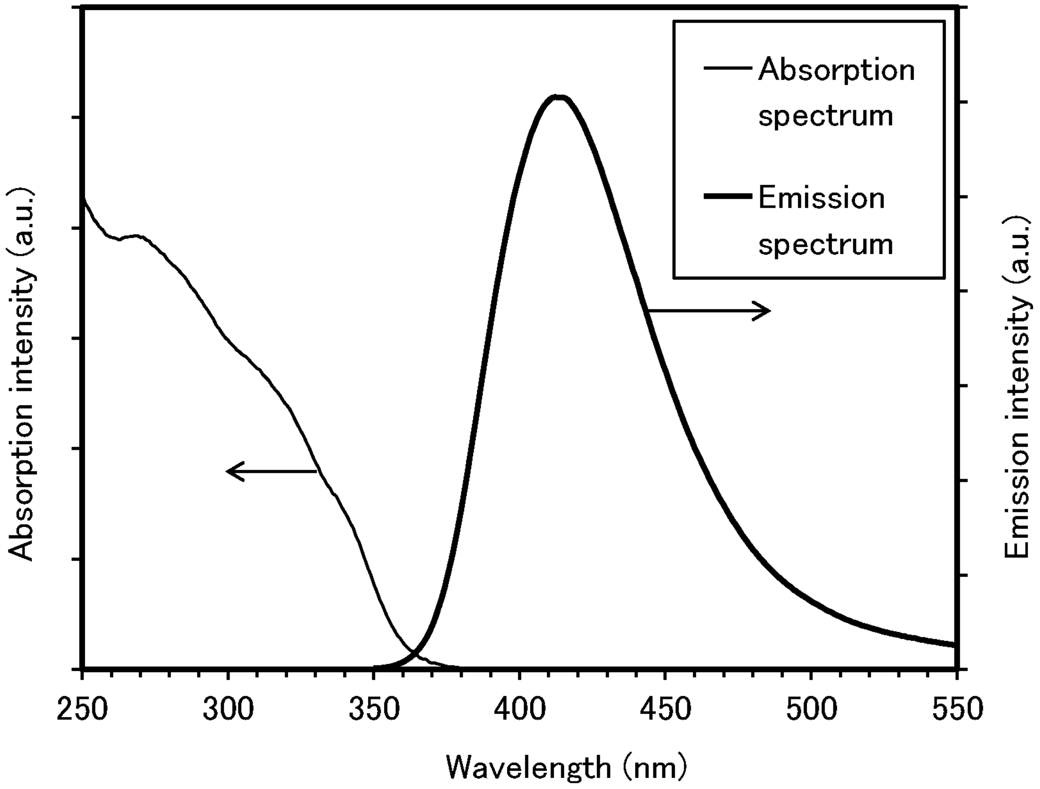
FIG. 59 shows an absorption spectrum and an emission spectrum of a thin film of 8mpTP-4mDBtPBfpm-$d_{10}$.

Next, the absorption spectrum and emission spectrum of a solid thin film of 8mpTP-4mDBtPBfpm-$d_{10}$ were measured. The solid thin film was fabricated over a quartz substrate by a vacuum evaporation method. The absorption spectrum of the thin film was calculated using an absorbance ($-\log_{10}$ [% T/(100−% R)]) obtained from the transmittance and reflectance of the thin film including the substrate. Note that % T represents transmittance and % R represents reflectance. The absorption spectrum was measured with a UV-visible spectrophotometer (U-4100 manufactured by Hitachi High-Technologies Corporation). The emission spectrum was measured using a spectrofluorometer (FP-8600DS manufactured by JASCO Corporation). FIG. 59 shows the measurement results of the obtained absorption and emission spectra of the solid thin film. The horizontal axis represents the wavelength and the vertical axes represent the absorption intensity and the emission intensity.

From the results in FIG. 59, in the solid thin film of 8mpTP-4mDBtPBfpm-$d_{10}$, absorption peaks were observed around 275 nm, 312 nm, and 345 nm, and an emission peak was observed around 412 nm (excitation wavelength: 340 nm).

The ionization potential value of a thin film of 8mpTP-4mDBtPBfpm-$d_{10}$ was measured in the air with a photoelectron spectrometer (AC-3, produced by Riken Keiki Co., Ltd.). The obtained ionization potential value was converted into a negative value, so that the HOMO level of 8mpTP-4mDBtPBfpm-$d_{10}$ was −6.28 eV. From the data of the absorption spectrum of the thin film, the absorption edge of 8mpTP-4mDBtPBfpm-$d_{10}$, which was obtained from Tauc plot with an assumption of direct transition, was 3.51 eV. Thus, the optical energy gap of 8mpTP-4mDBtPBfpm-$d_{10}$ in the solid state was estimated at 3.51 eV; from the values of the HOMO level obtained above and this energy gap, the LUMO level of 8mpTP-4mDBtPBfpm-$d_{10}$ can be estimated at −2.77 eV. This reveals that 8mpTP-4mDBtPBfpm-$d_{10}$ in the solid state has an energy gap as wide as 3.51 eV.

The glass transition temperature (Tg) of 8mpTP-4mDBtPBfpm-$d_{10}$ was measured. Note that Tg was measured with a differential scanning calorimeter (DSC8500 produced by PerkinElmer Japan Co., Ltd.) in a state where a powder was put on an aluminum cell. The result showed that the Tg of 8mpTP-4mDBtPBfpm-$d_{10}$ was 121° C.

Furthermore, the electrochemical characteristics (oxidation reaction characteristics and reduction reaction characteristics) of 8mpTP-4mDBtPBfpm-$d_{10}$ were measured by cyclic voltammetry (CV). An electrochemical analyzer (ALS model 600B, manufactured by BAS Inc.) was used for the measurement. The solution for the measurement was prepared by using dehydrated N,N-dimethylformamide (DMF) (produced by Aldrich Corp., 99.8%, catalog number: 22705-6) as a solvent, dissolving a supporting electrolyte, tetra-n-butylammonium perchlorate ($n\text{-}Bu_4NClO_4$) (produced by Tokyo Chemical Industry Co., Ltd., catalog number: T0836), at a concentration of 100 mmol/L, and then dissolving the object of measurement at a concentration of 2 mmol/L.

A platinum electrode (PTE platinum electrode, manufactured by BAS Inc.) was used as a working electrode, another platinum electrode (Pt counter electrode (5 cm), manufactured by BAS Inc.) was used as an auxiliary electrode, and an $Ag/Ag^+$ electrode (RE7 reference electrode for nonaqueous solvent, manufactured by BAS Inc.) was used as a reference electrode. Note that the measurement was performed at room temperature (20° C. to 25° C.).

In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the oxidation potential Ea[V] of 8mpTP-4mDBtPBfpm-$d_{10}$ was not observed. Therefore, the HOMO level is estimated to be lower than −6.2 eV. In contrast, the LUMO level was found to be −3.01 eV from the measurement result of the reduction potential Ec [V]. In addition, the results of repetitive measurement of the oxidation-reduction wave showed that when the waveform of the first cycle was compared with that of the hundredth cycle, 87% of the peak intensity were maintained in the Ec measurement, which confirmed that 8mpTP-4mDBtPBfpm-$d_{10}$ had high resistance to reduction.

Example 7

Synthesis Example 6

In this example, a method for synthesizing 8-(1,1':4',1"-terphenyl-3-yl)-4-[3-(dibenzothiophen-4-yl-1,2,3,6,7,8,9-$d_7$)phenyl]-[1]benzofuro[3,2-d]pyrimidine (abbreviation: 8mpTP-4mDBtPBfpm-$d_7$) shown as Structural Formula (529) in Embodiment 1 is specifically described.

[Chemical Formula 100]

(529)

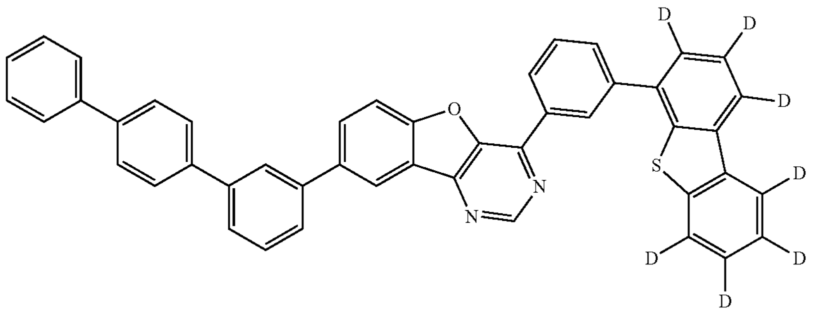

Step 6-1; Synthesis of 4-(3-bromophenyl)dibenzothiophene-1,2,3,6,7,8,9-$d_7$ Into a 200 mL three-neck flask in which the air was replaced with nitrogen were put 4.1 g (15 mmol) of molybdenum(V) pentachloride (abbreviation: $MoCl_5$) and 63 mL of deuterated toluene (abbreviation: toluene-$d_8$), and the air in the flask was replaced with nitrogen again. Then, 10 g (29 mmol) of 4-(3-bromophenyl)dibenzothiophene was added thereto, and the mixture was refluxed under a nitrogen stream at 100° C. for 4 hours. After the reaction, TN hydrochloric acid was added to the mixture, and the precipitated solid was removed by suction filtration. The filtrate was subjected to extraction with toluene, and the obtained organic layer was washed with a saturated aqueous solution of sodium hydrogen carbonate and saturated saline, and then was dried with magnesium sulfate. This mixture was separated by gravity filtration, and the filtrate was concentrated to give a brown oily substance. The obtained oily substance was purified by silica gel column chromatography (hexane), so that 7.9 g of the target oily substance was obtained in a yield of 77%. The synthesis scheme of Step 6-1 is shown in (f-1) below.

[Chemical formula 101]

(f-1)

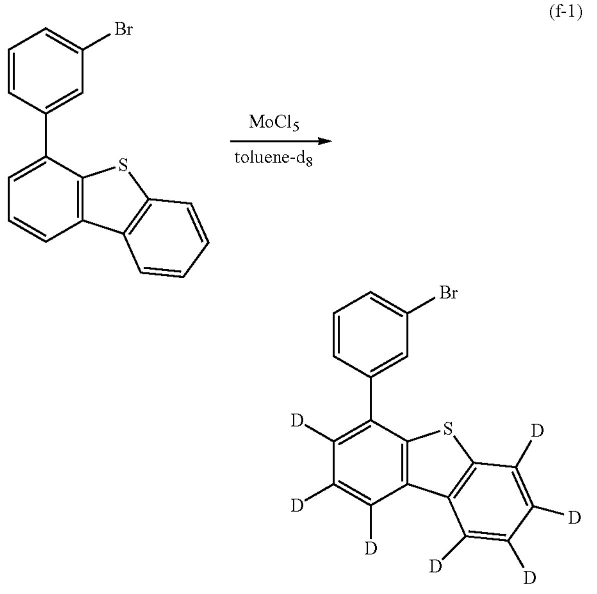

Figure 60A:
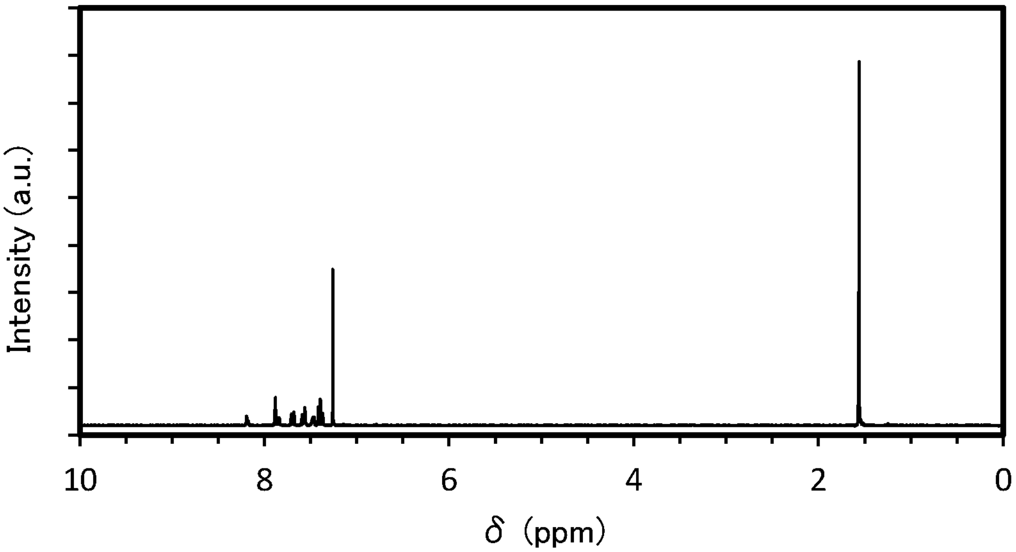
FIGS. 60A and 60B show $^1$H NMR spectra of an organic compound obtained in Example 6.

Analysis results by nuclear magnetic resonance ($^1$H-NMR) spectroscopy of 4-(3-bromophenyl)dibenzothiophene-1,2,3,6,7,8,9-$d_7$ obtained in Step 6-1 are shown below. In addition, FIGS. 60A and 60B show $^1$H-NMR charts.

$^1$H-NMR. δ ($CDCl_3$, 300 MHz): 7.37-7.42 (m, 1H), 7.56-7.60 (m, 1H), 7.68-7.71 (m, 1H), 7.88-7.89 (m, 1H).

Figure 60B:
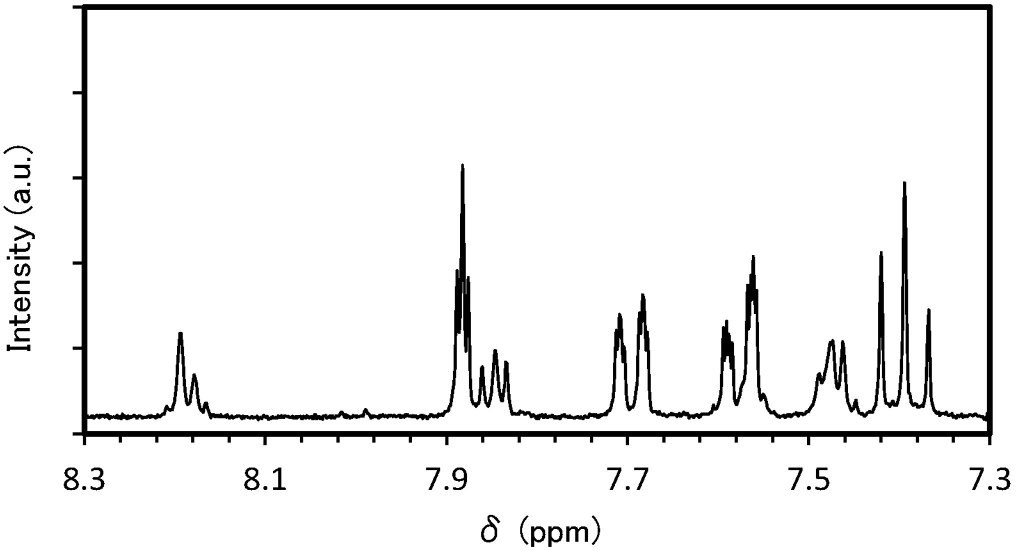
Figure 61A:
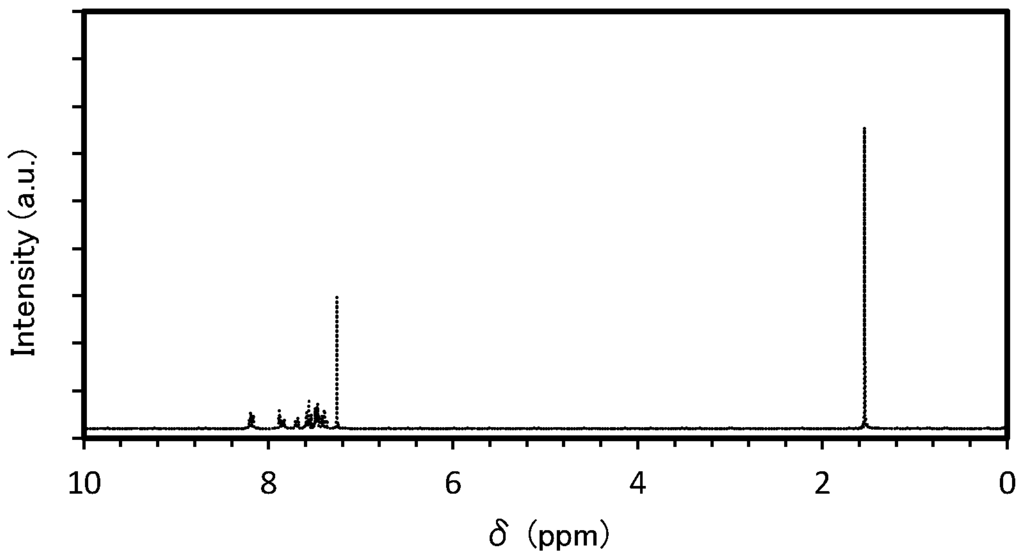
FIG. 61A shows a $^1$H NMR spectrum of the organic compound obtained in Example 6.
Figure 61B:
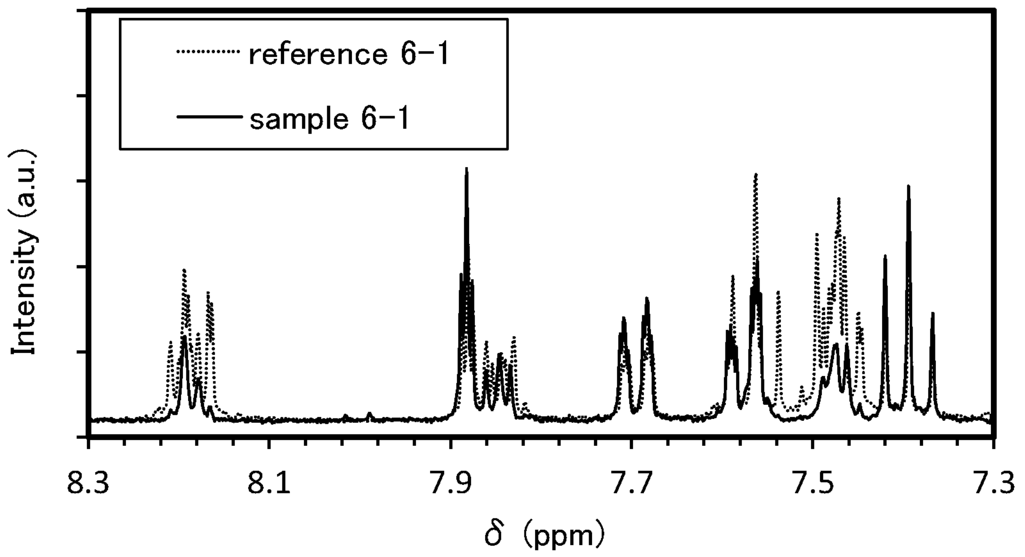
FIG. 61B shows $^1$H NMR spectra of the organic compound obtained in Example 6 and reference 6-1.

In FIG. 60B, peaks that appear around δ=7.81 ppm to 7.86 ppm, δ=8.16 ppm to 8.21 ppm, or the like are assumed to be protium that was not deuterated and remained in Synthesis Scheme (f-1). The deuteration rate of 4-(3-bromophenyl) dibenzothiophene-1,2,3,6,7,8,9-$d_7$ was estimated. FIG. 61A shows the $^1$H-NMR chart of 4-(3-bromophenyl)dibenzothiophene, and FIG. 61B is an enlarged view of δ=7.30 ppm to 8.30 ppm, which compares 4-(3-bromophenyl)dibenzothiophene-1,2,3,6,7,8,9-$d_7$ (sample 6-1) and 4-(3-bromophenyl)dibenzothiophene (reference 6-1). From the results, the deuteration rate of 4-(3-bromophenyl)dibenzothiophene-1,2,3,6,7,8,9-$d_7$ was estimated to be approximately 68%.

Step 6-2; Synthesis of 2-[3-(dibenzo[b,d]thiophen-4-yl-1,2,3,6,7,8,9-$d_7$)phenyl]-4,4,5,5-tetramethyl-1,3,2-dioxaborolane Into a 200 mL three-neck flask were put 7.9 g (23 mmol) of 4-(3-bromophenyl)dibenzothiophene-1,2,3,6,7,8,9-$d_7$ obtained in Step 6-1, 7.5 g (30 mmol) of bis(pinacolato) diboron, 8.7 g (89 mmol) of potassium acetate, and 113 mL of N,N-dimethylformamide (DMF). The mixture in the flask was stirred under reduced pressure and degassed. After that, the mixture was heated at 60° C. under a nitrogen stream, 0.93 g (1.1 mmol) of [1,1'-bis(diphenylphosphino)ferrocene]dichloropalladium(II) dichloromethane adduct (abbreviation: $Pd(dppf)_2Cl_2{\cdot}CH_2Cl_2$) was added thereto, and then the temperature was raised to 100° C. and the mixture was stirred for 4 hours. After a predetermined time elapsed, toluene and water were added to the mixture, and the precipitated solid was removed by suction filtration. The filtrate was subjected to extraction with toluene, and the obtained organic layer was washed with saturated saline and dried with magnesium sulfate to give the mixture. This mixture was separated by gravity filtration, and the filtrate was concentrated to give a black oily substance. The obtained oily substance was purified by silica gel column chromatography (the ratio was changed from toluene: hexane=1:1 to toluene 100% to perform a gradient), so that 6.9 g of the target white solid of 2-[3-(dibenzo[b,d]thiophen-4-yl-1,2,3,6,7,8,9-$d_7$)phenyl]-4,4,5,5-tetramethyl-1,3,2-dioxaborolane was obtained in a yield of 77%. The synthesis scheme of Step 6-2 is shown in (f-2) below.

[Chemical Formula 102]

(f-2)

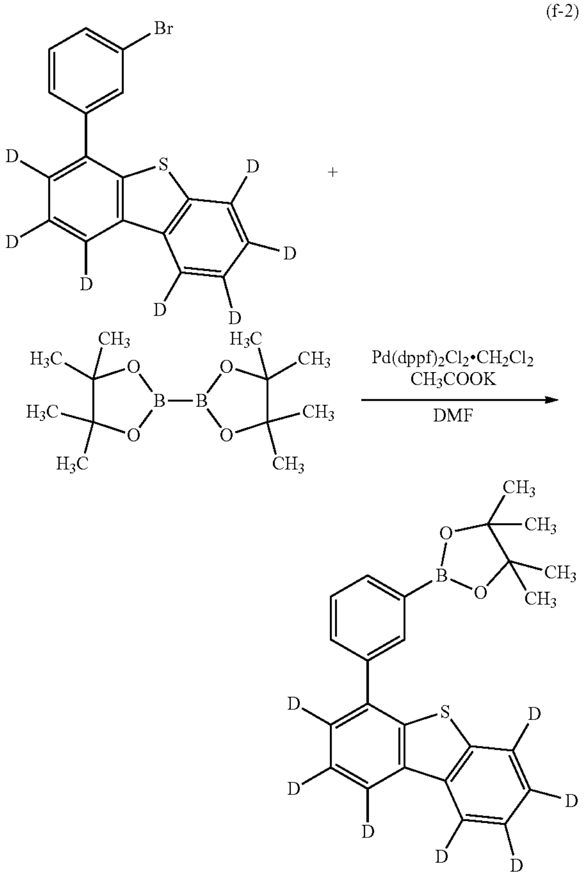

Figure 62A:
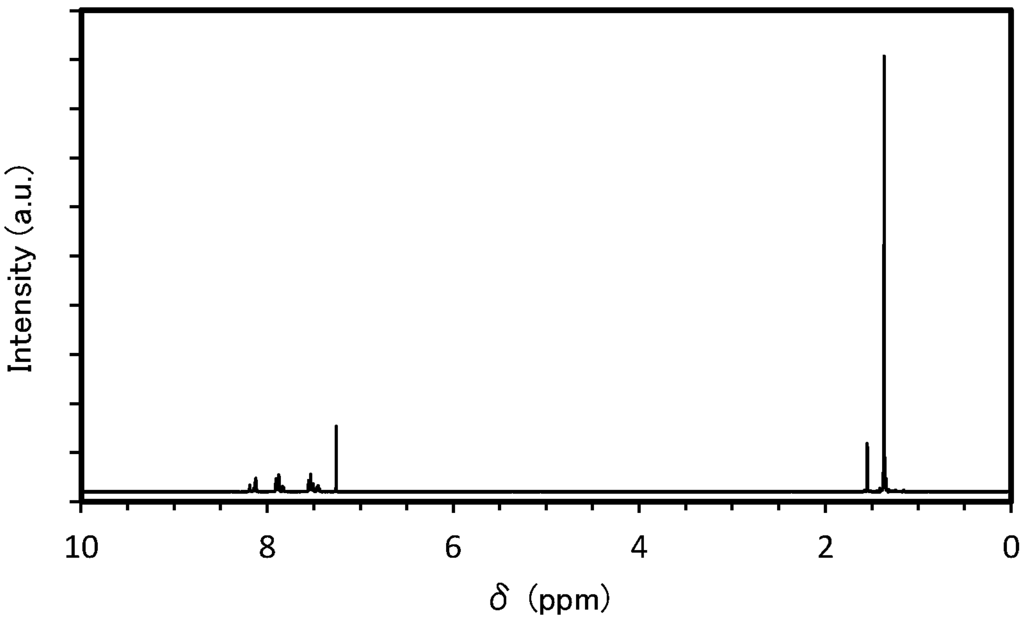
FIGS. 62A and 62B show $^1$H NMR spectra of an organic compound obtained in Example 7.

Analysis results by nuclear magnetic resonance ($^1$H-NMR) spectroscopy of 2-[3-(dibenzo[b,d]thiophen-4-yl-1,2,3,6,7,8,9-$d_7$)phenyl]-4,4,5,5-tetramethyl-1,3,2-dioxaborolane obtained in Step 6-2 are shown below. In addition, FIGS. 62A and 62B show $^1$H-NMR charts.

$^1$H-NMR. δ ($CDCl_3$, 300 MHz): 1.37 (s, 12H), 7.51-7.56 (m, 1H), 7.89 (dd, J1=7.0 Hz, J2=1.8 Hz, 2H), 8.12 (s, 1H).

Figure 62B:
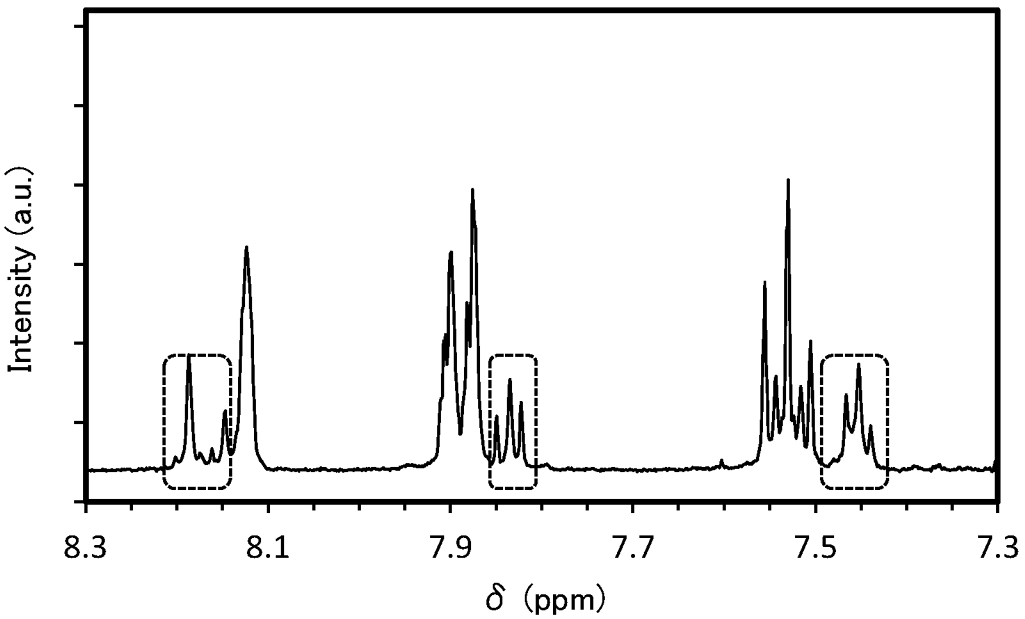

In FIG. 62B, signals that appear around δ=7.4 ppm to 7.5 ppm and other regions surrounded with dashed lines are assumed to be peaks derived from protium that were not deuterated and remained in Synthesis Scheme (f-2).

Step 6-3; Synthesis of 8-chloro-4[3-(dibenzothiophen-4-yl-1,2,3,6,7,8,9-$d_7$)phenyl]-[1]benzofuro[3,2-d]pyrimidine Into a 200 mL three-neck flask were put 5.7 g (15 mmol) of 2-[3-(dibenzo[b,d]thiophen-4-yl-1,2,3,6,7,8,9-$d_7$)phenyl]-4,4,5,5-tetramethyl-1,3,2-dioxaborolane obtained in Step 6-2, 2.9 g (12 mmol) of 4,8-dichloro[1]benzofuro[3,2-d]pyrimidine, 5.1 g (37 mmol) of potassium carbonate, 100 mL of toluene, 22 mL of ethanol, and 18 mL of water. The mixture in the flask was stirred under reduced pressure and degassed. After that, the mixture was heated at 60° C. under a nitrogen stream, 2.8 g (2.4 mmol) of tetrakis(triphenylphosphine)palladium(0) (abbreviation: $(Pd(PPh_3)_4)$ was added thereto; then, the temperature was raised to 90° C. and the mixture was stirred for 13 hours. After the reaction, this mixture was suction-filtered, and the obtained residue was washed with water and ethanol. The obtained residue was dissolved in toluene by heating, followed by filtration through a filter aid in which Celite, alumina, and Celite were stacked in this order. The filtrate was concentrated and then recrystallized with toluene to give 5.0 g of a white solid in a yield of 89%. The synthesis scheme of Step 6-3 is shown in (f-3) below.

[Chemical Formula 103]

(f-3)

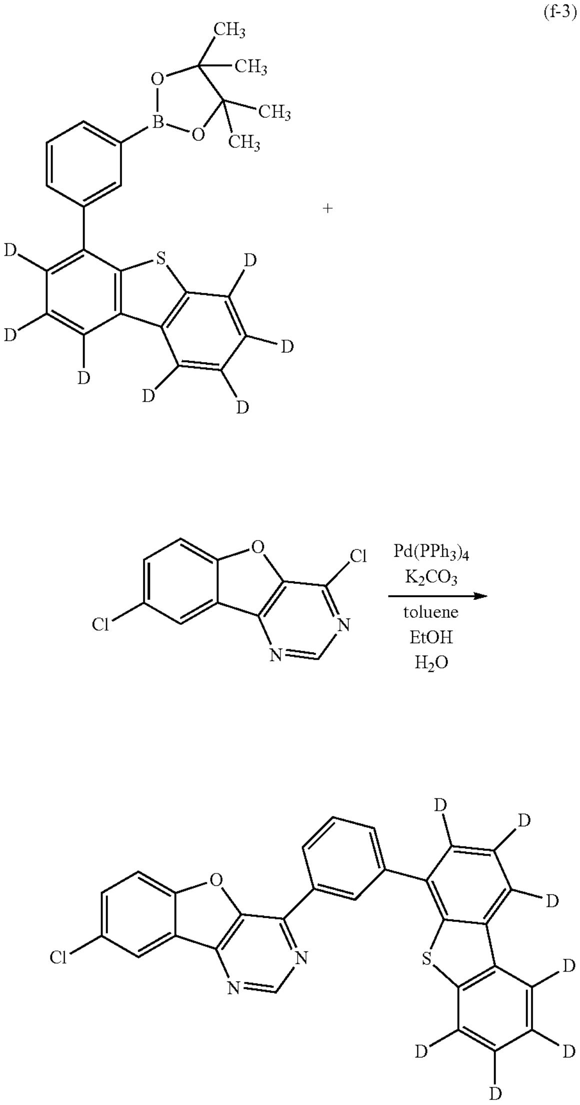

Figure 63A:
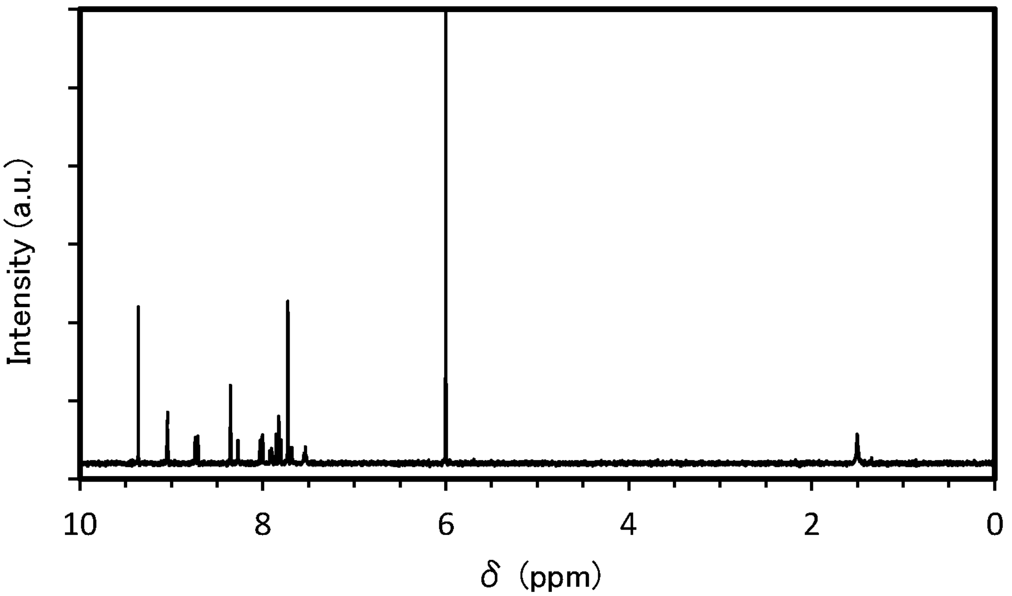
FIGS. 63A and 63B show $^1$H NMR spectra of the organic compound obtained in Example 7.

Analysis results by nuclear magnetic resonance ($^1$H-NMR) spectroscopy of 8-chloro-4[3-(dibenzothiophen-4-yl-1,2,3,6,7,8,9-$d_7$)phenyl]-[1]benzofuro[3,2-d]pyrimidine (sample 6-2) obtained in Step 6-3 are shown below. In addition, FIGS. 63A and 63B show $^1$H-NMR charts.

$^1$H-NMR. δ (C2D2Cl4, 300 MHz): 7.73 (d, J=1.5 Hz, 2H), 7.83 (t, J=8.1 Hz, 1H), 8.01 (dt, J1=5.7 Hz, J2=2.1 Hz, 1H), 8.35 (t, J=1.3 Hz, 1H), 8.72 (dt, J1=7.9 Hz, J2=1.5 Hz, 1H), 9.04 (t, J=1.6 Hz, 1H), 9.36 (s, 1H).

Figure 63B:
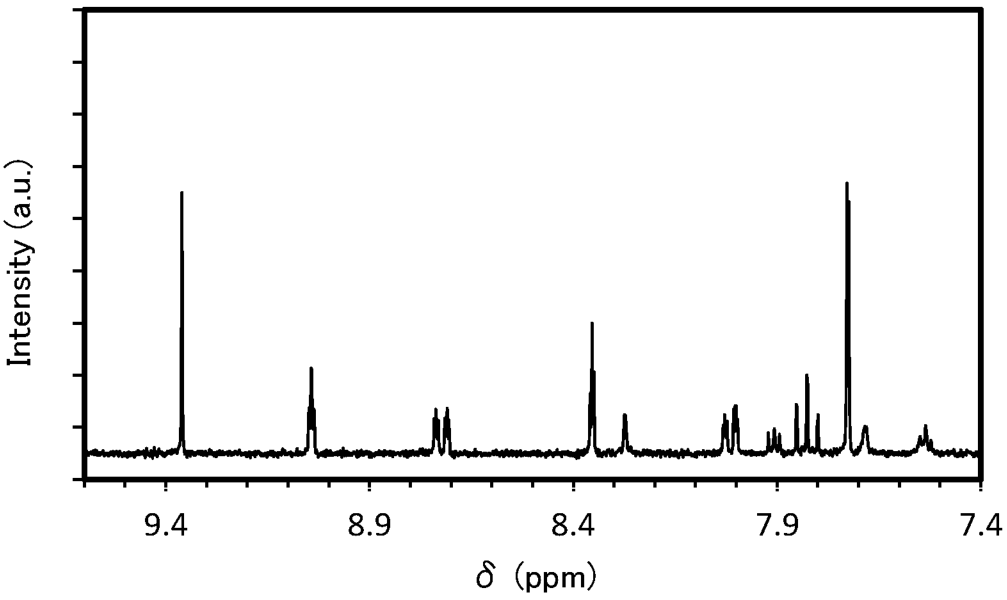

In FIG. 63B, signals that appear around δ=7.5 ppm to 7.6 ppm, δ=8.2 ppm to 8.3 ppm, or the like are assumed to be peaks derived from protium that was not deuterated and remained in Synthesis Scheme (f-3).

Figure 64A:
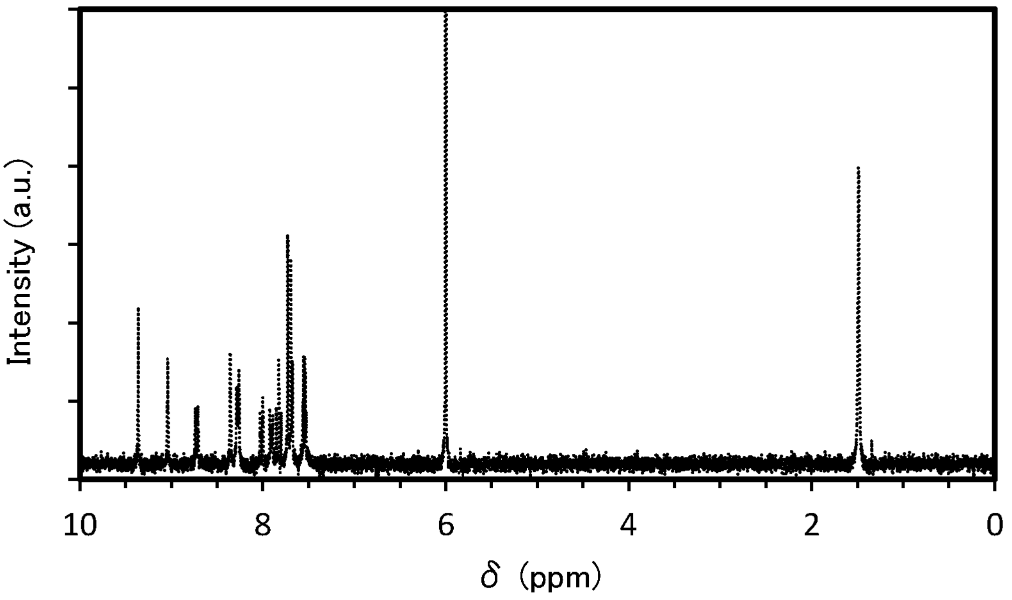
FIG. 64A shows a $^1$H NMR spectrum of reference 6-2.
Figure 64B:
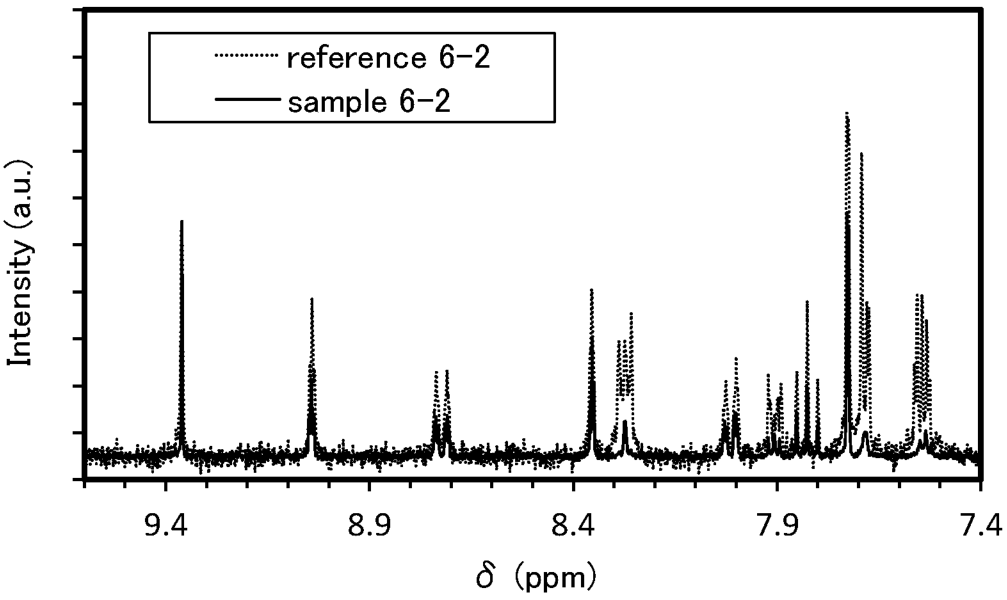
FIG. 64B shows $^1$H NMR spectra of the organic compound obtained in Example 7 and reference 6-2.

Here, the deuteration rate was estimated from $^1$H-NMR. FIG. 64A shows the $^1$H-NMR chart of 8-chloro-4[3-(dibenzothiophen-4-yl)phenyl]-[1]benzofuro[3,2-d]pyrimidine, and FIG. 64B is an enlarged view of δ=7.40 ppm to 9.60 ppm, which compares 8-chloro-4[3-(dibenzothiophen-4-yl-1,2,3,6,7,8,9-$d_7$)phenyl]-[1]benzofuro[3,2-d]pyrimidine and 8-chloro-4[3-(dibenzothiophen-4-yl)phenyl]-[1]benzofuro[3,2-d]pyrimidine (reference 6-2). Here, in sample 6-2 and reference 6-2, the peak appearing in δ=9.36 ppm is a peak derived from [1]benzofuro[3,2-d]pyrimidine. The deuteration rate of sample 6-2 was calculated using the peak as the reference (100%). As a result, the deuteration rate of 8-chloro-4[3-(dibenzothiophen-4-yl-1,2,3,6,7,8,9-$d_7$)phenyl]-[1]benzofuro[3,2-d]pyrimidine was estimated to be approximately 74%.

Step 6-4; Synthesis of 8-(1,1':4',1"-terphenyl-3-yl)-4-[3-(dibenzothiophen-4-yl-1,2,3,6,7,8,9-$d_7$)phenyl]-[1]benzofuro[3,2-d]pyrimidine (abbreviation: 8mpTP-4mDBtPBfpm-$d_7$)

Into a 200 mL three-neck flask were put 2.5 g (5.3 mmol) of 8-chloro-4[3-(dibenzothiophen-4-yl-1,2,3,6,7,8,9-$d_7$)phenyl]-[1]benzofuro[3,2-d]pyrimidine obtained in Step 6-3, 2.3 g (6.4 mmol) of 4,4,5,5-tetramethyl-2-(1,1':4',1"-terphenyl)-3-yl-1,3,2-dioxaborolane, 4.1 g (19 mmol) of tripotassium phosphate, 1.2 g (16 mmol) of tert-butylalcohol (abbreviation: tBuOH), and 60 mL of diethylene glycol dimethyl ether (abbreviation: diglyme), and the mixture in the flask was stirred under reduced pressure and degassed. After that, the mixture was heated at 60° C. under a nitrogen stream, 0.19 g (0.86 mmol) of palladium(II) acetate (abbreviation: $Pd(OAc)_2$) and 0.40 g (1.1 mmol) of di(1-adamantyl)-N-butylphosphine (abbreviation: cataCxiumA) were added to the flask, and then the mixture was stirred at 130° C. for 16 hours. After the reaction, water was added to the mixture and suction filtration was performed, and the obtained residue was washed with water and ethanol. The obtained residue was dissolved in toluene by heating, followed by filtration. The filtrate was concentrated and purified by silica gel column chromatography (the ratio was changed from toluene 100% to toluene:ethyl acetate=30:1 to perform a gradient). The resulting solid was recrystallized with toluene to give 2.4 g of a white solid in a yield of 67%. Then, 2.3 g of the obtained white solid was purified by a train sublimation method. In the purification by sublimation, the solid was heated at 350° C. for 6 hours under a pressure of 2.9 Pa with an argon gas flow rate of 15 mL/min. After the sublimation purification by sublimation, 0.82 g of a target pale yellow solid was obtained at a collection rate of 44%. The synthesis scheme of Step 6-4 is shown in (f-4) below.

[Chemical Formula 104]

(f-4)

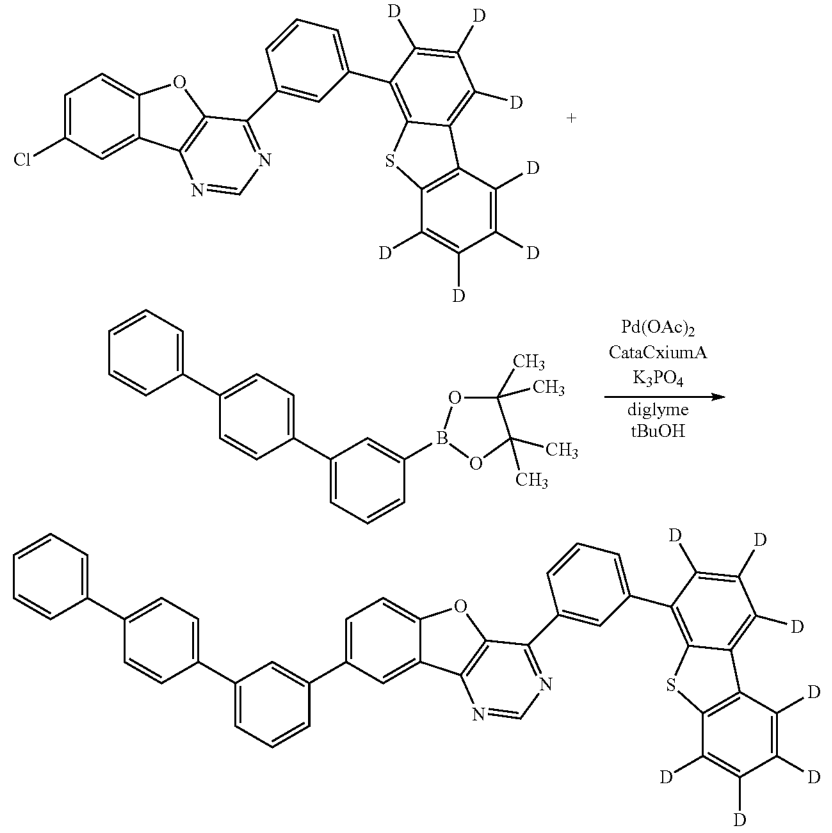

(529)

Figure 65A:
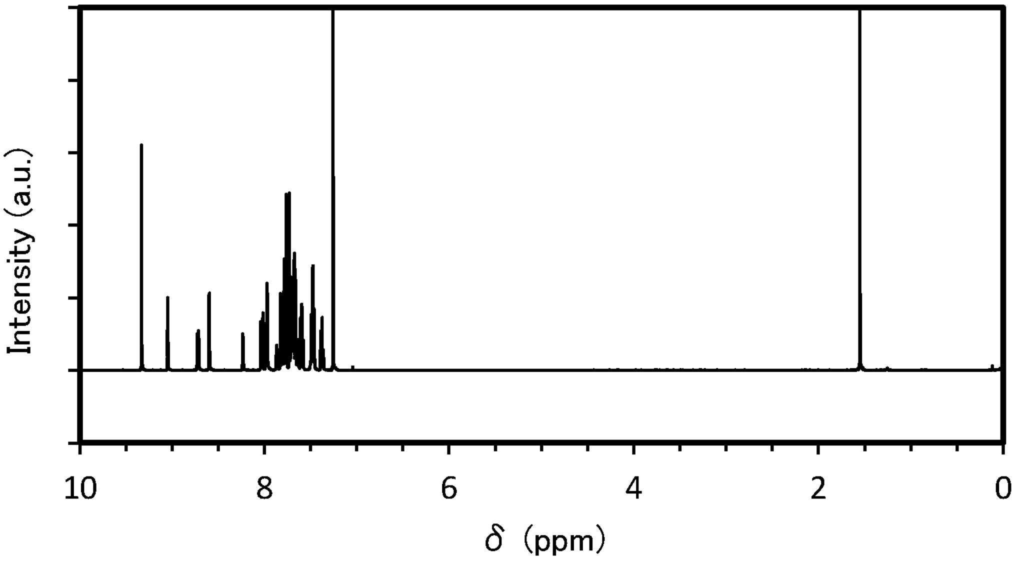
FIGS. 65A and 65B show $^1$H NMR spectra of 8mpTP-4mDBtPBfpm-$d_7$.

Analysis results by nuclear magnetic resonance ($^1H$-NMR) spectroscopy of the pale yellow solid obtained in the above are shown below. FIG. 65A shows the $^1H$-NMR chart. The results reveal that 8mpTP-4mDBtPBfpm-$d_7$, the organic compound of one embodiment of the present invention represented by Structural Formula (529) above, was obtained in Synthesis example 6.

$^1H$-NMR. δ ($CDCl_3$, 500 MHz): 7.36-7.39 (m, 1H), 7.46-7.51 (m, 2H), 7.60 (t, J=7.45 Hz, 1H), 7.66-7.73 (m, 6H), 7.77-7.83 (m, 4H), 7.97-7.99 (m, 2H), 8.03 (dd, J1=8.59 Hz, J2=2.29 Hz, 1H), 8.60 (sd, J=1.72 Hz, 1H), 8.71-8.73 (m, 1H), 9.50 (t, J=1.72 Hz, 1H), 9.33 (s, 1H).

Figure 65B:
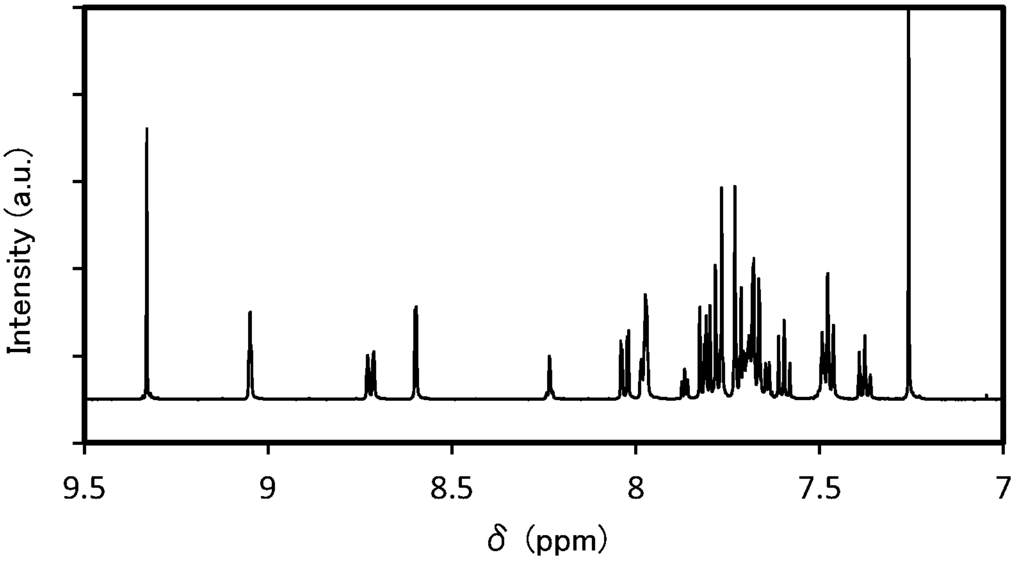
Figure 66A:
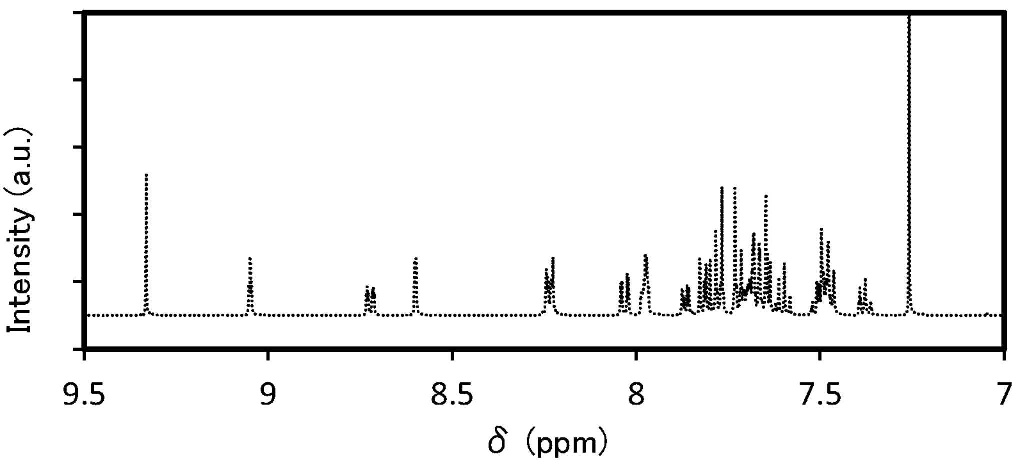
FIG. 66A shows a $^1$H NMR spectrum of 8mpTP-4mDBtPBfpm.
Figure 66B:
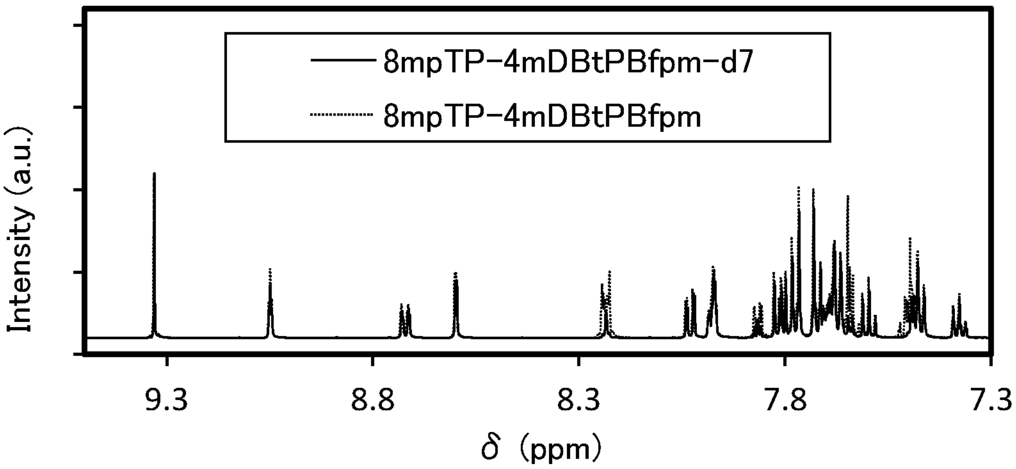
FIGS. 66B and 66C show $^1$H NMR spectra of 8mpTP-4mDBtPBfpm-$d_7$ and 8mpTP-4mDBtPBfpm.
Figure 66C:
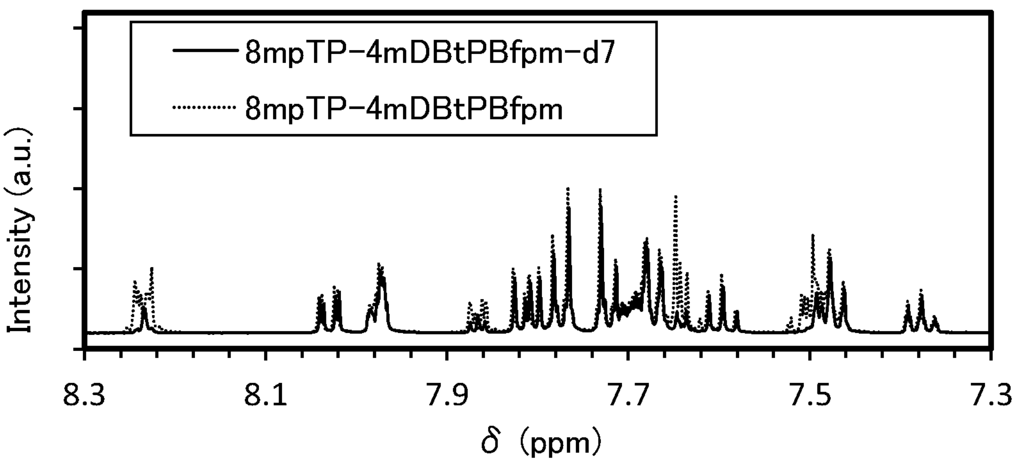

In FIG. 65B, peaks having low intensity were observed around δ=7.64 ppm to 7.65 ppm, 8.22 ppm to 8.25 ppm, or the like. They are assumed to be protium that was not deuterated and remained in Synthesis Scheme (f-1). The deuteration rate of 8mpTP-4mDBtPBfpm-$d_7$ was estimated using a signal in δ=9.33 ppm (s, 1H) as the reference. FIG. 66A shows the $^1H$-NMR chart of 8mpTP-4mDBtPBfpm that is a non-deuterated substance of 8mpTP-4mDBtPBfpm-$d_7$. FIG. 66B is a diagram of δ=7.30 ppm to 9.50 ppm, which compares 8mpTP-4mDBtPBfpm-$d_7$ and 8mpTP-4mDBtPBfpm that are normalized with a signal in δ=9.33 ppm. FIG. 66C is an enlarged view of δ=7.30 ppm to 8.30 ppm in FIG. 66B. In FIG. 66C, peaks that appear around δ=7.64 ppm to 7.65 ppm, δ=8.22 ppm to 8.25 ppm, or the like are assumed to be peaks derived from protium that was not deuterated and remained in Synthesis Scheme (f-1). Using the peak as a reference, the deuteration rate of 8mpTP-4mDBtPBfpm-$d_7$ was estimated to be approximately 68%.

<Characteristics of 8mpTP-4mDBtPBfpm-$d_7$>

Figure 67:
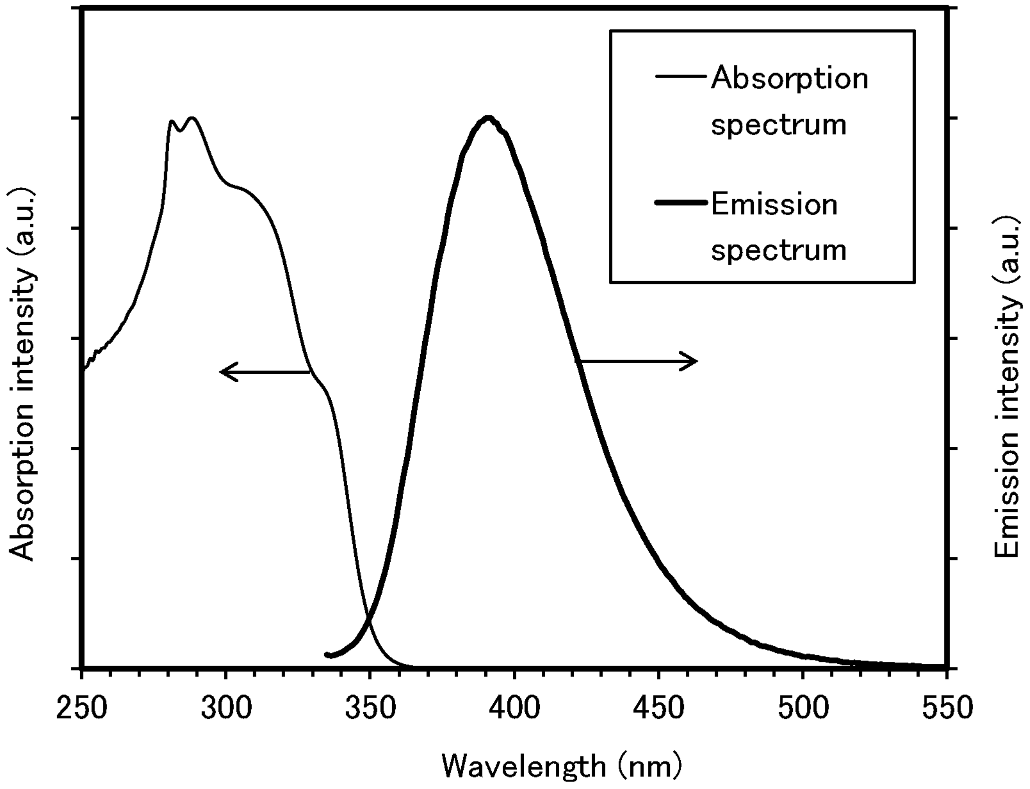
FIG. 67 shows an absorption spectrum and an emission spectrum in a toluene solution of 8mpTP-4mDBtPBfpm-$d_7$.

Then, the ultraviolet-visible absorption spectrum (hereinafter, simply referred to as "absorption spectrum") and emission spectrum of a toluene solution of 8mpTP-4mDBtPBfpm-$d_7$ were measured. The absorption spectrum was measured at room temperature with an ultraviolet-visible light spectrophotometer (V-770DS, produced by JASCO Corporation) in a state where the toluene solution was put in a quartz cell. The emission spectrum was measured at room temperature with a fluorescence spectrophotometer (FP-8600DS, produced by JASCO Corporation) in a state where the toluene solution was put in a quartz cell. FIG. 67 shows obtained measurement results of the absorption spectrum and the emission spectrum. The horizontal axis represents the wavelength and the vertical axes represent the absorption intensity and the emission intensity. The absorption spectrum shown in FIG. 67 is a result obtained by subtraction of an absorption spectrum of only toluene in a quartz cell from the measured absorption spectrum of the toluene solution in the quartz cell.

As shown in FIG. 67, in the toluene solution of 8mpTP-4mDBtPBfpm-$d_7$, absorption peaks were observed around 310 nm and 333 nm, and an emission peak was observed around 391 nm (excitation wavelength: 300 nm).

Figure 68:
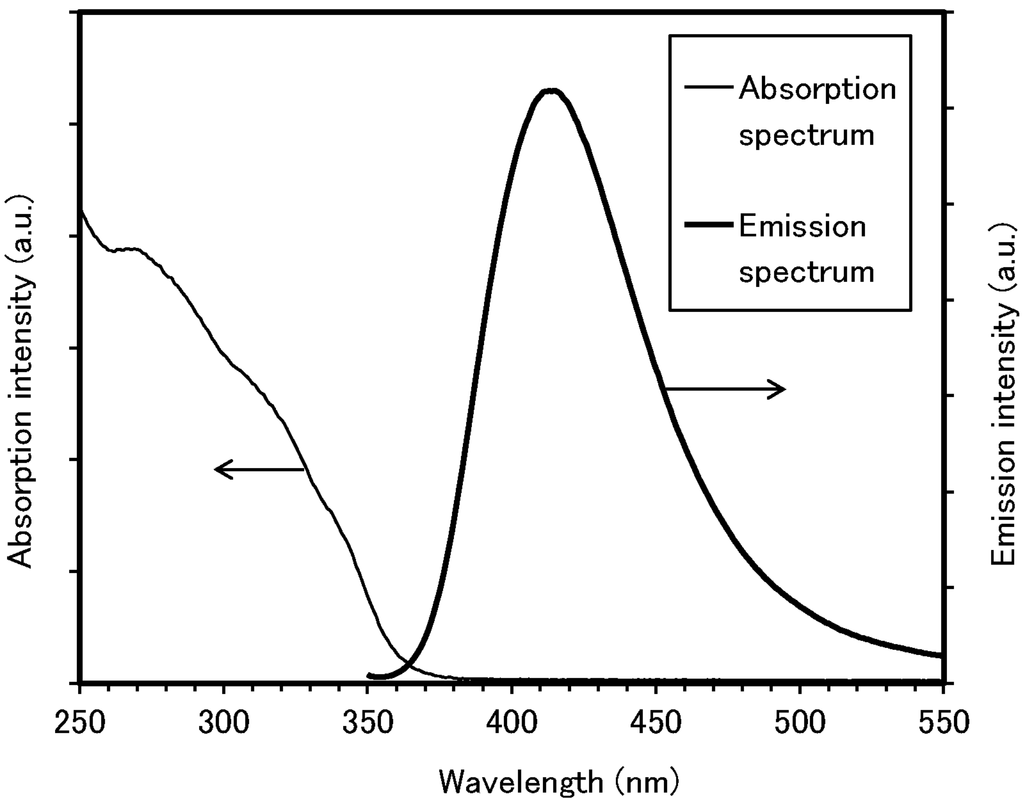
FIG. 68 shows an absorption spectrum and an emission spectrum of a thin film of 8mpTP-4mDBtPBfpm-$d_7$.

Next, the absorption spectrum and emission spectrum of a solid thin film of 8mpTP-4mDBtPBfpm-$d_7$ were measured. The solid thin film was fabricated over a quartz substrate by a vacuum evaporation method. The absorption spectrum of the thin film was calculated using an absorbance ($-\log_{10}$ [% T/(100−% R)]) obtained from the transmittance and reflectance of the thin film including the substrate. Note that % T represents transmittance and % R represents reflectance. The absorption spectrum was measured with a UV-visible spectrophotometer (U-4100 manufactured by Hitachi High-Technologies Corporation). The emission spectrum was measured using a spectrofluorometer (FP-8600DS manufactured by JASCO Corporation). FIG. 68 shows the measurement results of the obtained absorption and emission spectra of the solid thin film. The horizontal axis represents the wavelength and the vertical axes represent the absorption intensity and the emission intensity.

From the results in FIG. 68, in the solid thin film of 8mpTP-4mDBtPBfpm-$d_7$, absorption peaks were observed around 273 nm, 317 nm, and 340 nm, and an emission peak was observed around 415 nm (excitation wavelength: 340 nm).

The ionization potential value of a thin film of 8mpTP-4mDBtPBfpm-$d_7$ was measured in the air with a photoelectron spectrometer (AC-3, produced by Riken Keiki Co., Ltd.). The obtained ionization potential value was converted into a negative value, so that the HOMO level of 8mpTP-4mDBtPBfpm-$d_7$ was −6.28 eV. From the data of the absorption spectrum of the thin film, the absorption edge of 8mpTP-4mDBtPBfpm-$d_7$, which was obtained from Tauc plot with an assumption of direct transition, was 3.50 eV. Thus, the optical energy gap of 8mpTP-4mDBtPBfpm-$d_7$ in the solid state was estimated at 3.50 eV; from the values of the HOMO level obtained above and this energy gap, the LUMO level of 8mpTP-4mDBtPBfpm-$d_7$ can be estimated at −2.78 eV. This reveals that 8mpTP-4mDBtPBfpm-$d_7$ in the solid state has an energy gap as wide as 3.50 eV.

The glass transition temperature (Tg) of 8mpTP-4mDBtPBfpm-$d_7$ was measured. Note that Tg was measured with a differential scanning calorimeter (DSC8500 produced by PerkinElmer Japan Co., Ltd.) in a state where a powder was put on an aluminum cell. The result showed that the Tg of 8mpTP-4mDBtPBfpm-$d_7$ was 121° C.

Furthermore, the electrochemical characteristics (oxidation reaction characteristics and reduction reaction characteristics) of 8mpTP-4mDBtPBfpm-$d_7$ were measured by cyclic voltammetry (CV). An electrochemical analyzer (ALS model 600A, manufactured by BAS Inc.) was used for the measurement. The solution for the measurement was prepared by using dehydrated N,N-dimethylformamide (DMF) (produced by Aldrich Corp., 99.8%, catalog number: 22705-6) as a solvent, dissolving a supporting electrolyte, tetra-n-butylammonium perchlorate ($n\text{-}Bu_4NClO_4$) (produced by Tokyo Chemical Industry Co., Ltd., catalog number: T0836), at a concentration of 100 mmol/L, and then dissolving the object of measurement at a concentration of 2 mmol/L.

A platinum electrode (PTE platinum electrode, manufactured by BAS Inc.) was used as a working electrode, another platinum electrode (Pt counter electrode (5 cm), manufactured by BAS Inc.) was used as an auxiliary electrode, and an $Ag/Ag^+$ electrode (RE7 reference electrode for nonaqueous solvent, manufactured by BAS Inc.) was used as a reference electrode. Note that the measurement was performed at room temperature (20° C. to 25° C.).

In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the oxidation potential Ea[V] of 8mpTP-4mDBtPBfpm-$d_7$ was not observed. Therefore, the HOMO level is estimated to be lower than −6.2 eV. In contrast, the LUMO level was found to be −3.00 eV from the measurement result of the reduction potential Ec [V].

Example 8

In this example, light-emitting devices (light-emitting devices 8A and 8B) of one embodiment of the present invention described in the above embodiments and a comparative light-emitting device 8 are fabricated and the measurement results of the characteristics are described.

Structure formulae of organic compounds used for the light-emitting devices 8A and 8B and the comparative light-emitting device 8 are shown below.

[Chemical Formula 105]

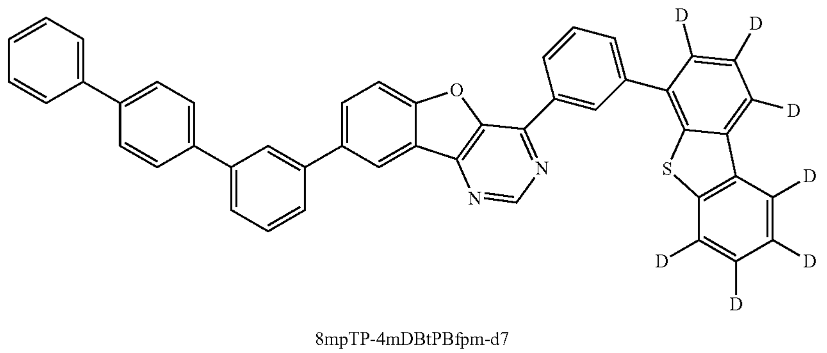

8mpTP-4mDBtPBfpm-d7

-continued
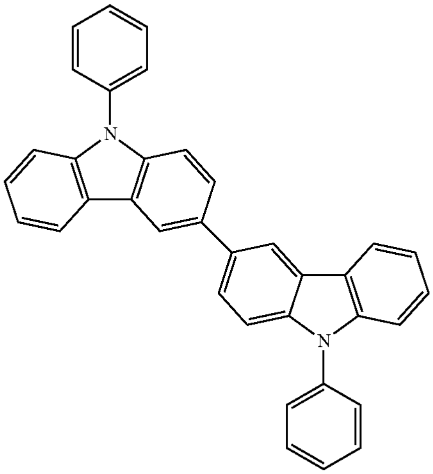
PCCP
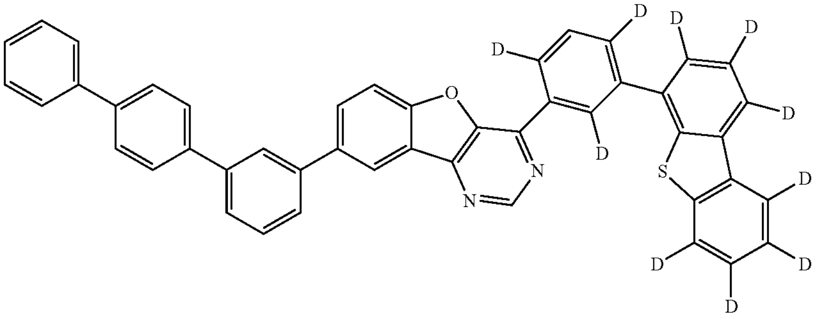
8mpTP-4mDBtPBfpm-d10
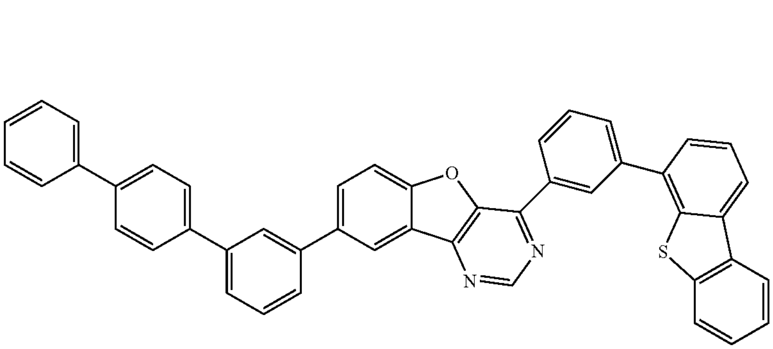
8mpTP-4mDBtPBfpm -continued

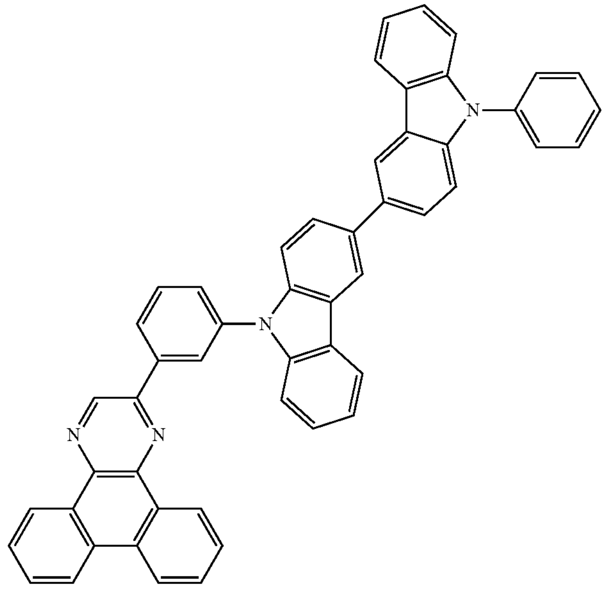

2mPCCzPDBq

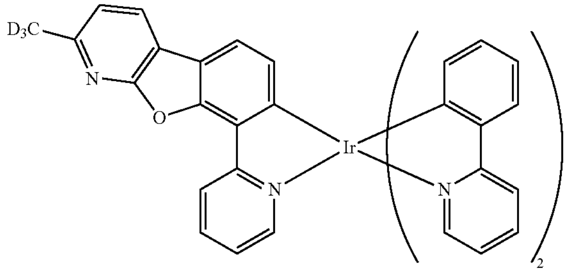

Ir(ppy)$_2$(mbfpypy-d3)

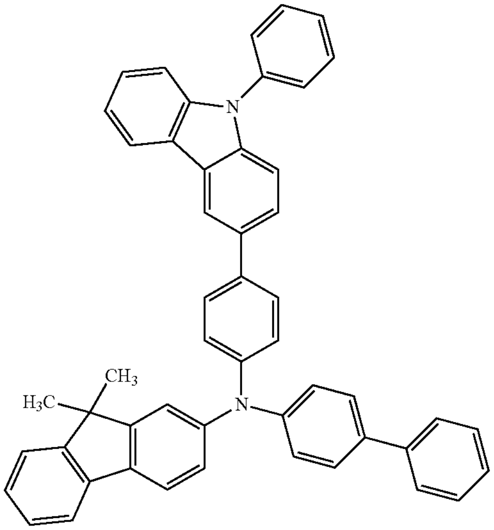

PCBBiF

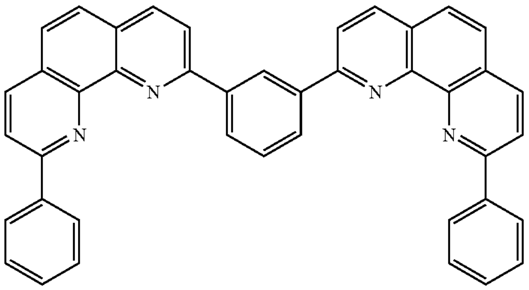

mPPhen2P

<Method for Fabricating Light-Emitting Device 8A>

In a light-emitting device 8A, as illustrated in FIG. 42, the hole-injection layer 911, the hole-transport layer 912, the light-emitting layer 913, the electron-transport layer 914, and the electron-injection layer 915 are stacked in this order over the first electrode 901 formed over the glass substrate 900, and the second electrode 902 is stacked over the electron-injection layer 915.

First, indium oxide-tin oxide containing silicon or silicon oxide (abbreviation: ITSO) was deposited by a sputtering method over the glass substrate 900, whereby the first electrode 901 was formed. The thickness of the first electrode 901 was set to 110 nm and the area of the electrode was set to 4 $mm^2$ (2 mm×2 mm).

Next, in pretreatment for forming the light-emitting device over the substrate, a surface of the substrate was washed with water and baking was performed at 200° C. for 1 hour. Then, the substrate was transferred into a vacuum evaporation apparatus where the pressure was reduced to approximately 10-4 Pa, and vacuum baking was performed at 180° C. for 60 minutes in a heating chamber of the vacuum evaporation apparatus. After that, natural cooling was performed to 30° C. or lower.

Then, the substrate provided with the first electrode 901 was fixed to a substrate holder provided in the vacuum evaporation apparatus such that the surface on which the first electrode 901 was formed faced downward. Over the first electrode 901, N-(1,1'-biphenyl-4-yl)-N-[4-(9-phenyl-9H-carbazol-3-yl)phenyl]-9,9-dimethyl-9H-fluoren-2-amine (abbreviation: PCBBiF) and a fluorine-containing electron acceptor material with a molecular weight of 672 (OCHD-003) were deposited by co-evaporation to a thickness of 10 nm such that the weight ratio of PCBBiF to OCHD-003 was 1:0.03 using a resistance-heating method, whereby the hole-injection layer 911 was formed.

Next, PCBBiF was deposited by evaporation to a thickness of 50 nm over the hole-injection layer 911, whereby the hole-transport layer 912 was formed.

Next, over the hole-transport layer 912, 8-(1,1':4',1"-terphenyl-3-yl)-4-[3-(dibenzothiophen-4-yl-1,2,3,6,7,8,9-$d_7$)phenyl]-[1]benzofuro[3,2-d]pyrimidine (abbreviation: 8mpTP-4mDBtPBfpm-$d_7$), 3,3'-bis(9-phenyl-9H-carbazole) (abbreviation: PCCP), and [2-$d_3$-methyl-(2-pyridinyl-κN) benzofuro[2,3-b]pyridine-κC]bis[2-(2-pyridinyl-N)phenyl-κC]iridium(III) (abbreviation: Ir(ppy)$_2$(mbfpypy-$d_3$)) were deposited by co-evaporation to a thickness of 40 nm such that the weight ratio of 8mpTP-4mDBtPBfpm-$d_7$ to PCCP and Ir(ppy)$_2$(mbfpypy-$d_3$) was 0.5:0.5:0.1 using a resistance-heating method, whereby the light-emitting layer 913 was formed.

After that, over the light-emitting layer 913, 2-{3-[3-(N-phenyl-9H-carbazol-3-yl)-9H-carbazol-9-yl] phenyl}dibenzo[f,h]quinoxaline (abbreviation: 2mPCCzPDBq) was deposited by evaporation to a thickness of 10 nm, and then 2,2'-(1,3-phenylene)bis[9-phenyl-1,10-phenanthroline] (abbreviation: mPPhen2P) was deposited by evaporation to a thickness of 20 nm to form the electron-transport layer 914.

Next, lithium fluoride (LiF) was deposited by evaporation to a thickness of 1 nm over the electron-transport layer 914, whereby the electron-injection layer 915 was formed.

Next, 200 nm of aluminum (abbreviation: Al) was deposited by evaporation over the electron-injection layer 915 using a resistance-heating method to form the second electrode 902, so that the light-emitting device 8A was fabricated.

<Method for Fabricating Light-Emitting Device 8B>

Next, a method for fabricating the light-emitting device 8B is described. The light-emitting device 8B is different from the light-emitting device 8A in the structure of the light-emitting layer 913.

That is, in the light-emitting device 8B, over the hole-transport layer 912, 8-(1,1':4',1"-terphenyl-3-yl)-4-[3-(dibenzothiophen-4-yl-1,2,3,6,7,8,9-$d_7$)phenyl-2,4,6-$d_3$]-[1] benzofuro[3,2-d]pyrimidine (abbreviation: 8mpTP-4mDBtPBfpm-$d_{10}$), 3,3'-bis(9-phenyl-9H-carbazole) (abbreviation: PCCP), and [2-$d_3$-methyl-(2-pyridinyl-κN) benzofuro[2,3-b]pyridine-κC]bis[2-(2-pyridinyl-κN)phenyl-κC]iridium(III) (abbreviation: Ir(ppy)$_2$(mbfpypy-$d_3$)) were deposited by co-evaporation to a thickness of 40 nm such that the weight ratio of 8mpTP-4mDBtPBfpm-$d_{10}$ to PCCP and Ir(ppy)$_2$(mbfpypy-$d_3$) was 0.5:0.5:0.1 using a resistance-heating method, whereby the light-emitting layer 913 was formed.

Other components are the same as the light-emitting device 8A.

<Method for Fabricating Comparative Light-Emitting Device 8>

Next, a method for fabricating the comparative light-emitting device 8 is described. The comparative light-emitting device 8 is different from the light-emitting device 8A in the structure of the light-emitting layer 913.

That is, in the comparative light-emitting device 8, over the hole-transport layer 912, 8-(1,1':4',1"-terphenyl-3-yl)-4-[3-(dibenzothiophen-4-yl)phenyl]-[1]benzofuro[3,2-d]pyrimidine (abbreviation: 8mpTP-4mDBtPBfpm), 3,3'-bis(9-phenyl-9H-carbazole) (abbreviation: PCCP), and [2-$d_3$-methyl-(2-pyridinyl-κN)benzofuro[2,3-b]pyridine-κC]bis[2-(2-pyridinyl-κN)phenyl-κC]iridium(III) (abbreviation: Ir(ppy)$_2$(mbfpypy-$d_3$)) were deposited by co-evaporation to a thickness of 40 nm such that the weight ratio of 8mpTP-4mDBtPBfpm to PCCP and Ir(ppy)$_2$(mbfpypy-$d_3$) was 0.5:0.5:0.1 using a resistance-heating method, whereby the light-emitting layer 913 was formed.

Other components are the same as the light-emitting device 8A.

The structures of the light-emitting devices 8A and 8B and the comparative light-emitting device 8 are listed in the following table. Note that X in the table refers to 8mpTP-4mDBtPBfpm-$d_7$, 8mpTP-4mDBtPBfpm-$d_{10}$, or 8mpTP-4mDBtPBfpm.

TABLE 3

| | Thickness [nm] | Light-emitting device 8A | Light-emitting device 8B | Comparative light-emitting device 8 |
|---|---|---|---|---|
| Second electrode | 200 | | Al | |
| Electron-injection layer | 1 | | LiF | |
| Electron-transport layer | 20 | | mPPhen2P | |
| | 10 | | 2mPCCzPDBq | |
| Light-emitting layer | 40 | | X:PCCP:Ir(ppy)$_2$(mbfpypy-d3) | |
| | | 8mpTP-4mDBtPBfpm-d7 | 8mpTP-4mDBtPBfpm-d10 | 8mpTP-4mDBtPBfpm |
| | | | (0.5:0.5:0.1) | |
| Hole-transport layer | 50 | | PCBBiF | |
| Hole-injection layer | 10 | | PCBBiF:OCHD-003 (10.03) | |
| First electrode | 110 | | ITSO | |

In the above manner, the light-emitting device 8A, the light-emitting device 8B, and the comparative light-emitting device 8 were fabricated.

<Device Characteristics>

The light-emitting device 8A, the light-emitting device 8B, and the comparative light-emitting device 8 were sealed using a glass substrate in a glove box containing a nitrogen atmosphere so as not to be exposed to the atmosphere (a sealing material was applied to surround the devices and UV treatment and heat treatment at 80° C. for 1 hour were performed at the time of sealing). Then, the initial characteristics of the light-emitting devices were measured.

Figure 69:
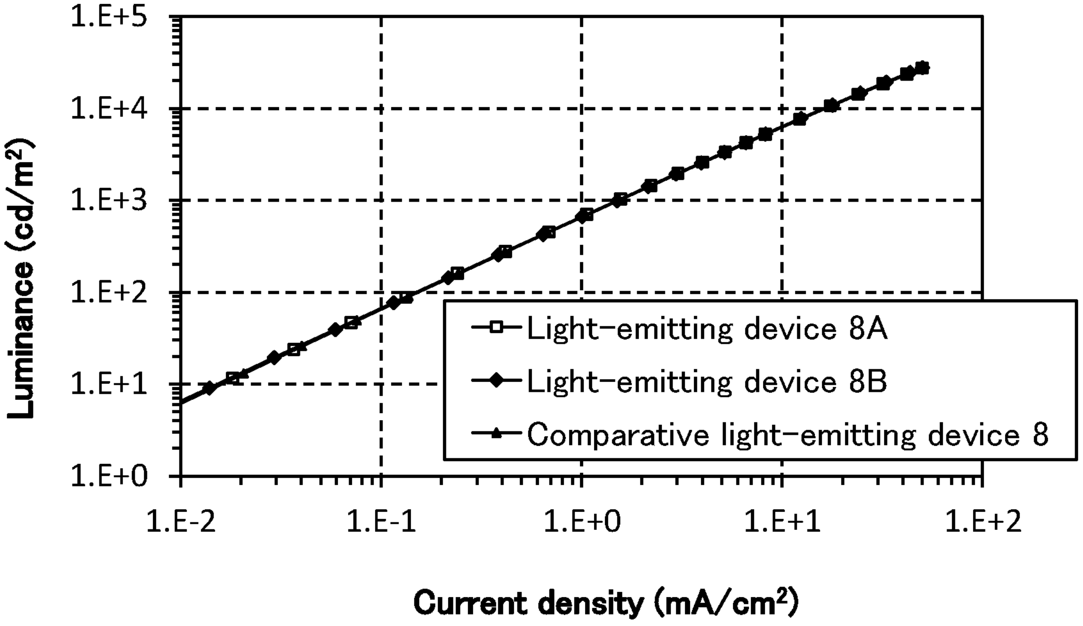
FIG. 69 shows luminance-current density characteristics of light-emitting devices of an example.
Figure 70:
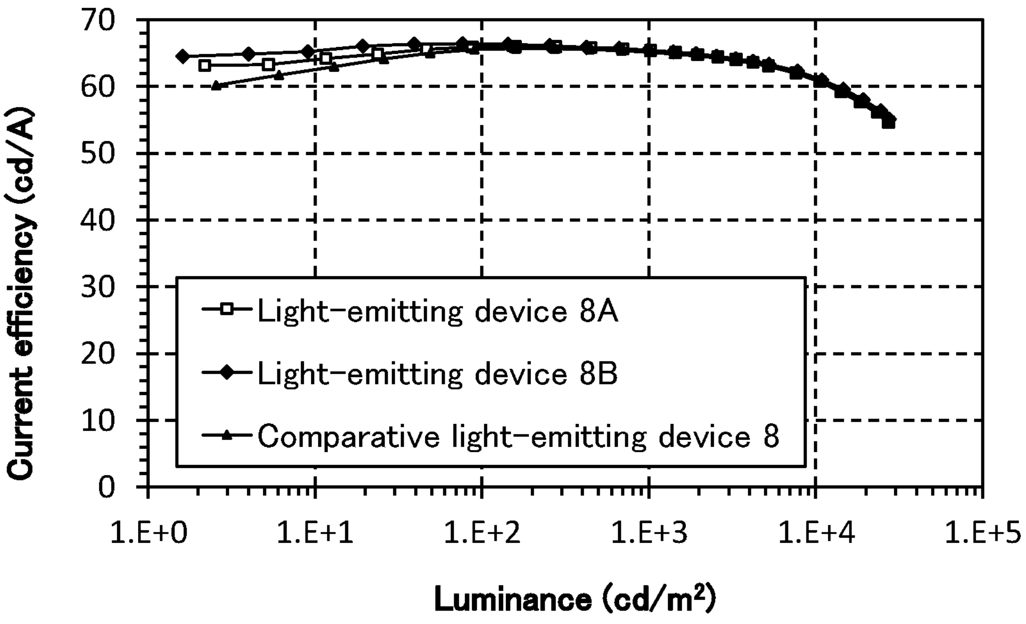
FIG. 70 shows current efficiency-luminance characteristics of light-emitting devices of an example.
Figure 71:
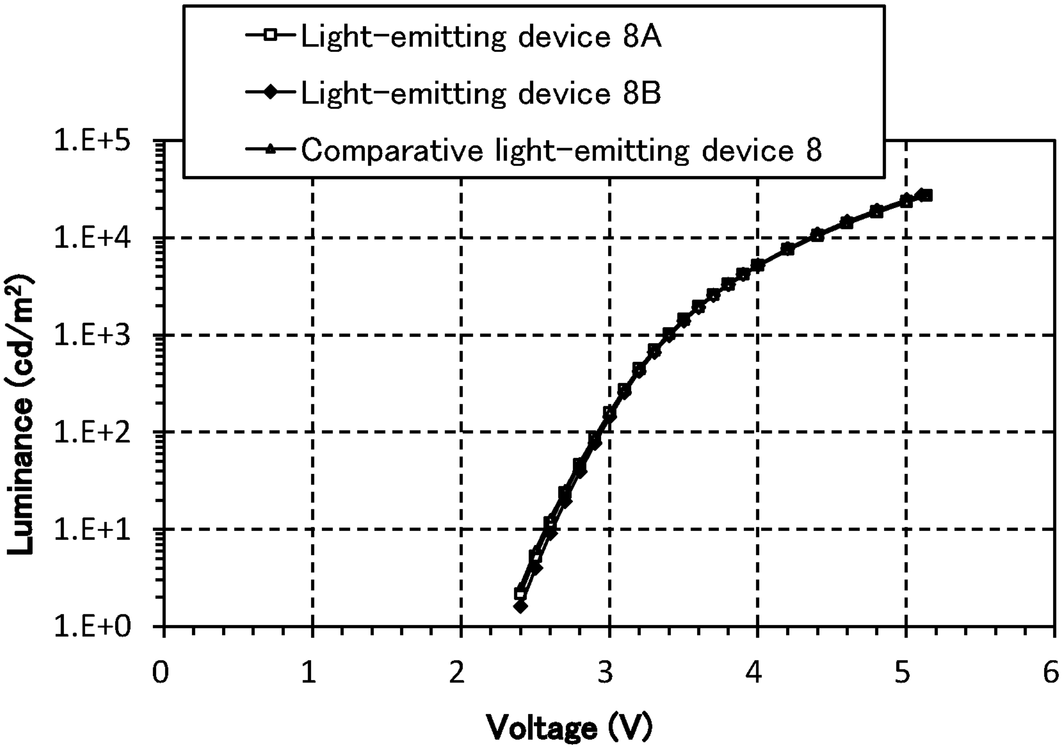
FIG. 71 shows luminance-voltage characteristics of light-emitting devices of an example.
Figure 72:
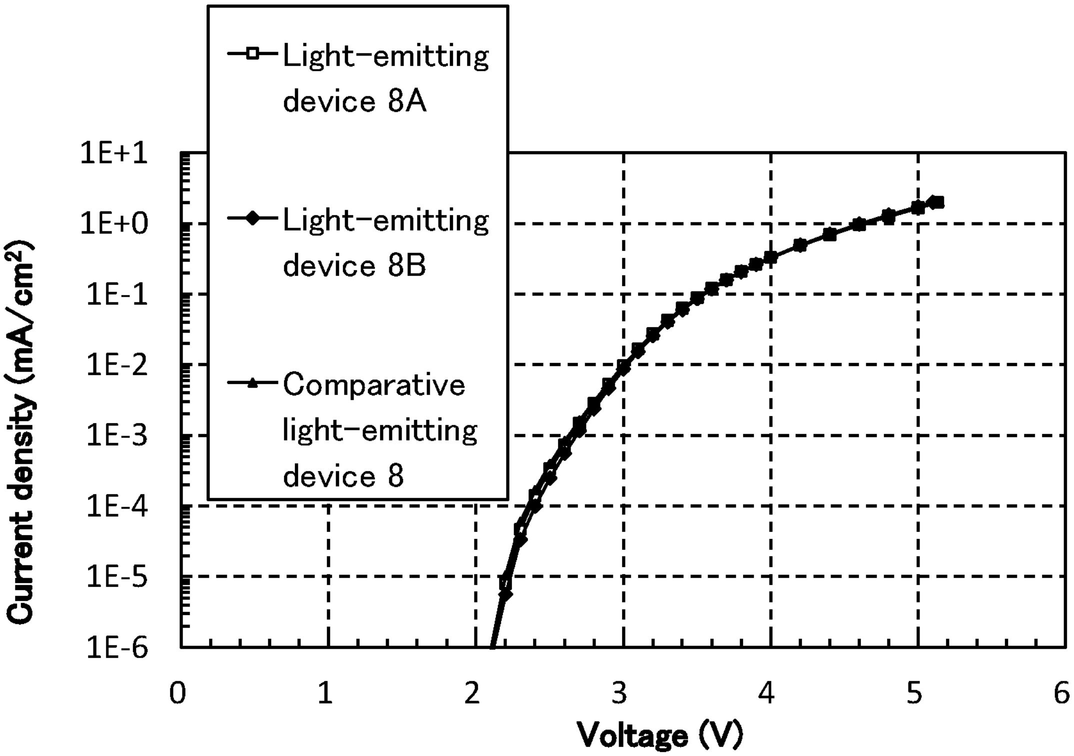
FIG. 72 shows current density-voltage characteristics of light-emitting devices of an example.
Figure 73:
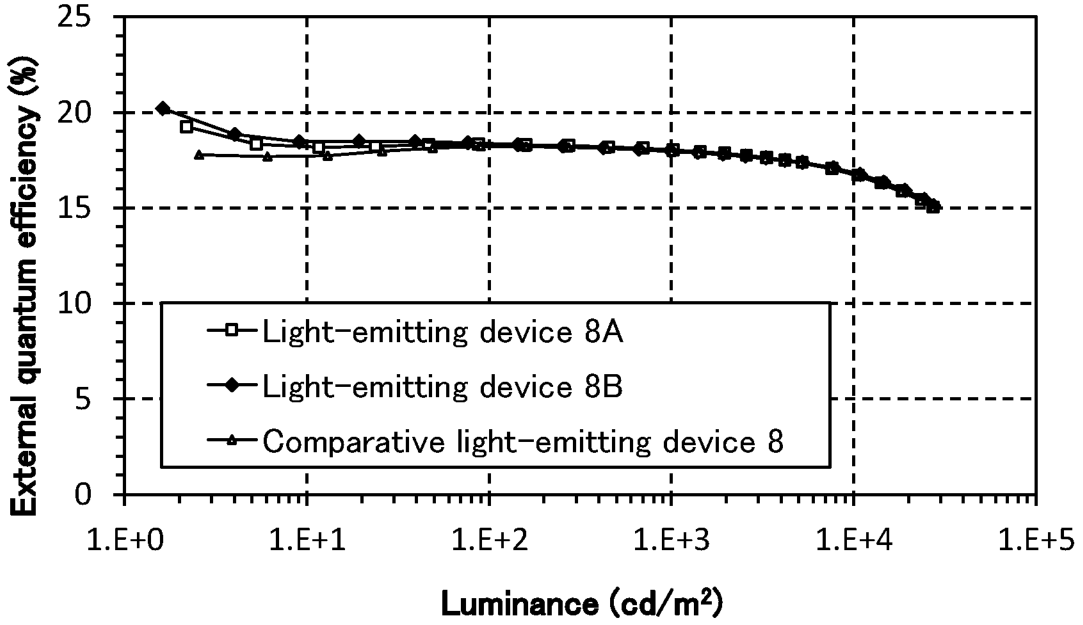
FIG. 73 shows external quantum efficiency-luminance characteristics of the light-emitting devices of an example.
Figure 74:
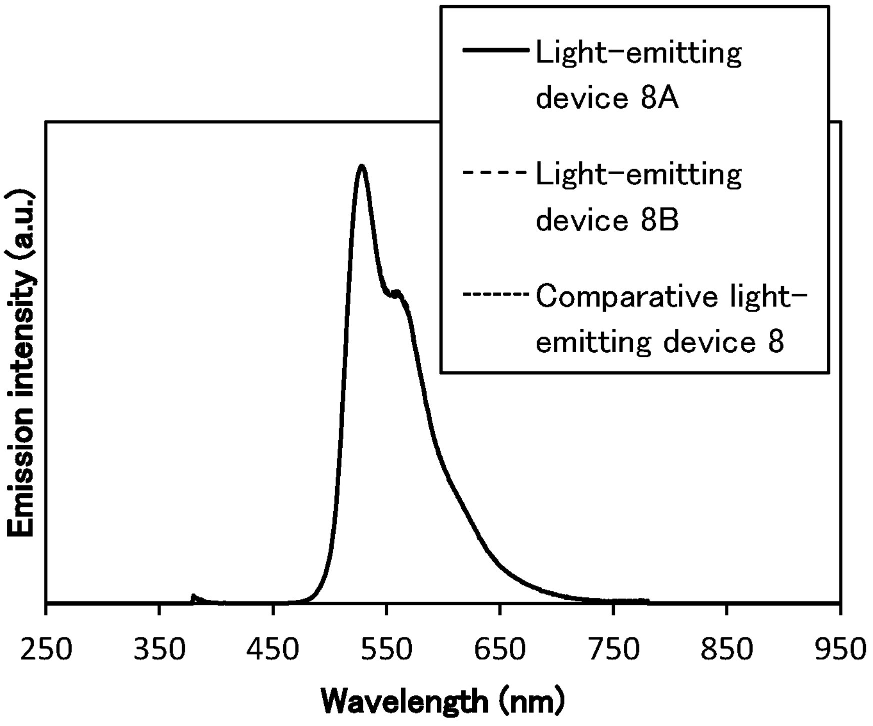
FIG. 74 shows emission spectra of light-emitting devices of an example.

FIG. 69 shows the luminance-current density characteristics; FIG. 70, the current efficiency-luminance characteristics; FIG. 71, the luminance-voltage characteristics; FIG. 72, the current density-voltage characteristics; FIG. 73, the external quantum efficiency-luminance characteristics; and FIG. 74, the emission spectrum of the light-emitting devices 8A and 8B and the comparative light-emitting device 8. The following table shows the main characteristics of the light-emitting devices at a luminance of approximately 1000 cd/m$^2$. Note that luminance, CIE chromaticity, and emission spectra were measured with a spectroradiometer (SR-UL1R manufactured by TOPCON TECHNOHOUSE CORPORATION). The external quantum efficiency was calculated from the luminance and the emission spectra measured with the spectroradiometer, on the assumption that the light-emitting devices had Lambertian light-distribution characteristics.

TABLE 4

| | Voltage (V) | Current density (mA/cm$^2$) | Chromaticity x | Chromaticity y | Current efficiency (cd/A) | External quantum efficiency (%) |
|---|---|---|---|---|---|---|
| Light-emitting device 8A | 3.40 | 1.57 | 0.371 | 0.602 | 65.4 | 18.0 |
| Light-emitting device 8B | 3.40 | 1.50 | 0.371 | 0.602 | 65.5 | 18.0 |
| Comparative light-emitting device 8 | 3.40 | 1.54 | 0.372 | 0.601 | 65.1 | 17.9 |

It was found from FIG. 69 to FIG. 74 that the light-emitting devices 8A and 8B that were light-emitting devices of one embodiment of the present invention had the similar device characteristics to the comparative light-emitting device 8.

Therefore, it can be said that a light-emitting device containing the organic compound of 8mpTP-4mDBtPBfpm-$d_7$ or 8mpTP-4mDBtPBfpm-$d_{10}$, which contains deuterium, does not impair the driving characteristics and emission characteristics compared with a light-emitting device containing an organic compound of 8mpTP-4mDBtPBfpm that does not contain deuterium.

<Results of Reliability Test>

Figure 75:
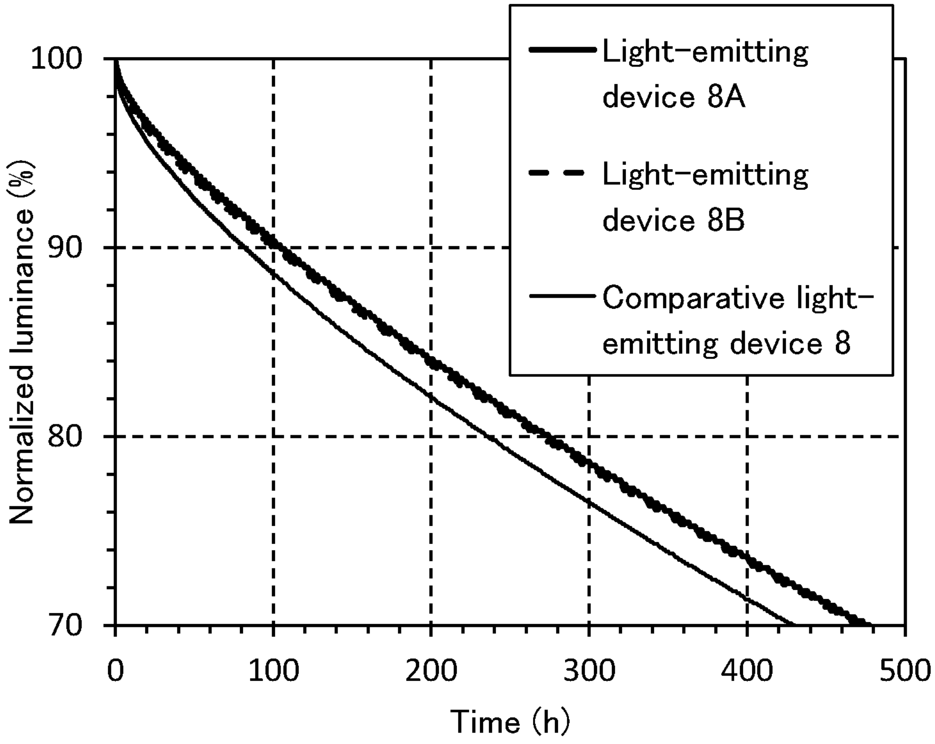
FIG. 75 shows a driving time-dependent change in luminance of light-emitting devices of an example.

Furthermore, a reliability test was performed on the light-emitting device 8A, the light-emitting device 8B, and the comparative light-emitting device 8. FIG. 75 shows a time-dependent change in normalized luminance at the time of constant current density driving (50 [mA/cm2]). In FIG. 75, the vertical axis represents normalized luminance (%), and the horizontal axis represents time (h). The value of LT80 (h) that is elapsed time until the measurement luminance reduces to 80% of the initial luminance was 274 hours and 268 hours in the light-emitting device 8A and the light-emitting device 8B, respectively. On the other hand, the value of LT80 (h) in the comparative light-emitting device 8 was 236 hours.

Therefore, it was found from FIG. 75 that in the light-emitting layer 913, the light-emitting device 8A containing 8mpTP-4mDBtPBfpm-$d_7$ with deuterium or the light-emitting device 8B containing 8mpTP-4mDBtPBfpm-$d_{10}$ with deuterium had higher reliability than the comparative light-emitting device 8 containing 8mpTP-4mDBtPBfpm that did not contain deuterium.

Example 9

This example describes measurement results of the characteristics of fabricated light-emitting devices (a light-emitting device 9A, a light-emitting device 9B, and a light-emitting device 9C) of one embodiment of the present invention described in the above embodiments and a comparative light-emitting device 9.

Structural formulae of organic compounds used for the light-emitting device 9A, the light-emitting device 9B, the light-emitting device 9C, and the comparative light-emitting device 9 are shown below.

[Chemical Formula 106]

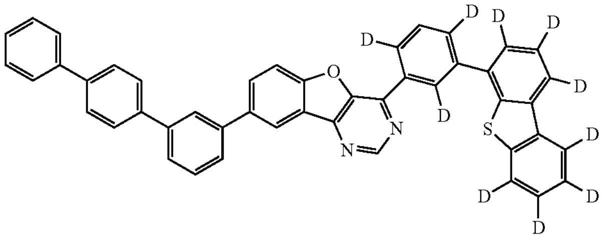

8mpTP-4mDBtPBfpm-d10

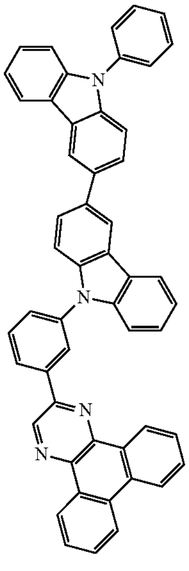

2mPCCzPDBq

-continued
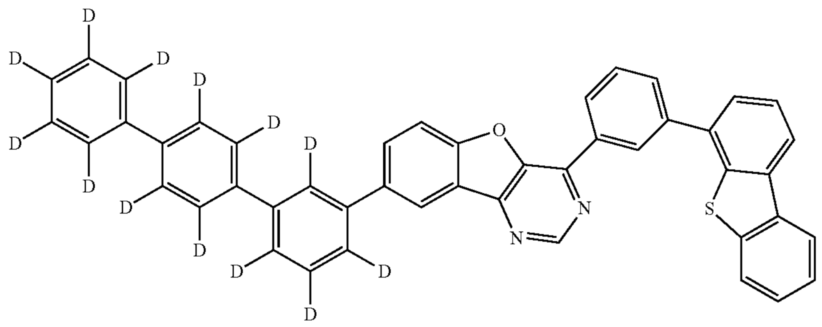
8mpTP-4mDBtPBfpm-d13
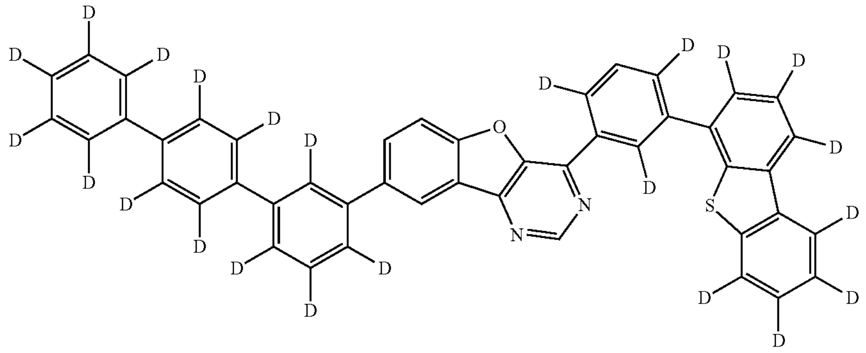
8mpTP-4mDBtPBfpm-d23
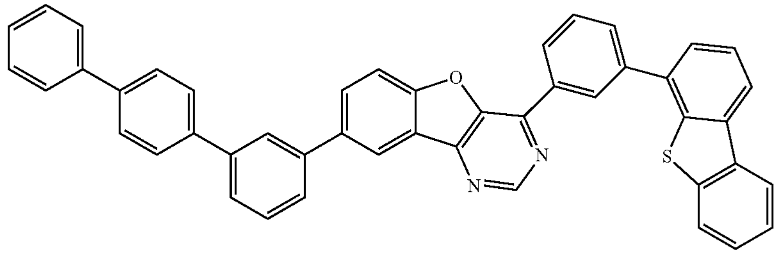
8mpTP-4mDBtPBfpm
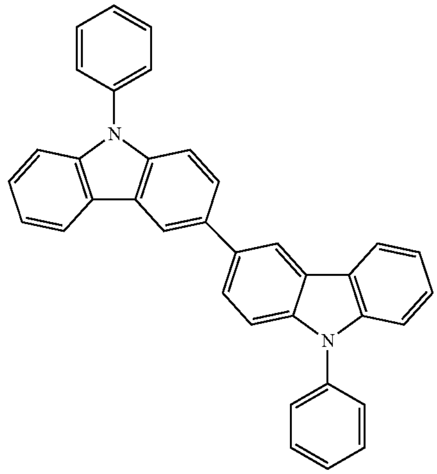
PCCP
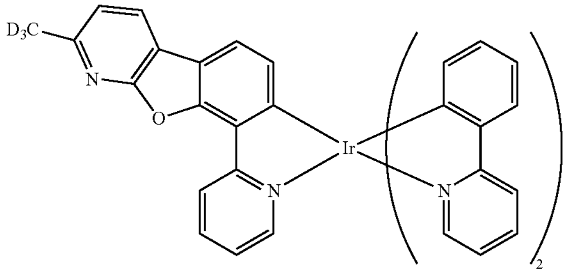
$Ir(ppy)_2(mbfpypy-d3)$ -continued

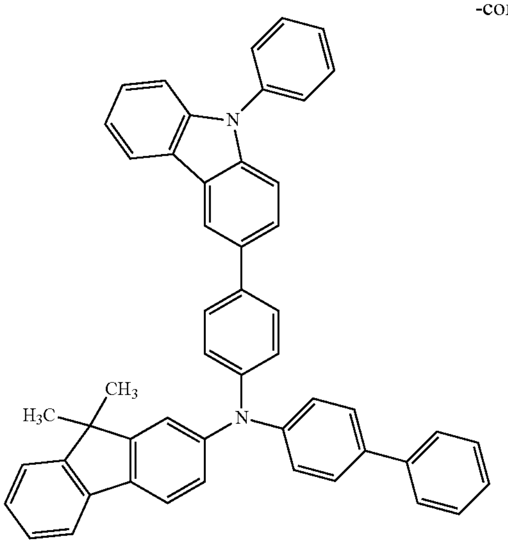

PCBBiF

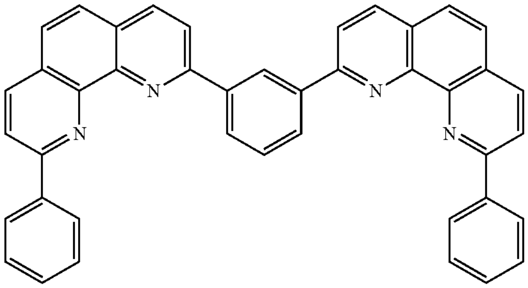

mPPhen2P

<Method for Fabricating Light-Emitting Device 9A>

In a light-emitting device 9A, as illustrated in FIG. 42, the hole-injection layer 911, the hole-transport layer 912, the light-emitting layer 913, the electron-transport layer 914, and the electron-injection layer 915 are stacked in this order over the first electrode 901 formed over the glass substrate 900, and the second electrode 902 is stacked over the electron-injection layer 915.

First, indium oxide-tin oxide containing silicon or silicon oxide (abbreviation: ITSO) was deposited by a sputtering method over the glass substrate 900, whereby the first electrode 901 was formed. The thickness of the first electrode 901 was 70 nm and the electrode area was 4 $mm^2$ (2 mm×2 mm).

Next, in pretreatment for forming the light-emitting device over the substrate, a surface of the substrate was washed with water and baking was performed at 200° C. for 1 hour. Then, the substrate was transferred into a vacuum evaporation apparatus where the pressure was reduced to approximately 10-4 Pa, and vacuum baking was performed at 180° C. for 60 minutes in a heating chamber of the vacuum evaporation apparatus. After that, natural cooling was performed to 30° C. or lower.

Then, the substrate provided with the first electrode 901 was fixed to a substrate holder provided in the vacuum evaporation apparatus such that the surface on which the first electrode 901 was formed faced downward. Over the first electrode 901, N-(1,1'-biphenyl-4-yl)-N-[4-(9-phenyl-9H-carbazol-3-yl)phenyl]-9,9-dimethyl-9H-fluoren-2-amine (abbreviation: PCBBiF) and a fluorine-containing electron acceptor material with a molecular weight of 672 (OCHD-003) were deposited by co-evaporation to a thickness of 10 nm such that the weight ratio of PCBBiF to OCHD-003 was 1:0.03 using a resistance-heating method, whereby the hole-injection layer 911 was formed.

Next, PCBBiF was deposited by evaporation to a thickness of 50 nm over the hole-injection layer 911, whereby the hole-transport layer 912 was formed.

Next, over the hole-transport layer 912, 8-(1,1':4',1"-terphenyl-3-yl)-4-[3-(dibenzothiophen-4-yl-1,2,3,6,7,8,9-$d_7$)phenyl-2,4,6-$d_3$]-[1]benzofuro[3,2-d]pyrimidine (abbreviation: 8mpTP-4mDBtPBfpm-$d_{10}$), 3,3'-bis(9-phenyl-9H-carbazole) (abbreviation: PCCP), and [2-$d_3$-methyl-(2-pyridinyl-κN)benzofuro[2,3-b]pyridine-κC]bis[2-(2-pyridinyl-N)phenyl-κC]iridium(III) (abbreviation: $Ir(ppy)_2$(mbfpypy-$d_3$)) were deposited by co-evaporation to a thickness of 40 nm such that the weight ratio of 8mpTP-4mDBtPBfpm-$d_{10}$ to PCCP and $Ir(ppy)_2$(mbfpypy-$d_3$) was 0.6:0.4:0.1 using a resistance-heating method, whereby the light-emitting layer 913 was formed.

After that, over the light-emitting layer 913, 2-{3-[3-(N-phenyl-9H-carbazol-3-yl)-9H-carbazol-9-yl]phenyl}dibenzo[f,h]quinoxaline (abbreviation: 2mPCCzPDBq) was deposited by evaporation to a thickness of 10 nm, and then 2,2'-(1,3-phenylene)bis[9-phenyl-1,10-phenanthroline] (abbreviation: mPPhen2P) was deposited by evaporation to a thickness of 20 nm to form the electron-transport layer 914.

Next, lithium fluoride (LiF) was deposited by evaporation to a thickness of 1 nm over the electron-transport layer 914, whereby the electron-injection layer 915 was formed.

Next, 200 nm of aluminum (abbreviation: Al) was deposited by evaporation over the electron-injection layer 915 using a resistance-heating method to form the second electrode 902, so that the light-emitting device 9A was fabricated.

<Method for Fabricating Light-Emitting Device 9B>

Next, a method for fabricating the light-emitting device 9B is described. The light-emitting device 9B is different from the light-emitting device 9A in the structure of the light-emitting layer 913.

That is, in the light-emitting device 9B, over the hole-transport layer 912, 8-(1,1':4',1"-terphenyl-3-yl-2,4,5,6,2',3',5',6',2",3",4",5",6"-$d_{13}$)-4-[3-(dibenzothiophen-4-yl)phenyl]-[1]benzofuro[3,2-d]pyrimidine (abbreviation: 8mpTP-4mDBtPBfpm-$d_{13}$), 3,3'-bis(9-phenyl-9H-carbazole) (abbreviation: PCCP), and [2-$d_3$-methyl-(2-pyridinyl-κN)benzofuro[2,3-b]pyridine-κC]bis[2-(2-pyridinyl-κN)phenyl-κC]iridium(III) (abbreviation: $Ir(ppy)_2(mbfpypy-d_3)$) were deposited by co-evaporation to a thickness of 40 nm such that the weight ratio of 8mpTP-4mDBtPBfpm-$d_{13}$ to PCCP and $Ir(ppy)_2(mbfpypy-d_3)$ was 0.6:0.4:0.1 using a resistance-heating method, whereby the light-emitting layer 913 was formed.

Other components are the same as the light-emitting device 9A.

<Method for Fabricating Light-Emitting Device 9C>

Next, a method for fabricating the light-emitting device 9C is described. The light-emitting device 9C is different from the light-emitting device 9A in the structure of the light-emitting layer 913.

That is, in the light-emitting device 9C, over the hole-transport layer 912, 8-(1,1:4',1"-terphenyl-3-yl-2,4,5,6,2',3',5',6',2",3",4",5",6"-$d_{13}$)-4-[3-(dibenzothiophen-4-yl-1,2,3,6,7,8,9-$d_7$)phenyl-2,4,6-$d_3$]-[1]benzofuro[3,2-d]pyrimidine (abbreviation: 8mpTP-4mDBtPBfpm-$d_{23}$), 3,3'-bis(9-phenyl-9H-carbazole) (abbreviation: PCCP), and [2-d3-methyl-(2-pyridinyl-κN)benzofuro[2,3-b]pyridine-κC]bis[2-(2-pyridinyl-κN)phenyl-κC]iridium(III) (abbreviation: $Ir(ppy)_2$(mbfpypy-d3)) were deposited by co-evaporation to a thickness of 40 nm such that the weight ratio of 8mpTP-4mDBtPBfpm-$d_{23}$ to PCCP and $Ir(ppy)_2(mbfpypy-d_3)$ was 0.6:0.4:0.1 using a resistance-heating method, whereby the light-emitting layer 913 was formed.

Other components are the same as the light-emitting device 9A.

<Method for Fabricating Comparative Light-Emitting Device 9>

Next, a method for fabricating the comparative light-emitting device 9 is described. The comparative light-emitting device 9 is different from the light-emitting device 9A in the structure of the light-emitting layer 913.

That is, in the comparative light-emitting device 9, over the hole-transport layer 912, 8-(1,1':4',1"-terphenyl-3-yl)-4-[3-(dibenzothiophen-4-yl)phenyl]-[1]benzofuro[3,2-d]pyrimidine (abbreviation: 8mpTP-4mDBtPBfpm), 3,3'-bis(9-phenyl-9H-carbazole) (abbreviation: PCCP), and [2-d3-methyl-(2-pyridinyl-κN)benzofuro[2,3-b]pyridine-κC]bis[2-(2-pyridinyl-N)phenyl-κC]iridium(III) (abbreviation: $Ir(ppy)_2$(mbfpypy-d3)) were deposited by co-evaporation to a thickness of 40 nm such that the weight ratio of 8mpTP-4mDBtPBfpm to PCCP and $Ir(ppy)_2$(mbfpypy-d3) was 0.6:0.4:0.1 using a resistance-heating method, whereby the light-emitting layer 913 was formed.

Other components are the same as the light-emitting device 9A.

The structures of the light-emitting device 9A, the light-emitting device 9B, the light-emitting device 9C, and the comparative light-emitting device 9 are listed in the following table. Note that X in the table refers to 8mpTP-4mDBtPBfpm-$d_{10}$, 8mpTP-4mDBtPBfpm-$d_{13}$, 8mpTP-4mDBtPBfpm-$d_{23}$, or 8mpTP-4mDBtPBfpm.

TABLE 5

| | Thickness [nm] | Light-emitting device 9A | Light-emitting device 9B | Light-emitting device 9C | Comparative light-emiting device 9 |
|---|---|---|---|---|---|
| Second electrode | 200 | Al | | | |
| Electron-injection layer | 1 | LiF | | | |
| Electron-transport | 20 | mPPhen2P | | | |
| layer | 10 | 2mPCCzPDBq | | | |
| Light-emitting layer | 40 | X:PCCP:$Ir(ppy)_2$(mbfpypy-d3) | | | |
| | | 8mpTP-4mDBtPBfpm-d10 | 8mpTP-4mDBtPBfpm-d13 | 8mpTP-4mDBtPBfpm-d23 | 8mpTP-4mDBtPBfpm |
| | | (0.6:0.40.1) | | | |
| Hole-transport layer | 50 | PCBBiF | | | |
| Hole-injection layer | 10 | PCBBiF:OCHD-003 (1:0.03) | | | |
| First electrode | 70 | ITSO | | | |

In the above manner, the light-emitting device 9A, the light-emitting device 9B, the light-emitting device 9C, and the comparative light-emitting device 9 were fabricated.

<Device Characteristics>

The light-emitting device 9A, the light-emitting device 9B, the light-emitting device 9C, and the comparative light-emitting device 9 were sealed using a glass substrate in a glove box containing a nitrogen atmosphere so as not to be exposed to the atmosphere (a sealing material was applied to surround the devices and UV treatment and heat treatment at 80° C. for 1 hour were performed at the time of sealing). Then, the initial characteristics of the light-emitting devices were measured.

Figure 76:
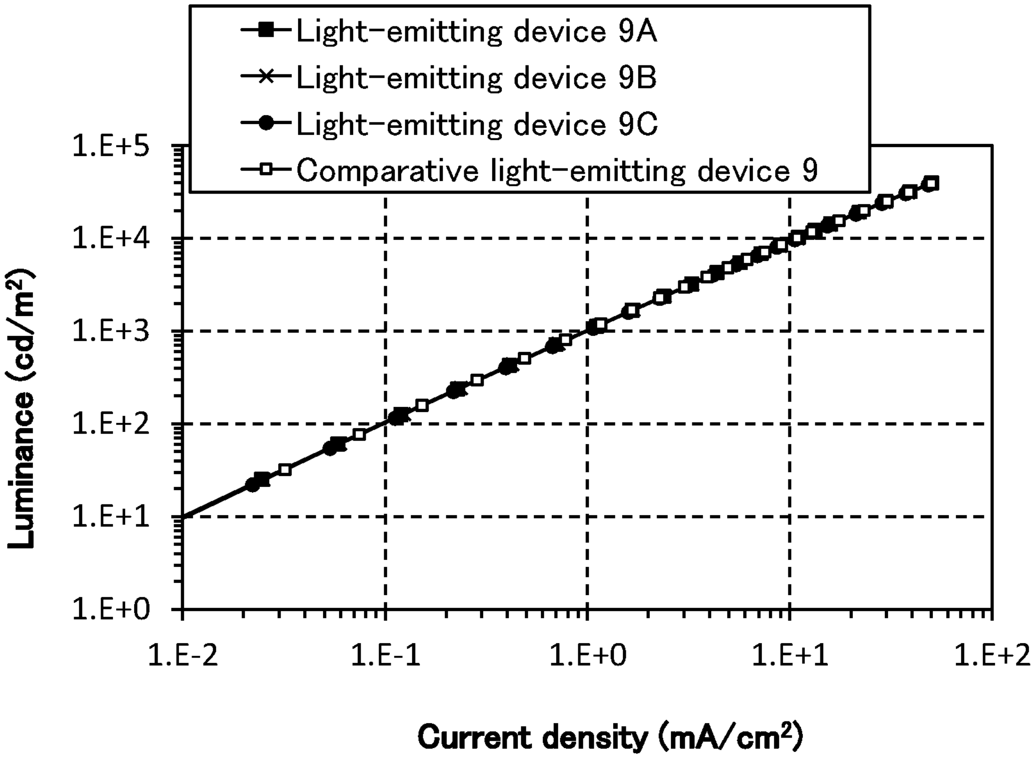
FIG. 76 shows luminance-current density characteristics of light-emitting devices of an example.
Figure 77:
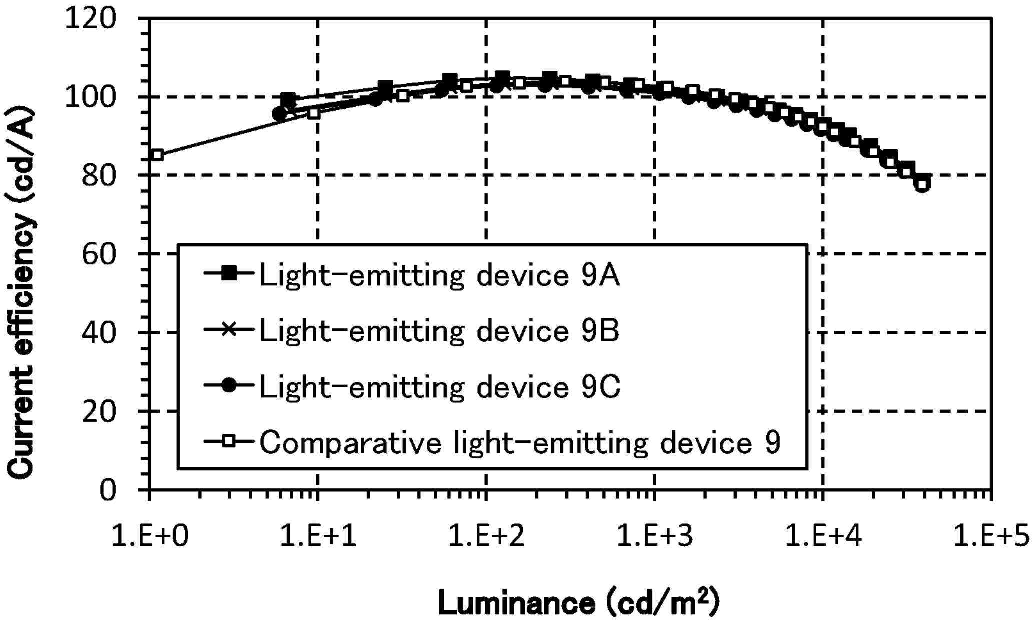
FIG. 77 shows current efficiency-luminance characteristics of light-emitting devices of an example.
Figure 78:
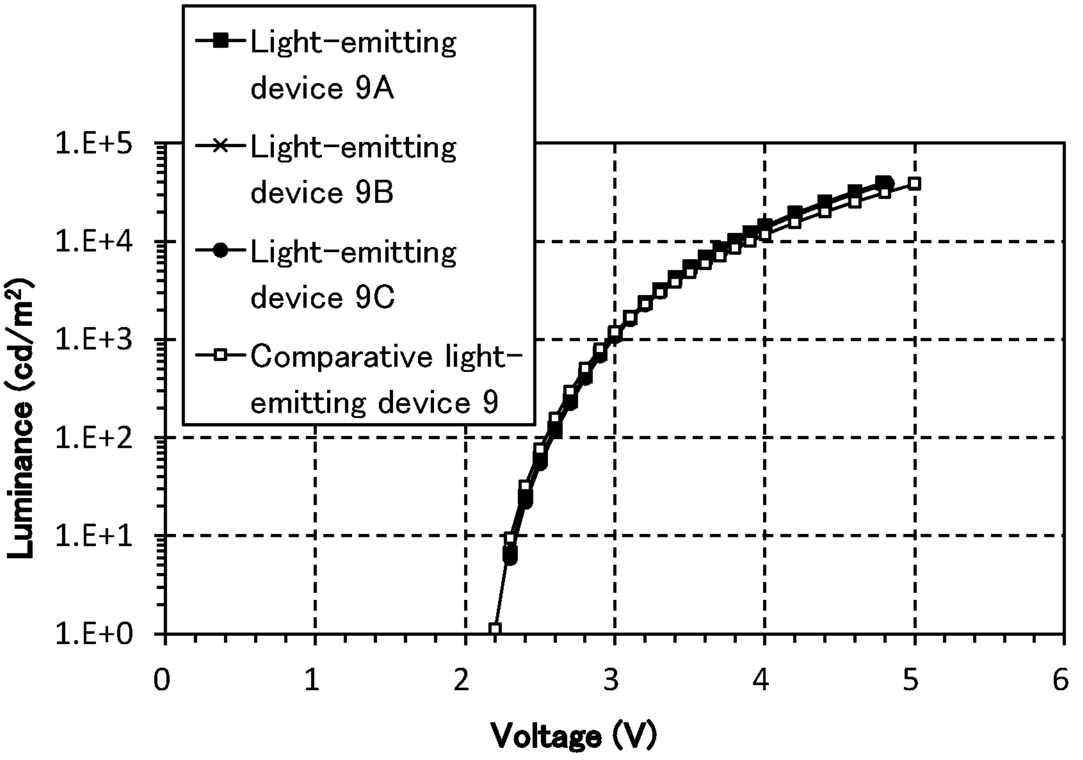
FIG. 78 shows luminance-voltage characteristics of light-emitting devices of an example.
Figure 79:
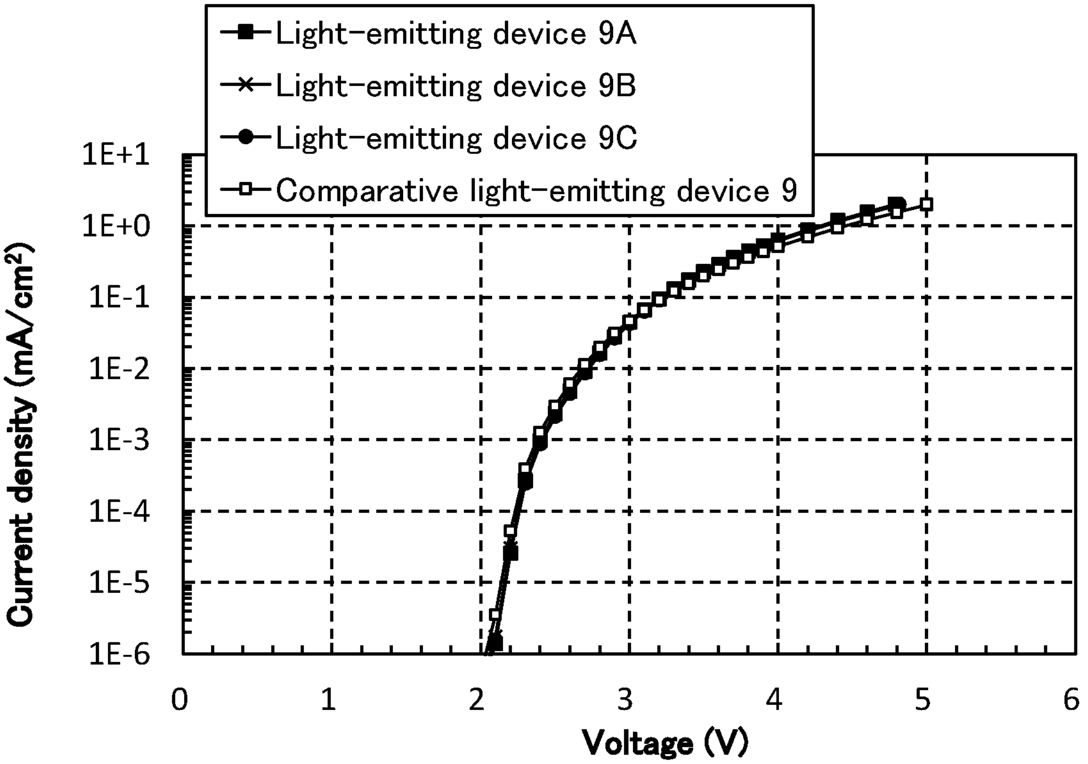
FIG. 79 shows current density-voltage characteristics of light-emitting devices of an example.
Figure 80:
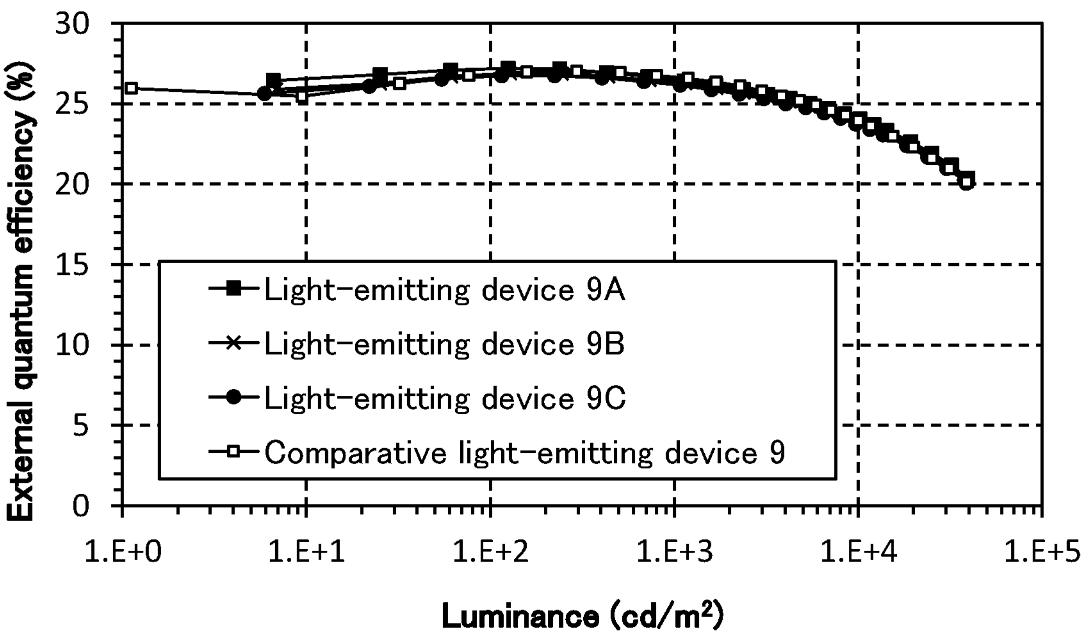
FIG. 80 shows external quantum efficiency-luminance characteristics of light-emitting devices of an example.
Figure 81:
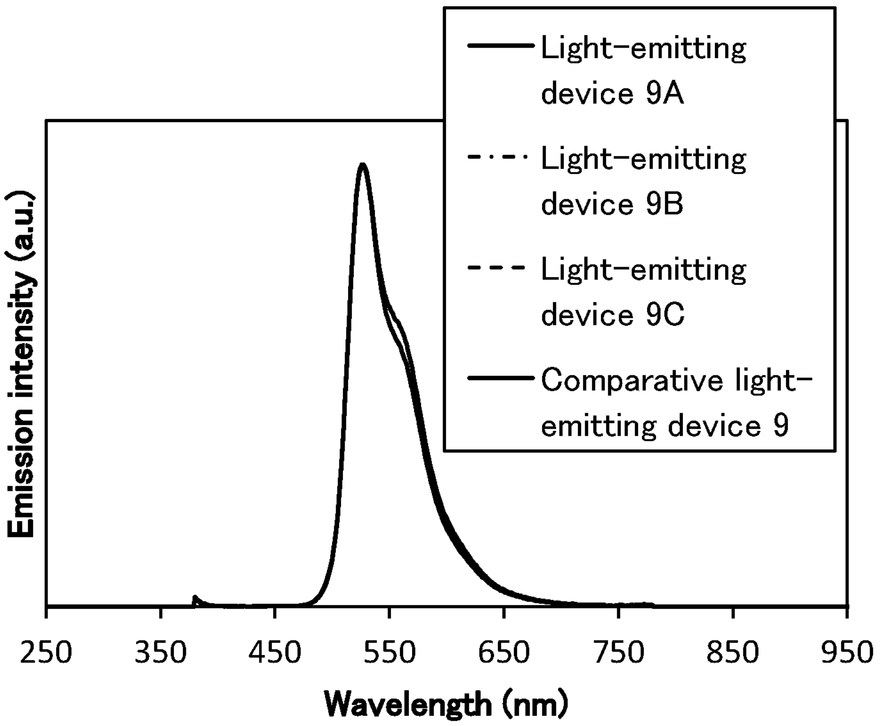
FIG. 81 shows emission spectra of light-emitting devices of an example.

FIG. 76 shows the luminance-current density characteristics; FIG. 77, the current efficiency-luminance characteristics; FIG. 78, the luminance-voltage characteristics; FIG. 79, the current density-voltage characteristics; FIG. 80, the external quantum efficiency-luminance characteristics; and FIG. 81, the emission spectrum of the light-emitting device 9A, the light-emitting device 9B, the light-emitting device 9C, and the comparative light-emitting device 9. The following table shows the main characteristics of the light-emitting devices at a luminance of approximately 1000 $cd/m^2$. Note that luminance, CIE chromaticity, and emission spectra were measured with a spectroradiometer (SR-UL1R manufactured by TOPCON TECHNOHOUSE CORPORATION). The external quantum efficiency was calculated from the luminance and the emission spectra measured with the spectroradiometer, on the assumption that the light-emitting devices had Lambertian light-distribution characteristics.

TABLE 6

| | Voltage (V) | Current density ($mA/cm^2$) | Chromaticity x | Chromaticity y | Current efficiency (cd/A) | External quantum efficiency (%) |
|---|---|---|---|---|---|---|
| Light-emitting device 9A | 3.00 | 1.11 | 0.328 | 0.638 | 102.1 | 26.4 |
| Light-emitting device 9B | 3.00 | 1.13 | 0.329 | 0.637 | 101.3 | 26.3 |
| Light-emitting device 9C | 3.00 | 1.07 | 0.329 | 0.637 | 100.8 | 26.2 |
| Comparative light-emitting device 9 | 3.00 | 1.17 | 0.337 | 0.631 | 102.4 | 26.6 |

It was found from FIG. 76 to FIG. 81 that the light-emitting device 9A, the light-emitting device 9B, and the light-emitting device 9C that were light-emitting devices of one embodiment of the present invention had the similar device characteristics to the comparative light-emitting device 9. Therefore, it can be said that a light-emitting device containing the organic compound of 8mpTP-4mDBtPBfpm-$d_{10}$, 8mpTP-4mDBtPBfpm-$d_{13}$, and 8mpTP-4mDBtPBfpm-$d_{23}$, which contains deuterium, does not impair the driving characteristics and emission characteristics compared with a light-emitting device containing an organic compound of 8mpTP-4mDBtPBfpm that does not contain deuterium.

<Results of Reliability Test>

Figure 82:
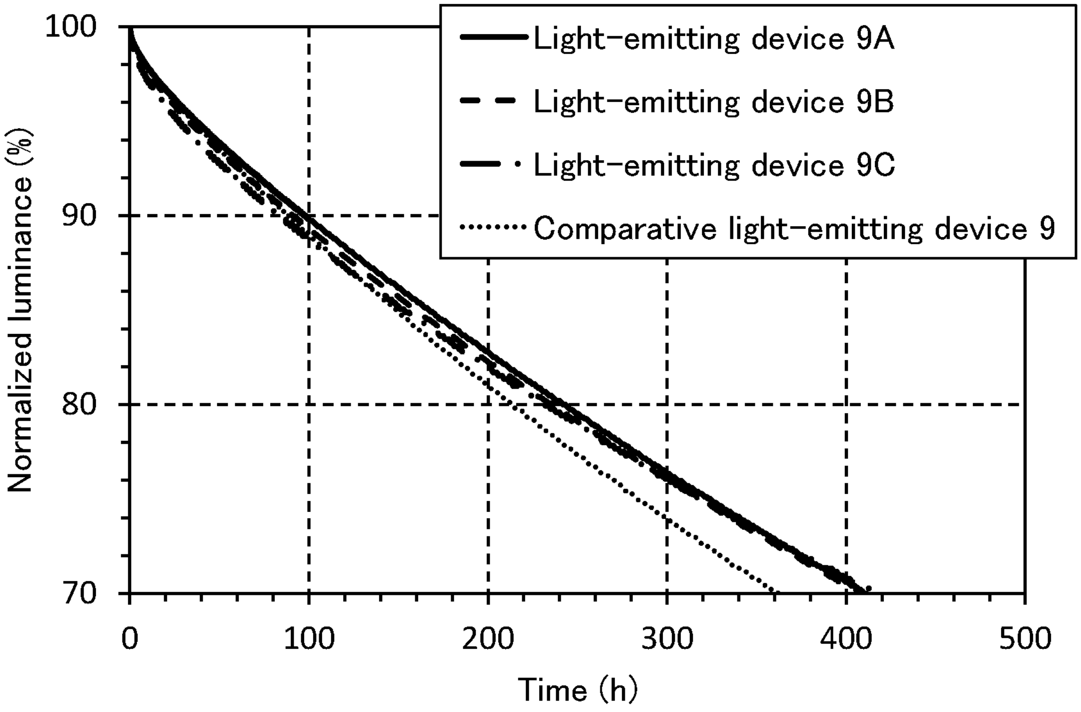
FIG. 82 shows a driving time-dependent change in luminance of light-emitting devices of an example.

Furthermore, a reliability test was performed on the light-emitting device 9A, the light-emitting device 9B, the light-emitting device 9C, and the comparative light-emitting device 9. FIG. 82 shows a time-dependent change in normalized luminance at the time of constant current density driving (50 [mA/cm2]). In FIG. 82, the vertical axis represents normalized luminance (%), and the horizontal axis represents time (h). The value of LT80 (h) that is elapsed time until the measurement luminance reduces to 80% of the initial luminance was 242 hours, 235 hours, and 231 hours in the light-emitting device 9A, the light-emitting device 9B, the light-emitting device 9C, respectively. On the other hand, the value of LT80 (h) in the comparative light-emitting device 9 was 213 hours.

Therefore, it was found from FIG. 82 that in the light-emitting layer 913, the light-emitting device 9A containing 8mpTP-4mDBtPBfpm-$d_{10}$ with deuterium, the light-emitting device 9B containing 8mpTP-4mDBtPBfpm-$d_{13}$ with deuterium, or the light-emitting device 9C containing 8mpTP-4mDBtPBfpm-$d_{23}$ with deuterium had higher reliability than the comparative light-emitting device 9 containing 8mpTP-4mDBtPBfpm that did not contain deuterium.

This application is based on Japanese Patent Application Serial No. 2021-172966 filed with Japan Patent Office on Oct. 22, 2021 and Japanese Patent Application Serial No. 2022-102968 filed with Japan Patent Office on Jun. 27, 2022, the entire contents of which are hereby incorporated by reference.

What is claimed is:

1. An organic compound represented by General Formula (G1):

(G1)

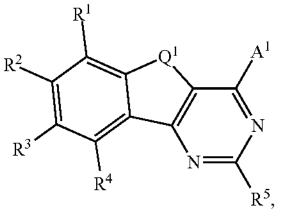

wherein:

Q' represents sulfur or oxygen;

$R^1$ to $R^4$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms, and $R^5$ represents hydrogen;

$A^1$ comprises an aryl group having 6 to 100 carbon atoms or a heteroaryl group having 2 to 100 carbon atoms; and deuterium is substituted for at least one of hydrogen contained in $R^1$ to $R^5$ and $A^1$.

2. The organic compound according to claim 1, wherein the organic compound is represented by General Formula (G2):

(G2)

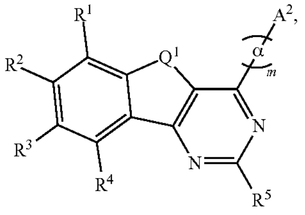

wherein:

α represents substituted or unsubstituted an arylene group having 6 to 25 carbon atoms, or a substituted or unsubstituted heteroarylene group having 2 to 25 carbon atoms;

m represents an integer of 0 to 4;

$A^2$ represents a substituted or unsubstituted aryl group having 6 to 30 carbon atoms, or a substituted or unsubstituted heteroaryl group having 2 to 30 carbon atoms;

$R^3$ represents an aryl group having 6 to 100 carbon atoms and including a substituted or unsubstituted substituent, or a heteroaryl group having 2 to 100 carbon atoms and including a substituted or unsubstituted substituent; and at least one of hydrogen contained in α, $A^2$, and $R^3$ is deuterium.

3. The organic compound according to claim 2, wherein each of the arylene group having 6 to 25 carbon atoms and the heteroarylene group having 2 to 25 carbon atoms is independently represented by any one of Formulae (α-1) to (α-20):

(α-1)

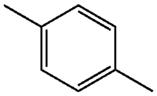

(α-2)

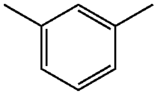

(α-3)

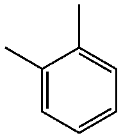

(α-4)

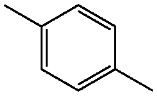

(α-5)

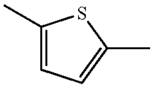

(α-6)

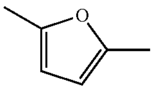

(α-7)

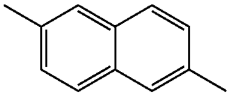

(α-8)

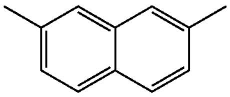

-continued (α-9)

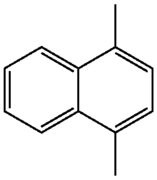

(α-10)

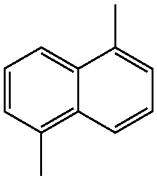

(α-11)

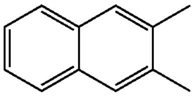

(α-12)

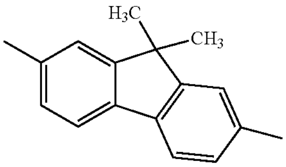

(α-13)

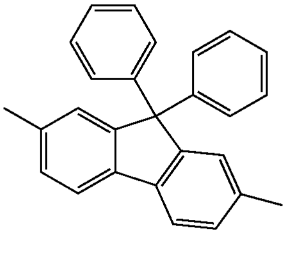

(α-14)

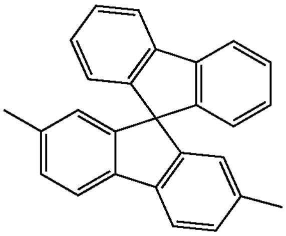

(α-15)

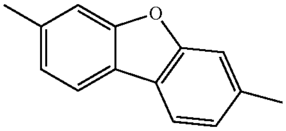

(α-16)

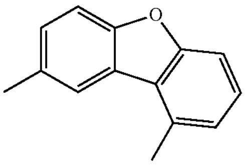

-continued (α-17)

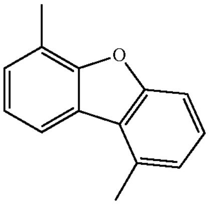

(α-18)

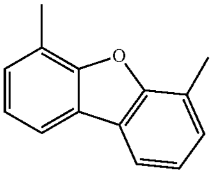

(α-19)

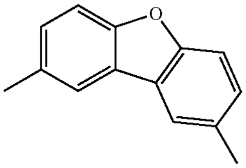

(α-20)

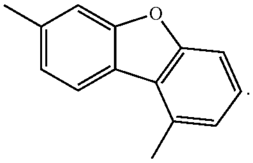

4. The organic compound according to claim 1, wherein the organic compound is represented by General Formula (G3):

(G3)

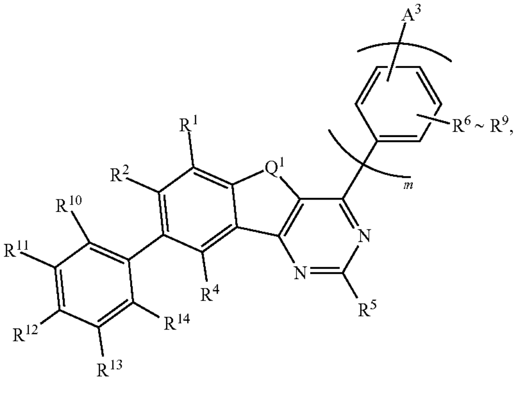

wherein:

$R^6$ to $R^{14}$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms;

$A^3$ represents a substituted or unsubstituted aryl group having 6 to 30 carbon atoms, or a substituted or unsubstituted heteroaryl group having 2 to 30 carbon atoms; and at least one of hydrogen contained in $A^3$ and $R^6$ to $R^{14}$ is deuterium.

5. The organic compound according to claim 1, wherein the organic compound is represented by General Formula (G4):

(G4)

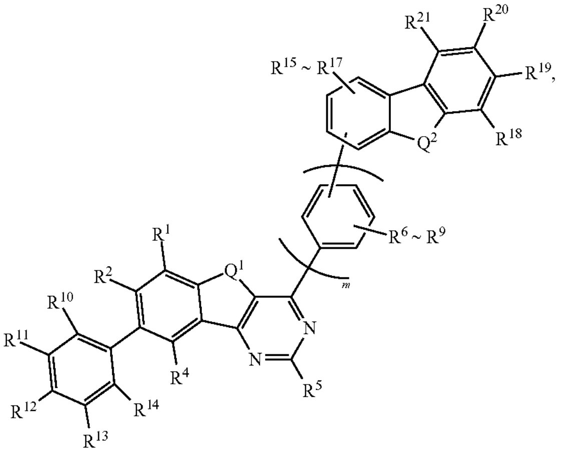

wherein:

$R^6$ to $R^{21}$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms; and at least one of $R^6$ to $R^{21}$ is deuterium.

6. The organic compound according to claim 1, wherein each of the aryl group having 6 to 30 carbon atoms and the heteroaryl group having 2 to 30 carbon atoms is independently represented by any one of Formulae (Ar-1) to (Ar-80):

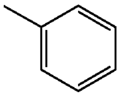

(Ar-1)

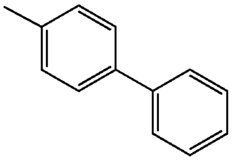

(Ar-2)

-continued
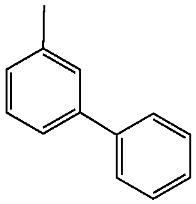
(Ar-3)
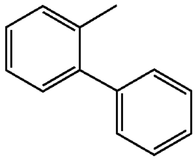
(Ar-4)
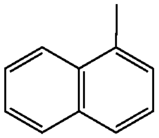
(Ar-5)
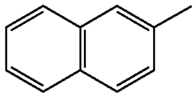
(Ar-6)
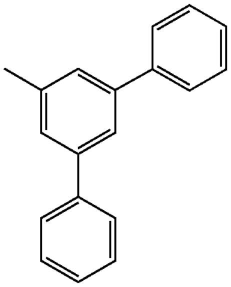
(Ar-7)
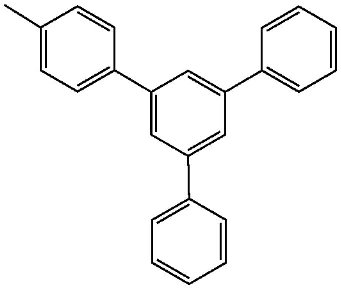
(Ar-8)
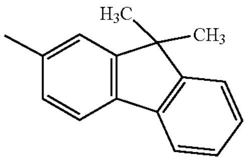
(Ar-9)
-continued
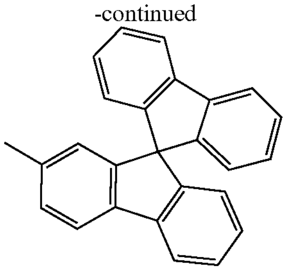
(Ar-10)
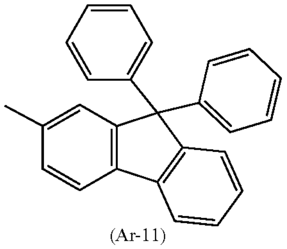
(Ar-11)
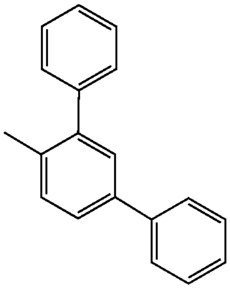
(Ar-12)
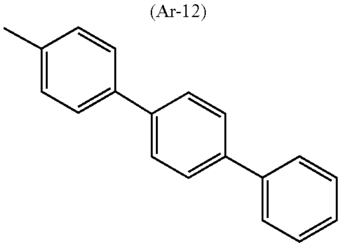
(Ar-13)
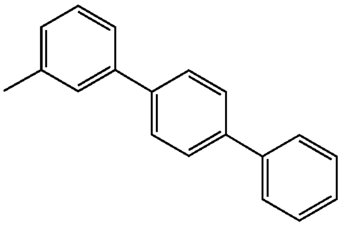
(Ar-14)
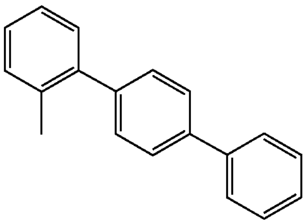
(Ar-15)
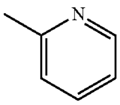
(Ar-16)

-continued
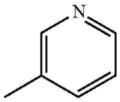
(Ar-17)
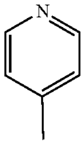
(Ar-18)
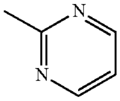
(Ar-19)
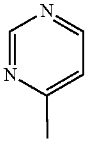
(Ar-20)
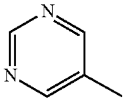
(Ar-21)
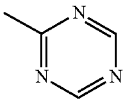
(Ar-22)
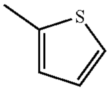
(Ar-23)
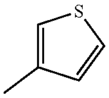
(Ar-24)
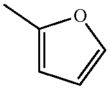
(Ar-25)
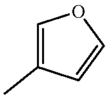
(Ar-26)
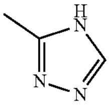
(Ar-27)
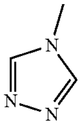
(Ar-28)
-continued
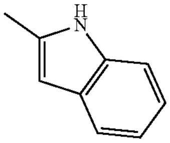
(Ar-29)
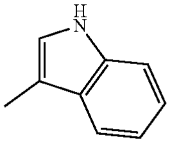
(Ar-30)
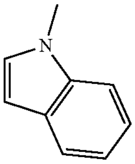
(Ar-31)
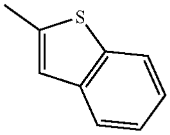
(Ar-32)
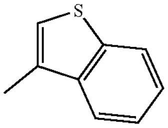
(Ar-33)
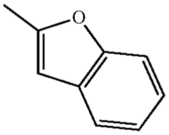
(Ar-34)
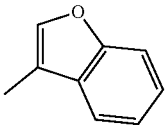
(Ar-35)
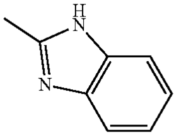
(Ar-36)
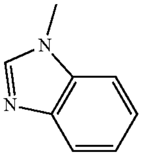
(Ar-37)
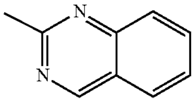
(Ar-38)

-continued
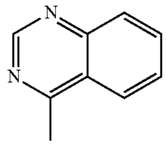
(Ar-39)
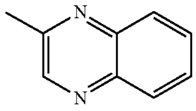
(Ar-40)
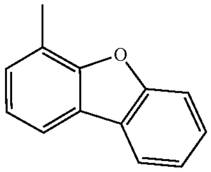
(Ar-41)
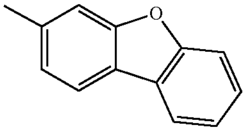
(Ar-42)
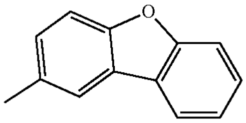
(Ar-43)
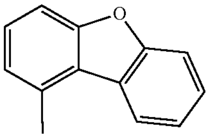
(Ar-44)
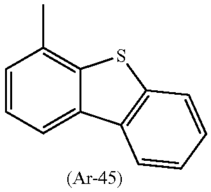
(Ar-45)
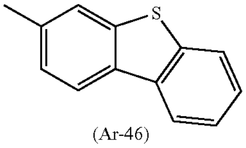
(Ar-46)
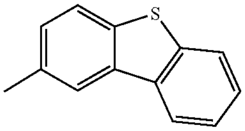
(Ar-47)
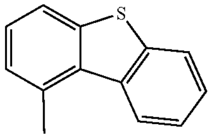
(Ar-48)
-continued
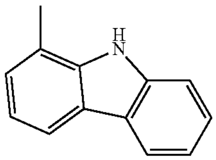
(Ar-49)
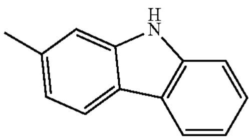
(Ar-50)
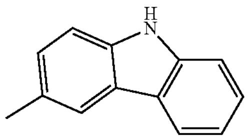
(Ar-51)
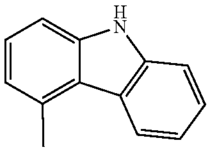
(Ar-52)
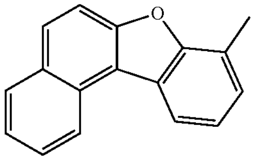
(Ar-53)
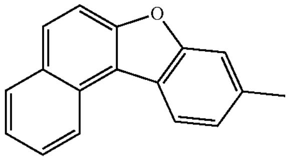
(Ar-54)
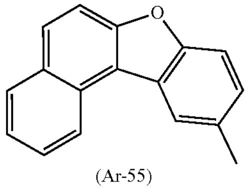
(Ar-55)
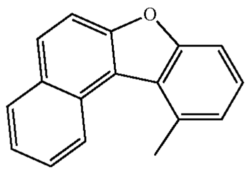
(Ar-56)

-continued
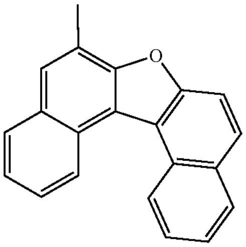
(Ar-57)
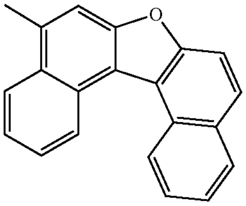
(Ar-58)
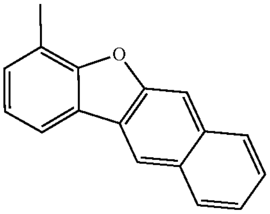
(Ar-59)
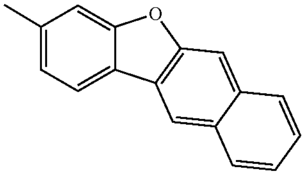
(Ar-60)
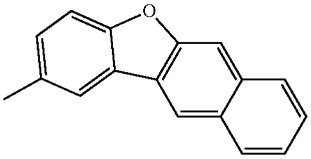
(Ar-61)
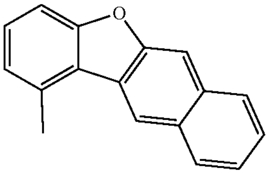
(Ar-62)
-continued
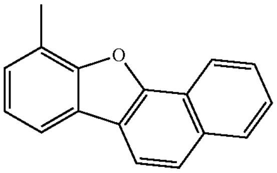
(Ar-63)
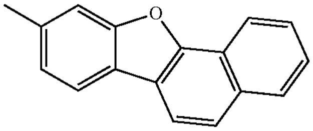
(Ar-64)
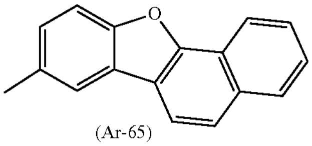
(Ar-65)
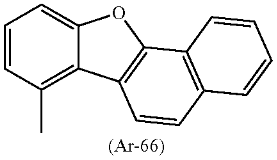
(Ar-66)
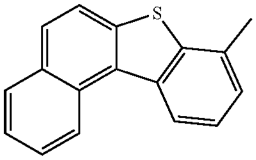
(Ar-67)
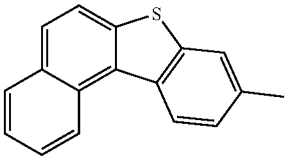
(Ar-68)
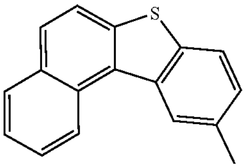
(Ar-69)
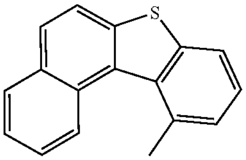
(Ar-70)

-continued

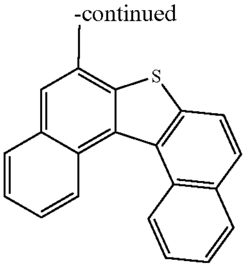

(Ar-71)

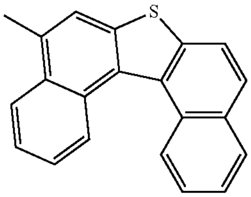

(Ar-72)

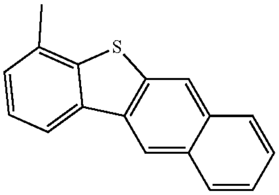

(Ar-73)

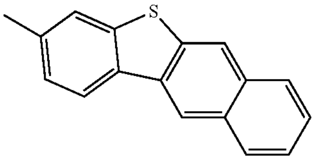

(Ar-74)

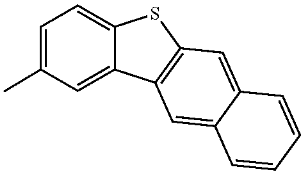

(Ar-75)

-continued

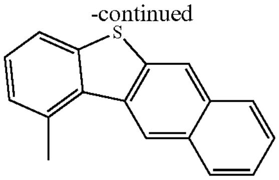

(Ar-76)

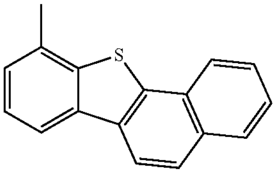

(Ar-77)

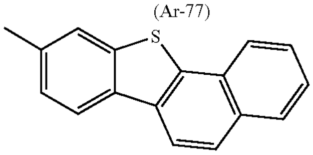

(Ar-78)

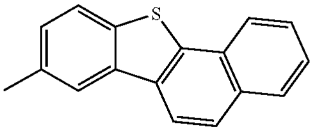

(Ar-79)

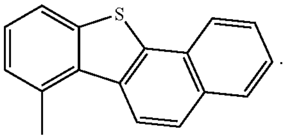

(Ar-80)

7. The organic compound according to claim 1, wherein $A^1$ and $R^3$ have the same structure.

8. The organic compound according to claim 1, wherein one or more hydrogen other than hydrogen directly bonded to a benzofuropyrimidine skeleton is deuterium.

9. The organic compound according to claim 1, wherein all hydrogen contained in a molecule structure is deuterium.

10. The organic compound according to claim 1, wherein the organic compound is represented by Structural Formula (100), (101), or (128):

(100)

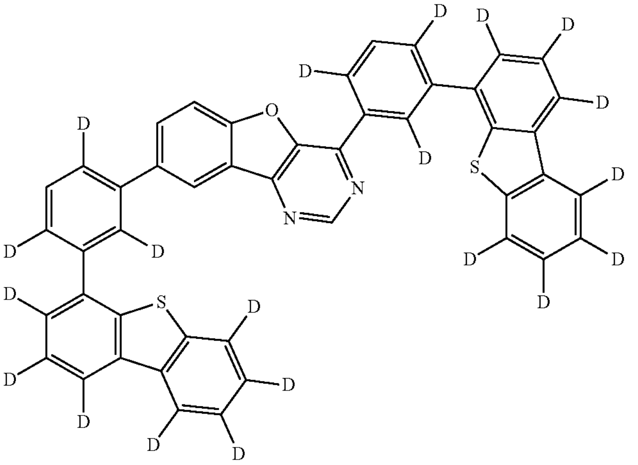

-continued (101)

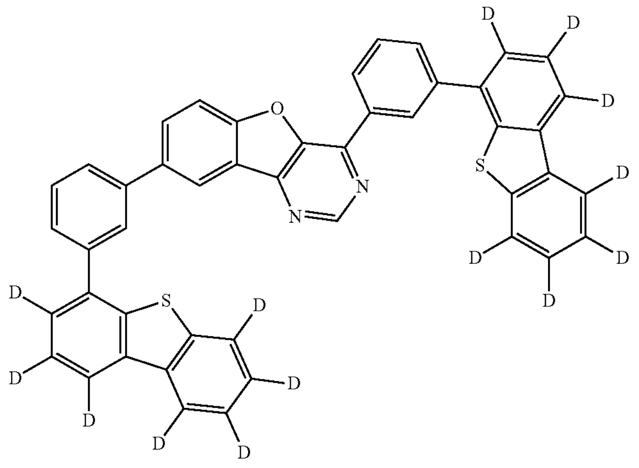

(128)

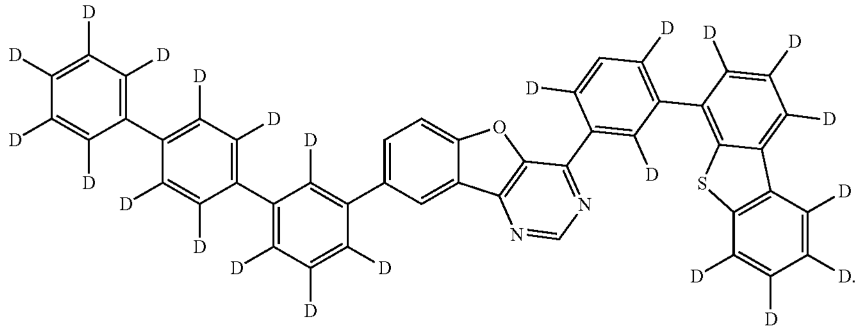

11. A light-emitting device containing the organic compound according to claim 1.

12. A light-emitting apparatus comprising a light-emitting device containing the organic compound according to claim 1 and at least one of a transistor and a substrate.

13. An electronic appliance comprising:

a light-emitting apparatus comprising a light-emitting device containing the organic compound according to claim 1 and at least one of a transistor and a substrate; and at least one of a sensor unit, an input unit, and a communication unit.

14. A lighting device comprising:

an electronic appliance, the electronic appliance comprising:

a light-emitting apparatus comprising a light-emitting device containing the organic compound according to claim 1 and at least one of a transistor and a substrate; and at least one of a sensor unit, an input unit, and a communication unit; and a housing.

15. An organic compound represented by General Formula (G1):

(G1)

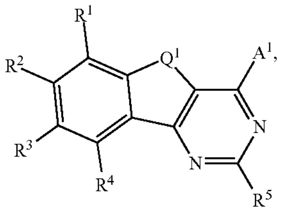

wherein:

$Q^1$ represents sulfur or oxygen;

$R^1$, $R^2$, $R^4$, and $R^5$ each independently represent hydrogen, deuterium, a substituted or unsubstituted alkyl group having 1 to 10 carbon atoms, a substituted or unsubstituted cycloalkyl group having 3 to 10 carbon atoms, a substituted or unsubstituted polycyclic alkyl group having 6 to 10 carbon atoms, a substituted or unsubstituted aryl group having 6 to 30 carbon atoms, or a substituted or unsubstituted heteroaryl group having 2 to 30 carbon atoms;

$A^1$ represents an aryl group having 6 to 100 carbon atoms and including a substituted or unsubstituted substituent, or a heteroaryl group having 2 to 100 carbon atoms and including a substituted or unsubstituted substituent;

$R^3$ represents an aryl group having 6 to 100 carbon atoms and including a substituted or unsubstituted substituent, or a heteroaryl group having 2 to 100 carbon atoms and including a substituted or unsubstituted substituent; and deuterium is substituted for at least one of hydrogen contained in $A^1$ or at least one of hydrogen contained in $R^1$ to $R^5$.

16. The organic compound according to claim 15, wherein each of the aryl group having 6 to 30 carbon atoms and the heteroaryl group having 2 to 30 carbon atoms is independently represented by any one of Formulae (Ar-1) to (Ar-80):

(Ar-1)

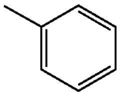

(Ar-2)

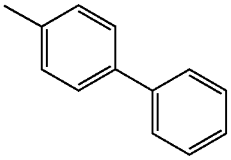

(Ar-3)

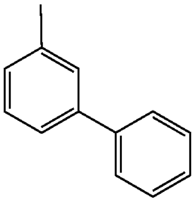

(Ar-4)

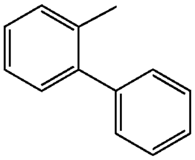

(Ar-5)

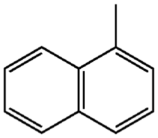

(Ar-6)

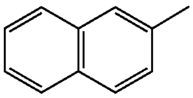

-continued (Ar-7)

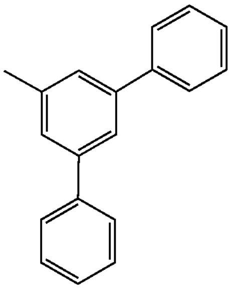

(Ar-8)

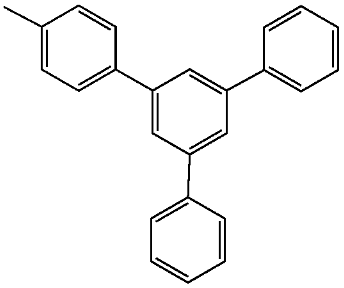

(Ar-9)

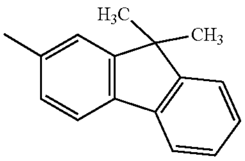

(Ar-10)

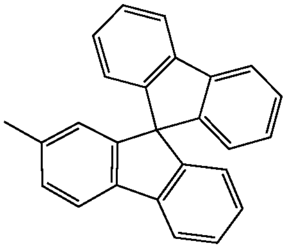

(Ar-11)

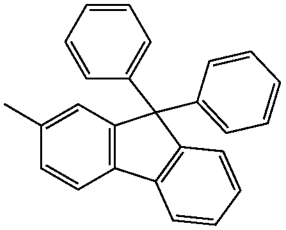

(Ar-12)

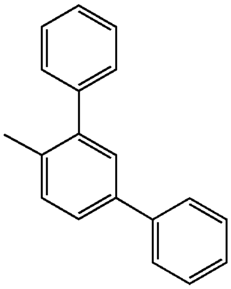

-continued
(Ar-13)
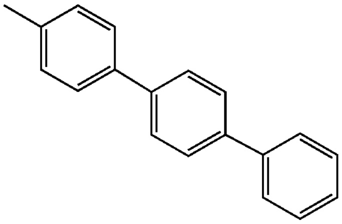
(Ar-14)
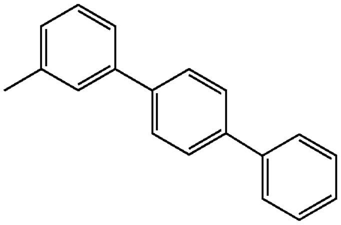
(Ar-15)
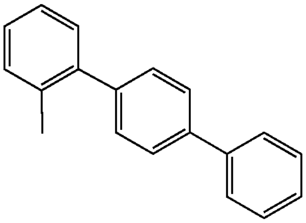
(Ar-16)
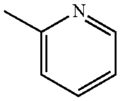
(Ar-17)
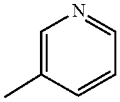
(Ar-18)
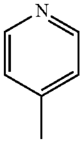
(Ar-19)
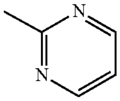
(Ar-20)
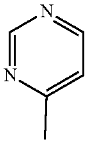
(Ar-21)
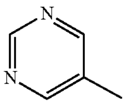
(Ar-22)
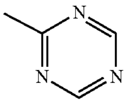
-continued
(Ar-23)
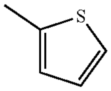
(Ar-24)
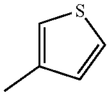
(Ar-25)
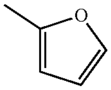
(Ar-26)
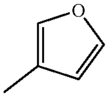
(Ar-27)
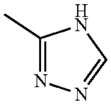
(Ar-28)
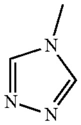
(Ar-29)
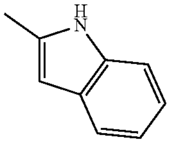
(Ar-30)
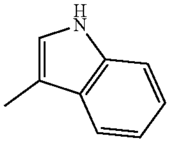
(Ar-31)
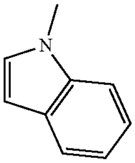
(Ar-32)
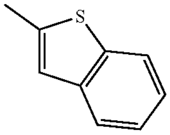
(Ar-33)
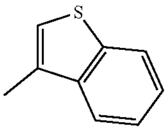
(Ar-34)
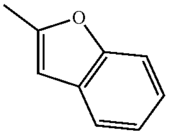

-continued
(Ar-35)
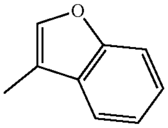
(Ar-36)
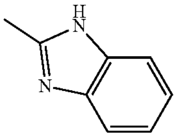
(Ar-37)
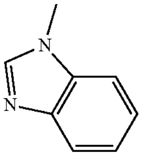
(Ar-38)
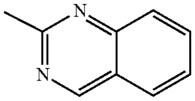
(Ar-39)
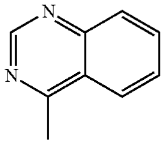
(Ar-40)
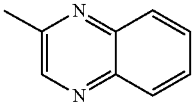
(Ar-41)
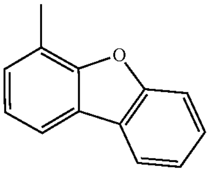
(Ar-42)
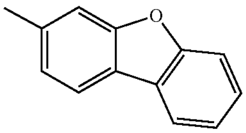
(Ar-43)
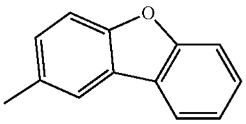
(Ar-44)
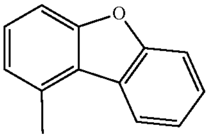
-continued
(Ar-45)
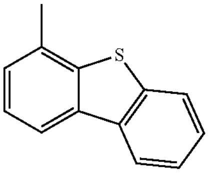
(Ar-46)
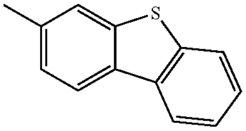
(Ar-47)
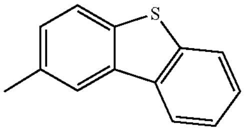
(Ar-48)
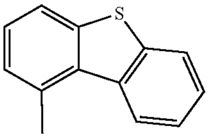
(Ar-49)
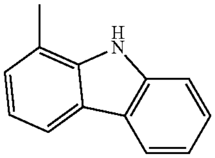
(Ar-50)
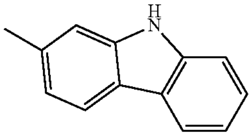
(Ar-51)
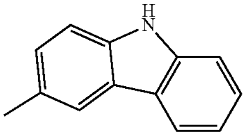
(Ar-52)
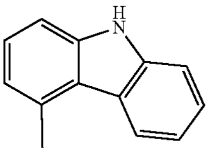
(Ar-53)
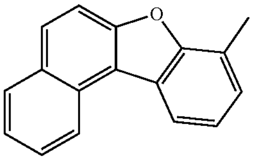
(Ar-54)
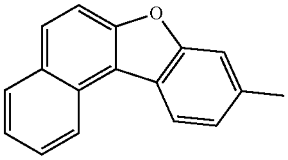

-continued
(Ar-55)
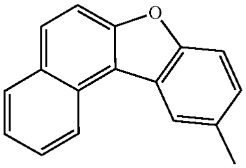
(Ar-56)
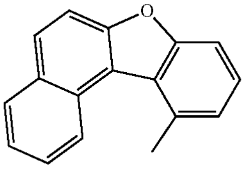
(Ar-57)
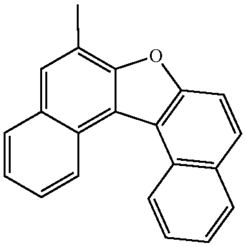
(Ar-58)
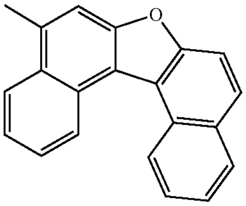
(Ar-59)
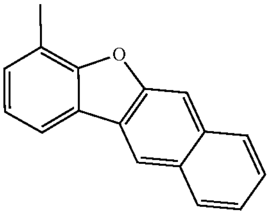
(Ar-60)
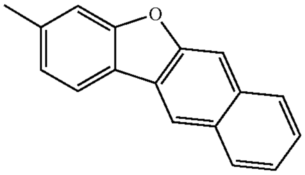
(Ar-61)
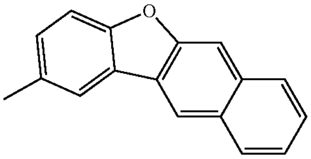
(Ar-62)
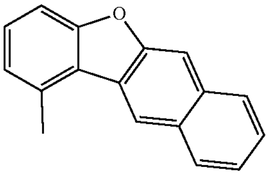
-continued
(Ar-63)
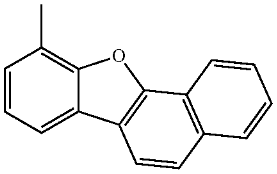
(Ar-64)
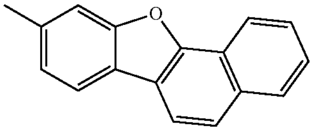
(Ar-65)
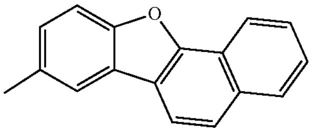
(Ar-66)
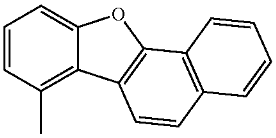
(Ar-67)
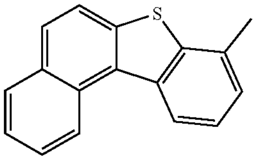
(Ar-68)
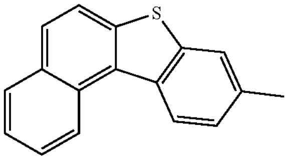
(Ar-69)
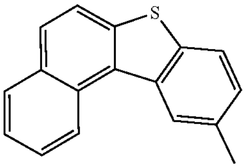
(Ar-70)
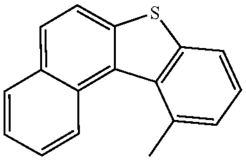
(Ar-71)
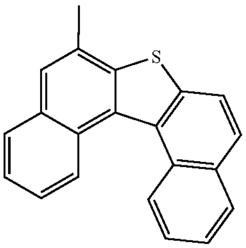

-continued (Ar-72)

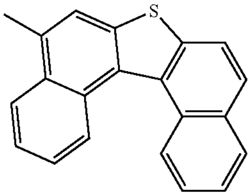

(Ar-73)

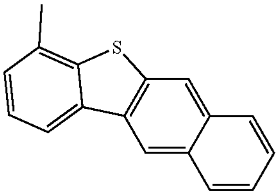

(Ar-74)

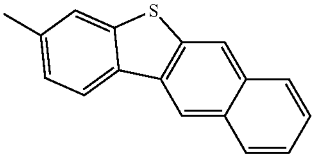

(Ar-75)

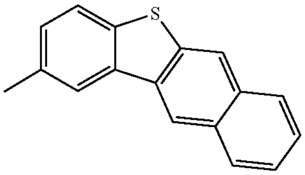

(Ar-76)

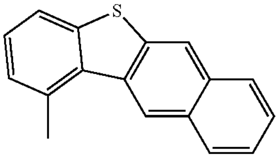

(Ar-77)

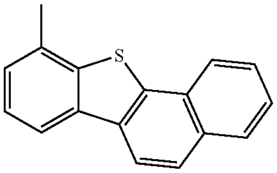

(Ar-78)

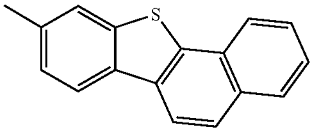

-continued (Ar-79)

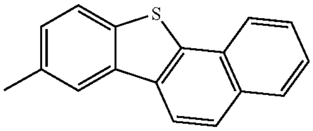

(Ar-80)

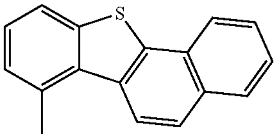

.

17. The organic compound according to claim 15, wherein $A^1$ and $R^3$ have the same structure.

18. The organic compound according to claim 15, wherein one or more hydrogen other than hydrogen directly bonded to a benzofuropyrimidine skeleton is deuterium.

19. The organic compound according to claim 15, wherein all hydrogen contained in a molecule structure is deuterium.

20. A light-emitting device containing the organic compound according to claim 15.

21. A light-emitting apparatus comprising a light-emitting device containing the organic compound according to claim 15 and at least one of a transistor and a substrate.

22. An electronic appliance comprising:

a light-emitting apparatus comprising a light-emitting device containing the organic compound according to claim 15 and at least one of a transistor and a substrate; and at least one of a sensor unit, an input unit, and a communication unit.

23. A lighting device comprising:

an electronic appliance, the electronic appliance comprising:

a light-emitting apparatus comprising a light-emitting device containing the organic compound according to claim 15 and at least one of a transistor and a substrate; and at least one of a sensor unit, an input unit, and a communication unit; and a housing.

* * * * *